US010022382B2

(12) United States Patent
Achiron et al.

(10) Patent No.: US 10,022,382 B2
(45) Date of Patent: *Jul. 17, 2018

(54) RNA POLYMERASE I INHIBITORS AND USES THEREOF

(71) Applicant: Tel HaShomer Medical Research Infrastructure and Services Ltd., Ramat-Gan (IL)

(72) Inventors: Anat Achiron, Tel-Aviv (IL); Roi Mashiach, Kiryat-Ono (IL); Michael Gurevich, Rechovot (IL)

(73) Assignee: Tel HaShomer Medical Research Infrastructure and Services Ltd., Ramat-Gan (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/626,198

(22) Filed: Jun. 19, 2017

(65) Prior Publication Data

US 2017/0290842 A1 Oct. 12, 2017

Related U.S. Application Data

(63) Continuation of application No. 14/742,907, filed on Jun. 18, 2015, now Pat. No. 9,688,697, which is a continuation-in-part of application No. PCT/IB2014/066402, filed on Nov. 27, 2014.

(60) Provisional application No. 61/910,060, filed on Nov. 28, 2013.

(51) Int. Cl.
*A61K 31/551* (2006.01)
*C07D 471/12* (2006.01)
*C07D 513/14* (2006.01)

(52) U.S. Cl.
CPC .................................. *A61K 31/551* (2013.01)

(58) Field of Classification Search
CPC ... A61K 31/551; C07D 471/12; C07D 513/14
USPC .......................................... 514/218; 540/575
See application file for complete search history.

(56) References Cited

U.S. PATENT DOCUMENTS

| | | | |
|---|---|---|---|
| 2007/0117770 | A1 | 5/2007 | Drygin et al. |
| 2008/0248001 | A1 | 10/2008 | Bourke |
| 2009/0093455 | A1 | 4/2009 | Nagasawa et al. |
| 2009/0093465 | A1 | 4/2009 | Pierre et al. |
| 2014/0086839 | A1 | 3/2014 | Achiron et al. |
| 2015/0284410 | A1 | 10/2015 | Achiron et al. |

FOREIGN PATENT DOCUMENTS

| | | |
|---|---|---|
| EP | 0983256 | 3/1997 |
| WO | WO 98/52933 | 11/1998 |
| WO | WO 03/081201 | 10/2003 |
| WO | WO 2007/022474 | 2/2007 |
| WO | WO 2008/081435 | 7/2008 |
| WO | WO 2008/131134 | 10/2008 |
| WO | WO 2009/046383 | 4/2009 |
| WO | WO 2010/113096 | 10/2010 |
| WO | WO 2012/123938 | 9/2012 |
| WO | WO 2015/079411 | 6/2015 |

OTHER PUBLICATIONS

Advisory Action Before the Filing of an Appeal Brief Dated Mar. 28, 2016 From the US Patent and Trademark Office Re. U.S. Appl. No. 14/005,583.

Applicant-Initiated Interview Summary dated Mar. 14, 2017 From the US Patent and Trademark Office Re. U.S. Appl. No. 14/005,583 (4 pages).

Communication Pursuant to Article 94(3) EPC dated Apr. 5, 2016 From the European Patent Office Re. Application No. 12710797.7.

International Preliminary Report on Patentability dated Jun. 9, 2016 From the International Bureau of WIPO Re. Application No. PCT/IB2014/066402.

International Preliminary Report on Patentability dated Sep. 26, 2013 From the International Bureau of WIPO Re. Application No. PCT/IL2012/050061.

International Search Report and the Written Opinion dated Jul. 9, 2012 From the International Searching Authority Re. Application No. PCT/IL2012/050061.

International Search Report and the Written Opinion dated Feb. 15, 2015 From the International Searching Authority Re. Application No. PCT/IB2014/066402.

Notification of Office Action dated Sep. 30, 2014 From the State Intellectual Property Office of the People's Republic of China Re. Application No. 201280023297.2 and Its Translation Into English.

Office Action dated Jan. 17, 2016 From the Israel Patent Office Re. Application No. 228464 and Its Translation Into English.

Office Action dated Jul. 17, 2016 From the Israel Patent Office Re. Application No. 228464 and Its Translation Into English.

Office Action dated Jun. 24, 2015 From the State Intellectual Property Office of the People's Republic of China Re. Application No. 201280023297.2 and Its Translation Into English.

Official Action dated Apr. 3, 2015 From the US Patent and Trademark Office Re. U.S. Appl. No. 14/005,583.

Official Action dated Jan. 11, 2017 From the US Patent and Trademark Office Re. U.S. Appl. No. 14/005,583. (28 pages).

Official Action dated Jul. 12, 2016 From the US Patent and Trademark Office Re. U.S. Appl. No. 14/742,907.

Official Action dated Dec. 13, 2016 From the US Patent and Trademark Office Re. U.S. Appl. No. 14/742,907. (8 pages).

Official Action dated Apr. 14, 2016 From the US Patent and Trademark Office Re. U.S. Appl. No. 14/005,583.

Official Action dated Dec. 31, 2015 From the US Patent and Trademark Office Re. U.S. Appl. No. 14/005,583.

Restriction Official Action dated Nov. 28, 2014 From the US Patent and Trademark Office Re. U.S. Appl. No. 14/005,583.

Search Report dated Sep. 30, 2014 From the State Intellectual Property Office of the People's Republic of China Re. Application No. 201280023297.2 and Its Translation Into English.

(Continued)

*Primary Examiner* — Brenda L Coleman

(57) ABSTRACT

Provided are novel compounds which are capable of inhibiting an activity of RNA polymerase I, and uses thereof in treating diseases or disorders modulated by RNA polymerase I, preferably autoimmune diseases such as multiple sclerosis and proliferative diseases.

10 Claims, 16 Drawing Sheets

(56) References Cited

OTHER PUBLICATIONS

Supplementary European Search Report and the European Search Opinion dated Mar. 17, 2017 From the European Patent Office Re. Application No. 14865441.1. (11 Pages).
Achiron et al. "Zinc-Ion Binding and Cytokine Activity Regulation Pathways Predicts Outcome in Relapsing-Remitting Multiple Sclerosis ", Clinical and Experimental Immunology, 149: 235-242, 2007.
Banti et al. "Synthesis and In-Vitro Antitumour Activity of New Naphthyridine Derivatives on Human Pancreatic Cancer Cells", Journal of Pharmacy and Pharmacology, JPP, 61: 1057-1066, First Published Jan. 8, 2010. Abstract.
Bratrude "The Anti-Inflammatory Diet and Multiple Sclerosis", Swedish Medical Center, 4 Pages, Aug. 12, 2013.
Cavanaugh et al. "Mammalian Rrn3 Is Required for the Formation of a Transcription Competent Preinitiation Complex Containing RNA Polymerase I", Gene Expression, 14(3): 131-147, 2008.
Cavanaugh et al. "Rrn3 Phosphorylation Is a Regualtory Checkpoint for Ribosome Biogenesis", The Journal of Biological Chemistry, 277(30): 27423-27432, Jul. 26, 2002.
Costelloe et al. "Long-Term Clinical Relevance of Criteria for Designating Multiple Sclerosis as Benign After 10 Years of Disease", Journal of Neurology, Neurosurgery, and Psychiatry, 79(11): 1245-1248, Nov. 2008.
Drygin et al. "Targeting RNA Polymerase I With an Oral Small Molecule CX-5461 Inhibitis Ribosomal RNA Synthesis and Solid Tumor Growth", Cancer Research, XP002678820, 71(4): 1418-1430, Published Online Dec. 15, 2010.
Drygin et al. "The RNA Polymerase I Transcription Machinery: An Emerging Target for the Treatment of Cancer", Annual Review of Pharmacology and Toxicology, 50: 131-156, 2010.
Haddach et al. "Discovery of CX-5461, the First Direct and Selective Inhibitor of RNA Polymerase I, for Cancer Therapeutics", ACS Medical Chemistry Letters, XP055350883, 3(7): 602-606, May 8, 2012. P.602, Compound 7c.
Haegert "Multiple Sclerosis: A Disorder of Altered T -Cell Homeostasis", 2011: Article ID 16130, . 6 pages, 2011.
Kalita et al. "Inhibition of Nucleolar Transcription as a Trigger for Neuronal Apoptosis", Journal of Neurochemistry, 105(6): 2286-2299, Jun. 1, 2008.
Leuenroth et al. "Triptolide-Induced Transcriptional Arrest Is Associated With Changes in Nuclear Substructure", Cancer Research, 68: 5257-5266, Jul. 1, 2008.
Liu et al. "Triptolide, A Component of Chinese Herbal Medicine, Modulates the Functional Phenotype of Dendritic Cells", Transplantation, 84(11): 1517-1526, Dec. 15, 2007.
Pittock et al. "Benign Multiple Sclerosis: A Distinct Clinical Entity With Therapeutic Implications", Current Topics in Microbiology and Immunology, 318: 1-17, 2008.
Reagan-Shaw et al. "Dose Translation From Animal to Human Studies Revisited", The FASEB Journal, 22: 659-661, 2007.
Russell et al. "RNA-Polymerase-I-Directed rDNA Transcription, Life and Works", Trends in Biochemical Sciences, 30(2): 87-96, Feb. 2005.
Wang et al. "Triptoilide T-Cell Inflammatory Responses and Ameliorates Experimental Autoimmune Encephalomyelitis", Journal of Neuroscience Research, 86:2441-2449, 2008.
Communication Pursuant to Article 94(3) EPC dated Jan. 17, 2018 From the European Patent Office Re. Application No. 14865441.1. (5 Pages).

POL1-I
RAM-0; Compound 1

POL1-I/1
RAM-2; Compound 2

POL1-I/4
RAM-1; Compound 4

POL1-I/3
Compound 5

POL1-I/2
RAM-3; Compound 3

Compound 1

Compound 10

RNA POLYMERASE I INHIBITORS AND USES THEREOF

RELATED APPLICATIONS

This application is a Continuation of U.S. patent application Ser. No. 14/742,907 filed on Jun. 18, 2015, which is a Continuation-in-Part (CIP) of PCT Patent Application No. PCT/IB2014/066402 having International Filing Date of Nov. 27, 2014, which claims the benefit of priority under 35 USC § 119(e) of U.S. Provisional Patent Application No. 61/910,060 filed on Nov. 28, 2013. The contents of the above applications are all incorporated by reference as if fully set forth herein in their entirety.

SEQUENCE LISTING STATEMENT

The ASCII file, entitled 70149SequenceListing.txt, created on Jun. 19, 2017, comprising 574,287 bytes, submitted concurrently with the filing of this application is incorporated herein by reference.

FIELD AND BACKGROUND OF THE INVENTION

The present invention, in some embodiments thereof, relates to therapy and, more particularly, but not exclusively, to novel RNA Polymerase I inhibitors and to uses thereof in methods of treating medical conditions including, for example, autoimmune diseases multiple sclerosis and proliferative diseases such as cancer.

Autoimmune diseases are caused by an autoimmune response, i.e., an immune response directed to a substance in the body of the subject. The characteristics of the autoimmune diseases vary and depend on the site affected by the autoimmune response.

Multiple sclerosis (MS) is the most common demyelinating disease of the central nervous system (CNS) affecting young adults (disease onset between 20 to 40 years of age) and is the third leading cause for disability after trauma and rheumatic diseases, with an estimated annual cost of 34,000 USD per patient (total life time cost of 2.2 million USD per patient).

The disease is characterized by destruction of myelin, associated with death of oligodendrocytes and axonal loss. The main pathologic finding in MS is the presence of infiltrating mononuclear cells, predominantly T lymphocytes and macrophages, which surpass the blood brain barrier and induce an active inflammation within the brain and spinal cord. The neurological symptoms that characterize MS include complete or partial vision loss, diplopia, sensory symptoms, motor weakness that can worsen to complete paralysis, bladder dysfunction and cognitive deficits, which eventually may lead to a significant disability. The associated multiple inflammatory foci lead to myelin destruction, plaques of demyelination, gliosis and axonal loss within the brain and spinal cord and are the reasons which contribute to the clinical manifestations of neurological disability.

The etiology of MS is not fully understood. The disease develops in genetically predisposed subjects exposed to yet undefined environmental factors and the pathogenesis involves autoimmune mechanisms associated with autoreactive T cells against myelin antigens. It is well established that not one dominant gene determines genetic susceptibility to develop MS, but rather many genes, each with different influence, are involved.

Clinically, in 85% of MS patients the illness is initiated with a relapsing-remitting course (RRMS), and in about 10-15% of MS patients have an a-priori primary progressive course (PPMS) without relapses. RRMS is characterized by inflammatory attacks associated with neurological deficits with periods of remissions between the relapses that vary in time. After a period of 10 years, about 50% of RRMS patients will progress to a secondary progressive MS (SPMS) course, characterized by permanent neurological dysfunction, with or without relapses and progressive disability.

Benign MS (BMS) is a clinical variant of RRMS in which the patients develop low neurological disability if at all after a disease duration of at least 10 years. Accordingly, this group of MS patients do not experience devastating accumulating disability over-time and when these patients are examined neurologically and scored by the Expanded Disability Status Scale (EDSS) they receive a score that is equal to or lower than 3.0. This low EDSS score signifies mild disability and when this low disability occurs more than 10 years after disease onset, the course of MS is defined as benign. Prediction of patients that will have BMS is currently impossible and the definition of these patients is retrospective. The molecular events accountable for the BMS variant of disease are not understood.

WO 2008/081435 discloses methods and kits for predicting the prognosis of a subject diagnosed with multiple sclerosis and methods of selecting a treatment regimen of a subject diagnosed with multiple sclerosis.

Achiron A, et al., 2007 [Clinical and Experimental Immunology, 149: 235-242] describe genes of the zinc-ion binding and cytokine activity regulation pathways which predict outcome in relapsing-remitting multiple sclerosis.

WO 2010/113096 discloses methods of predicting clinical course and treating multiple sclerosis.

Current approved drugs for the treatment of MS are either general anti-inflammatory agents or immunomodulators and consequently result only in moderate beneficial effects suppressing disease activity.

CX-5461 (see, Table 1 hereinunder) is a small molecule that was designed to selectively inhibit rRNA synthesis by inhibiting RNA Polymerase I (POL I or POL1), without affecting mRNA synthesis by RNA Polymerase II (POL II), and without inhibiting DNA replication or protein synthesis (Russell J, Zomerdijk J C. Trends Biochem Sci 30:87-96, 2005; Drygin D, et al. Annu Rev Pharmacol Toxicol 50:131-156, 2010).

The inhibition of POL1 results in nucleolar stress which causes the release of ribosomal proteins (RP) from the nucleolus and subsequent activation of p53, resulting in cell apoptosis [Kalita K, et al. J Neurochem 105:2286-2299, 2008]. In a previous study [Drygin D, et al. Cancer Res 71:1418-1430, 2011], the antiproliferative activity of CX-5461 was studied in cell lines and it was shown that CX-5461 inhibited POL-I activity in human cancer cell lines.

Recent studies indicate that disruption of the SL1/rDNA complex by CX-5461 results from the interference between SL1 and rDNA. SL1, a protein complex containing TATA binding protein-associated factors, is responsible for POL1 promoter specificity. SL1 performs important tasks in the transcription complex assembly, mediating specific interactions between the rDNA promoter region and the POL1 enzyme complex, thereby recruiting POL1, together with a collection of POL1-associated factors like RRN3 to rDNA (Cavanaugh A, et al. *Gene Expr* 14:131-147, 2008).

U.S. Patent Application Publication No. 2009/0093465 discloses a family of compounds, including CX-5461, as kinase modulators useful in the treatment of proliferative diseases such as cancer.

Recently, a role for inhibition of RNA polymerase I (POL1) pathway in the regulation of MS disease activity by suppression of inflammation and enhancement of apoptosis of autoreactive lymphocytes has been uncovered. The suggested mechanism by which POL1 pathway inhibition affects the disease process is demonstrated in Background Art FIGS. 1 and 2A-B.

The above findings have supported a basis for direct targeting of RNA Polymerase-I transcription pathway as a strategy for selective induction of apoptosis in MS in order to transform the active disease of RRMS to the preferable BMS subtype. Administration of a specific POL1 inhibitor (POL1-I) was demonstrated to prevent animal Experimental Autoimmune Encephalomyelitis (EAE) when administered at disease induction and to reduce the disease severity when administered at clinical disease onset [Achiron et al. 2013, J Neuroimmunol 263:91-97], thus confirming that a POL1 inhibitor acts specifically by inhibiting the polymerase I associated molecules.

WO 2012/123938 discloses uses of family of compounds, including CX-5461 and derivatives thereof, in the treatment of autoimmune diseases such as MS.

Additional background art includes Leuenroth S J and Crews C M (Triptolide-induced transcriptional arrest is associated with changes in nuclear substructure. Cancer Res. 2008; 68:5257-5266); Liu Y, et al. (Triptolide, a component of Chinese herbal medicine, modulates the functional phenotype of dendritic cells. Transplantation. 2007; 84:1517-1526); Wang Y, et al. (Triptolide modulates T-cell inflammatory responses and ameliorates experimental autoimmune encephalomyelitis. J Neurosci Res. 2008; 86:2441-2449; EP 0983256; PCT/US1998/008562; WO9852933A1; Alice H. Cavanaugh, et al., 2002 (Rrn3 Phosphorylation is a regulatory checkpoint for ribosome biogenesis J. Biol. Chem., 2002; 277: 27423-27432); PCT Pub. No. WO 03/081201.

SUMMARY OF THE INVENTION

Based on the findings that inhibition of RNA Polymerase-I plays a role in regulation of MS and other autoimmune diseases, as well as cell proliferation, the present inventors have searched for POL-1 inhibitors (denoted herein as POL1-I) that would exhibit an improved effect as compared to the presently known POL1 inhibitors (e.g., POL1-I and structural analogs thereof).

The present inventors have uncovered that by modifying a structural feature of CX-5461 or analogs thereof, so as to reduce or even reverse its capability of participating in hydrogen bond formation, inhibitors which exhibit improved performance are obtained.

According to an aspect of some embodiments of the present invention there is provided a compound represented by general Formula I:

Formula I

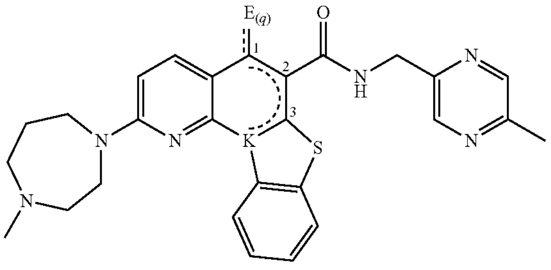

wherein ------ or the dashed line each independently indicates an optionally unsaturated bond, depending on the nature and valency of E;

E forms a chemical moiety other then carbonyl, capable of interfering with a hydrogen binding capacity of the compound;

Q equals 1 or 2; and

K is N or $N^{(+)}$, depending on the nature and valency of E.

According to some embodiments of the present invention, E forms a chemical moiety selected from the group consisting of thiocarbonyl and a substituted or unsubstituted imine.

According to some embodiments of the present invention, q is 1, K is N, E is linked to carbon 1 of the ring via an unsaturated double bond, and another unsaturated double bond is present between carbons 2 and 3 of the ring, the compound being represented by Formula Ia:

Formula Ia

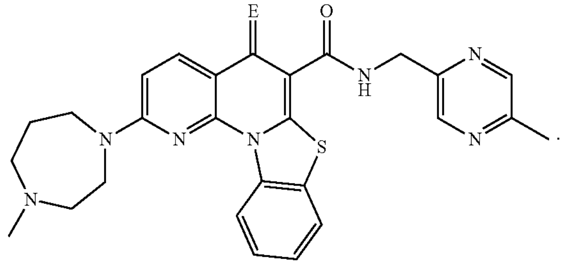

According to some embodiments of the present invention, E forms a substituted or unsubstituted imine, the compound being represented by Formula Ib:

Formula Ib

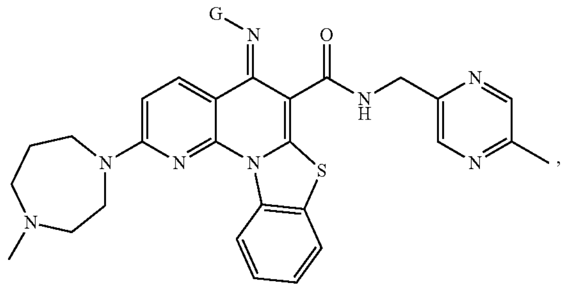

wherein G is selected from the group consisting of hydrogen, alkyl, cycloalkyl, aryl, heteroaryl, heteroalicyclic, alkoxy, thioalkoxy, thiol, hydroxyl, aryloxy, and thioaryloxy.

According to some embodiments of the present invention, G is aryl.

According to an aspect of some embodiments of the present invention there is provided a compound as described herein, for use in the treatment of an autoimmune disease.

According to an aspect of some embodiments of the present invention there is provided a compound as described herein, for use in the manufacture of a medicament for treating an autoimmune disease.

According to an aspect of some embodiments of the present invention there is provided a method of treating an autoimmune disease in a subject, the method comprising administering to the subject a therapeutically effective amount of the compound of Formula I as described in any one of the respective embodiments herein.

According to some embodiments of the present invention, the autoimmune disease is multiple sclerosis.

According to some embodiments of the present invention, the multiple sclerosis is a relapsing-remitting multiple sclerosis (RRMS) or benign multiple sclerosis (BMS).

According to some embodiments of the present invention, treating the multiple sclerosis comprises changing the course of the disease from the RRMS to BMS.

According to some embodiments of the present invention, the autoimmune disease is treatable by inhibiting an activity of RNA Polymerase I.

According to an aspect of some embodiments of the present invention there is provided a compound as described herein, for use in the treatment of a proliferative disease or disorder.

According to an aspect of some embodiments of the present invention there is provided a use of the compound as described herein, in the manufacture of a medicament for the treatment of a proliferative disease or disorder.

According to an aspect of some embodiments of the present invention there is provided a method of treating a proliferative disease or disorder, the method comprising administering to a subject in need thereof a therapeutically effective amount of the compound as described herein.

According to some embodiments of the present invention, the proliferative disease or disorder is treatable by inhibiting an activity of a protein kinase.

According to an aspect of some embodiments of the present invention there is provided a compound as described herein, for use in inhibiting an activity of RNA Polymerase I and/or for treating a disease or disorder treatable by inhibiting an activity of RNA Polymerase I.

According to an aspect of some embodiments of the present invention there is provided a use of a compound as described herein, in the manufacture of a medicament for inhibiting an activity of RNA Polymerase I and/or for treating a disease or disorder treatable by inhibiting an activity of RNA Polymerase I.

According to an aspect of some embodiments of the present invention there is provided a method of inhibiting an activity of RNA Polymerase I, the method comprising contacting the RNA Polymerase I with an effective amount of a compound as described herein.

According to some embodiments of the present invention, contacting is effected in vitro.

According to some embodiments of the present invention, contacting is effected in vivo.

According to some embodiments of the present invention, the method is being for treating a disease treatable by inhibiting an activity of RNA Polymerase I.

According to an aspect of some embodiments of the present invention there is provided a compound as described herein, for use in inhibiting an activity of a protein kinase and/or for treating a disease or disorder treatable by inhibiting an activity of a protein kinase.

According to an aspect of some embodiments of the present invention there is provided a use of a compound as described herein, in the manufacture of a medicament for inhibiting an activity of a kinase and/or for treating a disease or disorder treatable by inhibiting an activity of a protein kinase.

According to an aspect of some embodiments of the present invention there is provided a method of inhibiting an activity of a protein kinase, the method comprising contacting the protein kinase with an effective amount of a compound as described herein.

According to some embodiments of the present invention, contacting is effected in vitro.

According to some embodiments of the present invention, contacting is effected in vivo.

According to some embodiments of the present invention, the method is being for treating a disease treatable by inhibiting an activity of a protein kinase.

According to some embodiments of the present invention, there is provided a method of monitoring an efficiency of the compound of claim 1 in treating a disease associated with a subject, the method comprising:

(a) administering to the subject a therapeutically effective amount of the compound, and (b) comparing a level of expression of at least one gene involved in the RNA polymerase I pathway in a cell of the subject following treating with the compound to a level of expression of the at least one gene in a cell of the subject prior to treating the subject with the compound, (i) wherein a decrease above a predetermined threshold in the level of expression of the at least one gene following treating with the compound relative to the level of expression of the at least one gene prior to treating with the compound indicates that the compound is efficient for treating the subject;

(ii) wherein an increase above a predetermined threshold in the level of expression of the at least one gene following treating with the compound relative to the level of expression of the at least one gene prior to treating with the compound indicates that the compound is not efficient for treating the subject; or (iii) wherein when a level of expression of the at least one gene following treating with the compound is identical or changed below a predetermined threshold as compared to prior to treating with the compound then the treatment is not efficient for treating the subject;

thereby monitoring the efficiency of the compound in treating the disease in the subject.

According to some embodiments of the present invention, the disease is selected from the group consisting of an autoimmune disease and a proliferative disease or disorder.

According to some embodiments of the present invention, the compound is:

Compound 10

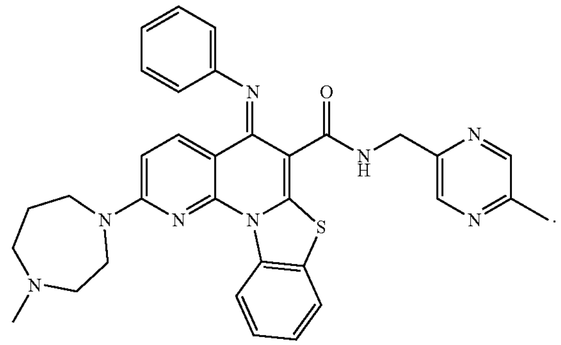

According to some embodiments of the present invention, the at least one gene involved in the RNA polymerase 1 pathway is selected from the group consisting of POLR1D, LRPPRC, RRN3, pre-rRNA and NCL.

According to some embodiments of the present invention, the at least one gene involved in the RNA polymerase 1 pathway is selected from the group consisting of POLR1D, LRPPRC, RRN3 and pre-rRNA.

According to some embodiments of the present invention, the cell is comprised in a biological sample.

According to some embodiments of the present invention, the biological sample is a blood sample.

According to some embodiments of the present invention, the level of expression of the at least one gene is determined using an RNA and/or a protein detection method.

According to some embodiments of the present invention, the detection method is selected from the group consisting of RT-PCR, oligonucleotide microarray, immunoprecipitation, Western blot analysis and FACS.

According to some embodiments of the present invention, the level of expression of the at least one gene is determined by hybridizing the cell or fractions or extracts thereof of the subject with an oligonucleotide which specifically hybridizes with a polynucleotide expressed from the at least one gene and/or by contacting the cell or fractions or extracts thereof of the subject with an antibody which specifically binds a polypeptide expressed from the at least one gene.

A "compound" as described herein refers to a compound having Formula I as described in any one of its respective embodiments, and further to any other compound described in the following description as being contemplated by embodiments of the present invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIG. 6A shows the results of a representative experiment and FIGS. 6B-D show the mean results of 3 independent experiments. Error bars represent mean±SEM.

DESCRIPTION OF SPECIFIC EMBODIMENTS OF THE INVENTION

Figure 1:
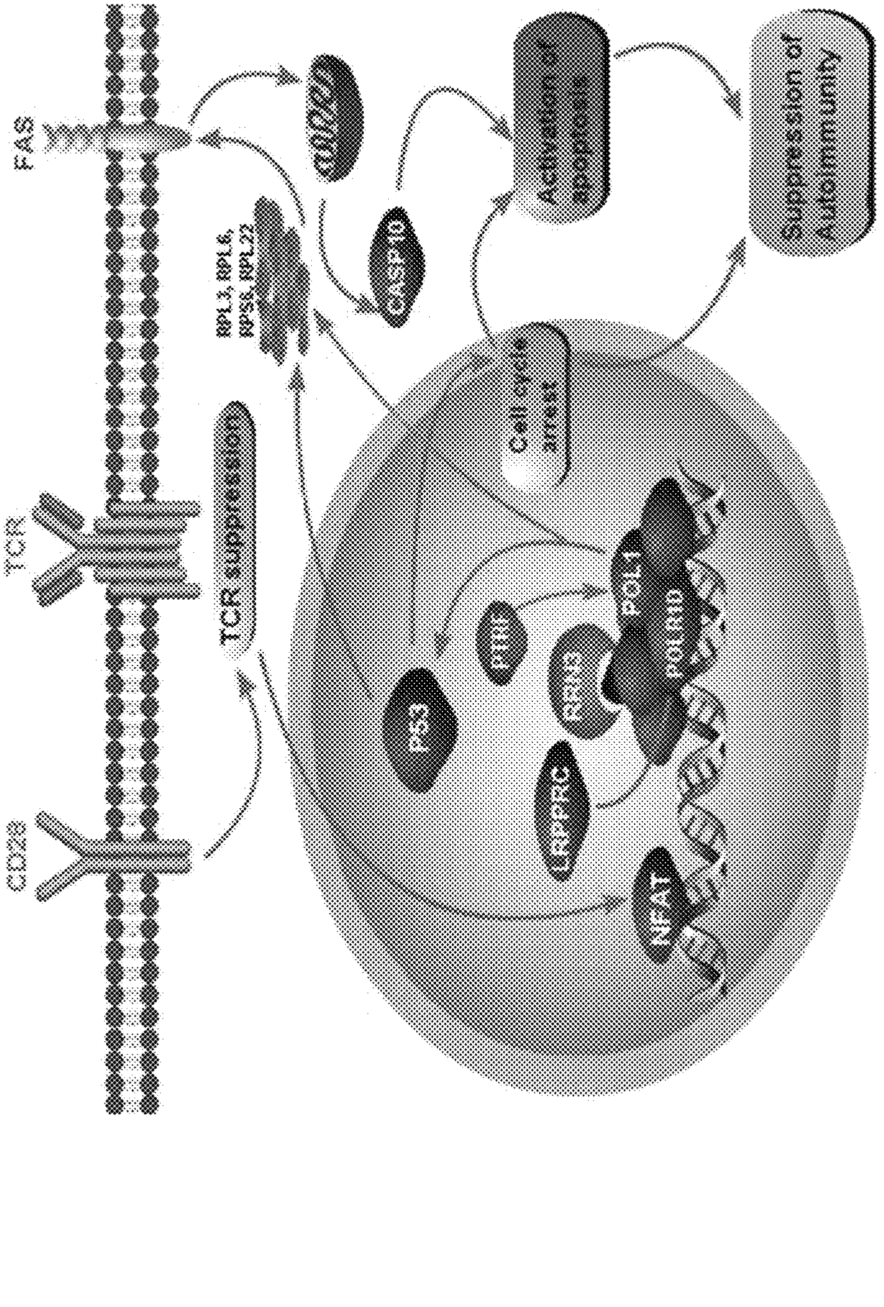
FIG. 1 (Background Art) presents a schematic illustration of POL1 molecular mechanism, showing the effect of POL1 on apoptosis and proliferation.
Figure 2B:
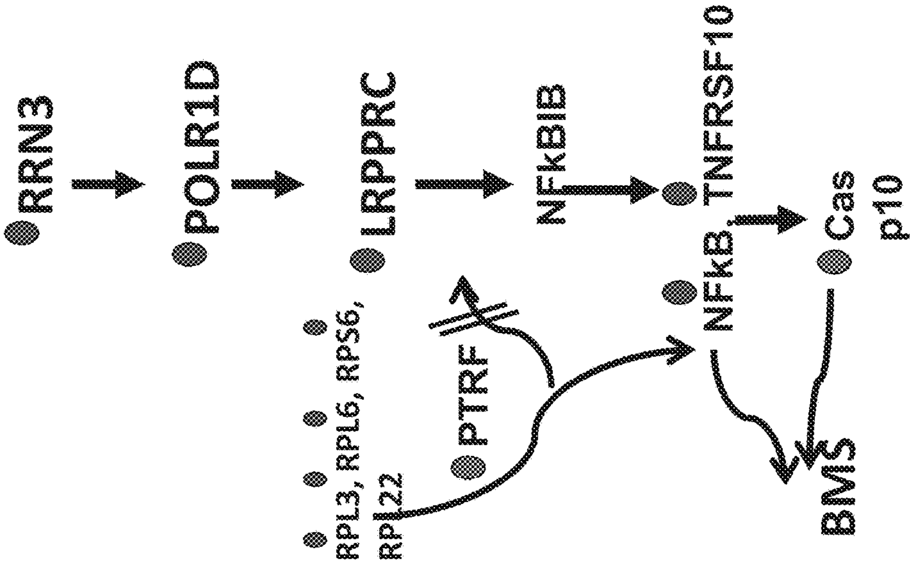
FIGS. 2A-B (Background Art) present schematic illustrations of the effect of POL1 inhibition on multiple sclerosis.
Figure 2A:
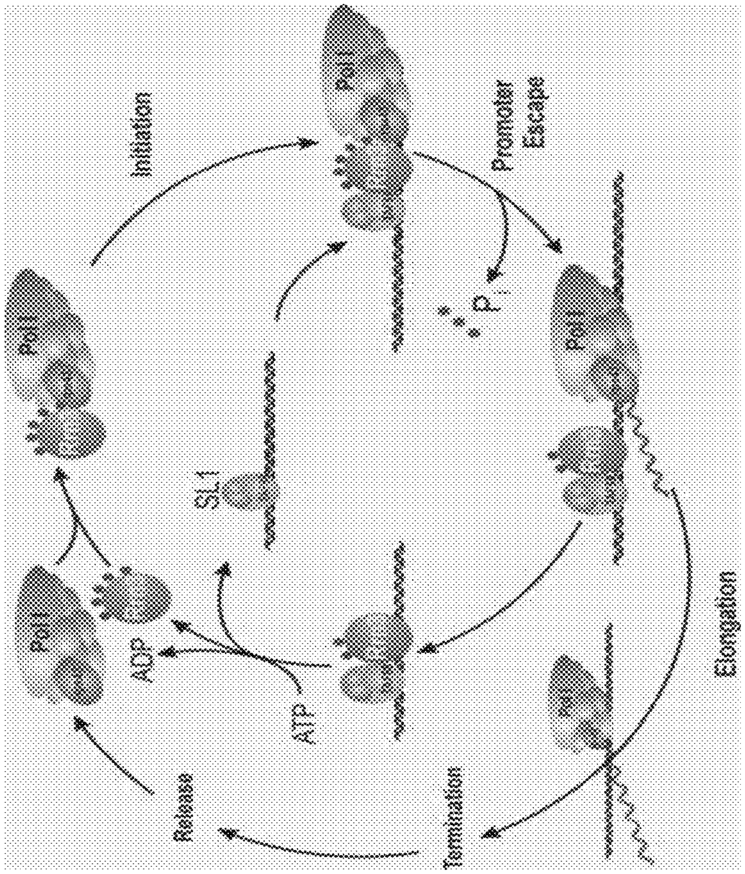

The present invention, in some embodiments thereof, relates to therapy and, more particularly, but not exclusively, to novel RNA Polymerase I inhibitors and to uses thereof in methods of treating medical conditions including, for example, autoimmune diseases multiple sclerosis and proliferative diseases such as cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Embodiments of the present invention stem, at least on part, from previous findings that demonstrated a characterizing gene expression signature in blood sample of RRMS and BMS subjects, whereby the major operating pathway was RNA Polymerase I (POL1). These findings have previously led the present inventors to explore a role for POL1 inhibitors in the treatment, and optionally personalized treatment, of MS.

Led by the fact that the current commercial products for the treatment of autoimmune diseases, and particularly MS, are used intramuscularly, intradermally or as intravenous injections for drug delivery, and lead to uncontrolled plasma peaks, undesired side effects such as flu like reactions and painful local reactions, and thus are accompanied by a high rate of non-compliance to these treatments, the present inventors have explored utilizing inhibitors of POL1-I, which are characterized by oral bioavailability, and improve patients' compliance and benefit patients in the aspect of side effects and pain relief.

As described hereinabove, a POL1 inhibitor, termed CX-5461, and structural analogs thereof, and their use in inhibiting a protein kinase activity and an abbrant cell proliferation, has been previously disclosed. See, for example, U.S. Patent Application Publication No. 2009/0093465.

A family of such POL1 inhibitors, including CX-5461, for use in the treatment of autoimmune diseases has been disclosed in WO 2012/123938.

In a search for POL1 inhibitors that exhibit an improved therapeutic effect, such as, for example, an improved (wider) therapeutic window, the present inventors have devised and successfully prepared and practiced a novel family of POL1 inhibitors, which can be used to treat autoimmune diseases such as multiple sclerosis, proliferative diseases such as cancer, and other medical conditions which are associated with inhibition of POL1 and/or a protein kinase.

According to an aspect of some embodiments of the present invention there are provided compounds which can be collectively represented by Formula I:

Formula I

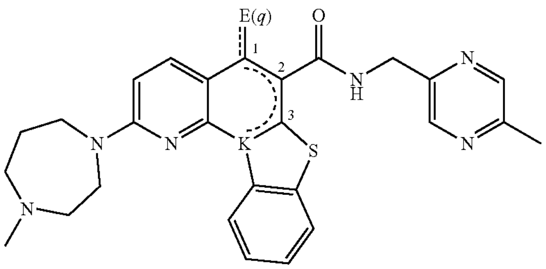

wherein ----- or the dashed line each independently indicates an optionally unsaturated bond, depending on the nature and valency of E;

E forms a chemical moiety other then carbonyl, capable of interfering with a hydrogen binding capacity of the compound;

Q equals 1 or 2; and

K is N or $N^{(+)}$, depending on the nature and valency of E.

Compounds represented by Formula I feature structural similarity of CX5461 (POL1-I, RAM-0, Compound 1; See, for example, FIG. 3A and Table 1 hereinbelow), yet the structure of CX5461 is modified so as to longer include a carbonyl (oxo substituent) at a position equivalent to variable E in Formula I.

The variable E therefore represents a chemical group that, when attached to the carbon marked as carbon "1" in Formula I of the quinazoline ring, forms a chemical moiety other than carbonyl (C=O). E is therefore a chemical group other than oxo (=O).

The chemical group of variable E in Formula I herein can be attached to carbon "1" via a double (unsaturated bond), in which case, q is 1. In such cases, the valency of E is such that is suitable to be attached via an unsaturated bond to carbon "1" (as in the case of, for example, an oxo group =O that forms a carbonyl C=O group.

In such cases, the electronic structure of the quinazoline ring of CX-5461 is maintained, such that an unsaturated (double) bond also exists between carbons "2" and "3" of the ring, and K is nitrogen in a neutral form (N).

Compound exhibiting such structures are represented by Formula Ia:

Formula Ia

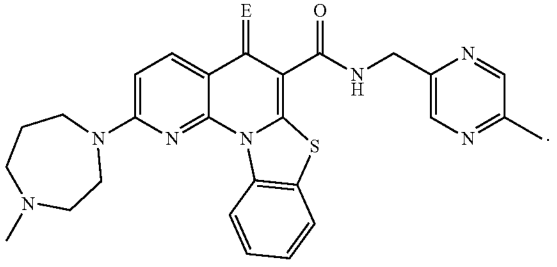

Exemplary chemical groups formed by "E" in such cases include, but are not limited to, thiocarbonyl (C=S), formed of thioxo (=S) group; and imine (e.g., C=N-G, with being as defined hereinafter), formed of e.g., a corresponding =N-G group.

Alternatively, the group represented by variable E is attached to carbon "1" via a single bond, and q is 2. Thus each E group is attached to the ring via a single bond (saturated bond). In such cases, the electronic structure of the quinazoline ring is maintained, such that an unsaturated (double) bond also exists between carbons "2" and "3" of the ring, and K is nitrogen in a neutral form (N).

Compound exhibiting such structures are represented by Formula Ic:

Formula Ic

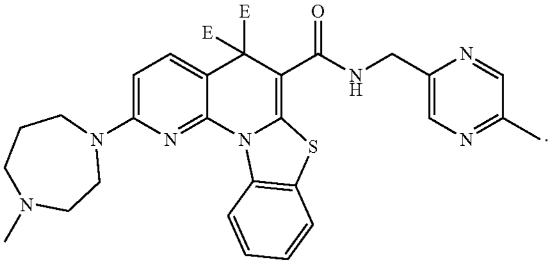

Exemplary chemical groups formed by "E" in such cases include, for example, two halides, preferably two fluorides, as explained hereinafter.

Further alternatively, the group represented by variable E is attached to carbon "1" via a single (saturated) bond, and q is 1. In such cases, the electronic structure of the quinazoline ring undergoes a rearrangement (a tautomerization rearrangement), such that an unsaturated bond exists between carbons "1" and "2" of the ring, and between carbon "3" and K, and K is a positively charged nitrogen $N^+$.

Compound exhibiting such structures are represented by Formula Id:

Formula Id

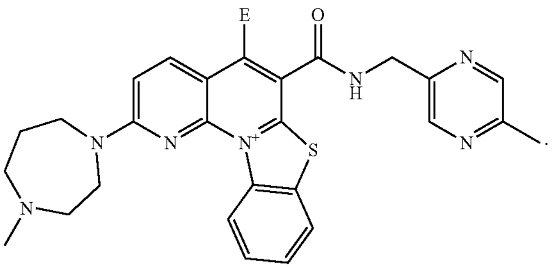

Exemplary chemical groups formed by "E" in such cases include, for example, halides, preferably a chloride.

While the above formulae provide an exemplary illustration for some preferred embodiments of the invention, generally, the chemical moiety formed by variable E is selected so as to modulate the hydrogen bonding capacity of the compound.

As used herein and known in the art, a "hydrogen bond" is a relatively weak bond that forms a type of dipole-dipole attraction which occurs when a hydrogen atom bonded to a strongly electronegative atom exists in the vicinity of another electronegative atom with a lone pair of electrons.

The hydrogen atom in a hydrogen bond is partly shared between two relatively electronegative atoms.

Hydrogen bonds typically have energies of 1-3 kcal $mol^{-1}$ (4-13 kJ $mol^{-1}$), and their bond distances (measured from the hydrogen atom) typically range from 1.5 to 2.6 Å.

A hydrogen-bond donor is the group that includes both the atom to which the hydrogen is more tightly linked and the hydrogen atom itself, whereas a hydrogen-bond acceptor is the atom less tightly linked to the hydrogen atom. The relatively electronegative atom to which the hydrogen atom is covalently bonded pulls electron density away from the hydrogen atom so that it develops a partial positive charge ($\delta^+$). Thus, it can interact with an atom having a partial negative charge ($\delta^-$) through an electrostatic interaction.

Atoms that typically participate in hydrogen bond interactions, both as donors and acceptors, include oxygen, nitrogen and fluorine. These atoms typically form a part of chemical group or moiety such as, for example, carbonyl, carboxylate, amide, hydroxyl, amine, imine, alkylfluoride, $F_2$, and more. However, other electronegative atoms and chemical groups or moieties containing same may participate in hydrogen bonding.

By "modulating the hydrogen bonding capacity" it is meant altering the number and/or strength of hydrogen bonds that the compound may form intramolecularly or intermolecularly, as compared to a carbonyl moiety at the same position.

For example, the group formed by variable E can be, for example, a stronger donor for a hydrogen bond compared to carbonyl, a weaker donor for a hydrogen bond, compared to carbonyl, or be a stronger or a weaker acceptor of a hydrogen bond, compared to carbonyl.

Without being bound by any particular theory, it is assumed that hydrogen bonds may form upon a keto-enol-type tautomerization of the amide group attached to carbon "2" in Formula I, which results in a hydroxyl group (—OH), the latter participates in hydrogen bonding.

The hydroxyl group thus formed is a strong donor of a hydrogen bond and may form a hydrogen bond intermolecularly, with, for example, a hydrogen bond acceptor group of a targeted molecule (e.g., a targeted enzyme such as POL1).

The hydroxyl group may also form hydrogen bond with a carbonyl, when it is the substituent of carbon "1", so as to form a six-membered ring structure, by intramolecular hydrogen bonding.

Alternatively, both a carbonyl at carbon "1" and the hydroxyl group may participate in hydrogen bonds with compatible groups of a targeted biomolecule (e.g., a targeted enzyme).

The modification of substituent E so as to no longer include a carbonyl group may therefore alter the compound's hydrogen bonding capacity by, for example, reducing or increasing the probability of hydrogen bond formation intramolecularly, reducing or increasing the probability of hydrogen bond formation intermolecularly, and/or reducing the strength of an intermolecular or intramolecular hydrogen bond.

In some embodiments, group E is selected such that the chemical moiety formed therewith increases the probability of forming a hydrogen bond intermolecularly and reduces the probability of forming a hydrogen bond intramolecularly (e.g., due to the formation of a group that forms a less stable hydrogen bond with the hydroxyl).

In some embodiments, E is such that the energy of a hydrogen bond formed between a highly electronegative atom therein and hydrogen of the neighboring hydroxyl is lower than the energy of a hydrogen bond formed with the same hydroxyl by carbonyl's oxygen.

In some embodiments, the energy is lower by at least 0.1 kcal/mol, and can be lower by, for example, 0.1, 0.2, 0.3, 0.5, 0.7, 0.8, 1, 1.5, or 2 kcal/mol, including any subranges and intermediates between these values. A person skilled in the art would recognize which groups are encompassed by this definition based on art-recognized tables that define the energies of hydrogen bonds formed with a hydroxyl group.

In some embodiments, the electron density on such an electronegative atom is lower than an electron density of carbonyl's oxygen, that is, the atom is less electronegative than the oxygen in carbonyl.

Without being bound by any particular theory, it is assumed that by interfering with the hydrogen bond capacity of the compound, by e.g., reducing the number (e.g., from 1 to 0) and/or strength of intramolecular bonds, and at the same time increasing the number and/or strength of intermolecular bonds, the compound may better interact with the targeted biomolecule (e.g., POL1), even more electively, and also may have a weaker or no interaction with an unknown off-target protein. It may also further exhibit improved water dissolution kinetics, which facilitates its administration.

In some embodiments, E is an imine group, which can be substituted or non-substituted, as depicted for compounds represented by Formula Ib:

Formula Ib

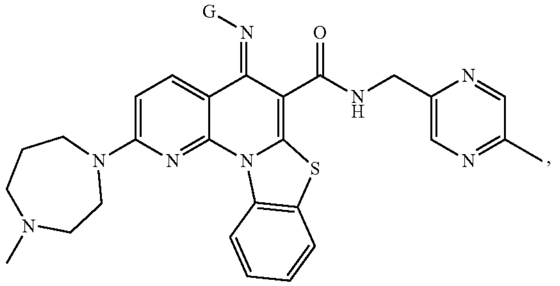

wherein G can be, for example, hydrogen, alkyl, cycloalkyl, aryl, heteroaryl, heteroalicyclic, alkoxy, thioalkoxy, thiol, hydroxyl, aryloxy, or thioaryloxy.

Exemplary such compounds are presented in Table 1 hereinafter as Compounds 3, 4, 5, 6, 7, 8 and 10.

In some embodiments, G is an electron withdrawing group.

Without being bound by any particular theory, it is assumed that electron withdrawing groups reduce the electronegativity of the imine's nitrogen and hence result in a weaker hydrogen bond intramolecular interaction with the presumably formed neighboring hydroxyl described hereinabove, and increase the hydrogen bond intermolecular interactions of the hydroxyl group.

In some embodiments, G is a bulky group as defined herein.

As used herein, the phrase "bulky" describes a group that occupies a large volume. A bulkiness of a group is determined by the number and size of the atoms composing the group, by their arrangement, and by the interactions between the atoms (e.g., bond lengths, repulsive interactions). Typically, lower, linear alkyls are less bulky than branched alkyls; cyclic moieties are more bulky than liner moieties; bicyclic molecules are more bulky than cycloalkyls, etc.

Exemplary suitable electron-withdrawing substituents of an imine include, but are not limited to, substituted or unsubstituted aryls, which, when substituted, preferably are substituted by chemical moieties and at position which strengthen the electron-withdrawing nature of the aryl; heteroaryls in which the heteroatom is positioned such that it exhibits electron-withdrawal with respect to the imine nitrogen; and bulky cycloalkyls substituted by one or more electron withdrawing substituents.

The phrases "electron-withdrawing substituent" or "electron-withdrawing group" are well known to those of skill in the art and are used herein interchangeably as their standard meaning which is a functional group that draws electrons to itself more than a hydrogen atom would if it occupied the same position in the molecule, as described in J. March, Advanced Organic Chemistry, third edition, Pub: John Wiley & Sons, Inc. (1985).

Exemplary electron-withdrawing substituents include, but are not limited to, halogen, pseudohalogen, haloalkyl, haloalicyclic, haloaryl, haloheteroaryl, carbonyl, ester, —C(═O)H and any combination thereof.

Figure 3A:
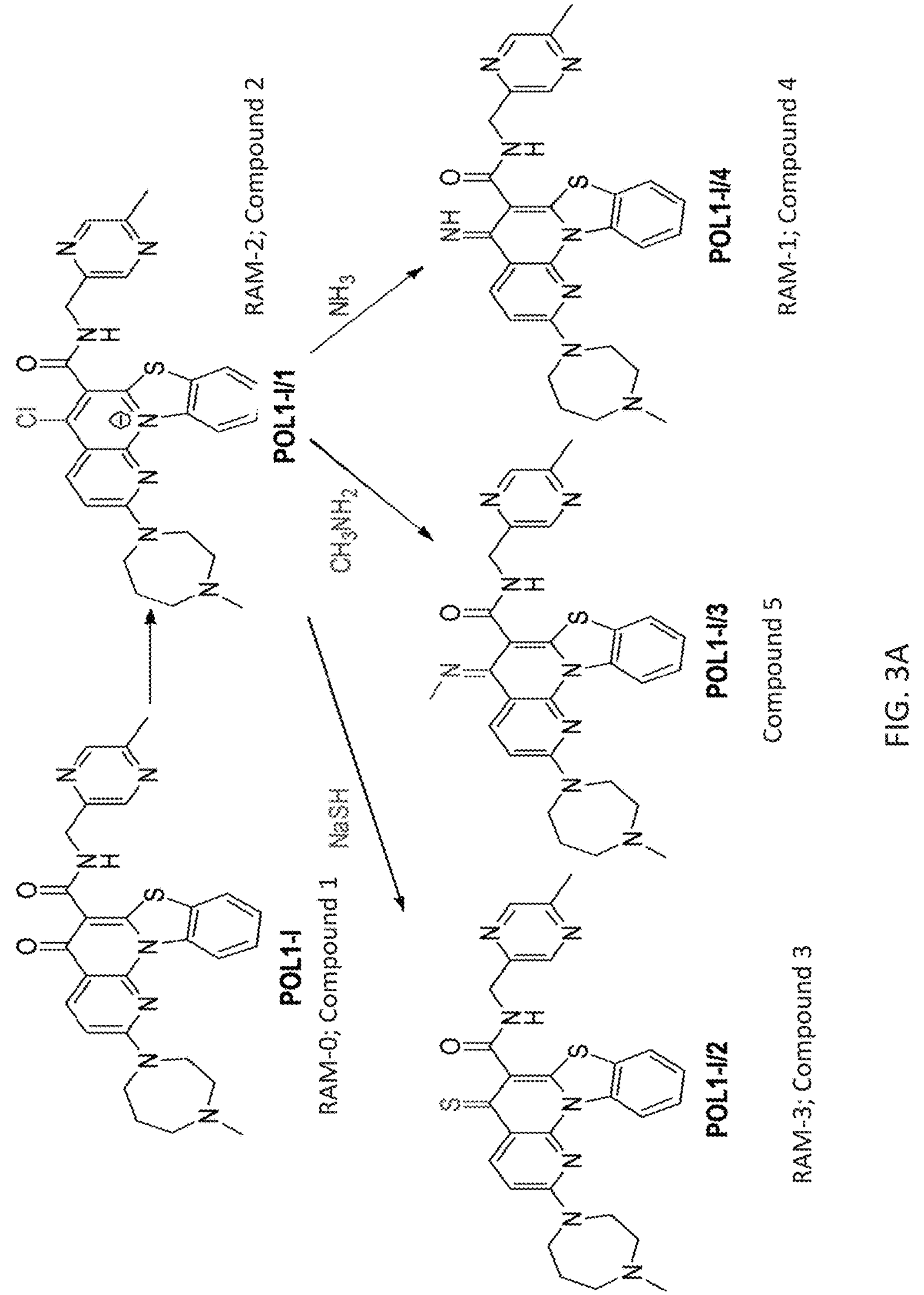
FIGS. 3A-B present chemical structures and synthetic pathways of exemplary compounds according to some embodiments of the present invention.
Figure 3B:
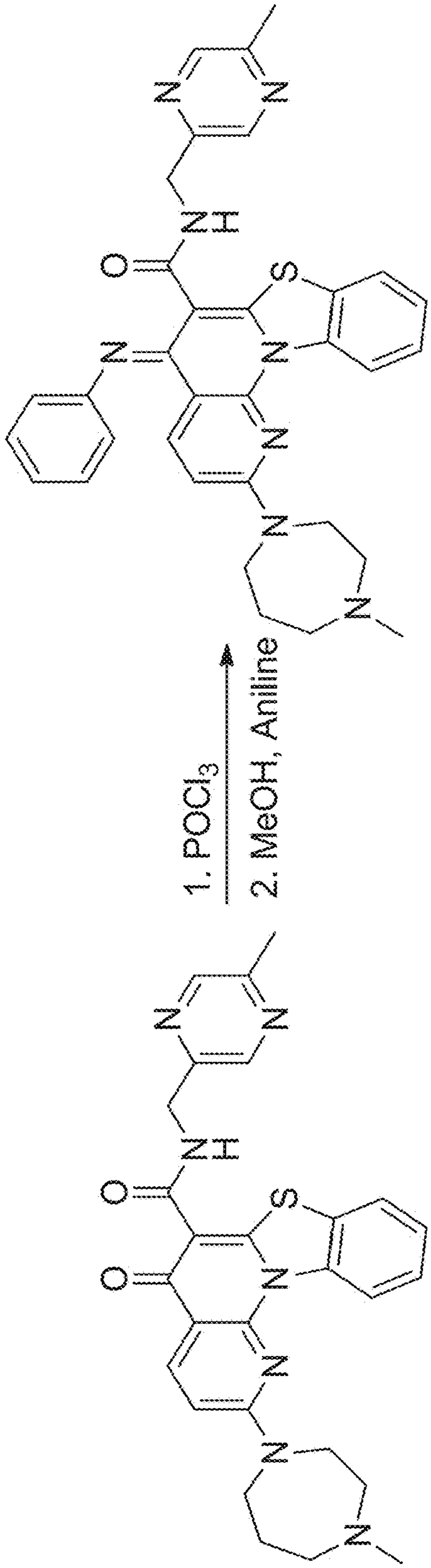

In some embodiments, G is aryl and the compound is Compound 10 (see, Table 1 and FIG. 3B).

It is to be noted that an inclusion of moieties that enhance the hydrophobicity of the compound, such as, for example, aryl, are assumed, without being by bond by any particular theory, to enhance the bioavailability of the compound, compared to compounds featuring a carbonyl moiety at the same position.

Thus, in some embodiments, there are provided compounds having Formula I as described herein, or Formula Ia or Ib, as described herein, which are characterized by higher hydrophobicity compared to corresponding compound in which E is oxo.

The term "hydrophobic" thus often translates into values such as Log P, which describes the partition coefficient of a substance between an aqueous phase (water) and an oily phase (1-octanol).

In some of these embodiments, the group denoted as E in these formulae increases the Log P of the compound, compared to CX-5461, by at least 0.5, or by at least 0.6, 0.7, 0.8, 0.9, 1, 1.2., 1.5, 2, 3, or 4 and any intermediate value therebetween.

According to some embodiments of the present invention, additional compounds, featuring or encompassing the main structural features described herein for compounds represented by Formula I are encompassed by the present embodiments.

According to some of these embodiments, there are provided compounds represented by Formula II:

Formula II

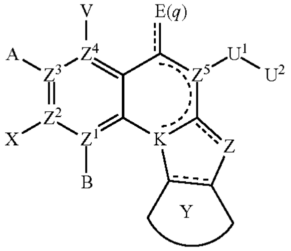

wherein E, q and K are as defined for any one of the embodiments of Formula I hereinabove;

------ indicates an optionally unsaturated bond;

each of B, X, A or V is absent if $Z^1$, $Z^2$, $Z^3$ and $Z^4$, respectively, is N; and each of B, X, A and V is independently H, halo, azido, —CN, —$CF_3$, —$CONR^1R^2$, —$NR^1R^2$, —$SR^2$, —$OR^2$, —$R^3$, —$W^0$, -L-W, —$W^0$, -L-N(R)—$W^0$, $A^2$ or $A^3$, when each of $Z^1$, $Z^2$, $Z^3$ and $Z^4$, respectively, is C;

Z is O, S, $CR^4_2$, $NR^4CR^4$, $CR^4NR^4$, $CR^4$, $NR^4$ or N;

each of $Z^1$, $Z^2$, $Z^3$ and $Z^4$ is independently C or N, provided any three N are non-adjacent;

$Z^5$ is C; or $Z^5$ may be N when Z is N;

Y is an optionally substituted 5-6 membered carbocyclic or heterocyclic ring;

$U^1$ is —C(═T)N(R)—, —C(═T)N(R)O—, —C(═T)-, —$SO_2$N(R)—, —$SO_2$N(R)N($R^0$)—, —$SO_2$—, or —$SO_3$—, where T is O, S, or NH; or $U^1$ may be a bond when $Z^5$ is N or $U^2$ is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, ═O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or ═O; $R^2$ is H, or C1-C10 alkyl, C1-C10 heteroalkyl, C2-C10 alkenyl, or C2-C10 heteroalkenyl, each of which may be optionally substituted with one or more halogens, ═O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, ═O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (═O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, V, A, X and B is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member.

According to some embodiments of the invention, $Z^1$ is N, and each of $Z^2$, $Z^3$ and $Z^4$ is C.

According to some embodiments of the invention, U is —W or -L-W, where W is an optionally substituted 5-6 membered unsaturated or aromatic azacyclic ring, optionally containing an additional heteroatom selected from N, O and S; or W is an optionally substituted 5-7 membered saturated azacyclic ring containing an additional heteroatom selected from N and S.

According to some embodiments of the invention, $U^2$ is -L-N(R)—$W^0$.

According to some embodiments of the invention, Y is an optionally substituted phenyl ring.

According to some embodiments of the invention, the compound with the proviso that when $Z^1$ is N, $Z^2$ and $Z^4$ are C, $Z^5$ is C, $U^1$ is —C(O)NH—, $U^2$ is -L-W, and L is an ethylene linker, one of V, A, and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

According to any one of the embodiments of the invention, compounds having a general structure represented by Formula III, are also contemplated:

Formula III

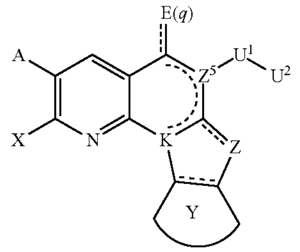

wherein E, q and K are as defined for any one of the embodiments of Formula I hereinabove;

and wherein:

------ indicates an optionally unsaturated bond;

each of A and X is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;

Z is O, S, $CR^4_2$, $NR^4CR^4$, $CR^4NR^4$ or $NR^4$;

Y is an optionally substituted 5-6 membered carbocyclic or heterocyclic ring;

$U^1$ is —C(=T)N(R)—, —C(=T)N(R)O—, —C(=T)-, —$SO_2N(R)$—, —$SO_2N(R)N(R^0)$—, —$SO_2$—, or —$SO_3$—, where T is O, S, or NH; or $U^1$ may be a bond when U2 is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, =O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O; R2 is H, or C1-C10 alkyl, C1-C10 hetero alkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—W0;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided that one of $U^2$, A, and X is a secondary amine $A^2$ or a tertiary amine $A^3$, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

According to some embodiments of the invention, with the proviso that when $U^1$ is —C(O)NH—, $U^2$ is -L-W, and L is an ethylene linker, one of A and X is independently an optionally substituted aryl, heteroaryl, or 7-membered azacyclic ring, optionally containing an additional heteroatom selected from N, O and S as a ring member, if W is pyrrolidin-1-yl, N-methyl-pyrrolidin-2-yl, piperidin-1-yl or morpholin-1-yl.

According to some embodiments of the invention, at least one of A and X is a tertiary amine $A^3$.

According to some embodiments of the invention, $A^3$ is selected from the group consisting of imidazole, imidazoline, pyrroline, piperidine, piperazine, morpholine, thiomorpholine and homopiperazine.

According to some embodiments of the invention, $U^1$ is a —C(=T)N(R)—, T is O, and $U^2$ is -L-W or -L-N(R)—$W^0$.

According any one of the embodiments of the invention, compounds having a general structure represented by Formula IV, are also contemplated:

Formula IV

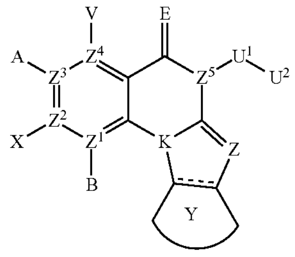

wherein E is as defined for any one of the respective embodiments of Formula I, and K is N; and wherein ------ indicates an optionally unsaturated bond; and each of B, X, A or V is absent if $Z^1$, $Z^2$, $Z^3$ and $Z^4$, respectively, is N; and each of B, X, A and V is independently H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$, when each of $Z^1$, $Z^2$, $Z^3$ and $Z^4$, respectively, is C;

each of $Z^1$, $Z^2$, $Z^3$ and $Z^4$ is independently C or N, provided any three N are non-adjacent;

Y is an optionally substituted 5-6 membered carbocyclic or heterocyclic ring;

$U^1$ is —C(═T)N(R)—, —C(═T)N(R)O—, —C(═T)-, —$SO_2$N(R)—, —$SO_2$N(R)N($R^0$)—, —$SO_2$—, or —$SO_3$—, where T is O, S, or NH; or $U^1$ may be a bond when $Z^5$ is N or $U^2$ is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, ═O, or an optionally substituted 3-7 membered carbocyclic or heterocyclic ring; or $U^2$ is —W, -L-W, -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or ═O;

$R^2$ is H, or C1-C10 alkyl, C1-C10 heteroalkyl, C2-C10 alkenyl, or C2-C10 heteroalkenyl, each of which may be optionally substituted with one or more halogens, ═O, or an optionally substituted 3-7 membered carbocyclic or heterocyclic ring; $R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, ═O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (═O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided that one of $U^2$, V, A, X and B is a secondary amine $A^2$ or a tertiary amine A3, wherein the secondary amine $A^2$ is —NH—$W^0$, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring, optionally containing an additional heteroatom selected from N, O or S as a ring member.

According to any one of the embodiments of the invention, compounds having a general structure represented by Formula V, are also contemplated:

Formula V

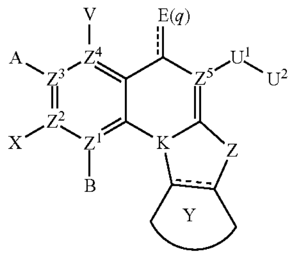

wherein E, q and K are as defined for any one of the embodiments of Formula I hereinabove;

and wherein: ----- indicates an optionally unsaturated bond;

A and V independently are H, halo, azido, —CN, —$CF_3$, —$CONR^1R^2$, —$NR^1R^2$, —$SR^2$, —$OR^2$, —$R^3$, —W, -L-W, —$W^0$, -L-N(R)—$W^0$, $A^2$ or $A^3$;

Z is O, S, $CR^4_2$, $NR^4CR^4$, $CR^4NR^4$ or $NR^4$;

Y is an optionally substituted 5-6 membered carbocyclic or heterocyclic ring;

$U^1$ is —C(═T)N(R)—, —C(═T)N(R)O—, —C(═T)-, —$SO_2$N(R)—, —$SO_2$N(R)N($R^0$)—, —$SO_2$—, or —$SO_3$—, where T is O, S, or NH; or $U^1$ may be a bond when U2 is H;

$U^2$ is H, or C3-C7 cycloalkyl, C1-C10 alkyl, C1-C10 heteroalkyl, C2-C10 alkenyl or C2-C10 heteroalkenyl group, each of which may be optionally substituted with one or more halogens, ═O, or an optionally substituted 3-7 membered carbocyclic or heterocyclic ring; or $U^2$ is —W, -L-W or -L-N(R)—$W^0$, $A^2$ or $A^3$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or ═O; $R^2$ is H, or C1-C10 alkyl, C1-C10 heteroalkyl, C2-C10 alkenyl, or C2-C10 heteroalkenyl, each of which may be optionally substituted with one or more halogens, ═O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, ═O, or an optionally substituted 3-6 membered carbocyclic or heterocyclic ring;

each $R^4$ is independently H, or C1-C6 alkyl; or R4 may be —W, -L-W or -L-N(R)—$W^0$;

each R and $R^0$ is independently H or C1-C6 alkyl;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (═O), or C1-C6 alkyl;

W is an optionally substituted 4-7 membered azacyclic ring, optionally containing an additional heteroatom selected from N, O and S as a ring member;

$W^0$ is an optionally substituted 3-4 membered carbocyclic ring, or a C1-C6 alkyl group substituted with from 1 to 4 fluorine atoms;

provided one of $U^2$, A, and V is a secondary amine $A^2$ or a tertiary amine A3, wherein the secondary amine $A^2$ is —NH—WO, and the tertiary amine $A^3$ is a fully saturated and optionally substituted six-membered or seven-membered azacyclic ring optionally containing an additional heteroatom selected from N, O or S as a ring member, or the tertiary amine $A^3$ is a partially unsaturated or aromatic optionally substituted five-membered azacyclic ring optionally containing an additional heteroatom selected from N, O or S as a ring member.

According any one of the embodiments of the invention, compounds having a general structure represented by Formula VI, are also contemplated:

Formula VI

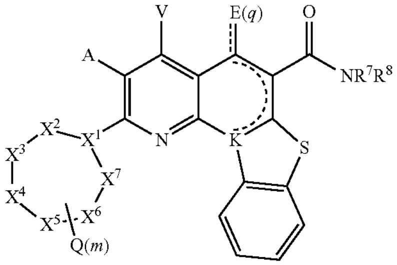

wherein E, q and K are as defined for any one of the embodiments of Formula I hereinabove;

and wherein:

$X^1$ is CH or N;

$X^2$, $X^3$, $X^4$, $X^5$, $X^6$ and $X^7$ independently are $NR^4$, $CH_2$, CHQ or $C(Q)_2$, provided that: (i) zero, one or two of $X^2$, $X^3$, $X^4$, $X^5$, $X^6$ and $X^7$ are $NR^4$; (ii) when $X^1$ is N, both of $X^2$ and $X^7$ are not $NR^4$; (iii) when $X^1$ is N, $X^3$ and $X^6$ are not $NR^4$; and (iv) when $X^1$ is CH and two of $X^2$, $X^3$, $X^4$, $X^5$, $X^6$ and $X^7$ are $NR^4$, the two $NR^4$ are located at adjacent ring positions or are separated by two or more other ring positions;

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing one additional heteroatom selected from N, O and S as a ring member;

$R^1$ is H or C1-C6 alkyl, optionally substituted with one or more halogens, or =O;

R is H, or C1-C10 alkyl, C1-C10 hetero alkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or R4 may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in —$NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4, or 5;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, $X^1$ is CH and two of $X^2$, $X^3$, $X^4$, $X^5$, $X^6$ and $X^7$ are $NR^4$.

According to some embodiments of the invention, wherein $X^1$ is CH and one of $X^2$, $X^3$, $X^4$, $X^5$, $X^6$ and $X^7$ are $NR^4$.

According to some embodiments of the invention, $X^1$ is CH and none of $X^2$, $X^3$, $X^4$, $X^5$, $X^6$ and $X^7$ are $NR^4$.

According to some embodiments of the invention, wherein $X^1$ is N and none of $X^2$, $X^3$, $X^4$, $X^5$, $X^6$ and $X^7$ are $NR^4$.

According to some embodiments of the invention, $X^1$ is N and one of $X^4$ or $X^5$ is $NR^4$.

According any one of the embodiments of the invention, compounds having a general structure represented by Formula VIII, are also contemplated:

Formula (VIII)

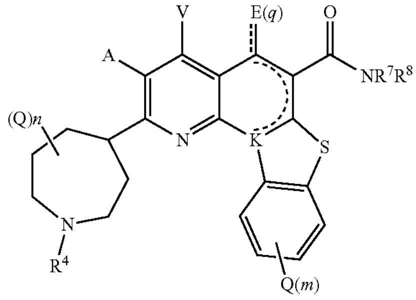

wherein E, q and K are as defined for any one of the embodiments of Formula I hereinabove;

and wherein:

A and V independently are H, halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O; $R^2$ is H, or C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or R4 may be —W, -L-W or -L-N(R)—$W^0$;

each R is independently H or C1-C6 alkyl;

$R^7$ is H and $R^8$ is C1-C10 alkyl, C1-C10 heteroalkyl, C2-C10 alkenyl, or C2-C10 heteroalkenyl, each of which may be optionally substituted with one or more halogens, =O, or an optionally substituted 3-7 membered carbocyclic or heterocyclic ring; or in $NR^7R^8$, $R^7$ and $R^8$ together with N may form an optionally substituted azacyclic ring, optionally containing an additional heteroatom selected from N, O and S as a ring member;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, $R^7$ is H and $R^8$ is a $C_{1-4}$ alkyl substituted with an optionally substituted aromatic heterocyclic ring.

According to some embodiments of the invention, the optionally substituted aromatic heterocyclic ring is selected from pyridine, pyrimidine, pyrazine, imidazole, pyrrolidine, and thiazole.

According to some embodiments of the invention, $R^7$ and $R^8$ together with N in —$NR^7R^8$ form an optionally substituted azacyclic ring selected from the group consisting of morpholine, thiomorpholine, piperidine or piperazine ring.

According to any one of the embodiments of the invention, compounds having a general structure represented by Formula VII are also contemplated:

Formula VII

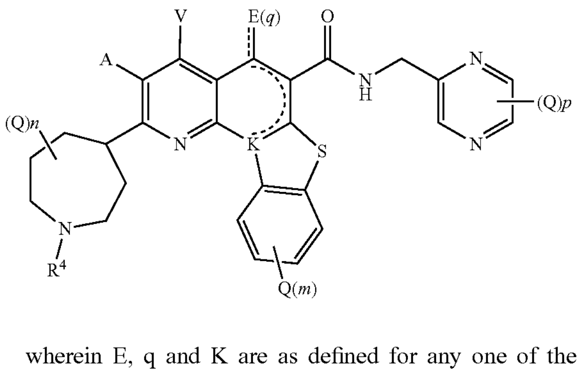

wherein E, q and K are as defined for any one of the embodiments of Formula I hereinabove;

and wherein:

A and V independently are H, halo, azido, —CN, —$CF_3$, —CONR1R2, —NR1R2, —$SR^2$, —$OR^2$, —$R^3$, —W, -L-W, —$W^0$, or -L-N(R)—$W^0$;

each Q is independently halo, azido, —CN, —$CF_3$, —$CONR^1R^2$, —$NR^1R^2$, —$SR^2$, —$OR^2$, —$R^3$, —W, -L-W, —$W^0$, or -L-N(R)—$W^0$;

in each —$NR^1R^2$, $R^1$ and $R^2$ together with N may form an optionally substituted azacyclic ring, optionally containing an additional heteroatom selected from N, O and S as a ring member;

$R^1$ is H or C1-C6 alkyl, optionally substituted with one or more halogens, or =O; R2 is H, or C1-C10 alkyl, C1-C10 hetero alkyl, C2-C10 alkenyl, or C2-C10 heteroalkenyl, each of which may be optionally substituted with one or more halogens, =O, or an optionally substituted 3-7 membered carbocyclic or heterocyclic ring;

$R^3$ is an optionally substituted C1-C10 alkyl, C2-C10 alkenyl, C5-C10 aryl, or C6-C12 arylalkyl, or a heteroform of one of these, each of which may be optionally substituted with one or more halogens, =O, or an optionally substituted 3-6 membered carbocyclic or heterocyclic ring;

each $R^4$ is independently H, or C1-C6 alkyl; or $R^4$ may be —W, -L-W or -L-N(R)—$W^0$;

each R is independently H or C1-C6 alkyl;

m is 0, 1, 2, 3 or 4;

n is 0, 1, 2, 3, 4 or 5;

p is 0, 1, 2 or 3;

L is a C1-C10 alkylene, C1-C10 heteroalkylene, C2-C10 alkenylene or C2-C10 heteroalkenylene linker, each of which may be optionally substituted with one or more substituents selected from the group consisting of halogen, oxo (=O), or C1-C6 alkyl;

W is an optionally substituted 4-7 membered azacyclic ring, optionally containing an additional heteroatom selected from N, O and S as a ring member; and $W^0$ is an optionally substituted 3-4 membered carbocyclic ring, or a C1-C6 alkyl group substituted with from 1 to 4 fluorine atoms.

According to some embodiments of the invention, A and V are independently H or halo.

According to some embodiments of the invention, $R^4$ is H or C1-4 alkyl.

According to some embodiments of the invention, m and n are each 0.

According to some embodiments of the invention, p is 0 or 1.

Methods of synthesizing the compounds of some embodiments of the invention are described in Example 1 in the Examples section the follows.

According to some embodiments, compounds represented by Formula I as described herein, or by any one of Formulae II-VIII are prepared by converting a compound encompassed by these formulae into a corresponding chloride such as depicted for Compound 2 herein (see, Table 1) and the chloride is thereafter reacted with a suitable precursor (e.g., an amine) to form the desired compound (e.g., a corresponding imine).

For use as pharmaceutical agents, the compound of some embodiments of the invention is sterile.

According to some embodiments of the invention, the compound is purified using known methods.

According to some embodiments of the invention, the compound has 95-99.9% purity.

For any of the embodiments described herein, the compound may be in a form of a salt, for example, a pharmaceutically acceptable salt, and/or in a form of a prodrug.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more amino groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt", as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per one molar equivalent of the compound.

As used herein, the term "prodrug" refers to a compound which is converted in the body to an active compound. A prodrug is typically designed to facilitate administration, e.g., by enhancing absorption. A prodrug may comprise, for example, the active compound modified with ester groups, for example, wherein one or more hydroxy groups of the active compound is modified by an acyl (e.g., acetyl) group to form an ester group, and/or wherein one or more carboxylic acid of the active compound is modified by an alkyl (e.g., ethyl) group to form an ester group.

Further, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the heterocyclic compounds described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, except in embodiments wherein a specific stereoisomer is explicitly required, as well as any isomorph thereof.

As used herein throughout, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, cycloalkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, alkenyl, alkynyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, lone pair electrons, alkyl, alkenyl, alkynyl, cycloalkyl, aryl, heteroaryl, heteroalicyclic, halo, hydroxy, alkoxy, aryloxy, thiohydroxy, thioalkoxy, thioaryloxy, sulfinyl, sulfonyl, cyano, nitro, azide, phosphonyl, phosphinyl, oxo, carbonyl, thiocarbonyl, urea, thiourea, O-carbamyl, N-carbamyl, O-thiocarbamyl, N-thiocarbamyl, C-amido, N-amido, C-carboxy, O-carboxy, sulfonamido, hydrazine, and amino, as these terms are defined herein. Representative examples are piperidine, piperazine, tetrahydrofuran, tetrahydropyran, morpholine and the like.

A "hydroxy" group refers to an —OH group.

As used herein, the terms "amine" and "amino" refer to either a —NR'R" group, wherein R' and R" are selected from the group consisting of hydrogen, alkyl, cycloalkyl, heteroalicyclic (bonded through a ring carbon), aryl and heteroaryl (bonded through a ring carbon). R' and R" are bound via a carbon atom thereof. Optionally, R' and R" are selected from the group consisting of hydrogen and alkyl comprising 1 to 4 carbon atoms. Optionally, R' and R" are hydrogen.

An "azide" group refers to a $—N{=}N^+{=}N^-$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "disulfide" group refers to both a —S-thioalkoxy and a —S-thioaryloxy group.

A disulfide bond describes a —S—S— bond.

A "carbonyl" group refers to a —C(═O)—R' group, where R' is defined as hereinabove, or where R' and C form a part of a cyclic moiety such as cycloalkyl, aryl, heteroaryl and heteroalicyclic, as defined herein.

A "thiocarbonyl" group refers to a —C(═S)—R' group, where R' is as defined herein.

A "C-carboxy" group refers to a —C(═O)—O—R' groups, where R' is as defined herein.

An "O-carboxy" group refers to an R'C(═O)—O— group, where R' is as defined herein.

An "oxo" group refers to a ═O group.

A "thioxo" group refers to a ═S group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(═S)—O—R' and —O—C(═S)R' groups.

An "ester" refers to a C-carboxy group wherein R' is not hydrogen.

An ester bond refers to a —O—C(═O)— bond.

A "halo" group refers to fluorine, chlorine, bromine or iodine.

A "sulfinyl" group refers to an —S(═O)—R' group, where R' is as defined herein.

A "sulfonyl" group refers to an $—S(═O)_2—R'$ group, where R' is as defined herein.

A "sulfonate" group refers to an $—S(═O)_2—O—R'$ group, where R' is as defined herein.

A "sulfate" group refers to an $—O—S(═O)_2—O—R'$ group, where R' is as defined as herein.

A "sulfonamide" or "sulfonamido" group encompasses both S-sulfonamido and N-sulfonamido groups, as defined herein.

An "S-sulfonamido" group refers to a $—S(═O)_2—NR'R''$ group, with each of R' and R" as defined herein.

An "N-sulfonamido" group refers to an $R'S(═O)_2—NR''$ group, where each of R' and R" is as defined herein.

An "O-carbamyl" group refers to an —OC(═O)—NR'R" group, where each of R' and R" is as defined herein.

An "N-carbamyl" group refers to an R'OC(═O)—NR"— group, where each of R' and R" is as defined herein.

A "carbamyl" or "carbamate" group encompasses O-carbamyl and N-carbamyl groups.

A carbamate bond describes a —O—C(═O)—NR'— bond, where R' is as described herein.

An "O-thiocarbamyl" group refers to an —OC(═S)—NR'R" group, where each of R' and R" is as defined herein.

An "N-thiocarbamyl" group refers to an R'OC(═S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(═S)—NR'— bond, where R' is as described herein.

A "C-amido" group refers to a —C(═O)—NR'R" group, where each of R' and R" is as defined herein.

An "N-amido" group refers to an R'C(═O)—NR"— group, where each of R' and R" is as defined herein.

An "amide" group encompasses both C-amido and N-amido groups.

An amide bond describes a —NR'—C(═O)— bond, where R' is as defined herein.

A "urea" group refers to an —N(R')—C(═O)—NR"R'" group, where each of R' and R" is as defined herein, and R'" is defined as R' and R" are defined herein.

A "nitro" group refers to an $—NO_2$ group.

A "cyano" group refers to a —C≡N group.

The term "hydrazine" describes a —N(R')—N(R")R'" group, with each of R', R" and R'" as defined hereinabove.

Treatment of Autoimmune Diseases:

According to an aspect of some embodiments of the present invention any one of the compounds as described herein is for use in the treatment of an autoimmune disease in a subject in need thereof.

According to an aspect of some embodiments of the present invention any one of the compounds as described herein is for use in the manufacture of a medicament for treating an autoimmune disease in a subject in need thereof.

According to an aspect of some embodiments of the present invention there is provided a method of treating an autoimmune disease, which is effected by administering to the subject a therapeutically effective amount of any one of the compounds as described herein.

As used in the context of this aspect of the present embodiments, the phrase "treating" refers to inhibiting or arresting the development of the autoimmune disease (e.g., multiple sclerosis) and/or causing the reduction, remission, or regression of the autoimmune disease and/or optimally curing the autoimmune disease. Those of skill in the art will understand that various methodologies and assays can be used to assess the development of autoimmune disease, and similarly, various methodologies and assays may be used to assess the reduction, remission or regression of the autoimmune disease.

As used herein, the term "subject" includes mammals, preferably human beings at any age which suffer from the pathology (the autoimmune disease) or which have been diagnosed as being afflicted by the pathology.

According to some embodiments of the invention, the term "subject" encompasses individuals who are at risk to develop the pathology or are suspected of having the pathology. As used herein the phrase "autoimmune disease" refers to any disease caused by an autoimmune response, i.e., an immune response directed to a substance in the body of the subject.

It should be noted that since autoimmunity can affect any organ or tissue of the subject, e.g., the brain, skin, kidney, lungs, liver, heart, or thyroid of the subject, the clinical expression of the disease depends upon the site affected.

Following is a non-limiting list of autoimmune diseases or disorders (including autoimmune-related diseases or disorders) which can be treated by the compound of some embodiments of the invention: Acute Disseminated Encephalomyelitis (ADEM); Acute necrotizing hemorrhagic leukoencephalitis; Addison's disease; Agammaglobulinemia; Alopecia areata; Amyloidosis; Ankylosing spondylitis; Anti-GBM/Anti-TBM nephritis; Antiphospholipid syndrome (APS); Autoimmune angioedema; Autoimmune aplastic anemia; Autoimmune dysautonomia; Autoimmune hepatitis; Autoimmune hyperlipidemia; Autoimmune immunodeficiency; Autoimmune inner ear disease (AIED); Autoimmune myocarditis; Autoimmune pancreatitis; Autoimmune retinopathy; Autoimmune thrombocytopenic purpura (ATP); Autoimmune thyroid disease; Autoimmune urticaria; Axonal & neuronal neuropathies; Balo disease; Behcet's disease; Bullous pemphigoid; Cardiomyopathy; Castleman disease; Celiac disease; Chagas disease; Chronic inflammatory demyelinating polyneuropathy (CIDP); Chronic recurrent multifocal ostomyelitis (CRMO); Churg-Strauss syndrome; Cicatricial pemphigoid/benign mucosal pemphigoid; Crohn's disease; Cogans syndrome; Cold agglutinin disease; Congenital heart block; Coxsackie myocarditis; CREST disease; Essential mixed cryoglobulinemia; Demyelinating neuropathies; Dermatitis herpetiformis; Dermatomyositis; Devic's disease (neuromyelitis optica); Discoid lupus; Dressler's syndrome; Endometriosis; Eosinophilic fasciitis; Erythema nodosum; Experimental allergic encephalomyelitis; Evans syndrome; Fibrosing alveolitis; Giant cell arteritis (temporal arteritis); Glomerulonephritis; Goodpasture's syndrome; Granulomatosis with Polyangiitis (GPA) see Wegener's; Graves' disease; Guillain-Barre syndrome; Hashimoto's encephalitis; Hashimoto's thyroiditis; Hemolytic anemia; Henoch-Schonlein purpura; Herpes gestationis; Hypogammaglobulinemia; Idiopathic thrombocytopenic purpura (ITP); IgA nephropathy; IgG4-related sclerosing disease; Immunoregulatory lipoproteins; Inclusion body myositis; Insulin-dependent diabetes (type1); Interstitial cystitis; Juvenile arthritis; Juvenile diabetes; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease, chronic; Meniere's disease; Microscopic polyangiitis; Mixed connective tissue disease (MCTD); Mooren's ulcer; Mucha-Habermann disease; Multiple sclerosis; Myasthenia gravis; Myositis; Narcolepsy; Neuromyelitis optica (Devic's); Neutropenia; Ocular cicatricial pemphigoid; Optic neuritis; Palindromic rheumatism; PANDAS (Pediatric Autoimmune Neuropsychiatric Disorders Associated with *Streptococcus*); Paraneoplastic cerebellar degeneration; Paroxysmal nocturnal hemoglobinuria (PNH); Parry Romberg syndrome; Parsonnage-Turner syndrome; Pars planitis (peripheral uveitis); Pemphigus; Peripheral neuropathy; Perivenous encephalomyelitis; Pernicious anemia; POEMS syndrome; Polyarteritis nodosa; Type I, II, & III autoimmune polyglandular syndromes; Polymyalgia rheumatica; Polymyositis; Postmyocardial infarction syndrome; Postpericardiotomy syndrome; Progesterone dermatitis; Primary biliary cirrhosis; Primary sclerosing cholangitis; Psoriasis; Psoriatic arthritis; Idiopathic pulmonary fibrosis; Pyoderma gangrenosum; Pure red cell aplasia; Raynauds phenomenon; Reflex sympathetic dystrophy; Reiter's syndrome; Relapsing polychondritis; Restless legs syndrome; Retroperitoneal fibrosis; Rheumatic fever; Rheumatoid arthritis; Sarcoidosis; Schmidt syndrome; Scleritis; Scleroderma; Sjogren's syndrome; Sperm & testicular autoimmunity; Stiff person syndrome; Subacute bacterial endocarditis (SBE); Susac's syndrome; Sympathetic ophthalmia; Takayasu's arteritis; Temporal arteritis/Giant cell arteritis; Thrombocytopenic purpura (TTP); Tolosa-Hunt syndrome; Transverse myelitis; Ulcerative colitis; Undifferentiated connective tissue disease (UCTD); Uveitis; Vasculitis; Vesiculobullous dermatosis; Vitiligo; Wegener's granulomatosis (now termed Granulomatosis with Polyangiitis (GPA).

According to some embodiments of the invention, the autoimmune disease is multiple sclerosis.

According to some embodiments of the invention, the subject is diagnosed with multiple sclerosis.

The diagnosis of "multiple sclerosis" can be made when a subject has experienced at least one neurological attack affecting the central nervous system (CNS) accompanied by demyelinating lesions within the brain or spinal cord, which may have, but not necessarily confirmed by magnetic resonance imaging (MRI). The neurological attack can involve acute or sub-acute neurological symptomatology (attack) manifested by various clinical presentations like unilateral loss of vision, vertigo, ataxia, incoordination, gait difficulties, sensory impairment characterized by paresthesia, dysesthesia, sensory loss, urinary disturbances until incontinence, diplopia, dysarthria, various degrees of motor weakness until paralysis, cognitive decline either as a monosymptomatic or in combination. The symptoms usually remain for several days to few weeks, and then partially or completely resolve.

Further details on the diagnosis of multiple sclerosis according to 2010 McDonald Criteria for Diagnosis of MS are provided in Polman C H., et al., 2011 ("Diagnostic criteria for multiple sclerosis: 2010 revisions to the McDonald criteria" Annals of Neurology, vol. 69 (2): pages 292-302) which is fully incorporated herein by reference in its entirety.

For example, the diagnosis of multiple sclerosis can be made upon (I): Clinical presentation of ≥2 attacks, with objective clinical evidence of ≥2 lesions or objective clinical evidence of 1 lesion with reasonable historical evidence of a prior attack; (II): Clinical presentation of ≥2 attacks, with objective clinical evidence of 1 lesion, additional data have to include dissemination in space, demonstrated by: ≥1 T2 lesion in at least 2 of 4 MS-typical regions of the CNS (periventricular, juxtacortical, infratentorial, or spinal cord); (III): Clinical presentation of 1 attack, with objective clinical evidence of ≥2 lesions, additional data have to include dissemination in time, demonstrated by: Simultaneous presence of asymptomatic gadolinium-enhancing and nonenhancing lesions at any time; or A new T2 and/or gadolinium-enhancing lesion(s) on follow-up MRI, irrespective of its timing with reference to a baseline scan; (IV): Clinical presentation of 1 attack, additional data have to include dissemination in space and time, demonstrated by: For DIS: ≥1 T2 lesion in at least 2 of 4 MS-typical regions of the CNS (periventricular, juxtacortical, infratentorial, or spinal cord) and for DIT: Simultaneous presence of asymptomatic gadolinium-enhancing and nonenhancing lesions at any time; or A new T2 and/or gadolinium-enhancing lesion(s) on follow-up MRI, irrespective of its timing with reference to a baseline scan; (V): Clinical presentation of Insidious neurological progression suggestive of MS (PPMS), additional data have to include 1 year of disease progression (retrospectively or prospectively determined) plus 2 of 3 of the following criteria: 1. Evidence for DIS in the brain based on ≥1 T2 lesions in the MS-characteristic (periventricular, juxtacortical, or infratentorial) regions 2. Evidence for DIS in the spinal cord based on ≥2 T2 lesions in the cord 3. Positive CSF (isoelectric focusing evidence of oligoclonal bands and/or elevated IgG index).

According to some embodiments of the invention, the subject has relapsing-remitting multiple sclerosis (RRMS).

According to some embodiments of the invention, the subject has a primary progressive multiple sclerosis (PPMS).

According to some embodiments of the invention, the subject has a secondary progressive MS (SPMS).

According to some embodiments of the invention, the subject has benign multiple sclerosis (BMS).

According to some embodiments of the invention, the subject has a progressive-relapsing course of MS.

According to some embodiments of the invention, treating the subject refers to changing the disease course of the subject from a typical RRMS course to a BMS course.

According to some embodiments of the invention, treating the subject refers to suppressing the activity of typical RRMS course.

According to some embodiments of the invention, administering the compound is performed after diagnosing the subject as having the autoimmune disease.

According to some embodiments of the invention, the autoimmune disease is multiple sclerosis and the diagnosis comprises appearance of brain lesions characteristics of the multiple sclerosis.

According to some embodiments of the invention, the compound prevents the appearance of additional neurological attack(s) and/or brain lesion(s) as compared to the number of neurological attack(s) and/or brain lesion(s) present at time of diagnosing multiple sclerosis.

According to an aspect of some embodiments of the present invention the compounds as described herein, in any one of the embodiments thereof are useful in inhibiting an activity of RNA Polymerase I, or in modulating a RNA Polymerase I pathway. These compounds are therefore useful in the treatment of any disease or disorder that is associated the RNA Polymerase I or which is treatable by modulating (e.g., inhibiting), a RNA Polymerase I activity or pathway, as is described in further detail hereinafter.

Such diseases and disorders include, in addition to autoimmune diseases as described herein, also proliferative diseases or disorders, as described herein, and any other medical conditions which would be recognized by any person skilled in the art.

Treatment of Proliferative Diseases or Disorders:

According to some embodiments of the invention, any of the compounds described herein are useful in treating a proliferative disease or disorder and/or in modulating (e.g., inhibiting) a protein kinase activity.

As used herein the phrase "proliferative disease" refers to diseases manifested by abnormal cell proliferation, and includes, for example, benign tumors, pre-malignant tumors, and malignant tumors, such as cancer.

As used herein the terms "cancer" and "malignant tumor" are interchangeably used. The term refers to a malignant growth or tumor caused by abnormal and uncontrolled cell proliferation (cell division). Exemplary cancers include, without limitation, cancers of the colorectum, breast, lung, liver, pancreas, lymph node, colon, prostate, brain, head and neck, skin, liver, kidney, blood and heart (e.g., leukemia, lymphoma, carcinoma).

The terms "treat" and "treating" and "treatment" as used herein refer to ameliorating, alleviating, lessening, and removing symptoms of a disease or condition. In some embodiments, "treating" is effected by a compound as described herein, which, when administered to a subject in need thereof, exhibit a biological effect such as apoptosis of certain cells (e.g., cancer cells), reduction of proliferation of certain cells, or lead to ameliorating, alleviating, lessening, or removing symptoms of a disease or condition. "The terms "treat" and "treating" and "treatment" as used herein in some embodiments, also can refer to reducing or stopping a cell proliferation rate (e.g., slowing or halting tumor growth) or reducing the number of proliferating cancer cells (e.g., removing part or all of a tumor). The terms "treat" and "treating" and "treatment" as used herein also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Also provided herein are methods and uses of any one of the compounds described herein, for modulating the activity of a protein kinase, which are effected by contacting a system comprising the protein kinase with a compound as described herein in an amount effective for modulating (e.g., inhibiting) the activity of the kinase. The system in such embodiments can be a cell-free system or a system comprising cells. Also provided are methods and uses utilizing the compounds as described herein for reducing cell proliferation, and optionally inducing apoptosis, which are effected by contacting cells with a compound as described herein in an amount effective to reduce proliferation of the cells. The cells in such embodiments can be in a cell line, in a tissue or in a subject (e.g., a research animal or human). Protein kinases are a family of enzyme which catalyze the transfer of a gamma phosphate from adenosine triphosphate to a serine or threonine amino acid (serine/threonine protein kinase), tyrosine amino acid (tyrosine protein kinase), tyrosine, serine or threonine (dual specificity protein kinase) or histidine amino acid (histidine protein kinase) in a peptide or protein substrate. Thus, included herein are methods and uses which are effected by contacting a system comprising a protein kinase with a compound as described herein in an amount effective for modulating (e.g., inhibiting) the activity of the protein kinase. In some embodiments, the activity of the protein kinase is the catalytic activity of the protein (e.g., catalyzing the transfer of a gamma phosphate from adenosine triphosphate to a peptide or protein substrate). Systems in such embodiments can be a cell-free system or a system comprising cells (e.g., in vitro).

In some embodiments, the protein kinase is a serine-threonine protein kinase or a tyrosine protein kinase. In some embodiments, the protein kinase is a protein kinase fragment having compound-binding activity.

In some embodiments, the protein kinase is, or contains a subunit (e.g., catalytic subunit, SH2 domain, SH3 domain) of, CK2, Pim subfamily protein kinase (e.g., PIM1, PIM2, PIM3) or Flt subfamily protein kinase (e.g, FLT1, FLT3, FLT4).

In some embodiments the protein kinase is a recombinant protein. The protein kinase can be from any source, such as cells from a mammal, ape or human, for example. In some embodiments, the protein kinase is a human protein kinase.

In some embodiments, any of the compounds described herein is also useful in the treatment of a condition related to inflammation or pain. Conditions associated with inflammation and pain include without limitation, acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjogren's syndrome, spastic colon, systemic candidiasis, tendonitis, urinary tract infections, vaginitis, inflammatory cancer (e.g., inflammatory breast cancer) and the like.

In some embodiments, any of the compounds described herein is also useful for modulating angiogenesis in a subject, and for treating a condition associated with aberrant angiogenesis in a subject.

Pharmaceutical Compositions:

In any one of the methods and uses described herein, and any one of the embodiments thereof, a compound as described herein can be administered to the subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the compound of some embodiments of the invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to some embodiments of the invention, the compound is administered by oral administration.

Conventional approaches for drug delivery to the central nervous system (CNS) include: neurosurgical strategies (e.g., intracerebral injection or intracerebroventricular infusion); pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active ingredients are contained in an amount effective to achieve the intended purpose. More specifically, a therapeutically effective amount means an amount of active ingredients (the compound of some embodiments of the invention) effective to prevent, alleviate or ameliorate symptoms of a disorder (e.g., an autoimmune disease such as multiple sclerosis) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide tissue or blood levels of the active ingredient which are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The doses shown herein with respect to the mouse animal model can be converted for the treatment other species such as human and other animals diagnosed with the autoimmune disease. Conversion Table approved by the FDA is shown in Reagan-Shaw S., et al., FASEB J. 22:659-661 (2007).

The human equivalent dose is calculated as follows: HED (mg/kg)=Animal dose (mg/kg) multiplied by (Animal $K_m$/human $K_m$).

According to some embodiments of the invention, the compound is provided at an amount equivalent to a range of from about 3-30 mg/kg/day in mice, including any intermediate subranges and values therebetween.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is detailed herein.

Monitoring Treatment Efficacy:

As shown in Examples 2 and 3 in the Examples section which follows, treatment with the compound of some embodiments of the invention (e.g. Compound 10) suppresses transcription of genes of the RNA polymerase pathway e.g. pre-rRNA. Thus, the teachings of the invention can be also used to determine efficiency of the compound of some embodiments of the invention in treating a disease, e.g. autoimmune disease (e.g., multiple sclerosis) and/or a proliferative disease, by determining the effect of the compound on the expression level of at least one gene of the RNA polymerase I pathway. This can be used to develop a tailored treatment of a disease by monitoring drug efficacy. This system is based on measuring the level of genes of the RNA polymerase I pathway during treatment with the compound and the ability to perform an ongoing fine-tuning drug efficacy assessment.

Thus, according to an aspect of some embodiments of the invention, there is provided a method of monitoring treatment efficiency of the compound of some embodiments of the invention, the method comprising:

(a) treating the subject with the compound according to the method of some embodiments of the invention, and (b) comparing a level of expression of least one gene involved in the RNA polymerase I pathway in a cell of the subject following treating with the compound to a level of expression of the at least one gene in a cell of the subject prior to treating the subject with the compound, (i) wherein a decrease above a predetermined threshold in the level of expression of the at least one gene following treating with the compound relative to the level of expression of the at least one gene prior to treating with the compound indicates that the compound is efficient for treating the subject;

(ii) wherein an increase above a predetermined threshold in the level of expression of the at least one gene following treating with the compound relative to the level of expression of the at least one gene prior to treating with the compound indicates that the compound is not efficient for treating the subject; or (iii) wherein when a level of expression of the at least one gene following treating with the compound is identical or changed below a predetermined threshold as compared to prior to treating with the compound then the treatment is not efficient for treating the subject;

thereby monitoring treatment efficiency of the subject having disease or disorder as described herein.

As used herein, the phrase "level of expression" refers to the degree of gene expression and/or gene product activity in a specific cell. For example, up-regulation or down-regulation of various genes can affect the level of the gene product (i.e., RNA and/or protein) in a specific cell.

It should be noted that the level of expression can be determined in arbitrary absolute units, or in normalized units (relative to known expression levels of a control reference). For example, when using DNA chips, the expression levels are normalized according to the chips' internal controls or by using quantile normalization such as RMA.

As used herein the phrase "a cell of the subject" refers to at least one cell (e.g., an isolated cell), cell culture, cell content and/or cell secreted content which contains RNA and/or proteins of the subject. Examples include a blood cell, a cell obtained from any tissue biopsy [e.g., cerebrospinal fluid, (CSF), brain biopsy], a bone marrow cell, body fluids such as blood, plasma, serum, saliva, spinal fluid, lymph fluid, the external sections of the skin, respiratory, intestinal, and genitourinary tracts, tears, saliva, sputum and milk. According to an embodiment of the invention, the cell is a blood cell (e.g., white blood cells, macrophages, B- and T-lymphocytes, monocytes, neutrophiles, eosinophiles, and basophiles) which can be obtained using a syringe needle from a vein of the subject. It should be noted that the cell may be isolated from the subject (e.g., for in vitro detection) or may optionally comprise a cell that has not been physically removed from the subject (e.g., in vivo detection). According to specific embodiments the cell is comprised in a biological sample (e.g. a blood sample). Thus, according to a specific embodiment, the method further comprises obtaining the biological sample from the subject. It should be noted that a specific cell type may be further isolated from the biological sample directly obtained from the subject e.g. a white blood can be isolated from a blood sample. Methods of isolating specific cell types are well known in the art including, but not limited to, density gradient centrifugation, flow cytometry and magnetic beads separation.

According to some embodiments of the invention, the white blood cell comprises peripheral blood mononuclear cells (PBMC). The phrase, "peripheral blood mononuclear cells (PBMCs)" as used herein, refers to a mixture of monocytes and lymphocytes. Several methods for isolating white blood cells are known in the art. For example, PBMCs can be isolated from whole blood samples using density gradient centrifugation procedures. Typically, anticoagulated whole blood is layered over the separating medium. At the end of the centrifugation step, the following layers are visually observed from top to bottom: plasma/platelets, PBMCs, separating medium and erythrocytes/granulocytes. The PBMC layer is then removed and washed to remove contaminants (e.g., red blood cells) prior to determining the expression level of the polynucleotide(s) therein.

According to some embodiments of the invention, the level of expression of the gene(s) of the invention is determined using an RNA and/or a protein detection method.

According to some embodiments of the invention, the RNA or protein molecules are extracted from the cell of the subject. Thus, according to specific embodiments, the method further comprises extracting a RNA or a protein from the cell prior to the comparing.

Methods of extracting RNA or protein molecules from cells of a subject are well known in the art. The extracted RNA can be further processed to a cDNA. Methods of and commercially available kits for converting RNA to cDNA are well known in the art and include e.g. the use of the enzyme reverse transcriptase. Once obtained, the RNA, cDNA or protein molecules can be characterized for the expression and/or activity level of various RNA, cDNA and/or protein molecules using methods known in the arts.

According to specific embodiment, the expression of the POL1 pathway gene can be determined at the nucleic acid level using RNA or DNA detection methods.

Thus, according to some embodiments of the invention, detection of the expression level of the RNA of the POL1 pathway is performed by contacting the biological sample, the cell, or fractions or extracts thereof with a probe (e.g. oligonucleotide probe or primer) which specifically hybridizes to a polynucleotide expressed from the gene of the POL1 pathway (e.g., including any alternative spliced form which is known in the art). Such a probe can be at any size, such as a short polynucleotide (e.g., of 15-200 bases), an intermediate polynucleotide of 100-2000 bases and a long polynucleotide of more than 2000 bases.

The probe used by the present invention can be any directly or indirectly labeled RNA molecule [e.g., RNA oligonucleotide (e.g., of 17-50 bases), an in vitro transcribed RNA molecule], DNA molecule (e.g., oligonucleotide, e.g., 15-50 bases, cDNA molecule, genomic molecule) and/or an analogue thereof [e.g., peptide nucleic acid (PNA)] which is specific to the RNA transcript of the gene involved in the POL1 pathway. According to specific embodiments, the probe is bound to a detectable moiety.

Oligonucleotides designed according to the teachings of the present invention can be generated according to any oligonucleotide synthesis method known in the art such as enzymatic synthesis or solid phase synthesis.

According to specific embodiments, the contacting is effected under conditions which allow the formation of a complex comprising mRNA or cDNA of a gene involved in the POL1 pathway present in the cell and the probe. The complex can be formed at a variety of temperatures, salt concentration and pH values which may vary depending on the method and the biological sample used and those of skills in the art are capable of adjusting the conditions suitable for the formation of each nucleotide/probe complex.

Thus, according to an aspect of the present invention there is provided a composition of matter comprising a biological sample of a subject, and a probe capable of detecting a polynucleotide expressed from a gene involved in the POL1 pathway.

Non-limiting examples of methods of detecting RNA and/or cDNA molecules in a cell sample include Northern blot analysis, RT-PCR [e.g., a semi-quantitative RT-PCR, quantitative RT-PCR using e.g., the Light Cycler™ (Roche)], RNA in situ hybridization (using e.g., DNA or RNA probes to hybridize RNA molecules present in the cells or tissue sections), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface [e.g., a glass wafer) with addressable location, such as Affymetrix microarray (Affymetrix®, Santa Clara, Calif.)].

For example, the level of RRN3 in a sample can be determined by RT-PCR using primers available from Santa Cruz Biotechnology Inc. (sc-106866-PR), or Taqman Gene Expression Assay HS00607907_ml (Applied Biosystems, Foster City, Calif., USA), according to manufacturer's recommendation.

For example, the level of human pre-rRNA (Accession No: NR_046235, SEQ ID NO: 68) in a sample can be determined by RT-PCR using the RT2 qPCR Primer Assay for Human RNA45S5 (330001, Cat. N PPH82089A-200, Qiagen).

As mentioned, according to specific embodiments, the expression of the POL1 pathway gene can be determined at the amino acid level using protein detection methods.

Thus, according to some embodiments of the invention, detection of the expression level of the protein of the POL1 pathway is performed by contacting the biological sample, the cell, or fractions or extracts thereof with an antibody which specifically binds to a polypeptide expressed from the gene of the Pol I pathway (e.g., including any variants thereof which is known in the art). According to specific embodiments, the contacting is effected under conditions which allow the formation of a complex comprising polypeptide of a gene involved in the POL1 pathway present in the cell and the antibody (i.e. immunocomplex).

The immunocomplex can be formed at a variety of temperatures, salt concentration and pH values which may vary depending on the method and the biological sample used and those of skills in the art are capable of adjusting the conditions suitable for the formation of each immunocomplex.

Thus, according to an aspect of the present invention there is provided a composition of matter comprising a biological sample of a subject, and an antibody capable of detecting a polypeptide expressed from a gene involved in the POL1 pathway. According to a specific embodiment, the composition further comprises a secondary antibody capable of binding the antibody.

The antibody used by the present invention can be any directly or indirectly labeled antibody. According to specific embodiments, the probe is bound to a detectable moiety.

The detectable moiety used by some embodiments of the invention can be, but is not limited to a fluorescent chemical (fluorophore), a phosphorescent chemical, a chemiluminescent chemical, a radioactive isotope (such as $^{[125]}$iodine), an enzyme, a fluorescent polypeptide, an affinity tag, and molecules (contrast agents) detectable by Positron Emission Tomagraphy (PET) or Magnetic Resonance Imaging (MRI).

Non-limiting examples of methods of detecting the level and/or activity of specific protein molecules in a cell sample include Enzyme linked immunosorbent assay (ELISA), Western blot analysis, immunoprecipitation (IP), radio-immunoassay (RIA), Fluorescence activated cell sorting (FACS), immunohistochemical analysis, in situ activity assay (using e.g., a chromogenic substrate applied on the cells containing an active enzyme), in vitro activity assays (in which the activity of a particular enzyme is measured in a protein mixture extracted from the cells) and molecular weight-based approach. For example, in case the detection of the expression level of a secreted protein is desired, ELISA assay may be performed on a sample of fluid obtained from the subject (e.g., serum), which contains cell-secreted content.

As described above, the level of expression of least one gene involved in the RNA polymerase I pathway in a cell of the subject following treating with the compound is compared to the level of expression of the at least one gene in a cell of the subject prior to treating the subject with the compound.

As used herein the phrase "following treating with the compound" refers to any time period after administering the compound to the subject, e.g., from a few minutes to hours, or from a few days to weeks or months after drug administration.

According to some embodiments of the invention the level of expression is determined following administration of the first dose of the compound.

According to some embodiments of the invention the level of expression is determined following administration of any dose of the compound.

As used herein the phrase "prior to treating with the compound" refers to any time period prior administering the compound to the subject, e.g., from a few minutes to hours, or from a few days to weeks or months prior to drug administration.

According to some embodiments of the invention the level of expression is determined prior any dose of the compound (e.g., when the subject is naïve to treatment).

According to some embodiments of the invention prior to treating refers to when the subject is first diagnosed with autoimmune disease, e.g., multiple sclerosis.

According to some embodiments of the invention prior to treating refers to when the subject is suspected of having the autoimmune disease (e.g., multiple sclerosis), or diagnosed with probable autoimmune disease (e.g., probable multiple sclerosis).

According to some embodiments of the invention prior to treating refers to upon the onset of the autoimmune disease.

According to some embodiments of the invention the effect of the treatment on the subject can be evaluated by monitoring the level of expression of at least one of the polynucleotides described hereinabove and below. For example, downregulation in the level of RRN3 in the subject following treatment can be indicative of the positive effect of the treatment on the subject, e.g., switching from a typical RRMS to a BMS course of multiple sclerosis.

As described above, a decrease above a predetermined threshold in the level of expression of the at least one gene following treating with the compound relative to the level of expression of the at least one gene prior to treating with the compound indicates that the compound is efficient for treating the subject.

As used herein the phrase "a decrease above a predetermined threshold" refers to a decrease in the level of expression in the cell of the subject following treating with the compound which is higher than a predetermined threshold such as a about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression prior to treating with the compound.

As described, an increase above a predetermined threshold in the level of expression of the at least one gene following treating with the compound relative to the level of expression of the at least one gene prior to treating with the compound indicates that the compound is not efficient for treating the subject.

As used herein the phrase "an increase above a predetermined threshold" refers to an increase in the level of expression in the cell of the subject following treating with the compound, which is higher than a predetermined threshold such as about 10%, e.g., higher than about 20%, e.g., higher than about 30%, e.g., higher than about 40%, e.g., higher than about 50%, e.g., higher than about 60%, higher than about 70%, higher than about 80%, higher than about 90%, higher than about 2 times, higher than about three times, higher than about four time, higher than about five times, higher than about six times, higher than about seven times, higher than about eight times, higher than about nine times, higher than about 20 times, higher than about 50 times, higher than about 100 times, higher than about 200 times, higher than about 350, higher than about 500 times, higher than about 1000 times, or more relative to the level of expression of the at least one gene prior to treating with the compound.

As described, a level of expression of the at least one gene following treating with the compound which is identical or changed below a predetermined threshold as compared to prior to treating with the compound is indicative that the treatment is not efficient for treating the subject.

As used herein the phrase "changed below a predetermined threshold as compared to prior to treating with the compound" refers to an increase or a decrease in the level of expression in the cell of the subject following treating with the compound, which is lower than a predetermined threshold, such as lower than about 10 times, e.g., lower than about 9 times, e.g., lower than about 8 times, e.g., lower than about 7 times, e.g., lower than about 6 times, e.g., lower than about 5 times, e.g., lower than about 4 times, e.g., lower than about 3 times, e.g., lower than about 2 times, e.g., lower than about 90%, e.g., lower than about 80%, e.g., lower than about 70%, e.g., lower than about 60%, e.g., lower than about 50%, e.g., lower than about 40%, e.g., lower than about 30%, e.g., lower than about 20%, e.g., lower than about 10%, e.g., lower than about 9%, e.g., lower than about 8%, e.g., lower than about 7%, e.g., lower than about 6%, e.g., lower than about 5%, e.g., lower than about 4%, e.g., lower than about 3%, e.g., lower than about 2%, e.g., lower than about 1% relative to the level of expression of the at least one gene prior to treating with the compound.

Non-limiting examples of genes involved in the RNA polymerase I pathway which can be used according to the method of the invention include RRN3, LRPPRC, POLR1A, POLR1B, POLR1C, POLR1D, POLR1E, PTRF, NIP7, ISF1, TAF1A, TAF1B, TAF1C, TAF1D, UBTF, TTF1 NCL and RNA45S5 (45S Pre-rRNA).

Sequence information regarding gene products (i.e., RNA transcripts and polypeptide sequences) of the genes of RNA polymerase I pathway which can be used for detection thereof can be found according to the following access numbers.

According to some embodiments of the invention, the at least one gene involved in the RNA polymerase 1 pathway is selected from the group consisting of POLR1D, LRPPRC, RRN3, pre-rRNA and NCL.

According to some embodiments of the invention, the at least one gene involved in the RNA polymerase 1 pathway is selected from the group consisting of POLR1D, LRPPRC, RRN3, and NCL.

According to some embodiments of the invention, the at least one gene involved in the RNA polymerase 1 pathway is RRN3.

According to some embodiments of the invention, the at least one gene involved in the RNA polymerase 1 pathway is LRPPRC.

According to some embodiments of the invention, the at least one gene involved in the RNA polymerase 1 pathway is POLR1D.

According to some embodiments of the invention, the at least one gene involved in the RNA polymerase 1 pathway is pre-rRNA.

According to some embodiments of the invention, the at least one gene involved in the RNA polymerase 1 pathway comprises RRN3 and POLR1D.

According to some embodiments of the invention, the at least one gene involved in the RNA polymerase 1 pathway comprises RRN3 and LRPPRC.

| Affymetrix ProbSet/SEQ ID NO: | Representative Public ID/SEQ ID NO: | Representative polypeptide Public ID/SEQ ID NO: | Gene Symbol | Gene Title |
|---|---|---|---|---|
| 216902_s_at/1 | AF001549/18<br>NM_018427/19 | NP_060897/38 | RRN3 | RRN3 RNA polymerase I transcription factor homolog |
| 211971_s_at/2 | AI653608/20<br>NM_133259/21 | NP_573566/39 | LRPPRC | leucine-rich PPR-motif containing |
| 220113_x_at/3 | NM_019014/22 | NP_001131076/40<br>NP_061887/41 | POLR1B | polymerase (RNA) I polypeptide B, 128 kDa |
| 207515_s_at/4 | NM_004875/23 | NP_976035/42 | POLR1C | polymerase (RNA) I polypeptide C, 30 kDa |
| 218258_at/5 | NM_015972/24 | NP_057056/43<br>NP_689918/44 | POLR1D | polymerase (RNA) I polypeptide D, 16 kDa |
| 200610_s_at/6 | NM_005381/25 | NP_005372/45 | NCL | nucleolin |
| 222704_at/7 | W93584/26 | NM_015425/46 | POLR1A | polymerase (RNA) I polypeptide A, 194 kDa |
| 218997_at/8 | NM_022490/27 | NP_071935/47 | POLR1E | polymerase (RNA) I polypeptide E, 53 kDa |
| 218859_s_at/9 | NM_016649/28 | NP_001263309/48<br>NP_057733/49 | ESF1 | ESF1, nucleolar pre-rRNA processing protein, homolog (*S. cerevisiae*) |
| 206613_s_at/10 | NM_005681/29 | NP_001188465/50<br>NP_005672/51<br>NP_647603/52 | TAF1A | TATA box binding protein (TBP)-associated factor, RNA polymerase I, A, 48 kDa |
| 214690_at/11 | AA004579/30 | NP_005671/53 | TAF1B | TATA box binding protein (TBP)-associated factor, RNA polymerase I, B, 63 kDa |
| 203937_s_at/12 | AW015313/31 | NP_001230085/54<br>NP_001230086/55<br>NP_001230087/56<br>NP_001230088/57<br>NP_001230089/58 | TAF1C | TATA box binding protein (TBP)-associated factor, RNA polymerase I, C, 110 kDa |
| 218750_at/13 | NM_024116/32 | NP_077021/59 | TAF1D | TATA box binding protein (TBP)-associated factor, RNA polymerase I, D, 41 kDa |
| 214881_s_at/14 | X56687/33 | NP_001070151/60<br>NP_001070152/61<br>NP_055048/62 | UBTF | upstream binding transcription factor, RNA polymerase I |
| 204771_s_at/15 | NM_007344/34 | NP_001192225/63<br>NP_031370/64 | TTF1 | transcription termination factor, RNA polymerase I |
| 208790_s_at/16 | AF312393/35 | NP_036364/65 | PTRF | polymerase I and transcript release factor |
| 219031_s_at/17 | NM_016101/36 | NP_001186363/66<br>NP_057185/67 | NIP7 | NIP7, nucleolar pre-rRNA processing protein |
| Not Applicable | NR_046235/37 | Not Applicable | RNA45S5 | 45S rRNA precursor for the 18S, 5.8S and 28S rRNA |

According to some embodiments of the invention, the at least one gene involved in the RNA polymerase 1 pathway comprises POLR1D and LRPPRC.

According to some embodiments of the invention, the at least one gene involved in the RNA polymerase 1 pathway comprises RRN3, LRPPRC and POLR1D.

According to some embodiments of the invention, the at least one gene involved in the RNA polymerase 1 pathway is RRN3 and NCL.

According to some embodiments of the invention, the at least one gene involved in the RNA polymerase 1 pathway is LRPPRC and NCL.

According to some embodiments of the invention, the at least one gene involved in the RNA polymerase 1 pathway is POLR1D and NCL.

According to some embodiments of the invention, the at least one gene involved in the RNA polymerase 1 pathway comprises RRN3, POLR1D and NCL.

According to some embodiments of the invention, the at least one gene involved in the RNA polymerase 1 pathway comprises RRN3, LRPPRC and NCL.

According to some embodiments of the invention, the at least one gene involved in the RNA polymerase 1 pathway comprises POLR1D, LRPPRC and NCL.

According to some embodiments of the invention, the at least one gene involved in the RNA polymerase 1 pathway comprises RRN3, LRPPRC, POLR1D and NCL.

According to some embodiments of the invention, the at least one gene involved in the RNA polymerase 1 pathway comprises pre-rRNA and RRN3.

According to some embodiments of the invention, the at least one gene involved in the RNA polymerase 1 pathway comprises pre-rRNA and LRPPRC.

According to some embodiments of the invention, the at least one gene involved in the RNA polymerase 1 pathway comprises pre-rRNA and POLR1D.

According to some embodiments of the invention, the at least one gene involved in the RNA polymerase 1 pathway comprises pre-rRNA and NCL.

According to some embodiments of the invention, the at least one gene involved in the RNA polymerase 1 pathway comprises pre-rRNA, RRN3 and LRPPRC.

According to some embodiments of the invention, the at least one gene involved in the RNA polymerase 1 pathway comprises pre-rRNA, RRN3 and POLR1D.

According to some embodiments of the invention, the at least one gene involved in the RNA polymerase 1 pathway comprises pre-rRNA, LRPPRC and POLR1D.

According to some embodiments of the invention, the at least one gene involved in the RNA polymerase 1 pathway comprises pre-rRNA, RRN3, and NCL.

According to some embodiments of the invention, the at least one gene involved in the RNA polymerase 1 pathway comprises pre-rRNA, LRPPRC and NCL.

According to some embodiments of the invention, the at least one gene involved in the RNA polymerase 1 pathway comprises pre-rRNA, POLR1D and NCL.

According to some embodiments of the invention, the at least one gene involved in the RNA polymerase 1 pathway comprises pre-rRNA, RRN3, LRPPRC and POLR1D.

According to some embodiments of the invention, the at least one gene involved in the RNA polymerase 1 pathway comprises pre-rRNA, RRN3, LRPPRC and NCL.

According to some embodiments of the invention, the at least one gene involved in the RNA polymerase 1 pathway comprises pre-rRNA, RRN3, POLR1D and NCL.

According to some embodiments of the invention, the at least one gene involved in the RNA polymerase 1 pathway comprises pre-rRNA, LRPPRC, POL1RD and NCL.

Qualifying the compound as being suitable for treating the autoimmune disease in the subject can be also performed by an in-vitro method.

As used herein the term “about” refers to ±10%.

The terms “comprises”, “comprising”, “includes”, “including”, “having” and their conjugates mean “including but not limited to”.

The term “consisting of” means “including and limited to”.

The term “consisting essentially of” means that the composition, method or structure may include additional ingredients, steps and/or parts, but only if the additional ingredients, steps and/or parts do not materially alter the basic and novel characteristics of the claimed composition, method or structure.

As used herein, the singular form “a”, “an” and “the” include plural references unless the context clearly dictates otherwise. For example, the term “a compound” or “at least one compound” may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases “ranging/ranges between” a first indicate number and a second indicate number and “ranging/ranges from” a first indicate number “to” a second indicate number are used herein interchangeably and are meant to include the first and second indicated numbers and all the fractional and integral numerals therebetween.

As used herein the term “method” refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Chemical Syntheses and Characterization of POL1 Inhibitors

Materials and Methods:

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (also referred to herein interchangeably as CX-5461, POL1-I, RAM-0 or Compound 1; see, chemical structure as presented in FIG. 3A and Table 1 below) was synthesized according to known procedures (see, for example, U.S. Patent Application Publication No. 2009/0093465 and WO 2012/123938).

All of the reagents were obtained from Sigma Aldrich.

$^1$H NMR analyses were performed using a Bruker Avance DPX-400 Ultra shield or alternatively Bruker Avance DMX-500. All the chemical shifts are referenced to the residual solvent signal.

All Mass Spectra analyses were performed on a Thermo Scientific LCQ Fleet mass spectrometer with an ESI source. All the spectra were recorded in the positive mode (unless mentioned otherwise) and were analyzed by the Thermo Scientific Xcalibur software.

General Synthetic Procedure:

POL1-I (CX-5461, Compound 1) is refluxed in phosphoryl chloride for several hours to afford the chlorinated analog 5-chloro-2-(4-methyl-1,4-diazepan-1-yl)-6-(((5-methylpyrazin-2-yl)methyl)carbamoyl)benzo[4,5]thiazolo[3,2-a][1,8]naphthyridin-12-ium (also referred to herein interchangeably as POL1-I/1, RAM-2, RAM Cl or Compound 2; see, FIG. 3A and Table 1 below).

The phosphoryl chloride is thereafter removed by evaporation and the crude product 2 is dissolved or suspended in an alcoholic solvent (e.g., methanol or ethanol). An amine or thiol compound, as desired, is then added and the resulting reaction mixture is stirred, possibly under reflux, until reaction completion. The solvent is then removed by evaporation and the resulting crude is purified, typically by preparative HPLC.

The chemical structure of the obtained product was verified by MS [ESI] and/or $^1$H NMR, as detailed hereinbelow.

An exemplary synthetic pathway of exemplary compounds according to some embodiments of the present invention is presented in FIGS. 3A-B.

5-chloro-2-(4-methyl-1,4-diazepan-1-yl)-6-(((5-methylpyrazin-2-yl)methyl) carbamoyl)benzo[4,5]thiazolo[3,2-a][1,8]naphthyridin-12-ium (POL1-I/1; Compound 2)

MS [ESI]: calcd. 532.1 found [M+H] 532.2.

Preparation of 2-(4-methyl-1,4-diazepan-1-yl)-N-((5-methylpyrazin-2-yl)methyl)-5-thioxo-5H-benzo[4,5]thiazolo[3,2-a][1,8]naphthyridine-6-carboxamide (Referred to Herein Interchangeably as POL1-I/2; RAM-3; or Compound 3)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Sodium hydrosulfide was then added (100 mg) and the resulting solution was stirred for 5 minutes. The obtained compound 3 was purified by preparative HPLC to yield 82.4 mg 80% yield).

$^1$H NMR (500 MHz, $CDCl_3$): δ=13.02 (t, J=5.58 Hz, 1H), 9.50 (d, J=7.01 Hz, 1H), 9.23 (d, J=9.38 Hz, 1H), 8.64 (d, J=1.13 Hz, 1H), 8.43 (s, 1H), 7.75 (m, 1H), 7.45 (m, 2H), 6.82 (d, J=9.42 Hz, 1H), 4.89 (d, J=5.61 Hz, 2H), 4.17-3.64 (m, 4H), 2.88-2.79 (m, 2H), 2.64-2.57 (m, 2H), 2.56-2.53 (s, 3H), 2.39 (s, 3H), 2.11 (m, 2H) ppm.

MS [ESI]: calcd. 530.6 found [M+H] 530.2.

Preparation of 5-imino-2-(4-methyl-1,4-diazepan-1-yl)-N-((5-methylpyrazin-2-yl)methyl)-5H-benzo[4,5]thiazolo[3,2-a][1,8]naphthyridine-6-carboxamide (Referred to Herein, Interchangeably, as POL1-I/4; RAM-1 or Compound 4)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Gaseous ammonia was then bubbled into the methanol for 1 minute and the resulting solution was stirred for 5 minutes. The obtained compound 4 was purified by preparative HPLC to yield 64 mg (64% yield).

$^1$H NMR (400 MHz, $CDCl_3$ ppm): 9.28 (d, J=8.21 Hz, 1H), 8.58 (m, 1H), 8.44 (m, 1H), 8.04 (d, J=8.72 Hz, 1H), 7.64 (dd, J=7.62, 1.35 Hz, 1H), 7.34 (m, 2H), 6.68 (d, J=9.23 Hz, 1H), 4.86 (s, 2H), 3.98-3.74 (m, 4H), 2.84 (m, 2H), 2.66-2.60 (m, 2H), 2.54 (s, 3H), 2.41 (s, 3H), 2.12 (m, 2H), MS [ESI]: calcd. 513.2 found [M+H] 513.3.

Preparation of (E/Z)-2-(4-methyl-1,4-diazepan-1-yl)-5-(methylimino)-N-((5-methylpyrazin-2-yl) methyl)-5H-benzo[4,5]thiazolo[3,2-a][1,8]naphthyridine-6-carboxamide (Referred to Herein, Interchangeably, as POL1-I/3; or Compound 5)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. Methylamine was then added (3 mL) and the resulting solution was stirred for 5 minutes. The obtained compound 5 was purified by preparative HPLC to yield 74 mg (73% yield).

MS [ESI]: calcd. 527.6 found [M+H] 527.3.

Preparation of Compounds 6 and 7 (see, Table 1) was performed similarly to Compound 5, using propylamine and isopropyelamine, respectively, and yielding 82 mg (76% yield) and 85 mg (79% yield), respectively.

MS [ESI]: calcd. 555.7 found [M+H] 555.4. MS [ESI]: calcd. 555.7 found [M+H] 555.3.

Preparation of Compound 8 (see, Table 1)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. 3 mL of Triethylamine and 100 mg of [Methoxylamine hydrogen chloride] were then added and the resulting solution was stirred for 5 minutes. The obtained compound 5 was purified by preparative HPLC to yield 34 mg (32% yield).

MS [ESI]: calcd. 543.6 found [M+H] 543.2.

Preparation of Compound 9 (see, Table 1):

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (Compound 1) (100 mg) was suspended in 3 mL of phosphoryl chloride, and the obtained mixture was refluxed for 3 hours. The phosphoryl chloride was thereafter removed by evaporation and the obtained crude product was dissolved in MeOH. 100 mg of urea were added and the resulting solution was left to stir for 4 hours. The title compound was purified by preparative HPLC to yield 78 mg (75% yield)

MS [ESI]: calcd. 537.2 found [M+H] 537.6.

Preparation of (E)-2-(4-methyl-1,4-diazepan-1-yl)-N-((5-methylpyrazin-2-yl)methyl)-5-(phenylimino)-5H-benzo[4,5]thiazolo[3,2-a][1,8]naphthyridine-6-carboxamide (Compound 10; See, Table 1 and FIG. 3B)

2-(4-methyl-1,4-diazepan-1-yl)-N-((5-methylpyrazin-2-yl)methyl)-5-oxo-5H-benzo[4,5]thiazolo[3,2-a][1,8]naphthyridine-6-carboxamide (100 mg) was suspended in 3 mL of phosphoryl chloride, and the resulting mixture was refluxed for 3 hours. The phosphoryl chloride was thereafter removed by evaporation and the resulting crude product was dissolved in MeOH. Aniline was then added (2 mL) and the resulting solution was stirred for 5 minutes. The compound was purified by preparative HPLC to yield 56 mg (50% yield).

MS [ESI]: calcd. 589.7 found [M+H] 589.4.

Compound 11 (see, Table 1) was prepared similarly to Compound 10, using 3-fluoroaniline instead of aniline.

MS [ESI]: calcd. 607.2 found [M+H] 607.5.

Solubility:

The solubility of Compounds 1 and 10 was determined by dissolving 50 mg of the tested compound in 0.5 mL of mQ water, at room temperature.

Compound 10 immediately dissolved in the aqueous solution, whereby Compound 1 dissolved only in a pH 4.5 buffered solution after vigorous stirring for 30 minutes.

Example 2

Cell Viability Assay

Cell viability was assessed by the 2,3 bis [2-Methoxy-4-nitro-5-sulfophenyl]-2H-tetrazolium-5-carboxanilide (XTT) assay (Biological Industries, Kibbutz Beit Hemeek, Israel), which measures the reduction of a tetrazolium component (XTT) into soluble formazan product by the mitochondria of viable cells. The intensity of the dye obtained is proportional to the number of metabolic active cells. On the day of measurement, cells were washed and XTT was added according to the manufacturer's instructions. Plates were incubated at 37° C. for 2-5 hours. The absorbance was read at 450 nm.

Mouse splenocytes were removed and spleenocytes were plated (250,000 cell/well) in DMEM+10% FCS+P/S+Q and 10 mg/ml Phytohaemaglutinin (PHA), in the presence of elevated concentrations (25-400 nM) of RAM-0 (Compound 1), RAM-1 (Compound 4), RAM-2 (Compound 2) or RAM-3 (Compound 3) for 72 hours. Cells cultured without PHA served as control. Control mice at zero are mice splenocytes with PHA stimulation.

Following incubation, cell viability was determined by XTT assay, as described above.

RNA samples from similar cultures were also prepared and tested by Q-RT-PCR for pre-rRNA expression levels as described in Example herein below.

Figure 4A:
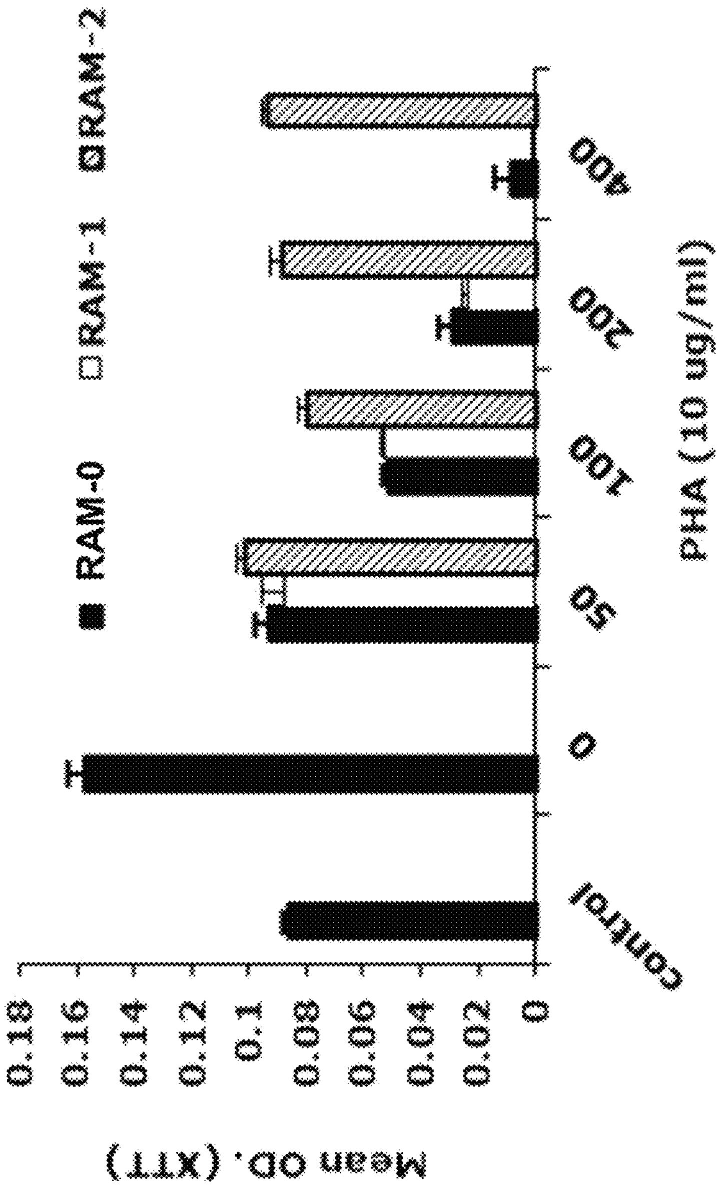
FIGS. 4A-C present bar graphs showing the effect of exemplary compounds according to some embodiments of the present invention in suppressing proliferation of mouse splenocytes, as determined in an XTT assay.

The obtained XTT data is presented in FIG. 4A (for Compound 1 compared with Compounds 2 and 4), in FIG.

Figure 4B:
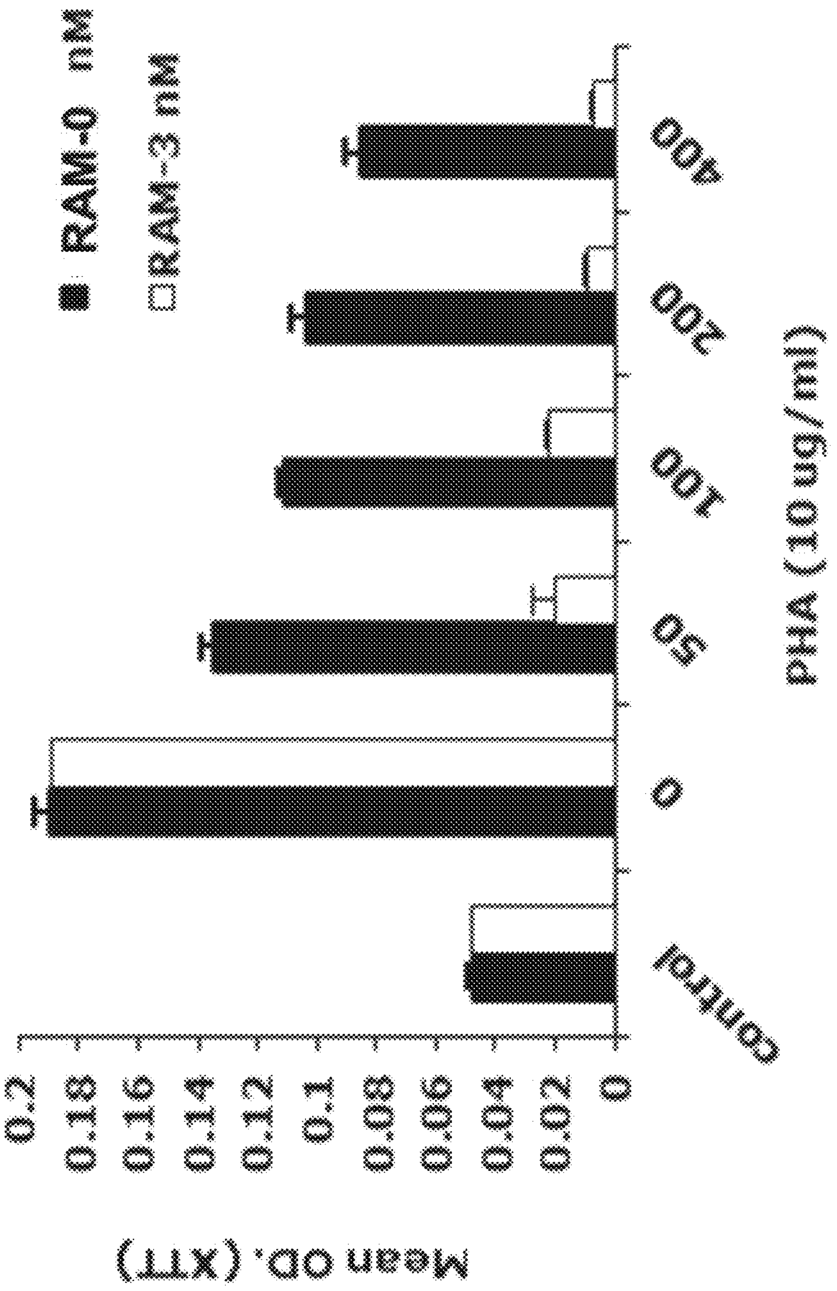
Figure 4C:
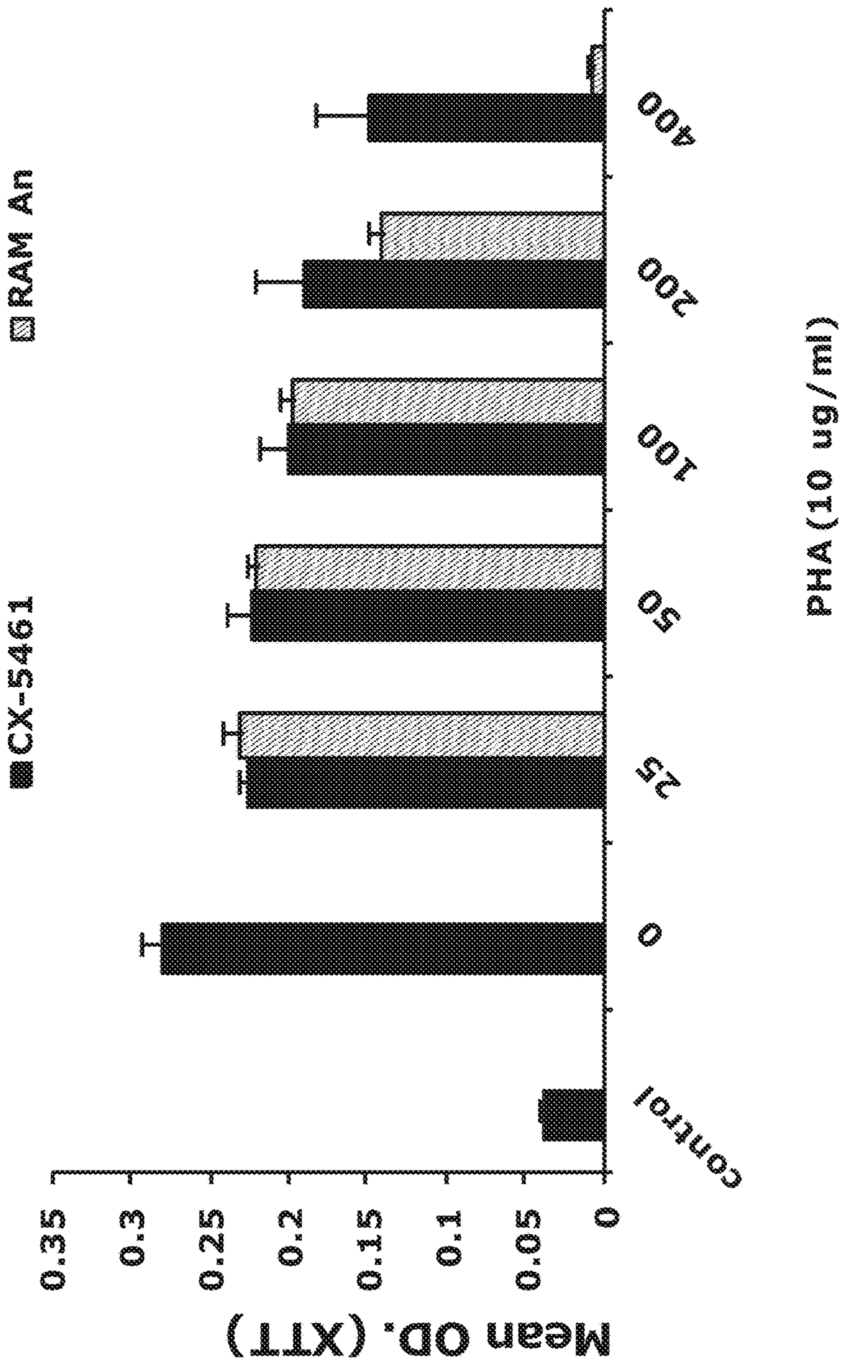

4B (for Compound 1 compared with Compound 3), and FIG. 4C (for Compound 1 compared with Compound 10).

As shown, PHA stimulation resulted in substantial increase in proliferation as compared to control. As shown in FIG. 4A, Compound 4 (RAM-1) exhibited a dose response curve similar to RAM-0 (Compound 1), while RAM-2 (Compound 2) showed no substantial effect. As shown in FIG. 4B, RAM-3 (Compound 3) was 6-folds more effective in suppressing proliferation compared to Compound 1 (RAM-0), suggesting much lower therapeutic doses of this compound. As shown in FIG. 4C, Compound 10 exhibits an improved performance is suppressing proliferation compared to Compound 1. As indicated below, this compound was also found to feature a larger therapeutic window and improved solubility and pharmacokinetic properties, compared to Compound 1.

$IC_{50}$ values as determined in these assays for Compounds 1-4 and 10, and for all other tested compounds, are presented in Table 1 below.

Figure 5:
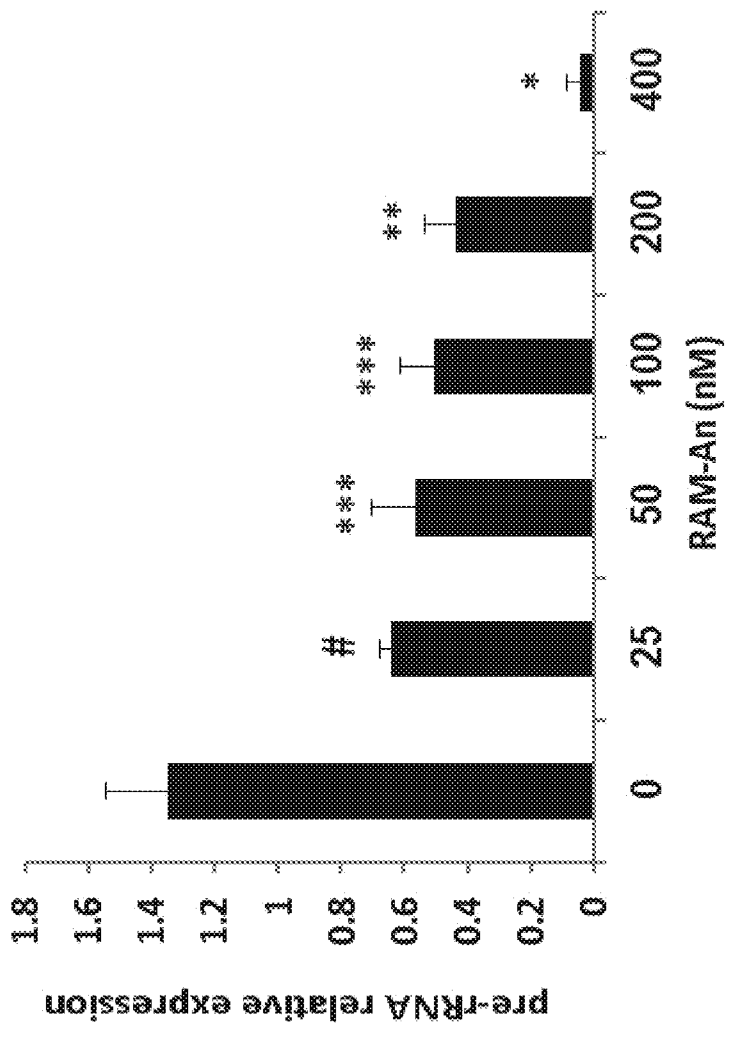
FIG. 5 is a graph showing mRNA levels of pre-rRNA in splenocytes of naïve mice following 72 hours stimulation with PHA in the presence of elevated concentrations of Compound 10. Bars represent mean±SEM; *p=0.0003, **p=$8.8*10^{-5}$, ***p<0.009 and #p=0.03.

The effect of Compound 10 on splenocytes proliferation was accompanied by suppression of pre-rRNA transcription, a key gene representing overall activity of the RNA polymerase I pathway. As shown in FIG. 5, 72 hours incubation with Compound 10 in concentrations of 25 to 400 nM resulted in a significant dose dependent decrease in pre-rRNA mRNA levels expressed by the splenocytes.

TABLE 1

| No. | Structure | Mw | Name | XTT |
|---|---|---|---|---|
| 1 | 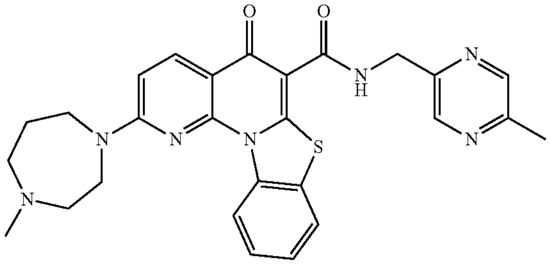 | 513.2 | CX-5461; RAM-0; POL1-I | $IC_{50}$ = 50 nM |
| 2 | 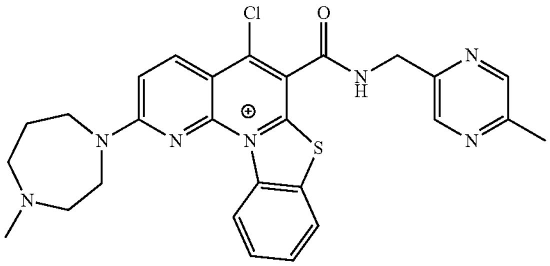 | 532.7 | RAM-2 POL1-I/1 | No Effect |
| 3 | 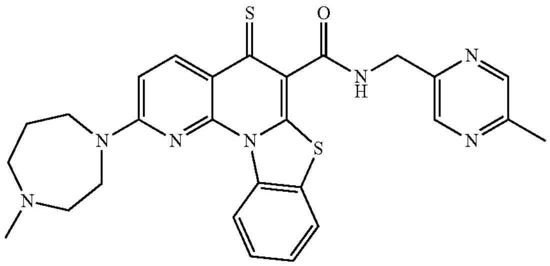 | 529.6 | RAM-3; POL1-I/2 | $IC_{50}$ = 20 nM* |
| 4 | 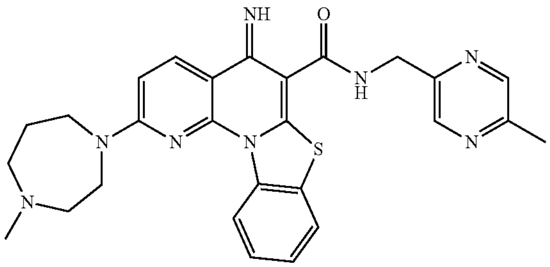 | 512.6 | RAM-1; POL1-I/4 | $IC_{50}$ = 50 nM |

TABLE 1-continued
| No. | Structure | Mw | Name | XTT |
|---|---|---|---|---|
| 5 | 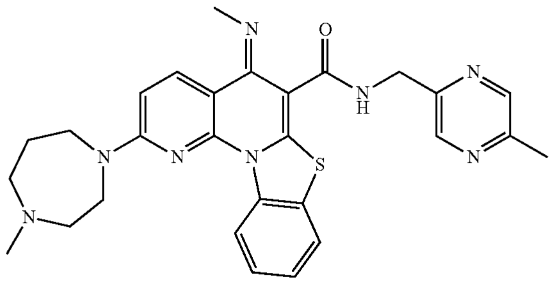 | 526.2 | RAM Me | $IC_{50}$ = 50 nM |
| 6 | 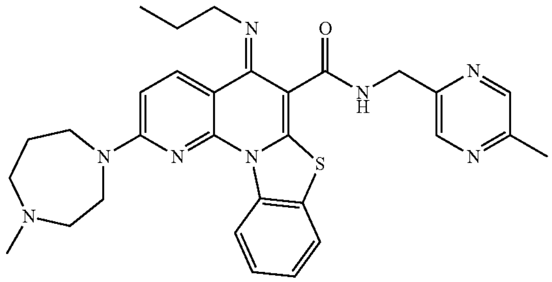 | 554.2 | RAM Pr | $IC_{50}$ = 50 nM |
| 7 | 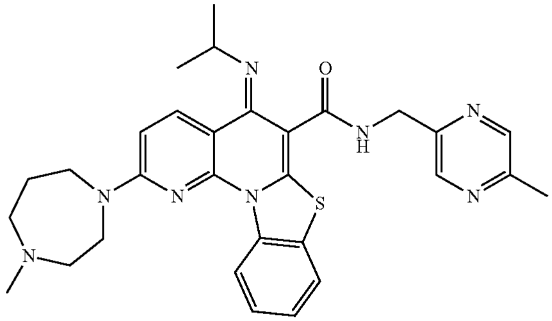 | 554.3 | RAM iPr | $IC_{50}$ = 50 nM |
| 8 | 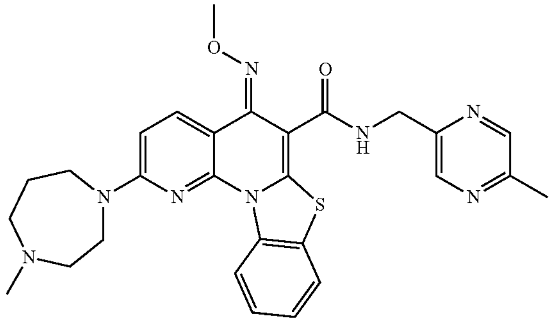 | 542.2 | RAM MeAM | $IC_{50}$ = 50 nM |
| 9 | 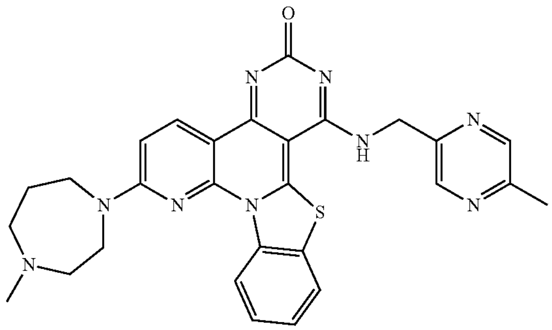 | 555.2 | RAM urea | No Effect |

TABLE 1-continued

| No. | Structure | Mw | Name | XTT |
|---|---|---|---|---|
| 10 | 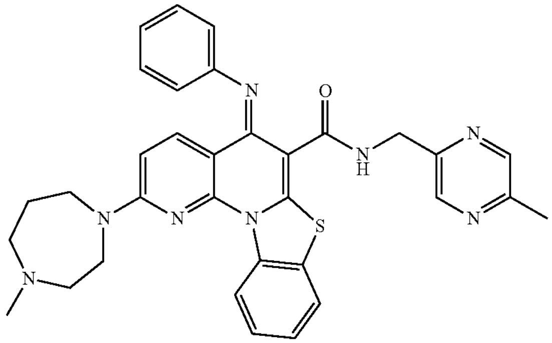 | 588.2 | RAM An | $IC_{50}$ = 40 nM |
| 11 | 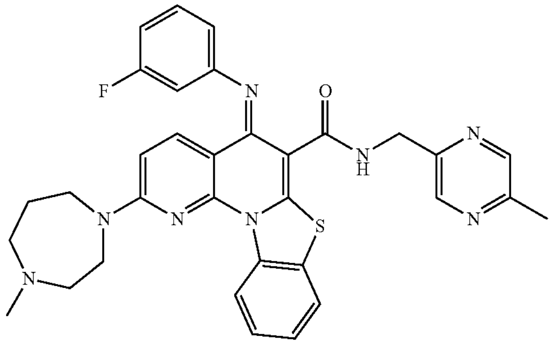 | 606.2 | RAM 3Fan | ND |

*Compound 2, although effective, was found to decompose in some of the experiments conducted.

Example 3

In Vivo Assays

Experimental Methods:

Mice: Eight-weeks-old female C57BL/6J mice (15-20 g, Harlan laboratories, Rehovot, Israel) were used in all experiments. Animal maintenance and experimental protocols were performed in accordance with the Israeli Council for Animal Care guidelines and approved by Sheba IRB Animal Care Committee. Mice were kept in an SPF environment, maintained on a 12-h light/dark cycle at a constant environmental temperature with free access to food and water in their home cages.

Induction of MOG35-55 EAE (Prevention Model): EAE (Experimental Autoimmune Encephalomyelitis) was induced in 8 week old female C57BL/6J mice (15-20 g, Harlan laboratories, Rehovot, Israel) by immunization with an emulsion containing 300 μg of purified myelin oligodendrocyte glycoprotein (MOG) peptide (MEVGWYR-SPFSRVVHLYRNGK, corresponding to residues 35-55; obtained from (Difco, Detroit, Mich.) in saline and an equal volume of complete Freund's adjuvant containing 5 mg H37RA (Difco, Detroit, Mich.). 0.2 ml of the inoculum was injected subcutaneously. In addition, 300 ng of *Bordetella pertusis* toxin (Sigma) in 0.2 ml saline was injected intraperitoneally at the day of induction and two days later.

Oral gavages with the tested compound, at various concentrations ranging from 3 mg/kg-30 mg/kg in PBS or 50 mM $NaH_2PO_4$ (PH 4.5), or with vehicle only, were initiated at day of immunization. Mice were monitored daily for clinical signs of EAE, scored as: 1, flaccid tail; 2, forelimb weakness and poor righting ability; 3, hind limb paralysis; 4, quadriplegia; 5, moribund. Animal reaching a score of 4 were scarified using $CO_2$.

Treatment was stopped once 30% of the vehicle-treated animals scored 1 on the EAE score. The experiment was terminated after 28 days.

Toxicity: The lethal dose for 50% of animals ($LD_{50}$), was determined for the EAE model, and was estimated in a continuous administration model. The animals were evaluated for signs of acute toxicity and survival during the entire administration period in the EAE model. Various concentrations were evaluated for efficacy, and when 50% mortality was observed in a specific concentration, this concentration was determined as the $LD_{50}$.

The therapeutic index ($LD_{50}/ED_{50}$), which is also referred to herein as Safety Margin (SM), was then determined based on the EAE model. $ED_{50}$ is the minimum effective dose observed for 50% of the tested animals.

Bioavailability: Determination of the level of the tested compound in serum was done following oral gavage. Blood samples (0.5 mL) were collected and immediately centrifuged at 5,000 rpm for 10 minutes. The serum was separated and stored at −20° C. until fluoprometric analysis by Tecan SpectraFluor, based on the specific excitation/emission values of the tested compound was conducted. The pharmacokinetic parameters including serum maximum concentration (Cmax), the time needed to reach Cmax (Tmax), and half-life (T1/2), were calculated to evaluate oral bioavailability. The serum concentration after oral gavages was calculated according to a calibration curve for each compound in the serum.

The Pharmacokinetic properties of compound 10 were quantified by the LCMS method described below. The concentration of Compound 10 was calculated with a calibration curve. The serum was prepared for analysis using protein precipitation. 15 μL of water were added to 15 μL of serum and a $H_2O$: MeOH: $CHCl_3$ (90:120:30) solution was added. The supernatant was subjected to LCMS analysis equipped with a PHENOMENEX® C-18 RP column.

RNA Extraction: For in vivo experiments spleens from EAE mice were isolated at day 17 post immunization and splenocytes were re-stimulated for 72 h hours in the presence of 5.0 μg/ml MOG35-55. For in-vitro experiments spleens from intact mice were isolated and splenocytes were stimulated with for 72 h in the presence of PHA. RNA was extracted from splenocytes of both the in-vitro and in-vivo experiments by robotic ABI PRISM, Applied biosystem 6100 Nucleic Acid Prep Station. To avoid genomic DNA contamination samples were treated with DNase I (Roche). The quality and integrity of the total RNA preparation was confirmed using a NanoDrop 2000c Spectrophotometer (Thermo Scientific).

Quantitative RT-PCR of Pre-rRNA: Complementary DNA was obtained from the extracted RNA by the High capacity cDNA reverse transcription kit (Applied Biosystems, CA, USA) following manufacturer's instructions. To confirm the role of POL1 pathway suppression by POL1-Inhibitors, the expression level of pre-rRNA transcript, a key gene of the RNA polymerase I pathway, was evaluated by Q-RT-PCR (n=3 per group). All PCR reactions were performed on a Light Cycler 480 instrument (Roche Diagnostic). The pre-rRNA, specific primers used were Forward: tttcttgtaagcgtcgaggtg (SEQ ID NO: 69) and Reverse: agcaggcacctaggagacaa (SEQ ID NO: 70) with a quantification probe (Roche, Probe ID #1, cat. no. 04684974001). For sample normalization, actin expression level was used as an internal control.

Statistical Analysis: All statistical analyses to evaluate differences between groups are performed by T-test and p value <0.05 is considered significant.

Figure 6A:
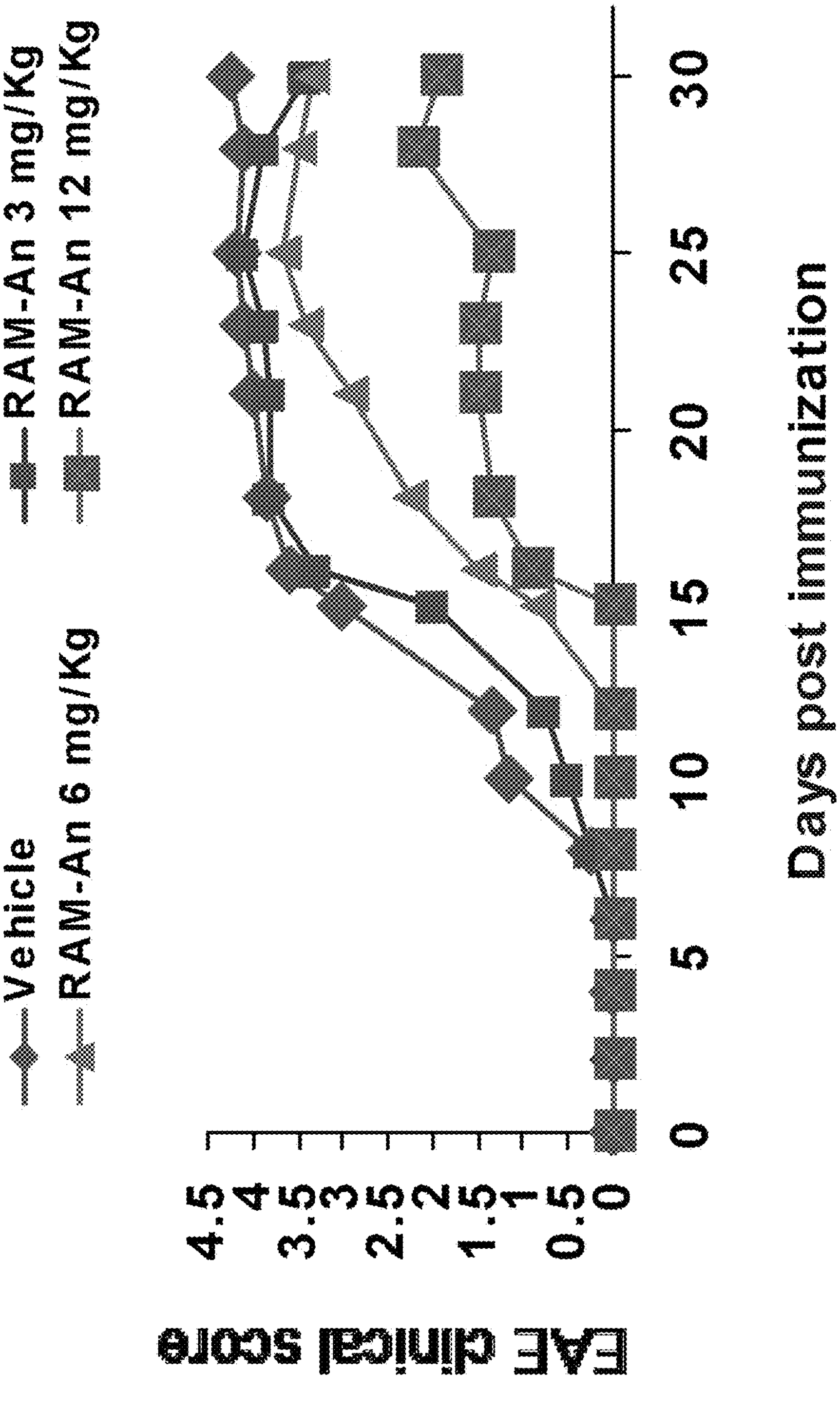
FIGS. 6A-D present plots showing the effect of various concentration of Compound 10 (RAM-An) on the EAE clinical score and disease incidence, as observed in an EAE prevention mice model, following daily (FIG. 6D) or every other day administration (FIGS. 6A-C).
Figure 6B:
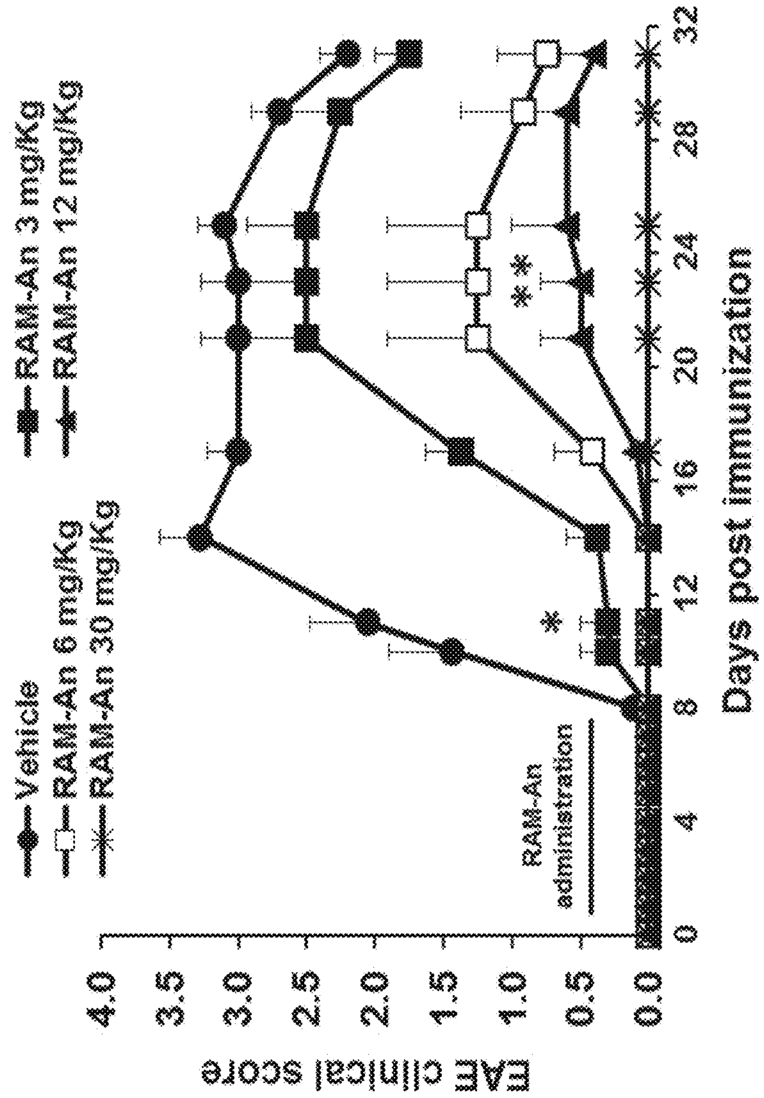
Figure 6C:
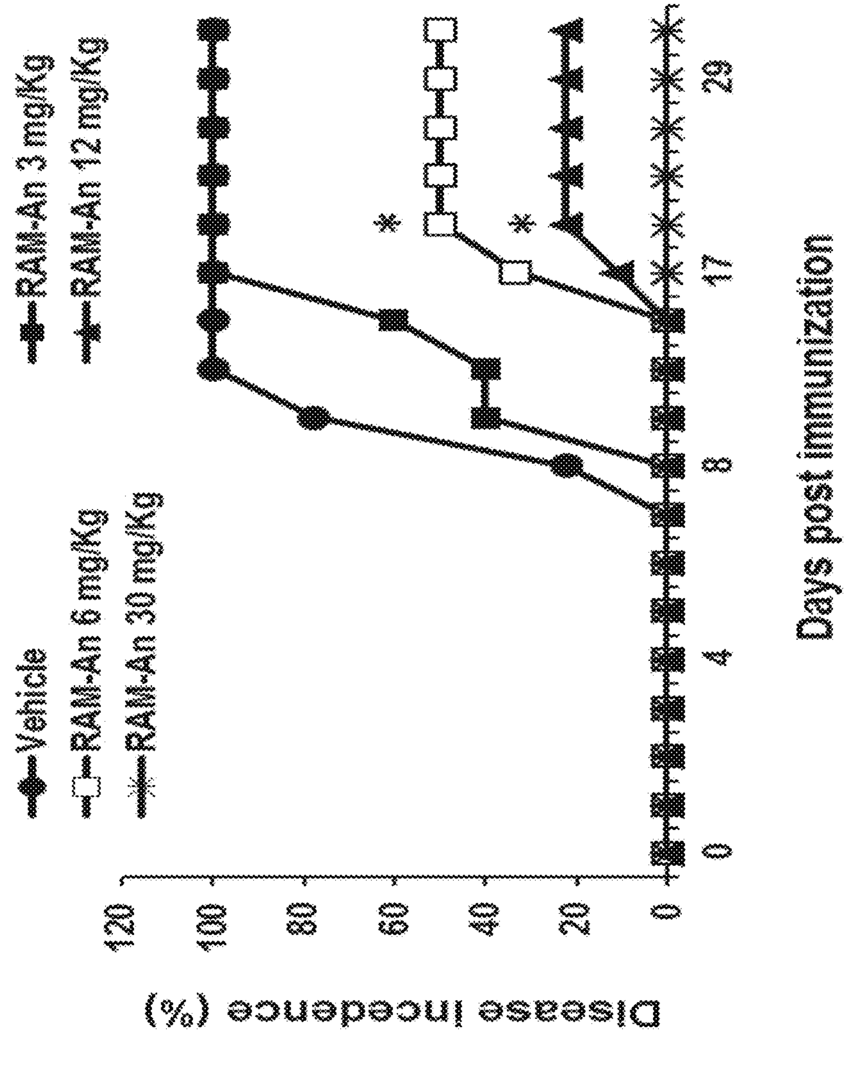

Experimental Results:

FIGS. 6A-C present the minimal clinically effective dose and optimal dosing schedule for Compound 10 by evaluating its efficacy in an EAE immunization model by oral administration at alternate days starting at the day of immunization. As shown in FIG. 6A administration of 12.0 mg/kg of Compound 10 significantly delayed disease development by 10 days; p<0.001, and suppressed EAE severity (as shown by decreased activity at 23 day post immunization, p=4.57E-05).

As also evident in FIG. 6B, the disease incidence gradually decreased with elevation of the dose and ranged between 98% at a dose of 3 mg/kg and 22% at a dose of 12.5 mg/kg (p<0.0001 for 6.125 and 12.5 mg/kg as compared to the vehicle treated group). Moreover, administration of 30 mg/kg completely inhibited disease development. Notably, mice in all treated groups showed 100% survival without apparent signs of toxicity.

As summarized in Table 2 below, analysis of 15 mice per group showed that mice treated with Compound 10 remained free of disease for 10 additional days as compared to mice treated with vehicle. Even following disease onset, the treated mice reached the peak of disease 6 days following the vehicle treated group and the peak itself was significantly lower in the Compound 10 treated animals ($p=4.8*10^{-6}$).

TABLE 2

Effects of Compound 10 in EAE, immunization model

| Treatment | No. of mice | EAE onset (dpi) | Peak of EAE (dpi) | Max clinical score | Cumulative disease score * |
|---|---|---|---|---|---|
| Vehicle | 15 | 9.5 ± 0.4 | 14.4 ± 1.2 | 3.8 ± 0.1 | 30.3 ± 2.4 |
| RAM-An/ 589.555 12.5 mg/Kg | 15 | 19.2 ± 0.6 | 20.4 ± 0.7 | 1.2 ± 0.4 | 7.2 ± 1.9 |
| p-value | | $1.3*10^{-12}$ | $2*10^{-4}$ | $4.8*10^{-6}$ | $3.3*10^{-7}$ |

* The cumulative scores represent the summation of each single score recorded for each mouse from the day of immunization (day 0) to the day of sacrifice (day 31).
dpi—days post immunization As shown in FIG. 6A, the minimal effective dose was 6 mg/kg.

Figure 6D:
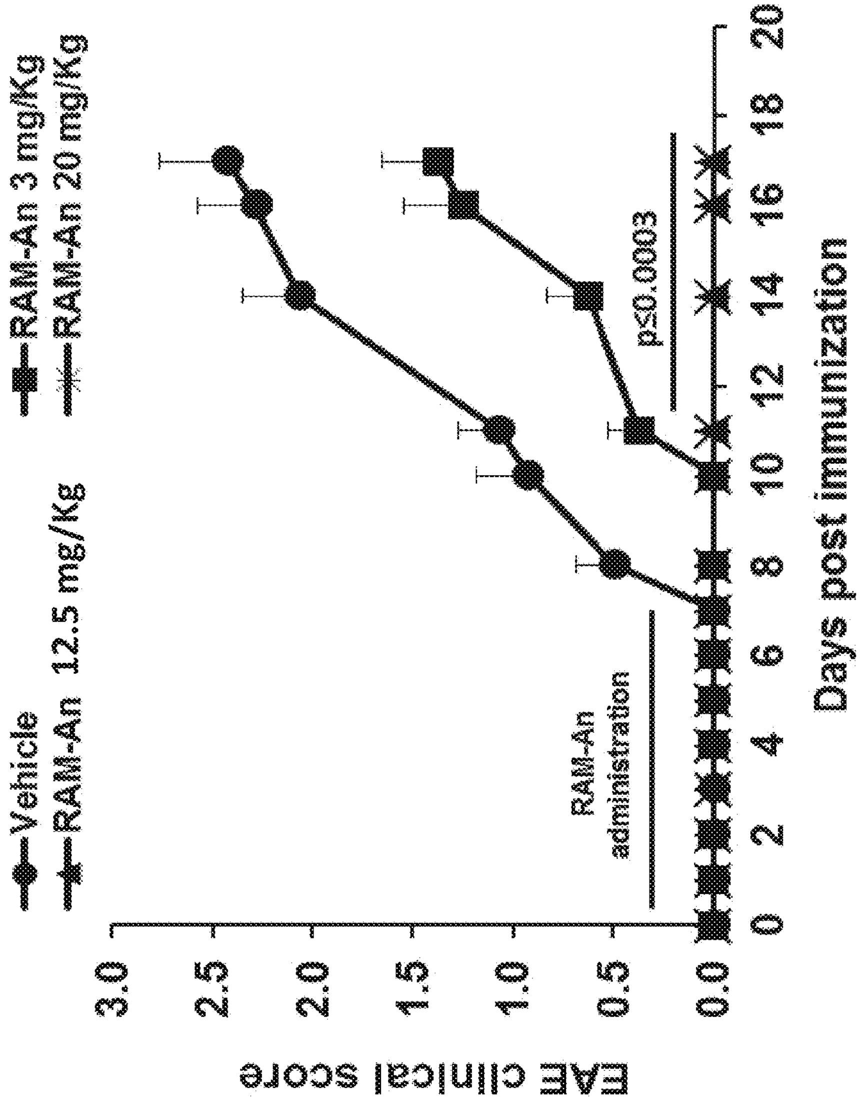

FIG. 6D demonstrated that the minimal effective dose was even lower in daily administration regimen in which efficacy of Compound 10 was evaluated using daily doses of 3.0, 6.0, 12.5 and 20 mg/kg starting at the day of immunization until disease onset at the vehicle treated group. Thus, daily administration of Compound 10 at a dose of 12.5 mg/kg resulted in complete inhibition of EAE (p≤0.0003 as compared with vehicle treated at 11-17 days post immunization and the minimal effective dose was 3.0 mg/kg.

Table 3 below presents comparative data for the effective and toxic doses as determined in the EAE prevention model assay described hereinabove, as determined for Compounds 1 and 10.

TABLE 3

Compounds effective and toxic doses as determined in the EAE prevention model

| No. | Structure | EAE | | |
|---|---|---|---|---|
| | | $ED_{50}$ | $LD_{50}$ | SM |
| 1 CX-5461; RAM-0; POL1-I | 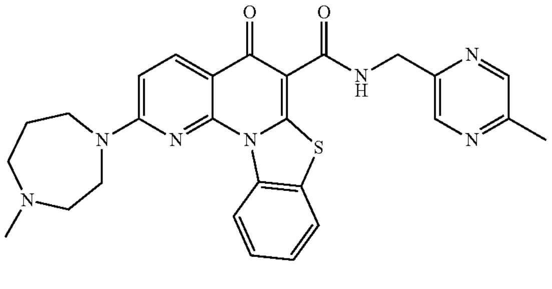 | 12.5 mg/kg | 25 mg/kg | 2 |

TABLE 3-continued

| Compounds effective and toxic doses as determined in the EAE prevention model | | | | |
|---|---|---|---|---|
| | | EAE | | |
| No. | Structure | $ED_{50}$ | $LD_{50}$ | SM |
| 10 RAM An | 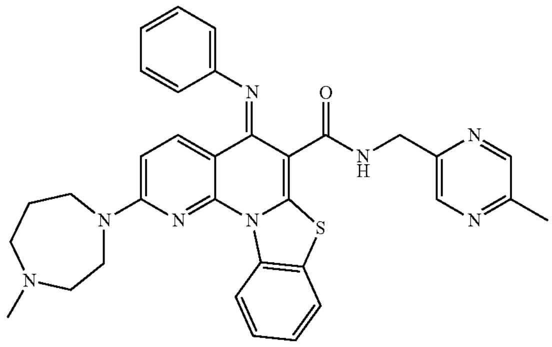 | 3 mg/kg | 30 mg/kg | 10 |

Compounds 2 and 9 were not tested; Compounds 3-7 were found relatively toxic during these preliminary studies.

It is shown in Table 3 that Compound 10 exhibits a substantially superior therapeutic index compared to CX-5641 (Compound 1).

Figure 7:
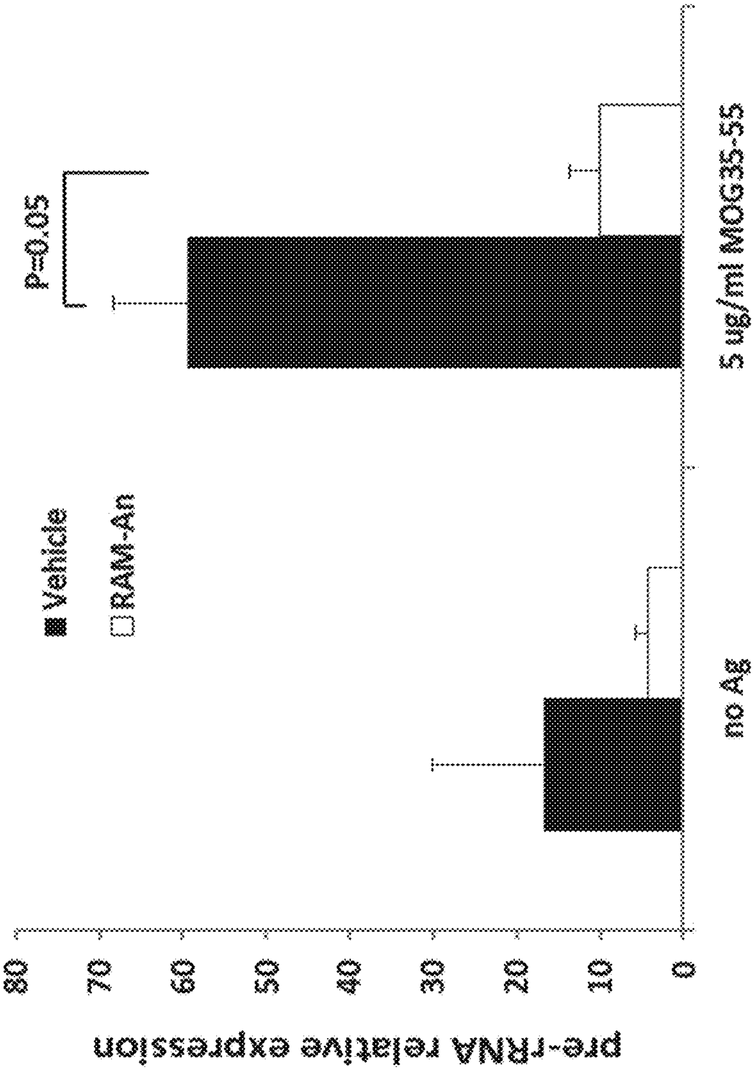
FIG. 7 is a graph showing mRNA levels of pre-rRNA in splenocytes isolated from spleens of EAE mice treated with 12.5 mg/Kg Compound 10 (RAM-An) for 17 days following immunization with MOG 35-55, as compared to vehicle-treated control mice. Bars represent mean±SEM.

The effects of Compound 10 in the EAE mouse model were accompanied by suppression of pre-rRNA transcription. As shown in FIG. 7, treatment with Compound 10 resulted in a significant decrease (5.9 folds) in pre-rRNA mRNA levels expressed by splenocytes 17 days following immunization, as compared to treatment with vehicle-control (p=0.05).

Figure 8A:
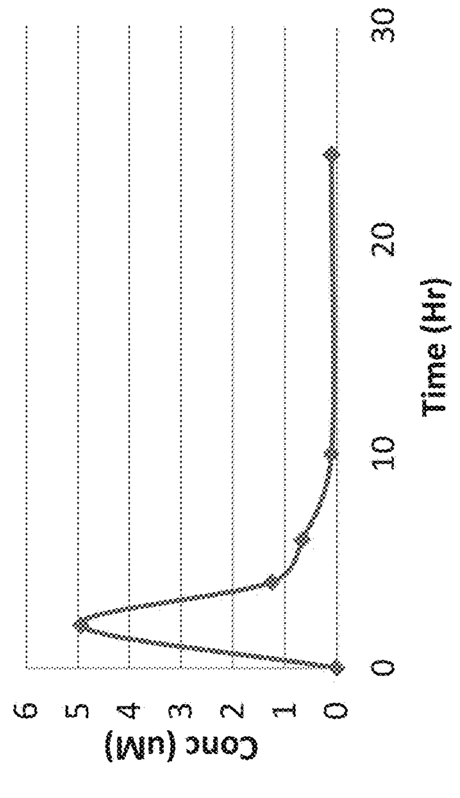
FIGS. 8A-B present graphs showing the time-dependent profile of Compound 10 (FIG. 8A) and Compound 1 (FIG. 8B) in mice serum following administration by oral gavage.
Figure 8B:
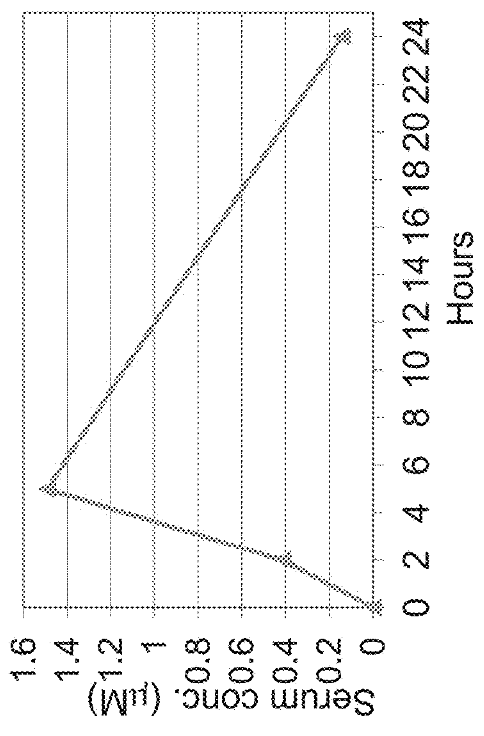

FIGS. 8A-B present the data obtained in the bioavailability assay for Compounds 1 and 10. As shown therein, Compound 10 exhibits a more favorable pharmacokinetic compound to Compound 1, as reflected by the higher Cmax, the lower Tmax, and the faster clearance.

Figure 9A:
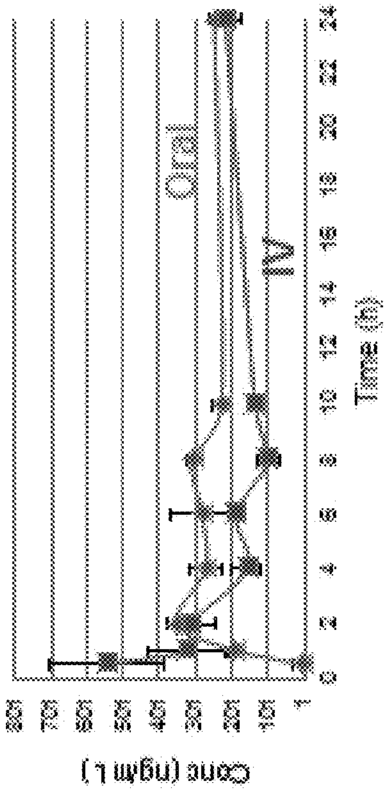
FIGS. 9A-B present graphs showing the bioavailability profile of Compound 10 for 24 (FIG. 9A) and 168 hours (FIG. 9B) in the serum of naive C57Bl female mice following single administration of 12.5 mg/kg by IV and of 12.5 mg/kg by oral gavage.

FIG. 9A presents the data obtained in the bioavailability assay for Compound 10 after oral and IV administration up to 24 h. As shown therein, Compound 10 is rapidly absorbed following both oral and IV administration; Compound 10 reaches maximal concentration after 0.5 h following IV administration and maximal concentration after 2 h following oral administration in healthy C57B6J, female mice.

Figure 9B:
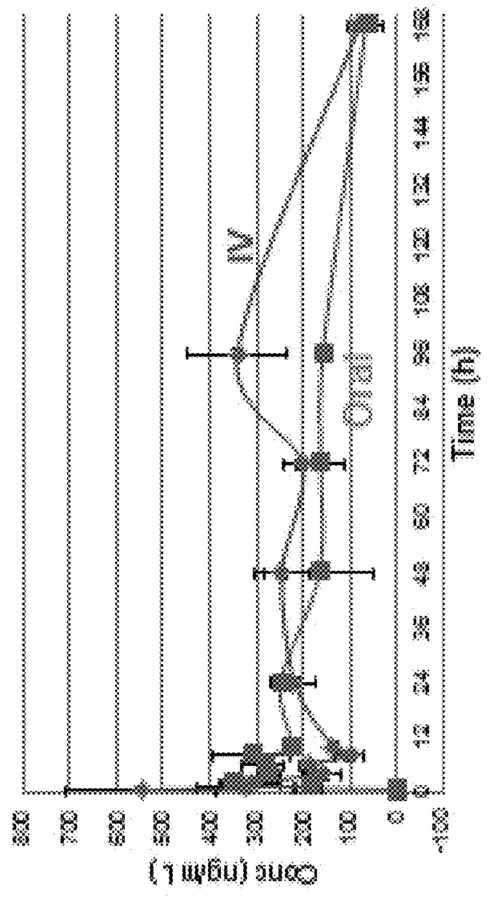

FIG. 9B presents the data obtained in the bioavailability assay for Compound 10 after oral and IV administration up to 168 h. As shown therein, the calculated bioavailability of Compound 10 is AUC(oral)/AUC(IV)=72%.

Compound 10: Single Dose Toxicity

The toxicity of oral administration of a single dose of Compound 10 was tested in naïve mice using range from 3 mg/kg to 500.0 mg/kg. No effect on survival was observed at 24 h. No behavioral changes were observed at 24 h.

Compound 10 Chronic Toxicity

Compound 10 was well tolerated when administered to EAE mice every alternate day until disease onset at a dose of 30 mg/kg. No effect on survival was observed. No behavioral changes were observed.

Example 4

Experimental Methods:

Cell-Free Polymerase I Transcription Assay:

Cell-free Pol I transcription assay was performed according to Drygin et al. (2010). Briefly, a reaction mixture consisting of 8 units of HeLa scribe nuclear extract (Promega) in transcription buffer and $MgCl_2$ (4 mM) was combined with POL1-Inhibitor (200 nM) and 10 mg/ml a-amanitin (Sigma) for 20 minutes at ambient temperature. Following, 10 ng DNA template (GENEWIZ, Inc.; http://www(dot)genewiz(dot)com(dot)cn) corresponding to the (−160/+350) region on human rDNA was added and the reaction was incubated for 5 minutes at ambient temperature. Transcription was initiated by adding rNTPs mix to a final concentration of 1 mM and the reaction was incubated for 1 hour at 30° C. Afterward, DNase I (Ambion kit) was added and the reaction was further incubated for 25 minutes at 37° C. DNase activity was terminated with adding an inactivation solution according the manufacturer's protocol. The samples were then subjected for RNA isolation (following the same procedure described in Example 3 hereinabove). Pellets of RNA were re-suspended in DEPC-treated double distilled water and subjected for reverse transcription by a High capacity kit (Applied Biosystems). The resultant transcripts were analyzed by qRT-PCR in a Light cycler 480 system using primer pairs (Sigma) and probe for real-time PCR. Primers were designed from the Assay Design Centre of the Universal ProbeLibrary (Roche Applied Science, USA) as follows: Pol I forward primer: tcaggcgttctcgtctcc (SEQ ID NO: 71), Pol I reverse primer: caccacatcgatcacgaaga (SEQ ID NO: 72).

Transcription by polymerase II from CMV promoter was tested similarly using the template provided HeLa scribe kit of Promega, further processing as described above and analysis of transcript with template specific primers: POL II forward primer: ctatgcgcacccgttctc (SEQ ID NO: 73), Pol II reverse primer: gtagcgaagcgagcagga (SEQ ID NO: 74). Probe ID: #70, cat. no. 04688937001 (Roche), was used for both reactions.

Figure 10:
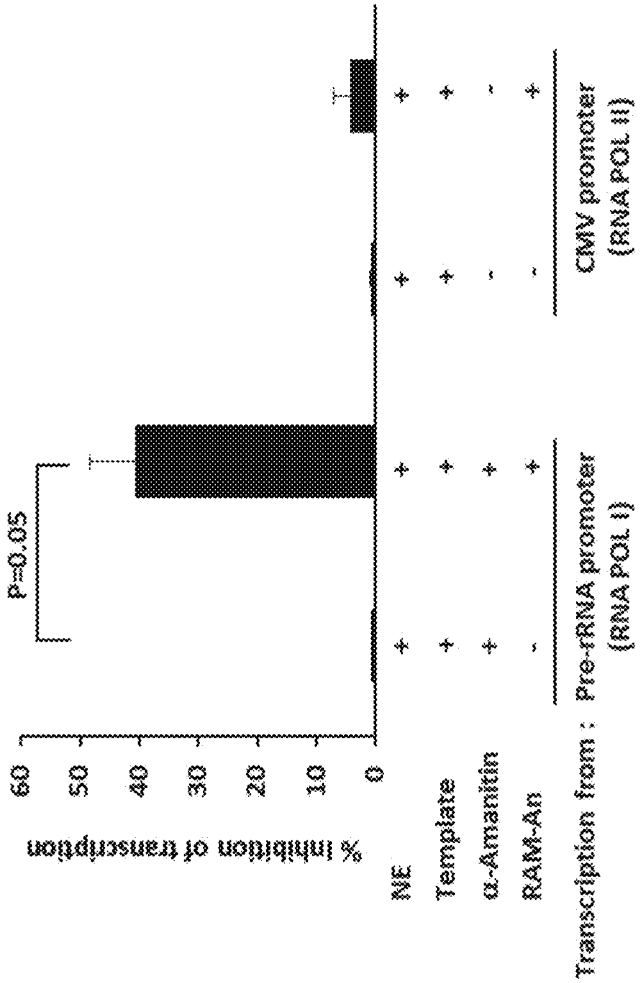
FIG. 10 is a graph shown effect of Compound 10 (RAM-An) on POL1 activity in cell-free transcription assay.

Experimental Results:

The analysis of the POL1 cell free assay showed that addition of 200 nM Compound 10 resulted in about 40% inhibition of Pol I transcription from the pre-rRNA promoter (p=0.05, FIG. 10), whereas Compound 10 only minimally affected Pol II transcription by 5% from the CMV promoter. These data indicate that Compound 10 directly targets the Pol I machinery.

In addition, viability, proliferation and apoptosis of splenocytes isolated from mice 14 days post immunization and incubated for 72 h with MOG 35-55 were assessed by XTT, BrdU and flow cytometry (Annexin V and propidium iodide double staining) assays, respectively. The results indicated that treatment with Compound 10 (Ram-An lot no. 589.555) reduced viability, suppressed cell proliferation specifically more affecting cells with high proliferation index, and induced apoptosis in CD4+ lymphocytes, as compared to treatment with the vehicle (data not shown).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating relapsing-remitting multiple sclerosis in a subject, the method comprising administering to the subject a therapeutically effective amount of the compound represented by Formula Ib:

Formula Ib

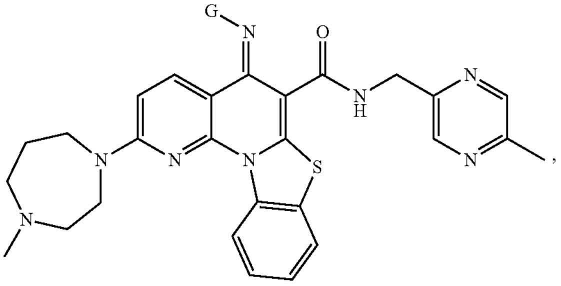

wherein G is selected from the group consisting of hydrogen, alkyl, cycloalkyl, aryl, heteroaryl, heteroalicyclic, alkoxy, thioalkoxy, thiol, hydroxyl, aryloxy, and thioaryloxy.

2. The method of claim 1, wherein G is aryl.

3. The method of claim 1, wherein said compound is selected from:

Compound 4

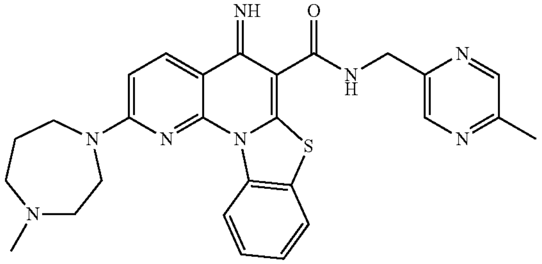

Compound 5

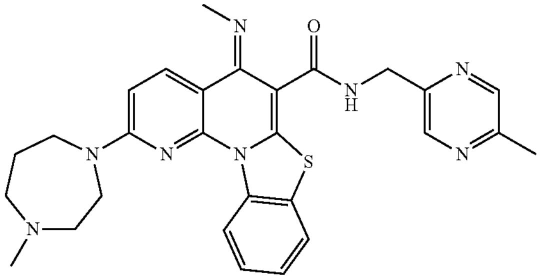

Compound 6

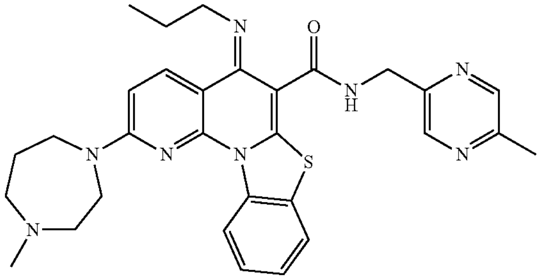

-continued

Compound 7

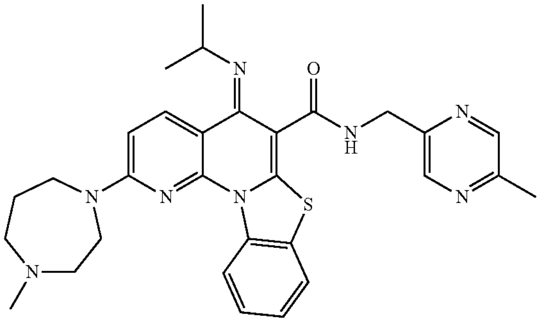

Compound 8

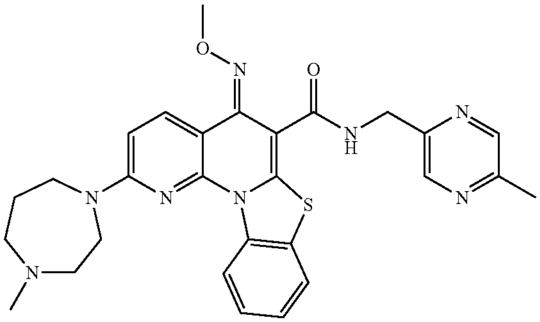

Compound 10

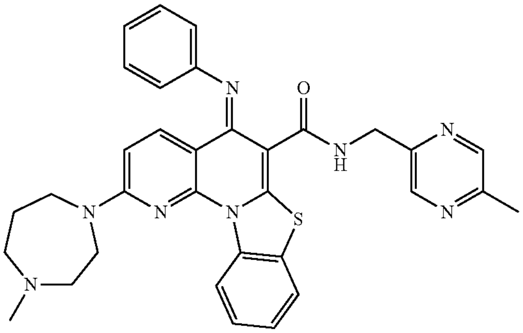

and

Compound 11

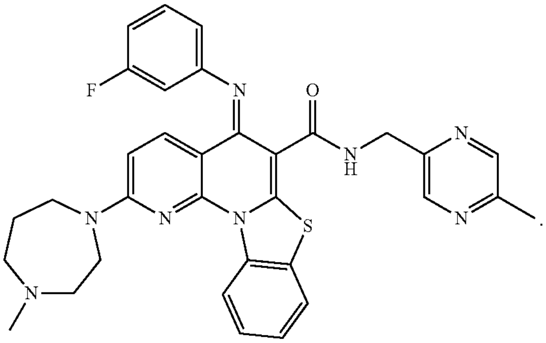

4. The method of claim 1, wherein said compound is:

Compound 10

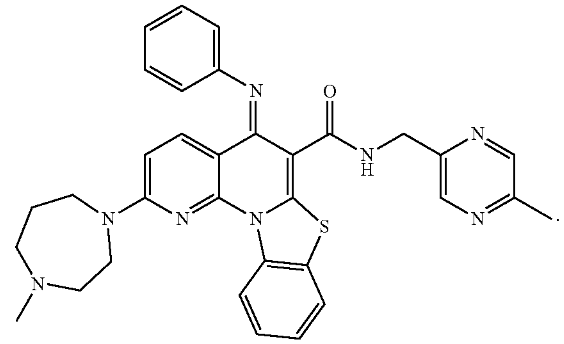

5. The method of claim 1, wherein treating said relapsing-remitting multiple sclerosis comprises changing the course of the disease from said relapsing-remitting multiple sclerosis to benign multiple sclerosis.

6. The method of claim 1, wherein treating said relapsing-remitting multiple sclerosis comprises treating a subject experiencing an acute neurological attack involved with multiple sclerosis.

7. The method of claim 6, wherein said acute neurological attack comprises a clinical representation selected from unilateral loss of vision, vertigo, ataxia, incoordination, gait difficulties, sensory impairment characterized by paresthesia, dysesthesia, sensory loss, urinary disturbances until incontinence, diplopia, dysarthria, motor weakness, paralysis, cognitive decline and any combination thereof.

8. The method of claim 7, wherein said treating comprises ameliorating, alleviating, lessening and/or removing said clinical representation.

9. The method of claim 1, wherein said treating comprises suppressing an activity of a typical RRMS course in the subject.

10. The method of claim 1, wherein said therapeutically effective amount is an amount equivalent to a range of from about 3-30 mg/kg/day in mice.

* * * * *

SEQUENCE LISTING

```
<160> NUMBER OF SEQ ID NOS: 74

<210> SEQ ID NO 1
<211> LENGTH: 296
<212> TYPE: DNA
<213> ORGANISM: Artificial sequence
<220> FEATURE:
<223> OTHER INFORMATION: Affymetrix ProbSet target nucleotide sequence

<400> SEQUENCE: 1

gatgaccaga tcatcaactg gctgctagaa ttccgttctt ctgtcatgta cttgacaaaa      60

gactttgagc aacttatcag tattatattg agattgcctt ggttgaatag aagtcaaaca     120

gtagtggaag agtatttggc ttttcttggt aatcttgtat cagcatagac tgttttcctc     180

agaccgtgtc tcagcatgat tgcttcccat tttgtgcctc cccgagtgat cattaaggaa     240

ggcgatgtag atgtttcaga ttctgatgat gaagatgata atcttcctgc aaattt         296

<210> SEQ ID NO 2
<211> LENGTH: 476
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (58)..(58)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t

<400> SEQUENCE: 2

tttccttcaa cttgtggatg caggcaaggt ggatgatgcc agagctctcc tacagagnat      60

gtggtgcnaa ttgctgaaca aaccccgatt ttgttgttgt tcctccttag gaattctagg     120

aaacaaggaa aggcatcaac tgtgaaatct gtgttagaat tgattcctga attaaatgaa     180

aaggaagaag catacaattc cctcatgaaa agctatgtct cagagaaaga tgtcacatct     240

gctaaagcac tgtatgaaca tttgactgca aagaatacaa aattggatga tctgtttcta     300

aagcgttacg catctttgct gaagtatgct ggagagcctg tccctttcat tgaaccccct     360

gaaagctttg aattttatgc acagcagcta agaaaattga gggaaaactc ttcttgaaat     420

aaccaggcga tactttgttt tgtatatatt tgtgattctg tgtctacatg ttattt         476

<210> SEQ ID NO 3
<211> LENGTH: 533
<212> TYPE: DNA
<213> ORGANISM: Artificial sequence
```

<220> FEATURE:
<223> OTHER INFORMATION: Affymetrix ProbSet target nucleotide sequence

<400> SEQUENCE: 3
aggcttagca ggatgggcgc agtggctcac gccactaatc ccaacatttt aggaggccta 60
ggcaggagca atcacttgtg cctgggagtt ctagactagc ctgggcgaga cttcatctct 120
acaaaaaaag caacaacgac aaaaaaaatt agccaagcat agtggcacac ccctgtagtc 180
ccagctactt gggaggctga ggtgggagga ttgcttgaac ccaagaggtc gaggctgcag 240
tgagccaaga ttgtgccact gcactccagc ctgggtgaca gagcaggacc ctgtctctat 300
tttataaatt aaaaaaggct gggtgtggtg gctcacaccc ataatcccaa cactttggct 360
cagcagattg cttgaaccca ggaattcaag tccaatctgg gcaacatggg gaaaccccag 420
ctctacaaaa aaaattagcc tggtgtggtg gcacatgcct gtagttccag ctactcagga 480
ggctgaggtg ggagaatctc ctgagcctgg aaggtccagg cagtgagcca aga 533

<210> SEQ ID NO 4
<211> LENGTH: 411
<212> TYPE: DNA
<213> ORGANISM: Artificial sequence
<220> FEATURE:
<223> OTHER INFORMATION: Affymetrix ProbSet target nucleotide sequence

<400> SEQUENCE: 4
ccaggcatat gacatggatc cccctgggga accaggctga tctctttcca gagggcacta 60
tccgaccagt gcatgatgat atcctcatcg ctcagctgcg gcctggccaa gaaattgacc 120
tgctcatgca ctgtgtcaag ggcattggca aagatcatgc caagttttca ccagtggcaa 180
cagccagtta caggctcctg ccagacatca ccctgcttga gcccgtggaa ggggaggcag 240
ctgaggagtt gagcaggtgc ttctcacctg gtgttattga ggtgcaggaa gtccaaggta 300
aaaaggtggc cagagttgcc aacccccggc tggatacctt cagcagagaa atcttccgga 360
atgagaagct aaagaaggtt gtgaggcttg cccgggttcg agatcattat a 411

<210> SEQ ID NO 5
<211> LENGTH: 441
<212> TYPE: DNA
<213> ORGANISM: Artificial sequence
<220> FEATURE:
<223> OTHER INFORMATION: Affymetrix ProbSet target nucleotide sequence

<400> SEQUENCE: 5
gcacgaggaa gaccataccc taggaaattc tctacgttac atgatcatga agaacccgga 60
agtggaattt tgtggttaca ctacgaccca tccttcagag agcaaaatta atttacgcat 120
tcagactcga ggtacccttc cagctgttga gccatttcag agaggcctga atgagctcat 180
gaatgtctgc caacatgtgc ttgacaagtt tgaggccagc ataaaggact ataaggatca 240
aaaagcaagc agaaatgaat ccacattcta gtcctttatg cagtatacaa ggagaactgt 300
cctgtaggat attctcttcc tgatggtgca gaacccagaa ttagaagttt gtggttacag 360
catactctgt ccttcagaaa ggcgtgattc tagctgttga ccccttgcag ctgttggaat 420
ctctgcaaga acctctgtat t 441

<210> SEQ ID NO 6
<211> LENGTH: 528
<212> TYPE: DNA
<213> ORGANISM: Artificial sequence
<220> FEATURE:
<223> OTHER INFORMATION: Affymetrix ProbSet target nucleotide sequence

<400> SEQUENCE: 6
ggtttggttt tgtagacttc aacagtgagg aggatgccaa ggaggccatg gaagacggtg 60
aaattgatgg aaataaagtt accttggact gggccaaacc taagggtgaa ggtggcttcg 120
ggggtcgtgg tggaggcaga ggcggctttg gaggacgagg tggtggtaga ggaggccgag 180
gaggatttgg tggcagaggc cggggaggct ttggagggcg aggaggcttc cgaggaggca 240
gaggaggagg aggtgaccac aagccacaag gaaagaagac gaagtttgaa tagcttctgt 300
ccctctgctt tccctttcc atttgaaaga aaggactctg gggtttttac tgttacctga 360
tcaatgacag agccttctga ggacattcca agacagtata cagtcctgtg gtctccttgg 420
aaatccgtct agttaacatt tcaagggcaa taccgtgttg gttttgactg gatattcata 480
taaacttttt aaagagttga gtgatagagc taacccttat ctgtaagt 528

<210> SEQ ID NO 7
<211> LENGTH: 488
<212> TYPE: DNA
<213> ORGANISM: Artificial sequence
<220> FEATURE:
<223> OTHER INFORMATION: Affymetrix ProbSet target nucleotide sequence

<400> SEQUENCE: 7
aagagtcccc atcaagactt cttccctgag tcaagtacag cgtagcatag tcctccaccc 60
acccaacctc tctgcctggc cagggtcctg gccctgccac tgtgtggcga ggtgtccttc 120
tagaccacat cagccccaag gctgggagca gtcgctccag ggccgcagca gttcactccc 180
acacatagaa cccaggtcac tgctggggcg attgaacagg ttgcctggct tttctctgct 240
gtcagtttgg tgtggaggcc tatgttctgc cccatacacc ccacaggccc tgcttatggg 300
aaggaacaca ggcctccagc ccagaggact gtgccgccct gttcttggcc gtccacgttt 360
cctctccctc tagcaccagc aatacatttc cctggcatgg acagaaaaga cagagaggac 420
ttgtacaaag gctttgtaaa accagaggct agcttctatc tttgtctact gttatttcag 480
ctcagggc 488

<210> SEQ ID NO 8
<211> LENGTH: 566
<212> TYPE: DNA
<213> ORGANISM: Artificial sequence
<220> FEATURE:
<223> OTHER INFORMATION: Affymetrix ProbSet target nucleotide sequence

<400> SEQUENCE: 8
gtggccgccg gcagtgaaga agatcacaaa ctgggcaccc tgtccctccc gctgcctcca 60
gcccagacct cagaccgcct ggcaaagcgg aggaagatta cctagacgca tgctttccag 120
acagggcgtt ttggctgcat cacagccact ggctggtcct attcatttcc atttttatgt 180
atgttttgaa aagaaaaggt ccggggatgg tggctcacac ctgaaatccc agcactttgg 240
gaggccgagg caggaagatc attgagctca ggagtttgaa accagtctgg acaacatggg 300
gagaccccat ctctaccgga ggaaaaaaaa aagagtcagg cctggtggtg tgcgcctgta 360
atcccagcta ctcgggaggc tgaggcagga cgattacttg agcttgggaa atcaaggttg 420
cagtgagcta tgattgtgtg gccacactcc atcctgggtc acagagtgag accttgtctc 480
aaaaaagtaa cataaggaaa aaagaagcct tgctttagca caggtatgaa gccagaagcc 540

-continued

```
agcatctcaa ctgtgcttgt cttatg                                          566


<210> SEQ ID NO 9
<211> LENGTH: 459
<212> TYPE: DNA
<213> ORGANISM: Artificial sequence
<220> FEATURE:
<223> OTHER INFORMATION: Affymetrix ProbSet target nucleotide sequence

<400> SEQUENCE: 9

gggaacatca acggtggaaa tcacttggga tgagactgat catgaaagaa ttacaatgct      60

caacaggaag tttaaaaagg aagagctttt ggacatggat tttcaagcct acttagcttc     120

ctctagtgaa gacgaagagg agatagaaga ggagctacaa ggtgatgatg gagtcaatgt     180

agaagaagat gggaaaacaa agaaaagtca gaaggatgat gaagagcaaa ttgctaaata     240

caggcagctc ttgcaggtta ttcaagaaaa agaaaagaaa ggcaaagaaa atgatatgga     300

aatggaaatt aaatgggttc caggtcttaa agaaagtgca gaagagatgg tcaaaaacaa     360

attggaagga aaggataaac tgaccccttg ggaacaattt ttagaaaaga agaaagagaa     420

aaaaagactg aaaaggaaac agaaggctct tgctgaaga                            459


<210> SEQ ID NO 10
<211> LENGTH: 387
<212> TYPE: DNA
<213> ORGANISM: Artificial sequence
<220> FEATURE:
<223> OTHER INFORMATION: Affymetrix ProbSet target nucleotide sequence

<400> SEQUENCE: 10

gagtcttaga ttttgccgga tgcactaaga atataactgc ttggaaatac ttggcaaaat      60

atctgaaaaa tatcttaatg ggaaaccacc ttgcgtgggt tcaagaagag tggaactcca     120

ggaaaaactg gtggccaggg tttcatttca gctacttttg ggcaaaaagt gattggaagg     180

aagatacagc tttggcctgt gagaaagctt ttgtggctgg tttactgtta ggaaaaggtt     240

gtagatattt ccggtatatt ttaaagcaag atcaccaaat cttagggaag aaaattaagc     300

ggatgaagag atctgtgaaa aaatacagta ttgtaaatcc aagactctga tactgaattt     360

tagttatttc acagttgtag ctacaca                                         387


<210> SEQ ID NO 11
<211> LENGTH: 530
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t
<220> FEATURE:
<221> NAME/KEY: misc_feature
<222> LOCATION: (452)..(455)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
```

<400> SEQUENCE: 11
gaaagtgaga cgacattgag aaaatgaaat agaaactttc tgganaaata ttttaatagt 60
gataataaca tcagatttta atataacatt ccagagaatt gtggaaaata ctgcatatat 120
atgtatagac tctgacacat atttacatat atatcaagtg tgcttagaaa aatgtatatt 180
gtaaagcagg tgagcttcat ttgattttat ttttcagagt atgaacattc taagagaaag 240
ttaaaacaat agcaaattgt ataattgtat ccagaaatgt atactcatcn tattttaaag 300
ctaaatttat tttttaaact agatcccttc attattcttt atgccccaga gtaaatccca 360
gatggatcaa agatctaaac ataatctttc atatgtaaaa atataaaagt attagtagaa 420
aacanatatg aatgctttga tgatcttgga annnnaangt caatttttgc agcatatggt 480
ggacaaagga gataatttct ttaatgtatc aatagctctt gcaaagcaaa 530

<210> SEQ ID NO 12
<211> LENGTH: 407
<212> TYPE: DNA
<213> ORGANISM: Artificial sequence
<220> FEATURE:
<223> OTHER INFORMATION: Affymetrix ProbSet target nucleotide sequence
<220> FEATURE:
<221> NAME/KEY: misc_feature
<222> LOCATION: (52)..(54)
<223> OTHER INFORMATION: n is a, c, g, or t
<220> FEATURE:
<221> NAME/KEY: misc_feature
<222> LOCATION: (57)..(59)
<223> OTHER INFORMATION: n is a, c, g, or t

<400> SEQUENCE: 12
ccctcccagg agttgactcc ggatgcatgc gcccagggcg tcccatcaga gnnncgnnng 60
atgctccgtg actacatggc caagctacca ccccagaggg acaccccagg ctgtgccacc 120
acacctcccc actcccaggc ctccagcgtc cgggccactc gctcccagca gcacacaccc 180
gtcctctcta gctctcagcc cctccggaag aagcctcgaa tgggcttctg aggacacaag 240
gtgggctgcc ctcaagcccc agagagcccc tcatccttcc tctgggacca gatgtgcctt 300
ccacagttga aacttgagaa gcagagctcg ccaccttctg gaggccactg tgatgatgag 360
ccaagcaatt tggagccaag ttgaagggac agggcaacaa aatacag 407

<210> SEQ ID NO 13
<211> LENGTH: 427
<212> TYPE: DNA
<213> ORGANISM: Artificial sequence
<220> FEATURE:
<223> OTHER INFORMATION: Affymetrix ProbSet target nucleotide sequence

<400> SEQUENCE: 13
gtatgggtca tttcaaagag ggcttatgag gctgtgaaac ccagagctct taacgctgtg 60
accaaagatg gaagttctct ataggaagcc atagcactcc taatgtttgg tgctatgttt 120
tcctgaggag atataaaacg taataatcca tgattgttgc catgtgagag ttttaaaggt 180
taatcaaaat ttctcttctt cagggcaaac ttgaagataa atcttttgac tccagctctt 240
tagaggatct aaagtgacct tgatggacag tggaagaaat cacaacatgg aattcctcga 300
ataacaattt attgacttta aataattttg tctaatgcta catatacaca attaaaaaac 360
ctttacacta tttctagaaa gtcagcatgt atttttggct cgaagtttct ctagtgtttt 420
ctgtgga 427

<210> SEQ ID NO 14
<211> LENGTH: 413
<212> TYPE: DNA
<213> ORGANISM: Artificial sequence
<220> FEATURE:
<223> OTHER INFORMATION: Affymetrix ProbSet target nucleotide sequence

<400> SEQUENCE: 14
ggagcactac aaaaagctgg ccgaggagca gcaaaagcag tacaaggtgc acctggacct 60
ctgggttaag agcctgtctc cccaggaccg tgcagcatat aaagagtaca tctccaataa 120
acgtaagagc atgaccaagc tgcgaggccc aaaccccaaa tccagccgga ctactctgca 180
gtccaagtcg gagtccgagg aggatgatga agaggatgag gatgacgagg acgaggatga 240
agaagaggaa gatgatgaga atggggactc ctctgaagat ggcggcgact cctctgagtc 300
cagcagcgag gacgagagcg aggatgggga tgagaatgaa gaggatgacg aggacgaaga 360
cgacgacgag gatgacgatg aggatgaaga taatgagtcc gagggcagca gct 413

<210> SEQ ID NO 15
<211> LENGTH: 514
<212> TYPE: DNA
<213> ORGANISM: Artificial sequence
<220> FEATURE:
<223> OTHER INFORMATION: Affymetrix ProbSet target nucleotide sequence

<400> SEQUENCE: 15
gcaggtgtta cagttgtcct tgtggataaa gaaaatatta acaacacacc aaagcatttt 60
agaaaggatg ttgatgttgt ttgtgttgat atgagcatag aacagaagtt accaagaaag 120
cctaaaacag acaaatttca ggtacttgct aagtcacatg cacataaatc agaagccctg 180
cacagtaaag ttagggagaa aaagaataaa aagcatcaga ggaaagctgc atcctgggag 240
agccagcggg caagggacac cctgcctcag tcagaatccc accaggagga gtcctggctt 300
tctgtgggtc cagggggtga aattacagaa ctaccagcat ctgctcataa aaacaagtct 360
aagaaaaaaa agaaaaagtc cagtaaccgg gaatatgaga cactggccat gcctgaagga 420
tcgcaagcag gcagagaggc cgggactgat atgcaggaat cccagcctac tgtgggcttg 480
gatgatgaaa ctccacaact actaggacct actc 514

<210> SEQ ID NO 16
<211> LENGTH: 529
<212> TYPE: DNA
<213> ORGANISM: Artificial sequence
<220> FEATURE:
<223> OTHER INFORMATION: Affymetrix ProbSet target nucleotide sequence

<400> SEQUENCE: 16
ccccgcttgg acacagtccg agtggaatgg gaagggaatg gtcaatccct gtcctggttg 60
tccaagtcgg gatctcagag gaaattgcag tgattccacg gttaggcccc cctgggggggg 120 ctgccttccc ctcagcctct ccccacacca cccacccagc tgctgtcatt ccgctcactg 180
agctcttctt cattctcacc ctgatccctg ggggactcaa agccaaaact gcccaaagag 240
gaaagattga atcctaaagg ggatccttgc ccccatggga ggccccctac tagaaggacg 300
tgaaagcagc ttttggggga aactgaggca gtggggaaga cagagcagaa tgagccctca 360
ccctggctgg gggtccagca caggctgtat ctgcagaggg tcccagagga acgctggagc 420
caagagaagc cctgggaagg aggggtgggg aacgacatgc atgtgaggga tggcacactg 480
atgtgtttat gcacctgtac acaggagcgc atggccatgg ctttggaaa 529

<210> SEQ ID NO 17
<211> LENGTH: 481
<212> TYPE: DNA
<213> ORGANISM: Artificial sequence
<220> FEATURE:
<223> OTHER INFORMATION: Affymetrix ProbSet target nucleotide sequence

<400> SEQUENCE: 17
atggggtttc agatctttgt gacgaaatag aatactgttt catatttgaa tcagagggct 60
tcttgttctg agaaataggt tcaaaatcat tggaaccagg aacaagaata gcttattgtt 120
atctgtgata acactgtttt ctaaacacaa ggattttctt ttttattaat atgcaacata 180
gacattgcca taacagaata ataaaccaca tgtggggttt taaaaatgaa atttggctaa 240
taggagcaat tcagctattt ttctatacag taattggtgt gtggtataga agaaaaacgg 300
gttcaaaccc cacttctgcc acctaccagc tatatggcct tgaatgagtc attcagcttt 360
aataaggttc attttcttct gtttaaaaag acacaaaact tgaaaatcag ctttggccat 420
ctacctgaga attagaaagt ctgatttttg gaattagaaa tcatgattgt aggctgggca 480
c 481

<210> SEQ ID NO 18
<211> LENGTH: 202004
<212> TYPE: DNA
<213> ORGANISM: Homo sapiens

<400> SEQUENCE: 18
aagcttgcag taagccgaga tcgcgccact gcactccagc ctgggtgaca gagggagact 60
ccatctcaaa aaaaaaagag agaaagtaaa ggaataaaag aatggctacc ccatagacgg 120
agcagccgtg agggctgctg gttgcccatt tttatggtta tttgttgatg atatgctaaa 180
caaggagtgg atttttcatg cctcctcttt ttagaccata tagggtaact tcttgatgtt 240
gccgtggcat ttgtaaactg tcatggtgct ggtaggagtg tagcagggag gatgatggga 300
ggtcagtctt gtctctattt tggttttggt gggttttggc cagctccttc actgcaacct 360
gttttatcag caaggtcttt atgactggta ttttgtgctg accttctatg tcatcctgtg 420
acttagaatg ccttaaccat cagggaatgc agcccagtag tttcagcctc atttttcccg 480
gctcctattt aagatggagt tgctctggtt cacacacctc tgacatgatc attgcccact 540
gcggcttcca cctcccgggt tcaagagatc ctcctgcctc accctcccaa ggtgctggga 600
ctacaggtgt gtgccaccag ctcagctaat ttttgtattt tttgtagaga tggtgttttt 660
ccatgttgcc caggctggtc tcaaactcct gggctcaagc aatccttctg tctcagcctc 720
ccaaagtact gggattacag gcatgtccca ccatgcccag actaatattt acttttaatc 780
agactaagat agggttacta cttgagttgc tatggctcca gctgaaagaa agcccgtgca 840
gtcatatcac gcgtaaacat ttgctttatg ctaaaaatat ggtggacctg gcattacagc 900
tattacaaat ctcctaagat gtctcgggta gtgtattagt tacttttcat actgctatga 960
agaaatactg gaaactgggt aatttataaa gaaaaagagg tttaatgtac tcacagttcc 1020
acaaggctgg agaggcctca gaatcatggt ggaaggcaaa gaaggagcaa aaaggtatgt 1080
cttccatggc agcaggcaag agagcacgtg cagggaaact gccctttata aaaccatcag 1140
atttagtgag atgtattcac tatcacgaga acagtatggg aaaaacctgc ccccatgatt 1200
cgattacctc ctaccgggtc cctcccacga cacatgggga ttatgggaac tacaattcaa 1260

-continued

```
gatgaaattt gggtggggac gcagccaaac catatcgggt agcaacaacc tagggtcagt   1320
tttgcaggtg gtaaagccat ttaccaagat agttgtgggt aaagaagggc agatttatta   1380
gagaaattgt gaaaatatgt tgcagtgggc agctcagcag agaaggggct acctgcaaag   1440
aggcaagggc tggaggaaag ttttataggg tcctgctgaa gggtgctacg tgtggaatga   1500
ggtcattgtg cccgcaggtt gtttgtgatt agctgtctct aacaattgtt catacaataa   1560
ttgttcatta ttgttctcaa cttggggctc tccccaacct ggggaccctt ccttattgtt   1620
gcttacttat caggtctcca cataaaggtg tggaaacttc attcattcat atcttcaaca   1680
caaattgtag gtagcctgtt ttttaaaaca tttattcaac aaatatttag tccaagccac   1740
tattacttac taccttctct actattgtat ggacttttaa ctatctctga cactattcac   1800
tattcttcca cattctctat tatttatacc tatggtaaaa tttgccagtt tgaccataca   1860
actaatactc acagggaata tatagagtct agaagaaaat atacaggtcc ttaaaggctg   1920
ccctgccaac aaaaccataa cgcaggaaca aacatcacaa ctatgccaaa taatcaatcc   1980
tacaatgtcc aaaatttttac tttaaaactg gaattaccag acttcctttc tgcattaacc   2040
agtttaacta gacagtaacg aaatattcct actttatgct gtgatagttt gtttgtttgt   2100
ttgtttgttt atttatttat ttatttattt aagacagagt ttcgctcttg ttgcccaggc   2160
tggagtgcag tggcacgatc tcagctcacc acaacctccg cctcccaggt tcaagcgatt   2220
ctcctgcctc agcctcccga gtagctggga ttacaggcat gtaccaccac gcccgggtaa   2280
ttttgtattt ttagtagaga cggggggttt ctccatgttg gtcaggctgg tctagaactc   2340
cagacctcag gtgatacccc tgcctcagcc tcccaatgtg ctgggattac agctgtgaag   2400
ccaccgcgcc cggctgctgt gatagttgag atgtaaacca aaaataaaat tctaagccac   2460
ccaatccgac tgaatggacc cttcctgttg agcaaggaca ttccaaagta aactgaaaag   2520
accagcttag gccatgatgg gaaggggagg tgtcaacatg cctcattcta ccttcctccc   2580
tctggaatcc agacacaact gaccagcatt aacattaaaa cagagatctt aagctgggca   2640
cagtggctca tgcctgtaat cccagcactt tgggaggcca aggtgggatc acctgaggtc   2700
agaagttcaa gaccagcctg gccagtatgg tgaagccatg tctctactaa aaatacaaaa   2760
ttagccggac attgtggtgc acgtctgtca tcccagcaag gcaggcgaat cacttgaacc   2820
caggaagcag aggttgcagt gagccaggat catgccattg cactccagcc tggtcaacag   2880
agcgagactc cgcctcatta aaaaaaaaaa aaaaaaaaaa ttagccgggc gtggtggcgg   2940
gcacatgtag tcccagctac tagggaggct gaggcaggag aatggtgtga accagggagg   3000
cggagcttgc agtgagccga gattgtgcca ctgcactcca gcctggacag aagtgcattt   3060
cataatgcat tttaattgca ttagcagtga tttaattttt ttagatgcta aaacttatgg   3120
gtgaaagtgg attaaatgta gccaaatgca acatcaaaat cttcaggcac aaaaacccat   3180
taactttttc atactctcag aaggtgaacc taatttcaaa tgaaagctgc ctccagaata   3240
tattgttaag cgtattctag atataattca ttttggcaaa catactgtag aaattcacat   3300
aacattttac tgtactaaaa gtaaattgcc catgtaacaa aaaatatctt ttcagagctt   3360
gaaatgaatt ttaaaggatg actgatggtc cctggaagag aaacagtaaa caaataaggt   3420
ttgtagcaat gatgtatgag ttagaaattg cagttccaga tgatctcttt attaaagaga   3480
cgatctacac ttaatttgat caagtgttat gaacatagtt catgttaagt ctccatttaa   3540
atacaacctg aaataccaaa gttaattttc ttttctttct ttcttttttt tttttttag   3600
aaggagtctt gctctgttgc ccttcctgga gtgcagtgac gtgatcttgg ctcactgcaa   3660
```

-continued

```
cctccacctc ctgggcttga gcgatcctac tgcctcagcc ccccaagtag ctgggaggac   3720
aggcgcaagc cacggcactc agctaatttt tgtatttttc gtagagatag ggtttcacca   3780
tgttgcccaa tttggtctcg aactcctgag ctcaagtgat ccgcccgcct tggcctccca   3840
aagtgctggg attacaggca tgagccaccg tgcctggcca gaaaattgta aacacacaca   3900
aactctcaag tggcctaatt ccctctcacc aaaccaatca caatacagat aaaagagaat   3960
aacttgtgtt catttttgta caaacaaaaa agatataaat tgtgaatgat gcatgatttt   4020
taattacaag taaactgggc aaatgcttct gcattattta aagctaaaag gtgatcagtg   4080
gaaactttcc tctgttagta ctctaatact tttatattt atcggctcac tacaacctgt   4140
gcctaccagg ttcaagcgat tctcctgtct cagccacctg agtagccgag accacaggca   4200
cgcactacca tgtccggcta attttgtatt tttaatagag acagggtttc accgtgttgg   4260
ccatgctggt cttgaactcc tgacctcaac cgatccgcct gccttggcct cccaaagttc   4320
tgggattaca agcgtgagcc acagcgccca gccttattat aattgttact atttaaatct   4380
cttttgctct ctccttcaag agagacctca tcccattcag ttgcttccat ttatttattc   4440
atcttctgcc tcctgggctc gagagatcct ccagcgtgag tctcccaagt agctgggact   4500
acaggctcac accaccaagc ttggctaaat tttgtaggtt ttggagagac aggctcttgc   4560
cacgttgcct aggctggtct caaactcctg ggctcagatg atccacctgc cttcgcctcc   4620
caaagcactg ggacatgagc caccacgccc agccgcaagt acttttacac aaaatgcaaa   4680
caccattctt ccatcataaa agtgatacca cagcttccgt gaagttttgc caggtagtac   4740
tcataattac cttgggtaaa ctttttgatg ttaaactgta tcttcttatt acgagttttt   4800
ccattgtatt aactgctttt acaacaacac aaataacaag ttattttaca aaccatttag   4860
aaatttctgt actatggtcc cagtaatgta aaatatatta atgcctatta cattcagata   4920
aattatacac ttggaaacca catacttatg acttacagaa acttacataa acaaattata   4980
gaaattacat gctcaatttt taggtatata gtcttaaatt aagcttaaat atacattctc   5040
aagataaatt aacagttcag ggcttcacaa cttgaaatct gtggaagatg acattggaga   5100
caacagaact ctggtggaat tcttagatgg aatttgccga aacttttttt tttttttttt   5160
tttgagatgg agtgtcgctc tgtcgcccag gctggagtgc agtggcgcaa tctcagctca   5220
ctgcaagctc tgcctcccgg gttcacgcca ttcttctgcc tcagcctccc gagtagctgg   5280
gactacaggc gcccaccgcc acgcccggct aattttttat atttttagta gagatggggt   5340
tttactatgt tagccaggat ggtctcgatc tcttgacctt gtgatctacc cgccttggcc   5400
tcccaaagtg aaacttttct ttaaaataga gatgggatct tgctgtattg cccaggctgg   5460
tctcagactc cttgccttaa gcagtcctcc cacctcagcc tcctaaagtg ctgggattac   5520
aagcgtgaag cattacatcc aagtgaaact tcttgagatg gttacataat gtctaaatct   5580
gctggtgtag aagttaataa agtgtagaac tgaataacta ttaaatatta gatcaagttt   5640
ctcatgttta tcttaacgta taacgattta tcttaaagca ctgattttca caaaataaca   5700
tcagtgtgaa attggaaaag aagccaaata ttttatttca cgtatctggg aaatgaggtg   5760
ctttagtcaa ctgaatctgc ccaaaactaa aaagcattaa ttaaaaagta cttaactcag   5820
aaattataaa aataggagac atcaataaaa tacattctac acagaatacg ccaaccatac   5880
actactcttt tttgataata aaaaatgtat ttactgagcc agttgtggtg gctcacgcct   5940
ataatcccag caccttggaa ggccaatgag agtggatcag ttgaggccag gagtttgaga   6000
```

ccagcctggc caacatggtg aaatgccgtc tctactaaga atacaaaaat gagccgggca 6060
cggtggcacg cacctgtaat cccaggtact ccgaaggatg aggcaggata attgtttgaa 6120
ctcaggaggt ggaggttgca gtgagccaaa atcatgccac tgcactccag cctgggtgac 6180
agagtgagtc tctgtctcaa aaaaaaaaaa aaaaaaaaag aaaaaaagtc agttgcagtg 6240
gctcacgcct gtaatcccag cactttggga ggctgaggca ggcggattac aaggtcagga 6300
gatcgagacc accctggcca acatggtgaa acctcctctc tactaaaaat gcaaaaatta 6360
ggctgggcac ggtggctcac acctgtaatc ccagcacttt gggaggccga ggcgcggaga 6420
tcacgaggtc aggagattga gaccatcctg gctaacacag tgaaaccctg tctctactaa 6480
aaatacaaaa aattagctgg atgtggtggc agcacttgta gtcccagcta cttgggtggc 6540
tgaggcagga gaatggcgtg aacccgggag gcagagtttg cagtgagccg agatcccacc 6600
actgcactcc agcttaggcg acagagccag actgtgtctc aaaaacagga aagaaaacaa 6660
aagaaaattt ggactattgc caattacaaa tatttttaga gaagaattca aaacagtaac 6720
tgtggatgat ggaaacaata gttatgataa aagtctgatg aaacttccca gttcacaagg 6780
aaatttaatt acttatgtgc agcattttaa gacagtaatc agaatcatga ctgacagcat 6840
catatcaggg ccagcagact tttataaatt tcatacaatc ttcagaaata ataacttttt 6900
ttttttttt tggatagatt ctacctttgt cacccaggcg ggagtgcagt ggcatgatct 6960
cggctcacta caacctccgc atcctgggtt caagcagttc tcctgtctca gcctcccgag 7020
tagctgagat tacaggcatg tgccaccagg catggctaat ttttgtattt ttagtggaga 7080
cagggtttca ctctattagg ctggtctgga actcccgacc tcaggtgatc cacgtgcctt 7140
tgtctcccaa agtgctggga ttacaggcat gagtgacagt gcccagccat tcgtgacatg 7200
tttatacaaa tataacttta gcaaatattt agcataacta tcaaaattac aaatcatatt 7260
aaatttgtat aaatgtatgc aattttcgga acacgcatat caacaacata cccataaata 7320
taactgagat gagatctaat gtcacctcac ttgacagtgc cctcccatgc agtatcgcca 7380
catttgacaa tgcctgccca tttaatctac caaataaatc gaatcactta atacctctac 7440
aagatgagag atacattctt tagactcccc aagggatgca gctgaaaaaa atcccaaagt 7500
tagttttaag ccaaaaagac ttgatttagg attttgacac tggagaaacc catcaaagat 7560
gtcaagtttg aaaacacttg atcaaaacag aatcacaggt cactattaaa agagtattaa 7620
tttaaccaga gacttccaaa gcaatacaga aacttacatg gatataaaaa ccctaaccct 7680
tttaaaggtc agatttgcta agtgatcaaa aggggtactt gaattgaatc gacacaggaa 7740
gagtgtgtac agggttatga gtgtaggcag gtggttactt tggtcatatc tccatttgcc 7800
acctgattac acatgagaat ggcatcttta ctcaccagaa agccagtatt ataggaggtg 7860
taggaggcat tcttggactt gagacaagaa cattgttgtg tagaaatttc attgactgtg 7920
ttaaaattat tctccatggg ctggagaaca cataacatgg cctttagaat gagacgggca 7980
ttgattggat gcaaggtctc cacacttact agctgtgtga cattggacag agtgcttcat 8040
cattccgaga ctcagttttt aaaggaaaaa caactaacta ccttgcaagc ttgctagcag 8100
gtttaagtgt aataatgtgt gggaatgact gcaccgtgac taacatgcag tgacagctta 8160
attaatgtta acccttatca ttatcatata agaatgtgag ttacataaga gaggagtcct 8220
gtcagttcgt tctctgctgt gtccccaaga ccatgaatca tggctggcat gtagtaggca 8280
tttaataata tatgttcaac aagtatttgg cagtcttgga gggcagaaaa ggaggtgggg 8340
aagattttta aataacattc tttaaaaagt cacattgtcc tacaataccg atttttcttg 8400

-continued

```
catatttagg aaattgaggg tttttttcta aaacatgcgg acatatggga aataggatgc   8460
aacatttgca ctaatgtttc agacacagtt agaggtttcc aagagatttt gcgctgggga   8520
ggctgcttgc tacaagctcc caaagctctg ggaggacata gtattcattc ctccctcagc   8580
agaagcggtg aggcaagaag ctctggggag cacccagcgt tggactttta gcatagtgtg   8640
tcaggtcttc atagtttggg cccagggcac agagaagtca cagctctccg gcatcctgtg   8700
acctttaccc tctttgccaa gggaaaatgt ggcccaccaa agcaagaaac ttgagggcat   8760
gggtcacccc agccctggca tctgcccaga gcccgagaag gaaggaacaa tgatcctcca   8820
gctacctcac ggggctggca caggtgacca ctgccctggc atcacccagc tgtgtccggc   8880
agcctgaacc ccatctgtgg ggatgcgagg aggaaaatac aaaagtcctt aggtgaacac   8940
tgagaaggca gatgcagcag aaacctccag gccagaacta cccagtcttg gacctatggt   9000
ggagatagag catagctggc gatcatgtgt acttacactc taaggtcacc tggttgcact   9060
atggcctcat ctgtggctct gaaaatgaag atttggaagg agatcatcac agctaatgtt   9120
taacaagccc ctcctgtgtg ccaaatcatt cacccctcac cacaaccgaa tgagctaagg   9180
attctcatta tatatagttt atggagaggg aagtgcagac ataaagaggt gaattatctt   9240
acccagatca cacagctgat aagtggtgga ggcagaatag aatctaaaca gtgtggctcc   9300
ggagcccaca tgcattgatt cgacaagtgt ttattgagca cctgccgcgg acaaggcctt   9360
gtgtgattaa atagggttat aattagtaat ataaaaatga gaaatcacta atgcttttta   9420
gacttaacat tttgtttttt tgtaggtttc aggcacagaa ctgtatatcc aataatagtg   9480
aaatggatcc cactaattat gacagaaatg atgatacatt taaatgactt ggatgtttta   9540
taggtatgat ctcgtgaaat cttgagagaa actgaatgac gaatgaaact attgttcctg   9600
tttcacacag aagaaaactg aggttaaaag gggtaaagta attttgcatg gcatgaagta   9660
gaaattcaaa gtacaggaat ttgaacttgg ttctgtcctt ttctgaagcc cttgaccact   9720
atagactcaa acatcacctt gtttttccac tcattcaaca cttttttttt taaattatct   9780
aataggttgg cactcatcat gagcccctgt tctcattctg caaatggtga agctctctat   9840
tgtcctgacc ccacagttcc tgtcccatga ccagggccag ctcaccaagg agctgcagca   9900
gcatgtaaag tcagtgacat gcccatgcga gtacctgagg aaggtgagtg agtgcagaca   9960
gatggggcct ggtgcccttg agcagttccc gggtctcagc tgccacacat ctcatagccg  10020
gtgatgctgg gggaagctta cgcagtcaca gtactggctt cttcctcttt ttctttccat  10080
acaagtggct tagggatggg gtagagtagt tgacttattt ggatgaaaac cactatcttc  10140
tgtcagaaac tcaaaaggaa tcattgctgg catggtaacc taaagaaaaa caaccagaca  10200
agtgcccaac gacacttaaa aaggtgattt attatcttgc caagtttagg ctgggcatgg  10260
tgactcatgc ctctaatccc agcattttgg gaggctgagg ctggtggatc accggaggcc  10320
aggactttga gaccagcctg accaatatgg caaaacctcg tccctactaa aaatacaaaa  10380
attagccggg catggtggtg tgagcctgta gtcccagcta ctcaggaggc tgagacagga  10440
gaattgctta gattcaggag gtgggggttt tagtgggccg agatcacgcc attgcactcc  10500
agactgtgcg acagagcgag actctgtcaa aaaaaaaaaa aaaaaattat cctgcaaaat  10560
ttgaaaagga aattcaaatc aacagcttct aaactacttt ttaacatgac tcataataat  10620
acattctata gtacatatgt atgttctata actttgaata aaagagttaa ccacatcaca  10680
tttattttat aacatgtaat acatattttt tattctcctt catttgtttt gaatgctctg  10740
```

-continued

```
tgcagtctac aaaaagtcca atagtaataa ttaaattagt cattaagttg aacattatct  10800
tgtcttttaa aatgataatc tcaaaaatga tcttttattt ttgagattta tatagataca  10860
cacacacaca cacacacaca cacacacaca cacacacaca cacacacaca catatttttt  10920
gagacagagt ttcactctgt cccccaggct ggagtgcaat ggcacaatct tggctcactg  10980
caacctctgt ctcccgggtt caagcaattc ctctgcctca gcctctgagt agctgggact  11040
acaggtgtgt gccaccatgc ccagctaatt tttgtattct tagtagagat ggggtttcac  11100
catattggcc aggctcgtgt caactcctga cctcgtgatc tgcccaccgc ggcctcccaa  11160
agtgctggga ctataggtgt gagccgctgc acccggtcca agtaaaatta ttttaacaat  11220
atactatgaa gagaaaaaca ctggctatga aagaatatgc atagttttac cctgtttaaa  11280
aataaagatt gaaagaatac atatgcaaat aagtttactt ttatttttgg taacacttta  11340
ctgcattgtc tgaatattga caatcagtat gcattatgaa gctacctggc taacattgtg  11400
tactcactgt gtgtgccagg ccctgggttc aatgctctac atgcacttat atttcattta  11460
attctctctg caacctgaga tggtatagcc acctcatttt acagagttga aactgaggct  11520
cagagactga aagttaagcc tgaggttgca gtcaataaga ggcagagctg gaactgaaac  11580
ctacctgtgt ctgaccacca gttcgtgttc tgacggcagg ctagtctgca tcacagagtg  11640
tggagtagat ggtgcatgcc tgctaggatg ggctaggtat cactgtaggt aagaaacagc  11700
cccaaactat ggaaatgtac accactgaag gctcttttcc tgcccatgct gcacatcctc  11760
catggctctc ctgtgccctg tgccccacat gccctcatcc tgccacgaga ataaaggagc  11820
agcctccata tgggagctgt cagctgctct aagagatgaa ggagagagtg gcccgtctca  11880
atggctccca actcttttgc ctcgaggtga cacgcttcac ttccacgcac atctcctggg  11940
tcaaagcaaa tcccatgggt acatccactt tcaagtggcc caggagagaa cctgaaatac  12000
tcggtggact ccattaaggc cgtcatatgg tgtcagcctg catgggagac tgtggagggg  12060
cagaggagga gagtggggaa ctgatgggaa atgacaggag gactaagtca ccgcagattt  12120
gctttatctt cagccaggtg gagtttgtcc cagagccgca caaaatcatc accagcatga  12180
ttaaacggag tagacttcag aaaaagcagt ttggtcggat gtaatcagca gtgaactcag  12240
aatcaattga gtgacattga gtcagtaaat ctctgactgc ctcagttacc ccatatgata  12300
gttttgagga tgggaacatt gagagagttg atttggaagg atatcaagag taaaaattcc  12360
aacattttta gttcctttaa gttaaatcca ggcactgtct ttcctgcaag tctcctgttc  12420
ctttcagatt gcacaggtga gagtgctcag attagggctg gaggttgtaa accattgctc  12480
ccacactgac agtgccccg tgtcgtgcgt gtattctgcg cattttcctg tgctaaacac  12540
tctcccaaaa catcgtgggg cctgattctt cctctttgtt ccaatggccc tgggtgactc  12600
aagtgcccat tcaatgacca ggacacagag gtcttagaga gatgctcctt gaggccccag  12660
gtgcgagcct gtaccctgcc ggagcatgag gcaagggaca gggcatcgtc tgtggggata  12720
gtgggggtag tgggggtagt ggtcagccag atttggtgac tctacttgct caccagacga  12780
tcctacacct gccacctccg atggatccac tgcctctgtg cctgcctgta ctgctgatgc  12840
tccagtggat aactcagcat cccagcctag gcccaatgcc actgaagatg gacctgcccc  12900
ctggggaccc aggagtccta ccactcagct gtccccagga gtgcccagac cctcattctt  12960
atccaggacc taggagccct acccctggcc ttccctcatc agccgtaaat gatgatttac  13020
tgctgttacc atcatcactg ccttcagtga ccaagggcct tccaaggtgc cagctctgga  13080
acgaaggatg cccttgggag gtgatgacac tcaggtacac gggtgctcaa cagattgctt  13140
```

cctcctatcc tcagacggtc tttgcatgca tgcagccatt ggcactccca ttgtgtggaa 13200
ggaaaccagc ccagggtcac acagctggtc agcagcaaca tagctggtct caaatctaag 13260
gtgcctgacc atgcctccat gagggaccgc ctccaaggga ggttgatcct ggctttgggg 13320
agcctttcct gggctgcacg aataacctcc attgttcgag accccaaact ctgctcacat 13380
cttcctttcc ctatctctgc ttgggctatg atcacggtga ctctagcagc ccttcatgga 13440
cattatagta ctctctgcca ttcacttttg ctctaatctg acttcaaccc ccacttactt 13500
ggtctctcct tttacaacca ccacaaccga aatctagggc tgcttttttt tttttttttt 13560
tttgagacag agtctcattc cattctgtca cccaggctgg agtgcaatgg tacgatctcg 13620
gctcactgca acctccgcct cccgggtcca agggattgtc ctgcctcagc ctcctgagta 13680
gctgggatta caggcgtgtg ccaccatgcc tggctaattt ttgtattttt agtagagacg 13740
gggtttcacc atgttggtca ggctggtctc gaactcctaa cctcgtgatc cgcctgcctc 13800
agcctcccaa agtgctggga ttacaggcgt gagccaccat gcccagccaa atctagggca 13860
ggaacatggc tgcagcatat aaaaagaatt gaattccata cttttgttaa ccctgttttt 13920
tgtttgtttg tagttgttgc tgtttttgag acagagtctc gctctgtcgc ctaggctgga 13980
gtgcagtggt gcaatctcgg ctcactgcag actctgcctc ccgggttcaa actattctcc 14040
tgcctcagcc tcccaagtag gtgggactac aggcgcccac caccacaccc ggctaatttt 14100
tgtattttat tagagacagg gtttcaccat attggccagg ctggtctgga actcctgacc 14160
ttgtgatccg cccacctcgg cctcccaaag tgctgggatt acaggcgtga gccaccacac 14220
ccagcccctg ttttgttttt gttttgcttg cttcttaggg ttgtttttct atttatggta 14280
aaggcattgg ctttccattt gtagcatcaa tagaatattt cctgtttaca ataaccttat 14340
gtcatagtaa atggtaaagg gatttaaagc agtggttttc agctgccaga ggcctgagag 14400
agtttgggca tactctgtgt gatcgggcag aaggcctgtg ggaagtttag cagaggacag 14460
ggccaggaaa ggtgatggac agtgggggtc tgtcctggtc accaggcccc tgggtcctgc 14520
ccacctgctt ggagctcccc acccatcaca catgatgctg ccaagccctc tgggtattgt 14580
gggcaaatac cttaggagag aagctgatga actttgtttc ttgaaatgca cagattcctt 14640
ggacgtccct gagagctcag tcatgaaagt caacttggtt ttctcccccct catttgggtt 14700
cagaatttaa agtccacaca cacaggcagt aagatgatat agataaggac gtcatcactc 14760
ggtttcggat gttaaaatgt ctaggtgggt tagcggtgat ttgagatcac acaaccttgt 14820
gccacaaaga ggaattccca ggccagaggg agacatttta ttgccatgtt atgatctcat 14880
cattgagttg aaaggcaatc ttgtttcatt ttggattctt tcttatgttt atgtcttata 14940
agggcacttt gaatttccaa gcaaataata attttgaatt agcttttaat cattgacttc 15000
tagcacagtt atatgatcag aaacatgctg tgtgatttga ttgctctcaa atatattgag 15060
atttgctgga acaaaataag tcaggttaat ttttgtaaat gtaccaggca tgcttaaaat 15120
gaatgtatct acatttgttc ccgagataca ggttgatgga cggatggcta catggatgtg 15180
atggagatgg tttactatcg ggaccttccg caccctgctg atgttttgtt gcttaggata 15240
tgaatggctg agcggaggct gtaaaacctg gcactctgct tgggtatgag gttcttcctg 15300
ccatcctgcc atcatttgtt ttttatgttt tgtcgccata agtgaccttg aggaaccctg 15360
ggagctcagg aaggaaggag cgcccagaag cagggacagg gagctggttg gggaggacca 15420
gaaatcaggt ttgtgaaggt tccagagagg acctgtcttt gggaggagtg tgggagactg 15480 agatgggggga ggggtcattg gaatgatgcg ggcgctactt ggcattgtcc attgtgaggc 15540
actgtccatt gtgaggcacc accggggtca tcagggattg gtggagaggg agtataaagc 15600
cccagggttg gtaagggagg gcccagaccg aagaaggttt ggtggatagc agaacctttt 15660
tgtctccctc tgattgctcc taagcctcac gctcccttgc cccgcgtgtc ctgttgcttc 15720
cctgatcttc tccgtgacct gtagctaaac cttccaccag cgcttgagaa cttaatttga 15780
accggatcct ttcccagacc cctttcttct tctcctcctc ctcctccacc tcctccaggt 15840
gcccaacagc cccccttctcc tcctttccct tcccttactt ccccccttcc cctcccccttc 15900
ccctccccct cccctccccc tcccctcccc ctcccctccc caactcagat ccggccccgg 15960
tccccgtccc cttccctccc ccctgcccta agccacctcc acctctgtcc tggccgcctc 16020
agggcgccct gaaaggacca ggacatgcgg gtgcggtgga tgctcttttg gctcctcttt 16080
gggctcctac tggaatttat cagccatcag tgcatctctg tgagtagacg ctggacccgt 16140
ggggtttctt cctttttact gggctgtatc acgtggcatg aaattacaca gctcaggcct 16200
gtaatcccag cactttaggg ggccgaggtg ggcagatcac ttgagtccag gagttgaaga 16260
ctagccaggg catcatagcg aaaccccatc tctacaaaaa attccaataa agattagtcg 16320
ggcctggtgg tgcgtacctg ttatcccagt tactggagag gctgaggtgg gaggatcgct 16380
tgggcccagg agctggacgt tgcagtgagc cgagatggcc ccgctgcact cttgttttta 16440
acaaagaaaa tggaccaaaa caaagtgaaa tgtcatttga tttgtgtcat ctggtttgat 16500
gacttttttt tttttttttt tttttttaga cagagtctca ctctgtcgcc caggctggag 16560
tgcagtggca agatctcggc tcactgcaac ctccgcttct ggggttcaag caattgtcct 16620
gcctcagcct cctgagtagc tcagattaca acgcctggct aatttttgta tttttagtag 16680
accaccacgc ctggctaatt tttgtgtttt tagtagagat ggggtttcac catgttcgcc 16740
aggatagtct ccatctcttg acctcgtgat ctgcctgcct cagcctccca gtgctgggat 16800
tacaggcgtg agccaccgcg cctggccaaa atatataacc ttaagtgtaa gtttactaac 16860
tttggaaagt acatacacca gcataaacca acccccttc aagatctaca ttattttatt 16920
tatttattta tttattttga gacagtttct cccttgttgc ccaggctgga gtgcaatggg 16980
gcaatatcag ctcaccgcaa cctctgcttc ccaggttcga gcgattctcc tgcctcagcc 17040
tcccgagtgg ctgggattac agacatgtgg caccactccc agctaatttt gtatttttag 17100
tagagatagg gtttctccat gttggtcagg ctggttttga actcccgacc tcaggtgatc 17160
cgcccgcctc ggcctcccaa agcgttggga ttacaggcgt gaaccaccat gcccagccaa 17220
gatctacact attatgtcac cccagaaagt gaactctcag tcttcccagc cagtctcttt 17280
cttatcatag gttagcttgc ttattctgga atttcgcgta tacagatgca tgccatgcca 17340
taggtactct tttgtgtctg ctttgttctg ctcaacacca tgtttctgaa atcattacca 17400
ttgttgtatg gttctctaac ttcatcattt ccatttcaga ctcagcatat gctgagttca 17460
acctgttgaa gggctatctc tgtttaattc accatcttga aagaaacatt taaaattgag 17520
atgttttcaa gaatatatag ttaaatcctg aggaatcgac gtagaaatgt tatcacaagc 17580
tgtctgaact tactcagggg aagtcttcgt cttcactcac ataagagtct aatggaatta 17640
atatcaacaa tcttagagaa atcccacact attcatgcca ttttcatgat ctccaccttg 17700
ataatttttt tttttttttt tttttttttt tttttttttt tttgagacag agtctcgctc 17760
tgtcacccag gctgaagtgc agtggtgcga tctcggctca ctgcaacctc tgcctcccgg 17820
gttcaagtga ttcttctgcc tcagcctccc aagtagctgg aactataggc atgtgccacc 17880
atgccctgct aatttttgt atttttagta gagacgggtt tcaccgtgtt agctaggatg 17940
gtctcaatct cctgatctcg tggtccaccc acctcggctt cccaaagtgc tgggattgca 18000
ggcgtgagcc accacgccca gcccaccttg ttaattttta agcactaaaa tttgatactt 18060
atttgtgaat gaagtaatct cttcattgta tttttttttt tttttactta tgctgagatt 18120
taaatgacaa agattcatat aatccaagag agaagtatta tttagaggga ttcttttacc 18180
atgtgatata taataaatgc atccaatgtt atacatcaat ttaaaaaaca agtaaataac 18240
tttaaagaaa agataactac tggccaggtg cagtggctca cacctgtatt cccagcactt 18300
tgggaggcca aggcaggtgg atcatgaggt caggagttgg agaccagcct ggccaagatg 18360
gtgaaaccct gtttctacta aaaatacaaa aattagccga gcgtggtggc aggcgcctgt 18420
aatcccagtt actcagtagc tgaggcagga gaatcgcttg aacccgggag gcggaggttg 18480
cagtgagttg agatcatgcc actgcaatct agcctgggtg acagagcaaa actttgtctc 18540
aaaacaaaaa gaaaagaaaa gataagataa ttactttata cttagcttgt cttacccatg 18600
agtgacgggc tgcatgtggc ccaggacagt tttgaatgca gttcaacaca aatttgtaaa 18660
ctttcttaaa acattaggag attttggcca ggtacagtgg ctcatgcgtg taatcccagc 18720
actttgggag gctgaggcgg gcagattacc tgaggtcagg agttcgagac caccctgacc 18780
aacatggcaa aaccccatct ccacaaaaaa tacaaaaatt tgctgagtgc actgtcaggc 18840
acctgtactc ccagctactc aggaggctga ggcaggagaa tcacttgaac ctgagaggca 18900
gaggttgcag tgagccggga gcacaccact gcactccagc ctgggtgaca gagtgagacc 18960
ccatctcaaa aacaacaaac aaaaacaaaa acaaaaaaat ggctgggcac ggtggctcac 19020
acctgtaatc ccagcacttt gggaggccga ggcaggcaga tcgcctgtca ggagttcaag 19080
gccagactgg ccaacatggt gaaacctcat ctctactaaa aatacaaaaa tgagtcgggc 19140
atggtggcag agacctgtaa tctcagctac tcgggaggct gaggcaggag aatggcttga 19200
gcccaggagc tggaggttgc agtgagccga gattgcacca ctgcactcca gcctgggcga 19260
ctgagtggag cggaactctg tctcaaaaaa aaaaaagagg tttttttag atcatcagct 19320
attgttagtg ttagtgtatg ttatgtgtgg ctcaagacaa ctttgcttct tttaatatag 19380
gcagggaagt caaaagattg gatatccctg ctttatacca agaaagacaa caccccacat 19440
ttgcaatgcc tgaaaacact accagccatc tgaaaaacat gtgacttcta acttctgttc 19500
ttttttgtag cagtggaatc ccacggtgat atctgaggga tgtggttacc ttttggagga 19560
ggttgacggt ttctaaggat gattctttct gagtgaaata ttgtcagtgt cattgacctt 19620
ttcattattt caactattat tattccaggt tatcaatact ctggctgacc atcatcatcg 19680
tgggactgac tttggtggaa gtccttggtt acatgtcatt attgcatttc cgacaagtta 19740
taaagttgtc attaccctct ggatagttta cctttgggtg agtatactaa ctttctgtag 19800
aggtatactt gtaatcacaa ataagaataa attatataaa acaattcaca tttctggact 19860
tcattatgaa tatgtggttt tacccaaaaa atcagggaaa tgatttatta gtataagaat 19920
tatgaaaaca tctgccattt gcattatgaa aattaaatag gtcggtgttt gtttaataga 19980
atgtcaacag agcttttggt caaaaataag tttttttaac ctttgtgcta tttatcacaa 20040
atggagtatg aggtttcgtc acttaaatag gaaattcttt ctaaactctt ctgctttata 20100
gttctatcgt atgggtggaa ggaaagcttc caatctcctc tctgaagatt cactgcagaa 20160
atgagctgac aacagacagc ttaacaggaa aagaaaaaca tagaacaggc ataaacatgg 20220

-continued gaaccagctg aaaaatgaga ctgctagaag ggccggatgg ctgatgctta aagagcaccc 20280
tcttctgagg ggagagggag atagatggag atgtaggcca tttagagggg cagcaaatga 20340
tttttagggg aaatgaaaga ggccaaggaa caaacaattg gcctgagaca aagttcctgt 20400
gaggtcatag ggacgaggtg acaaactgcc ggaaggtgaa gggcagaact gcactgcgtc 20460
tcatgatgca gagaaagccc cagagactct tagaactgcc ctccaagaga atcaatgaaa 20520
agtgtgtctg ggcagggtaa ttttgaatga catcattcaa agtgcatgtt ccgacttgga 20580
actggagaga gatcagtatg tcaaaagtct gtacttggta agaatttggc tgctaagttg 20640
tgccataatt tgtcttttga gcctttttc ctttgggtaa gttgagctct acattttgtc 20700
ttgccattca tgacagtaaa aatgtggttg tctgggggct gaacctcctt ctgaacaatg 20760
atccaagata aaagtactaa taccacaatg ctttttata ttcaagggaa gaggaagtat 20820
gtttcagttt taccacctag ataattacac gtcatttggc actgcctttc aagatatgta 20880
gaaaacagaa aatatatgag ttatgaagat atctaggcac atttaacatt ctctatgcca 20940
cttagtcctg aacagagaat tttcggtata aattggagga agcttttttc tttttttttt 21000
ttcttttctc accccgaaga cgagtctcct tctgttgccc aggctggagt ataatggtgt 21060
gacctcggct cactgcaacc tccacctcct ggcttcaagt gattcccctg cctcagcctc 21120
tcaagtagct gggattgcag gtgcccacca ccatgcccag ctaatttttg tatttttagt 21180
agagtcgggg ttttaccatg ttggccaggc tagtctcaaa acccgacctc aaatgatcca 21240
ccaacctcag cctcccaaag tgctgggatt acaagcgtga gccaccacgt gagccagggg 21300
aagtttttaa atttaccact ttttaacaat tccacttagg aaagttcagt tgagctgttg 21360
gacttggaca acttcgcacc tctcatcttt gtccttgtca tctagtcatc tataccatta 21420
cctccttagc agggacatca tgggtgccat gaagcattca tgcgtgatgg catttcttgg 21480
cttctcattt cttcatgtgt ttgacatttc ccctagctcc aaactgggcc agctaccttt 21540
cctatgaaat ctagcagtag ctgtgggatt gacgtggttg ctcttttcat ctttttagat 21600
tacccattgc ttctctcgaa atcctagtac atgatttttt ttttatccta tgtgcagaaa 21660
tcaggaaaaa acaaattcta caaagaattt gaaagatatt atttcaggcc aggtgtggtg 21720
gctcatgcct gtaatcccag cactttggga ggctgaagca gatggatcat ttgaggtcag 21780
gagttcaaga ccagatgggc caacatggtg acaccccatc tctactaaaa agacaaaaat 21840
tagccaggca tggtagcagg cacctgtaat cccagctact tgggaggctg aggcacaaga 21900
atcgcttgaa tctgggaggt ggaggttgcc gtgagccaag gtagcgccac tgcacttcag 21960
cacggttgag agtgacactc tgtctcaaga aaaaagtcat ttcaatgacc acctcaggag 22020
attcataggt atctgaccca catctgagat gggatttgca ttgcatttta gctatgatga 22080
gaagaaatat ttaatatctt agaagattaa aagcatactg tgataaatatg gaaatcttgg 22140
tgggaattca gtcattagtg agaatgtttt gcgttaagtt caaaccagcc tcaatgaagc 22200
tgatgtgagg gaagggaaag tgaactctga gtagagcagg gacagaagga agatgctcca 22260
gtgcagatca ggaaggagca ggggatgaaa tgttacaaat tctagaactc agagagctga 22320
aggtaattac ttccttttca agttgtgaaa catgttaacc tgtggtaaaa tacttataag 22380
atgataatta ccatctaacc gtgttgaagt gtacagttca gttgtgtgaa gtatattcat 22440
gtcatttttt tttttttttt ttttttgag acgaagtctc actctgtcac caggctggag 22500
tgcagtggtg ggatcttggc tcactgcaac ctctgcctcc tgggttcaag cagttctcct 22560
gcctcagcct cccgagtagc tgggactaca ggcgtgcatc accatgctca gctaattttt 22620

-continued gtatttttag tagagacggg gtttcaccat gttgcccagg atggtctcca tctcttgacc 22680
ttgtgattca cccgcctcgg cctcccaaag tgctgggatt acaggcgtga gctaccgcat 22740
ctggcctatt tttttttttt tttttttttt tttttttgag acagagtttc aattttgttg 22800
cccaggttgg agtgcaatgg cacaatctca gctcaccaca agcttttcct gctgggttca 22860
agtgattctc ctgcctcagc ctcccgacta gctgggatta caggcatgca ccaccatgcc 22920
tggctaattt tgtattttta gcagagacag cgtttctcca tgttggtgag gctggtctca 22980
aactcccgac ctcaggtgat ccgcctgcct cggcctccca aagtgctggg attacaggag 23040
tgagccaccg tgccagcctc atgtcattct tgtgtgtgtg tgtgtgtatg tgacagagtc 23100
tcattctgtc gctcaggctg gagtgcagtg gtgtgatctc ggctcactgc aacctccgcc 23160
tcccagcttc aaacggttct ctgcctcagc ctcccgagta gcttggatta caggcgcccg 23220
ctgccatgcc cggctaattt ttgtattttt agtagagacg gggtttcacc atcttggcca 23280
ggctggtctt gaactcctga ccccgtgatc cacctgcctc ggcctcccga agtactggga 23340
ttatacgcat gagccaccgt gcccagccgt cattcttata ttattatttc ctaggtgtct 23400
ctcctgaaga ctatcttctg gtctcgaaat ggacatgatg gatccacgga tgtacagcag 23460
agagcctgga ggtccaaccg ccgtagacag gaaggtatgg ctctgttgga atccgcatag 23520
tgtggaaatg agtttgccct ggaaagggaa agaacagctt cttgccctca ggtttctcac 23580
cttctcctct cctcactctc accaagggct gaggtccatt tgtatgcaca caaagaaaag 23640
agtttcttcc tttcgaggaa ataaaattgt cctgaaagac gtcattactc tacggagaca 23700
tgtggaaaca aaagttagag ctaaaatccg taagaggaag gtgacaacga aaatcaacca 23760
tcatgacaaa atcaatggaa agaggaagac cgccagaaaa cagtaagatg tgccttgaca 23820
caaatactgt tgtatgaacc atgtgccaat caaagtagac aactgtaaag tccttgagaa 23880
tattttctac aatatttgtg gcaaattcag tgggttcaaa attgagtttg tcctttctgc 23940
ttcattagtt taagctgtat aattcctttc ccttcctaca ttcttgtttt catttttttcg 24000
gaggaagagg agttgctagt actggcattg gttttccttt ctcttttttt tttttttttt 24060
ttcctgagat ggagctttgc tgttgttgcc caggctgtag tgcaatggca caatctcagc 24120
tcactgcctt ttgggttcaa gcaattctcc tgcctcagcc tcccaagtag ctgggattac 24180
aggtgcccac caccacgccc agctaatttt tgtattttta ctagagatgg ggtttcacca 24240
tgttgtccag gctggtctcg aacttctgac ctcaggtaat ccacctgcct cagcctccca 24300
aagtgctggg attagaggcg tgagccacca cagccagcct tttttttttt tttttttttt 24360
tttaattttg cgatagagtc tcgctctgtc gcccaggctg gagtgctatg gtgcaatctt 24420
ggctcactgc aacctctgcc tcccagtttg aagcaattct gcctcagctt cccgagtagc 24480
ttggattaca ggtgtgtgcc accacatttg accaattttt tttttttttt tttttttga 24540
gacagagtct cactctgtca cccaggctag agtgcagtgg catgatcttg gctcactgca 24600
acctccacct cccaggttca agcgattctt atccctcagc ctcttgagta gctgggacta 24660
caggcatatg ccaccatgcc cggataattt ttgtattttt agtagaggcg gggtttcacc 24720
atattggcca agctggtcta gaactcctga catgatccgc acacctcggc ctcccaatgt 24780
gctgggatta caggcgtgag ccaccgtgcc cggcccaatt tttgtatttt tagtagagac 24840
aggggttcac catgttggcc aggctagtct tgaactcctg acctcaggtg atctgcctac 24900
ctcagcctcc cagtgtgagc caccgcaccc agcctggatt gttgaattca atgcttgggt 24960

-continued

```
caccrccaga ttcattttca cagtctttca tgttttggtc atatgacatt gtattttgct  25020
gccatatgac tgatcttttt ttgttaaatg tgagatactt gttaaaaaat gtttagcaat  25080
gaattgaggc ctagtagcat gttatcttgc tgcagaagag atgggagtct acttctgggg  25140
gatggtcagg ggtcctccat acaagctgca attgaagtcg tcggtgcagg ctcagtccct  25200
acaaaggcca gggtatttcc tgtccacctt tattctgatg catgactctt ctgggtctca  25260
accagagcca gcggacttca gtatgggtcg ctttcattgg cagaccctca atccacttgt  25320
tttccatcta atcccacgca tgtgtgcaaa agctgctgtg cttctttgca tctcagtagt  25380
tccttctgga attcagcaat gaaactcagg gaaatgggtt ccaaatgcga ggctgacttt  25440
cgtcctgggt ttccttcttc tccatcttca cctcatgtct gtttactgcc atgttagcaa  25500
tttgatgtat tcaatcatgg gttttatatt ctgtttggtg tcccccattg ttctcattgg  25560
agatcagaag cttcagatgc acttatgtca actcaagagt agaatgcttc cttagcttcc  25620
ctccagagtc aggttttgtg tttctagttc ccaagtgcac agcaggagta gtgatgtcct  25680
cactggcttc tcatttgcat taagctgtga gcttctttag cgtggggaca ggaccctgct  25740
cccattgcat tctcagcacc acaccacaca ctccttgttt gaggccactc cagacagcat  25800
gtgctgaagg atgccttgtg gtcagaaaca agttcattaa ctttctcttt gaagtgtttt  25860
cgcccctgtt tcctagcgtt ctgggaattt tacacatcct tcctataaag ccaagtatca  25920
ggtgagatcc ttaggatcag gaccatgaat caagtggtgt gagggcaaca cagcaaactt  25980
accctttttta ggccgtttcc tttttctgcc ctcaatctct gtgaactgaa ccttgttaaa  26040
gtcagtcaac accagggtgg atggtttgcc gttgtcacct attttcagga cataacaccc  26100
tgacttagga gccattccga tcatttctaa ttcaatagat gcgcccagca ttcagattgc  26160
cttttctctc aaccaggatc tttaaagttg atgacaagag ttccagtcct gaatcatggc  26220
aaagtgcagt agtgaactgc ggggttattc tggaaggatc tctctatggc tgatggtctc  26280
agttccggca tcagcctctg actgagaatc aggtctcaca caggaggagt cagatgagga  26340
gcaatcctct gcttccgatg gagttagttg tgatgaattg gtgaggtctg gtttttcaca  26400
ctgaactaaa atgagctttc gctgtgtcaa gcacaagact gaccccagag acacacatag  26460
tgcacctcat agaagctttt aatagtcttt atatttacta aagaatagga ctaactatgg  26520
aactatgaag atgagctgga aatgacaggt gacttgccag caggccagag tgtgactttt  26580
ttttgtccct caatgggagg tgtcaattct ccccttcggtt gtgagaatca gttggttcat  26640
ttgtgggaag gttgcagggg ggaatctttg aatcacagcc ttcagatgcc agaagggcag  26700
agggaatccc acacgggctg gtggatcatg tgtgtgcatt tctctccctt ctaatctgag  26760
gaaactaagc gtgaaagaat gtgagcatgc agaaaaggag aggcaggtat cagaggcaga  26820
ggaaaatggg aaattggata tgaaagaaat acacacctac aagtgagttc agaaactgta  26880
ccccaccctc ttgggaaacg cccattggag tgttgttttt aacctttgta cagtatttag  26940
acccagtaaa tgcagaaata gaaacaaacg gtcagaagac atatcgtgag agagagcgag  27000
agagagttca caaaacagaa aacaaagtac cttaatattt accagtgacc aaaagatgtg  27060
aagtagcaaa acgtctcctg accccattgc cagctagact gtgtggaaac tcggttcata  27120
ccagccattc taggggtggg gtgagttgtt gtcatcctta ggaaagtgtg ttgttgtagg  27180
atcaaccaca tccttcaaaa ggactatgcc tgtttataag cccagctgtt tctgccctgt  27240
gaaacacggt aaggatatta atacaaagag aatacagctt tatgataaaa gatgctcaat  27300
gaaggatgaa ttagggatgt actgagaatg gggaaggaaa ctatcatctc agaagtcagc  27360
```

```
aggcagtaag caagaggagg aatcaataca gcaacagttt ggatcagact gtacagtttt  27420
tttgtttttg tttttgtttt tctgagatgg agtctcgctg tgtcacccag gctggagtgc  27480
aatgacgtga tcttggctca ctgcaacctc cgcctcccag gttcaagtga ttcccctgcc  27540
tcagcctccc gagtagctgg gattacaggt gcctgccacc acgcctggct aatttttttgt  27600
atttttagta gagaaggggt ttcaccatat tagccacaat ggtctcaatc tcctgacctc  27660
gtgatccatc cgccccgccc tcccagagtg ctgggattac aggcgtcagc caccgtgacc  27720
ggctcagact gtactcttct agccatctga aatacgtttt ctaggtagag atagattgtg  27780
taagggtaca gttgtgagga taacagaaac atggcagatt atttaaaatc atcctgaaag  27840
tggtgcttta tctgatgaaa gtgattgtaa tccataggaa aatgtttcaa cgtgcgcaag  27900
agttgcggcg gcgagcagag gactaccaca aatgcaaagt aaggagcttc ctccctgcag  27960
ttgcaggata gttcagtgct gatgcagatg atgccacggc ccttagactc tctcaacatt  28020
caatttctca tgtgttggct ttttcagatc ccccttctg caagaaaggc tctttgcaac  28080
tgggtaagtt tgcttgtttt ccttgctttt ggacatagtc tgccaggtca ggacatggat  28140
acatttttct ccctacagct ctgtgctcaa gccctgcaga gggagatggc agagagaaag  28200
gctgcctaca agcatcacag tcccatccct gttggtaacc gtgttgcgca aaaacacctt  28260
catccccacc cagtggggcc cctgatctaa tattctaagt gtcagaggtt ccgtatttgt  28320
aatagcagat gggccctgac tgtaaactag tgaagagtga atgtaactta ttacccacag  28380
ggacaattcc aaatgaaggc cttaaatgat gctcagctaa gctggttctt gtgtggcctc  28440
tgtaccttca aaagctgccg agtcctatga ttacacgtga tgggacttgt acacttgaag  28500
tgaaacacag ttttaaaact tgctttgttt agaattccca cctcattttt ccatggacaa  28560
aagtattctt tatgtcctag tgcacttaca atttggtatt acctgggagt gaaaagaaat  28620
attacagcca tgcctaagtg acttcttgag gtgagattgt tctgtcagaa aaccctctcc  28680
cagttcccct gcagctcttc aggaatccac atctctccag agctctttgt tctcatgggt  28740
ggcacctcca gagtgaagaa gatcctttgt caagaaggga aacagagggg aaatgagagg  28800
gtcctgcagg cagagctgga atcaacttcc actctgcctc ttgcaagctg tgtgaccctg  28860
ggcacaattt ctccttcctc tggaaacctc tgttttctta gatttggagc agggtggtca  28920
cactgacctt gcagagttct gagaatcaga gacagaacat aaaaggcctg gaaaacattc  28980
tccaaaaaga agctgcaaca tgtgtggaca gtgggctttt catgcctctc ttactgtctc  29040
ttactgtctg ttgacctggt gcaagaaaca tgctctggtg atggctgtga gggaggaatg  29100
aggatagaca tagacactcc tgtgtctcaa acatgcttct ttattactct gttatgactc  29160
tgtcttccct ggggcaggac cccagcctgc ctacatttgc agacagacac agtggcatgt  29220
ggagacaaca gtgtgtccca atgactttcc tttaccctcc agctgtcggc agtactcagt  29280
ggaagggtga tattatgaca ctgatacttc tattttgaaa cctggaggat ggaaaggtgc  29340
aaaaatctat caccagcaac agaaggtgca gactgtgttg gtggcggtaa ttttgtccat  29400
caaatgaata tgtgtgaaaa cattccctcc tttggcccta caggtcagaa tggcggcagc  29460
ggagcatcgt cattcttcag gattgcccta ctggccctac ctcacagctg aaactttaaa  29520
aaacaggatg ggccaccagc cacctcctcc aactcaacaa cattctataa ctgataactc  29580
cctgagcctc aagacacctc ccgagtgtct gctcactccc cttccaccct cagcggatga  29640
taatctcaag acacctcccg agtgtgtgct cactcccctt ccaccctcag cggatgataa  29700
```

```
tctcaagaca cctcccgagt gtgtgctcac tcccttcca ccctcagcgg atgataatct  29760
caagacacct cctgagtgtc tcctcactcc ccttccaccc tcagcggatg ataaactcaa  29820
gacacctccc gagtgtctgc tcactcccct tccaccctca gctctaccct cagctccacc  29880
ctcagcggat gataatctca agacacgtgc cgagtgtctg ctccatcccc ttccaccctc  29940
agcggatgat aatctcaaga caccttccga gcgtcagctc actccccttc caccctcagc  30000
tccaccctca gcagatgata atatcaagac acctgccgag cgtctgcggg ggccgcttcc  30060
accctcagcg gatgataatc tcaagacacc ttccgagcgt cagctcactc cccttccacc  30120
ctcagctcca ccctcagcag atgataatat caagacacct gccgagcgtc tgcgggggcc  30180
gcttccaccc tcagcggatg ataatctcaa gacaccttcc gagcgtcagc tcactcccct  30240
tccaccctca gctccaccct cagcagatga taacatcaag acacctgcct tccaccctca  30300
gcggatgata atctcaagac accttccgag cgtcagctca ctccccttcc accctcagct  30360
ccaccctcag cagatgataa tatcaagata cctgctgagc gtctgcggat tccgcttcca  30420
ccatcagccg atgataatct caagacacct tccgagcgtc agctcactcc ccttccaccc  30480
tcagctccac cctcagcaga tgataatatc aagacacctg ccgagcgtct gcgggggccg  30540
cttccaccct cagcggatga taatctcaag acaccttccg agcgtcagct cactcccctt  30600
ccaccctcag ctccaccctc agcagatgat aatatcaaga cacctgccga gcgtctgcgg  30660
gggccgcttc caccctcagc ggatgataat ctcaagacac cttccgagcg tcagctcact  30720
ccccttccac cctcagctcc accctcagca gatgataata tcaagacacc tgccgagcgt  30780
ctgcgggggc cgcttccacc ctcagcggat gataatctca agacaccttc cgagcgtcag  30840
ctcactgccc ttccaccctc agctccaccc tcagcagatg ataatatcaa gacacctgcc  30900
gagcgtctgc gggggccgct tccaccctca gccgatgata atctcaagac acctccctta  30960
gctactcagg aggctgaggc agaaaaacca cgcaaaccca agaggcagag ggcggctgag  31020
atggaaccac ctcccgaacc caagaggcgg agggtcggtg acgtggaacc gtcacgcaaa  31080
cccaagaggc ggagggccgc tgacgtggaa ccatcatcac ccgaacccaa gaggcggagg  31140
gtcggtgatg tggaaccgtc acgcaaaccc aagaggcgga gggccgctga cgtggaacca  31200
tcatcacccg aacccaagag gcggagggtc ggtgacgtgg aaccgtcacg caaacccaag  31260
aggcggaggg ccgctgacgt ggaaccatca ttacccgaac ccaagaggcg gaggttgagc  31320
tgagaagagg ccagtgcact caagcctgag caataagaat aaaaccgagt agaacaaaat  31380
aaaaaattca aaaaacaaaa caaaacccac actccaaaaa ctaacaaaga ataaataaat  31440
aatataaaaa taaaataaat actgcagtcc ttatgttatt gctttgtttc gatatctggt  31500
atgattgcct gagggacctg aggtttttaa tcataggggt ttttttttaa tctttagaag  31560
tggttggtta tgtaaaatat tattattttt ttttttgaga ctggattttg ctgtgtcacc  31620
caggctggag tgcagtggct cgatcacagc tcactgcagc ctcaacctcc tgggcttcaa  31680
gcaatcctcc tgcctcagcc tcccaagtag ctgggatcac agatatgtgc caccacgcct  31740
ggccaatgtt aaaaaatcct ttaacttttt tgtagagatg cactcctgga ctcaagcgat  31800
cctcctactt gtcccgacca ccagcccctt tctgataaac aaacatttac actgtttatt  31860
atctgatgcc atttctatct tcttccttgt cgtccagaca tcgaataatt aggtttcttc  31920
agggttttct ttttcaagtg ctcagtgtta aagatcactc acattagggc cagacaccat  31980
ggctcatgcc tgtaatccca gcactttggg aggccgaggc gggcagagca cttgaggtgg  32040
ggagtttgag accagcccgg ccaacttggg gaaaccccac ctctactgaa aaaaatacaa  32100
```

-continued

```
aaattagctg ggcgtgatgg tgcatgtctg tagtcctagc cacttgggag gctgaggcat  32160
gagaatcgct tgaacccagg aggcagaggt tgtagtgagc caagatcacg tcagcacact  32220
ctagcctggg tgacagagtg agactctgac tcaaaaaata aataaaataa atatcactta  32280
catgagatat acccaagggg tggtctacag agacttggaa gcagtggtta ttgcaacagg  32340
ggcacggaag tcatctggct atgccagggt gcccagggga tactcggggt gggtggcatg  32400
gtgctgctgg ggactcatcg cacaggacgc tctgattgac gcactgccag gagtagcgct  32460
ctgtcttggg gctgcagccg gcctcctcag ctcgagtgta acatcagtcg tggccatggc  32520
agcacctgcg gatgtcacat gggcaggaca gcaggtgggt gaagctctct cctggccctc  32580
ctctcttgcc aggaccatgg gtgactgaag acccccaggg aggcacagca tcctcttatc  32640
taagattttt ttttttttaa gagacagggt ctttaaaaaa gtcctgcagt ctgcagtcgc  32700
ccaggctgga ctgcagaggc acaatcatag ctcacggcag ccttgaactc ctgggctcaa  32760
gcgatcctcc cacttcagtg tcccaagtag ctgagactac aggcacacgc cagcatgtcc  32820
ggctggtttt ttagtttgta tttcctttga gacagcatat ctctctgtcg ctcaggctgg  32880
ggtgcaatgg ctcaatcagc tcactttagc cttgaactcc cgggctcaag tgatactgcc  32940
acctcaactt cccaagtatg ctactacagg aacacaaact cctttttttaa atttttgtg  33000
gatatggggt ctcactatgt tgcctaggct ggtcttgaac tcccaggctc aagcagtcct  33060
acctcagcct ccccaaatgc tgggattaca ggtgggagct actgtacgcc tggccttatc  33120
taagctgttt ccctgaaaat gcccgtcttg ggtaatgatt ccattggccc caccatgccc  33180
tgtcctgcct tcctggctgt gcccaagctt ggtccctgcc tgcctgcctc actctctggg  33240
tctcgagctc ctgtgacaca tgactcctct ctcttcctgg agtgatccaa gccctgccac  33300
ttcctgactt tgcccacact gtaccctctg cctggggcaa cttcatgtct gcccattgtc  33360
ccttaggcct cagcccaggc acaagcccct gcctccggag gtcatccagg cctcaccagg  33420
ctacaccctc tcgtaaaatt ggattccctc ccttcagggc aggtttataa tgaaatcctc  33480
ctcagaggcc aggtgcggtg acacccatct gtaatcccag cactttggga ggctgaggtg  33540
ggaggatcac ttgaggccag gggtcgaga ccagcctggg caacataaga gagactcttg  33600
tctctcttgt ctctataaca aatttaaaaa ttagctcacc aggccaggct cagtggctca  33660
tgcctgtaat cccaacactt tgagaggccg aggcaggtgg atcacgaggt caggagttcg  33720
agagcagcct gaccaacacg gcgaaaccct gtctctacta aacatacaaa attagccagg  33780
catggtggca cgcacctgta atcccagcta ctcgggaggc tgaggtagga gaattgcttg  33840
aaccccggag gtggaggttg cggtgagcca agatcacgcc attgcagtcc agcctgagca  33900
acagagcaag actctgtctc gagagaataa aaacacacaa aaaattaact cgccaggatg  33960
gcacatgcct atagtcctaa ctacttggga ggctgaggtg ggaggattcc cttcagccca  34020
ggagtttgag gctgcagtga gccactgtga ttgtgccact gcactctaac ctgggcaaaa  34080
gcgagacccc aggctagagt gcatgatttt gggtcactgc aacctccacc tcccaggttc  34140
aagtgattct cctgcctcag cctcttgagt agctgggact acaggcatgt gccaccacgt  34200
ctgggtaatt tttgtatttt tagtagagac agggtttagt agagaccatg gtgaaacccc  34260
atctctatta aacaaatctc tactaacccc atctctacaa aaaacagctg ggcgtggtag  34320
tgcacacctg taattccagc tacttgggag gctgaggcac gagaatcatt tgcatcttgg  34380
aggcagagtt tgcagtgagc tgagatcgca ccactgcact ccagccggga tgacagagca  34440
```

-continued

```
agaccctgtc tcaaaaaaaa aaaaagggcc gggcgcggtg gctcacgcct gtaatcccag  34500
cactttggga ggccgaggcg ggcggatcac gaggtcagga gatcgagacc atcctggcta  34560
acacggtgaa accccgtctc tactaaaaat acaaaaaatt agccgggcgt ggtggcgggc  34620
gcctgtagtc ccagctactc gggaggctga ggcaggagaa tggcgtgaac ctgggaggcg  34680
gagcttgcag tgagccgaga tcgcgccact gcactccagc ctgggcgaca gagcgagact  34740
ccgtctcaaa aaaaaaaaaa aaaaaaaaaa aagaaaaaag aacaaacaac agcaacaaca  34800
acaaaaaaac ctctgtgtca atcacagcct tcgagctagg ggagaggcgg ccgaattctg  34860
ccctccgcta acgagctata gctttgtgga aatgggcgag tggcgtgccc ttgtgagcct  34920
cagggccgca tctgtaaaat gggcataact gtcatgcctg tctttaagaa cagccttggg  34980
ggtaaatgag tggaactaat ggaaagatct cagcccacaa ccttccacag aacaggcgct  35040
tctcacacag taagtagcag gagtgcagag gctgcaggca tgaatccagt cagactgcag  35100
actgcctggg ttcaagtccc agctcccacg tcttggtaac taagtggcct cagacaagtt  35160
acttagtatt tcttcttctt cttttttttt ttttttcaga cggagttttg ctctgtcacc  35220
caggctggag tgcagtggtg tgatctcggc tcactgcaac ctccgcctcc cgggttcaag  35280
caattctcct gcctcagctt cctgagtagc tggaattaca ggcacctgcc accacatcca  35340
gctaattttt gtatttttag tagagacagg gtttcaccat attggccagg atggtctcga  35400
actcctgacc tcgtgatctg cctgcctcag cctcccaaag tactgggatt ataggcgtga  35460
gccaccgcac ctggacacat tacttaatat ttctgtgcct tggtttcttc atctgtgaaa  35520
tgggattgtt gtgagaatgc aaagggattc ccagggcagt tcctagtgca tagtctggct  35580
gcctttgtgt gtgtgtgtgt gtgtgtgcat gtgtgtgtgt gtttaatata gagacagggt  35640
ctcactatgt tgcctaggct ggtttcaaac tcctgggctc cagtgatcct cctgcttcca  35700
cccaaagtgg tgggataaca ggtgtgagtc accacacctg gtcactttat attattttt  35760
tcttttgaga cagggtctcg cactgttgcc gaggttggaa tgcagtggtg caatctcaac  35820
tcactgcaaa ctccgcctcc cgggttcaag tgtttctcct gcatcagcct cttgagtagc  35880
tggtactata gtcaccgggc tccttgcctg gctaagtttt gtatttttag tagagatgcg  35940
gtttagtgat tctcctgcat cagcctcttg agtagctggt actataatca cttagctcct  36000
tgcccagcta atttttgtat tgttagtaga gatgcggttt ccttttttttt tttttttttt  36060
gagatggagt ttcgctcttg ttgcctaggc tggagtgcag tggtgctatc tcggttcacc  36120
acagcctccg cctcctgggt tcaagcgatt ctcctcctca gcctcccgag tagctgggat  36180
tacaggcatg tgccaccgca cctggctaat tttgtatttt tagtagagac ggggtttccc  36240
catgttggtc aggctagtct cgaactcctg atgtcaggtg atctgccttc cttggcctcc  36300
caaagtgctg ggattacagg catgagccag catgccaggc tggccctttt tttttttttt  36360
ttaatcactt aacatatatc ttggagaact ttccattttg ggagttaaag agatttgttt  36420
gtttgtttgt tttgagacag ggtctccctc tgtggcccag gctggagctg gaccttggct  36480
cagtccaact tccacccccc gggctcaagc aatcctccca cttcagcctt ccaagtagct  36540
gggtctatgg gcacatgcca ccacatcccg ctacttttta tagtttttgt agagatagga  36600
ttttaccatg ttgcccaggc tggtcttgaa ctcctgagct caagtgatcc acctgcttca  36660
gcctcccaaa ttactgggat tacaggcatg agccatcttg cccagcctgt tttttattta  36720
atatctacta agtgccaact accatagagg acataaagat gattcagtct ctgcagaagt  36780
cattttcttt ctctttcctg ttgtacagca caaaattaat ggactaaata gtctgtcact  36840
```

-continued agataaagaa gccctaagta atcaggcact tgctgcagtt tttacaaagt ttaaaaagcc 36900
atatgaaaca cagtatactc caagtaataa gaggcaaaat atgtgaagtg ttactgctgg 36960
ggaatttacg gactattctt ttctacaata tatctgctgt ggtctgaatg tgttccccaa 37020
gattcatatg ttaaaactta accaccagtc tggtagtatt aagaggtggg gcatcattaa 37080
gtcatgaggg catgggatta gtaacctcat aaaaaggttg gcgggaacga gctaggccct 37140
ttcattgccc ttacatccct ctgtcacttg aagacacagc actggtcccc ccgggaggac 37200
atagcagcaa ggtgccgtat tggaaatggc caccatgccc tcaccagata ccaacctgct 37260
ggtaacttaa tcttggcctt cctagcctcc agaactgtga gaaagaaatt tctgggtttt 37320
gtttgtttgt atgagacagg gtctctgtca cctaggctgg agtgcagtgg cacgatctcg 37380
gctcactgca acctctgcct cctgggttca agtgattctc ccacctcagc ctcccgagta 37440
gctgggatta caggtatgca ccaccacacc cagctttttt tttttttcat agcgttgtac 37500
agatagggtt tcgtcatgtt gcccaggctg atctcgaact cctaaggtca cacgatccac 37560
ctgccctggc ctcccagcat gctgggatta aaggcgtgag ccactgtgcc tggccaaaat 37620
ttccgttttt tataaataac ccagtctctg gtactttctt atagccgcac gaacagataa 37680
agactgtacc tatctgttga ctgggcgcag tggctcacgt ctgtaatccc agcacttcgg 37740
gaggcttaga caggtggatc acgaggtgag gagatcgaga ccatcctggc taatatggtg 37800
aaaccccgtc tctactaaaa atacaaaaaa tttagctggg ctcggtggcg ggcgcctgta 37860
gtcccagcta ctcaggaggc tgaggcacga gaatggcatg aacccgggag gcggagcttg 37920
cagtgagccg agatcatgcc actgcagtcc gtcctgggcg aaagagcgag actccgtctc 37980
aaaaaacaaa caaacaaaca aacaaacaaa aaagaccgtg cctttctgtc tgtctccctc 38040
ataggtcagt ttccacctga ttgtaaccac atcaagtatc ctagtatatt tcatatttac 38100
agaaaaataa atgggcaaat actgtcattt acagagaacc tgccctgtcc tgtacactgt 38160
gacatatttt gtggtttgtg attatgtgct ctgatcctta cgatagctct aaaatagctc 38220
aaaaagttat tcccattttg tacataagaa aattgaagtt ctggaaacat aaggcaattg 38280
cccaaagtaa tagagtaaat gacaaagcta ggatttcttt ctttcttcca ttaattaatt 38340
aattatttga gatagggtcc ctgttgtggg atgcagtggg gagatcatag ctcactgcag 38400
tctcgacctc ctgggctcaa ctgatcctca cgtctcagcc tcctgagtag ccgggactac 38460
aggtgcacac caacactatg gctaattctt gtatttttct gtagaggtct gcctaggcta 38520
ggcagagatt ctggctaggc tggtctcaaa ctcctgggct caagcaattc tcctgcctca 38580
ccctcccata tagctgggac cgcaggtgtg tgccaccact cccagctgac ttgtttatac 38640
cagtggttct taattggaag agttttgtac cccggggaca tttggcaaca tctggagatg 38700
tttttgaatg ttacagtggg gaggagggga atgctactgt cacctactgc gtagaggcaa 38760
gggatgctgc tgaacatccc acaatgcaca gaacagcctc ctccccaccc aacagagaag 38820
tatctggttg gcccaaaatc tcaatgatgc caagtctaag aaactgcttt gtatttctct 38880
gagatactgg gatgaggaac gctctaaatt agttgtcttt gaggataatg tatgcataca 38940
tacacatata tgtgtataca tgtatataac taaagatata tagttgagat cttgcatttg 39000
tgttaatgaa tgtagttttt ataaagataa ttgactcata cattaattgt tgactctttg 39060
gaaaggaaaa aggacaaatg agatacatgc tattggtttt gttatttaga aattgttcgt 39120
gtggatcctc cctaccattc agccatttgc aaaccattag ttgagcataa cttaatccct 39180
tctagttcac agcaaagatt catcaaaagc catttggtat actgtcacct catctctcta 39240
ccagtgttga ttagattaca ggagggttac aggagggcac cttatccaaa ttggccaatg 39300
ataaattctt ttttggtacc ttactatata tttgtatcct cagaacaaat tctcctttct 39360
gcttaagctg gcttgacttc atttctttca ctagcaagct aagaggcttt ggccaacaga 39420
actactctag gggtagctgt aaaatttatc tctaaggaaa ggctgctctt ttgaaaacac 39480
agtttaatgg gtcttctggg tatatgacga tagtaaagca aaattttgtt ctggaatgaa 39540
gaagctgatt acattgttgt attacaaaca atatattact cagtgaagtg aaaggccaca 39600
ctgtgggcag ggtggtgact ttgcagatag catgttaatc cttgcatgct ttttgttgtt 39660
tctcttttttg gagggggagg gtcttaattt tctttggccc tcccccaccc cctttatttt 39720
ctctggggaa ggcaagactg gataaggagg cttttatcct gccaagatga gttggcccac 39780
aggacaattt gactgaatag aggctccaca aagaacggac atggccaaag aattacaaca 39840
ggaaattatg catttagttt taaggcttcc tttttctcct tttttttttt ttttttttga 39900
gaccgagtct tgctctgttg cccaggctgg agtgcagtgt tgcgatctca gctcactgca 39960
acctctgcct cccgggtcca agcgattctc cagcctcagc ctcccgagta gctgggatta 40020
caggtacctg ccaccacacc tggctaattc gtatttttgg tagagatggg gtttcaccat 40080
gttggcccgg ctggtcttga actcctggtc tcaagtgatc cacccgcctc agcctcccaa 40140
agtacaggga ttacaggcat gagccacagg gcctggccag tatttttctt gtataatgct 40200
cagagtttcc tttaaatctt tttaaaaact tggcagcctt agtcttagct gtgctttggg 40260
aaaataagga gctgcactca agcttaagaa gatattgctg gaagtgtaca ttggcacagc 40320
cttcgaagct tcttggtgcc ctcctgtaac ccaatcgaca ctggctagag agatgaggtc 40380
atattgcatc aaatggcttc cagtgattct ttgctgtgga caagaaagtt gctctttttc 40440
tttgagaaag ttgctctttt tctttgagag ggagttttga tgcctaggct ggagtgcaat 40500
ggcagtgatg tcggctcact gcaacctctg cctcccaggt tcaagtgatt ctcctgcctc 40560
agcctcccga gtagctggga ttacaggaat gtgccaccat gccaggctaa ttttgtattt 40620
ttagtagaga cagggttttt ccatgttggt caggctggtc tcgaactccc gacctcaggt 40680
gatccaccca tgttggcctc caaaagtgct gggattacag gcgtgagcca ccacgcccag 40740
ccaagaaggt cactctttat gctcaacaaa tgtattgcaa atggctgaaa ggtagggagg 40800
atccagatga acaatttcta aataggaaaa ctaatagcca gacacgatgg ctcacacctg 40860
taatcccagc attttaggag gtcgaggcag gcagatcacc tgatgtcagg catttgagac 40920
cagcctgggc aacacggaga aaccccatgt ctactaaaaa tacaaaaatt agccaggtgt 40980
ggtggcgggc atgtgtagtc ccagctactc aggaggctga ggcaggagaa tcacttaaac 41040
ccgggaggca gaggttgcag tgagctgagc ttgtgccact gtactccagc ctgggcaaca 41100
gagagagact ctgtctcaaa aaaaaaaaaa aaaaatcgta gatatccaat ttgttccttt 41160
ctcctttcct aaaagctttt tgtgcccccct ccaacccaac agttccaccc tagaaaaaca 41220
cttgtacaca tacatcagga aacgatacaa gaatattcag gctggtcgcg gtggcttgcc 41280
tataatctca gcattttggg aggccgaggt gggaggacgg cgagagatca tgccactgcg 41340
ctccagcctg ggcaacagag ggagactccg tctcaaaaaa aaaaaaaaaa aaaagcataa 41400
tgttgaaaac aaacagcagt ataatacagc atggagataa ctttataaaa tgcaaagaca 41460
aataaaagta aatatagtgc attgtttagg agtataaata tggtaattat gcaaagaaaa 41520
ctaaaatgac ttttaaaaat catgatggtg actatttttg ggaggaaagc aggtagaagg 41580

-continued tgggatctga gagcagcaca cagtaagtgt caattgtcct agttaatgtt cggcttctta 41640
aattgggtga tatgttcaca ggtgttcatt atgttctttt tttttttttt ttttttgaga 41700
cggagtctga ctctgttgcc caggctgggg tgcagtggtg cgatctcggc tcactgcaag 41760
ctccacctct tgggttcatg ccattctcct gcctcagctt cccaagtagc tgggactaca 41820
ggtgcccgcc accacacccg gctaattttt tttttttttg tatttttagt agagacgggg 41880
tttcaccgtg ttagccagga tggtctcgat ctcctgacct cgtgatccac ctgcctcggc 41940
ctcccaaagt gctgggatta caggcgggag ccgctgcgcc cagcccatta tgttcttata 42000
acttacatta acatattatt ttatatatgt caagcttttt ttccctttttt tttttttaag 42060 agatgagatt ttgctttgtc acccaggcca gagagtgtcg tggtgcagtc atagctcaca 42120
gcagcctcca actcctgggt tcaagtgatt ctcccacctc tgtctgccaa ataattggaa 42180
ctacaggcat gtgccaccat gcctgggtaa gttttttttt ttaatttttt atttattatt 42240
atactttaag atttagggta catgtgcaca atgtgcaggt tagttacata tgtatacatg 42300
tgccatgctg gtgcgctgca cccactaact cgtcatctag cattaggtat atctccgaat 42360
gctatccctc cccccctcccc ccaccccaca acagtcccca gagtgtgatg ttccccttcc 42420
tgtgtccatg tgttctcatt gttcaattcc cacctatgag tgagaatatg cagtgtttgg 42480 tttttgttc ttgcgatagt ttactgagaa tgatgatttc caatttcatc catgtcccta 42540
caaaggatgt gaactcatca tttttatgg ctgcatagta ttccatggca tatatgtgcc 42600
acattttctt aatccagtct atcattgttg gacatttggg ttggttccaa gtctttgcta 42660
ttgtgaataa tgccgcaata aacatatgtg tgcatgtgtc tttaaaacag catgatttat 42720
agtcctttgg gtatcctggg taagtttttt aaaagtgtta tttgtagaga cggagtctgg 42780
ctgtgttgcc tgggctggtc tcaaactcct ggcttcaagg tatcctcctg cctcagcctc 42840
ccaaagctct ggcattacag gtgtgagcca ctgcacccag actcagactt tttttaaggg 42900
aaagaatggg agtgtaggtg gggagacaca ctttgggagg ccaaggtggg aggatcactt 42960
gggccggggg ttcaagacca gtctgggcaa caaagtgaga cctcgtattt accaaaaata 43020
caaaaaatta gctgggcttg gtggtgtggg tttgggaggc tgaggtgaga ggattgcata 43080
agctgtagga gcccgaggct gcaacgagct gtgatcgcgc cattgcgctc taacttgggc 43140
tagacaatga gatcctgtct caaaccaaaa caaaacaaaa cagataattg tcaaattgct 43200
gttttgctat tgttgctttt tgtttttgct tcgctttgcc ttggaagtga agaagagatt 43260
ctcatttaaa cagttatctt gaagtatctt tgtgaactag ggtgcaatta tttcctctgt 43320
ccttgagaca cagatgattc ctgtccaaca ttcccaagga actcagtaag gaccaaatag 43380
agactcagga aagacagtta ctgattttac actgttgcaa aacagagcta tggtttatgt 43440
ttaacaaact gctggtgggg cgtggtggct catgtctgta atcccagcac tttgggatgc 43500
caaggtgggt ggatcacttg aggtcaagag ttcgagacca gcctggccaa catggtgaaa 43560
ccctgtctct actaaaaata caaaaattag cagggcatgg tggtgcatgc ctgtaatcct 43620
agctactggg gagggtgagg cacaagaatc gcttgaacct gggaatcgga ggatgcagtg 43680
agccgagatc acgacactgt actccatcct gggtgacgga gcgagactgt ctcaaaaaaa 43740
acacaaaaaa caaaaaaacc aaattgctgt attttatttt gtgaaatagg gtctagctct 43800
gttgtccagg ctggagtgca ggggtgcaat cacagctcac tgcagccttg acctccaggg 43860
ctcaatcgat cctccctcct cagttttcaa gtagctgaga ctacaggtat gcaccaccat 43920
atgctgccca ggctggtctt gaactcctgg agagagatac atacacacac acacacacac 43980
acacacacac acacacacac actttttttt ttttttgag acacagtttc gctcgtcacc 44040
caggctggag tgcaatggca caatcttggc tcattgcaac ctctgcctcc tgggttcaag 44100
ctattatcct gcctcggcct cccaagtagc tgggattagt aaggcactgc caccatgcct 44160
ggctaatttt gtatttttag tagagacagg gttttgtcat gttggccagg ctggtctcaa 44220
acttctggcc tcaggtgatc cacttgcctc ggcctcccaa agtgttggga taacaggcat 44280
gagccactgc gccgggccca tacatatgca ttttaaaaaa tttatttatt tatttcgaga 44340
cagggtctca ctctgttgcc caagcaggag tgcagtggtg ctatctccca ggctcaagca 44400
atcctcagcc tcccgagtag ctgggactac aggtgtgtgc catcacaccc agataatttt 44460
tattattttt attttttaaa ttttttgtag agatggagtt tcaccgtgtc acccaggctg 44520 gatattttttg tatttttgat aggcctgtac agtttccaaa gttgcaacct ttcccccctcc 44580 ctgagagtag gggcagcccc ggctctccct ctacatcctc cacagtcccg aggttttggc 44640
ctctgtttcc tctgtttcct atgcttggaa caccagtcgc tcttttgttg gtctggctga 44700
cttctgttcc tcttttaaaa atttaagttt ggccgggtgc ggtggctcac gcttgtaatc 44760
ccagcacttt gggagtccga ggcgggtgga tgacctgagg tcatgagttc aagaccagcc 44820
tggccaacac agtgcaaccc cgtctccact aaaaatacga aaattagccg ggtgtggtgg 44880
catgcgcctg taatcccagc tacttgggag gctgaggcaa gagaattgct tgaactgggg 44940
aggcggaggt tgcagtgagc tgagatcacg ccactgcact ccacctgggc aacagggcaa 45000
gactcggtct caaaagaaaa taaataaata aataaataaa taaataaata aataaataaa 45060
gtcaaggggg taacacctct tggtaactct cctgttgttt ctcatgccag catcatcaca 45120
gccttgaggc tctggggtag gtcacttcgt cgagctcgtt tccatgagga taacgttatc 45180
ttgggtgtct gtgagaatgc tgcactgagt atagagccca ggctcctggg tcagccgggt 45240
tcgaatcccc tttcctccgt gaagatctgg gtcagtcaca agtgcttcag tttcttcgat 45300
ctgactgagg gaggctttga ctccaaaaaa ttaacacttg agtgtacctg gccacagctt 45360
agcacatcca gggtgtttcc accctttctt tgggatcctc agggctggat ggagccgatc 45420
cttcccgtct ctccttacac tcgcgcactc acgctggctg gaacaagtcc tccaagtaga 45480
acgaagagcg cgttttagcg gcgctctagc ccgccgagag catacgccct ccccacacgg 45540
ggcccctgat tgtctgaagg ttgcgctggc acgcgcaact tccgggacag aggctgtggc 45600
tggaaggagc tgggcatccg gcctgaggcg cagcggtcgc gttagttcgg cccaatggcg 45660
gcaccgctgc ttcacacgtt gtttgtcggg agatgcggcc gcttcgtcct ctgcagtcaa 45720
gacgctgggc gcgtcgagga ctgggtaaga ttcaggccgc ttccttctgc gcgtctggga 45780
ccaaagctca ggaccgcgct tagaggagcg gattgaaagg atgtgggaca aagctaatgg 45840
cgtgtgatag gagcacgggg tcgagggtca tctcacgttc acagaaatga gctcattcct 45900
cctaactggg taatagacat gggtggggcc tggaaaagtg agtatgttct ctgttctgga 45960
ggcccacttt cccgactgtg tctcttcgtg atttcccagg cctgggtact gccttctgcg 46020
ccttgacccc tcttccttcc ctcttcttcg tccaaatttg gaagggattt ccctgggcta 46080
tgtgggttat cagccgaacg ttgtcactca tggcaaattg aatattacat cttttttgtt 46140
tgaaatttgt ttcgacacac gtatttgttt cgcagtcttt attttgctcc acttttaaaa 46200
tccctaaccc ccatagcact cttggcgttt aactttcaga gtcattagga tgctatgttt 46260
tttcattaat ttactacgtg taagtgaagc aaaccttgta aaacaattag cgtaatatga 46320
ttcctaatat ttatcgagct cctgcttact gtgttaaaca ctggggacag tggtttatcc 46380
aaagacacta atgtccctgc tttctacaga gcttacagca tagggtggga aggcagtaca 46440
caggccaata aataaacgaa cacgatgatt tcagttatac aacaaggtaa tgggggaggg 46500
agaagggaga gaaggagtgt tcgagatttc tcattgggaa gacatctgtc atttcagctt 46560
ctacttgaat gaagacaaaa atctaggccg ggcgcggttg ctcacgcctg taatcccagc 46620
actttgggag gccgaggtgg gcggatcacc tgaagtcagg agttcgagac cagcctggcc 46680
aacatgcgaa acctcgtctc tactgaaaat acaaaaatta gccaggcgtg gtggcagggt 46740
gcctgtaatc ccagctactc aggaggctga ggcaggagaa ttgcttgaac ccggagatgg 46800
aggttgcagt taagctgaga tcacaccact gcactccagc ctgggcagca gagcaagact 46860
ccatctcaaa aaaaaaaaaa aatccagcca cgtagagatt tgggaaaaga gtatttccaa 46920
tagagtgaac agtaagtgaa atgagaaaca gcttggcttg tttgaagagc agaaaagaca 46980
tgatggctgt agtaaaacaa gttgttggag atgaggtgag agaggtaggc gggggccaga 47040
ttaatgtagg attttaaaga ccacactgag agatttggat tgttactgta agtgcagtgg 47100
gaagacagtt attggttgct gagcaaagga gggattgttg gttaagagtg gaagcaggga 47160
gaccagtaaa gaggccttaa caatagtccc actgaattat gttggttcaa taaaggttgg 47220
ctattataat ttttattatt ttcatgaact taatagcttg ttaatcttgg ttccacagga 47280
tttcaaatat gcgtgcatta gagaatgatt ttttcaattc tcccccaaga aaaactgttc 47340
ggtttggtgg aactgtgaca gaagtcttgc tgaagtacaa aaaggtaaga ggagataatg 47400
tgtgaggttt gcttttggtc aggtcagaat acaactattg ctgttatact aaagaccaat 47460
agaaatagca agattaatta agataccagt tgaaatcaaa tatttaataa tagcatgatg 47520
ccgtcagtgc aaaattagag taatagtgtc cttttttttcc cccaccttgg cccatttcac 47580
aggtaataat gagagagtaa taatgtcttt actgaggttt cacctcttca aatgctttat 47640
ttacaaagca tcttttaact ttagcaagtg ctagaattaa aaacaattac agcattttat 47700
ttatttattt atttgtgctg gagtcttcct ctgtcaccca ggctggagtg cagtggcgtg 47760
acctcagctc actgcatcct ccacctccca ggttcaagca attctcctgc ctcagtcttc 47820
tgaatagctg ggttacagg cacgcaccac cacacctggc taattttta attttttaa 47880 tagagacggg gtttcaccat gttggcctgg ctggtctcaa actcctgagc ttgtgatcca 47940
cccgccttgg cctcccaaag tgctgggatt acagatgtga gccaccatgc ctggcctaca 48000
gcattttatt ttttgaggaa cttacctaag cattactttg ggacagtaaa ccggttctct 48060
gaatagggat ttttgttttt gtggtagttt agaagcattt ctactatatc tcagcagtag 48120
agggaaaatg ttaagtaacc gtatgtttat atgaaatatc catttgtatc catatttgag 48180
tgaatacttt tttagatcct cctgaattag atcattagag ctggctgttt tttcccctca 48240
tgctttttga gaattcgcag gagtatcaac tattatattc aaatgtcaat acagaagtat 48300
agctaaatgt agtttatcat tttcctttt ccaagccctc tggctgcact aacatgagtg 48360
tttaaatttt tgtagtcatg attttataat ccgcaattga catgtgaaag ttagtgttcc 48420
ttttataatt tcatctgatg ttaaagtacg gttaaaagtc ttgctgttga tactaaacag 48480
gaaacaaaag cataacttaa ttctttcccc ttcttgttaa gggtgaaaca aatgactttg 48540
agttgttgaa gaaccagctg ttagatccag acataaaggt aattaatttt gtgtttgatc 48600
attagcaaaa ttattgccac tttatacaga catagtttgc tctttgggtc ccattctgtt 48660

-continued ctgcagaact tgctctctcc atggtcctcc cttactttaa tctggtggtt ctcaaccagg 48720
gacagtttta cccccctagaa gacatttggt gatggctgca gatatttttg tcacaactgg 48780
gaggaaaggg tgctactggc atctagtggg tgaatgacag agatgctgct aaacatctca 48840
cagtgcacag ggcagcctcc cataaccaag agtgatccag ccccaaatga caacagtgtt 48900
gaggctggga aaccctgctc taatgcttcc tttctattag attactacct ctttcctcca 48960
tgctgcatgc aactcttttg tctctttaaa gctaaaacaa accaaaaaaa aaaaacaaac 49020
cactgtttca gcatttccag gttcgagata cacctatcat gtagtaaaac cttaatacat 49080
tttgtttcac cattcttcct ttactgccca gttttgaaga gaatggttta ttaccatggc 49140
agtggtagtt agattgcctg gaatgaaatt ccaattttat tatccagtgt gtgatcttga 49200
gcaaattgtt ttaacctctc tgcctctatt ttccactgtg tgaaaccaag aaaacaatag 49260
agatttaaaa aatatggagt gttttgtttt ttaagagatg tggtcttgct gtgttgctct 49320
agctattcac aggtgtgatc atagtgcact acagccttga actcctggcc tcaaatgatc 49380
ctttctcttc agccttctaa aaagctggga ctataggtgc atgccactgt gcctggcttt 49440
aaacatggaa atacttaaca aggattcaat gagctaatat gcaagaagca cttagaacag 49500
tctctgactc aaagtaaggg cagtaattgt catctgttgt ttttgttcca gctgactgtg 49560
ctgtatcatt tctcactcac atttaagtcc actgttctta tcactgtagt aattaccctg 49620
acagattacc catgtttttt ttttacatgc tgatttcagt ggactttttt tgagacaaag 49680
tctccttctt gtcacccagg ctggagtgca gtggtgtgat atgggctccc tgcaaccttt 49740
gcctcctggg ttcaagcaat tctcctgcct cagcctccca aatagctgag attacaggca 49800
cccgccacca tgcctggtta attttttat ttttagtaga aacggggttt caccatgttg 49860
gccaggctgg tcttgaactc ctgacctcag gtgacctgcc tgcctcggcc tcccaaagtg 49920
ctgggattac aagtgtgagc cactgagccc agcctcagtg gacttacttt tttaagcctt 49980
gtattccttg tatcagccga cactgttggc cacccacttc ttaaaacttc agtgtttctg 50040
atcctcctgt cttctgatcc tttaatctct ctctttttt tttttttttt tttttgctc 50100
tgtcgcccag gctggagtgc aatgacgcaa tcttggctca ctgcaagctc cacctcccga 50160
gttcaagtga ttctcctacc tcagcctccc gagtagctgg gactacacgc gcccgccacc 50220
acccccagct aattttttgt atttttagta gagatggggt ttcaccatgt tagccaggat 50280
ggtatcgatc ttctgacctc gtgatccacc cgccttggac tcccaaagtg ctaggattag 50340
aggtgtgagc caccacaccc ggccagtgat cctttaagct ctagtatctc tcgataggtt 50400
cttgatctta aatttggtgt tgattgggct tcaaaacttg actcttttct cactctgttg 50460
attcttctgt gtgatctcct catctccctt catggctttg aaatctacct gtgtcctaat 50520
atatttgtgt ctgtagccaa gattgctctt gtgggctcca gacttatttc attttcattt 50580
ttggggatgg gcagaacaga gtcttgctct gtcacctagg ctgtagtgta gtgggatgat 50640
cttggctcac tgcaacctct gcctcctggg ttcaagccat cctcccacct cagcctcctg 50700
agtagctgtg ccaccacgcc cagctaattt ttttgtattt tcagtagatt tggggtttca 50760
ccatgctggc caggctggtc tcgaactcct gacctcaagt gatccacccg cctcagcctc 50820
ccaaagtgct gggattatag acgtgagcca ctgcacccgg cctagacttg tttcttaact 50880
gtctgttaga tgcatttacc cagaatcatc atagatgctc caaacttatc atgtccactc 50940
ttggctgggc tccatctttc atggagcttt ccctggttct ctctaagcac atggttgttc 51000
cttcattgag tctatttccc acacttccag atctctctag ttacagatct ggtttacaag 51060
gccctccatg gtctatttgg tgcttctttg ttccccagat ttattatctg ttggcttggt 51120
cactatacat gccagccata ctgaacattt ttcagttttc tgaaaacata cttttccttc 51180
tgtaagaagc agaacttcca gaaaagactc aactgtgtta ctgtttaaag acagctgaag 51240
catcactttc tctttaaagc ttttcctgac ccctgcctcc tttcccagat acaaagggac 51300
attttctttg tgttccactg tattttgtat cagcagttct cattcttggt attttgacat 51360
accaagaatt gcactagttg tgtggagtgt tgcaagtaga actttttttcg tcttgagaca 51420
gggtctcgct gtgtcaccca ggctggagtg taatgggccc gatcatggct cactgcagcc 51480
tcaacctccc aggctcaagc aatcttccca cctcaggctc ccgagcacct gggaccacaa 51540
gcatgtgcta ccatgcctgg ctaatttttc tagagacgag gtctccctat gttgcccagg 51600
ctggtctcaa attcctgggc tcaagcagtt tcctcctgcc ttggcctccg aaaagtgctg 51660
ggattacagg catgagccac tgttcctgcc tgctagtaga aataataata gttcagtact 51720
aaagcatcaa agtctgcaac tgatttactt tttttttttt ctttttgaga catagttttg 51780
ctcttgttgc ccaggctgga gtgcagtggc atgatcttgg ctcactgcaa cctctgcctc 51840
cgagtttttt aagtaattct cctgcctcag cctcccgagt agctgggatt atgggcatgc 51900
accaccacgc ccagctaatt ttgtattttt agtagagacg ggtttctcc atgttggtta 51960
ggctcgtctc gaactcccaa cctcaggtga tccacccacc tcggcctccc aaagtgttgg 52020
gattacaggt gtgagccacc acccccagcc tgatttactt ttaaaaatgg tacagtttaa 52080
atgttatcct tatagttttg ttgcagtctt tttagtggaa aagagatagg atagattatt 52140
ttatttacac actaacttag cttgttttct acatgccttt ggccttagtg agctaccgtt 52200
aatgttatcc ttaacagttt tggacatatg aaattaccat agtacaaatg agttgtggtt 52260
ttactttatt ttactgccag gctacttggg atttcatcag aaaatggttg atctgtggga 52320
gtttgacaca tggatatggc atagtaagca ctcagtagct gaattaaggt ggggaaaagg 52380
ggacagcttc ttctccgcat atagggaggc atgtgggatg gtggacagag gatagccttg 52440
accgagacag atgggtttgg acctgcttct ttactggcct cttggttggg cagattgctt 52500
attaatcgtt cttagcctca gcttcctgaa cagcaaaatg ggaataacta aacatcttgc 52560
agagttctta ggattagaag aagatatata tgcggagtgt caggcaccat gcctggcata 52620
tggtgtattc tcactaaatg ataactccat atgaatatcc ctgtaggtat gatgaccttg 52680
tgttgctttt atttatatgt ctaagccttc cacaaattag ggcttttttc ttaatggttt 52740
ttgtcctgtg cagtatatat gcatgaatat aattaatata gtaatatttt acataattga 52800
cactgtattt tataccttgc gtttcaaatt tagcagttct tctcatgtca ctaacaatta 52860
ctatgaacag taatttgatt gcctgaaaaa tatttcatgg aggaatgggg ctatcattta 52920
tacagaacaa acacatcata atatatttaa actcagccac agatttggtt tagaaaagtt 52980
atgtttattc atgaccccaa ttgatcagcc tagactgaat tttatcagca tgcttcctgg 53040
tcagcttgaa tatagaggaa atagaggtag ctattgttcc tttgtgatct tctaatattt 53100
caatctgcta gaattctgca gtttttaaaa gtcccaggtg tcaacatttg aggtgatttc 53160
actttttcag ggcaaacaaa agtgatcagg ctgaagtatt gcatttaagt ctttctcctg 53220
tgtattagag ttactagatt actttcttaa aacgattaag tttattgtga catctttttc 53280
tgttttaata cccagttttg atttccttcc aagtttgtga ccttttcccc ccaacctatt 53340
cttgataaat gattgatata agatagctgt aaatttctgt tatcttagag gatttgtgat 53400

-continued

```
tttgaaagta ctctttgttt aacttaagga tgaccagatc atcaactggc tgctagaatt  53460
ccgttcttct gtcatgtact tgacaaaaga ctttgagcaa cttatcagta ttatattggt  53520
aagttcacca tttattttac tgtcaagtat gtaattcaga actttggtaa tagtatatgt  53580
tatattaata acatgctgct tttatctttc ttccccccact ctagagattg ccttggttga  53640
atagaagtca aacagtagtg gaagagtatt tggcttttct tggtaatctt gtatcagcat  53700
agactgtttt cctcagaccg tgtctcagca tgattgcttc ccattttgtg cctcgtaagt  53760
cattactctt tgcttgcttg gaattttctt ttcttttctt tttaatactt ctttgttaaa  53820
ataccacctt ccccttatat atgagagact gctaccatgg aagattccag atgcatattg  53880
gcaccaggtc tggtagacat atattccccg taatgacccc tatggaggtg tctagattca  53940
tttgttgctg tgagtttgat gaattataac ttgctttatt gaactcctgg tgaaatctag  54000
gaatttttag ccatttaaaa actataaagt tgcattactt tttttcagat tgtgcattta  54060
attaatcatt gggctaactt tggattatgg aaaaataact tttttatag ctgttcattg  54120
tctaggtcaa taactttttt tgtatagcca ttcattgtct agatcaatga cagaacaaca  54180
tattttcttt ttccctcaaa agcccgagtg atcattaagg aaggcgatgt agatgtttca  54240
gattctgatg atgaagatga tagtaagtat aaaaaggttt aaagcctggg cacagtagct  54300
tacacccata atcccagcat tttgggaggc caagatggga ggatcacttg aggccaagag  54360
tttgagacca gcctgggcaa catagtgaga ccttgtctct gcaaaaaaac atttttttttc  54420
aaatattttc ttaaaaaagg cttaaagtag aactaggcag ggtagtgtgt gtctttagtc  54480
acagctacct gggaggctta agtgggtgga ttgcttgagc ccaggagttc aagctctgcc  54540
tggtggcaag actctgtctt ctttaaaaaa aaaaaagtaa agcacagaat acctggcatc  54600
tattctaata agtagactgc aacaaatgac aacttttgat gtaatctttt tgttatattt  54660
accattgata tgcagtcagt tgtcctgaat gcattattta tataattagt ccatttaatt  54720
ttcattgatg ctggtggaga aaagtcttga aattattatt tctctgataa attattccgt  54780
tttggttagc atgtgttttt agcttcaagt atgtcacttt ttgtttgttt gtttgttttt  54840
tgagacagag tctcgctctg ttgcccaggc tggagtacag tggtgtgatc ttggttcgct  54900
gcagccttca cctcctaggt tcaagtgatt ctcctgcttc agcctcctga gtagatggga  54960
ctacaggcgt ttgccaccat gcccggctaa tttttgtatt tttagtagag atggggtttc  55020
accatattgg tcaggctggt ctcgaactcc tgacctcagg tgatccaccc acctcggcct  55080
cccagagtgc tgggattaca ggcgtgagcc actgtgcccg gccagcattt atttttagtt  55140
tcaagcatgt cgcccttcag ttttgttttg atgctcatac tctgaacttt tcttctttca  55200
gatcttcctg caaattttga cacatatcac agagccttgc aaataatagc aagatatgta  55260
ccatcatgag tatacttttc cttattttga atgtttaatt ctcaagaaaa ttgtaatcaa  55320
ttagtaaaaa ttataaaatg ttaatagtat taaagcttga gtcttacatt gcattttttt  55380
tttttgtatc cacttgagga aacattacat tctacaaaaa gtggcatttc cattttctat  55440
ttattctctt taattgtttt tcaaagttcg tatgcagatt ctcccccaat tttgtatggt  55500
ggttggaatt ttgtttttat cttcaacaga tatgctatcc aaaatttttc agtgagaaac  55560
ccctgggtgt gtttgtgtca tgccatatga ataaaaattg cacttctaag aaaagctttt  55620
caggtttgtg ggtttctttt ggaggggtgg atttctagtt ccctctgtct gttgattatt  55680
tgttaactta aaaaaatcca acttgattat tttttcttct tttaaaaata atatacatgt  55740
gtagtgggaa atgtcagcaa aagtgctgtt atgtttctgt gggagagaag ctccctcttt  55800
```

```
gatttgctgt tgatatcaga gttaacagaa gcttattttc tctaagttgt tatagacttt  55860
ctcagaagct atacattgta agttccagtt ctggccgggc gcggtggctc acacctgtaa  55920
tcccagcact ttgggaggct gaggcgggcg gatcacctga ggtcgggagt tcgagactag  55980
cctgaccaac atggagaaac cccgtctcta ctaaaaatac aaaattaggt gggcgtggtg  56040
gcgcatgcct gtaatcccag ctgtttgggg ggctgaggca ggagaatcgc ttgaacccgg  56100
gaggcagagg ttacagtgag ccgagattgt accactgcac tccagcctgg gcaacaagag  56160
cgaaactccg tctcaaaaaa caaaaaaagt tccagttctt tgaggtaagg gttcctgttt  56220
gcctcctatg tctatcgata tttgctttta gaatggtagt tttccttttt attccttttc  56280
tagaaagtaa agtcaacatg gattgattta attttttaaa aatagggcac cgtggtttct  56340
catgccaata ctggtggaaa aatttccatt tgttcgaaaa tcagagagaa cactggtaag  56400
aaatcttttc attgagaaca tcatggaaaa gttgtttgta tgatttcatt ttagatgata  56460
ttaggtcttt ttctttcttt ttctgtcttt atttttattt ttcttttttg agaccgagtc  56520
tcactctatc gcccaagctg gagtgcaatg gcgtcatctt ggctcactgc aacctctgcc  56580
tctcgggttc aagcaattct cctgcctcag cctccccatt agctgggact gcaggcacct  56640
accaccatgc ccagctaatt tttgtatttt tagtagagac aaggtttcac catattggcc  56700
acactgttat cgaacgcctg accttgtgat ctgcctgcct cggcctccca aagtgctggg  56760
attggtgaac caccgtgccc ggctgatgtt aggtcttttt cttaaaggtt actttgtctt  56820
ctagacttta aactgatgtc taagaatttg actcagattc ctttcttata aagcggctat  56880
tggggattcg cagtgccttt ttctgttatt actatgtgca agtcaaggtc tgagttcatt  56940
tccggaatat ctgtagtggc tttatgctca tacgggcaag aattactaga agataatagt  57000
tcatgtatta ctaattgtga acatgcctta ttttaacctg aaaacaaagc cttccataga  57060
agaattctgc ttaagttttt gtacaatgtt cagatcatct gtgcagtttt taataattaa  57120
tagtggttgc cttagtagaa aaccgaatct agtagcatac aaaaagaatt acgtaccatg  57180
accaagtgcg actgatgtta ggaatgcaag attgattttt tttttcgggg gtggggggac  57240
agtctctgtc tgtcacccag gctggagtgc agtggcacca tctcagctca ctgcagcctc  57300
tgcctccagg gttcaagtga ctctcccacc tcagcttccc aagtaggtgg gactatagac  57360
atggggcacc acaccccact aatttttgtg tttttggtag agatggggtt ttgccatgtt  57420
ggccagactg gtcttgaact cctgacctca agcgatctac ccgtctccac ctcgcaaagt  57480
gttgggatta gaggcgtgaa ccaccgtgac cggctgagat tgagttagta cctgaaaatg  57540
aattaataaa atattttgta gcaatagaac aaaggacaaa aaccacataa tcatctcagt  57600
agatgcagaa gtgtgtgaca aacaccaata tccctttatg agaaaaacag aaggaaattt  57660
tctcaacctg ataaagggca tctgaaaaac ccacagctaa catcatattc agtggtgaaa  57720
gaccaaaagt tttttcctaa gacaaagaac aaaacaagga tttccgctct tgctgcttgt  57780
ctagccaagg cagttaggca agaaaaagaa ttaaaagcat ccagatggaa aggaaggcgt  57840
aaactctctt ttgcatggtg attttatatg tcattctaag aagtttacac acacacaaga  57900
aattttagag ataataaatg agttcagcat ggttacggga cagaagacta acatacacta  57960
accagttgtt caagacaatt gaatagggga gaatagtcat ttcaacaaat gctgctggca  58020
gaagtggata tgaacatgca aaagagtgaa gcatatggat atccatatac aaaaatgaac  58080
tcaataaaag ccctacatga agtgtaaaaa ctgtaaaact ctgagaagaa aacgagtaca  58140
```

ttttcataat gttggattag gcagtaattt ccagatttga tgcctaagca caagcaacca 58200
aagaaaaaat gcatcaattg tacttcaaaa ttaaacgttg ttatgcttca taggacatct 58260
tcaagaagat gaaaagaatc cccaaataat gggaggaaat atttctaaat tttatgtctg 58320
gtaatggact tgtatatgta aagaactctt ataattgaat aataaaaggg caaatagccc 58380
aactgaagag ggcaaaggat ctgaataggc atttctgcaa aacacatgaa aagaagctca 58440
acatcattag ccatcaggga aatgatttca cttaatgccc acaaggatgg ctataatcag 58500
aacgagaaga cagtaacaag tgttcacaag gatatggaga aatgggaacg ttggaactgt 58560
catatgttgc tgtgagaatg taaaatggtg cagccgtttt ggaaaatagc ctggcatttc 58620
ttcaaggtta aatgtagaat taacacgtga ctcagcagtt ccatttctgg gtttataccc 58680
aagagaaatg aaaatatatg tccacagaaa aacttgtaca tggatgttca tagcagcagc 58740
atccataata gcctcaagta gaagcaactc aaatgtctgt caactgatga acagatgaca 58800
aaacatggta caatggaata ttactcagca atgaaaagga atgctttata tgttacaaca 58860
tgattggacc ctaaaaacat gccaaaaggc tgtgtattat atgactccat tgataggaaa 58920
ggaatggttt acatgttaca acatgattga accttaaaaa catgccacaa actgtgtatg 58980
actccattga tatgagagga atggtttaca tgttacaaca tgattgaacc ctaaaaacat 59040
gtattatatg actccattta tatgaaatgt ctcaaagagg cagattcata gaaagactag 59100
tggttgccaa ggtcttcatt ttttaggggt gcactaatgg atgtaggatt tctttttaga 59160
gtgattaaaa tgttacaaaa ttgctggctg ggtgcagtgg cttatgccca taatcacagc 59220
acttcgggag gctgaagtgg gaagatccag gagttgaaga ccagcctggg caacatagtg 59280
agaaaatgtc tccctaaaag gaagaattaa cctcatgtgg tggtgtgcac ctgtagttct 59340
agctactagg gaggctgagg aggaaggatt gcttatcccg ggaattcaag gttgcagtga 59400
gctatgattg cacccactgt acctcatcct gagagagaga gcaagaccct gtctctaaaa 59460
gaaaaataaa tgttctgaaa ttgattatgt tgacggtcac ataactgaat atattaaaaa 59520
cttaaattgt atactttaag ttggtgattg tatgatatat gagttttatc aatacagcta 59580
cttaaaaacc tatagttatg caaattaaaa atttcattta ctggggataa ttgaaatgat 59640
tataccgaac ataatacatg tagaaacagt atagtttttg tattgctgga tagtctgttt 59700
ttttcttttt caatatttga aactaaaggt catgtaattg atgtttttct tacataactg 59760
tgaaatattt attctctgtt gaaatgtttt atcttacgtt ttctccttta ggaatgttac 59820
gttcataact tactaaggat tagtgtatat tttccaacct tgaggcatga aattctggag 59880
cttattattg aaaaactact caagctggat gtaagtattg agtaatctat ttttattttc 59940 tttttttat tttttatttt tttattttca tttactgact tgaatttgtt ataatcacag 60000
tatgtggaaa caatagtcag tgatagaaaa gaatccactt ggccaggcat ggtggctcat 60060
gcctttattc ccagcacttt gggaggccga ggcaggcaga tcacctgagg tcaggagttc 60120
aagaccagcc tggccaacat ggcgaaaccc cgtctctata aaaaaaaaaa aaaaaaatta 60180
gccaggcatg atggtgggtg cctgtaatcc cagctactca ggaggctgag gtgggagaat 60240
tgcttgaatc cgggaggcag atcttgcagt gagctgagat cgtgccactg cactccagcc 60300
tgggcgacag agcgagactc catctcaaaa aaaaaaaaag aaaagaaaag aaaagaaacc 60360
actagcacca ttctttgctt cctttctttg aatgtgtctt gaactccatc tgtgcatgtg 60420
ctgggagttg tagacagttc cttctcatga ttggagaaca aggcgttaaa tacatagtta 60480
tccaaatgta aaagtatggt tgtggaaaat gccatgaatg aaacatacat tatgagttag 60540
agaacctgat agaatcacag tggggtcagg aagggattcc tacggaagtg atttttcctg 60600
tttggccttt cttaagggca gattataatt ataaacagtt aaaactttgt ttaaggaggc 60660
ccgcactaag gtgcagtggg aatgaaagga agtggtagat tctagtgaca ttgtgaggaa 60720
aggtgaactg gtccttgaga ctggtttgga ggaggggagg cagacagtaa gggaaaggaa 60780
tccttcaata gttgctccct gtggaatcga atcttggtgt tgccattaat ggtagttaga 60840
aatatgaaga ggaggctggg tgtggtggct cacgcatgta atcccagcac tttgggaggc 60900
cgaggcgggc ggatcacgag gtcaggagat cgagaccatc ctggctaaca tggtgaaact 60960
ctgtctcact aaaaatataa aaaattggcc gggtatggtg gtgggcacct atagtcccag 61020
ctactcggga ggctgaggca ggagaatggt gtgaacctgg gaggtggagc ttgcagtgag 61080
cccagattgt gccactctgc tccagcctgg gtgacagagc aagactctgt ctcaaaaaaa 61140
aagaaaaaaa aaatatgaag aggaggcagt tggaagagta gttccatctt ggccaggttc 61200
agttgctggt gggcagccta ccagagaata ctcacaggca gtcgtggctg cagatgggga 61260
cctgagcata aacctttgga aagatgcagt ttaggacagg ggaggagaag ggtgatcaga 61320
agtatgggga aaaccaagag tctggatgct caggaagaat ccgctggaag gaggagtttg 61380
gtcagcagca tcagatactg ctgtcatttt ttagaaagat gaaaagagca acagtccttg 61440
gatttagtgg ttagaaggta gtctttgttg ctttctggag gaccatgtca gtgaagacgc 61500
agaaactgca tttcgggaga ggatgtggat ggtggggaag cagaattggg gctgttagag 61560
accttggtgc agggttgtgg tggaaggagg ggatggagca gggctaagag gcgtggttta 61620
ggagtgggga gatgtgagca ggtttgtgga ctgaggggag aggagctttg gtggaggaaa 61680
acattgatgc tataggaaag caggaagatg gaacaaggtc ttagaagagc tggagcttgg 61740
gctcactggt gcagtgctcc cttggagttg cacctctctg gccaactgta tatgtactct 61800
ttatagtctt tctctggtat atacttaagg aacattttag aatgtttaca aagaaggtca 61860
ggcatagtta ataaaaaatg gcatggtttg agtggtatgt taagatattt gaatggtgat 61920
ataccaaaat aaatattgca tcatgcacat ttggcttgca gttcatcatt tttctgctca 61980
attgattgac gatatgttta ttacacaatg tgtctgtgag tgtcttgtgc atagagattg 62040
tattagtcca ttttcacact gctgataaag acatagctga gcctgggaag aaaaagagat 62100
gtttttgttt gtttgtttga gatggtgtct cgctctgttg cccaggctgg agtgcagtgg 62160
tgcgatctcg gctcactgca acctccacct cccgggttca agcagttctc ctgcctcagc 62220
ctcctgatta gctgggatta caggcacgtg ccaccatgcc cggctaattt tttgtatttt 62280
tagtagagat ggggtttcac tgtgttagcc aggatggtct caatctcctg acctcatgat 62340
ccatccacct cggcctccca aagtgctggg attacaggcg tgagccactg cacctggcca 62400
aaaaagaggt ttaattggac ttacagttcc acatggctgg ggagccctca gaatcatggc 62460
gggaggtgaa aggcacttct tacatggtgg cggcaagaga aaatgaggaa gatgtaaaag 62520
tggaaacccc tgataaaacc atcagatctc gtgagactta ttcactatca tgagaacagt 62580
atgggggaaa cctaccctat gattcaaatt atctcccacc agtccccccc ccaacaacat 62640
gtgggactta caggagtaca attcaagatg agatttgggg ccaggcgtgg tggctcatgc 62700
ctgtaattcc agcactttgg gaagctgagg ccggtggatc acctgaggtc aggagttcga 62760
gaccagcctg actaacatgg agtaacccca tctctactaa aaatacaaaa ttagctgggc 62820
acagtggcac atgcctgtaa tcccagctac tcaggaggct gaggcaggag aatctcttga 62880

-continued

```
acctgggggg cggagtttgc ggtgagccaa gatcttgcca ttgtattcca gcctgggcaa  62940
caagagcaaa actctgcctc aaaaaaaaaa aaaaaaaaaa gtgagatttg ggtggggaca  63000
cagagccaga ccatatcaga gctagaataa atgttgaatt tgttgaggct acctgacata  63060
gagcatcatg tgatagttgt cgattttata taagtatgta gtaaaagggg cttggtttat  63120
tatatttaaa ttccttcatg acctaggtca gtttacaggc ttgcaccata attgtgtatt  63180
gtgttggggt gtgatataag gcactaatct ggacaccttg aacgtgtgta tatcagatga  63240
atttccatcc caaaataaca tagttgtatt ttttaaatcc ttttattctt ttttcccccc  63300
cctttgttat aggtgaatgc atcccggcag ggtattgaag atgctgaaga aacagcaaat  63360
caaacttgtg gtgggacaga ttccacggaa ggattgttta atatggttag cagtttatta  63420
atgaaagtgg agatgaagtt tatcataatc aaagggtgga aacagctagt gctgctcatc  63480
tttgttaagg ctttagattg aaagaattaa aatagtttag caaacttgaa aacgattcct  63540
tatatgagta atttgctgcc atgtcattta gcacttagca taattggtct atttccaagg  63600
ctttgaattt gggtttggtg aagtatgttt cacttttgtt gttgtaactt tcagtgtttg  63660
tttttgtaag ccagatgctg tctgtgaggg cgtggctaat ggaaaagcat aactgtttaa  63720
tttctgcatt ttaccacttg tacactttat agcattactt cttacgagta gctgggacca  63780
cagattacca tgcctggcta atttttgtgt ttttagaaga ggcggggttt caccatgttg  63840
gccagactgg ttgtgaactc ctgaccgcaa gtgatctgcc cgcctcctgc cccgcaaagc  63900
gttgggatta caggtgtgaa caactgtgcc tggcccacgt tcccttctca gtacacttgg  63960
agagaaaaca gattgctgcc tgccagccca gctaggtgct ctgaaaatgt catcctgcct  64020
ttggtcacta ggtggtggtc ttcccttaag cctttctcta ttaaaatctc atatggggta  64080
attaacagta tttcctttat tctttccaag ggttgagttg taactagccc aaaccaactt  64140
attaatctag aattttaaaa actttaggct ttgacttttc ttcttcttct tcttttttt  64200
tttggtgggg gaaagaatat agaaggcttt tccttctctg caacgatttt gtggcttcct  64260
agaggtcagg agagtgttgg tcatgggaaa gaaggttgaa ttcagtctgc ccacatgggc  64320
gtgcctagct ttagaacagc gctatttagg agaagttgga agttacaccc tttggtgaga  64380
agctgtgtct gtttttttcc atgattggca taattaactc aaataccagc tgtacattag  64440
tccgtatttc tgttcatggt tgagttcagt gtgtccagag accggaaggt gctttgcact  64500
cacaggagtg cccatgtgga gctccatggg atgtgaatta ttgttggtca ctagttctgg  64560
ctgacattgg aatcacttga agagttttta taatatgtgg attccaaagc cctgtcacaa  64620
acctattgaa tttgtacctc ccaggttgaa ttttttgttg ttttttgttt gtttgttttt  64680
tgagatggag tctcactctg tcacccaggc tggagtgtag tggcatgatc tcagctcact  64740
gcaacctctg cctcctgggt tcaagtgatt ctcctgcctc aacctcccaa gtagctggga  64800
ttacaggcac ctgccaccac gcctggctaa tttttgtatt tttagtagag agagggtttc  64860
tccatgttgg ccagtctggt ctcgagctcc tgaccttggg tgatccaccc gcctcggcct  64920
cccaaagtgc tgggattaca tttacaggcg tgagccactg tgcctggccc tgggttgatt  64980
ttgatgctta gctaggtttg ggatccattg gattatttaa cacccgaggt gccttttgtt  65040
tctaatgata ttctctcaac gtgttttaaa aatgaagccc atgagatagt tatgagatag  65100
tagaactttt ccctacattg gtgaagtaaa aatcttggga ttttgatagt cagattatct  65160
taggcattaa aaaatatcac accgatgccc tctcttttta tagggattcg cagaggcatt  65220
tttggaacat ctttggaaaa acttgcagga tccaagtaat cctgccatca tcaggcaggc  65280
```

tgctggaaat tatattggaa gctttttggc aagagctaaa tttatttctc ttatgtaagt 65340
agcctaattt gccgagtact ttttaatatc atgctttaaa aagagtatag cattgtctca 65400
agtcagaaat atctcccata tgtttttggc atgtttttaa agtgaataaa attcctactc 65460
tgtgcaagat gtttatattt ctaagtggtg attttagaat aaagtgtctc ctttttttata 65520 tataaaaccc tgtatgtaag gcttttgtca tctcttttgt gtggttgcac ttaaagatcc 65580
atttgttttg tggatagagg acagtgttgt atactgtttt gattcttttt gtaggtttgt 65640
catttttttc atttgcattc caaatctatt gtatctgtta aagctgaaga aaaacccttt 65700
taaaggtaat agacctatct aggaggccag tttctttcag tggcccatga agatatcttt 65760
ggacaaggat gctgttgaaa cccttcccca agaacaaaat tattcaccca taggacttga 65820
ctggatgcat cagggaatac tgaagtccac cagactgtct ttctcttgag acgtgttggt 65880
gaacatgtcc tatttggcca atcaccctaa gaggggtgcc tttgagatgg ttaggagaac 65940
ctgctttcca tcccttggga cgttcttagg ggctcacctg ttcctagaag gtcagagcta 66000
ctctgccttg taattggaag gttgtcttcc tacgcaccca tccttatcct tcctttcttt 66060
gcttttcctc tgtacccatg ggtattattt aaagaaacct atgaacttac ttagcatggt 66120
ttgtaatgaa aggcagttgt gtgtttttat gttattctgg ttttttttatg aagtgtaaag 66180 ttgacttgaa tttttctttt ctctagtact gtaaaaccat gcctagatct tttggttaac 66240
tggctgcaca tataccttaa taaccaggat tcgggaacaa aggcattctg cgatgttgct 66300
ctccatggac cattttactc agcctgccaa gctgtgttct acacctttgt ttttagacac 66360
aagcagcttt tgagcggaaa cctgaaagaa ggtcagtgtt gtgggagtgc tggactggat 66420
tttccttgtg ttcttgtcac ccttcagaat ggtgattcat tactttttttg agatttttat 66480 aaaaactgga ttcagaaaac tgcatgtaca ctcaaacttc taataataat ttcaagcagc 66540
tcataggccc ctacaaaccc cttaagatag atttgagctt gagaacccta caaacccctt 66600
aagatggatt tgaggttaag aaagaggttt ctgcctttga aggtttgaaa tgtgaagatg 66660
tctccagagg tgaggctgag ccctgggctg tgccagcgcc ctgtacaaag cttcagttgg 66720
atgcaccttc tctttgttgt ccttgtaaca gcccagtaaa tggcaggtat tctcccttta 66780
cagacagcac caaagcacgg ggaagtcatt ttcccaagat cacatggtta ctggcaggat 66840
tagaaaactg aagccaggtt cagctgaccc taaagtttga gtttatatag attacactct 66900
gcctgaagcc ttgagactta attgaccagt attgttttgc taatttctaa gagttactta 66960
taattcaaat ctatcagttg aaacttacta gattagcgta ttttagttga agagagtctc 67020
caagaacagt gtttataagt cattgtaaat tgttctgttt atgtttatga ataattcata 67080
tggttttgtg ggtcacttcc tctaaaccag ggtctgtcaa ccctgcatga ttgccatttg 67140
ggctgcatca tccttcatcg tcgggggctg tcctctgcac tgtaggatgt ttaacagcct 67200
ccacctacta gctgccaaca gcagtccctg accacccccca gctgtgacaa ctaaaagtgt 67260
ctccagacac tgccaggtgt cctctgtggg ggttgcagtc tccttaggtt aacagccaca 67320
gctctaaact gacagttgta cgtgttgcat tatatatgtt tacctacatc ctacatgctt 67380
ctaaaagatg ttgtatgaac tagtaggatg aggttttatc acaaggtaag taaatacaag 67440
ctctgctttt ctttgtataa attaatgcca ggaatctgaa ttaaatatct tgtttttgta 67500
agcagtgaca tcccatttag gtaattttta ttgaaatatg catcaaagaa actcctaaga 67560
aaatatactt aagtacaagt tggtcagctt gcctcttaaa ataaatgtga tgtctttatt 67620

-continued ttactcatgt aggaaagaat tgtattcact aagtctaaga aagtggcttc tgtctaaatt 67680
tgccgtccgt tgaggtagaa ggcaaatttg gagttttctt gtttagaaaa aaaactacag 67740
atgactactg tgcacctgaa aacagcactc agcttcacta acgagacatg caagctagaa 67800
tcaaattgct gttttgtttt gttgcctgtc gtgattgtta gctgaaacca aatcacaagg 67860
tctttttctc cctctgtatt agctcagcat acactgagct tacaaacgta tgaacttcac 67920
gttgtcgtgg aatcttacag cctgctactt cctaagtttc ctttagagaa gctgccttgg 67980
tgaccaatga atgtggttag cctagtgata ctcttctggg ccatatactg tgtgactatc 68040
tgcatggacc tttattgaaa gcatttctgc aaataatttt tttaagtttt ttttaaatgt 68100
gtgataattt gtgcttttaa agatatctta cacttttcac ttatttgtac ctttaaaaat 68160
cttttttttt tttaaaccaa aggtttgcag tatcctcaga gtctgaattt tgagcggata 68220
gtgatgagcc agctaaatcc cctgaagatt tgcctgccct cagtggttaa cttttttgct 68280
gcaatcacaa agtaagttat ttatgctttc ttgatgggag ttatttaaaa tatttttatt 68340
tatgtttctc tagtattgta agagtctgtt aaatttctat gaaattagta acattataaa 68400
aggccaggcg tggtggctga cgcctgtaat ctcaacattt tgggaggctg aggtgggagg 68460
attgcttgag gccaggagtt aaaagaccag cttgagcaac atagtgagac cctatctcta 68520
taaaaaaatt ttaaaaatta gctgggtgtg gttgcctgtg cctgtagtcc caactactca 68580
ggaggctgag gtaggagaat cacttgaacc caggaggcag aggttgcagt gagctgagat 68640
cgtgccattg cactccagcc tgggtgacaa gggcaagact ccatcaaaaa aaaaaaaaaa 68700
aaaaggaatt tctgcaatac gctacaacat gaatgatttt gtaggacatt acgctaagta 68760
aaataagcca gtcacagaaa aacaaatact gtatggttct acttaaagga agcccataga 68820
gttgtcaaaa ttagagagac agaaagtaga atggtggtcc ccagcggctg cagaaagaca 68880
gagtggggaa attattgttt aatgggtaca gagttttcat tttacaggat gaagacttgt 68940
ggatatggat ggtggtgatg gttgcacaac aatatcaatt tattttatac cactgaaccg 69000
tgcacttcaa aatggttaag atggtaagtt ttatgttgtg tattttacca taataaaaaa 69060
aattgtagag ggaaaaacag tctgcctcca cttttgatat gggactgcta acatcttcca 69120
ccctccctct ccccctctgc cccacatctg ggcaagctaa gaaagcctgc tgctctctcc 69180
tctggcacca gctggaaatt catacccaac aagccctagc cctcccacca gacccacatt 69240
tcatccccat ccccatcgca tccccatccc catccccatc cctaaccacc ataaatgcta 69300
agggagtttc cttgcctggt tttctgaaac catttttgga cctgcttggg aatctgccct 69360
gctctctcag aaagcttcat tatatgagca ataaaccttt tcctaccctc ttggtgcatg 69420
tggtgtatca tcagtcttga catctaaaac aaattttggg tggtggggtc catgtctttg 69480
cagggtgacc acaatagtac ctggcacatt atgtgtttaa taaacagaga ttactgtcat 69540
atttatttta ttttattttt tgagatgaaa tttcactctt ttttcctagg ctggggtgta 69600
gtggtgcgat cttggctcac tgcaacctcc acctcccggg ttcaagtgat tctcctgcct 69660
cagcctccca aggagctgag attacaggca tgcgccacca cacctggcta attttgtatt 69720
tttagtaggg atggggtttc accacgttag ccagactggt ctcgaactcc tgacctcaga 69780
tgatccaccc accttgacct cacttacagg cgtgagccac cgcgccttgt ctctgttata 69840
tttatttctc tatttaaatt gatggatata tgcaaacctg atcattatca tacttatgcc 69900
ttgacacaag agaggcaata aactaatcta agtgatgctt gtgatgccaa agatgtcaga 69960
acactttctg ggccaatggc agatacctca tgtcaccaga tgctaagggt ccacaataaa 70020
aagcgttgaa tgaaaatttt gaggataaat atctccaggt tgaggaagaa ggttgcacat 70080
atcgggtgct caataaatat ttgtcgaatg aatgaatgag tgaatggccc cagtgtgtgg 70140
ggcttgggaa gtgattggat ataggcagag aaaaggaaca agtcaaaaat aattcagaaa 70200
tcaagaacaa gcaagttgcc ttgatatact tcattcctac acttggcaaa ctttagtgat 70260
taaggaaaca atgttttaaa aaaagttttg gtgatgagac attcaggaag atctatcaat 70320
aaatagcaaa cctggtcctt tttaagacac tgtgtataaa aaaattccaa aaagattaaa 70380
atcagtgcag aaaccaaaga accatttttt tctatatcat attgatcatt tcaagtggaa 70440
ctgttagcta tcttagaaaa attgtggttc tcaattggtt ttgcctctat ctctgaacca 70500
ccattcctaa aggaaaacat tcaaccagaa aatttcagca catcacaatc tctctgaaga 70560
ttaagaagtc tctgtgaagg actgaatgta taaattgaaa aatttttgct gtcacattta 70620
ggtaaaagag aaatcgttct tcatatcccc ttcctttcca tctgtagctc acctatgtca 70680
actttcctct cagaagtgaa ataaaattaa agctatgaca ctgagtgtca gtcatggagg 70740
gacacgttcc ccacttagcc tttgctgaag tgtttccaga gacaactgtc taatgccagg 70800
tccccactta gtgggctgca cttttctact catttgcaca taatccagaa gtcacatttt 70860
gggttcacag tttccactgg ggtaacctca ttaggcctgg ccacctctgt gcttcttgtg 70920
aagtctctga tttgaaggat tagtatcctt tccagactgt gtgggttgac tttcacccat 70980
ctggagttgc ttggaacaaa gataactacc tcaactcctt gtcatgaaag caaaaaaaaa 71040
atagcattag agttctgaga acaggatgtc attacgggtt gtgccttgtc agctacaggt 71100
aagatatttg agtggctcct caagcctccc caactccctc tccaacctcg ctacacagtc 71160
ttcccaggtc tggtatttga cctccagact gccgcccaga aagcaactca gagctcagca 71220
acaccatgat gatgaaacac aaatatgtgg gcccccaact ttggagactc cactggttgc 71280
ttttgtgcag ctctttctat atatgacttt caaaatggca gccaaccctc tcaactgttg 71340
gttgatctga atatgtaaag ttcagccttc aaacccagca aacagtcagc tataggatag 71400
agttcaggtg ctggggaatg accacggttg gctgctacgt tgggaaccct ggtgacatca 71460
tatatggacc tgggaatgta aagaaacgta ggaaatctga atttatgact tttctaatct 71520
ctctatcggg atcctttttt ggaatcaaga tgattttcct tctaaaaggt cattttatta 71580
cagtaatggg cagggtagac atacctcact agcgtactct caaaatttct tgcatgcata 71640
tgctttctcc ggcatgcata tgctttctac tacaatgtga acaagcctac gaaagctagc 71700
ctaatggagg atgagagacc acgtggagga gagctgaagt gccccagcca gcagctagcc 71760
tacacccaca gctattttgc ttgtgttcca ctcgtcctat ttgcataata ttgttcttta 71820
agttaaccca ttcttaattt attgttttaa tcttaagcaa taatattcaa gaactaatga 71880
gttttgtgta ttcattatat ttttccataa tatatattat actaataaat gcccattcaa 71940
atttttgttt gagtgctcaa gtgggtatca tttaaaataa tcttatatac tatatataac 72000
agccaaggtt tgggcaacac aacagaaact gcatgagttt attttatcag aattttttaa 72060
acggtatggg agaactaaaa aagtaaaaaa gggaaccctt gagttaacaa ggagataaga 72120
actacgtaaa gcagttactg tcctgaagga ataaagggaa gagcatgggg ttattagaac 72180
ctagaagttt ggaaccacca ggagctggga ccctatgagg agagggttgg cccctgacaa 72240
tgctggtgtc tctaagggag ctcctgaggc tgattctagc agtgtaggga aagaaactgg 72300
aaactggaac aatttcctct gtaatcaatg acccttgcca gggtaaagaa tcactgctga 72360

-continued

```
agagatgcta ctggaaaagc aagcaaacaa aaaggagggt gtcccttccc cttcttcctt  72420
ccttccagtc tccctcatga cagagcatct ggctggtgac gggaaaaggt gctccacaga  72480
gcaccacccc aacatcacac gggcatctgc tgacccacag ctgactgcag atgaggaagc  72540
tcagcctagg tcacacaaac gcctcccagc tgagtctagc ctaaattgcc aacctgccaa  72600
atcatgaact aataagtgac tattgtttta agccactacc tttaagggaa ttcagtatgc  72660
agcaatagct atctgatcca tataggccta caaggctata gaaaaactat cacatgtaat  72720
cccagcactt tgggaggcca gggcgggtgg atcaactgag gtcaggagtt cgagaccagc  72780
ctgaccaaca tggagaaacc tcgtccctac taaaaacaca aaattagcca ggcatggtgg  72840
tgcatgcctg taatcccagc tacttgggag gctgaggcag gagaatcact tgaacctggg  72900
aggcagaggt ttcagtgagc caagatcgca ccattgcact ccagcctggg caaaaagagc  72960
gaaactctgt caaaaaaaag aaaaagaaag aaagagagag agagagagag aaagcagaga  73020
ggctactgca gagaaaagtc tagaaggatg ggttcatggg ttcatcgaga gacaatagct  73080
taacaaccag cacaccatag ttggcaaaac actatcattg aaaaaaaaac atgctcaaaa  73140
ggggaaatgc cagtttgggt aaatatgctt ttgtgttgga gagaaagaat ttggaacagg  73200
cttttcagac ccccttaagg cccaacaaac aaattataat ttagacaagt ctgggattct  73260
tcacagctca gcttgtggtg atggtattag cttcacaact ccaaacaagt taagctgtct  73320
gtgtgaaatc tcctcaacaa cacctcactg gcaaacctgg aggtgctgaa aacagagctt  73380
tcaattcttg tttgcaacca agggagttga gttggcagat gggcactgtg tccagccttg  73440
ggaaaggaca tcgcagactt tgcatcctaa gaactcataa ccacaacggc aaggtaagac  73500
acaagctctt gaaagtttcc atcacagtgc agcacaaatg accttggcta tgtgccctgt  73560
tattgctggt ccctgcttaa aaatctcctg tgacttccaa ccacacaaat ttcctacctg  73620
gttgcaaaaa tgcccttgat aattcacccc tccctctatc ttgcccccttt tacaatgtgg  73680
cttggcagct cctcccatca agagttaaaa tctatttcct caccccttga atctaggctg  73740
gccatgggac ttgctttggc caatagatgt ggcagaaatt atggcgtgac agttctaagc  73800
atgagtctca agaggctttg catgcagcaa ctttctctta gaaccctgcc accatgtgaa  73860
caatcctgcc tgggctagcc taatggagga tgagagacca tgtggaagag agctgaggtg  73920
ccccagccaa caaccagcct accccagaag cagaggcatc tgctgaccca cagctgactc  73980
cagatgcata agggagctca gcctagatcc agaacgcctc ccagctgagt ctagcctaga  74040
ctgccagcct gccaaatcat gaagtaataa gggactattg ttttaagtca ctaccttttg  74100
ggggaatttg atatgcaaca atagctctct gatacatata ggcctacaag tctatagaaa  74160
aactatgctg cctctctctc cagccacaca atttctttct cttctcattt actattctaa  74220
ttcctctgtg ttatagtctg tgtcccaaaa ttcatgtcaa aatcctaatc tccaaggtaa  74280
tggtattaga aggtaaatct ttggtaggtg atcaggtcat gagggtggag ccctcatgaa  74340
tgggattagt aaccttataa aagagaaccc agagagctca tttgctgctt ctgccatgtg  74400
aagatacagt gaaaaaagaa gcaggccctt gccagatacg agtttgccaa tgccttgatc  74460
ttggaattcc cagcctccag aactgtgagc agtaagtttc tattgtttat aagctaccca  74520
gcctatggca ttttgttacg gcagcctgaa tggactaaga cagtctacct agaccattat  74580
ttccctttca tcatccacca gccaattcca gcacatcttt tagatctcag cttaaatact  74640
ccctccaaga cctccctcta tctctaatat gaatgaaatc catatctcaa gttcttcaca  74700
gaatcctcta ctctttcctt catggcattt gtcataattt gtaattatat atctagcaaa  74760
```

gttctttgtt gttaaacatc tacctcctcc actctcctag aaactccaca aggacatccc 74820
tgcacccagt gcctaggcaa tgccagacac atagcagatg ctccattaat tatctgtcga 74880
atgactgaat ggcttccaag ttagttaact gggcaccctt gataacagat tctggcctat 74940
ttgaaggatc aaagaagaaa gtggtgctac cttctcccct gccactatct tgcccacttg 75000
tggtgccagt tcaggaggtt tggaatggat gtggctaatg atagacgtag acctattgcc 75060
tttcttggat cataattctg ccaggctctg agtccatgtg gcatcgatgg ctaattgtcc 75120
tccaaaattt atcctctctt cttccattta taccctccca tggagtttta acagggcatg 75180
tggtcaccct actgggatct cacttctcag cttcccttgc aactggatgt ggccttgtga 75240
ctaaattctc atgaacagaa tgtgagtgca agtgatgtgt cagtatcttc atcactttcc 75300
taaaaaggga actgctggtc ctccacttcc tctctttcac ccttccaatg agccagaaca 75360
tgcatgtgat gctggtgagt cagcttcagt cacatgaata aaaacaaact ccaggagatg 75420
actaagcaat aagacagaag gaacccaagt ccctagacga gttcacagaa ccaagctacc 75480
tatccaaccc tgggcccacc tggattataa catgagaaaa acataagtcc taatcatatt 75540
tttgaagcac tgcattttag ggcttctttg tgacagcagc ctaccctcta gtctaatcaa 75600
tatacctcac caagtctcct gctcctaagg gagacaaaga agcaaaatga gtctcaaaac 75660
atcatccaaa tggaatagat acagacctgt aatcccaaca ctgtgggtgc ccaaggcggg 75720
tggatcactt gaggtcagga gtttgagacc aacctggcca acatggcaaa accctgtctc 75780
cactaaaaat acaaaaatta gccggacgtg gtgttgtgca cctgtaatcc cacctaccca 75840
cgaggctaag ccgggagaat tgcttgaacc caggaggggg aggttgcagt gagccgagat 75900
catgccactg cactccagcc tgggtaacag agtgagactc tgtctcaaaa aaataaataa 75960
aaataaaaat aaatagacca ttaattaata gatatagcct tggtctgtga ccaaagctca 76020
gaatgttatg atattccttt cctatgtcac ctcaacttgc ccctgtcatc agacaggaca 76080
aattccccac tggtcctttg cactcacagc tgttacattt gaaatgggag cttagccttc 76140
cctgccctgg ttcctcctta gactcatttg ggaaaacagg aaacgtaatt atttctgcca 76200
ttacctttat ctcatggagc ctgacagagt gtaaccaatg gtaggaatta aaacattcta 76260
attgccaact cacaacaact cccgaaaaaa atcattttaa ctcattatac atattaaatt 76320
atgacatgct taatgtccaa acctaataga ttcagtactc aggaaatccc ttatacaggt 76380
agacaccttt cctcctgtac tttaagaaaa tcttacatca atatgcggga cttctcaaat 76440
ttttctatca cagttttctt aataggaagg agaatttgtg ccaaaagatg tatggaaatt 76500
tagcacaaag tagccctcta caagcggagg atttctttaa agcattgtgt tttatctcaa 76560
gattccatgg caaatgttta tcttctctgc ttgttttagt atgaaatagt tttcatttgc 76620
ttgtcatcat ttttaaggag ttgaaaatac aatcaacctc actcatcata aaataaaagc 76680
aaattaaaac tactatgaca tattttcacc tacaaaattg agaacatttt aaaatgtgat 76740
aatagttcta ttaacaaggg tgtgagaaga caattctcag gcagggcatg gtggctcaca 76800
cctgtcatcc cagagctttg ggaggctaaa gtgggaggat cgcttgagct caggaattca 76860
agatccacct aggcaacata gtgagactct gtctctacaa aaagtaaaat ataaattagc 76920
tgggtgtggt ggcatgcggc tatcatccca gctactgggg aggctgaggc gggaggattg 76980
cttgaactgg ggaagaccag gttgccatga gccatgatca cgccactgta ttctagcctg 77040
ggtggcagga ccggaccctg tcccaaaaaa aaaaaaaaaa aaaaaaaaat ccctcttccc 77100

-continued tgattggtgg gactgtaagc tggtgcaacc tcttgggagg agcaggtggt tagaaaacat 77160
gtatcaaatt tttatgcaaa atttaaatag acccacaatt agaccctagg aatttattct 77220
ccagatattc tcatgcatgc gtgcaaggta tatttgcaaa gatttgtatc cagcactatc 77280
tgtaattgca aaaatccaga agcaacctca gtgtcaatcc ttagaagact gtgtacatga 77340
gatactgtac atgttggttg ggttctccga gaagcgcatg cccggataga atgcaaaaga 77400
ttcattaggg agtaacacct ctgccagaaa agcagaagag ataggattgg gcaggagggg 77460
ccattagagc acaatttaga gctaccacca tttcagaagg cagcaaagat tgcctgttag 77520
agaaatggtc aggcccttgt accctcagtc actggatggg agccactcca agaagagcat 77580
gaccatgact taacagctaa ggggaccctg aaagagctgc caggttaagg ctatcagctc 77640
ctcactcccc acagctggac agagagcctt tgtttaagga ggatctgagc agctcatctc 77700
caggtctggc acaagggtta cccataggat gaagatggaa gacatgaatc tatatgtatt 77760
agtatggaac aatctccatg atagattttt aagtgaaaga gcaatagtaa attgcaaaag 77820
agaacataac gttttgggac taggcagaag tgataaccga acaacagtgt gaatggagta 77880
aaatgtcacc gaattgtaca ctttaaagtg gctaattttg ctatgtgaat ttcacctcaa 77940
ttttttttt tttttttgag atggtgtttc actcttgttg tccaagctgg agtgcaatgg 78000
caaagtctcg gctcaccaca acctccgcct cctgggttca agcaattctc ctgcctcagc 78060
ctcttgagta gctgggatta caggtgcgtg ccaccacgcc cggctaattt tgtattttta 78120
gtagagacgg ggtttctcca tgttagtcag gctggtcttg aactcccgat ctcaggagat 78180
ctgcctgcct cggcctccca aagtgtggga ttacaggcgt gagccaccgc gcctgacccc 78240
atctcaatgt tttaaaagag agagaataca gcatgctgtc atttgtgtta attttaaaaa 78300
ggaaatgaat ttatgtgcat gtataaatgc tagacatgga atctctctga aaggagccat 78360
gaaacactca tactatgatc tccagtcagg aaagagactt aattttcact gtacgccctt 78420
ggtgctgctt aaatttttat catgtgcatg taattacacc ctgtctttaa aaatcattaa 78480
agatgtttaa ttgttctgat gaaggaatac attacttgcc atcaagaaaa atgaatgaaa 78540
aattttctgc gagacaattt ttagcaagac actgttgtat tgatcattca agttcagaaa 78600
attcagcctc cgtcaagggg cacaaacatc atatatcagg ttcagtttgt cctctctctc 78660
agagtcaaag tgctttagga acatagacac aataagtttc tggaaccaaa tggcaaatat 78720
caaaacttgc tagaacagga gaaaagtgta tcttattgaa aattcaccag ctgctatacc 78780
attcagcatt gggaaaatca gcatagcttc ttagacttca ttattttaaa gatggcaaaa 78840
tagccaagtc atggatgtct cccccttca tcaaaatgta aagaactagc tgcctctggg 78900
actctccacc aattttcaag cacgtctttt gaacccattt gatggtgtca ctcaataagg 78960
gcaccttttt caacttggct gcctcttttt gacccaaaat aatttcaacc cttttctgca 79020
gctccgggct tcaccaggct ttctattatt gcatatacct ttcatagtga ttctaaaccg 79080
acctcgaatg aagagacaaa tgattttttta tctattggtt tgattgcact tctccttgta 79140
ctgctccaag acaaggcttg tcttttgagt tgcaaaaaat actagcgctc tatttccaaa 79200
gtcaaacaag tggcttttca atgtctctgc aagtgttttg tttcatgcag tcagtgctga 79260
cttttctcga tggagagaca tatggtttgg gcccatttta gcaactctat aataaaactg 79320
attataaaaa taagcatcta agaatatctt aggcttttaa gattgacacc actgcttgct 79380
actcaattgc tagttgtggt tggcagtgca cgcagtgtct ttgtggtcaa gttcattgtg 79440
gcaagctcag aggtcatgtc agatcacaac acagggactt tgaattgggt ggacatccat 79500

```
tcattacgtg gcacacgtca cgagcttcaa ggttttgctt caaaaactct tctgtcttct  79560
aggtgaaagt ataagtttaa acttactgct ctttaagaaa gtaaatgaaa aatgacacta  79620
aagtcccaaa agccagaatt gtcagcaatc ctaggtgcag ttcattcatt cattcattca  79680
cgtattcatt caataaatat ttatggaggg cctatttacc tggcagcact tcatgaggcc  79740
ctggaaatac aatagtgagc aataaaaaca cactccttca ccaggtggag ctatagtcta  79800
ctagggagat atagatgtta aacaaattat cacacaggcc gggcatggtg gctcacacct  79860
gtaatcccag cactttggga ggccgaggca ggtggatcac ctgaggtcag gagtaggagt  79920
tcaagaccag gctgactaac atggtgaaac cccatcttta ctaaaaatac aaaattagct  79980
aggcatggtg gtgcatgcct gtgatccaag ctacttggga ggctgaggca ggagaattgc  80040
ttgaaccggg gaggcagagg ttgcaatgag ctgagatcgc accattgcac tccagcctgg  80100
gcaacaagag cgaaactcca actcaaaaaa aaaaaaaaat tatcacacaa acaagtacat  80160
aattctatat tgtgaagtgt cccaaagaaa aatatgccac tcttaataag tacaggaggc  80220
ttaatttgga aagttagaaa agtgatgttt aaagtgagaa ctgtaagaca agtcactttg  80280
tcagtgcaaa gtggaaagaa agtattttaa gtagcaagga gagcatgagt aaagaccacg  80340
gagaaggaaa gcgaggatgc agttagagac atgaaaggac tgcattggtg gggcaccggg  80400
atgaaggaga tgatgaagaa gatgtaacca gaaaggctgg cagggacaag gtcatgctgg  80460
gtcttgcagg ccagcatgag cacttgagat tcttaaagta attgcaaggg agcctttgag  80520
ggttttaatg agggcagtat ctttatcaga tgtgcacttg tttggggttt ctctggattt  80580
tgttgaaaga acaatttaag cagaaggcag attaggaaat aggagaatcg agaggctgta  80640
tatgttgaga cgcagtggta gtctagggtg acaatgcagg aaatgggaag cagtggatga  80700
actggggata tgttttgaag gtagaataga tgatggctgg gaagacagtg actattcaag  80760
ggcagggggg ttgggggagg tatcaagaat gtttagaata tagctaacca catacccttt  80820
tagaaacagt cttctctgaa catttctcct gtctccaagc ctcagtttcc tcatctatga  80880
aataagaaca ctactacttc ctttttaagg ttgttaaact ggttaaatga gattatgcag  80940
ggaaagcatc actagtcagt gctcaaaaat gtgcttttta aatttcctcc ctttgcctct  81000
tattctcaac tttgtccttt gtaatattat tgttctttaa gtgggcttgg ttttgtccta  81060
tctttgccca ttcactcact gctccccatc cacccaaatc ccctctgtat tctgtttatg  81120
caagactgag tttacccctt ctcagtccat tgacttatct ctcctcactc attgacttgt  81180
cccaggcaat ttattctgca atcttggaca aaaatctgga ttttcagcca ggtgcagtgg  81240
ctcacacctg taaacccagc actttgggag gccaaggcgg gtagatcatt tgaggtcagg  81300
agtttgagac cagcctgacc aacatgacga aaccctgtct ctactagaaa tacaaaaatt  81360
agctgggtgt ggtgacgtgt gcctgtaatt ccaggcatgc ctgtaatccc agctactcgg  81420
gaggctgagg caggagaatc gcttgaaccc aggagacgga ggttgcagtc aggcgagctc  81480
acgccactgt attccagcct gggcaacaaa gcgagacttc atctcaaaaa aaaataataa  81540
taattcatta tgtaatccag ctttgaaaca ctctttggct acacttttgt atgctttaag  81600
gaggaacaaa acacagatgg tctccaactt acattggtta aatctacaat ttttcagctt  81660
tacaatggtg caaaaacaat gtgcattcag tagaaactgt acttcaagta cccatacaac  81720
cattctggtt tgccccttca gtacaatgtt caatgaatta tgtgagatat tcaacacttt  81780
attataaaac aggctttatt ttagatgatt ttgcccaacc ttaggctaat gtaagtgttc  81840
```

taagcatgtt taaggtaggc taggctaagc tatgatgttc agtaggttag gtgtattaaa 81900
gcaagtttta cttaagatat tttcaagtta cagtgggttt attgagatgc aacctcattg 81960
taagtcaagg aacatctgta cttcagaagt catcaaagct gcatgagcag gacacaagtc 82020
atatgaaaag ccaggtagac ataatgctat aaaaaatccc tccattgggc cgggcacggt 82080
ggctcatgcc tgtaatccca gcactttggg aggccgggga gggtggatca cgaggtcagg 82140
agattgagac catcctgact aacacagtga aaccccgtct ctactaaaaa tacaaaaaat 82200
tagccaggca tggtggcggg cacctgcagt cccagctact cgggaagctg aggcaggaga 82260
atggcaagaa cccgggaggc ggagcttgca gtgagccgag atcacgccac tgcactccag 82320
cctgggtgac agagcaagac tccatcaaaa aaaaaaaaaa atccctccat tgtcagagtg 82380
tgagcttcca gctcattatc ccagaagccc gagatagcag cagttctcag atcttgtgat 82440
aaaggtcatc tcctatcctg gggctctcag gaccataatg caagagtctc cctctaaacc 82500
tgccagcccc agggcttttc ccgccttcct catcctaagt cctgaaaagt tcactgggcc 82560
aaatggtgaa ccacgcactt attgccccat aacccttggt acaaatgtct ccaaatatat 82620
ccatcaagcc tacaggtagt actgagaata acaacagtag ctaacattga ttggacactt 82680
ctaagcccct taaatccatt atcttactta attctcacaa cactgatcaa gagttggata 82740
aaataatcca ctctcaagcc agcaaatcta aaccagccac tcttccgtat ggattcctgc 82800
tcttatggta acaagggctt gccttcccca cctttattct taacccttct ggaaaacctc 82860
tgctcctcct tttctgagat ggaaaaattt ataagtgaaa aaccattcca tctttcgagg 82920
tgtggaggga ggaaaacaat cactcctgcc ttcaactaag agtgtgaaaa ataagcttaa 82980
ctaaacctga aatacatttt caaatgcctt tgaaaagact tataaatcaa atcacattg 83040
tccatctctc tgctcttcaa aattatcatg catgcacctg aagtttaagc aaagaaatcc 83100
attaaacaaa caaacctaaa atcataaaac ccagatttag agatttatcc gctcagtcta 83160
atgaatgccc aattcagaat acaattttgt cttcaaagag ccctgaaggt tcttatcttt 83220
cttatctttc tatagtgtta acagaaatat tacatctttg aaaagaagaa aaacattatt 83280
cccagagcta aaacagaaaa ggctttgaac tattttaggg ataaatcaac tcacagttac 83340
caataaacca aaaagaataa aaaagactgt ttcaaaccaa gttgactact cttacatata 83400
ttcaagtgtc aacttacaaa tcagtcttta aatatacacg tacactttct aactctcctg 83460
aaatgtcacc caagccccca ttcaatcagc taaaaacaat ttaattcttt ctctagggag 83520
gaaatcaggt tatcagataa gtaaacctta aataccattt ctaggcctga tgtggtggct 83580
catgcctgta atcccagcac tttgggaggc taaggcaggt ggatcacttg aggtcaggag 83640
tttgagaaca gcttggccac atggtgaaac cctatctcta ctaaaaatac aaaacttagc 83700
caggcatggt gacaggcacc tgtaatccca actactcaag ataatctgca taccaattgt 83760
gggtagacat aggtttttgt ccagagccct ccacagaccc atcccttacc taccattgtc 83820
tctcgggctt caaccttatt tgaaagtctt aatttgcagt tccacatact gcaaacacaa 83880
gacccagtct ttctggttct tattttacct ggagattaaa atacaggctg ggcgtggtgg 83940
ctcatgcctg taatcctagc actttgggag gccaaggtgg gtggattgct tgaggccagg 84000
agtttaagac cagcctgggc aacatggtga aacccctgtc tctactaaaa atacaaaaat 84060
catccgggtg tggtggtgtg tgccgacagt cccagctact caggtagctg aggcataaga 84120
atcgcttgaa accaggaggc agaggttgca gtgagctgaa atctcaccac tgcactccag 84180
cctgggcaac aaggcaagac tgtctccaaa aaaaaaatta agtttctgtc ttacaatatc 84240
ataagaaaat ggctggacag gttttcacca aagttggagg gtacttttgt gatgggtttg 84300
gtttaaattg gtttaaaata taagacacat agtccataga gaattcacct atggactatg 84360
ctgctaagag aatctcaaag agatgcactg ttatgctcca gagttttgtg agaggccact 84420
aaggtcagga gacacatgcc atatatatca agatgctgtc aacagagaaa accagtgagg 84480
tttcaaacag aagccccgct ccattcaacc aggcagccac tcctcattgc aggtgctgac 84540
ctgggctttg gctgcttctc acatgggcaa ctctatacac tctattcctg ggagaagggc 84600
agcaaagacc cacttattaa atgatgttta acaatcctcg gccgggcgcg gtggctcacg 84660
cctataatcc cagcactttg ggaggccgag gtgggcggat catgaggtca ggagatcgag 84720
accatcctgg ctaacaaggt gaaaccctct ctctactaaa aatacaaaaa aattagccgg 84780
gcgtggtgtc gggcacctgt agtcccagct acccaggagg ctgaggcagg agaatggtgt 84840
gaacctggga ggtggagttt gcagtgagcc gagatcatgc cactgcactc cagcctgggt 84900
gacggccgtc tcaaaaaaaa aaaaaaaata tcctccaggc aattgtgtga cagctggaat 84960
gaaaaatcag gggcaaattg tacatataag ggaacaattg ttcatatttg tgtaagctac 85020
cctccggagt ctacaagtta aaaggcacac tttaatcaat ttggcaactt gcatggcatt 85080
ttcctccact atttgtagga tgctggtatc tccttaacag ctactgtttt cctatgcaac 85140
acacaatgac ttcttgaaca catggcagct tttcatttgt tcatttaaca aatacttatt 85200
gagttactac tatgtgccaa acaccattat aaaggtactg aggatacagc ggtgaacaag 85260
atggacaaaa atccctgcct ttgtactaca ttcttgagtg ggtgtgagga gacaatgaac 85320
caaagaatga acaaactgtg tattgtgcag gtgtgtcatg ggaaaaaaat gaaggaggga 85380
agaaaagcgg aaaagcagaa aatgtcagga atgcacttcc gtggcgggtg gccagacagg 85440
tggccaagaa gtgacatttg aactaaagaa ggtataagtg agcaagctat gagggaattt 85500
ggcaaaacaa tttcggaggc ggaggtcaca gccagcaggt gcaaaggcct ggggcaggag 85560
tgggtccagg gcatgggacg gatggggaga aggtcagcat ggctgaagga agtagggggt 85620
aagctcaaac aagtcgcagg tgggaaactg agtgtattgg accttgtagg caattttaag 85680
aactttagtt tccactcatt aacatggaaa accactggaa ggttttgagc aaaggaataa 85740
cataatctgc cttttttttct tcaaatgctg tgaaacaaat acttatttga ccctatcacc 85800
atttctacct ttggaaaggc tatggtgtgt tactggatgt tgaggatagc ttactcttca 85860
atgtgcagta accaaactga attcattctt tctcaagatg agagaaagat aagccaggta 85920
tggtggcttt cttagataag ccaggtatgg tggctcacgc ctgtgagctg aggcgagagg 85980
atcacttgag gccaggagtt gaagaccagc ctgggcaaca tagtgagacc cctcatctct 86040
taaaaatttt tttttagtta gccagacatt gtggcatccg cctgtaatcc cagctctttg 86100
ggaagctgaa gtgagctatg atcacgccac tgcaccccag cctgggtgac agagtgagac 86160
ccccatctct aattttgaaa aaaagactgg atagggcctg gttaatacaa ctaactcccc 86220
aaaattcaag tttttcatat aggtcttttt taaaaaatag ctttaattga cataaaattc 86280
acccatttaa agtttacaat tcaatggatt tttatatatt cacaatgtag tacaaccatc 86340
attataattt tttttttttt tttagacaga gtctagctct attgtccaga gctggagtgc 86400
agtggcgtga tctcagctca ctgcaacctc catctcctga gttcaagcga tcctcccact 86460
ttggcctccc aagtaactag gattacaggc atgtgccatc acgcctggct aagttttgta 86520
tttttagtag agatggggtt tcaccacgtt ggccacgctt gtctcaaact cctggcttca 86580

-continued

```
agtgatccac ctgcctcggg tccaaagtgc tgggattaca ggcatgagcc acagcacctg  86640
cccgtaatct acgttagaac tttttatcat cccatcaccc atttaagtct ttacccatta  86700
gccatcactc cccattttct caacccttcc cgcaaaaccc ctacccagcc ttgggcaacc  86760
actaatctac tttctataca tttgcctatt ctgaacattt catatcaatg gaatcatact  86820
acatgtgaca ttttgcatct ggcttcttag aataagattt tcaaggttcg tctatgttgt  86880
agcatatatc agcacttcag tccttttgag ttttttttta acaatcttta ccattttcaa  86940
gtgtatcgtt tcatggcagt aagtatattc acactgttgt gtaaccatac ccaccatcca  87000
tctccagaac tcttgtcacc tctccaaact gaaactctgt acccattaaa caacaattcc  87060
cattccccac cccaccccag tccctggtat ggcaaccacc attgtacttt ctgtctctat  87120
aaatatgact actcatactt catttttttaa attgccaagt aatgtttcat tgtatggata  87180
tactgtacaa caatttaact atccattcag ctaatggaca tttggggttt ttttaacctt  87240
ttggctatca tgaataatgt tctgatactt cgtgtgtgtg tatagataga tagataaatt  87300
aaatagaaga tagaagagag agagagagat tggagacagg gtctcactct gtcactcagg  87360
ctggaatgca gtggcaggga cacatctccc tgcagcctca acctcccagg ctcaagtgat  87420
cctcccacct cagcctccca agcagctggg actacacgca tgtgccacca cacctgacta  87480
atgtatgtat ttacttattt atttatgtat tgtaaagaca gagtctagct atgttgccca  87540
ggctggtctc aaactcctga cctcaagtga tccttcctac ctcagcctcc caaagtacca  87600
agattacagg catgagcccc cgtgcccagc ctgatacttt ttttttaag tattattcca  87660
gttgccttgt tgaaaataga ccccaagaaa gcaaatctca aacagagaaa actgctagga  87720
agttcttgct ggaatccagg tgagaacgga tagaggctca catttaaatg aagtagtcag  87780
aaatagccac atttggatgt atttttatac aattcctgct cctgaagtct tccccactcc  87840
tttttttttt tttttaacca ttactacaat tgctttgctg ccttttttgct gatttattgg  87900
atcacgtgtt taaaaccctg atgtgaacac ctacatttat ccttcttact gggtatgtgt  87960
taggtattta acaaagtctt agttctcctg gagtctgcct gcatgaacca accaaatata  88020
aatctgcaaa atgggaactc tacagtgtct cttcagtttt gctgtcaaga tttcacagcc  88080
tcagcttcta aaattatttc atcaagttca atggatacat attcttgaac tcttttctag  88140
cctatatttt ccaacaatgt tgctaactat atttccatac cagccttctt atctaacata  88200
ctggttaaaa tgtcaaaaag cagagggttt aaaaagcttt tctcggtgga atgtgcttct  88260
ccttcataca tgatataact tgatttgaac aatgtcacaa agatattttc tctgttagat  88320
taaaattttg tttgcatgaa tttttcaata gctttaagca gttgaatagc aatatatgca  88380
ggaagaagct gagagactta tgtaatagat atttcatgta tctataaccc acactgctgc  88440
ccaggaaatg tgcgctgcat taatagagag gattttttcc tgctgaatac cttgaggagt  88500
tggccaacac gtttgggagt agaagtagaa agggccaggt gtgatggctc atgcctgtaa  88560
tcccagcact ctgggaggcc aagtggggag gattgcttaa gcccaggact ttgaggccag  88620
cctgggcaac agagtgagac tccatctcta aagaaaaaaa atcataaaaa actaaaattc  88680
tctgccaaaa tggacacaga aaaaactgac aatccagaga aagataatat gcaatgaagc  88740
tagacatggc caaattagaa aatgatattg agagagaaca agagcaagaa agaggagccc  88800
tcagcattga gagggctgag gaagcacaga aatgactgat gggttggtta gttagttact  88860
ttttgtgaag tgtgcaatgt aaatttcact ttggtctccc caccggaatc atcaactaaa  88920
gtctacactg ctatatcggc tatctattgc tgtgtaacaa attattccaa aactcagtgg  88980
```

cttaaaacaa cacatttatt atctcacagt ttctgtgggt taggaattcg aagatgggcc 89040
ccctgcttca gggtctccca tgggttgcta tctaggtgta agctaggtct catctcaaga 89100
ctcaactggg gcaggatcca cttccaagtg cacccacatg attattggca ggattcgttt 89160
cccatgaact gttgtcagaa gccgctttca gatccttgcc acgtgggcct ctccgaaggg 89220
cagctcacaa cacaacagct tgatttatca gagcaagcag gcaatgaggc agaacaggga 89280
cctctcttag ggacatgcag cactcccacc ctcaaacata gaaataaaga aaaatcttaa 89340
gttcctttaa gaaaaattcc aggcacttag ctagccctta aaaaataaat aaggccgggc 89400
acgggggctc atgcctgtaa tcctagcact ttgggaagcc gaggcagttg gatcacttga 89460
agtcaggagt tcaagaacag cttggccaac atgacaaaac cccatctcta ctgaaaatac 89520
aaaattagcc aggagtggtg gcgcatgcct gtagtcccag ctactcagga ggctgaagca 89580
ggagaattac ttgaacccag gaggtggagg ttgcagtgag ccgagatcat gccattgcac 89640
tccagcctgg gcaatggaga aagactctgt ctcagaaata aataaataca tcaataaaca 89700
acttaataag caagaagata atagtagctt agaataatgg gcaaaaaagt taaaatcatg 89760
ggatgtttgg cttccctata aaaactaatg ttcatagatt gtttttcaaa aatgaggact 89820
ccccactaaa tgggtccagc aacacacaag gtccagcaac acaactcaga taagggggac 89880
ctgaaggcta aactcttaac acttttctca gttctaaatt tcttcctaag gggagtagag 89940
gaagtcacac cccaggccag aactaacatt ccactgatct caaattttta gacaaggctt 90000
ctcctcctaa gccaattaca aatcaaaaca tctttaaatc tacctttgac ccatgggttc 90060
ccactttgag acgtcctgcc tttttaggtc aaaccaatgt agagcctccc atatattgat 90120
ttataacttt gcatgtaacc tctgccttcc tgcaattaca aatccttacc tataagccat 90180
ccgggagctt gggacttaag cattaactaa ttatctttgc ttggtgcccc tccaataaat 90240
accccacttc ctcttgctac aatcccaata tcaatgtttg gttttgctgt gctgggcagg 90300
gggacccaag ttaggttcag tatcagcaag aaggcaagac agagtgtgtg ctagcaagac 90360
agaagtccgt gtgtttggta acctaatctc aaactgaaat gccatcacct ttgctgtgtt 90420
ctactgatta aaagctagtc acccatatgt tcattgcagc actattcaca aaagcaaaga 90480
cattgaatca acctaggtgc ccatcaatgg agaattggaa aaagaaaatg tggtacatat 90540
ataccatgga atactacaca tccataaaaa ggaacaaaat catacccttt gcagctacat 90600
agatgcagct ggcagccatt ttcctaggtg aattaacgta ggaatggaaa accaaatact 90660
gcatgttctc atttataagc aagagctaaa cgttgggtac acatggatat aaacatatga 90720
acaataaaaa ctggggacta cagctgggca tggtggctca cacctataat cccagcactt 90780
tgggaggcca agctgggcgg atcacttgag gtcaggagtt caagaccagc ctggccaaca 90840
tggcaaaacc ctgtctctac taaaaataca aaaattagca gggcgtggtg gcaagcacct 90900
gtaatcccag ctactcagga ggctgaggca tgaggatcac ttgaatttgg aaggtggagg 90960
ttgcagtgag ccaagatcat gccactgcac tccagcctgg gcaacagagc aagactctgt 91020
ctcaaaaaaa aaaaaaaaaa aaaaaaaaaa aaaaaaaacg gggactgcta gatgagagag 91080
aaagggagag acaaaagggc tgacaaacta tgctcactat ttggatgaca gaaccagtca 91140
taccccaaac atcagcaaca gacaacatac ccatgtaaca aacctgcaca tgtatcccct 91200
acatctaaaa taaaagttga aattataggc tgttcgcagt ggctcatgcc agtaacccca 91260
gcactttggg aggctggggc agaaggatca cttgagccta ggaaatcaag accagcctgg 91320

```
gcaacatagg gagacttcct ctctacaata aaattaaaaa ttagccaggc attgtgatgt  91380
gcacctgtgg tcccaactac ttggaaggct gaggtgggag gattgcttga gcccaggagt  91440
tcaaggctgc agtgagccgt gattgtgtca ctgtactcat cctgggccac agagcaagac  91500
cctgtctcaa aaaaagagac agctcactgt cagctcactg caaccccccac ctcctggatt  91560
caagcgattc tcctgcctca gcctcccaag tagctgggac tacaagagcg caccaccata  91620
cccagctaat ttttgcattt ttttttttta gtagagacaa ggtttcacta tgttggccag  91680
gctggtcttg aactcctgac ctcgtgatcc gcccgcctca gcctcccata gtgctaggat  91740
tacaggcgtg agccaccgta cctggccgag aaattatttt ttaagtgaaa ataaaaaaat  91800
aaaagctagt cactaggtcc agcccacagt cagggcaagg ggtcacaaaa ggacgtgaat  91860
atgaggtggc agggatcatt tggggtcatc ttagaagctg tctaccacaa tgttccacta  91920
tgaattattt cagaggattc acacctgggg caaggaggta catcgatagc atgcaaccag  91980
aaggagtcct gagacagtca tttgcagaaa ccctggtgaa gttttggttt tccttggcca  92040
tgcaatcagg ggctactcac tggctgatgg actcagctga cacccagatt aatttgagaa  92100
ctgtatccac agtcattaac tacggggcag tgcccaactg tccccaagcc agaagtaaga  92160
ggtatgcatc ttcacgacct caatgacaaa cttgatcata taaaataggc agcattaatt  92220
gacctggttc aggctacgcc ggaggtggac taccacctgg aaacagagag acattgcaga  92280
agcttccctg aggttcccct tgcagccttc aggggtgaat tctttgacac tgggtgtttg  92340
aaatggagca atcaaggccc cagcaaaaaa cagatgcaca ctccaatggg gtaattgagg  92400
acagtttagg aaagagatta tttacagaag tgtggacagg attaagagaa aacaaggatg  92460
tggagcacgc tggtattatc aacagtgggg tctaaaaggg aaggagagag agagagagaa  92520
tcctggaacc cagagagagc tgtcgctgta agacagaact gcccaacagg aactgtggcc  92580
tttagggaga aactgagcta ctgcaaactc tcagcccgga aggaaagaag ccaaaggaat  92640
aaataccctg acctcccctt ccaccctcca atctcctact gggtccccac tggccagtct  92700
ggctccctgg gcacaccaga gttgagaaga acggacagcg gatttggagg cgcaagaaga  92760
aagtatccaa aacctagaca gaaagccagg cagcttcaca tgagcttttt aaaagtgtag  92820
aagtcataaa aattctcctg gaaatgagca aacacatggg ctttcagaag atgaacacaa  92880
aatagctttt aaaatgaaag tctgctctgg aagggaaaag gtggttcctg gcaatgtgca  92940
gaggaggatt aaagtcccca ccctcaactc cagcctgctg cgtcttccaa gagagaattc  93000
cccagagcct ggactaggga agcattggcg ccactgggaa aagctgctac agcccttgtt  93060
gggcggctct ttctcacagc tactgaagct gcctttgcaa agattatgac agtgagagaa  93120
tctggtgttg ctgactccat cttgtttcta gcctcacagg ctaactgtcc tcactcattc  93180
ctgggcatag gccaagttaa tcatgagatg aattttttta ttttatttat ttgctttttg  93240
agacaaggcc tcactctgtc gcccaggatg gagtgcagtg gcatgatcac ggctcaccac  93300
agcctcgaac tccctggtct cagggtggtc ctcccacctc agcctccaga gtagctagga  93360
ctgcaggcgc atgttaattt ttttgtattt tttgtggaga tggggcttcg ccatgttgcc  93420
cagtctggtc ttgaactcct gggctcaagc gatctgcctg ccttggcatc ccaaagtgct  93480
gagattgcag gtgtgagcta ctgcacctgg ataggtattt agtttatagt ttaatttgaa  93540
agcaaggatg ataatagtgt tccactaaaa ctgattccct cattgtttca gggctgaaac  93600
cacctttgta aaactaagga aaggccacaa gattagggag gggcctgaat tctgctaaaa  93660
tggaggcata gtcttaggca tagttttaga accagccatt gttctataag tcacaagatt  93720
```

-continued tgtgacttcc ccaattgctc ctatagataa catcactatt atagaaccta ggattggtct 93780
tttgagatgt ttttcagact ttgcattctg gcaaataact gaccccacct ggacttgtaa 93840
ctcatgactc aactggtcct gtggccccta cccagaggtg gactcagagc accaggacca 93900
tttcccacac ctctattgca tccccaacta atcagcagca tccattgcct agtcctctgc 93960
ccaccaaact atttttgaaa aaccacaggc tgggtgcggt ggctcatacc tgtaatctca 94020
gcactttggg aggccaaggt gaggggatca cctgaggtca ggagttcgag accagcctga 94080
ccaacatgga gaaaacctgt ctctaccgaa aatacaaaat tagccgggca tggtggcaca 94140
tgcctgtaat cccagctact tgggaggctg aagcaggaga atcacttgaa cccgggggc 94200 ggaggttgtg gtgagccaag agcacaccat tgcacaccag cccaggcaac aagagcaaaa 94260
ctccacctca aaaagaaaag aaaagaaaaa ccacaacctc caagtttttg gggagactga 94320
tttgagtgat aactccagtt cttccacatg gccagcctca agttaattaa actctttctt 94380
cactgcaata ccacagtctc agcaaactgg ttttgtctat gcagtgggta ggaaggttga 94440
gtaatcacac tacagttctt tctggattcc aggagtctct ctccccttcc cttttagacc 94500
tggttggtaa gggctctgtg ctgttgacag ttccagagta cctcacatcc tttgtttcat 94560
ttaacccagt ccatgcttct gtaaatactc tctttgctaa actctcctca agtaattgat 94620
tttaatgtgc atccattgcc tgccaggacc tgattagtcc atttcaagca tccaatatca 94680
aagaatgcac ccaaaacaaa gacgctgtta ggaaacacag aactgggcac tgcaaaggtc 94740
tttgagcatg acacaaggat gttgcaagag cggcaggccc agaaggcaag tggggattga 94800
agaaccttaa cagcatattc acggggctca gtcctaggat tcagcatcat gacatatcac 94860
ctccaagctt ccatgctttc atttgtatag ctaagacttg acaagactag tgagggtgtc 94920
cgatgatgag gacagtcaag gatgttaaat tcctgactat acattaacaa ggaggaaaaa 94980
aactaacaaa cctgcatcag tgtgaagacc agaaaggcct gtccacagag ccagatgaca 95040
aggtacaaca ggatgctgtt gaaaaaaatc agactagata agagcaggtt gctgtgtgag 95100
caaactcaga ccatacaaga gaactatagg cccctctcct ccagcccaga attcctgccc 95160
tgagtgatgc taaatcagaa ggaagaaaag caggagatga tattggctac cctccgggga 95220
caggaagcat cacctggttg gactaccaga ctgccattca cacttatata catggagtca 95280
gtcgggtatg actcagtccc ctgaggccaa atgtcagcga ggagagtggg aggagcaaat 95340
ctctctcctc cattagagtt gtctccggaa caaacccagg tctcaaggca aaggcctcac 95400
acactatttt gctattttgt cacccacgta aagttttcag aaacaggatc cctgtagctc 95460
atcaggcact caggtgcatc aaagctgaat tcagggtaaa gattgatgct gtggcccagt 95520
gaagctgaga tgcccatact ctctctgttc aggttataga gaaaatgggc actttgtgat 95580
cacttatacc cataataaaa aacaatttgt gtgcatctca tgagcaagaa aaataaacag 95640
gaaaaaagaa agcaacccaa ctacttgtaa gtataaggaa atccaaccca tatttgttca 95700
tataactgaa aggtccaggg gcaaacctgc aggtatggtt tgatgcaggt gccaacatct 95760
tttgccagga cccagtgttt ctcacaccct ttcttttttc ttttttctt tccttctttc 95820 tttctttttc tttttgtctt tccttctttc tctttttttt ttttaacagg atctcactct 95880
gtcacccaag ctggagtgca atggtgcaat ctcagctcac tatagcctca acctcccagg 95940
ctcaagcaat cctcccacct cagcctcctg agtggctagg accacaggca tgcaccacaa 96000
tgcccagcta attcttttca ttatttatag aaacagggag tctcactatg ttgccagggc 96060

-continued tggtctcgaa ctcctgggct catgtaatcc tcccacccac ctaagcctcc caaagttctg 96120
ggattacagg tgtcagccac catgcctgac ctcacaccat ttcttaactc cattcttctc 96180
actccatttc ttaatttcat tcctttataa agcttctctt cttactattt caagatggct 96240
gcccaattca tgtgcagagg aaagagaagt tctttctctt tactctgaca gttgaataaa 96300
aaatccaaag cctggctctc tttggtccat ccctgaatca gtcattatgg cctggggaat 96360
ggagtatgct aattgactta agggaatcag ggcccagcac tggagtgaag gtggggctaa 96420
tgccacctaa tccactggag agtaccaaaa gtgtgcttcc ccaaaggaaa ttcacaatac 96480
tgtgggaaag gatgaattga tgctgagtca ctatgaatga caaatgcaaa agataaacat 96540
accaggcccc actccttgca ggaagcaaaa gatcctagag ggagaggctg acatggaaca 96600
ggatgtctga ccaataaaac ttcttccaat gaggattcac agacatagtc ataccttcca 96660
ggttaagtaa ggctcaattc caggcagctg tctgtctcag ctcctcatgc acatccgtcg 96720
cttctgtcta cccagcattt gtttctccct tattcagttc tcattgctgt gtaacaaatt 96780
gacagaagtg catcaactaa agcaacacaa atgtattatc tcacagctct ataggtcaaa 96840
atccaagcac ggctcaaccg gattctctgc tcagggtctc atggggctga aatcaaggtg 96900
tcagctggag ctgtagtctt atctaaagct cagggtcttc ttccaggatg attggttgtt 96960
ttcagacttc cgctccttct gattatcttg agataggagg caggacttga ctctggaggt 97020
ggggcttgga caccggacca agttcaggac taactaaaac agagctggga gggaagcagc 97080
tttccctaag acacacccac cagtgtgcca ggtcagttta ccattgacac ggcaatacct 97140
gggagttacc accccttcc atggcaatga cctgatgacc taaagttact accccttctc 97200
tagaaagttc tgcagaaacc acccttgaat ctgcatataa ttaaaagcag gtataaatat 97260
gactgcaaaa ctgcccagag atgccactct ctggttacag ggtagccctg ctctgcagga 97320
gccgtcatgg agctgtaaca ctgcaggagc tgtaacacca ccgcttcagt aaagctgttt 97380
tcttctacct ccagcttgcc cttgaattct ttcctgggca aggccaagaa ccctcacagg 97440
ctaagcccca gtttggagtt catctaccct gcatcaatat gactgaggtc tttttcttg 97500 ctggctatcg accagagacc tctctcacct cctaaagaca aacctaggtc cttgccctgt 97560
ggcctctcca taggctttct cacactttga gcatctctga cttcaggaag ggcctagtcc 97620
cttttaaagg tgcacctgat taggtcaggc ccacccagat gctctccctt ttgattaact 97680
caaaatcaac taactagtag cccagtcagg gcagggctat tccatcacat cctctaattg 97740
tgcagcactg gagaggagga gattgcacag attgtgcaca ccagggagca gggatcttgg 97800
gggccatctc agaattctgc ctaccacatg ttagtaattg atctcttctg gaatcagtcc 97860
tttcctgctc agtcaatgtt atttgtggta ggatttaggg taatcagacc tagccttggc 97920
caattggtgt aaccattgtc tgggccacag tggtcagatc agaaatgggc acctgcctca 97980
agcaagccca atcagaccta acctggggac ttttgctgaa gtaactagga aagatctctc 98040
tctctctctc tctctctctc tctctctctc tctctttctt gttattgcgg aagtgttagg 98100
ctgtaaactt agagctgatg gtggacacca tgtgctttga ttcaaatgac cccccaaaac 98160
tcatgttgaa actgaatccc aaaagtggga gcattgagag gtgggacctt taagaagcga 98220
ttgtatccct cttgagggca gagcctttac tgaccaccta atgttttatt aaagcttgtt 98280
ctgcaccacc cctatcccta ccatcaccat ctggagctct cgatcctttc ctccagattt 98340
ctttgctcca taatatttat cactatctga tacaggggtg tgtggatgtg aacatgtata 98400
tgtgtgcatg tgtgtgttta tggtccgcct ctcccagtcc ccggtagact gtaagcttca 98460
tgaaagcagg gctttgtgta ctgttgtttc tgtagcatga ggtctgccaa aaaagtaggt 98520
tccccataaa tgtttgttaa atgaatatat tctgattcta tctccccctc ctccagaatg 98580
gatctaaagc ttcccaatct ttgcctgagt gagtgtccta ctgagttcaa ttttgtttca 98640
gaaaggacgt gtgtatgttc acccatatgc tgcacaaata tgtaatggac accagccatg 98700
accagcctac tggggactgc ttggcagtag caacatggca gcgaacaaga cagatgagcc 98760
tcctgcccac agaagcttac attcgggtgg aatacaggct ggtgagttgt catgccgatt 98820
cctccaaccc aaaacccttg ccagtatggc aggtcctgga gctggactgg ccaccattga 98880
gaatccaccc aactgcccat cagcatctca agttccctgt tgcaagatgc cagggagcat 98940
gagagaggac cgtgggggag agtgagctct caatgaacct ggtgtggcag ggagaagacg 99000
aagatggggc agatccccag gggaagaca acttaagggc agatttgttg aactaagtta 99060
cttcaaaggg tcttccatct tccagcatga gcagagaaga tgaccacaca cctgggggag 99120
agtcagatgg cttcttcaat tggaacgttc ttccctaagg atgagctaat atagcacatg 99180
acctgaaaat ccttctggga gactccaggt aaaagggcct tgactgcacc agggagagaa 99240
gctaagttgt agatttgggg gaaatgagtg ttagaacagt gagtgctcaa gggaagtagt 99300
taagtgagcc atgagataca aagtctgcca tggcaaagta ggtggaacaa ccatgttatg 99360
agtataagtt ctgaccccag ctttcctgtg atttctacga cccttggtct tgaagatggg 99420
aaataaatgg gtgcatgaca gaagttaaag actattatcg ggtatcaagt accatagcac 99480
tttttggagg cagaagagct tgacaaatgg gcatagtgta catagtaaat gatggtaagg 99540
gtaaaggata aaatgtatca tcttcctgtc atcagaatgg gaccagcact gtgtaaggtg 99600
ggcatgttaa tgacatgata tataagacag cttttgctac aataacaagg aactccctag 99660
gcctggcacg gtggctcatg cctataaccc cagcactttg ggaggctaag gcgggtggat 99720
tacctgaggt caggagtttg agaccagcct ggccatcatg gcgaaaccct gtctctacca 99780
aaaaatacaa aaattagcca agcaaggtgg cactgcctgt aatcccagat actcgggagg 99840
ctgaggcact agtggtgctt gaacccagga ggcagaggtt gcagtgagcc gagatcactc 99900
cactgcactc cagcctgggt gacaaagtga gactccatct caaaaaaataa caataactta 99960
aaaaaagaga aatagctctc aaatcccaat agatccctat aacaaatatt tgtttcttgc 100020
ttctgagtct tcagattggc tgtgattaca ctgggtttgg cttggctgag ctcagctagg 100080
ttctgctgag ctcagcttgg ctccaaggtt tgggttgagt tcaggtctgc tccacatgtc 100140
ccttcacatg agaagcaatt gccaagaggt caagtcaaat catgcagcac atttaaaact 100200
tctgctgggg gaaaatgtgt ctgctcacat tccaatgacc aaagcccaaa gttagaaggg 100260
caaggaatta gactctacct attgagatgt actacaaagt cacatggcaa aaagcttata 100320
attctaataa aggaactaag cagaatcact aggagcaatc acctagtccg ccacacatgg 100380
agatgtgcca cagggactca gagactggaa ggaattcccc agggccagag ttctcctggg 100440
aaactacagc ctccaccatt gcctcccaga tttcatcagc atctctgtag tctggctcat 100500
cagaggccac aacggagata aaggcaaata aagacttcag ctgctggcaa gctgcagata 100560
tctccatgga tcagccaagc ccatgtctct ttctgaaaca atcagtaatc ggggaagcga 100620
ccacagaaaa gcgtaataca aactacctat ggtattggaa gaatcccagg aatcgttgga 100680
ggtcttgaat gaatttgaag agggtactca gttcaagact actttaagac acacactttg 100740
tagatgtccc aactagatac tgtgtggcct gggaattctg caatgtttac tttttttcaa 100800
ttatattatg ttataatata tttataagaa atatatatca tatataagat tatatatagc 100860
ttatatatct atatataatc tagatatatt atatatctaa atataatctt tgatatatat 100920
ctcatatatt atcttataca tatgatatat tatcatatac atgagttata cgtatctcat 100980
atatattatt ttcttatata tatgaaatat atctcatata tataagatat gagagctata 101040
tatctcatat atagatagat atagatatct atctacatct atattcccag gccacacagt 101100
gtctagttgg gacatctaca aaatgtgtgt cttaaactag tcttgaacga gtaccctctt 101160
caaattcatt caagacctcc aacgattcct gggattcttc caataccata ggtagtttgt 101220
attacgcttt tctgtatatg agatatatat ctcatacaca gatagatata gatcattcca 101280
tcacccaggc tggagtgcag tggcacaatc atagttcatt gcagcctcaa aattctgggc 101340
tcaaccgatc ctcccacttc agcctcctga gtggctggga ctacaggtgt gtgccaccag 101400
gcgggggcta atttttcttt ttttggagac agagtctcac tctgttgccc agactcagat 101460
gtagtggtgc aatctcagct cactgcaacc tccacctccc aggttcaagc agttctcctg 101520
cttagcctcc caagtagctg ggactacagg cacgtgcaac cactcccagc taattttttg 101580
tattttacta gagacgaggt ttcaccatgt tgcccaggct ggtcttgaac tcctgagctc 101640
agatacctgc ccgcctcagc ctcctaaaat actgggatta caggagtgac ccacccactg 101700
cccccagcct tttttttttt tttttttttt tttttttttt ttggtaggga caggatttcc 101760
ctatgttgcc catgctggac atgaactcct ggcctcaagt gatcctcctg cctcagcctc 101820
ccaaagtgct aagattatag gtatgagcca ccacgcctgg cccaatattt ctaaaggccc 101880
ctcaagaggc aaaagtgggc aaaggacttt taaggacaaa aaatgcctag tattgaatat 101940
taagttgttt actgtgttgt aactctcttc catgacttca gtaaagcaga gtaagcacac 102000
acatgcccca agacacagta acctctgttt ggtagtacag cccatcacaa gcagctgtgg 102060
ctgaacccct gggtaccagg actagagagg ataacttcat tgtaagttcc actggatgtt 102120
aggctgaagt tgcagccccc atcaagccag gcttggtgtc tggagcgggc ctgaaggtag 102180
agattctgca aaaggatcta actggggtga tattcaaaaa atttagaagc cagaatggca 102240
caggtcctga ctgataagaa ccagagccaa catgctgtga tctgcataca agtgccagtg 102300
atccctgcct ccagctgagg agggctgtga aggatggagg ctagaaatcc atcaggagag 102360
ctgacattga aaggtgaatg ggagcagcac ctgccagcgt gacctgctgc tttcctgcat 102420
gcaaaggact gtgcatttca acctgagacc ctggggttcc tgcagggcat cagctagatt 102480
tgtcttcctg cctggggcga tcaccaatta tatgtgctgt gaggcaaact gtcctcccac 102540
cagaggagga ggtgaaggga tttacagaat ctctctctga tctgacttat tagagaagtt 102600
aaaggacacc tgtccaggag gcagcacagt gcagagataa agaagtcagg attcaaattt 102660
gtcctatctg ggaagcttag acaagagctc cttaacctct ctcacactca gtcccctcat 102720
ctggaaaatg ggaatcctaa cagtgcctac ctggcaggag catggccaca atgaaatgag 102780
ctaatgacac agtgaaagcc cttagacagc ctgacccaga gtcagccctc tgtaatggga 102840
gtcattattc aagatgggag gaaagaaaca ggaattagat cagaaacaaa tgaccagaaa 102900
gagagatgaa atacaaaagc tacatgaagt cggcagtgtg aagcctgact cgcaggagag 102960
tggattttgt tactgtttgc tttttcttgt ccaggataat ccaagactgg cagaaagtga 103020
gaataccgat tgagatccaa ggacatcctc atgggagtct gtgcagacac gttttcatca 103080
agaacccctc tccaagcagc tggtccagcc cagctaaact gggggctgct gtttgtaaga 103140
aaattaatgc tctgggccaa gcacggtggc tcatgcctgt aatctcagca ctttaggagg 103200

-continued ccaaggcagg cggatcactt gaggccagga gttcaagacc agcctggcca acgtggtgaa 103260
atcccgtctc caccaaaaat gcaaaactta gctgggcatg gtggcgcatg cctgtaatcc 103320
cagctactca ggaggctgag gcaggagaat cacttgaacc cgggaggtgg atgttgcagc 103380
gaaccaagat catgccactg cactccagcc tgggtgacag agtgaggctc catctcaaaa 103440
acaaaaacaa aaaaaattaa tgttctgtac ctgaggagca cccatttgct gctacttccc 103500
tgccaggatg aaggaaaacc aagtcagaca ttaaataaca cgtgcaggat cacaggatca 103560
cacctttcac actgcagtct tagttttcta taaaaccacg tgacctctga aaatacactc 103620
cagcctctgc aacacctact catgacgctt tgtaaaatcc accgcctttt agggacacca 103680
agattttcgg aaacatgcag ttttcttacc tccagatgag atgtctactg tggataggtg 103740
actaggagga gaacccaagg tgtgctgatg gcagaacaga agcacctagg atgccaccag 103800
ggaaacgccc tgacaagcag ctgtgatgct gtcttcgaga aggtgtttgc aaacaccact 103860
gctgcccccc ttccctgagc cctgacttcc taaacctaag gctaaaagca tcctggcaat 103920
tcccggaagt aacttcattc tagcaggatc gagccagtgg gtggagtttt ctcagcccgc 103980
caggatcaca tcagtgactg acttacccaa tgtactttta tttttattt caaccaattc 104040 cccaaagccc agagcaactt aaaaccagaa gagccaccac catctccacc aaaaacaggg 104100
aatattttga gagtttaatg ataacttcac agccatccat tcagctgagt cccaaggaaa 104160
tggaagacac ctgaaaaatg tatttttaaa ttgatttaac gttgagccat gttaaatgtt 104220
ttaacttcca accaatgcaa tgcccaccaa aacatcaatt agtcccagca atcaggcaag 104280
aatattggct tctgctcagg gattcattta tttcagctct gctaaatatc gtagaggaga 104340
aatccaatgt agcctgtagc ttcaagaaag tgaaattaag cccaagtaga aactagatga 104400
ggccctggct aaaatggtgc cttttcttgc actgcctctc tctggtatct ctctaaagtg 104460
agggcagcaa cttgattgta agggtctcgt gctgttaaca gaaaacaccc ttccttcccc 104520
acaggttctc tgtctccaag ctggaaaaca aaagaggctg caatgggaca gagaagggct 104580
tcctgctgag gagatgagtg ggcttaagaa tttgcaagat caaaaatcaa aacaattaaa 104640
cccatggaga tagagtagaa ggagagtgaa cagaggctgg gaagggtaat gggagagttg 104700
gtggggagga ggcagatggt taacgggtac aaaaaaaaca gaaagatgag taagacctac 104760
ttttccatag cacaacagga tgactatagt caacagtaat ttttttttt tttgagataa 104820 cgtcactctg tcacccaggc tagagagcag tggcatggtc tctgcccact gcaacttctg 104880
gctcctcagt tcaagcgatt ctcctgcctc agcctcccga gtagctggaa ttacaggcgc 104940
acaccaccat gtccagctaa tttttgtatt tttatagaga tggggtttca ccatgttggc 105000
caggctggtc ttgaactcct gacctcaggt gatccacctg cttcggcctc ccacagtgct 105060
gggattacag gcatgagcca ctgcacccga ccctatagtc aataataatt taatcgcaca 105120
ttttaaaata actaaaagag tacaattgga ttgtttgtaa cacaaaggat aaaggtttga 105180
ggtaatggat accccatttt acatgatgtg attattacac atcgcatgcc tgtatcaaaa 105240
catctcatgt accccataaa tatatatacc tactatgtac taatgaaaat taaaatttaa 105300
aaaaattaaa aataatttgc aagatcattt ttaataatta tttttcattt ggggtgcatt 105360
ttcaccatca aggccccagg gtttccctgc cctagatgag ggtctggatc cagggaaggg 105420
tgtcccacca tctggagcat cctgtctcta cacatgttgg ccagctgctt ggggcaacac 105480
aggacgatgc gctcaggcca ctcaccacag gagcttggcc attagaacca gcaggggaca 105540
accaagccaa agaccccacg actggagagc tcctaaaagc aaatacaaaa taagagtaca 105600
catgaagttc tggcagcaag cagaaggtag acacatgatg tccaactccc cgagtctctc 105660
tctggggcca cttgatgcag agccttgatt tgttcgtctc ttaaatggga acaatgatcc 105720
ccaaagagga ggaggggtgg gggagtgaga attaaatgag attgtgtcag tcagcatgta 105780
ctagggagct tgttagaaac accaattcca ggatcccctg gagattctga tttagcaagt 105840
ctgccaggag acccaggaat ttgtatttta agcatctctc ccaggtgatt ctgataatta 105900
agcaacttta ggaaagaaaa gattagggct ctggtccata ggaagggttc atccaatggc 105960
agccctcact taggcccttg ggtgaatga aggaggggca tccaggatct tgcccagcca 106020
gggacatgca ggaaacatct ttttaagggg ccctcatcac tttctgacac tgctgtttca 106080
agggaaaact ggtcacacct ttctgcaggg gatttgacaa catccattaa aaaaaaaaat 106140
ttaagacaga gtctcgccct gtcacccagg atggagtgca atggcgccat ctcggctcac 106200
tgtagcctct gtctcccagg ttcaagcgat tcctctgcct cagcttccct agtaactggg 106260
actaaggcat gtgccaccac acctggctaa tttttgcatt tttagtagag acggggtttc 106320
accatattgg ccaggctcat ctcaaatttc taaccccaag tgatccacct gcctcagcct 106380
cccaaagtgc tgggattaca ggcataagct gccacatccg accaacatcc atcaaaatta 106440
taaatgcaga ccctgtgatc tagcaatctc actttgaaga gtttatccta cagacatact 106500
tgcacagatg caaattatat caggtcagga gctgcagcat tgttcataac agcaaaaaaa 106560
aaaaaaaaat agaaacaact gcaaggtcca tctacagacc tctggttgaa tacagttacg 106620
gcatagccat aaaaccaaca atggcacagc tcctgtgcac agatacagaa ctccctccaa 106680
agtatattgt taggtgaaaa atacaaggtg cagaataagg tgtataataa gcttttgtga 106740
aaagtgcaga gatcatctat atttgatttg ctgtgtatgc atagaatatc tctggacaaa 106800
tacacaagaa gctgctaaca ttggttgcct ctggggaggg aacagggtgg ctgggggaca 106860
ggggctggag gaaaagattt caccacatgc cttgcagact ttatatattc ggaaccctgt 106920
gcattatcta ttgcacatat tatctattca tgcaaaacgc tataacattt acaaataact 106980
ttcaaatata tgcatatcat atttcaatgg aaagtttttt ttgttgctgt ttgtttgttt 107040
gtgatggagt tttgctcttt tgcccaggct ggagtgaact ggcatgatct cagctcactg 107100
caacctctgc ccccagtgtt caagcaactc tcctgcctta gcctcccgaa tagctgggat 107160
tacaggtgcc ccccaccaca cccggctaat ttttgtattt ttagtagaga cggggttttg 107220
ccatgttggc caggctggtc tcaaaactcc tgacctcagg tgatccgccc acctcggcct 107280
cccaaagtgc taggattaca ggcatgagcc aatgtgccca gcctcaatga aaagtgtttt 107340
aaagtaataa tataatacat caaaaggcat gatttatgtt ttcaagtgcc acctctggcc 107400
acttgtggct gtagaaatgg ggaatactcc aattcaccat ccctatgtga aggcaggaca 107460
gggagacatt caagtcagga aaaggtggag tggaggtttt agtcaagcac caagtcctct 107520
gacttctctg ggcacttgcc catgccggta cctactcctg agacactgtc tacctcgcta 107580
agcccatctt cttctcacct tgtgtctcac ctgagacatc actgacttta ggaggtttcc 107640
tgacccatgt gtgttcccca tctcagcacc cagcacctgc ctcatgttca ccagggtaca 107700
tgtcttccct ccccgccagg ctgcactgag agctcaatga gggcagggaa catctctgtt 107760
ccccatcttg ttagaagcta tctccccaga gcatggtcca aatgtggtgt taagaacaga 107820
agttatcaca aagaagtgag aaagtgaagg ggaaatgggg agagctgtaa gaaaggcatg 107880
ggggagaaaa aggaaagaag gccatgttcc caggatccaa tgccactccc tggggaggct 107940
tctctatctt agctcagccc tcagtcacta tcaccctccc tggtcttgtc agatttgaaa 108000
tatcttcttc atttacaaga gggccttatc tatcttggtc acctctgtat tcccagcccc 108060
tactgcggac ttggaacata gtaggtgccc agtaaacatg ggttgaatta attaatattg 108120
gacaggccag gcttggtggc tcgcgcctgt aatcccaaca ctttgggagg ctgaggtggg 108180
cagatgacct gaggtcagga gttcaagacc agcttggcca acatggtgaa gccccatctc 108240
tactaaaaat acaaaaatta accaggtgtg gtggcacaca cctgtgatcc tagctactgg 108300
gaggctgagg tgggaggatc gcttgagcct gggaggtgga ggttgcagtg agccgagatc 108360
gcggcactgc actccagcct gggcgacagg gcgagactct gagtcaaaat aataataata 108420
ataatagttc attattattg gatagtgagg agggagtttg caaaggagcg gctaaaatga 108480
aattagtcct gagtttctga tgttatgcgt tctgggtagg ggcgggagaa ctggaagatg 108540
tttaatgccc cccacccaag ggcagccata gttgagaatc actaattctg aagcttggta 108600
gggaagcttg atagggactt tgggtttttc actgagggca gaatccccag tgactgtcag 108660
agacctcgct ctgaatctta agaacctccc caccccaggc ctgacaggga ggacaaggaa 108720
ggagagtggg gctgggacgc ggggcagagg gcggctctgc tcacctgcgg gagaacgcga 108780
ggatgaggtt ctagtgggac cggcgctagc gggcgcgtcc tgccaggagt gagtcttggc 108840
gccatctagc gcctgctgga ggctctgcag ctgcagtgga ctgagccgcc ggcgctgggc 108900
gtgggtcacc gccgcggcgt tctccggacc cagggaggcg atctgctccg cggacagctc 108960
ctgcaggagg caaaggggca gcaccctcac acggggcccc tccccggatt tcccacatct 109020
cgggcgtccg cgcaggatgc acacaacttt gccatcccct tgtgtgtatc atgtgtggtc 109080
ctctttaaga tatttcctta aaattagatc actcttgcac taccaaagta aatgcattta 109140
aaaatagaaa atttaaaatg gaagtttcca aaaatggaaa gccggcagac ttgccataag 109200
caagcattaa ataggagccg caaaataaaa ataaaacaat attgttgaat cctagctaga 109260
tttgtccgcc aacaatatct gaacccctgg cctcttggaa aaaaaagaga gagagagaga 109320
atataaaatg tactatacag ggttaaattg acacttcctt cttgaagtat ttagaagtac 109380
taatggagag ttgaaaaggg aagcatgatt tcctccctat gtggcaatgt tgtttaatgc 109440
aatgcaggac agcttcccag tgcttcaagt cttccacctc ctgaaacact gatgtggagg 109500
gggaaacaca ggccttaaag atcagaggcc tgaattcgag cccctgctct gccacatact 109560
tgctgtgtca ccttgaacaa attacacagc ctccgtgggc tttggggata aatgtgagac 109620
ggcatagaga actcatctcc tctgctgact gattctgatc ctttggtttg actgcctgag 109680
caccatgtga tgagctctgt gagggctcca tggagggaaa atgcagtcat ctattggtga 109740
tatctgctat ggacaacatg agttggaaat tctgccagcc agactatgtc ttcaaggact 109800
gtgaacaagg tgtcttctga agtcacttcc agatcaaagg acttggtgac tcgttccaat 109860
gggactggaa tacgaagggg actctatatc atcatgttta ttttctaaag gccctgaaga 109920
atctgggaaa gatgcttatg ctccctcatc ccttcctctc ctgtcagtca ccctctcctc 109980
ctcttttgtc caggtagata cttccctgga atcatatccc tctgtgtaaa gcccttccag 110040
gaaccccact ccagaacaca gttcaggctc ctggaaaaaa ctctgcccac ctctccagcc 110100
tcacacatgg cattcttcac tccaggagag tgggtgccaa tatttacagt tccctagagg 110160
cagcatcttc ctgtgcacct ctttctgcct ggaacactgt ttcttcttca tcgccagctg 110220
ttctccaaga ttcagcatct ggtcggtcaa gcgccatggc tcatgcctac aatcccagca 110280

-continued ctttaggagg ctgaggcaga atgattaacg gagctcagga gttcgagacc agcctgggca 110340
acacagtgag acccccctc tctacaaaaa gtttttttaa ttagccaagt gtgtagtcct 110400
agttacttag gctgacgtga gaggattgct tgagcccagg ggatcaaggg tgcagtgagc 110460
catcattgtg ccactgcact cccttgggca acagagtgag actttgtctc aaaaaaatta 110520
aaattcagca tcacctcctc tcctctcact acacacacac acacacacac acacacacac 110580
acacacacac ggtggggtgg tcagagaggt acttttttgg cttccatata ccattaacac 110640
agagtctgta ttctaaaaat tatctctttt atcaatgttg ctgacttgcg acccacaggc 110700
cagattgaat ctctaggcct acggcactgt gttttcaaaa ataaattcag attggctgcc 110760
aacatttaat tatcaagcaa ttccatatga aaatgaagat ttctgacttc ttctcgaaaa 110820
aagtgaaaag gaaaattcag caatcttggg cccacatggc cacactgcat gaatgtgcta 110880
ggaatgagaa gcagcctcca catttagaca aggctctcca gttcacttcg gtctctaccc 110940
agcctactgc accttatgtt accttttagg cccctgaagg cactatgtga taaccccttc 111000
acctgtgcat ccttaggtgc acctaccctg gagcctgcca caatgtaggt gatcagtagg 111060
gatttctgga atagataaat acctgtacaa ggaagcagca caacagcact ccaaacaaga 111120
ccaagagaaa gtgcttagca aaatgccagc atccaagacc aagctgcttg tcccatgcag 111180
agtgccccag aggggaagca ggtatttgct caatggcttt gaggactgct atttattgcc 111240
ctcaaacagc tattatgcct gcaatgtgct cggaactgtc caggatgctg aagtgattga 111300
aggttggctt tctttttttt tttttgagac agagtctcgc tctgtcgccc aggctagagt 111360
gtagtggagc gatcttggct cactgcaagc tccgcccccc gggttcacac cattctcctg 111420
cctcagcctt ctgagtagct gggactacag gcacatgtga ccaccccagc taattttttt 111480
gtatttttag tagagacagg gttttaccat gttagccacg atggtctcaa tctcctgacc 111540
tggtgatcca ccctcctcgg cctcccaaag tgctgggatt acaggtgtga gccactgcac 111600
ccggcctcag ctatctttct tgaaatgaac aagtgatgtg gcactggggg agtttgtcga 111660
gcctggtttg tgtgttttat ccagaagtgc tggacaaaat gtgttcccac attacgcagc 111720
aaacaggaac accagaatga ctgcctcctc atcagagcag actattccca ccaaacactc 111780
ccctaatctt gtatacagac agaaaaaaag gacctgtcat tagataccct gcttcccttc 111840
cttcaaatga tccaatttca ccctctcaat tttttcatag cagtttttca cctgtcctct 111900
tgtgattttc ctaatacttt tctttaaatc aactaaaaat atatatatat agaaaaaaat 111960
atatatatat agagagagag agatggtttc gctcttgttg cccaggctgg agtgcaatgg 112020
tgtggtcttg gctcattgca acctctgtct cccgggttca agtgattctc ctgcctcagc 112080
ctcccaagta actgggatta caggcatcca ccaccacgcc cagctaattt tgtatttttc 112140
atagagatgg ggtttcacca cattggccag gctggtctca gactcctgac ctcaggtgat 112200
tggcctgtct cagcctccca aaatgttggg attacaggtg tgagccacca tgcctgacct 112260
aaatcaacta aaatattttt atttaattat atcttaaaag gaaatgttac agaggtccac 112320
aatccctcat ctgcaattcc aaagtccaaa aataatctga aaactgcaag ttttccccca 112380
aagtttaagt caaacttatt tatcagcaaa acttgacctg aagtaatgtg aggctattta 112440
tttatagtct ctatttattc caattagtgt ggcttgtcac agatttcttc acagaaatat 112500
taatgtgttt gcttacaagg tgcttcccca gacactgctg ggggtatgaa gttacataca 112560
gtaaatgtac agggtgatct tttcaaaatc tgagaaattc tgaattctga actatatctg 112620
tccccagggg ttttcgtaag ggtttatgaa cctgtcatac caccataagt agaaaatcag 112680
taccacctgc tagaagaaga gaagatgacc gtaaaaataa atataattaa actacatatt 112740
gtaattttaa gaaaaatgtt ttttaaaaac acctaaactc acacagatct cctctgaccc 112800
catcagcaga gcctggtcac aagcctctaa attccaaggc ccatcacctg tttccctgtg 112860
tgatttgaaa tggggtcaag ctcccatttc tccttgaaga actgagcacc tactttgaat 112920
atctcatcag gaaggcattt tattgctgat ggctggaaat atggcatcaa atccttgtca 112980
agcatccgga gctctgcctt agttaatcca gctggggaga aaaaggaatc acgggggttt 113040
agttcaagcc atcagaactc cgcttgtttt attaatggtg ctgcataatg ttcagatctg 113100
agtgttctag gcaggcatca ttccttacaa aaggccctgg aaatcacact ggggaatcaa 113160
gttccttcat caactcagaa aaaaaaaatg tgggtcacat tagccctgat tggcctccta 113220
cagtgaaacg catgcccaga aggaacttca atttacacac tttcaaattt tgtataaacc 113280
tacttagggg ccaattaaat cacattctaa actagcggtt ttccaaactt tagtgtacac 113340
aagaatctcc aaaagagctt gttttaaaag cagatttgca gacccaccct ctgcaacttc 113400
aaatcatgaa atgtaggttc tactgtaacg ccactgatgt ttgctacaca tggccaagga 113460
taatgtttta ttttgtgtcc ccacatttaa gtttggaaag agagagaaag gtatgctcag 113520
ggtgagtctt acctgcaatg gtcccaagct cctgcaagac agaactggtc cactcagtgg 113580
gatccccaaa cacaacttca gccttcctct taaactcggc taagacatgt gtgctgcaga 113640
gcagggtccc aattctggcc actaccaccc tggtagtggt taaagaggga gggatataat 113700
atgagcttgg actcttcagc caaaaacaaa caaacacaca cacacacaca cacacataca 113760
cacacacact gcacagtagg ctcagcaggg acagcagatc cagcttatcc cattagccca 113820
gtgggatttt agcccagaaa ggtgccaagt gtcaggaggt ggaatatctg gatggatgga 113880
tggatggatg gatggatgga tggatggatg gatggatgaa ttaacccatt tgccattttg 113940
cacattcata ttttagttac ctgaattctg agatctttat aagtgggatt tcagtgatgt 114000
ttatagcaca cagggttgca ccaagtccta ccaaatgaaa gctcttcagg tcctggatac 114060
tgtatcctga atcatccagg taccettgca aaatggattc agcctaaaaa atagtaagaa 114120
taaaagataa accatccagg aatgatcaag gtccccaggc ctgaggggat aaataagctg 114180
ttgctgtagt ctcctgactg atctcccatc ctactcctct ggaatcccca ctccaaacca 114240
tcctggcctc tgcatccaag ttcatgtcct taagatacta cttcaactga gtatgtcccc 114300
taatctatga aagtgtcttc aggcaatgaa tctcttacat ccttcaccaa tattaaaggc 114360
acttgtgtcc tgtgtgtctg ctgcttattt ccttcagtca ctcttatgac cctcagacag 114420
tttggacata caacttcttc tgcatcagga tccaaacttt tccagcatct ttttccacaa 114480
cgtttcttct cccttttttt tttttttttc gtttttttgga gacggagtct tgctctgtca 114540
cccaggctgg agtgcagtgg cacagctcgc tgcaacctcc acctccccag gttcaagcaa 114600
ttctcgtgct ttagccaccc aagtagctag aattacaggt gcacatcacc acatctggct 114660
ttttgtattt tttgtagaga cggggtttca ccatgttgcc caggctggta tcaaactcct 114720
gacctcaagt gatccaccca cctcggcctc ccaaagtgct gggattatag gcatgagcca 114780
ccgcacccag cctttccaca acctccaaca aaaccttata atttcctgtc tctttgcctt 114840
tgttcaaacc agtcctttca tctgaaatgc ccttctgcac ttccaagtgc agacattctt 114900 ttttttttt ctttggttca actcaaatgt caccttcttc atgaggtttc agccagaatg 114960
attttttctt cctctatggt cctacagaaa tatgtttacc ccttaatgat tttttcttcc 115020

-continued tctgtggtcc tacagaaata tgttcacccc ttcaattcca atgtttactc ttcaattcca 115080
agagtagcac acaaaatgct ttggtgttaa actattttaa actaagcctt gatttaaggc 115140
ggctgacaca taagtctcca taattctagc acagtggcta ttcatcattc ataacttcct 115200
ctggagaacc acctctcttg tattcctgct tcatgtggtt cagtcaaagc taactgcacc 115260
aagttccagg agtgatgaat ttcaattcat accttagcct agctgcagtc actggttctg 115320
gattggacat gtgatttaac cagagtcaac cagaactttg agtggagcat taggggaaga 115380
gctttcttta ctctggactt gaacttagaa ggatatacac aaggatctgc tggaacctac 115440
cacatgcagg catagagcct gtctctcaat gaagccaaca caaagaaaag caaagttcaa 115500
aaacatgata agagacagat tcccacccag agtgttgaag atcctggatc cagctgtatc 115560
tgaacactac ccctgaactt tccagtaatg ggagtcaata aattcctttt tttttttttt 115620
tttttgagac aaggtctcac tctgtcaccc agcctggagt gcagcggcat gatctctgct 115680
cactacaacc tccctctccc aggttcaagc gattctcatg cctcagcctc cccagtagct 115740
gggattacag gcaggcatga acatgcctgg ctgatttttg tatttttagt agagaagtag 115800
tttcactgtt gggccaggct ggtctcaaac tcctgacctc aagtgatctg cccgtttcag 115860
cctcccaaag ttctaggact acaggtatga gccactgcac agtgcaccca gcccctttat 115920
ttgttcaagc cagtttgtgt tgggttttct gccacttgta actaaacatg tgctgattca 115980
ttttatctac ctatgtagga cctgaggagg catccaagcc aatcctatga agatcagcta 116040
caaaataaag tctgggctgg gcacggtggc tcacacctgt aatcccagca ctttgggagg 116100
ccgaagcagg aggatcactt aaagtcagga gtttgagacc agcctggctg acatggtgaa 116160
agcttgtctc taccaaaaaa tacaaaaatt agccaggcat ggtggcacgt gcctgtggtc 116220
ccagctactt gggaggctga ggtgggagga ttgcttgagc ctgggaggtg gaagttgcag 116280
tgatccaaga ttgtgccact gcactccagc ctgggtgaca gagggagact ctgtctcaca 116340
aaataaagtc tggttccttc agtgctcatg ggagcaagta aaagagatta taagacctca 116400
caaggcaaag atgaggagac atccaaggag agacccctaa gtggaagcga aaatcacagg 116460
ctatagtcaa tcttcccaac tctctttgct ttttttgtt ttttttttt gagacagcgt 116520 ctcactgtgt cacccaggct ggagtgcagt gacatgatct tggcttactg caacctccat 116580
cccccagggt tcaagtaatt cttatgcctc tgactcccaa gtagctggga ttacaggcgc 116640
ccgccaccac acccaactaa ttttttgtgt ttttagtaga gacagggttt caccattttg 116700
gccaggctgg tctcaaactc ctggcctcaa gtgatctacc cacctcagcc tcccaaagtg 116760
ctgggatcac aggcatgagc caccatgccc gacccccatc tccgtttaat gttagtcatc 116820
cccatcacac aatatagatc attaaggtgt tgagagaaag tgttgaggaa gattgtgaaa 116880
tgttgcaatg aaattccgtc ttcatgggct ggtgcttccc acccctcagg tgtgtttaaa 116940
tgctacctac tcagagaaaa ctgccctctg gactctttca tctcaaacag cccttcttcc 117000
cactattccc atgagcacct tgtccatttt ccgcatcact tatcgtgatt tttcaaattt 117060
ttcactttga ttactcactt ttttgtctgt atcaccaagt aggctcccaa aagaaaagga 117120
ccatatccag gtagtttacc aatgagtccc cagcacctag cataatgcct gccacagagt 117180
aggagttcaa taagtacttc ttgagtaagt aaatgaatga gtgaatgaat gaatgaatga 117240
aacaacatct gagtgagtga cttacaaaag tcgtgggcaa tatatattat ttgacatgct 117300
tcattttgct gccttcatgt aatagactgg cttcaggaag atttctcatg tttctgaaaa 117360
tcggactggt cagtgtcctc atcaagttgt cctccatgat tacaaagctc acagctacta 117420

-continued tgggggcggg ggatgcagta acaccatgct tagacttata tgtctttgac ttaatgggac 117480
tgtatatcca aagtggtaat agctaacatt tattgtagct aacatttctt gagtgcatac 117540
tgtgtgctgg caccactttg accactttac acatactatc tcatctaatc ctcctaaata 117600
acactatgag gtaagtatta atagtatccc tagtttgcag atgagcaaac tgaggcaagg 117660
agaggttaag taactaggcc aagatcacac agctagaaaa tgatcgttct ggccaggcgc 117720
cgtagctcct gcccgtaatc ccagcacttt gggagacaaa ggcgggcaga tcacctgagg 117780
tcgggagttg gagaccagcc tgaccaacat ggagaaaccc cgtctctact aaaaatacaa 117840
aataagcagg gtgtgatgat gcatgcctgt aatcccagtt actcaggagg ctgaggcagg 117900
agaattgctt gaacccggga ggcagaggtt gcagtgagtg gagattacac tccagcctgg 117960
gcaacaagag caaaactcat tctaaaaaaa aaaaagaaga agaagaaaga gaaaagaaaa 118020
tgatggttct aggatcaaaa cccaggcagt ctgattccag ggcccatact cttagccagt 118080
gaaggtgttt ggctatggag aaaagatgga gattcaagtt agttttcaaa tttttcttat 118140
taagtcttca taatcaggtt tcactagttg actcagagca atttgggctc ctcaactatc 118200
aggcacgctc actttaaaat gaaagtgcaa aaatacaatt taaataaaat tactttgaag 118260
atatggtatt aaattgtcct tgccactgaa acccggaaaa tgcaagctca gcctgcaagg 118320
tgataagtta aaataaattt ccttgagtga cgagaccagt gtatatgtaa tgattccaag 118380
acaattaata ccaacacttt taggcaatat taactgttga aaaatgaata gctttaagat 118440
ttcaatctct ctgttcatcc ctctggcttc tataatagtt ttttccctta tattggtttt 118500
tgagctgaac tatctgttaa tgtagttccg tcaggtctga ctattaatct agaaacctgc 118560
atttaaggtt gattgggagc taaagttgaa gaactgacta caaatgatac atgcaaatgt 118620
taggttttca tatcctcttc aaacatattg ataaatctca ctgccatcca tgagaattaa 118680
aatcggtgcg aagggaagga gataccctag tttctgcatg tatttttctg tttctccgag 118740
cctgcaaata gaatgatttt aatagcacag tgtgatgtgg cacttctcaa actagtcaaa 118800
accagtttta gagtcaaaga accatgggat tatagaatat cagactggaa ggaacctcag 118860
attgttgggg ctaaccctct catcttgcaa aggaggagac taacccagag aaaggggctg 118920
taatgatgat aatgttgatg atgacaatgc aatgatgtca atatcaacat aaaaacagct 118980
aatttttatt gactactatg taccagacat tgttcaaaat gttttcaagt attaactcat 119040
gtaatcttca tggccaggat ctgcatgttg cccagctcca ggggtgcacc attcacagtg 119100
tattctgttt gaatggtgcc actcagagtt atgaaacatg gccaccgtga ttacaaaaag 119160
ctcaaaagag tagggggaca ttcattggtt ttggctgctc agcgtccaca ctttttcttt 119220
ggaaaattac cctccattag cttcctattg ctactctacc aaattacccc aaacatagtg 119280
gctttaaaac tacacgttta ttctcttata gttctggaga ctgtatgtcc taaaatggac 119340
tagaaggatg ggttccttct gggagttcta agaagaattc attttcttgc tttttctagc 119400
ttcaagaggc cacctgcatt tccttggctc atagccccat cctccatctc caaaatcagc 119460
agcagagcac cttcagatct ctttctaggt ccctctgctt ccattatcat gtcaccttct 119520
ctatctatga ccctccttgc tccttcttaa aaggaccctt gtgattacat tgggcccacc 119580
caaataatcc aagataacct cctcatctca agatccttaa tcgcatcttc aaagtccctt 119640
ttgctccata agttaacata gtcacagctt ccaggggttc agacatggac atctttcggg 119700
gaccttaatc agcccaccac atatccttcc ccactcggct catgtggtca tgagatgctg 119760
ataagatgga ctccgctccc tgatgcaggc ctcgccaacc aacatattca acccctgacc 119820
agagtggttg ctcaggggcg ggcaactaca tgagtggagt caatgctgag gcttttccaa 119880
aaactaataa agaagaggca catttttatg ggcttgttaa ttaggttgta tataagccta 119940
gtgctgaaaa tgaccactga gagagctgcc taagaacgaa gataacatgg aagggctaac 120000
acttcccttt ccagcagtac agtggattag acaccctaaa ctcctctccc aatcaaaaca 120060
attaaaattc tgggaagaac ttcttcttta gcccatgaag gattaattaa cataggaatt 120120
ggccacccac cataaacaac tagaaaattt aacaaaatac atcagacaac tgcatccgga 120180
tatggaacaa cagaatcata atcccagaag aagaaaaaca aacaagatga gccttaaaat 120240
taccctcact tactgccaaa aagcagtttc caagacatgg atcaggaaga ggaaccaaaa 120300
caagcccagt ggcccagctg agtggaggat acagatatcc aagttcagag aggccacggc 120360
acttatcact tgggcaaagt attggagagg aggaaactgc agagggttcc agaaagctgc 120420
agagatgtct agtactgact gctattttgc acatgcaaag agtgaaactc cacataggca 120480
ggaaaagagt catcagtaat cagaaaggat taggctgagc aacttccaga gctcatatgg 120540
agctggaaat agttcacatt ctcaccagcc aaagtagaga gatcttgaaa tacatggagc 120600
attaggtaac atcctcaaag gaatcatgtc acagtaatga tgataaatta acaacagaat 120660
aaaggtcact ctggttttac cctaacaaaa ctcaaaagga agcatcaaaa ggatcaagct 120720
gatttgaaag taacttaagt gtatgacaga acaaagccca atactcttca aagaaataca 120780
actaaatcaa atactcaaca atgtaaaatc cacaatgctc atcacccaat caaaattgct 120840
aggcttgcaa acaaaaaaag aaaatatgac tcataactaa gagaaaaatc agtcaacaga 120900
aacagactca aaaatgacca tcatgaggaa attaacagta aggatatgaa ggcagctctt 120960
ataaatatgg aatagttaaa agacccagaa acatccaccc acctgtcccg gggtccattc 121020
tgtttgccag cttagggaag ccacagtgtc tatggagctg aggtccagct gctccagctc 121080
actctcatta agagccagag caatgcgccc cagggagacg atatggtgtt ctctccagta 121140
agatggcatg tcccaaacct ttaggcaaaa aaagaaaata gattagactg aacactgtga 121200
tggtatttac aatgatttga atgtttgtgc ccctctaaaa tgcatatgtt aaaacctaat 121260
ctccaatgtg atagtattgg aaggttgggc cttgggagat gattaggtca taagggtgga 121320
gccctcatga gtgggattag tgcccttgta aaagagaccc cagagagcta gctacaagct 121380
agtccctttc caccatgtga ggacacagtg agaaagcacc atctatgaaa aacaagtcct 121440
taccagatac tggatctgcc agtgcttcaa tttttgattt ctcacccccc agaactgtga 121500
gaaataaatt tctgtttata agttaccagt ctatgatatt ttgttatagc agcctgaatg 121560
gacaaaggca gtatctaaaa tagacataag gaggctaggt gcggtggctc acacttggaa 121620
tctcagcatt tttggaggcc aaggcatgca gatcacatga ggccaggagt tcaagaccag 121680
cctggccaac ataacgaaac cctgcctcta ctaaaaatac aaaaaaaaaa aattagctgt 121740
gcatggtggc gcacatctgt aatcccagcc acttgggtgg ctgaggcaca agactcactt 121800
gcagaagttg cagttagcca agatggtgcc actgtactcc agcctgggtg acagagcgag 121860
accctgtctc aaagaaataa aaataaaaca gacataggga aacctattgt gcagcatggt 121920
gaccacagtt gataataatg tgttgaatgg ttgaaaattg tgaagagagt agatgttaaa 121980
tattctcaca acaaaaactg acaacggaca agtatgaaag gtgattgaca tgttagcttg 122040
ctttaaccat tccccaatgt atacatacat caaaacatca tattgtatat atgtatacac 122100
cataaatata tataatttgt atttgtcaac tatcccttaa taaaaaataa ataaaaatta 122160
aaaagacata gggtaaatct taatataaag ctctctttta aatcaataat aaaaacatga 122220
ctatatttgt tttaaaaaaa agatagacaa aagacatcaa caaggaattc acaaaagaaa 122280
aattaaatgt atggggaaaa ctttattctc agtcataatt aaagaaatat acattaaaaa 122340
caatcagacc atgttgattc atcacatgtc aagaagtata aagacttatc accatttacg 122400
atactggaaa gatacaaggt aagggatacc ctcatttgtt gtagttgaga atataagttg 122460
gtacatactc ttgagagggc aatttggcta tctgtatcaa aagcttttaa agtatttata 122520
ttctttgacc cagaaattcc acctctggga atttagcctg agtaaatgag acaagtaccc 122580
aacagtatat gtataaaggc atacattgag gcattttttt aatgcaacct gaaagtctaa 122640
caattagcta aataaataag aactaaccat aaataaaatg aagttgcccc tgtggatacc 122700
tccaccaagg attggttcca ggacttctta aagataccaa aatccatgga tattcaagtc 122760
ccttatataa aatagtgtag tatttgcata taatctatgc acatcctcat gtatacttta 122820
aatcatctct agattagtta taatacctga tgcaatataa gtgctatgta aatatgtaca 122880
aaatgttatg tcaaaaatgc tactgtattt ttatgtgtat tgttttttat tgttatattg 122940
ttatttggat catttttttct aaatacattc tacctgaggt tggttgaatc tgcagatgtg 123000
gaacccactg atatggaagg ctaattgtat tacaaagcta tttaaaatac tgatataggc 123060
tagatgctgt ggcttacgcc tgtaatccca acactttggg aggccaggca gacagatcac 123120
ttgaggtcag gagttcgaga ccagcctggc caacattgtg aaaccccatc tctactaaaa 123180
atacaaaaat tagccgggca tggtggcgga tgcctgtaat ctcagctact tgggaggatg 123240
aggcaggaga attgcttgaa cctgggaggc agaagttgca gtaagccaag accacactat 123300
tgtactccag cctgggcaac aagaacaaaa ctccatctca aaaaataaat aaataaataa 123360
aatactgaca tagatgtaca ttttggatat gaaaaaatat gcagtctgta ctgttgggtg 123420
tagaaagcaa gttattgaat agtaggtaag tataatatca tttttgtaaa acatgagata 123480
tatgtatgaa atatataaaa taatattttt tatatacata gttttggagt ctggtaagct 123540
tcaagtgaat ataccaaaat atcaacagtg cttatctgct gaacagtgct tatcaaaata 123600
tcaacagtga gtaaaagatt atcactgatt ttcttcttta ttattttctg acttttctac 123660
aataaacttg aagtactcat ataatacata aatacagtta tatttataat tttaagacat 123720
tgaattgttt aacccttgag ggtaactaga tattccacaa ccatgtaaag agctaaaaca 123780
gggctgggtg cagtggctca tgcctgtaat cccagcactg tgggaggcca aggtgagcag 123840
atctcttgag gctaggggtt tgagacaagc ctggccaaac aaaccccgtc tctactaaaa 123900
tacaattatt agccaggcat ggtggcttgt gcctgtagtc ccagctactc aggtggctga 123960
gacacaagaa tcacttgaac ccgggaggca gagtttgcag tgaacaacag atcgcgctgc 124020
tgccctccag cctgtacgac agagcaagac tctgtcttaa aagaaaaaga aaaaaaaaag 124080
aaagaaaagc taaaacaggc cacaaaggga ccttttcctt ttatttattt atttgagaca 124140
gagtctcgct ctatcaccag gctggagtgt agtgacgcaa tctcggctca tggcagcctc 124200
cgcctcccgg gttcaagcaa ttctcctgcc tcagcctccc gagtagctgg aactacaggt 124260
gcatgccacc tgtagagatg gggtttcacc atgtgggcca ggctggtctc gatctcttga 124320
cctcgtgatc cgcctcccaa agtgctggga ttataggcat gagccactgc acccagccta 124380
tttttattta tttttgagac aaggtatcag ctctgacgcc taggctagag tgcactggcg 124440
caatcttggc ttactgcaac ctccacctcc cgggttcaag ccattctcct gcctcagcct 124500

-continued cctgagtagc tggaactaca ggcacatgac accacgcctg gctaatgttt gcattttgag 124560
tagagacagg gtttcaccat gttggccagc ctggtctcga actcctgacc tcccgtgatc 124620
cgcccgcctc ggcctcccaa agtgttggga ttacaggcat aagccactgc acccagccaa 124680
caaagggacc tttttaaaga tggaaagcta cttccagtcc tctttttact cctttctgtt 124740
atattttcag acaaatttgc aaatgattct gagaaaacct gctgtgagca gcagctgggg 124800
ctctccaggt gaaggaataa agcctaattc ctgcaaaccg ccttggtcag aggcactggg 124860
acatccacag aacttgattc actgagcatc tgctagatgc caagacacat ctcatcccat 124920
tctctgccac agccctaaga gggaggaact ggaaatttcc tcctttctca gataaggaga 124980
tcacaatatc actgagctga tgcagtaaaa tttcaagatg atgtatggga aaactgctcg 125040
aggagggttc tatgtgcaga aatgctgaac tggttttggt gtttttcttt tttcctctgt 125100
ttaatgtttc ctccctgagg tgggcttcac ctgtattgct ttctccttca gggtcatcag 125160
ctgaggccgg ctgaaaccct ggacagctcc cagcagttcc acggtcctga tgaatgtgtc 125220
ttcctccatg caccgcaggt cctccagggc ccagcaggcg ttggcttcgg ccaacttgaa 125280
gatgtcatca gaagaggggg ccacgactcc atggcaacct gaagaaagga gagatgcagg 125340
gaaggagaag aggaaagaga atttcaggaa atgttagtgt attgaaatga gtaacattct 125400
ttgccagtca gatttatgca tggaagggac tacagagtaa aagcagagag caggaggcag 125460
ggaccagttt gaatcccact tctgccattt cttgctaatt actgggtaac aaagtcatgg 125520
aaatgccagc tttttgcaca tccacatgca caaactagga gcggtgcaac attacaatta 125580
aactacaaat tccttgaggg cagtaagagc tggtggtgaa cagtcctgac tttcgattca 125640
aatccaaggc tatttaacct ctctgtattt cagttttctt gtctataaaa tggaaataaa 125700
atcgcctcat aggatggttg tgaaaactaa atgtgttata tgtaaagcac ttagaacagt 125760
gccacgcata cagtaagcac tcgatacaca atttctgttg cctatcttac cccctatgcc 125820
tttgagtttg cagcccagca taaagattcc aaaattatgc agcagccttc ctataaaaat 125880
gggaagatgg gctgtgcggt ggcgcatgtc tttaatccca gcactttggg aggccaaggc 125940
agaaggatca cttgagccca ggaattcaag accagcctgg gcagcatggt aagacctcac 126000
ctctaaaaaa aaaaaaacta caaaatatta gctaggcatg gtggcacatg cctgtagtcc 126060
cagctaccca gcaggctgag gtgggaggat cacctgagcc tgggaggtca agattgcagt 126120
gagccgtgat cacacctatt ctccagcctg ggtaacggtg agaccctgtg tcaaaataaa 126180
ataaaaaata aaaaccagga agatgagttg ctgtccatga aaatcatagt gggggttgtg 126240
gctttcccat cccaagagaa aagagaaatg agcctattgc atttctcttg gcaacaggaa 126300
aaacatccat ttcggtcttt gaataatgtg aaccttacct actcaaacca gctaccaacc 126360
aacatgcaag tgagatattg tctttgctgg atctgatgtg cccaacctgg gagaaaactc 126420
taggatcctt aagagcaacc ctggatttct tatcttagcc gcagaccacc actgatgctg 126480
acagatgcac caaccccacc caaggccagg gtatttcccg agccccatgg cctctctctt 126540
ctcattgcac cttcaatgga aattcactgc attccaatca cgaggcaaaa gtagaccaga 126600
tcaaagatgc cagttgtggt cctcaaacat ctttatcata agccacttgg agaggactaa 126660
agacccatcc ctccctaggc caacccccag cccaccctct agtgaaaaca acatcagtga 126720
tagcacagaa ctagagaggg cagaatggtt gactagtata tcaggaactt ggtcttatca 126780
ctgtgtctgt ccagggctta gaatagagcc tggtacatcg taggtgttca gcaaatatct 126840
gtggagtgag tgaacacaca cacacaaatt aatataaaac caagcggtaa ttctgctaat 126900
ccatcaatca ctaaagcaca gcagcaatta atacccagaa ccaactaaag aacactcaaa 126960
ctatgcactg ataccagagc ttccttcccc tgagcatgga aagccttatt ttgtgtacca 127020
catgcacaca gtaagagctc tgcaatatga tgacatggac tgctagacct tgagggcagt 127080
gggagccagt ggtggtcacc accaactttg ggtacaaatc caagaactgc catttactaa 127140
ctctgtgact ttagacaagt cccttagtct cctaagcccc agtttccttc atttaaaaaa 127200
caagagaaca cccaagcctg gaaatctgca gccctaaatg ggaataggca ttcctgtttt 127260
cacgcccaaa tgttaggttt tggcctgcca catcccacta tcctgtaccc atataaaccc 127320
caaaccccag gctccatgag catacaagca gatgagcaga tgaacagaag agaagaggag 127380
cagaagagca gcatggcaga gaaaggagca tctgaaggcc aagaagagtt tggctgggga 127440
cagttggaga ggagattggt cacaggacag ccaaactcca ggggaagatc atcttcccac 127500
tccatcccct ttctagctcc ccatccatcc caccgagagc cacctccatt acccaataaa 127560
accccacatt caccaagaaa aaaaaaaaac gggagaacaa gataatgcat ggagggataa 127620
tcacccaagg tagacacaaa tccaattgtg atacttcttt gctcgatgtc acacgatgcc 127680
tccacccaga gtaaaagcca aagtcattag ggtttccttt aacagtcact acatggctgg 127740
ccttgtctct cactcccctc caaacacact ggcccttacc tcccactcat ggaagtggtc 127800
ctgttgcact ctctgcctgg aagactctaa ttgaaaatat ccacatggcc cactctccct 127860
tgggtcttca ttcaaatgtc accttctcaa taagatgttc cttcatgatt ctcttttcac 127920
atgacagtcc cctctcaaca ctcgtggtgc attcccttgc tttattttcc ttcttggcac 127980
ttttcataca atataccata tattttactt atgtatggaa atttattgtc ttgctaccct 128040
ccatttgaaa gtaagctctt tatttacaaa attggtgctt aacgaatatt tgttgggtgg 128100
atgaaagcaa gcactgactg tcaactacta tcactggggg tgattaactt tgtctcctca 128160
tgcctggccc cagtctgcac ttagtaggtg catggtaata ataataaaat atctaacact 128220
tggacaggca tggtagctca catctataat cccagcacta tgggagacca aggcaggagg 128280
atcacttgag gctcagagtt caagatcagc ctgggcaaca cagtaagacc ctatctctac 128340
aaaaaaataa aaaattatcc agatgtggtg gttcatgcct gtagtcccaa ctacttgtga 128400
agctgaggtg ggaggatccc ttgagtccag gaggtcgagg ctgtagtgaa ccatgattgc 128460
tgcactccag cctgggtggc agagcgaggc cctgcctcta taaaatcaaa ttttaggccg 128520
ggggcagtgg ctcacgcctg taatcccagt atttcgggag gccaaggcag gtggatcacc 128580
tgaggccagc gttcaagacc agcctggcca acattgtgaa accccgtctt tactaataat 128640
acaaaactta gccaggcgtg gtggcacatg cctataatcc cagctagtca ggaggctgag 128700
gcaggagagt tgctgtaatc tgggaggtgg aggttgcagt gggccgagat catgccacta 128760
tactccagcc tgggtgacac tccagcaaga ctccatctca aaaaataaaa aaaatcaaat 128820
tttaaaaata tataatactt attaaagatc tgctacatgc caggcattcc ggtaaacatg 128880
tttctgggtt taaacccatt aattctcaca ataacccagt gaggtagaga ctttcattat 128940
ccccatttga taaaggatga aaactgaggc acacagaggt taaagagctt acccaaagcc 129000
acacagccag taagtggcag actcaggagt gaaatgtagc cagcccggcc ctgtcactgc 129060
tatgttaaac cactaatcca tgttggtcct ctaagtcaat cctactgaaa tgtttgttac 129120
acatattcac gcattaaacc tactagcctg ggtatggagt atgggacatg attccaggtc 129180
actttacaaa agtgtaactc tttttttttt gagacagagt ctcgctgtca cccaggctgg 129240
agtgcagtgg tgccatctca gctcactgca accttcacct cctgggttca agcaatcctc 129300
gtgtctcagc ctcctgagta gctgagacta caggtatgca ccaccacacc cggctaattt 129360
ttgtgtttct agtagagaca gggtttcgcc atgttggcca ggctggtctc gaactcctga 129420
cctcaagtga tctgcctgcc tcaacctcac aaagtgctag gattacaggc ttgagcaacc 129480
gcacctgaac caaaagtgta attcttttgc ttatagattt tgtcattcta ttgctttgca 129540
gacatttcat ccagttccct gcataaggag gcctcttgat gtcagggacc ctgcccaaaa 129600
cattaattac tatgtcagca atggctcaga taccctgaaa acactcacca ggcatagggt 129660
catagctggg gatcttatca ctgctgttcc gaacagactg aaagacagcc cagaggaatt 129720
ctttagtggg cagggtcctg gccatcttgg aagctgcttg cagaaggatc tcaggaaact 129780
gtgtgaaaga agatgaaaga agaggaataa taattaaaac cccttaaata cagattgaaa 129840
ttagagttga aactgtcaca ctacttactg ccttcattct ttgttatagc aacttctcat 129900
ataaatctat tccctagtcc cactaatgtg gtctctataa agaatcctat aaaatgatac 129960
tcaacttcaa taaaaatcca ataaagtcta aaaaacataa gtaaatcact tttcacccat 130020
cagattgtca aaaataaaat gaagtgctaa tacttaatgc tgggcacatt catttttccg 130080
tgggactgtc aaactgtgca ctattagcag agcaatctgg taatatcgac aaaaaatgta 130140
ggttaggcga ggtgtggtgg ctcatacctg taatcccagc attttgggag gtcgaggcag 130200
gcaaatcact tgaggtcagg agctcaagac tggcctggcc aacatggtga aaccccatct 130260
ctactaaaaa tacaaaaatt agtcagtcgt ggtggcatga gcctgtcatc ccagctactt 130320
aggaggctga gacagaagga tcaccagagc ccaggaggct gaggttgtag tgagtcgaga 130380
gcatgccact gcactccagc ctgggtgatg ggagtacaac cctgtctcag aaaaaaacaa 130440
aaaaaatgta tgtgtaccta cccctttttt ggtttggtgc tatttctaag tttttactaa 130500
actttatatt tgacatagtt tggatgtgta ccccacccaa atcttattga aatgtaatcc 130560
ccagtgttgg aggtggggcc cagtgagagg tgattggatc atgggggcag atttctcatg 130620
aatggttaaa tacaatcccc ttggtactgt cctcacaata gtgcgtgcgt tctctcgaga 130680
tcttgttgtt taaatgcatg tagcacctcc cccatcacgc tcttgctcct gtgtcggcca 130740
agtaagatgt gtctgctccc ccttcgcctt ccgccatgat tgtaagtttc ctgaggcctt 130800
cccagaagct gggcagatgc cagcatcatg cttcctgtac agtcggcaga gccatgagcc 130860
aatcaatcct cttttcttgt ctcttttttt tttttttttt ttcagagtct tgttctgttg 130920
ctcaagctgg aatacagtgg tgtgatctcc actcactgca acctccacct cccaggctca 130980
agtaattctc gtgcctgagc ctcctgagta gctgggatta catgcatgca gcaccaagcc 131040
aggctaattt ttttttattt ttattgtaga caaggtttca ctatcttggc ctggctggtc 131100
tcaaactcct ggcctcaagt gattcgccca cctcggcctc ccaaagtgct gggattacag 131160
atgtgagcca ctgtgcctgg cagtgtttgt ttgtttgttt gtttagacgg agtctcgctc 131220
tatcacccag gctggagtgc agggcacgat ctcggctcac tgcaagctct gccccctggg 131280
ttcacgccgt tctcctacct cagcctcccg agtagctggg actacatgtg cccaccacca 131340
cgcccggcta attttttgta ttttttagta gagacggggt ttcaccctct tagccaggac 131400
ggtctcaatc tcctgacctc gtgatctgcc cgcctcggcc tcccaaactg ctgggattgc 131460
aggcatgagc cactgcacct ggcccttttt attttatttt ttttaattta acttttattt 131520
taagttcagg ggtacatggc aggtttgtta tataggtaag cttgtgtcat ggaggtttgt 131580
tgtacaaatt atttaatcac ccaggtatta agcctagtac ccattagtta tttttgctga 131640

-continued tcttctccct cctcccacct ttcactctcc aataggcccc agtatctgct gttccattct 131700
atgtgacaac gtgttctcat catttagctc ccacttataa gtaagaacat gcggtatttg 131760
gttttctgtt tctgcattag tttgctaagg atgatggcct ccagctccat ccatgtccct 131820
gcaaagaaca cgatctcatt ctttttatg gccacatagt attccatgta aacctccttt 131880
ctttataaat tacccagtct caggtatttc tttatagcaa tgcaagaatt gcctaacaca 131940
ggtcaggtgc ggtggctcac acctgtaatc ctagcacttg ggaggcccaa gcaggcagat 132000
cacctgaggt caagggttca agaccagcct ggccaacacg gtgaaacccc gtttctacaa 132060
aaaatacaaa aattcactcg gcatggtggt gtatgcctat aatccctgct actcaggagg 132120
ctgaggcagg agaatcactt gaacccagga ggtggaggtt gcagtgagcc gaaatcgtgc 132180
cactgcattc cggcctgggc aacacagcta gactccatct caaaaaagag aaagaaaaaa 132240
agaattgcct aacacaacat ttgtcatgaa aaggaggtga agaagggttg tctcaacatc 132300
ctgggtggag actagcaatg aggggactta ggggactttg ggttgccttg gagaaagtgc 132360
catttctcat ctagaacgaa tacactttgt caagacttgg gattttatta gaaggcctgc 132420
ccatgggccc agataatcca tcaggctcta caaacagcta tgcctcactg ggtcccggct 132480
cacccagaga gcaagcctct cagcctatgt agctcccctt tctagtctca tcttcagaat 132540
tagagtcaca gtctaagcca gcagttcttc aaccctggct gtacctaaga gtcacctggg 132600
acacccagag ccagccccta aagattctga ctcagtcggg ctgggctgga taccatggat 132660
tggtccctct tggaatctcc ccaggtgatt ctaatgtgca gctgaggctg aaggcaacca 132720
ctctaagaca gttaactttt agaaagcaat atgcatagcg gagtgaatgg cattttccat 132780
tttgtatttt ctaaagaaga gtgtgtatat gctcttgtgt ttttagtaga gacagggttt 132840
cgccatgttg gcgaggcttg ttatataggt atttttatac ctatataaaa cttgttatat 132900
agatattcag gatatttctg aaaggatgca gaagagattg gggacagcaa ttgcctctga 132960
agagggaggc tagggaacta gaagtctggg gtgggaggga gacttgcttc tcatcctatt 133020
acctttggtg cgattgggat ttgttaacca ggagcatgta ttacttgctt tattaaacat 133080
ttccagtatt taaaaaaaga gtatacagaa taatacaaca aaacacccat gtcctcacaa 133140
cccaacttaa gaaataaaac atcacaatat aaataataag tccctccttc actctttgcc 133200
ttcctccttc cccagaagta actgtcactc tgaatttggc attcactttt acacttctct 133260
tacatataaa cttggcttac atttgcttta aattaattca gctactattt atttatttac 133320
tttgtatcct actatagata ttcttttgca atctgggttt ttttttaact ctacactgtg 133380
tttttgagat ttcacagtgt tgatgcaaga ctttttcaat ttcagaagtt gatttttttta 133440 agattagata gatatatgga tgttctcact gatatgtggg agctaaacta tgaggaccca 133500
aaggcataag aatgatacaa tgggctttgg ggacttggat ggaagagtgg gaggggccaa 133560
gggataaaag actacaaata tgttgcagtg tatactgttc aggtgatggg tgcaccaaaa 133620
tctcacaaat caccactaaa gaacttactc atgtaaccaa acaccacctg taccccaata 133680
ccttatggaa aaataaaaat aataataaac atctaaacat aagaaaaaca aggaaggaaa 133740
aaaaatagat ggatatataa catttgtgca tcagggccgg gcatggtggc tcacgcctgt 133800
aatcccagca cttgggaggc cgaggcgggc agatcacttg aggtcaggag ttcaagacca 133860
ggctggccaa catggtgaag ccccatatct actaaaaata taaaaattag ctgggcatag 133920
tggcaggggc ctgtaatccc agctactcgg gaggctgagg caggagaatc acttgaaccc 133980
aggaagcaga ggttgcagtg agccgagatt gcatcactac actccagcct gggcaacaga 134040
gggagactcc atcgcaaaat aaaataaaat aataaaataa aaataaacat gtgtgcatca 134100
actgcttata actatatatt cagacatcca gaatatgatt ttactgtgac tggacttcag 134160
aatgtgctgc gtgtgatcct aggtgaagtt gtgtgtgttc aggccctgct gagcatgtgt 134220
gaccatgtgc accttgtgcc tgcaagtgca ggtatgagag tgtgtggatg tgctttgtgg 134280
gggatctgat tgtcattcag caaacattca ctcctttcct gccctccacc tccatggaag 134340
gagactcctt cctgccccat taaagttggt cttggtcatg taacttactt tggccattgg 134400
agtgtggcag aagtgacagc gtgccaactt ccaacctagg acttaaggag aattgtactt 134460
atcccttccc ttttttggta gtttcatacc ttcatggtaa gaaaaacaag ttctagagca 134520
gggctgcccc agcgacccac aaatcaggca gcaaggaaca tatgcgaatt gttctatgcc 134580
cttgagattg tgtggctttg ttatgcagca caaatgacta attcatgctt attttgcatg 134640
ccccttggtc tagactgtct aacttctgga gccttactcc tagaaaagcg tcatgcccaa 134700
atgtaatgat caataaagac ttgttattgg attaaatgtg cttgcacatg tgattgcata 134760
cactggacat acatgtgcat gtgcataggg caccagccag tgtgagagcc agaacagacg 134820
tgcgtgtgag atgcacacta atagcagagt ggtagctaag taatatctgt ctgcacacat 134880
ctgcctgggg ggccacacaa aagggcctga gttcatttag ctgtggactc actccctttt 134940
ccagaacctt gcacatcctg gaatggagct ggaaacatct tagcccttgg aggcagggag 135000
gaagcttcca gaaccataga cagcagtaaa cccaatgctg tataactgac cacactttct 135060
ctccccttca aactccttca gccttcttaa gatggagcac aacattacct ttgtggctat 135120
agagcttaat tcatctcctg agaaaagtac tagaaagggt cccaagtcct tcgtggtctc 135180
ggctgtccag tgctgaggga gtctaaaaag agataataac cagtaaagtg aaaaaacatg 135240
ctgtggtgga catctgttgc cttttccccc agcacccttt tctttcagga atagattgtc 135300
ttatactcat gtcaatcaca tggtcccact tccttgacca agaaaattgg catgtgatgc 135360
aggctgacca atcagagtca tccctgggag ttttgatgga actatcagag aagctctcct 135420
ttctctggta tctctggcag taggggagga tattggagga cattcatatt accaagtgga 135480
aaaagtaaag accacaccaa ggaacacaga gctgagggat gggaggaaca tattcctgaa 135540
gatatcattt gagacacggg attcagccat gcctgaagac caccagtgga gtttcccgtt 135600
acattccatt cctgaattca atacattccc gttctcttta gtttgaatta aattattgaa 135660
tttctgccat ttacatcaca gtgtgtcctt cttctccctc ctcaatagaa gagtaattat 135720
atatttcttc cttttacttt accataacag tcttctctta gaataagaaa aaacctttct 135780
cttgaacttg gcaggataaa ataaaggcac tgacccagaa tccactgtta ttcttgtata 135840
gatcataaat gcctacagtg aagagcatta cactatcttt ggcgacatct ctaaaggagg 135900
tctgcccaat tagcagtgac agctggtggg aatgcaaaat catacagcca ctttggaaga 135960
cattttgttg gtttcttaca aaagcaaaca tgtttttgcc atataaccca gcaaacacac 136020
tctttggtat ttacacaaag gagttgaaaa cttacgtcta catgaaaacc tgtatatgga 136080
tgttgatagc agctttatcc ataattgcca aaacttggaa gcaaccaaat gtccttctgt 136140
aggtgaatgg ctaaataaac tgtggttcat taagacaatg aaatatgatt cagcactaaa 136200
aagaaatgag ctatcaagcc aaaaaaagac ctggagaaaa cttaagtgca tattactaag 136260
tgaaagaagt ctatctgaaa aggctatcta ctgtatgatt ccaaatatat gatattctag 136320
aaaaggcaaa agtatcagtg gttgccagga attaggagtg agagaggaat gaacaggcaa 136380
agcccggaag gatttttagg gcagtgaaaa tactccgtat gatactataa tggtgaatac 136440
atgttattat atacttgtct gaacccatag aatgtaaagc accaagagtg aatcctaatg 136500
taaaatatgg actatggatg ataatgagaa tccaatgacg ataatgtcaa cataggttca 136560
tcagttctaa caaatgtaca actttggtgg gggatattga tcatggggag cttatgcgtg 136620
tacggggtca gagagatatg ggaaatctct atcttctcca tttttctgag aacctaaaac 136680
tagtattaaa aatagtctct agggtcaggc atggtggccc atacctataa tcccaacact 136740
gtgggaggct taggtgggtg aatcccttga gcccaggagt tcaagaccca cctaggcaac 136800
atggtgaaat tccatccctt aaaaaaaaat acaaaaatta gctgggtaca gtgatgtgca 136860
cctgtggtcc cagctacttg ggaggctcag gtgggaggat cacctgagcc cagggaggtt 136920
gaggctgcag tgagccatta ctgtgccaca gcactccagc ctgggtgaca gagcgagacc 136980
ccatttaaaa aaaaaatagt ctttaaacta ataataatac cactaccttg catctgtaaa 137040
gggccacctt ttccaaattt ccccttcata tgccaagctg tgtaagaaac aactctttga 137100
gatttttagg gcagctacta ttgattccac tttacagcaa atctgaagcc aaggccaggc 137160
gcggtgactc acgcctgtaa tcccagaact ttgggaggcc gaggtgggtg gattacgagg 137220
tcaggagatc aagaccatcc tggccaacat ggtgaaaccc agtctctact aaaaatgcaa 137280
aaaatagctg ggcgtggtgg cacatgcctg taatcccagc tactcgggag gctgaggcag 137340
gagaatcgct tgaaccaggg agtcagaagt tgcagtgagc caaggtcgtg ccactgtact 137400
ccagcctggc cacagagcga gactccgtct aagaaaaaaa aaaaaaatct gaagccaaaa 137460
gaagaaaggt cacatttcca aaataagcat aagaatttta tctcatccta agccagagac 137520
tctgtttgca gggcaggaga gccaaggttg agtgtccctc cacagagcat accacaccac 137580
caaaagccaa acccagccgc tcctcaccca tactgtccca ggagcttgag cctcactgca 137640
gccttttgct cagggttgag gtctgggcag tctctgaggc cgtgtagagc agtcgcccaa 137700
gccctggggg agatccccct gtcgatgatg gctgccggca agtgacacag caggttcccc 137760
atgatgtcca cagtgtactc atcagcaatg gagtcgtcct gaacccaaaa agtggagcca 137820
atgggcagtt ccaacagagc ataagatcgt gagccattag aaacacatcc tgtggggtgg 137880
gcactgtggc ttatgcctat aatcccagca ctctgggagg ccgaggcaga cagatcattt 137940
gaggccagga gttcgaaatc agcctggcca acatggtgaa accccatcta tactaaaaat 138000
acaaaaatta gccaggcatt gtggcacatg cctgtagtcc cagctactcg agaggctgag 138060
gcacaagaat tgcttgaacc cgggaggcag aggtcgcagt gagcctagat gatcatgcca 138120
ttgcactcca gcctgggtga cagaggaaaa ctctgtctca aaaaaaaaaa aaaaaaagtt 138180
ccgatcccaa acttcttaaa gattccagga tcttaactgc ctaccctgcc atggattcct 138240
agagatggaa caggacctga tcttccccag ggatgcaggc ctcagaaatc tggaaaaccc 138300
tggcttggca caccaggagc actcagtaat tgagcgctgc tgtcactgtt attgctctga 138360
gaatattcca gacttcaacc accattatac tattggcacc acaacaatga aaacagcact 138420
tcaaagtttg tatgccactt gaaagccttc aaagctcttt tgcactttca caaaatgaca 138480
aaaatagttc acatttattg tgtgtttcct atgtgcgggc accgtcctga gtatctgtgg 138540
gtctcaatct agtcatcttc aaagtaactg taagaagtaa gtactactat tatccatttt 138600
ttaaagaaaa agaaactgcc agctagtggc aaggctagga ttcacaccca gacaatctgg 138660
cctttgagcc tttacattaa ataatacatt gcccatgtca tgttttcaat actctatgag 138720

-continued gagactaggt atggtggctc atgtctgtaa tcccaacact ttgggaggcc gaggtggatg 138780
gatcacctga tgtcaggagt ttgagaccat cctggccaac atggtgaaac cctgtctcta 138840
ctaaaaatac aaaaaataac cgggtgtagt ggtacacacc tgtagtccca gctacttggg 138900
aggctgaggc aggagaatca gttgaacctg ggaggcagag gttgcagtga gctgagatcg 138960
tgctactgca ctccagcctg ggtgacagag tgagactctg tcccaaaaaa aaaaaaaaaa 139020
aaaaaactct aagggggatg tgctactccc cccaccttac agatgagaag actgaggctc 139080
agggaggaaa ggtgattcac ccaaagccac ataaccaatc actggcaccc agtctctggg 139140
tactgtgctc tttccattcc tccagagtag cctcccctcc tttgggccgt ggggcagaag 139200
tctccagaac caatggaaaa gattgttcca accagcaact ttagagtaag cttcaagacc 139260
caccagtcag acttctggcc atcacagcag gctcaagatc ctagccagat ccctcacagg 139320
gctccccaag atggccacag atacccagag ggaggggaca cccaggaaga gttttcttac 139380
caggcactgc tgcactttcc tgaggactga agtctttttg tgggaatcta aaaccaagga 139440
gtccaaccag ctcttcccca ggctgatcag aaagggcaca cactgggagg ctgggacaga 139500
agccaggtag cgggccctgg agagagatgg ggagaacaag aggaggaaca catggctgct 139560
cctgttggcc cctaaaatca gggttcgcct gcccaagagc tcatcccaaa gacattcttt 139620
aaatgtttgt tcttcccagt gatgctttgg ctccctgcag caggtagcaa gcttcccacc 139680
catcatgctc ctcttctatg ggtgggaaca aacttcccat catgctcctc ttccatgaat 139740
gggcaacaaa cttcccatca tgctctcttc tatgggtggg aacaaacttc ccatcatgac 139800
cctcttctgt gggtgggaac aaacttccca tcatgctcct cttctatgcc ccagagcatt 139860
gatcagagaa tgggttctcg taaatagaca tgttgattga tggactggtt gaggggagat 139920
gaaaaagaaa ggaaaaagta gatgaaaaaa gagacaacga ggagagagaa taactagaaa 139980
gtgagaaaga aagataagaa aaagagtgga aagagaaatt ctgtcatctc cagtccagaa 140040
ctctgccttc cactcttgat ccttcagctc ttgacaatgt attctcaaca gggtcaaagt 140100
caccctcaag aaggagaaac tggtttggat ggagataaaa aagactgtta tgacaacgat 140160
ctgtaaccca ctgaagctca ttcctactca aaatattttt cctcagtgta taatttcttt 140220
cattcaggag aaattaaaat tttctccttt ggaaggcatt aacaaaagtt gagaaagtct 140280
gcatgaaacc catccggcct actcaacccc accacttcac tgttccaaaa ccagatacaa 140340
cgtcttcccc caaacatgtt cttccgcctc tatgctatcc cacactcctt tttttcttta 140400
tcccaagcct gtcattgcta tctccttagc attatcccaa tctgttctta cttctggcca 140460
ggtgtggtgg ctcacagcta taatcccagc actttgggag gccaaggtgg gtcacctgag 140520
atcaggagtt tgagaccagc ctgagcgaca tggtgaaatc ccatctctac caaaaattca 140580
aaaaattagc tgggcatggt ggcatgcaca cctggggttt caactactct agaggctgaa 140640
gtggaagaat cacttgaacc tgggagacag aggttgcagt gagctgagat cgcaccactg 140700
cactccaacc tgggtgacag aatgggaccc cgtctcaaaa caacaacaac aaaaaaaatct 140760 attctaactt ctccattccc agtaccactg tcttatttat ttcttcattc atccagcaaa 140820
tatctacaaa gcaactacag taagccaggc actgttctag gcaccaaata taacaatgaa 140880
caagacacaa gtggtcctta attctagcag agagaagaaa cacagaaacc agtgaacaaa 140940
acaagacatt tgagctatta atagctggca tggtggctca cgcctgtaat cccagcactt 141000
tgggaggccg aggcaagcag atcatctgag gtcaggagtt tgagaccagc ctggccatca 141060
cggtgaaacc ctgtctctac caaaaaatac aaaaattagc caggcgtggt ggcgcacacc 141120

-continued tgtaatccca gctactgggg aggctgaggt aggagaatct cttgaaccca ggtggcggag 141180
gttgcaatga gccaagatta caccactgca ctccagcctg ggtgacagag ggagactctg 141240
tctcaaaaat aaataaatta attaattaat taattaatgt aaggaagaaa ataaaatggc 141300
tctgtaaaag agaatgacaa tggggataat caaacgagcc ccttctaagg cagttccatt 141360
tgagctgaga catgaatgag tggtagaagt gccatgccaa gatctgggtt actgaaataa 141420
tcttcagctg tctcccttct ttccattcag cctccctgca ttctatcctc tatgtgggta 141480
gtggctatga tctttctgaa atataaatct gatggctgca cacagaatat gtgtgaaaca 141540
cctcacttta caaagccccc atgatctgat gtcccttaac tctctggcct tctctcccct 141600
atctactctg cagatatacc cccatgtgtt cccagagtga ttggcttttc ttacccactg 141660
ctgaaccgga catccccatt ccactgcctg gaatgtccat cttaaactct ctatccagca 141720
ttagttcggt ctcccctgtc tctccagtct atgggtgata ttccctcctc tatgtccagt 141780
cctcattatc cctccccttt gcctctcctt tggaaggcaa taaaaaagtt gagaaaggct 141840
gcatgaaacc catctggcct agtcaaaccc accacttgac tgttcaagaa ccagattcaa 141900
catcttcccc caaacatgtt cttccacctc tgtcctaaca gaggtgtgta acagcacctg 141960
gctttcttgg aaagcaccta gtttttcttg gagaaccatc tccctcactc taagtccttg 142020
tggtttctct ccagctccag gggtgcaata cagattgaag tcagtcaaag ttacccatcc 142080
tcccaacctc actgattggt tcaaggaaaa caaattcgcc caattaaggt caatgagagt 142140
caaacccaag atgtgtattg agaatgatgg gaagagaaca tttttctatt ttccctgaat 142200
atgaaactgg gaaaatttaa ccttagatct tccagggttc ccacagagga acaacttgcc 142260
tgatagtgaa gccaacagag aaaagctggg acaagagaca aatgacatca tttgcacccc 142320
tagatcgagc catgcctgaa gtccctctct gaactttcca gttacctgaa caaaaaattc 142380
ccttttattg cataagccag tttcagtttc agttctgttg ctttcaacca aatatcaacc 142440
tgatataatt ggcttcatgt ttgtctattc cctctcccac catgagatta taaggtctta 142500
taaattaata ggaatttcta aatcttcaga tagaaaattt agctatctga gaactagcac 142560
acagcaagta ctcaatgaac tttttttttt ttttgaatga acgaagacaa taagagcaaa 142620
aaaaggtaga gggaaataaa gaaggagaga aggagagaaa caatgtccag atcatgtttg 142680
aaaagcaggg ccaccctgca ggcccaaaag ctcacacatg ccaggagaaa cgcctactgc 142740
tcccctcaac tctgattccc ctggagcctg gcacagccgc aaagccaggc cagatgggac 142800
ctgcctcact gacactcatt caggcttggg ttgctttggc ttggttttta gataacagga 142860
aaagcaagaa ggtctgtctc aaatgtctgt gtgatactca gaattgaaat cctggatctc 142920
aagggcttaa ctctctaagg catcctccac tctgcctctg gttcctgaag aaaacccagt 142980
ggggagagaa tcattttgac ttcagtgatt cccaccgatc tcactgatga gccagaaggt 143040
gggggctgat gttcacttac gggagtgcag ccaagaggaa aggtggcata gacaatctgg 143100
aaacttccca gtatttccac gccaaacaat taacctgaaa gattaagcag ttctggggat 143160
ttaatgcagt aagaagaaga acaaacacag tgctttccat gtgccaggta ctattctaag 143220
tgcttcatac gtgttcattt atgcaataga gcaccctatg atgtgagtac cactactgtg 143280
cccagtttat ggatgagaac gctgaggtaa taacaaacat gaacacggac atttaagtgt 143340
gagaatgctc atcgcaattt tgcttatatc tgcaagaaag ggagatataa ttttaatgtt 143400
cctcagcagg ggattggtta agtaaattat ggtatataca tacaatggaa tagtgcacct 143460

-continued actttgtttt aataaggtag atttatatat atattaacac taaatgatgt ctgtgctatt 143520
ttatgcatgt gcatatatat agttatatta tatataatgt aaaaaccaca aatgggctca 143580
tattgtacac acaattctgt taaactatat atatagctta actatacata tagttatata 143640
tagcttaact atacatatag ttatatatag cttaactata tatatagttt tatacatata 143700
tatatcttag ctatatatat aaacagaaca gcatgtatag tatgagctca cttgtgtttt 143760 tttttttgt ttttttttg agacagtctc actctgtcac ctaggctgta gtacagtggt 143820
gtaatctcag ctcactgcaa cctccgcctt ccaggttcaa gcagttctcc tgcgtcagcc 143880
tcccgagtag ctaggattac aggcaccccc caccatgcac ggctaatttt tttttttttt 143940
tgtattttta gtgggttttt ttggggtttt ttttttgtat tttttaaaaa tttttttagg 144000
ttggccaggc tggtttcgaa ctcctaacct caagtaatcc acccatctcg gcctcctaaa 144060
gtgctaagat tactggcgtg agcactgtgc ccggcccact tgtggttttt atattacata 144120
tagatacttt tttaaaattt ggtttagaga tagagtctca ctctgtcacc caggctgaaa 144180
tgcagtgact ccatcataac tcactgccac cttgaactcc caggttcaag tgatcctcct 144240
gcctcagttt cccaagtagc taggactaca ggcatgtgcc accatatttg gctaattttt 144300
gtattttttt gtagagttag agtcttgctg tatgtttccc aggttggttt caaagtccta 144360
tcctcaaatg aacctcccac ttcagcctcc caaagtgcta gaattacagg catgagtcat 144420
tgtgaccggc ctatatttta tatataaaag aaaactctca aaagtaatag caaactgttc 144480
tttatagtta cctctgaaac acagttgctc acctcagtat tattgacatt ttcgaccagg 144540
tacctctgtg tagtggtgct gtcctacgca ttgtaggatg ttgagctcca cccctggcct 144600
ctacccacta gaggccagta gctctgctcc ggttgtgaca accaaaaatg tttgcagaca 144660
tggccaaaag tcccctaaga gggcaaaaca gtactctgtt gagaacaact gctctgggga 144720
aaatttgggg aaattttact ttctctgtat tggttgtttg tgtgtgtgtg tgtgtgtgtg 144780
tgtgtgtgtg tgtgtgtgtg tgtaataatt atgtgttttc agaatgggcg tggtggctca 144840
tgcctgtaat cccagcactt taggaggctg aggctggtgg atcactggag gtcaggagtt 144900
caagaccagc ctggccaaca tgatgaaacc ccgtccctac taaaaataca aaaattagcc 144960
aggtgtggtg gtgcgcacct agaatcccag ttagacagga gactgaggca ggagaatcac 145020
ttgaacccag gggcggaggt tgcagtgaga ttgaaccact gcattccagc ctgggcaaca 145080
gagcaaggtc ctgtctcaat aataataata atgataataa taataataat aataataatg 145140
tgttttagta aaaatataaa cgagaaaggc aaattttcta attaactggt atttgaaggc 145200
tctgagagct ggaagcctag gaaagcacct tcactggggc aactcttcct gctcgaacat 145260
gtaggtcttc ctcaaagcag gtctagcttc catccatttg ctcagttatt ggcttgccca 145320
cctgggcagg tcttttaata tagttcagtg gtttgtacca gcaaactgat tagaaatgca 145380
aagtattagg cctcacccct tacctactat atgtaaaact ctgggagtgg ggcccccaat 145440
ttgtgttttt acagccttcc acacaatgct gatgcaagct caactttgag aatcactaac 145500
agaattaaca gtccaaggga atgagagagc ttcattaaaa ctttgcatat tcctgtaatg 145560
atcttgaagg attatacacc aagcactcta tgcttcctgg ttttctggga gataatttac 145620
tctttggaaa ttcttcattc tggtctgaaa cacaaggcca gagttgagaa ggtgcttttt 145680
aatatccatt acaggagtct gtaagccagc ggttcacacc aaaagttcaa atgctgtaag 145740
gcctgtgttt actagcttag acactgaaaa atcagtcact ggctgggtga agtggctcat 145800
gcctgtcatc ccagcacttt gagaggctga ggcaggagga tcacttgagc ccaggaattt 145860

-continued gagaccagcc tgggcaacat atcaagaccc tatctctgca aaaaataaat aaattagcca 145920
ggcatggtgg tgtgtgcctt tagttccagc tactcaagaa gttgagacgg aaggatctct 145980
tgagcccagg aggttgaggc tgcaatgaac catgattatg ccactgtact ccagcctggg 146040
tgacagggca agactgtgtc tcaaaaaaaa aaaaaaaaga aatcagttac tgcttctagt 146100
ctccccaaag gttaaatagc ctccataacc ttttagaaaa tgaagtttta agtgagaaag 146160
aaaatgttct cagagtactg tttgcattca cagctactcc tggaaagtgt tggaatatta 146220
gctgaaggag taccttccat cccacgggaa cataattatg aacacacaaa atactgtccc 146280
ttatgaatat attttaaggc ttaaatttga gtatggaata accaatctgt tgattctttg 146340
gctgtagtga tgtgggtatt tggagctgtt taaaaagaaa ctggaaaaaa cctggctcaa 146400
tctttggccc taagtcatca cttgcgtctg aatgattctg gcataaagat ctttagatgc 146460
cacagccaat ccaggcccag tgactggggt agggagagag aattagaagc tggaaaatgc 146520
tttaacggta cctgataggg tgaaagcagg gcgaagttgt tctgaaaatc ctggaaatgg 146580
gccagaaaga agtcagtgct catggcatca atgtgtgagc aggtcacgcc tttgaccagc 146640
tgcccagcac tagaaaacaa aacaaggcac tcgggagagg aaggaagtga ggaggagagg 146700
aaagaaagag cgagagaagg cagatatgat cagatacaag ctacagatgt gactgcctaa 146760
ctctcccacc tggaaaagta ggctgctctg gcagaaggct ctgaaaggcc tgttcagcac 146820
ccaggccgag ttacattttc ctacctcaaa agctcctcag gccttctggt ggtctttaac 146880
agaagctcat acaggaacag agcctgcaag aagagaatga tcgttagcac tgatggcaca 146940
ctcagcgtgt gcccaacact gtgaggccct atcaggaagg cattccacaa tcccatttta 147000
cagatgggga aatggaggct taacaggcta tgtgagttac ctaggactag accattgcta 147060
agtggcagtg cctggatttg aaccagtgtc aaggtaattc cagagcccca ctctcacact 147120
ccagatgatt ctctacaccc catgaggcag atgagaggca aagacattgg tggcagggct 147180
ggagttttac ttcctgtgct ttaggaagct gctgaccagt tgagaactcc ctgtgtctcc 147240
tattcacatg tgcacctgcc aggttctgaa caccaggcat cccagaataa accaggatgg 147300
gctagaaagc accagcaata aagtacctgc agctagcagc atgcactgtc ttcaaaccac 147360
cccccaatga gcactctaga acaatgccta gtagacaggg gagtcatttg ttttaaggaa 147420
cataatttta cagaatccct aacttgcaga cgcaatcaag tactacattt gtctatttta 147480
tagactctga aactttgagt atcattcccc agacagaata aattatgagc tagcattaga 147540
catggtagct gagagccaaa aagcagcaca aaagcccagg caaaaggaat ggacgatgga 147600
ggaaagttct ggacactgtt tgtggcccca gagattttcc tgggctcagg gtcaaattct 147660
gggaccctcc catggtcttc cccatctcag gaaacagcaa tcccatcagc tcaatggccg 147720
agacaaaagt atcttgaagt cttcggtggc agaatgtatt ttccaaaata aaactattgg 147780
ctgggtgccc tggttcacgc ctgtaatccc aggactttgg gaggccaagg cgggcagatc 147840
acttgaggtc aagagttcga caccagcctg gccaacatgg tgaaaccctg tctctataaa 147900
aaatacaaaa attagccggg catgatggtg tgtgcctgta atcccagcta cttcaggagg 147960
tggagccatg aggattgctt gaactcagga ggaggaggtt acagtgagcc aagattgtgc 148020
cactgcaccc cagcctgggt gaccgagaga gactctgtct caaaaaaataa aacagaataa 148080 aataaaacgg ttgccactgt cactaaattt agaggtggtt tgtgacacag caatagatca 148140
gcaggacatc atccagcctc atgagagacc ctgagcaaga gcgcctggaa cagacaggga 148200

-continued tttgtgtcgt ttcattcact tttgcacact cagcactgtg agcagtgcct ggcgcactgt 148260
tgggctgtgc ttgataaaca tttgctgggt gcatgtaatg aagactgact gaatacaaag 148320
gtagtcaacg atggtactaa ggcagagcat ccacttcaac agcaccatcc ccccaagcgg 148380
cctcaatgct cacagcattt aataatacac ataatagccg cgaatactta cagtacacag 148440
cccaggtggc atgtatcagt gaccctcatt ttattatcaa aattatcccc atttcgcaca 148500
tgagaaaact gaggccatat aaggaacttc tccaaagcta ataaataagt gggagccaga 148560
attcatgctc aggtcttgtc taactttttt tttaagagac agggtctcgc tctgtcgccc 148620
agactggagt ggagtagcat gaccataact cactgcattg cggaactccc atgctcatgt 148680
gatcctcctg tctcagcctc ctgagtagct gggaccacag acatgcatca ccatgcctgg 148740
ctaatttttt aactttttgt agagacagga tcttgcttgc tatgttgccc aggctggtct 148800
cgaactcctg gcgtcaagcg atcctcctgc ctcagcctgt ccaaattctt aacactatac 148860
tattctgcct cctatactaa tcccacagaa ataaatttct tttatcaaat taaccttaaa 148920
acagaccatt cattctcaca agacagatag tcagaaatac aggatcgatc tgtgtttcat 148980
ggtaatacct ggctccttcc aagttcctta tccttcagga ctgtagagtt gaatccaggt 149040
tgcctcctta aatcaaagag agacacttcc ttaaagaaag ccccttgtat ctccacgatg 149100
cctggggcag tgtcttccgc ttggaccatc tgccagaagc gagaagcaac aaaacaacat 149160
tgtaaaaaat gcattgagct ttgaggaagg gccaggcact acatcacagg caataaaatc 149220
catcagaacc gctcagcaac cctaggaagt ggagagtagc atcatcccca tttcacaggt 149280
gaggaaacag agacttaaag tgtgatgagt tgaaagtcag taagtgacat tcaagcccaa 149340
gtctgtctga ttccaaaacc cgtgctcctt atttctttat tttaactgta tgggctactt 149400
gctatctgca aggtattggt gttttaggcc aaacccctta ggttttaggg tttttttctt 149460
tttttgagat gggaatctcc ctctgtcgcc aggctggaat tcagtggcat gatattggct 149520
cgctgcagtc tccgcctcct gggttcaagc aatttccctg cctcagcctc ccgagtagct 149580
gggactacag aagtgcacta ccacacccgg ctaatttttc gtatttttag tagagacggg 149640
gtttcaccat gttggccagg ctggtctcaa tctcctaacc tcatgatccg cccaccttgg 149700
cctaccaaag tgctgggatt acaggcgtga gccacctcac ctggccaagt tttggtttct 149760
taacagattt tgccattgga cagaacggac ctgatagagc aagatgtcaa aagactccct 149820
gacaagtaaa aaaggggcca ggcatggtgg ctcacacctg taatcccagc actgtaggag 149880
gccggggcag gtagatcact tgagcccagg agtttgagac cagcctgggc aacatggcaa 149940
gaccccatct ctagaaaaac aaaaattagt gagcagcaca ggcctgtagt cccagctact 150000
tgggaggctg aggtgggagg atcccttgag ccccagaggt ggaggctgca gtgaaccaag 150060
atcacgccac tgcatgctgg ctggggtaat agagcaagac cctatctaaa caaacaaaca 150120
aaaaaacaga atacggacat ggctgtggac catgaaaagg gctttcagat gcaccctagg 150180
actttgggtt tatttttaga tttgaaaaac aaattttagg ccaggcacag tggctcacac 150240
ctataatccc agcactttgg gaggccgaag cagaaggatt atttgaggcc aggagttgga 150300
gaccagcctg ggcaacatag caatactcca tctctacaaa aaattaataa attagccaga 150360
catggtggct tgaggccagg agtttgagac tagcctgcgc aacatagcaa gaccatgtct 150420
ctacaaaaag ttaaaaaaat tagccaggca tggtgatgta tgcctgtggt cccagctact 150480
caggaggttg aggcaggagg attgcttgag cccaggagac tgtggtgagc tatgatcata 150540
ccactgtact ccagcctggg caacacagaa agactgtctc aaaaaaaaaa aaaaaacttg 150600
aacctgaagt gttataagat caggaaacct gatttaagaa aagtcttcca gattagactg 150660
tctggcagaa caaaggggtc tgggaagaat gacagcatga ctgaagggct ccgtctggaa 150720
aggaaggaag gtgtgccacc aggagaaggc agagccaccc cagacaccaa cagctgagac 150780
aatcccagcc ctgggttcat ggcccaaagt cacagcccac tcaccaaccc caaaaacata 150840
ccccctgtga catgtggctg agcaccagac atcttcctct caccttgctg aggatacctt 150900
gctgctgggc aggtgacaag tcggatacat actgggagac ggcacttctc aggacctgcg 150960
agatgtcctt gcgtttcatg ctgcagaagg cctgggtgct gaccccagcc agcagtgcgc 151020
ccatctggct gacattgtag aaagacagca cctggaagag gagcggctgc gcagtcaggc 151080
tctgctcccg cctttcacct ctccaacgtg cactcagccc atctatgtgc caagtatagg 151140
gatgggtgac accttagggg cacagcagtg agccagacag atgctgcctc cacaggcctt 151200
ccttccttct atcaagaaag agagttggcc aggcatggtg gctcacgcct gtaatcccag 151260
cactttgaga ggccaggcgg gtggatcacc tgaggtcaag agttcgagac cacctggcca 151320
acatggtgca accccatctc tactaaaaat acaaaaatta gccaggcatg gtagcaggtt 151380
cctgtaatcc cagctacttg ggaggctgag gcaggagaat tgcttgaacc caggaggcag 151440
aggttgcagt gagctgagat tgtaccattg cactccagac tgggcaacaa gagcaaaact 151500
ctgtcagaaa gaaaagaaag aaagaaagaa agaaagaaag agagagagag ggagaggaaa 151560
gaaagaaaga aagaaagaag agagagagag agaaagaaag aaagagagaa agaaaggaaa 151620
gaaagaaaga gaaagaaaga gagaaagaga gaaagagaga gagaaagaga gaaggaaaga 151680
aagaaagaaa gaaaggaagg aaggaaggaa ggaaggaagg aaggaaggaa ggaaggaaga 151740
aaggaaaaga aagaaaggaa ggaggaaaga aagaaagaaa gaaaaaagaa agaaaggaaa 151800
gaaagaaaga gagagagaga aagaaagaga aagaaagaaa gaaattatac ttgggttttt 151860
tttccttcct ttagagtgaa gatgctagat agttttccat ataatcaagg acatgctttg 151920
gttctatgaa aagacagctg agtgggttcc tttagttatt ctgtgtataa tgggtgatct 151980
catgctgtct tcaaagaagg caagaccttt tgacctcttg ccttctgagt aaaagtggcc 152040
tcacccctca gtaggaagag ttgggtatta ggaaagagac aaaccacttt gtcctgggct 152100
gggagggaac aaaaccgtct ccctcaactc cctaaaatca aattcagaga ggactgtcaa 152160
ggtggaccca tggagcccca gtcaaggtcc agaaacaagg attcaaagcc ttcaacataa 152220
agtcaccacg aggctagaag agaccagatg aatgggctgg cctggtacct gagtcagaaa 152280
gtgggagtgc gtgggcattg gtcatggtgc cataatggag acagtgagca caggagttaa 152340
acaagatggc tctgaggcca ggtgccctgg gttcaatccc agctgcgtaa ctttcacgtg 152400
gccttttcca gttcccttac acactctgta cctcacatga atgaactgga aaatgaagac 152460
tacagcacta ctgacttcag aggattgttg gattaagtta ttaattcact tagaacacaa 152520
cctggcacat agtaagtgtt cagtaaatgt ttgttattcc acaccctccc tcccttggcc 152580
ccgcgatgga ggaagcaggc taggaccagc cctcggagct gcagctgccc ttcatccctc 152640
cctcgccctc tctaccgaca tcctgctcca gttcccactt ggatttactt tggggaatgt 152700
ggttggaata tatctggctc agaaccatga cataccaaac ccagctttaa aaacttgaag 152760
aaatttaaaa agacttggat gccaagaaga aattccctac tccttctctt tgggaggcca 152820
aggcgagtag attgcttgag cccaggagtt tgagatctgc ctgggcaaca ttgcaaaatc 152880
ccatctctac aaaaaaatac aaaaatcagc ccggcgtagt ggcatgtgcc tgtggtccca 152940

-continued gctactcagg aggctgaggt gggaggatca cctgagcctg gggggtcaag gctgaagtga 153000
gccaagatca gatcacttca ctccagcctg ggcaacatag tgagaacctg tctcaaaaaa 153060
caaaaaaaga agaagaaacc ccccagttcc tgaggccaac tccagcactg ccttctggat 153120
gcatggattc tactctataa ctcttaaacc cctttaccgc ctgaatcaaa agcttttgtt 153180
ttcattttac cacctgaatc aaaagctttt gttttcattt ccaacctcag tgatgcgatc 153240
tcggctcact gcaagcaccg cctcccaggt tcacgccatt ctcctgcctc agcctcccga 153300
gtagctggga ctacaggcac ccgccaccat gcccagctaa tttttttttt ttttattttt 153360
agtagagaca tggtttcacc gtgttagcca ggatggtctt gatctcctga cctcgtgatc 153420
tgcctgtctc ggcctcccaa agtgctggga ttacaggcgt gagccatcgt gcctggccta 153480
gtgattttct tccttgtgag acactgtggt attttgcttt agaacaagca aaatggggcc 153540
ccttacattt tcaacatctt cacctcttcc catatcctcc ttcaagctgc atgggaggta 153600
ctaacactag aattacggtg ctaggttagt aaacatgacc tttaaggagt agtctctcct 153660
ttattctttg ggattcctac tactttttc tttttttttt ttaagacaga gtcttgctct 153720
gtagctcagc ccagtctgga gtacagtggc atgatctcgg ctcactgcaa cctcctctgc 153780
ctcctgggtt caagtaattc ttctgcttcg gccttccaag tagctgaaat tacgggtgtg 153840
caccatcatg gccagctaat tttctattt ttagtagaga cagggtttca ccatgttgtc 153900
cagctggtct caaaccccta gcctcaagtg atccattcat cttggcctcc caaagtgctg 153960
ggattacagg cataagccac catgcccagc ctactacctt ttgtcaaaat aaaaattgat 154020
gagttttgta tagttggtca gacacagtta aaactaaatt cacagtttag caattataat 154080
gggtgcttgt taaacatctg gtagtaaatt atgttgtttc aaagtaatta aaattaatat 154140
ccagaagcca aaaataaaca aatgtttgtt attattattt gattggaatg ggtcctaatc 154200
caatccttgt gagccagttt gcatcctggg aagtggccag gagtgtggac taaacgagaa 154260
ggacaccaaa agccaggcac ggtggctaat gcctgtaatc ccagcacttt gggaggctga 154320
ggcaggcgga ttacaaggtc tggagttcga gaccagcctg gccaacatgg cgaaacctcg 154380
tctctactaa aaacacaaaa attcgctggg tgtggtggtg ggtgcctata atcccagcta 154440
ctcggaaggc tgaggcagga gaattgcttg aacccggagg cggaggttgc aatgagctga 154500
ggttgtgcca ttgcattcca gcatgggcga caagggcaag actccgtatc aaaaaaaaaa 154560
ttagatgaca ccaaaatgct tagaactcaa gtctcccaga tttggagccc tctggactgg 154620
acccaaccca gggacattaa ttgtccccaa aagaatgtcc attttccacc ccaggagcag 154680
caagaacaca gattaagact cctgtcccca ccaaagagga ctgtctgcct gacagttccc 154740
tctctgcagc ccaagattgg aataaaatag catcatccct aatcccaaag taatggcaaa 154800
aaccgcaatt actttttgca tcaacctaat agcagcttaa cagcaggcag gaaaatcctg 154860
ggatgagtcc cacacgttga tcccactcag ggatggctaa tgccccttga gctcctactc 154920
tgtggtgtca cctggtggtc tagcttcttc atgtgtacca actcacataa tattcgcagc 154980
aatgctacag gataagtgct actgatttgt tgttgttgtt gtttaatttt ttttgaaatg 155040
gagtcttgct ctgtcgccca ggctggagtg tggtggcaca atctctgctc actgcaacct 155100
ctgcctccca ggttcaagcc atcctcctgc ctcagcctcc caagtagctg gaagtacagg 155160
catgcaccac cacgcccagc taatttttgt atttttagta gagacgggat ttcaccatgt 155220
tgatcaggct ggtcccaaac tcctggcgtc aggtgatcct cccacctcag ccttccaaag 155280
tgctgggatt gcaggtgtga gccaccttgc ccggcagtaa gtgctattgt tgtccacata 155340

-continued ttacaaatag agaaactgag tcaaagtgaa aatagcaaat tgcctagtgt cacacagcta 155400
gtaaatggca gagcaaggat ttgaacccag gcagtcctcc tcagcatcat cttcttactg 155460
attggttgcc ccctgctgtg tgtgtataac tgattgttat ggattaaata tttgtgtctc 155520
ccaagaattc atatgtcaaa gtcctaaccc ctaatgtgat ggcattggga ggtgagacct 155580
ttaagaggcc tttaagggtt agatgaggtc atgagataat gagggtcagg tggggccctg 155640
atccaatggg attagtttcc ttgtaagacg caacaccaga gagcttgctc tcatgtggtc 155700
aggtgagcac acagcaagat ggcggccacc tacaggccaa gagaagaggc ctcagaatga 155760
aacctacctt tctgacacct cgatgttgga cttcccagtc tccagaactg tgagaaataa 155820
atttatgttg tttacgtcac tcaatctaca gtatattttt atggcagcct ggcaggtcta 155880
atacacttag gtcatcttag gggaataaaa aagagtttaa aactccagct gaccttctca 155940
tgggccaagt atttggcaga caagatgatg acctggctct tggcccaacc tgagacctgg 156000
ttgagggtgg agatggctcc gtgcacagcc tcgggggaga gggattccag ttggctgtag 156060
gtcaaaccta caactgcatc cgacaaagaa cccagggtct cattgagggt ctggttctcc 156120
atggcaatgt ccaggagttc tgctttgagc tggaaggaga gcaaactgga atgagtgttg 156180
acaggaagca gggcggtggc tccctctgac catatccagg gctattagga ctccacagca 156240
cctcccttga ccctgttcca tcaaagcttt tgggctcaga aacgatgaag gaaagggact 156300
cctgccatgc ccagacagtg agacaccaca cggaggacac ctcttctggc cttagctttc 156360
atgtgccaaa aattcccttt gtacttcatt taaatattaa tttgttatta aatcaacctt 156420
aatccatgtc agaaagaaat gttcctttta taactacacc acactcttat agcatctgtt 156480
gtcctctggt gaccttgaac tctatatcca tatatacagg ctgttttcct ttcattaaat 156540
agccaggggc cttttcacga taatttataa tctgtgtaaa aataactttt tttttttct 156600 taagacagag ttttgctctt gtcacccagg ctggagtata atggtgtggt cttggctcac 156660
tgcaacactg caacctccac cttccgggtt caagcgattc tcctgcctca gtcttctgag 156720
tagctgggat tacaggcacc caccaccaca ctaatgtttg tatttttagt agagacaggg 156780
tttcaccatg ttggccaggc tggtctcaaa ctcctgacct aatgtaatcc acatgcctca 156840
gcctcccaaa gtgctgggat tagaggcatg agccaccaca tccagccaaa aataactctt 156900
cacagtacaa gaaagtaaaa gtctcctgaa catcctacca cataaaaata accatgatta 156960
gcaattgggt gtatatgctt ccaagatttc ttataccttt ataaatatag agacactaca 157020
tagtttttac agagttgtaa tatgaacaga agcacaattt actcttctta aaattatctc 157080
ttgcacctct ttgcacattt ctatgatcat tttaataatt attttattgc aatatgcctg 157140
cctaatgata gtaaagtgtg cgttacagct gctttcggta aggaatgtga taaagtcacc 157200
tactatacaa tgagctctgt aacaaaaaac aagaatggtt catattttaa cacccgaatt 157260
tacgtaataa cgtagtcatt tcaggcaggt gcacaaaacg ggtttctggc aatattgaaa 157320
tagccactgg ggggcagcag agtgaagtag aagaaacaac tgtcaaagcg cctgggttct 157380
ctaagttcgg caactgcctt acctagaaat cagtttccac atctgtaaaa cgaaggggtg 157440
gactacagtg gcagctccca aagtgtggag cacacccagc ggcatctgca acacctggga 157500
acttgttaga aacgcagatt gccaggctgc tcccggacct cctgaatcag agactgggtg 157560
gggctccgaa atccagggat ccccagactc cgggtcacag atggggacca ccgggaccct 157620
ggcctgttag gaaccagcca cagcaggagg tgagcagcag gccagtgagc attaccgcct 157680
gagctctgcc tcctgccaga tcagaagcgg cattagattc tcctaagagc aaaccctatt 157740
gtgcactgtg catgcaaggg acctagtctg tgcgctcttt atgagaatct aatgcctgat 157800
gatctgtcac tgtctctcat cacccccaga tgggaccgtc tagttgcagg aaaacaagct 157860
cagagctccc actgatttca cattatggtg agttctatag ttatttcatt atatattaca 157920
atgtaataat agaaataaag tgcacagacc gggcgtggtg gctcacgcct gtagtcccag 157980
tactttaaga ggccatggca ggcggatcac gaggttaaga gaatgagatc atcctggcca 158040
catggtgaaa ccccgtctct actacaaata caataaatag ctgggcgtgg tggcgtgcac 158100
ctgtagtccc agctactcag gaggctgagg cagagaattg cttgaacctg ggaggcagag 158160
gttgcagtga gccaagatcg tgctaccgca ctccagcctg gcaacagagc gacactccat 158220
caagaaagga gaggagaggg gaaggggaaa gggatggggg ggggaggggg agggagggag 158280
ggaaggagga aagaaagaaa gagagagagt gagaaagaga agaaagaaag gaaggaagga 158340
gggaagaaag aaagagagag acagaaagag aaagaaagaa agaaagaaag aaagaaagaa 158400
agaaagaaag aaagaaagaa agaaagaaag aaaaggaagg agaaggaagg tagggaggga 158460
gggagggagg gaggaaggga gggaaggaag gaagagcaca ataaatgtca tgcacttgaa 158520
tcatcctgaa acaatccccc ggccccagtc cacggaaaaa aattgtcttc cacaaaaccg 158580
gtccctgatg ccaaaaaatt gtcttccaca aaactggagc gctgccacaa gctgtatttg 158640
aacaggccct ccctgtgatt tagatgcacc ctccagtttg agaacaactg agctagatga 158700
tcccaaaggg ctccctcgta tctaattgca tgccaccttc tccttggtca gggctgccac 158760
atgttgagac ccctgggcct taaaatacat ttatcttctt atttttgctt gagcttgctt 158820
aggacggatt cttttccttg gaaacaaaaa tatgcattca caggctaggc tcggtggctg 158880
acgcctgtaa tcccagtact ttgggaggcc aaggcaggtg gatcacttga ggtcaggagt 158940
tcaagaccag cctagtcaac atggtaaaac cccatctcta ctaaaaacac aaaaaattag 159000
ccgggcatgg tggcatgcac ctgtagtccc agctactcca gaggctgagg caaggcgaag 159060
gttgcaatga gctgaaattg tgccacttga acccggaagg tggaggttgc agtgagctga 159120
gattatgcca ctgcattcca gcctgggtga cagaatgaaa ctcaaaaaaa aaaaaaaaat 159180
gaatcttata aaaaaaaaaa aaaagatgcg ctgaccaaaa tagatgacca cactctcaaa 159240
tgtcaaatgt gtttggggac tttatggtga tgtgtgggaa actgctgtga aattattgat 159300
ggctttatca aaatttcatt taatattatt ttcatgtcat cgtttcgatt ttaagcaaat 159360
tgaaaagggc cacaaaaagt ggaatggaag ggggtagaat tgagacttga ctggaaggaa 159420
gaagagagag atggagagga aggaaaatga gagagagcgt gtttgctcat ctggtcttgg 159480
gaactcataa ccaccctgca atccagtgtt ctcaatcctg gctgcattga aatcacctga 159540
gaagcattaa aatcaggcca tacctcaggc cacaccccag aacaataaca tcagattctc 159600
tgagggtggc acctggcagg gatgttacta atctagaggc aggtttgaga accactgctt 159660
tatctcctgc cgctccaggt gtgctcacca gagcagcggt tccagaatca cctggaagct 159720
tgttggaagt gcagcgtcag ctgggcgcaa tggctcacac ctgtaatcca aacactttgg 159780
gaggccaagg gaagaaggag gaagaagagg aagatgggag tcctgggcct caaccaagag 159840
ctcctgaatc agaatctgca tttaagatcc ccaggtgatc tgtatgcata tttaagttcg 159900
aagtagctgt ccctttcttt tcttttctgt tctttttttt agatagggtc ttgctctgtc 159960
atccaactag agtgcaaagt cactatcata gctcactgca ggctggcact cctgggctca 160020
agcgatcctc ctacctcagc ctcccaagta gctggcacta taggcacatg gctttttttt 160080

-continued ttttcttttg agacagagtc tcactctgtc acccaggctg gagtgcagtg gcacgatctc 160140
agctcgccac aacctctgcc tcccaggctc aagcaattct cctgcctcag cctcctgagt 160200
agctgggatt acaggcgcat gccaccacgc ctgtttttgt atttttagta gagacagggt 160260
tttaccatgt tggccatgct ggtctcaaac tgacctcagg tgatctgcct gccttggcct 160320
cccaaagtgc tgggattaca ggtgtgaacc accgtgccca gccatttttt tgtatttttt 160380
gcagagacaa gggtctcatg atgttgacca ggctggtatc aaactcctgg cctcaaatga 160440
tcctcccatc ttggcctccc aaagtgctgg gattacaggc atgagccacc gcgcctggct 160500
gagacagctt tctgattaaa ttttgatctc cccagggtct gttcctttgc tattttctgt 160560
ctgggcttcg atgttacact tacctcagta tttgagatgc catctgctgt gactggactt 160620
aaatcccgac taatgctgtg tgttttctcc caaaggctaa gctaggctgt tctccccatt 160680
tctctggcta gtgacactga ggcagaggcc tcagggcctt gcaccccagc tgtaccttct 160740
ggacgccagc ctggaagccc ctcaggtggc tgcacttgat catctggtaa agcaggactt 160800
gagccacagt ggcatccagc aattccaggt cattgtagaa acaaaccagc agccccagcc 160860
tgtgtgagaa gaggagggat ggtggtggag gtgtaaccgc agaaccagcc cattctggtt 160920
caattttgtg taataaaatg gtgagttgtt tttcagttgc cacggactcc caggttgaag 160980
gtcacataac ctgaacatcc tcagatgaac caaatgtgca accacaggcg gaacctaact 161040
gctcagacga gaccaaggaa tgggggctga attatgaagt ggacaccaca tggcatggtc 161100
cacgatccaa tcagaatgag tcctggcatc acctcatggc atgatccaat cagatcacac 161160
ctcccagcat caccttgtag caagacccaa tcagatcaag tctcattacc ctccgcctat 161220
aaaacctgcc ccagtcccca gctcagagac acagatttga gcactgtctt ctgtctcctt 161280
ggcagttgat tcacagtaac cgtttctctc tacaaaaacc tagtgcttca gtgtttggtt 161340
ttccattgcg catgggcaaa cagacccagt ttggttccat aacagagcgc tgagagctgg 161400
tggacacgac accccctccc cagtccaaac caatggggtc ttgattatat taatagcagc 161460
taccacttat caggtcttgc actgagccgt ttacctgcat tatctcatta cagcaaccct 161520
acaaggcagg tgctctcatt agccccattt cacagatggg gaaactgaga tttgatttgt 161580
ccaaggcaag tcggtggagc tgggacttaa atgtagatcc atccacctat gccatctctc 161640
cacctgggat gaataaaggg aataaggaaa gaaaggtgcc ggtagccaca gaaaactccc 161700
cattttccac attacaatca ctaaattcta gagctgatct caccctgagg gattctctga 161760
ggcagagatc tgtttctagg atgccttctg gtacccaccc agatgatgca aagatttcag 161820
aaggaaaaca aaaaagactg gaggaaaaca atggaagggc agaagtgaga ttggaaccct 161880
ggtataactg agagcaatgt ttctaatcat taagagcatt gattcaggcc tactgcagtt 161940
tgaagcccag ctctgtgaga tgtttgctct ccaccaagtt acttaacttc tctgtgaggc 162000
cgctatacac agttctgcag tgcacactct gtactcccat actgtacaga gacagggtgc 162060
ctctccctct ctgagcctct aataaatggg aggttttctt tgttcatcgt agcacatcat 162120
aataaacatg agtgaaagaa agaggatgat tgtgaaagtt aaatgagaag tggtatacca 162180
actgatttgc atacatcctg gtggaaacca agcactcatt cattaatgaa tgctcttaga 162240
gttagaatga agactaccta gttgaccaca gtcagcctgg ctccaccctc tcagagcgat 162300
attgacatat tcagacatgc ccacaggaga gctgccaggt ccagggaaaa gatttgaaag 162360
tgtgtctcat gaggaaaaga gatctgctta acttcgagta aagaagactc aggggaagtg 162420
agggctgaac gttaataacc acgttgagaa taactattca caacagccaa gacatggaat 162480
catcctaagt gtccaacacg tcagtggatg aatggatttt ttttttaatt tggtggatac 162540
acaatggaat gctcttcagc tttgaaaaag aaggaaattc tatcatatgg gaccccatgg 162600
atgaacttgg aggatcttat gctaagtgca ataagctagg cacagaaaga caaatactgt 162660
atgacctcat ttatattatg aatctgaaaa acaaataaac aaacgtcata ctcatggaag 162720
cagagcctta gaatggttgg taccaggggc tggaggtggg aagggagttg gagagacttg 162780
gacaaaggac acaatgtttc agttaaatag gaaaataggt tctggagatc tattgtacat 162840
gctgactaca gttaataaca atgtatcata tactcaaaaa ttgctaagag tagattttaa 162900
gtgttctcac cgcaaaaaaa gtatgtgagg taatgataac ttaattagct tgatttagcc 162960
attccacaat gaatatatat ctcaaaacat gttgcacacc atagatataa tttttattta 163020
tcaatttaaa aaaataaatt ataaaagaaa aataggcttg gcgtggtagt tcatgcctct 163080
aatcccagca ctttgggagg ccgaggcggg cggatcacaa ggtcaagaga tcaagaccat 163140
cctggccaac atggtgaaac cccgtctcta ctaaaaatac agaaattagc tgggcgtggt 163200
ggcgtgtgcc tgtagtccca gctacttggg aggctgaggc aggagaatca cttgaaccca 163260
ggaggcagag gttgcagtaa gccgagattg tgctactgca ctccagcctg gcgacagagt 163320
gagactccgt ctcaataaat aaataaataa aaagaaaaaa tattattcat tgagcactta 163380
ctatgtgtca agtgtgcaaa tccctacaaa gaccttaatg cagtaggcat atttttatct 163440
cccattttac agatggggaa gcggaagtat agagaggtga tgtaaaaata gcaaagatca 163500
caccattagt aagcagcagg gaaggattaa gccacgaagt ctggctcgag gtcccatgtt 163560
cttaatcatg aggctatttt tgtgtgtgtg aaaccataga aaaatgagac acatgctaat 163620
aagtgaaaat tactaaaggt aggtgaaaca gatgtaattg tttcctatga gtacattccc 163680
taagagtggc tcatttgaaa aaccttaagg taatatggga tgggagcagt gtggcaataa 163740
taagaccttg agagacggac acaagaggat tgaatgatgg cccagcacag tggctcacgc 163800
ctgtaatctc agcactttgg aagtccaaga tgggtggatc acttgaggtc aggagtttga 163860
gaccagcctg gccaacatgg cgaaacccag tctccactaa aaatacaaaa attagctggg 163920
tgtggtggca cacgcctgta atcccagcta cttgggaggc tgaggcagga ggatctcttg 163980
aatctggagg tggaggttgt agtgagctgg tattgcacca ctgccctcca gcctggacaa 164040
caaagtgaga ctctgtctca aaaaaaaaaa aaaaaaacag gattgaatgg gccaggcgtg 164100
gtggctcatg cctgtaatcc cagcagtttg ggaggccaag gcaggcagac cacctgaggt 164160
cagcagttca agaggtcagg agtttgagac cagcctgacc aacatggcaa aaccccatct 164220
ctactgaaaa tacaaaaaat ttagctgggc atggtggcac acatctgtag tcccagctac 164280
tctggaggct gaggcatgag gattgcttga acccaggagg tggaggttgc agtgagccaa 164340
ggtcacatca ctgcactcca gcctgggtga caggacaaga ctctgtctca aaaaaataaa 164400
taaataaaag gaaaaggagg gagtattgag ctgtactcac cacctccttc ccattgccca 164460
ctcccttcct gacacccctg gaatgtagag ttcctgtccc tcctcccctg ctgggaatgg 164520
ttttagggag gatcacatta cagtcactaa attctagagc tgatctcatc caggggctcc 164580
ccagctaaga gtctgataac aagtggttct catatatggg gacccatgag ttatttccaa 164640
cacttgactc aacttaaacg gaaatcacac attcactttg gaacaggacc cagtcctgag 164700
tatttaaaat gtttcatttc tgtgctgaga gacagaatta gcacttgata aggttgcata 164760
aaatgcctgg cacacaggag atgctcagaa agcatttatc ctttcaccca gcttcataac 164820

-continued ctcttcataa aaaaagttgc agacacctct cctcacatgc acagagaaat atgggactat 164880
tcaaagagat ggaccagcca cctcccttcc ctccctgggt gttttgctgc tcagagaatt 164940
ctgatgctta gatcacatct tgggaaaggg ctccaaggcc cagagctcat gcgcttgcct 165000
gtggatggtg gaggtattcc tcatgttaaa gttggaggag ctgatcctct ccagaaacgc 165060
ctgggccagc tcaggtgtga tgtcatagac catgtccagc tgcttggtgg cgttgtcata 165120
gctgataaac agcccaatct agttggtgga caaggacgag aatatcagtg aggagggtgg 165180
aagtggccca gtgtggcccc accctggtgg tctgcactgt gccccatcat ggacacttgg 165240
atacacctcc tggttctcat tgtcattgat gtcttttttt cttttctttt tttttttttt 165300
tttgagatgg agtctcactc tgtcgcccag gctggagtgc agtgacatga tctcagttca 165360
ctgcaacctc cacctcctga gttcaagcaa ttctcctgcc tcagcctccg gagtagctgg 165420
gactacaggt gcccaccacc acgcttggct aatatttgta tttttagtag atatggggat 165480
tcaccatgtt gtccagggtg gtctcgaact cccagcatca agtgatccac ccgcctcggc 165540
ctcccaaagt gctgggatta caggcgtaag ccaccatgcc tggcctcatt gtcattgatt 165600
tcttagtggt ctgtaactgc tactttagtt tcctcctcaa cctaactatt ctttaggaaa 165660
gaattatttt ttaatatctg agaaactggg ctttttaaaa gctaatcttt gcacatttat 165720
ttctagattt gttatatgga ggtcagagaa tgtggtccac aaactttctg ctttgaagaa 165780
tcagaatttt tttaatagat gaatgagttt ataaatggcc cttgggtgat ggaaaagagt 165840
atgtgttctc tttgtaagac acaaagtttg gtgcatatat attcaactta ttaaatatac 165900
tattcagatt cccaacattc ttgttccttt ttggcccaca tgtccaaggg tgccacgtgc 165960
aagtcttcta ctactacagg actcatatct atctattctt ccttgtattt ctagcagatt 166020
ataaattata tatataattt tggggggaca ctgactcact ctttttattt tatttttgtt 166080
tttattttta tttttatttt tattttttttg agatggagtc tcgctctgtc acccaggctg 166140
gagtgcagtg gcacaatctc agctcactgc aacttcagcc tcccgggttc aagtgatact 166200
cctgcctcag cctcctgagt agctgggatt acaggcatgt gcaaacatgc ccagctaatt 166260
attgtatttt tagtagagac ggggtttcgc catgttggcc aggctggtct tgaacacctg 166320
acctcacatg atccacccgc ctcagcctcc caaagtgctg ggagtagagg cgtgagccac 166380
tgcgcccggc caagacacag tctcactctt ttacccaggc ttgggtgcag tggtgtgatc 166440
atggcttatt gcagcctcga cctcctgggc tcaagtgatc ctcccacctc agcctcccaa 166500
gtagctgaga cctcaggcac acaccactac acctggctaa tttttaaatt tttttgtaga 166560
gatgaggttt cactatgttg cccaggctgg tcttgcactt ctgggctcaa gtgatcctcc 166620
cgccttggcc tcccaaagtg ctgggattac tggcatgggc cacggcagcc ggcacattct 166680
atattttgag acagtattat gctgtgctca aaggggctca taaagttgtc tctcctttgt 166740
ggatcgtact ctttgtccat ataaaattcc tttttaggct gggtgcggtg tctcacacct 166800
gtaataccag cactttggga ggctgaggca aggcagatca cctgaggtca agagttcaag 166860
accagcctgg ccaacatggt gaaacctcgt ctctgctaaa aatataaaaa ttagccaggc 166920
atggtggcat gtgcctgtaa tcccagctac tcaagaggct gaggcaggag aatcaattga 166980
atctgggaga aggaggttgc agtgagctga gatcacgcca ctgcacttta gcctggacga 167040
cagaacgaga ctccatttca taaataaaca aataaaataa aataaaattc ccttttagca 167100
gtgttattct tgacttctcc cttctctaca tttttagcga ataaaaagtt gcaaatgagt 167160
gcttgacctt agaaatttcc tctagggggc tcagctttct aagaatttaa gctgttacct 167220
actcaaagca actctacatt gagagagtaa atggcagtgg ggtgcggggt taattctagg 167280
actgcgggtt ataaaaatcg gaagacactt gaaatactcc cagcccccta ggtaaaagag 167340
agaaagctcg ttctgcctct ggtttcataa taaccacaca ttgctgggtc aatgggtcct 167400
tgaacaggcc agtcatttga tgcaaacact tctctcactg gccagaagag tcagggcaca 167460
tatgacttaa aaaagaagaa gaagaagaag aaaaattgga agcaaggccc acagtctctt 167520
catgaatccc tttgtgttgg cagcattctt tggagaccgc attcaagaat catgatgccc 167580
aagggatttt agtgtcattg ggtcaacatc aaaaggagag ggacaggttg actagtgagt 167640
taagtaatcc tagaatgtgt gtatttctcc actgtaaact ctagaattaa aatctaacca 167700
ttgctcatgc tcaagtagct attaacagaa gtagctataa atagaagtag ctattaatcc 167760
attttgcttt tgctttgagt tcatgatccc aaggatggga aactttatat cttttgtcct 167820
tggccttctc cagtacaaaa atacccttaa atgatttttg gttcatagcc aacaatccct 167880
ttaaatcatg tttgctcaca tcagagatgt gatcttagtt gtccacaatt ctttttcttt 167940
tcttagccct tccacactaa aacaatccca tgactgccca cttgaaactt tcttccaata 168000
gttttcttca gaggcccaag gtctattggg ctgaggaggg tacacaattt ccaaggcacc 168060
ttgactggct ggatgaacat tagagtttga gaatacacct taccccaagt gtattagtaa 168120
tggtgacata taaatgtact tttccaactt acttctatag gactaatttt cgtaatttct 168180
tcaaacgata ggtgaaccat gtatctgccc aaaacccata agtgttccgc actgacccat 168240
gaagcagagt catctacaaa aaataaagaa atgaataaat gagtacatac ataaataaaa 168300
gcctttacac tggtatgtga tagtcaacag catctttgct gtcaagacct acttcttgca 168360
ttcattaatt cgttattttg tttttcgggg ttttttgaga cagaatctca ctctgttgcc 168420
taggttggag tgcagtggtg tgatctcagc tcatctcaac ctccgcctgc cggttcaagc 168480
gattctcctg cctcagtctc ccaagtagct gggattacag gcacccacca ccatgcccag 168540
ctaatttttg tatttttagt agagacagag tttcaccatg ttggtcaggc tggtctcaaa 168600
ctcctgacct caggtgatct gcccgcctct tgcctcccca agtgctggga ttacaggcat 168660
gagccaccat gcccagccac attaatttgt tattaactca ttcaacaatc atatacgtag 168720
ggcctacctg tgagatcaca cgtaggatgt gaacacagat tcgcaccacc tcagaccttg 168780
ttactcaata gtgtggtctt tggaattgca acatctgtgt cacctggcca cttgttagaa 168840
atacagatta ttctttctgg ccaggcacct gtaatctcag cattttggga ggctgaggca 168900
ggaggattgc ttgaggccag gagtttgaga ccagcctgag caatatatca agaccctcat 168960
cgctacaaaa aaaaaaaaaa aaaaaaaaaa agccagctgt agtcccagct actcaggaaa 169020
ctgagaaggg aggattgctt gaaaccagga atttgaggct acagtgagct atgtgctcac 169080
tctactgcac tccagcctgg gcaacagagt gagaccctgt ctctttaaaa aagtaataat 169140
aattaaaaat aaataaataa ataagaaatg caggttattt ttaatactta aaacccacaa 169200
aatgtagttt tattttttca ttcgattggt tactaaataa tctggaaaca tgaggccaga 169260
tgtggtggct cacacctgta atcacgaaat cccgtctcta ctaaaaatac aaagaaaaat 169320
tagccaggtg taatcccagc tacttgggag gctgaggcag gagaatctct tgagcccggg 169380
aggtggaggt ggcagtgagc cgggatcaca tcactgcatt ccagcctagg tgacagagcg 169440
agactctgtc taataataat aataatgata ataatctggc aacatgaaat atgtttgact 169500
gtcttgcatc actaccacta gtaaggatca tcctcactga ttatcaccat gttactatac 169560
ttgaaccaaa gcaaactact tgtacctccc caaaacattc tccaaatctt ggctggcctt 169620
ggccctgctc accacctaca atgcttttcc ttaccccttc tgcatccaaa tcctacttta 169680
agatcaagct caaattttcc tctcccttaa agccttctct tatctccttc acgagaagta 169740
ctttctccct ccactgaatt cccagaggac tctctctgac accccgttct ggcttttgaa 169800
attccccatc actgagatgt cagtggaatt ttaaaaacca tcaagtcagc caggtgcggt 169860
ggctcaagcc tgtaatccca gaactttggg aggccgaggc aggtggatca caaggtcagg 169920
agatcgagag catactggtc aacatggcga aaccccatct ctaataaaac tacaaaaatt 169980
agccaggcgt ggtagcgcac gcctgtagtc ccagctactc aggaagctga ggcaggagaa 170040
tcacttgaac ccgggaggca gaagttgcag tgagctgaga tcataccact gcactccagc 170100
ctgagtgaca gagccagact ccatctcaga aaaaaaaaaa aaaaaaaaaa aaaatatata 170160
tatatatata tatatctcaa gtctaggatc agacttcaag tttcactgag ctggaagtgg 170220
ctgccaatgc tccccagctc tttagcaaaa gacatttaca cacgatattg tattggaggc 170280
atttggggaa aatgaaggaa gtggggagca tttacagggt gcagtgactc taacatcaag 170340
agctatttgc agaagccgtg ggcaatgaca gatgccaaaa caagatggag aaatcaactt 170400
ttatatagac tgattcacaa gaaaatatgg agtgcctctc ccaaaccagg aatcaaagat 170460
gttggggtga cacaggcaga ctcctacgat cctctagatg gggaccctgg acatttgcct 170520
tgcctatata gagggctgga aacttttgag gctagaacca cacattcaca aagaaccaag 170580
cttagttgtt tattttttaa cttattacta agcataaact gtatttctgt agatcaatca 170640
tccccaagct tgggattttt ttttttcttc ctctgttgtc caggctggag tgcagttgga 170700
tgatcatagc tcactgaagc ctcaaactcc tgcctcagcc tccctagtag ctaggactac 170760
aggcacacat caccacatca ggctaatctt ttaatttttt tgtatggggg gggggtctc 170820
actacattgc ccaggctggc cttgaactcc tggcctcaag caatcctcct tcctcagcct 170880
tccaaaatgc taggattaga ggtgtaagcg accacacctg gccagcaagg ttgggatatt 170940
tttaacagcc aaagtatttc cagttccctc aagggccttc atgaaaaaac aatttaagtc 171000
caaacagaat taattttaac tcactgtagt ttaataatga agcgcaccgt ataagaattt 171060
tagaaggaaa gtctgtgcct aattaaactc tggcaataaa gacagagaag tctgaaggta 171120
gagaggcttt ctcatggtta cccagtgtga gactctgatt cctggagacc acaattatgc 171180
accaggcaga gggaattcta ctatgcattt gagactttga ttatgatgtt gtttaatgtt 171240
cattatgcac aaatctcaga gctgaattcc aggaaaagat tgattggcat tccccatcct 171300
ccagccccat ctgctttcct tatgttttcc ccacaccgag ctcattcccg tctcagggcc 171360
tttgtatttc ctgggatttc tctctgggat gccctttctc cagagcctta cgtgactggt 171420
tccatctcct cattttggtc ttgattcaaa tgtcacccac ttgagaggtc ttccctgatt 171480
ccttagtcca agagttggca aactacaatc catggggcaa actctgccca tcacctgttt 171540
ttatacagcc catgagccaa aagtggtttt tacatttatt attttggact ttttttaga 171600
gacaaggtct cgctctgtca cccaggctgg agtccagtgg ctccatcacg gctcactgca 171660
gtctcaaact cctaggttca agggatcctc ccccccctcag cctccagggt agctgggact 171720
acaggcatgt accaggacac cggctatttt ttaaaaaatt ttttaagaaa tggggtcttg 171780
ctatgttgcc caggctggtc ttgaactttt ggcttcaagt aatcctcctg cctgggcctc 171840
ccaaagtgct gggattacaa gcatgagcca ctgcaccctg cctgcttttt accttttta 171900

-continued atagctgaaa ggaaaatcaa aagaagaatc ctatttggtg acacatgaaa attatgcaaa 171960
tttcagcatc cattagtaaa gctttactgg gacacaggca tgctcattca tctattgtct 172020
acagctgtct tcaagctgca gcgtcagagc tgaatagttg aggcagagat ggtaggctta 172080
caaagcctaa aatatttacc tggtccttta cagaaaacat ttgccaagcg ctcttctagt 172140
ctaaagtacc tgtaatatcc tttctgcctg ggtgcagtgg tttatgcctg taatcccagc 172200
actttgggag gccaagccag gtggatctgt tgaggtcagg agtttgagac cagcctggcc 172260
aacatggagg aatcacatct ctactaaaaa tacaaaaatc agctggacat ggtggcaggc 172320
acctatactc tcagctattc aggagctgag agaatcactt gaactctgga ggcagaggtt 172380
gcagtgagcc gagattgtgc cactgcactc cagcctgggt gacagagtaa gactccgtct 172440
caacaaacta ttttattttc ttcatagccg ctaccagtat ctaaatttct aagttctctc 172500
tctctcttta tttacttaca tgtttaaaaa aattgtctcc accaacactc ccacaataaa 172560
acaatagggc cgtaagagca gagactttgt tttgtttcct tctctatctt cagctattga 172620
tacataatgg gcttttaaaa agtttattct gtttacatta ctgacattaa aggtttaaca 172680
aattgaagct atctgagaaa ttgtttgtat tgctaatcta tatagccatt cttttctatc 172740
gctgttttgt ttgtttgttt gtttgtttgc ttgttttgcg acaaggtctc actacatcac 172800
tcaggctgga atgcagtggc acaatcccag ctcactgcaa gttctgcctc ccgggctcaa 172860
gtgattctcc cacctcagcc tcctgagtag ctgggaccac aggcgcacgc caccacacct 172920
ggcttttgtt tttttgtttg tttgttttgg taaagacaga gttttgccat gttggccagg 172980
ctggtctcaa actcctaacc tcaagtgatc tgcccgtctc agcctcccaa agtgctggga 173040
ttacaggtgt aagccaccgc acttggcccc aatttttcttt tcttttcttt ctttcttttt 173100
ttttttttt ttttgagaca gagtctcact ctgtcaccca ggatgcagtg caattgcatg 173160
atctcagttc actgtaacct ccacctcctg ggttcaagtg attctcctgc ctctgcctcc 173220
caaatagctg ggattacaga catgaaccac cacgccaggc taattttttg tatttttagt 173280
agagaagggg gttcaccatg ttggccaggc tggtctcgaa ctcctgacct cagttgatct 173340
gcctgactca gcctcccaaa gtgctggatt gtaggcatga gccaccatgc ccggcccacc 173400
tggccccatt tttaagtgta gagttgagcg ggagtaagta cattcacatc cacactattg 173460
tgcaaccgtc actaccagcc atatccagaa tatttgaac cttgcaaaat cgaaactgta 173520
ccaccattct aatttctgtc tctatgaatt tgactgctct aggacacaag gaggctttaa 173580
gcaacatcca tcaaataaat aaatcctgac ctacctgctt tggtagccag gacgctcaga 173640
gttaaatttc tgtgttttat tgcctagatt tcctaataaa attctcttct gtctctctct 173700
cttttttttt ttttcgagac ggagtctcgc tctgtcaccc aggccggagt gcagtggtgc 173760
aatctcagct cactgcaatc tctgcctccc cggttgaagc gattctcctg cctcaacctc 173820
ctgagtagct gggattacag gtgcccgcca ccacgctcgg ttaatctttg tatttttagt 173880
agagatgtgg tttcaccatg tcggtcaggc tggtctcaaa ctcctgacct ccggcaatcc 173940
tcctgccttg gcctcccaaa gtgctgggat tacaggcgtg agccaccacg cccagcctct 174000
tctctcattt taatatagat ttttttatac agattttgaa cttgtacccc tactcaaggt 174060
tcacattgaa tctaagttac catcattatt tatattccac tgaaaaacta ggacacaaca 174120
tagattatga aatacaaaca catcattatt tcagacttcc acatgtgcga attgcattga 174180
cgaaatggag tatgtgtttt actccataag ccacatcaaa ctgtttttcg aagcagtggg 174240
aggtggtaaa aatcagaaga gaacaacatc aaatccatgt tttcagagat gaaacacctc 174300
ttctgaagat attcttcccc caaaaagtga ccccacctcc aagtacaggc tcaccagtgg 174360
cattggagga tgtctgcagt attccagtca tccaggaata gagagctctc tgggaatgag 174420
ccgaggtttt gtcgtagaga tctttgaaca ctgcagatct aaatgacaca aacacaggca 174480
tcagctaata acaagcaggt gggggctgca ttaaaaaggg agtcacaaca gcaaatgtga 174540
cccaaagctg tcttgtgtta aaacccttcc ctctcctgga tgtggagaaa tagaaacgct 174600
tttacactgt tggttggaat gtaaattgat tcaaccattg tggaagacag cgtggtgatt 174660
cctcaagaat ctaggactag aattaccatt tgacccagca atcccatttc tgggtatgta 174720
cccaaaggat tataaatcat gctactataa agacacatgc acacgtatgt ttattgtggc 174780
actattcaca atagcaaaga cttggaacca acccaaatgt cctccaatga tggactggat 174840
taagaaaatg tgacacatat acaccatgga atactatgca gccctaaaaa aggatgagtt 174900
cgtgtccttt gcagggacat ggatgaagct ggaaaccacc attctcagca aactatcaca 174960
aggacagaaa accaaacacc gcatgttctc actcataggt gggaattgaa caatgagatc 175020
acttgggcac agcaagggga acatcacaca ccggggcctg ttgggggtg gggggagggg 175080 gtggggatag cattaggaga tatacctaat gtaaatgatg agttgatggg tgcagcaaac 175140
caacatggca catgtatacc tatgtatcaa acctgcacgt tgtgcacatg taccctagaa 175200
cttaaagtat atttaaaaaa aaaaaaacctt ccctttcttg aatgtaaatt ggttcaacca 175260
ttgtggaaga cagtgtagcg attcctcaga gatctagaac tagaaatacc atttgaccca 175320
gcaatcccat tatcgggtat atacccaaaa atatataaat cattctgtca caaagataaa 175380
tgcacacatg atcattgcag cactaatcac aatagtaaag acatgtagtc aacccaaatg 175440
cccatcaata atagactgga taaagaaaat gtggtacata tataccatgg aatactatgc 175500
agccataaaa atgaacaaga ttatgtcttt tgcagggaca tgaatggacc tggaagccat 175560
tatcctcagc aaactaacgc aggaacagaa aatgaaacac cccatgttct cacttgtaag 175620
tggaagctga acgatgagat cacatggaca cagggagggg aacaacacac actgggtcct 175680
attgtggggg tggggtgggg gagggagagc attaggaaaa atatctaatg catgctgggc 175740
ttgataccta ggtggtgggt tgataggtac agcaaaccac catggtacac gtttacctat 175800
gtaacaaacc tgcacatcct gcacgtgtac cccagaactt aaaaataaaa aatacccccca 175860 aacacactcc ttaggtatat gtaactattt ttcccatttt cctcttcccc ttcacagcta 175920
aacaccttcc aaagaatatt ccatacatat tgtctccact tcctcacctc ttggtccttt 175980
tttggggaag tgggggcagc tctgttgaga tataattccc acaccttaca attcacccat 176040
ttaaagtaca caattgggcc gggtgcagtg gctcacacct gtaatcccag cactttggga 176100
agccaaggca ggcggatcac ctgaggtcag gagtttgaga ccagcctgac caatatgatg 176160
aaactctgtc tctactaaaa atacaaaaag tagccaggcg tggtggcatg cacctgtaat 176220
cccagctact tgggaggctg agacaggaga atcacttgaa cctgggaggt ggaggttgca 176280
gtgagccgag atggggccat tgcactccag cctgggcaac aagagtgaaa ctctgtctca 176340
aaaaaaaaaa aattacataa ataaagtgca caattcagtg gttttcagca tataagacaa 176400
agagccaaag atgtttctga tggcatcatt tgagtctctg gatccagctg cgtctgaagt 176460
cagccctaca cctaaaacta ttcaattaca tgttccaata attccctttt tgcttcaagc 176520
cagtttgaat gggtttttct gccacttggg cttactgctt actcaggtga gcagtaacca 176580
ataaactctc tctcccaatg atgttctctt ccacaatctg catgaacgga ggagggaaga 176640

-continued gatgctgaat ttaaaaggaa tagtataata gcctgcagag caaaagggtt tcatttatat 176700
acatcttagt gaaaaaaact ggcaacctag agaaacgatg aggtcagcat actgtctgtt 176760
ttccttactg tcatttggct acaaaagata aaaggaatct cccacattgt tatcatcata 176820
ttggtctttt ccttcttcta aatcattttt agatttagaa agagtgcttt atggccataa 176880
agcactacga ttagtaaaag gagggagttg gcggtggttg caatgcctat ggcccttcaa 176940
gtcctagaca caatcctcga atttggttta catcaaagcg caatttcatg cagggctagg 177000
tgtaaccaat ctaagctggc atggcatctc aaaaggagaa gtcctccttt ttcagtgctc 177060
tgtcactcct tctgttgtcc ctcaagaaca aagtctcagt ttagtgccag tgaatcttta 177120
aaacacactc agattgtttt taaatcaatg gaacaagacc caggctcaga gcctttgtgc 177180
tgtggactga atgtttgcgt ttccccaaat ttcatgtgtt gaaatcctaa ttcccaacat 177240
gaaggtatta agaggtggag ttttgaggag gtgattaggt catgaggctg gatacctcat 177300
gaatgggatt agtgccctta taaaagagat cccagagggc ttgcccaccc cttccaccac 177360
aaggggacac agcgagaagg tgccacctat aaaccagaaa gcgagccctc accagacacc 177420
aagtctgtca gcaccttgat cttggacttc ccagcctcca gaaccatgag aaataaatgc 177480
ttcttgttta ctagccacac agtctatggt atttttgtta cagcagccca atctgactaa 177540
cacacttaag caagcaacat atctagctag gatttagtaa cacttttttt cccactgtat 177600
ttatttatgt gggttttttt gtttttgttt tttgtttgtt tgtttttgtt tttgagatgg 177660
agtctcactc tgtcgcccag gttggagtgc agtggcatga tcccagctca ctgcaacctc 177720
cacctcccag gttcaagcaa ttctcctgcc tcaagcctcc caagtagctg agattacagg 177780
cgcccaccac catgcccaac taatttttgt atttttagta gagacgtggt ttcattatgt 177840
tggccaggct ggtctcgaac tgctgacatc atgatccacc cacctctgct tcccaaagtg 177900
ctgggatcac aggtgtgagc taccacaccc agcctaactc tacagatgtt aagcttttgc 177960
tccaaaacgt gcatatcaac ctgtccccac ttgtcttctc cctgctgcca ggtgagatct 178020
ctttgcattc tcacggcagc ccctgaagga tactgtgatg agttaagaag gtgggagtgg 178080
ctgggtgcag tggctcatgc ccgtaatcca agcactttgg gaggccaagg caggtggatc 178140
acttgatgtc aggagttcga aaccagcctg gccaacatgg tgaaactcca tctgtacaaa 178200
aatacaaaaa ttagtcgggt gtggtaggcg cccctgtagt cccagctact tggaattgag 178260
gcaggagaat cacttgaacc tgggaggcag aggttgcagt gagccgagac tgcaccactg 178320
cactccaacc tgggcgacag agtgaaactc catctcaaaa aaaaaaaaaa aaaagttcgg 178380
aggaaccact cacaggttct taaaggcatc ctcgcgcagg tcccgaggga gccgctctgt 178440
gatgtctggc tggagaaagc tccctgagga ccccctcagc accttgccca ggatctccac 178500
acactccagg gagttcagca tctggaaaca cctctccagt gtgatgagaa acaggctgcg 178560
gttcacgcca gggctctgca aggctcgttc tcgaatctct cctaagtcga tgatgatgtc 178620
tttcaggtcc taaagcaatg acagaagcca gggtcagttt gagagctgcc tctcaatttg 178680
gaagccctgg gagggaccac acattgcaac agtggggaaa gtcaggatca ctgtttaaca 178740
ccatgctgct atgttgaaac ttctagaact ttccattccc tgcagaacaa agtcaaggcc 178800
tttacctgct ccactcactg tggagcctcc ccactctcca gatacacctg accagcatac 178860
atcaggccct tggtctacct ggaattctgc atctttcctt tttctggtga aatctagctc 178920
atcctttaag tctgggctcc attgccatca ccttcgtgaa gtctctgatc cctccaactt 178980
cctacttcag atcagatttc cctcccttat gtggccccag ggcatcttga accaaactct 179040
ataatgcatt aaagggactc atgcgtcttt cctccaagcc cgtggttctc atctctgggt 179100
gcacatcaga atcacctggg gagctttttt aaagttttat tttatttttg agacagggtc 179160
tcgctctgtc acccagtccg cagtgcagtg gtgtgattat agctcactgc agcctcaacc 179220
tcctgggatt gagcgatcct cccacctcag cctcccaagt agctgggact acaggcacac 179280
accaccatgc tcagctgttt tttgtagaga tggagttttg ccatgttgtc caggctggtc 179340
tcaaactact gggctcaagc aatctgccca caacctccca aagtgctagg gttacaggta 179400
tgagccacca tgcccagccc atctggggag attttgaaaa ggactgattg gcctggaaca 179460
gtggctcaca tctataaccc cagcatgttg ggaggctgag gcaggttgat cgcttgagcc 179520
taggagtttg agaccagcct aggcaacaca gggagacccc gtccctaaaa aataaatttt 179580
ttaaaattag ctgggtgtgc taatgcgcac ctgtagtcct agctgcttga gaggctgagg 179640
tgggaggatc acttgggctc aggatatcaa ggctgcagtg agctataatt ataccactgc 179700
actccagcct ggatgacaga gcaagcccct gtctctaaga aaaaaaaaaa aagcctccat 179760
tttactgagc attgactcta ctgtgccaag cttggagcaa acgcatcatc tgattaattc 179820
tcatgacaat cctaccggtt aagccccatg ggtactaggg tcaggcattc ccaggttcca 179880
gtcccagggc ctccattatc tgtgtgtcct gagcaaatga cttacctttt ttaagtccca 179940
gtttttaagg tctcagaggc cttgctttgt gatattcttg gatcactaaa ctcattttgt 180000
ggaaattaac tgttcctgtt ttttgtctcc cctccagacc gtgagctcct tgagtgcagg 180060
aggatctctg tgtccactgg tgcatagtaa tttttactag tggatgttta ttgacccaaa 180120
caaccaggag attctcagat ccttaattag gacccgtcat ttcttagtac tgacaaaaat 180180
atgaattagg ccaggcatgg tggctcacac ctgtaatccc agcactttgg gatgccgagg 180240
caggcaaatc acttgaggcc aggagtttga gaccagcctg gcaaaatctc gtctctacta 180300
aaaatacaaa aattagccag gcatggtggt gcacacttgt aatcccagct acttgggagg 180360
ctgaggcaca agaatcactt aaacccagga ggcagaagtt acagtgagct gagattgtgc 180420
cactgcactc cagcctgagt gacagagtga gactctaaaa caaaaataaa ataaaaaatt 180480
gtaaggctct tcattttaac tttggagaaa gtaagtgaga aaacttaggt cctaaagccc 180540
ccagggggtt ggaggaggca gaaggagaga ggaagagaca atgaagtgcc aaggcctaag 180600
tcaggctcca tttattcaat tcaacaaaca ccacgtggtg ctggacttcc tctatccccg 180660
ggatgccaag ggctcctcac caagccgtcc ttcttgtctt ctaagaggca tttcatggca 180720
gtgcggaact gctgggcgtc tgtcttcctc aggtcctcca gcagcttctg gggctggtgc 180780
agacgctgct ccaggtggtt ttccacggct gcctgtattt ggggtgttgg gagagtcggt 180840
gagaacagaa agagcaggag cacatggtca gcaccatggc cagcggccca gcccggcccc 180900
ctcattccct gcagagacca caactagtgg ccagcagtct ggtttggcca cctccaaatt 180960
tcctcattag ccgccaacat ttaaaaatga ggggccgggc gcggtggctc atgcctgtaa 181020
tcccagcact ttgggaggcc gaggcgggtg gatcacgagg tgaagagatc aagaccatcc 181080
tggccaacat ggtgaaaccc cgtctctact aaaaatacaa aaattagctg ggtgtggtgg 181140
cgcacgcctg tagtcccagc tacttgggag gctgaggcag gagaatcgct taaacccggg 181200
aggcggaggt tgcagtgagc cgagatcacg ccactgcact ccagcctggt gacagagcga 181260
gactccacct aaataataat aataataata ataataataa taataagggg attcctcaca 181320
agatcaagat ttccaacttc tcttgaaaaa gtaaaggttt ggcaacaccg ggcgcacatc 181380 ccccttttagg caataattgg caagccaagg gacagctgct tgttgaagta actctcaggc 181440
ccagccagcc cgattccccc attccatggc ctgcctggtc cctgtaggtg attgagtttc 181500
ccatcagcag cagctggcct ttgtccagga agtttagaac cccagatggc actgtgccca 181560
aacccaagct accagcgcag gagcaaaata caggcgaaat gaacatactc tgtggcgccc 181620
cctacagggc aaggagcaga agccatcagc ctctcctgaa agagatttcc tctgctgtct 181680
ggggaattgt tctctaaatc tccgttaaac agacatgccc agtgtgatgt catgggcaaa 181740
aggtgaactc tagacccaga caagccacat gcaaatcccc accttgacac ttactagctg 181800
tgtggcttgg acgagttact taactagggt tgctgggtaa aatacaggat gctcagttaa 181860
atttgaattt cgggaaaaac tacacatttt ttttttttta gtataagtat gtctcaaatg 181920
ttgcatagga catacttaac ttaaaaaatc actcattgtt tgccaggcaa ggtggcccac 181980
acctgtaatc ccagcacttt gggaggccaa gacaggcgga tcatgaggtc aggagtttga 182040
gaccagcctg gccaacatag tgaaacccca tctctactaa aaatacacaa attagccagg 182100
catgatggca tgcacctgta gtcccagcta ctcaggaggc tgaggcagga gaattgcttg 182160
aacctgggag gaggaggttg tggtgagctg aggtggcacc actgcactcc agcctgggca 182220
acagagcaag actctgtctc aaaaaaaaaa aaatcactca ttatttatct gaaattcaaa 182280
cgaaattgga catctgtttt ttgtttttgt ttttgtttta gagacggggt cttgctctgt 182340
tgcccaggct gaaatgcagt ggtatgatca tagctcaccg taacctcaaa ctcctgggct 182400
caagcaatcc tcctgcctca gccttccaag tagctgggac tacaggccac accaccacac 182460
tcagctaatt ttttgtttgt ttgtttgttt gtttttgtag agacaaggtc tcgctatgtt 182520
ggcaaggctt gtctccaact cctggtatca agcaatcctc ccacctatgc ctctcaaagt 182580
gctgggatta caggcatgag ccaccacgca gagtcacatc tgtattttta tttgctaaat 182640
cagcaacatt tcttctgggc ctcagttttc ttatctgcaa aatggaggca ataaaaggac 182700
ttaccacata gagttattac gaggattcag tgtgtaaagt gttttcaata gttgctagca 182760
cacagtaagt gctcaatagt gccagctatt attctctatc ttgaccaagg tgaataatgg 182820
cttaattaaa gcctcacccc taaaatgaaa ggtccttgtg ggtagtatca tgactgcctt 182880
gttccctact gagtcctcag tgtctagagc tatgcctggc agaaagcaga tgttaactca 182940
gtagatatta aatgaataaa taaatatggt atatacacag gaagaaacgt atcagattaa 183000
agtggataca tctcatgagt atccattact gctagagaga aaagtggcaa gcattgcttc 183060
tctttcagtt tccctgactg atgaagaaga aaagaaaagc agatgccatg tggggccaac 183120
agccacctcc agctagtggc tgtcctggga cctggcagac aacaagctct ctgagtatat 183180
ttgtgatatc aatgttggtt gatgtttcca ttttcattca aacataagta aaaatggaaa 183240
caatgaagac atatgtcaga actttattca ttaattaatg acataaatgg tcttttgcta 183300
aactgaataa ctttctcaat actgaaagaa tttttctcca attttctgtg ttatccacag 183360
tgtgatgata aagacacaac atgccacact aggctaacag tcaggcaggt gctgtgcagt 183420
tcaccgcagt caccaccaca ggcacgagcc ctattgcccc ttaaggcaaa tatcctttgc 183480
cacctatcaa cacgcttgtg ctattgtttt cattacagta gtacatttct tggacccatg 183540
gtagaaagac tgatcactat atccaaatat ccactctctc actgctcttt atcaattgaa 183600
cccttcaact tttagttggg tacatggctc ctttgcagta agatgtgact atggtgtgtg 183660
agccaatcta atgtgtgcag agggaattgt gtaacttgcg tcatatcctc agaagagaag 183720
atgctaccct tgtcttcttc ttcccaccca tcccctggat tggagaaagg aagaggtgtt 183780
tccaccacat gggcaataac tccccaggag atgacaaagc aaaaagataa aaggaacctg 183840
ggtccttgga taacctcatg gaatagagct gccttttctc tgtggctttc ccacttagct 183900
ctggactatt gtacgagaaa gaaataaact aaattgtttg agctgctgtc atctgggggt 183960
ctttttgtta tagcagctca gcctatatcc taatatacca tgtctccatc aaaggtggga 184020
aaatgaaaga aagacaaaat agcttatatc atgtttcaag aaaaactgga cagaaccctt 184080
ttccttgcag aagcaaagac tatctctaca tccagcccac ttctccaact tacctggccc 184140
ctgagtttgc aatccctgag cactgagatg ggaacatata gatgggtctc aggtacacac 184200
ctgcaggctg gggatggtga aggcaacatt ccgggaattc agataggcca ggactctgtg 184260
ggacaggtca tccgtccaca cgtgggagct tcagttgaag acagacagga aaagatcaca 184320
atgacagatt ctcctacaag cactactgta ctagctaagt gcccagggga caggtaggga 184380
tggaccaggg gtgttaggac tttgtacttg gaagtgggag gtttctcttt tcttttcttt 184440 cctttttct tttctcttt tttgaaacag ggtcttgctc tgttgcgcga tcacggctca 184500
ctgcagcctc aatctcccca gcccaagtga tcttccaacc tcagccaccc aagcagctgg 184560
gatcacaggt gcatgccaca acacccagct aatttttgt agagatgggg tctcactatg 184620
ttgcccaggc tggtctcaaa ctcctgggct caagcaatcc tcccacctct gcctcccaaa 184680
gtgctgggat tacaggagtg agctgctgca cccagcctga agtaaaaaat ttcttaacca 184740
ggcacagtga taggatagtt tccaattcta ggaatctgcc tggatcccat tctctcaaag 184800
ccaattccca aatttctaag ctgtatgcaa tattctaatt cccgtaacaa tctgcttaga 184860
ttgactacaa tccaaactga ttgtgttaga aagatgtaca tttaaaagca gacgctaggt 184920
acaccatgag aggctggaat agcatagtta ggagtgtggg ctccaaactg gatttgaatc 184980
ctagttccat cacttagttg tgtggcttga gacaatttga taaattttct tgtgcctcag 185040
tttcccttta tatgaaatat ggttaacaac tgtgagatta aaatttgttc acacatgaaa 185100
attgcgtaag actgtgccca acacacagta aatgcccatg aatagccttt tctcattttt 185160 ttttttttt ttggagacag agtctcactc tgttacccag gctggagtgc agtggtgcaa 185220
tctcagctca ctgcaacctc cgcctcccag gttcaagcga ttctcctgcc tcagccttcc 185280
aagtagctgg aattacaggc gtgcaccacc acatccagct catttttcta tttttagtag 185340
atactgagtt ttgccatgtt ggccgggctg ggctggaact cctggcctta agcgatcctc 185400
ctaccttggc ctcccaaagt gctgggatta caggataagc caccatgccc agcctatgaa 185460
aagccttttg taatcttacg tttgcttctt tgtttgtttg tttgtttgtt ttgcgatgga 185520
gtctcactct gttgcccagg ctggagtgca gtggctcaat cttggcttat cacaacctca 185580
gcctcccgcg ttcaagtgat cctcctgcct cagcctcctg agtagctggg actacaggta 185640
tgcaccacca tgcctagcta attcttttgt acttttagta gggacagggt ttcactatgt 185700
tggccaggct ggtcccgaac tcctgacttc atgatccgcc caccttggcc tctcaaagtc 185760
ctggaattat aggcatgagc caccgcgccc ggcctgtaat cttataaaga gatggatgga 185820
tggatggatg gatggatgga tggataaatt aataaacaaa taaaatactt agactgaaag 185880
aatatatcca aaagtaccca ttggtgttat cttagggaaa ggagtggtta tgggagtctt 185940
tcactttaac ataactgggt atccctgata tgaggcccca agacccctat ttcttatcga 186000
tcatagtact catcatatta gaattgttta ttaatattgg cgtttccaca ctacctagtt 186060
ccctgcccca tgtccctggt atctgtctgt atgcagctta taatgcaaca gtaaagggaa 186120
tgggtcctgg agccaggcca ctggttcaca tcccagttgt gtgtccttga tttacccttc 186180
ctggacctca gtttcaccat tgtgtgcaat gggataacaa tgggaactac attgtgtggc 186240
acttgtgagg attagattgt ttctatacca agcgcttagt agaataccca ctacatagaa 186300
agcactcaat aaatttcagc tcttaggccg gttgcggtgg ctcacacctg taatcccagc 186360
actttgggag gctgaggccg gcagatcacc tgaggtcagg agtttgagac cagcctggcc 186420
aacatggtga aaacccatct ctactaaaaa tacaaaaatt agccgggcat ggtgacaggt 186480
acctgttacc ccagctactc aggaggctga ggcaggaaaa ttgcttgaac cccggaggca 186540
gaggttgcag tagtgagcca agatagcacc actgcactcc atcctgggca acaagagcga 186600
aactccattc aaaaaaagaa aaaaaattgg cccttatgct agagtgagga ggaatgatgc 186660
ccgtggagca agggtgtttg ttgactttta acacattgtg cattgattga catttttgt 186720 aatgagcaca tattactttt tacaattaag agacttccat taagaatttt tattaaaaat 186780
ctataccatc ccttcccctc tcctctaggg cattttacct ttgaaactgt atgagatcca 186840
gcagtgctac aatgggagta aaatgaaaag acatctttaa aaggaatcat tccagagaga 186900
tcacagctac attctgtttg aaattcttag aagaagcaag tggagatcaa gggggcacat 186960
taccattcag atagcttcca tctattattt cttcctaaaa ggcaaagaga taacatcaag 187020
tataacaacc aaaagttggc aattccagta gaggggactc tgattaacag aaaatagaat 187080
actcaccgcc atgttttgca acaatggatg caaatctgta agaaagccat tgaatgtata 187140
actagaattg aattgtgtga ccttcaaaac tacaaatatg ggttagagga aaagccccag 187200
aaagccactc atgaaggaaa tttttagtga attttaatta taactgtcca ctctgagaaa 187260
accgtggctt gaaaaatcct cttagaataa tcctgaaaaa tcatacatgc acacacacac 187320
agcccaaaaa caacttacag catcatgtac ctaatgtatc tatcccacct cattccctaa 187380
actgtgtgga aaccacaaag ggtgattctt ccctcaggac ttaccctgcc tggaatttgg 187440
cactgtataa ctcgacactc catggctcag aaaaaggaat aggaaaaggg agtatgtcgt 187500
aggttcctga gacattctcc tgtagttaat ttaagcatag aagtgattca tgttttttt 187560 atatatatat atatacacac acacacatat atatacatgt atataaacat atatatatat 187620
atggacattc agaagacaaa aggaaaaacc aagtacaccc agaatccctt gaagtctttt 187680
ttaaaaataa ttttaaaact cacctacttt cctccatcta aacccccatt cttgtctaag 187740
acactatcat ctctctcctt ggtgactaca atggcctgtt tatcttacca ctacccccaa 187800
ctcctctcaa tccagcaaaa aggtatagtc aaaagtagac tctgggccaa gcatggtggc 187860
tcacacctgt aatcccagca ctttgcatgg ccaaggtggg tggatctctt gaggtcagga 187920
gttcgagacc agcctggcca acatagtgaa accctgtctc tactaaaaat aaaaaattaa 187980
ctgggtatgg tggtgcatgt ctgtagtccc agctacttgg gaggctaaga caggagaagt 188040
gcctgaatct gtgaggtaga ggttgcagtg agccaagatt gtgccactgc actccagcct 188100
gggcaacaga gcgagactct ggaaaaaaaa aagtatagac tctattttat ctgcaagaaa 188160
tttatatcca gaatacaaaa actactctta taattcaata agaagataga caagccaagg 188220
ggaaaaaatg ttaaaaagat atgaagttgg ccaggcgcag tggctcacgc ctgtaatccc 188280
agcactttgg gaggctgagg tgggcggatc atgaggtcag gagatccaga ccatcctggc 188340
taacacggtg aaaccccgtc tctaataaaa atacaaaaaa attagacggg cgtggtggcg 188400
ggcgcctgta gtcccagcta ctcaggaggc tgaggaagaa gaatggcgtg aaccctggat 188460
gcggagcttg cagtgagccg agatcacgcc actgcactcc agcctgggcg acagagcaag 188520
actccgtctc aaaaaaaaaa aaaaaaaaaa gatatgaagc taaacttcat aaaaacagat 188580
gtaaaaatgg ccaataagca cacaaatgat tatcacatta gctaacaaga actagcaaat 188640
taaactcaca acgagaccac tacaaagtca ctagaatggg caaaaatttc aaagactgac 188700
tatcaaatgt tggtgatgat atggaacaac aggaactctg atacagctgc ttggaaaaac 188760
tgtttgacag tgtcttacag agttaaatat acaataccct atgatcaaga aatgccaccc 188820
ctaggtattt aagcaagaga aatgaaaaca tgtctacaca aagatttata tagcttcatt 188880
catagtagcc agatattgga aacaatcaca tatccaataa caggtgaaag gttaaacatg 188940
gatctccatt cagtgggata ccattcagta ataacaataa aaagaaattc atcataattt 189000
tattctagct atgatggagt aattggcaat ggataaaccg tcctgcctta aacaattaaa 189060
aagctggctg aaatatgtgc atccaaaggt ttttcagaca ttgggcagca ggtagcacaa 189120
gactgagatc cctgagcaag gaaggcaaac aagctgagct ctataattgc tcctgctcac 189180
tgcctggagt ctccatccaa cagcacaagg agggagaatc caaacagagc ctacaggtct 189240
cactgagcag aagagacgga gtggaacttc agggaaatca aggcagctag aatccataag 189300
aagaatactt ggagaggagg aagttgcaca gagagaaagt tctggagatc tgaagaaggg 189360
tcttttgaga ctttggctga atatttatct acctttgcat gtaagaaacc tcctgaggct 189420
ggagaatgaa ccaccagtag gcagaacaat ccttggacct cacaggggaa tgagaatagc 189480
tcctgcaagc tgcaatggaa aaacctccaa acacattggg catcagggtc aatcatcaaa 189540
gaacaattgc ctccatgata ggccaaatta gccctaggct aaagtttatt ccagatctgc 189600
cctaacaaat ctcaaaagca agttctggaa ggatctaatt gattccaagt aactgaattg 189660
cattccagaa caaaacccaa caatatttaa agcagtatca taaaacccag aaacttcaga 189720
aaaccagaag atggagaaag aaaaaaaaga aaaaaaaaat ccagcaatgt aaaatccgaa 189780
gtgtccagat ctaatcaaaa attatcaggc aggccaagca cagtggctca tgcctataat 189840
cccagccctt tgggaggcca aggaaggtga attgtctgag ctcaggagtt tgtgaccagc 189900
ctgggcaaca tggtgaaact ctgtctttac caaaaatgca aaactttgcc agggatgtgg 189960
caggtgccca actactcagg aggctgaggt gggagggtca ctgaagcctg gaaagttgag 190020
gctgcaatga gccatgatta tgccactgca ctccagccag ggtgacagag cgagaacctg 190080
tctcaaagaa atttttttaat aaataaataa aaattaccag gcatactagg aagcaggaaa 190140
atatggctga ttatcaggag aaaaatccaa tcaatagaac agatccagaa atgacacaga 190200
agatccaatt aatggacaag gatgtttatt ataaatacac tctggaagtt caagaaagta 190260
gggaaaactg cgagcatgtt aaagggagag acatggtagg tgcgaaaaaa accccaagag 190320
gaacttctag agataaaaat acaatatctg aaatggaaaa tacacgggat agagttaaca 190380
gcatattaga cactgcagaa gaaaaattag tgaacttgaa gtcatagcaa aataaattat 190440
ccaaagtaaa atgcaggggg aaaaagactg aaaaaattaa gagggctctg gagcaatatg 190500
aaactatttg aaatatgtgt aactggagtc ccaggaaagg agggggtggc acaaaaaatat 190560
ctgaataaat cattagcagg gcacagtggc tcacgcctgt aatcccacat tttggaaggt 190620
tgaggtgggc aaatcacttg aggccaagag ttcaaaacca gcctggccaa catggtgaag 190680
ccccatctct ataaaaaaaa aaaaaaaaaa aaaaaaaaaa atagccaggt gtggtggctg 190740
taatcccagc tactcaggag gctgggcaca aaaatcactt gaacctggga ggcggaagtt 190800
gtagtgagcc aagattgcac cactgcactc cagcctaggt gacagaatga gactgaaaaa 190860

-continued aaaaagagag agagagaaag aaaaagaaag aaggaaagaa agagagaaag aaaaagaaag 190920
aaagaaagaa agaaagaaag aaagaaagaa agacagaaag aaaacatgac ctcatgacca 190980
aatttgtgta aagtttgata gaactacaga tccacagatc caagaagctc aaccaacccc 191040
aagcagagga atcatgaata aagccacgcc aaggcatata ataatcaaat tgctaaaaaa 191100
aaaaaaaaaa aaaaaaaaaa gatttttaaa aaaaatccag caaaaaggag ttgcatctag 191160
actatattga aaaactctta aaactaaaaa ataaataagc aatccaatca gaaaacgagc 191220
agaagatatg tgcagatata tcatcaaagt atatatacag atagcaaata aacacatggg 191280
aagatactca gcactgttag ccattaggaa aatgaccact gaaaccacag tataattata 191340
ggcctatcag atggctaaaa taaaaaaaaa aaaaccataa tgaagccagg cgcagtgaat 191400
catgcctgta atcccagcac tttggaaggc cgaggtgggt gaatcacctg agatcaggag 191460
tttgagacca gcctggccaa catggtgaaa ccccatctct actaaaaata caaatattag 191520
ccgggcatgg tggctcatgc ctgtagtccc agctactcag gaggctgagg caggagaatt 191580
gcttgaaccg aggaggcgga ggttgcagtg actgggaggc agaggttgca gtgagccaag 191640
attgcaccac tgcactccag cctgggcaac agagtgagac ttcaactcaa aaataaataa 191700
ataaatgtaa ccataatgcc attaactaga aagaatgagg agaaactgga tcactcacac 191760
attgctgatg agaatataag gtggtacagc tattctggaa aatagttttg ttgtttctta 191820
taaaattaaa tgtgtactta acgtacagcc caacaattac actcttgggc atttatccca 191880
gaaaaatgaa aatttatgtt cacataaaaa cctgtacaca ggctgggcat ggtggctcac 191940
gcctataatc ccagcacttt gggaggctga ggcgggtgga tcacgaggtc aggagatcaa 192000
gaccatcctg gctaacatgg tgaaacccca tctctactaa aaatacaaaa aattagctag 192060
gcgtggtggt gggcgcctgt agtcccagct acttgggagg ctgaggcagg agaatggcat 192120
gaacccagga gacagagctt gcagtgatgc agtgagccaa gatcacgcca ctgcattcca 192180
gcctgggtga cagtgtgaga ctccaactca aaaaacaaac aaacaaacaa acaaaacctg 192240
tacacaaatg ttcatagcat ctttattcat agtagctgaa aaattgaacc aatctaaatg 192300
tcattccgta ggtgaatggt taaactcact gtgtgtggta tgtccacgcc attgaatact 192360
actcagcaat gaaaaggaat gaactattga tacaggcaac aactttgatg cacctaaagg 192420
gaattatgca gagggaagaa agccaatcac tgaaagttat atactaatga ttccaattat 192480
aaagcattct tgaaataaaa ttatagaaat gcagactaga ttggtatttg ccatggggag 192540
agggagataa ggctgtcaag ggatgcatga aagaggcttg tgatcaccag gagagttctg 192600
ggtcctgatt agggtagctg atacattagt ctacacatgt cacaaaattg aagaaaacga 192660
tataaaatat acacacaaag gagtgcatgt aaaactagtg aaatctgaat aagccctgaa 192720
tttgtaccat gatttcctga attttatatg gtactattgt tacataacat gtaaccaatg 192780
ggggaaactg ggtgaagagt acacaggata tttcttttgc aacttcctat gaatctgtag 192840
ttatttcaaa ttcttttttta ttttcttgag agacagagtc tttctctgtc acccagcctg 192900
cagtgcagtg gcatgatcat ggctcactgc agccttgaac tcctgtgttc aagtgatcct 192960
ctggtctcag cctcctgaga agctgagact acaggcatgc actaccatgc ccagctaatt 193020
cttttagttc ttgtagaaat gggttcttgc tatgtttccc aggctgatct caaactcctg 193080
gcctcaagca atcctcccat ctcggcctcc caaagtgcta ggaatacagg catgggccac 193140
catccctggc cacacaattg ttttttaatt tagttatagt agtctgtacc actgtaggat 193200
gacaatagtt aacaataata tatagtttca aatagctaga aggaagatac tgaacagaaa 193260
gaaatgagaa atgtttgaga tggtagacat gctaattacc ctgactgatc accatacatt 193320
atacacatca aaacatcttt atgtacccca taaatatgta caattattat atgtcaattt 193380
ttttttttt ttttgagatg gagtctcact ctgtcaccca ggctggagtg tagtggcgca 193440
atctcggctc actgcaacct ccgcctccca ggtgcaagcg attctcctgc ctcagcctcc 193500
tgagtagctg ggataacagg catgcgccac cacacccagc taatttttgt atttttagta 193560
gagatggggt ttcgccatgt tggtcaggct ggtctggaac tcctgacctc tggtgatcag 193620
cccacttcag cctcccaaag tgctgggatt gctggcgtga gccaccgtgc ccggcgtata 193680
tgtcaatttt ttaaataaat aaaataataa atttttaagc acccaaaggg aaaaaaccca 193740
tattatatgc ataggaaaag gaatacacta ctgatatagg caacaacaca gatgaacctc 193800
agaaacatta tgcttatgct gagcaaaaga agccagtcaa aaaagaccac ataacatatg 193860
attccatttc tgtgaaactc taagttatct agaatatcta gattctaggt tatctaggtt 193920
acctagaata atcttcagtg acaggaaaca aattaggatt ggtctggggc attattaggg 193980
tacaatggga aaagtttatt gcaacagggc acaagggaac ttcttggagt gatggaaaaa 194040
ttttttttgt agatataggg tctcactata gtgcccaagc tggtctcaaa ctcctggttt 194100
caagcaatcc tcccttcgag cttcccaaag tactgggatt acaggtggat gccattgcac 194160
ccagccccca ttttttgtat cttgattgtg gtggttgtca cacagataca tacatttatc 194220
agatctcact gaactgtaca cttagtgtgc attgtattgc ctgtaaattt atacctcaca 194280
aaagtcagta tcaaacagaa atggaaaagc atggactgtg gagccagtca cctgttctga 194340
atcacgtctc cgccacttac tagctgtgca atgttggaca tatttctttc ttttttttt 194400
tctttttct tttttctttt ttttttttt gatatggagt cttactctct tgcccaggct 194460
ggagtgcagt ggtgcaatgt aggctcactg caacctctgc ttcccaggtt caagcgattc 194520
ttctgcctca gcctcctgag tagctaggat tacaggtacc caccaccaca ccaggctaag 194580
ttttgtattt ttagtagaga caggctccca ccatgttggc caggctgatc tcgaactcct 194640
gacctcaagt gatccaccca ctttggcctc ccaaagtgct gagattacag gtgtgagcca 194700
ctgagcccgg ccttggacga gtttcttaat ctctctgcac tccaattttc tcgtctgtaa 194760
aatgagatta atgatggtac cagcatcact gtgtcgtatg agggtaaaat gagttgttaa 194820
tagtgaatca cttcaaacag ggcttgacac aaagtcagct ctgtatacaa gtttattaaa 194880
taagcaaaga aaccagattg ctgttttcaa acagatgctg ttttgaaaaa caccatctca 194940
ataaactcat gtcaccctcc gcctctcccc attaccctca agataaagcc caaagctttt 195000
ccagtggctg tatcaccctc ctctttgccc ctcattcccc aaggttcctg cccgggccat 195060
ctgtctgtcc ctccaaggtg ctatcctccc cagattaaga ccctctcaca ggctgttcct 195120
cggcccagag gattcttccc cttcctcttt gcccggctaa gatcaattca ttgtaaattt 195180
caagtcttca atgaagcctt ccctgaattc tctgaccagg ccaaagcaat tagccagaag 195240
aaaaggccaa tacttctctt ttatagcacc aagcacagct ataatacata tttatgtttg 195300
tgtaattatt tcatgctttc attcttcaaa tatttgttga gtagtgctgt gagccaggca 195360
ttattctatg ctctgagaat acagcagttt acaaaactaa ctccctgctg gtgtgttgga 195420
atgaaccagg cagaaaatag ataatcaaat aactatatta tgtcagggag tgatgagtgc 195480
catggagaaa aatacaacag ggtaggaaaa aggagccaaa gaaggagcag gtactattat 195540
agacagtttg gtcagggaag acctgaggag gtgacattta agcagagacc tcaggaagtg 195600
aaggaatgaa ccacgggaat atctggagaa agaaagttcc agaaagaaaa gaaaatgaca 195660
gtgcaaaggc tttgatatta ggagcataat ttgcatgttc ttcagtaaat tgcacgaaga 195720
ggatataaca gtaggacatg gggttggaga ggtatcaggg ccagagtgag tagggtcttt 195780
caggccattg tgagcgctct gacttttact tggagggagg tgggagccac tgaagggata 195840
ttagccagga tggatgctct gacttgtttt tgtttttgtt ttgttttgtt tgagatggtg 195900
tctcactctg tcgcccaggc tagagtgcag tggcacaatc tcagctcact gcaacctctg 195960
cctccccggc tcaagtgatt ctcctgcctc agcctctcaa gtagctggga ttataggtgc 196020
ccaccaccac acccagctaa tttttatatt tttggtagag acgagatttc accctgttgg 196080
ccaggctggt ctcgaactcc taagctcaag tgatccaccc acctcagcct cccaaagctc 196140
tgggatgaca ggtgtgagcc actgtgcctg gccctgactt ttattttaac tggatcaagc 196200
acattgattg ctgtgttgag aataccctgg agtggaacaa tggctgtagc aggcagacca 196260
atctaggaaa gagatgacaa taacttggtc attgatagca gtgaaggtgg tgagaagtgg 196320
ttggattttg gaggtatttg gaaggcggaa ccaaaagatc gaatgtaggg aataaaagaa 196380
atagacaggt caaagacaac gccaaggatt tggcctgagc atgtagagag ggagatggga 196440
aaaccatagg agttccaagt ttagggaagg atccctggag ctcagttttg gacatactaa 196500
gcttgagaag ccttttagag tgcagatagc atagcaagta ggcagtttga tgtttgagcc 196560
tgcaggttag gggagaggtg ctgtcagaag cagctatcta aacagagata gtcagtggtt 196620
ttttgtgttt gctttttttgt ttgttcttct gttttggggg tttttttggg gtgggggaca 196680
gagtctcact ctgtcacgca cgctggagtg cagtggcacg atctcagctc actgcaacct 196740
ctgcctccca ggttcaagtg attcttgtgt ctcaacctcc cgagtagctg ggattacagg 196800
cttgtgccac cgcaccggct aatttttgta tttttagtag agacggggtt tcaccatgtt 196860
ggccaggctg gtctcaaact catgacctca agggatccac ctgacacagg ctcccaaagt 196920
gctgggatta caggcatgta atcccactgc acccggcccc agatagtcag catgtattta 196980
aaccctgaat gatatcacca agaaagtaaa tttacggaga aattaggtga gttttaagga 197040
ctgagaccca tggcaccccc attgccaaga cgttgagtag actaggtgca gccagagaaa 197100
tcaagactgt ggaaaactcc ccaaaacaaa caacctagtt tctttagcca atatattaca 197160
gagagagaga gaaagagaac ctattaactc aaaaacaaaa gattgatcac ttgtagaatc 197220
tagactttat ttggatcctg attcaaacac gtcatgtctg ggcacggtgg ctcacacctg 197280
taatcccagc actttgggag gccgaggcgg gcagatcact tgaggtcagg agtttgagac 197340
cagcctggcc aacatggtga aaacccatct ctactaaaga tacaaaaact tagctgggca 197400
tggtggcgca tgctaataat cccagctact cgggaggctg aggcaggaga atctcttgaa 197460
cccgggaggc agaggttgca gtgacccgag atcatcccat tgcactccaa cctggatgac 197520
aagagtgaaa ctctgtctcc aaaaaaaaaa aaaaaaagaa agaaacaaag caaacaaaca 197580
aaaaatacca taaaataaaa taaaaaatta ggccaggcac agtggctcac acctaatccc 197640
agtgttttgg gaggccaagg cggaggattg tttgaggcca ggagtttgag accagcctgg 197700
gcaacacagc atgactccat ctctataaaa acatttaaaa tttagcctgg cgtggtgatg 197760
cacacctgta gtcctagcca ctcaggaggc tgagatggga ggatctcttg agctccagaa 197820
ttcaaggctg cagtgagcta tgatcatgcc acagcactcc agcctgagtg acagaacaag 197880
atcctgtctc aaaaaaaccc aaaaaattgt gagacaattg aggaaatttg aacccctgat 197940
tagatatttg aagattttaa agaattattg ttaatagttt taagtttgat aatgaaactg 198000
tggttatatt tttaaaggag tccttattgt ttcaaggagg ggttagtaaa gtaccaccca 198060
cggaccaaat ggaaatggcc acctgatttt gcgtggctca tgagcttaaa atgatttttt 198120
aggttgttta aatagttttt taaaaccaaa agaataatat ttattgacat atgaaaattt 198180
cctgtgtgaa atttaaattt aagtgtctat aaataaagtt ttattggcac atgtccatgc 198240
ccattcattg gcctattgtc catggcagct tcctgctacc atagcagagt tgagtacttg 198300
ggacagggac cacacggcct ccaaagctca aaatatgtat tccatgttcc cttactgaaa 198360
aagcttgcca gcccttcttt tattttatgt atttatttaa ttgttttttt tttttaaga 198420
cagagtctct ctctgttacc cacgctgggg ttaccatgcc tcagcctccc aagtagctgg 198480
gactacaggc gcccgccact acgcccggct aatttttgt atttttagta gagacagggt 198540
ttcgccgtgt tggccaggat ggtctcgatc tcctgatctt gtgatctgcc cgcctcggcc 198600
tcccaaagtg ctgggattac aggcgtgagc caccgcgccc agccgccatc ccagcattct 198660
ttaatacaga tttccctcgt attgtctaac ttgttatgca aatggattat ttttccccca 198720
aggggacctc cacaaccagc tttgaaaaca attatgctta ctttactgcc caggacaaaa 198780
acagtaaaac ttttgaagtt cccagacacc aaaagccctg cattctaaca ggttttgagc 198840
aaacctgatc ccaaagcact ttgtaggtgt gttggcccac catcaccatc ctgtaactgg 198900
aatgctcaac tccaattaga agtcttcctg gtttgggtca tttggggctt tggggaacct 198960
ttgacccttt tttctccctt ccctttgggc agctgccctg ggacattggc cccattcaca 199020
attctccagt ttcccagaca atgtggcttc ttgtgctctt tgctcgggcc cctctattaa 199080
ccctacagag aggtttcagg ttactgaaac agacgccttg ctttctgctg tgcataatgt 199140
cctttttcca gcgagaaact gcagcccatc aggatctggt tttcattaaa ggcactttgg 199200
gtcacttttt tagcagattg gtcaaaagga ctgaaaggac tgggcagggc gatgatgatt 199260
tggaggtcaa tagctttctc tatgggccat accccttccc cactgaaaga ttcccccact 199320
gcagactgga ggaaatcagt caggcaagga tccctgtggt gaaaactact cgaaaacagc 199380
aacaataacc acaaacctga aatgaagaca atttcctgag aaactatgaa tgtttggatg 199440
tgcaaggtga tcaactttcc cagttgcccg ggaccaaaag gtttcccagg actcaaaact 199500
ttccattttg aaaccagaaa gtcacaggca aacccggagg agttggtcaa cccatggatc 199560
agagtcactt catcttctgt gaaatttgca aagatgctag gaggttcccc tcctgctggg 199620
acaccccagc ccagacacaa accattaatt cacaattaca tggagtttca ctgtctgcaa 199680
ggctgctcca tttaagctct gggtcatgaa cacataactc taggcatact gacactagct 199740
gggagatttt ccaccaaaaa aaaaaaaaaa aaatgccatt tcatgactat taatccaaaa 199800
taggtaaatg tgtctggctt atagaatacc agcctgatta caaatgcttg gtgttggaat 199860
ggcccagctc acagtggttg tagaagtcca gtaggcccag gctttgtggc tcactcctgt 199920
aaccccagca ctttgggagg ccaaggtggg aggatcactt gagtccagaa gttcaaaacc 199980
agcctgggca acatagggag actccatttc tacaaataat ttaaaaatta gctgggtgca 200040
tgcttgtagc cctagctact caggaggttg aggcaggaga attgcctgag cctgggaggt 200100
cgaggccaca gtgagccgcg atcacatgtc actacattcc agcctgggtg acagagcaaa 200160
accctggctg gaaaaaaaaa aaattcaagc agtcaagggg atgggagctt ggtggactag 200220
agatgcccag acttgagttc ctgtcccagc cctgccacta atagtgagat tttaggcaca 200280
gctattcccc ttcttctctc ctaagtctcc ggagaacaaa tggctttgga ttcaatgagg 200340

-continued

```
aaaagaagga aagaaaggaa gaaactggtc tcactgagca tcctctatga gccgggcatc 200400
acaccaaacc ctcctccctg ccatttactc tttccaccag ccttgaaggg ttaccgtact 200460
cagtttcaca gatgagttca gtgcacatga acgatcacac agcaagcgaa tggcagggag 200520
ggggttatga tgcagggctg tggggctccc tagtaacctt aatcccagca gtcatttaat 200580
gagacagaac taagtacacg cctctctaac atacattgtc tcgcttaatt cttgtagaat 200640
ctttgaggca agcattacca ttatctctac ttcacagatg agcaaatggg ttctgagagg 200700
tcaagtgacc tgcccaaggt cacacagcta tgcatgcaca gccaggtggc aaacccagag 200760
ctaaatgatt ccaacgctca ctggctttgc tctccagtgt cagctcagca gccctgaacc 200820
taaaactcca ggtggcaggt gccaccccag ggataagacc ccagctttaa cctgaaccaa 200880
accttaacca gctgtgtgct attgggcaaa ttccttaacc tctataggct tgcatttcct 200940
cctctgcata gtaggcatgg cactcatacc tccctggcaa aaaactatca actttatttg 201000
tttatttatt tatttattta tttatttatt tatttattca ttcatgagac agagtctccc 201060
tgtgtcgccc agaatggagg gcagtggcct gatctcggct cactgcaacc tccacctgcc 201120
ggattgatgc gattctcctg cctcagcctc cggagtagct gagattacag gcgcccgcca 201180
ccacacctgg ctaatatttg tatttttagt agagatggaa tttcaccact ttggccaggc 201240
tggtctcgaa ctcctggcct caagtgattc tcctgcctca gcctcccaaa gtgctgggat 201300
tacaggtgtg agccccggcc tttacctgca tttttccatt tcttccacac aactgttatg 201360
aggtaggcat tactttatac ataaaataca taaagaacta agcccagcac tggcacatat 201420
aagaatgcaa tgaatcgtag ctattattac taatgctatt gtttttactg ctgctatatt 201480
attataacaa ataatcattg tgatagttat tgcaacagtt gtcatcgctg ttattatatt 201540
actaagtagt tttggatccc ttttctcgaa gtttcatcgt cccccccctc caagtgccct 201600
ccaatcccag gagcccttaa agccgctgca cccacacttt gcccaccctc tttctctcgg 201660
tctgtccccc acgccatcca tcacctgcac cccttcccta gggaggccca gcggtgggcg 201720
cccacccgct cccccagcgc tttgccccgt gagtcctccg cccaggcccc cgcgcgcgcc 201780
tcacctgcgg agcccggctt ggccgcactg agtcccacgg gcgggcgggt ggcgcagggc 201840
ggggccgcgg ggctcatgcg gggagcgggc aggcaggaga gcggcggggc ggcgccagcc 201900
ggcagctctg cgacctcctc cctgcagcgg cccaggtggg aactcagcca gggcagcggc 201960
gggggtcaca gtccccgcct gggacttcct atctgtcgaa gctt                 202004
```

<210> SEQ ID NO 19
<211> LENGTH: 3796
<212> TYPE: DNA
<213> ORGANISM: Homo sapiens

<400> SEQUENCE: 19

```
gctgaaggtt gcgctggcac gcgcaacttc cgggacagag gctgtggctg gaaggagctg     60
ggcatccggc ctgaggcgca gcggtcgcgt tagttcggcc caatggcggc accgctgctt    120
cacacgcgtt tgccgggaga tgcggccgct tcgtcctctg cagttaagaa gctgggcgcg    180
tcgaggactg ggatttcaaa tatgcgtgca ttagagaatg actttttcaa ttctccccca    240
agaaaaactg ttcggtttgg tggaactgtg acagaagtct tgctgaagta caaaaagggt    300
gaaacaaatg actttgagtt gttgaagaac cagctgttag atccagacat aaaggatgac    360
cagatcatca actggctgct agaattccgt tcttctatca tgtacttgac aaaagacttt    420
gagcaactta tcagtattat attaagattg ccttggttga atagaagtca aacagtagtg    480
```

```
gaagagtatt tggcttttct tggtaatctt gtatcagcac agactgtttt cctcagaccg    540
tgtctcagca tgattgcttc ccattttgtg cctccccgag tgatcattaa ggaaggcgat    600
gtagatgttt cagattctga tgatgaagat gataatcttc ctgcaaattt tgacacatgt    660
cacagagcct tgcaaataat agcaagatat gtaccatcga caccgtggtt tctcatgcca    720
atactggtgg aaaaatttcc atttgttcga aaatcagaga gaacactgga atgttacgtt    780
cataacttac taaggattag tgtatatttt ccaaccttga ggcatgaaat tctggagctt    840
attattgaaa aactactcaa gttggatgtg aatgcatccc ggcagggtat tgaagatgct    900
gaagaaacag caactcaaac ttgtggtggg acagattcca cggaaggatt gtttaatatg    960
gatgaagatg aagaaactga acatgaaaca aaggctggtc ctgaacggct cgaccagatg   1020
gtgcatcctg tagccgagcg cctggacatc ctgatgtctt tggttttgtc ctacatgaag   1080
gatgtctgct atgtagatgg taaggttgat aacggcaaaa caaaggatct atatcgcgac   1140
ctgataaaca tctttgacaa actcctgttg cccacccatg cctcctgcca tgtacagttt   1200
ttcatgtttt acctctgtag tttcaaattg ggattcgcag aggcattttt ggaacatctc   1260
tggaaaaaat tgcaggaccc aagtaatcct gccatcatca ggcaggctgc tggaaattat   1320
attggaagct tttggcaaag agctaaattt attcctctta ttactgtaaa atcatgccta   1380
gatcttttgg ttaactggct gcacatatac cttaataacc aggattcggg aacaaaggca   1440
ttctgcgatg ttgctctcca tggaccattt tactcagcct gccaagctgt gttctacacc   1500
tttgttttta gacacaagca gcttttgagc ggaaacctga aagaaggttt gcagtatctt   1560
cagagtctga attttgagcg gatagtgatg agccagctaa atcccctgaa gatttgcctg   1620
ccctcagtgg ttaacttttt tgctgcaatc acaaataagt accagctcgt cttctgctac   1680
accatcattg agaggaacaa tcgccagatg ctgccagtca ttaggagtac cgctggagga   1740
gactcagtgc agatctgcac aaacccgctg gacaccttct tcccctttga tccctgtgtg   1800
ctgaagaggt caaagaaatt cattgatcct atttatcagg tgtgggaaga catgagtgct   1860
gaagagctac aggagttcaa gaaacccatg aaaaaggaca tagtggaaga tgaagatgat   1920
gactttctga aaggcgaagt gccccagaat gataccgtga ttgggatcac accaagctcc   1980
tttgacacgc atttccgaag tccttcaagt agtgtgggct ccccacccgt gttgtacatg   2040
caacccagtc ccctctgacg gcagaaattt gtgactgaga tgtgacattt gggattcccc   2100
atcacttgtc atgccctcag cacccagctt gtgccattgg gcattgatgg cattgaacta   2160
gagcgagtgc ctgcctcggc tgtggcactt ccaggttcga ctgaatcaag catctgaaga   2220
ctgggttttt ttgttgttgt tgttcccctt acagacaaaa tgaagactat catgtgcaat   2280
cttttacagt ggggttgatg atacatttgg aaggatttgc ttgtttaata tgtacatttt   2340
ttgtgttaac agctttttga cacaattact gggtaatttc taatataggc agcagactgt   2400
tttacgggtt gctgttttaa catgggtttt tgtcagatcc atggtcttag gacttgactg   2460
atgagctttc agtgaagaat cctctaagat aaaacttcta tttaaagact ttaactagaa   2520
agtgtttatt ttggctacat tgttcacctt ctgctgtatt ggtatttgtc tgttgggatt   2580
tcaagggagt gtagagaaga cagaaggaaa gctgagagct ggcccgacat ggtctgggac   2640
acagagttgg agctggcact gaagatctcc agggacttca gagaccaata aaagcccata   2700
gggaagagag agaggatata gggaaacaga atcagatgtg taatatactt ggcacagcga   2760
aaaaatggat ttaaaagaca aaaatggagg tccaggtaga tgtaattcac acagactgaa   2820
```

agtgagttcg ggcttgtgta aaacacatga gattggattt gaccccttgg ctctcaagtg 2880
tccccttaga tctagaactg ctccttggtg gccattagat cgagtcagtt ttgatctgca 2940
tcacttagtt attgggaatt tctttgttgg aaacaggaaa attttttag attatttggt 3000 gtacggtttt gctcacaaca ataggtggaa gttgctagtg cagtcttggt ctgatggctg 3060
tgtgcatcgc acattcggct tggtgaaatc cttctctaaa gcctcttttt gtatttttat 3120
aactaaacag aggaagtctt cagaagacct cgctttaaaa caaatttgtg caaacactgc 3180
tagagtcatt ttgaagctca agcattttca ctttgtttct tacatgtgta ctttttgtt 3240 tacttgtgaa aatggccatc tttaagcata tttattttct gccactttat ttaaaggcaa 3300
gcaatatttt cttgatcata aatattttgt aatgaaatac ttcctctttt ccagggcttt 3360
gtatgcactt gtataattac attgatggca atgtagagtt tgaatttcag tctgtaaata 3420 ctttttgga aaatagaaat ttttattgct ttaaagtttt ggatatgggt ggtttctttt 3480
tccgggtttg gtggaaagta atttgagaac tttaaggttg tctttttaac tgctggcaaa 3540
atgttgattt tttaatatta gataaaacga gtaaacgaaa ttccccagaa attagtagta 3600
agtggggtct ttgtgggttg ggaagtagtt ttaatgtaga aagacattta catataagtc 3660
tgtttaattt caaaggagtt tgtgaaaaaa aatccatggt gaaaatgaaa caatgacatg 3720
gttaatctgg aacttacgtt cttataccaa taaaaggtac ctcaatacat gttctttcaa 3780
aaaaaaaaaa aaaaaa 3796

<210> SEQ ID NO 20
<211> LENGTH: 719
<212> TYPE: DNA
<213> ORGANISM: Homo sapiens
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t

<400> SEQUENCE: 20
acataaagaa aattttcatt tatttttccc tcagatatac ttcaaaataa catgtagaca 60
cagaatcaca aatatataca aaacaaagta tcgcctggtt atttcaagaa gagttttccc 120
tcaattttct tagctgctgt gcataaaatt caaagctttc agggggttca atgaaaggga 180
caggctctcc agcatacttc agcaaagatg cgtaacgctt tagaaacaga tcatccaatt 240
ttgtattctt tgcagtcaaa tgttcataca gtgctttagc agatgtgaca tctttctctg 300
agacatagct tttcatgagg gaattgtatg cttcttcctt ttcatttaat tcaggaatca 360
attctaacac agatttcaca gttgatgcct ttccttgttt cctagaattc ctaaggagga 420
acaacaacaa aatcggggtt tgttcagcaa ttgcaccaca tctctgtagg agagctctgg 480
catcatccac cttgcctgca tccacaagtt gaaggaaaan atcagtgaca ggtttataaa 540
ttgcaaactg attggccaat ctctccgcca tgatggctta tctttcaaac tgctggtcca 600
actgctcctc tattactttc tggataagat gccaaggccg agtantcggg tcaatgactt 660
tatcctctga agtaagctat tntcatggtt tctattgcgg catctatgta atcattctt 719

<210> SEQ ID NO 21
<211> LENGTH: 6637
<212> TYPE: DNA
<213> ORGANISM: Homo sapiens

<400> SEQUENCE: 21
acatgctcct cctgtccttc tggcggagcg tgcttcccgc tgcggggacg ttcgagcaat 60
ggcagccctg ctgagatccg cgcgttggtt gctgcgtgcc ggggcggccc cgcgcctccc 120
gctctccctg cgcctcctcc ctggcggccc gggccggctg catgccgcct cctatctgcc 180
cgccgctcgc gccgggcccg tggccggagg actactgagc ccagccaggc tgtatgccat 240
tgctgccaaa gaaaaagata ttcaagagga gtccactttt tcttctagga agatttccaa 300
tcagtttgat tgggctctaa tgagactaga tctttctgtt cgaagaactg gccgcattcc 360
aaagaagctt ctacaaaaag tttttaatga tacctgccgc tcaggtggcc taggtggtag 420
tcatgccttg cttctactac gtagttgtgg ttctctcttg cctgaactaa agcttgaaga 480
gagaacagaa tttgctcata ggatatggga cacacttcag aaattaggtg ctgtgtatga 540
tgtgagtcac tataatgctt tacttaaagt ctatcttcaa aatgaatata aattctcacc 600
aactgatttc ctggcaaaaa tggaggaagc aaacattcaa ccaaatcgag tgacatacca 660
gagattgatt gcttcttatt gtaatgtagg agatattgaa ggtgccagca agattcttgg 720
atttatgaaa actaaggatc tcccagttac agaggcagta ttcagtgccc ttgtgacagg 780
gcatgccaga gctggtgata tggagaatgc agaaaacatt ctcacagtga tgagagatgc 840
cggaattgag cctggtccag acacatacct cgcattattg aatgcatatg ctgagaaggg 900
cgacattgac catgttaagc agactctgga gaaggtggag aagtccgagc ttcaccttat 960
ggaccgtgat ttactgcaaa ttatttttag cttcagtaaa gctgggtatc ctcagtatgt 1020
ctcagaaatt ttggaaaaag ttacatgtga aagaagatat attccagatg caatgaacct 1080
cattttactt ttagtcactg aaaaattgga agatgtagcg ttgcaaattt tactagcatg 1140
ccccgtatca aaggaagatg gcccaagtgt ctttggcagt ttctttttac aacactgtgt 1200
gactatgaat acgcctgtgg agaagctaac agactactgt aagaagttaa aggaagtcca 1260
gatgcactcc tttcctctgc agttcaccct ccattgtgct ttactcgcca ataaaactga 1320
tttggcaaaa gccttaatga aggctgtgaa ggaggaaggt tttcctatca gacctcacta 1380
tttctggcca ttgctagttg gacgtcggaa ggaaaaaaat gttcaaggta taattgaaat 1440
cctcaaagga atgcaagaat tgggagtaca tcctgatcag gaaacatata cagattatgt 1500
gattccatgc tttgatagtg taaactcagc acgagccatt ttgcaggaaa atggatgtct 1560
gtctgatagt gatatgtttt ctcaagctgg attgagaagt gaagcagcaa atgggaactt 1620
agactttgta ttatcatttt tgaaatcaaa tacattgccc atctcgctgc agtctataag 1680
aagtagccta ctgctaggct tcaggaggtc tatgaatata aatctttgga gcgagataac 1740
agaattgttg tacaaggatg gacgttattg ccaggagcct cgaggaccga cggaagctgt 1800
tggctatttt ctttataact tgattgacag catgagtgac tcagaggtac aggccaagga 1860
ggagcatttg agacaatact tccatcagct ggagaagatg aatgtaaaaa ttcctgaaaa 1920
tatctacaga ggcattcgta atctcctgga aagctaccat gttcctgaat tgattaagga 1980
tgctcacttg ttggttgaga gtaagaattt agactttcaa aaaactgtgc aacttacatc 2040
atctgaattg gagtccacac ttgaaacact aaaagctgaa aatcaaccta taagagatgt 2100
cctaaagcaa ctcatattag tgctttgttc agaagagaat atgcaaaaag cccttgaatt 2160

-continued

```
gaaagcaaaa tatgaatccg acatggttac tggtggctat gcagctttaa taaatttatg   2220
ctgtcgacat gataaagtag aagatgcctt gaacttgaaa gaagaatttg accgcttaga   2280
ttcatctgct gtccttgaca ccggcaagta tgtaggcctt gtaagagtat tggcaaagca   2340
tggcaagctc caagatgcta ttaacattct gaaggagatg aaagagaagg atgttcttat   2400
caaagataca acagccttgt ccttttcca catgctaaat ggcgcagctt taagaggtga   2460
aattgaaaca gtaaaacagt tgcatgaagc catcgtgact ctagggttag cagaaccatc   2520
caccaacata agtttcccat tggtcactgt acacttggaa aagggcgacc tatctactgc   2580
tcttgaggtc gccattgact gctatgaaaa gtataaagta ttaccaagga ttcatgatgt   2640
cttgtgtaaa ctggtagaga aaggcgagac tgatctaatt cagaaagcaa tggactttgt   2700
gagccaagaa caaggtgaaa tggtgatgct ctatgatctc ttctttgcct tcctacaaac   2760
aggaaattac aaagaggcca agaagatcat tgagactcca gggattagag ctcgatctgc   2820
aaggcttcag tggttttgtg acagatgtgt tgcaaataat caggttgaaa ctctggaaaa   2880
attagtggag ctgacacaga agctatttga atgtgataga gaccagatgt actacaatct   2940
gctaaaactg tataaaataa acggtgactg gcaaagagct gatgcagtct ggaataaaat   3000
ccaagaagaa aatgttattc ctcgtgaaaa gacattaaga ttattagcag aaatccttag   3060
agagggtaac caggaagttc cgtttgacgt acctgagttg tggtatgaag atgaaaaaca   3120
ttccctgaat tcttcgtcag cctcaaccac agaacctgat ttccagaaag atatattgat   3180
tgcctgccga ttgaaccaaa aaaaaggggc atatgatatt ttcctgaatg caaaagagca   3240
aaacattgtg tttaatgctg aaacctacag caatctcatt aaattactga tgtcagaaga   3300
ttattttaca caagcaatgg aagtgaaagc attcgcggag acccacatca agggcttcac   3360
actgaacgat gctgccaaca gccgcctcat cataacgcaa gttaggcggg attatttgaa   3420
agaggctgtg acaacactga aaacagtatt ggatcagcag cagacccctt ctaggttagc   3480
agtgacccgt gtcatccagg cattggccat gaagggtgat gttgaaaaca tagaagtagt   3540
tcagaagatg ttaaatggac tcgaagactc cattggactt tcaaaaatgg ttttcatcaa   3600
taacattgct ttggctcaaa taaagaataa taacatagat gccgcaatag aaaacattga   3660
aaatatgctt acttcagaga ataaagtcat tgaaccccaa tacttcggct tggcatactt   3720
attcagaaaa gtaatagagg agcagttgga accagcagtt gaaaagataa gcatcatggc   3780
ggagagattg gccaatcagt ttgcaattta taaacctgtc actgattttt tccttcaact   3840
tgtggatgca ggcaaggtgg atgatgccag agctctccta cagagatgtg gtgcaattgc   3900
tgaacaaacc ccgattttgt tgttgttcct ccttaggaat tctaggaaac aaggaaaggc   3960
atcaactgtg aaatctgtgt tagaattgat tcctgaatta aatgaaaagg aagaagcata   4020
caattccctc atgaaaagct atgtctcaga gaaagatgtc acatctgcta aagcactgta   4080
tgaacatttg actgcaaaga atacaaaatt ggatgatctg tttctaaagc gttacgcatc   4140
tttgctgaag tatgctggag agcctgtccc tttcattgaa ccccctgaaa gctttgaatt   4200
ttatgcacag cagctaagaa aattgaggga aaactcttct tgaaataacc aggcgatact   4260
ttgttttgta tatatttgtg attctgtgtc tacatgttat tttgaagtat atctgaggga   4320
aaaataaatg aaaatttct ttatgtactt atgtatgtgt gatgcatgtt caaagtctta   4380
ttgaccataa ctctgtgcac ttggttattg gacatttttg gagttttttt ctctgggaaa   4440
aatcgatagt gttttcttca atgctgctgc tgtgtgaagc catacttttt caggattctt   4500
cccctaattg gctctttggt ttccctgctc tgtttcattt atttcattaa aatgttattc   4560
```

ctttatttaa gattcactta ttagtctgct gtttctctga aaaattttag agctaggtat 4620
agtgaccgtg aactttctaa cgcataatat tctgtgatac agccattccg tacatgtgtg 4680
aagtcctgca taactttcga actttgttaa atgttggcac taggagtcat cagatctagg 4740
cttcatcatt ttccagtgag aagcagagac ccaaagggcc tgttacttgt gcttggtcag 4800
gggactgtct gtcatgcctg gaggctcttc ggcacacttc cccatctttc ccttctgcca 4860
ctgtggcttc aagcacctct gttcatagag cgtctctgaa attgagtctc ggtcatgact 4920
tatcccgaag tagagcaatg tgtttcctct cattgtagtt tcaggacttt gtcagtacaa 4980
gctctgccct aggcttgtta ctttatactc atatcctgaa aagatgtgat ttcatctatg 5040
aaggggtaaa atattggttt gtatttaatt gtttgaaata aaagtgatcc ctatattgaa 5100
tctcatgcct gttaatatct acactgtaag tagtgacttc aaaaaaattc taagataggt 5160
agtcaggaga gtttgccatt ataaaaggtg tcttaataat atggaatatt gacctaactg 5220
gagatgaggt aattaattac cgaaatgttg aaaatgtttt gagaactctc cccattttgg 5280
ggtattcctt gttcatttga atttggtgac tccctactgt tccagtttca gtgccaactt 5340
gggtcacact gttcacatca ggggagacct tgccttgggg acgtaggcgg gcctcttgca 5400
acttgtgctg ttgaccttct gtcttgtgga actctctctc ctgcatctgc tacctgcccg 5460
cagatggtgt gagggagggt tgatggcggg aagccaggaa gtagatgtca tcatggtatt 5520
ggccaggctt ttacttcaac tctttttgtg gcgttagatt taaggaagca gggggcatgg 5580
ccaacgttga gtcttggccc agtggacata gtgcggcttt cccttgagca ctgcccagat 5640
gcaggacctg cacatgttac aggtttgcca aaagcatctt tttttttttt tttttttttg 5700
agatagtctt gctctgttgc ttaagccaga gtgcagtggc gcaatctcag ctcactgcaa 5760
cctccgcctc ctgggttcaa gtgattcttg tgcctcagcc tcccacgtag ctgagattac 5820
aggcttgcac caccatgttc agctaatttt tgtatggtaa agacggagtt tcaccatgtt 5880
ggccaggttg gtctcgaact cctggcccca agtgatcctc cccctgcgct cgcttcagcc 5940
tcccaaagtg ctgggattac aggtgtgagc caccacgcct ggccaagagc ctcactcctg 6000
tctttagtga ttgcactgaa gcaggcctca ttttttttgca gtcatgctaa ccacaagtta 6060
gtcaacattc actaattgac attcattaga ataggtctcc aaggtgaggc ataacgttgg 6120
ggtgtaatct ggatttcgca gtcatctttt tggggaaact gaaagtacca tctcatttgc 6180
atgaagtgac tccacactgg ccctgtatat ggactctggt aaaatgtgag tgtggtacag 6240
aggaaatagg taagaccccc ttatctagcc ctctcggcag cagcgggggg gtgttacaaa 6300
ggactagctg ttcaaatatc ttttgtattg tattgattcc cctattgaat ataaatattt 6360
aaagtataat aactatactg taggtgggct tatgagtgtt ctaaatatct aatagctaaa 6420
ttgaaataag tagaaatata aacaatttag cagctttctg taatacattt acactcaaat 6480
tataagcagc taattctaaa aaagatgtca ctgtaaacta ttgagaacta tagtatttta 6540
tatataatta tatgttcatg tatttgaacc caaaataatt ttaactgaaa tgctttgaat 6600
aaagtatact gtaaatatca aaaaaaaaaa aaaaaaa 6637

<210> SEQ ID NO 22
<211> LENGTH: 5427
<212> TYPE: DNA
<213> ORGANISM: Homo sapiens

<400> SEQUENCE: 22

-continued

```
agatgcgacg aggttagcgg ggcccgacca ctccttggct tcccaggggt gagcctcgcg     60
agttaggagt tgggtagaga gtcagcccgg ggcccggcat ccgctttttc gttgaagcaa    120
cgactttggc cggatgactc cccagggtcg gcatcagcgt gggactggga acaggtgaag    180
ggaaacagaa gagagcctga gaagaccgct ctcctccgat cctaattgac tgagccaatg    240
agagccaaag aggtcacatg ctcaactggg cggggagcgg gtttccacct gcggcatctt    300
tcgcgagcgg ggagatgagt ggggcggaat atgggagaaa gggagggccc gccacgctct    360
ggctggacac ggccttaatc ggcccgttca ctcgacgttt ttggttctac gttgaccccg    420
agaaaccgaa accgcagggc ctagggcggg tggaacgaga gggaactaca tttcccagca    480
ggctgcggaa acgggactgc ggccactact tccggcgtgt accgagagac tggcgtccgg    540
cgtgtaccga gagactggcg tccggtgtgc aggtggccac atggatcctg gcagccggtg    600
gcggaacctg cccagcgggc ctagcctaaa gcacttgact gacccctctt atggaatccc    660
gcgggaacag caaaaggcag cgttgcagga gctgacgcgg gcgcacgtgg agtccttcaa    720
ctacgctgtg cacgagggtc tcggcctcgc ggtgcaggct atacctccct ttgaatttgc    780
tttcaaagat gagcgtatct cttttactat tctggatgct gttatcagtc cacctacagt    840
tccaaaaggg accatctgca aagaggccaa tgtttatcca gcagaatgcc ggggccgaag    900
gagtacctac cgtgggaagt tgacagctga tatcaactgg gcagtgaatg gaatctcaaa    960
aggaatcatt aagcagtttc ttggctatgt tcccatcatg gtgaaatcca agctttgcaa   1020
cttacgtaac cttcccccac aagccctcat tgagcaccat gaggaggcag aggaaatggg   1080
gggctatttt ataatcaatg gcattgaaaa agtcatccga atgttgatta tgcctcggag   1140
aaatttttccc attgcaatga taagaccaaa atggaaaacc agagggcctg gttatactca  1200
gtatggagtt tcaatgcact gtgtgaggga agaacattcc gctgtcaata tgaacctcca   1260
ctacttggaa aatggcactg ttatgttgaa ctttatttac cgaaaagaac tgttctttct   1320
tcctttggga tttgcactta aggcacttgt cagcttttct gattatcaga tctttcagga   1380
gctcatcaaa ggaaaagagg atgattcttt ccttaggaac tctgtttctc agatgttaag   1440
gattgtaatg gaagagggtt gttcgacaca aaaacaggtc cttaactacc taggtgaatg   1500
cttcagagta aaactcaatg ttcctgactg gtacccaaat gagcaagctg cggagttcct   1560
gtttaaccag tgcatctgta tccacttgaa atccaatact gaaaagtttt atatgctttg   1620
tctcatgacg cgaaagctct ttgctttagc caaaggagag tgcatggagg acaatcctga   1680
tagtttggtg aaccaggaag tcctcacacc gggtcagctc ttccttatgt tcctgaagga   1740
aaaactggaa ggttggttag tgtctattaa aatagctttt gataagaagg ctcagaagac   1800
cagtgtttcc atgaacactg acaatttgat gaggattttt acaatgggca tagaccttac   1860
aaaaccattt gaatacccttt ttgctactgg gaatctgcgt tctaaaacag gtcttggcct  1920
cctacaagat tctggacttt gtgttgtggc tgacaagctg aacttcatac gctacctctc   1980
ccatttccgc tgcgtgcaca gaggggctga ttttgccaag atgaggacca ccacagtacg   2040
caggctgctg ccagagtcct ggggcttcct ttgtcccgtg cataccccag acggggagcc   2100
ctgtggcctg atgaaccacc taactgccgt atgtgaggtt gtcacacagt ttgtgtatac   2160
ggcatctatt ccagctttac tgtgcaactt gggggtcact cccattgatg gagctcccca   2220
ccgatcatac agtgagtgct accctgtcct gctggacggt gtcatggttg gctgggtgga   2280
taaggatctt gctccaggca tcgcagattc tcttcgtcat tttaaggtgt tgagagagaa   2340
aagaattcct ccctggatgg aagtggtcct tatacccatg acaggaaaac caagtctgta   2400
```

-continued

```
cccaggattg ttcctttta ccactccttg tagactggta cggcctgtgc agaacttagc   2460
attgggcaaa gaagagctaa ttggaactat ggaacagatc ttcatgaatg tcgctatctt   2520
tgaggatgaa gtttttgctg gagttaccac acaccaggaa ctctttccac acagcctgct   2580
gagtgtgatt gccaacttca tccctttctc tgatcacaac cagagtccac ggaacatgta   2640
ccaatgccag atgggtaagc aaactatggg ctttccactt ctcacttatc aagaccgatc   2700
ggataacaaa ctgtatcgtc ttcagactcc tcagagtccc ttggtgagac cctccatgta   2760
tgattattat gacatggata actatccaat tgggaccaat gccatcgttg ctgtgatttc   2820
ttacactggc tatgatatgg aagatgccat gattgtgaat aaggcctctt gggaacgagg   2880
ctttgcccat ggaagtgtct acaagtctga gttcatagac ctctctgaaa aaattaaaca   2940
aggagatagt agcctggtgt ttggcatcaa acctggtgac ccacgcgttc tgcagaagtt   3000
agatgacgat ggattgccgt ttataggagc aaaactgcag tacggagatc cgtattacag   3060
ctacctcaac ctcaacaccg ggaaaagttt tgtgatgtac tataagagta aagaaaattg   3120
tgttgtggat aacatcaaag tgtgcagtaa tgacactggg agtggaaaat tcaagtgtgt   3180
ttgcatcact atgagagtgc ctcggaaccc aactatcgga gataaatttg ccagtcgcca   3240
tgggcagaag ggcattttaa gcagattgtg gccggctgag gacatgcctt ttactgagag   3300
tgggatggtc ccagacattc tgttcaatcc ccatggtttt ccatcccgca tgaccattgg   3360
gatgttaatt gagagtatgg ccgggaagtc tgcagctttg catggtctct gccatgatgc   3420
tacacccttc atcttctcag aggagaactc ggccttagaa tactttggtg agatgttaaa   3480
ggctgctggc tacaatttct atggcaccga gaggttatat agtggcatca gtgggctaga   3540
actggaagca gacatcttca taggagtggt ttattatcag cgcttacgcc atatggtctc   3600
agacaaattt caagtaagga caactggagc ccgagacaga gtcaccaacc agcctattgg   3660
gggaagaaat gtccagggtg gaatccgttt tggggagatg gaacgggatg cgcttttagc   3720
tcatggtaca tcttttctcc ttcatgaccg cctcttcaac tgctcagatc ggtcggtagc   3780
ccatgtgtgt gtgaagtgtg gcagtttact ctctccactg ttggagaagc cacccccttc   3840
ttggtctgcc atgcgcaaca gaaaatacaa ctgtactctg tgtagtcgca gtgacactat   3900
cgatactgtt tctgtgcctt atgtttttcg gtattttgta gctgaactgg cagctatgaa   3960
catcaaagtg aaactggatg ttgtttaact tgatgttgac cttttggatt aagaggacta   4020
tcagattaaa gcaaaatgta attttaattc aatgaagata tcattaccag gttactcttg   4080
agatttttca acggtgttag aactctcaac caagacctga aaccaagta tgcaaggttt   4140
ctgaatctct ctggtagatt aactattgac aatgattttc tgttatcttt gttcaaaaag   4200
ttcatgtctt ctcaaaatat gaaatattga taaatggaag agcatacggt gacaagtctc   4260
ctttccaacc ccaggttccc tacaccctgc tctcagcagg cagtgagtgt cacacacctg   4320
ttaatccatc ttgagcagga cagtactata caaatagaat gcaagctgta atgtaatttt   4380
atattttctt atagccacgt tgaagtaaaa acaaacaggt acagtgtttt ttaccagctt   4440
tatagaagta cagttgttac atatttaatg aatacaattt gatgggtctg actatatgca   4500
cacacctttg ataccatcac cacaatcagg gtaataaaca tacctgtcat ctccacaagt   4560
ttcctcctgc ccctttgttt tttgcttttt ggttgctgtt gagtttttgt tttgtcttct   4620
gtggtaagaa cacttaactc aagacctacc ctcttaacaa atctttaagt gcacgatata   4680
gtattgttaa ttccaggcac catgttgtac aacagatctt tagaccttac ttgtcttgca   4740
```

-continued

```
taactgaagc tttatacctg ttgaacaact ctccatttcc ctggccccta gcaaccaccc   4800

ttctaccctg tttctatgag tttgactatt acagatatct catatagtgg gatcatgcaa   4860

tatttgtcct gtgactggct tatttcactt agcatagtga aataagattc atccattttg   4920

gaagccaggc atggtgctgt gcatctatag tccctgctat ttgagaggct gaggtgggag   4980

gatcatttga gtgcaggagt tcaaggacag cctgggtaat ataggaagac cctgtcttga   5040

agaccctgac ctcaagtgat ccacccacct cggcctccga aagtgctagg attacaggtg   5100

tgagccactg tgcctggcct ccggtgagta ttttatattt agtctacact tccatacttg   5160

gctttttct gcttttatat tgatctgctt tcatagcagt gtgtagagtg ccacttatgt   5220

tttctttctt gtgtacagta ttttattgta tggatttacc atcccctgtg tatttaagtt   5280

gttccattct ttggccatta taactttttt ctgcaaatat tctggtgact tatctttggc   5340

cattataaac tgttgataat agatcatctt gtatatactt ctgcaattat aagatgtttt   5400

ttgatgatga aaaaaaaaaa aaaaaaa                                      5427
```

<210> SEQ ID NO 23
<211> LENGTH: 1138
<212> TYPE: DNA
<213> ORGANISM: Homo sapiens

<400> SEQUENCE: 23

```
agggctacta ggacgcacgc gcgagataga acctctagtc tcgtggagag attgaagatg     60

gcggcttctc aggcggtgga ggaaatgcgg agccgcgtgg ttctggggga gtttggggtt    120

cgcaatgtcc atactactga ctttcccggt aactattccg gttatgatga tgcctgggac    180

caggaccgct tcgagaagaa tttccgtgtg gatgtagtac acatggatga aaactcactg    240

gagtttgaca tggtgggaat tgacgcagcc attgccaatg cttttcgacg aattctgcta    300

gctgaggtgc caactatggc tgtggagaag gtcctggtgt acaataatac atccattgtt    360

caggatgaga ttcttgctca ccgtctgggg ctcattccca ttcatgctga tccccgtctt    420

tttgagtatc ggaaccaagg agatgaagaa ggcacagaga tagatactct acagtttcgt    480

ctccaggtca gatgcactcg gaacccccat gctgctaaag attcctctga ccccaacgaa    540

ctgtacgtga accacaaagt gtataccagg catatgacat ggatcccccct ggggaaccag    600

gctgatctct ttccagaggg cactatccga ccagtgcatg atgatatcct catcgctcag    660

ctgcggcctg gccaagaaat tgacctgctc atgcactgtg tcaagggcat tggcaaagat    720

catgccaagt tttcaccagt ggcaacagcc agttacaggc tcctgccaga catcaccctg    780

cttgagcccg tggaagggga ggcagctgag gagttgagca ggtgcttctc acctggtgtt    840

attgaggtgc aggaagtcca aggtaaaaag gtggccagag ttgccaaccc ccggctggat    900

accttcagca gagaaatctt ccggaatgag aagctaaaga aggttgtgag gcttgcccgg    960

gttcgagatc attatatctg taagaaagat ttgctggctg cggtggctca cacctgtaat   1020

cccagcactt tgggaggcca aggcgagtgg atcacggggt caagagagcg agaccatcct   1080

ggctaacatg gtgaaacccc gtctctataa aaaaaaaaaa aaaaaaaaaa aaaaaaaa     1138
```

<210> SEQ ID NO 24
<211> LENGTH: 817
<212> TYPE: DNA
<213> ORGANISM: Homo sapiens

<400> SEQUENCE: 24

```
gtcggggcgg gggctggggg tggagcctca tgccccgccc cgcggctggg ccctgccgcg     60
```

```
ccgctgcggc tcctcctccc tccttccgtc ctccgcgcct tccgtcggtc ggtccttgct    120

tcctgcttcg cctccgcgcc tcgcgctatg ggacagagcc cccgatccgc cagcaccacc    180

tgaggatcca gaaaccgccc cagcgatgga agaggatcag gagctggaga gaaaaatatc    240

tggattgaag acctcaatgg ctgaaggcga gaggaagaca gccctggaaa tggtccaggc    300

agctggaaca gatagacact gtgtgacatt tgtattgcac gaggaagacc ataccctagg    360

aaattctcta cgttacatga tcatgaagaa cccggaagtg gaattttgtg gttacactac    420

gacccatcct tcagagagca aaattaattt acgcattcag actcgaggta cccttccagc    480

tgttgagcca tttcagagag gcctgaatga gctcatgaat gtctgccaac atgtgcttga    540

caagtttgag gccagcataa aggactataa ggatcaaaaa gcaagcagaa atgaatccac    600

attctagtcc tttatgcagt atacaaggag aactgtcctg taggatattc tcttcctgat    660

ggtgcagaac ccagaattag aagtttgtgg ttacagcata ctctgtcctt cagaaaggcg    720

tgattctagc tgttgacccc ttgcagctgt tggaatctct gcaagaacct ctgtattctt    780

ctaataaatt ccctctttta tttaaactag aaaaaaa                             817
```

<210> SEQ ID NO 25
<211> LENGTH: 2732
<212> TYPE: DNA
<213> ORGANISM: Homo sapiens

<400> SEQUENCE: 25

```
ctttcgcctc agtctcgagc tctcgctggc cttcgggtgt acgtgctccg ggatcttcag     60

cacccgcggc cgccatcgcc gtcgcttggc ttcttctgga ctcatctgcg ccacttgtcc    120

gcttcacact ccgccgccat catggtgaag ctcgcgaagg caggtaaaaa tcaaggtgac    180

cccaagaaaa tggctcctcc tccaaaggag gtagaagaag atagtgaaga tgaggaaatg    240

tcagaagatg aagaagatga tagcagtgga gaagaggtcg tcatacctca gaagaaaggc    300

aagaaggctg ctgcaacctc agcaaagaag gtggtcgttt ccccaacaaa aaaggttgca    360

gttgccacac cagccaagaa agcagctgtc actccaggca aaaaggcagc agcaacacct    420

gccaagaaga cagttacacc agccaaagca gttaccacac ctggcaagaa gggagccaca    480

ccaggcaaag cattggtagc aactcctggt aagaagggtg ctgccatccc agccaagggg    540

gcaaagaatg gcaagaatgc caagaaggaa gacagtgatg aagaggagga tgatgacagt    600

gaggaggatg aggaggatga cgaggacgag gatgaggatg aagatgaaat tgaaccagca    660

gcgatgaaag cagcagctgc tgcccctgcc tcagaggatg aggacgatga ggatgacgaa    720

gatgatgagg atgacgatga cgatgaggaa gatgactctg aagaagaagc tatggagact    780

acaccagcca aaggaaagaa agctgcaaaa gttgttcctg tgaaagccaa gaacgtggct    840

gaggatgaag atgaagaaga ggatgatgag gacgaggatg acgacgacga cgaagatgat    900

gaagatgatg atgatgaaga tgatgaggag gaggaagaag aggaggagga agagcctgtc    960

aaagaagcac ctggaaaacg aaagaaggaa atggccaaac agaaagcagc tcctgaagcc   1020

aagaaacaga aagtggaagg cacagaaccg actacggctt tcaatctctt tgttggaaac   1080

ctaaacttta acaaatctgc tcctgaatta aaaactggta tcagcgatgt tttgctaaa    1140

aatgatcttg ctgttgtgga tgtcagaatt ggtatgacta ggaaatttgg ttatgtggat   1200

tttgaatctg ctgaagacct ggagaaagcg ttggaactca ctggtttgaa agtctttggc   1260

aatgaaatta aactagagaa accaaaagga aaagacagta agaaagagcg agatgcgaga   1320
```

-continued

```
acacttttgg ctaaaaatct cccttacaaa gtcactcagg atgaattgaa agaagtgttt   1380

gaagatgctg cggagatcag attagtcagc aaggatggga aaagtaaagg gattgcttat   1440

attgaattta agacagaagc tgatgcagag aaaacctttg aagaaaagca gggaacagag   1500

atcgatgggc gatctatttc cctgtactat actggagaga aaggtcaaaa tcaagactat   1560

agaggtggaa agaatagcac ttggagtggt gaatcaaaaa ctctggtttt aagcaacctc   1620

tcctacagtg caacagaaga aactcttcag gaagtatttg agaaagcaac ttttatcaaa   1680

gtaccccaga accaaaatgg caaatctaaa gggtatgcat ttatagagtt tgcttcattc   1740

gaagacgcta aagaagcttt aaattcctgt aataaaaggg aaattgaggg cagagcaatc   1800

aggctggagt tgcaaggacc caggggatca cctaatgcca gaagccagcc atccaaaact   1860

ctgtttgtca aaggcctgtc tgaggatacc actgaagaga cattaaagga gtcatttgac   1920

ggctccgttc gggcaaggat agttactgac cgggaaactg ggtcctccaa agggtttggt   1980

tttgtagact tcaacagtga ggaggatgcc aaagctgcca aggaggccat ggaagacggt   2040

gaaattgatg gaaataaagt taccttggac tgggccaaac ctaagggtga aggtggcttc   2100

gggggtcgtg gtggaggcag aggcggcttt ggaggacgag gtggtggtag aggaggccga   2160

ggaggatttg gtggcagagg ccggggaggc tttggagggc gaggaggctt ccgaggaggc   2220

agaggaggag gaggtgacca caagccacaa ggaaagaaga cgaagtttga atagcttctg   2280

tccctctgct ttcccttttc catttgaaag aaaggactct ggggttttta ctgttacctg   2340

atcaatgaca gagccttctg aggacattcc aagacagtat acagtcctgt ggtctccttg   2400

gaaatccgtc tagttaacat ttcaagggca ataccgtgtt ggttttgact ggatattcat   2460

ataaactttt taaagagttg agtgatagag ctaaccctta tctgtaagtt ttgaatttat   2520

attgtttcat cccatgtaca aaaccatttt ttcctacaaa tagtttgggt tttgttgttg   2580

tttctttttt ttgttttgtt tttgtttttt ttttttttgc gttcgtgggg ttgtaaaaga   2640

aaagaaagca gaatgtttta tcatggtttt tgcttcagcg gctttaggac aaattaaaag   2700

tcaactctgg tgccagaaaa aaaaaaaaaa aa                                 2732
```

<210> SEQ ID NO 26
<211> LENGTH: 583
<212> TYPE: DNA
<213> ORGANISM: Homo sapiens
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (492)..(492)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t

<400> SEQUENCE: 26
ttttgttgta aaaaaaacca agtttttttt ctttcctaat agctagttcc aatgatgtta 60
attacccgcc ctgagctgaa ataacagtag acaaagatag aagctagcct ctggttttac 120
aaagcctttg tacaagtcct ctctgtcttt tctgtccatn gccagggaaa tgtattgctg 180
gtgctagagg gagaggaaac gtggacggcc aagaacaggg cggcacagtc ctctgggctg 240
gaggctcgtg ttccttccca taagcagggc ctgtggggtg tatggggcag aacataggcc 300
tccacaccaa actgacagca gagaaaagcc aggcaacctg ttcaatcgcc ccagcagttg 360
acctgggttc tatgtgtggg agtgaactgc tgcggccctg ggagcnactg tccccagcct 420
tggggctgat gtggtctana aggacacctc ggccacacag tggaaggggc cagggancct 480
ggccaggcaa anaagttngg ttgggtggag gactatgcta cgctgtactt gactcnggga 540
agaagtcttg attggggncc tttnttggat ntggccccng ggg 583

<210> SEQ ID NO 27
<211> LENGTH: 1884
<212> TYPE: DNA
<213> ORGANISM: Homo sapiens

<400> SEQUENCE: 27
ggcggggcca cgccttttcc ggcccgcagc gcggcctggg ctcccgcgtg tttaaaagtg 60
cgcttgtggc tgctgctgtc ttaactcctg tgcttggcgg acagacaggc gagatggcgg 120
cggaggtgtt gccgagtgcg aggtggcagt attgtggggc gcccgacggg agccagagag 180
ctgtactggt ccagttctcc aacgggaagc tacagagtcc aggcaacatg cgctttacct 240
tgtatgagaa caaagattcc accaacccca ggaagaggaa tcaacggatc ctggcagctg 300
aaacagatag gctctcctat gtgggaaaca attttgggac tggagccctc aaatgcaaca 360
ctttgtgcag gcactttgtg ggaattttga acaagacctc tggccaaatg gaagtatatg 420
atgctgaatt gttcaacatg cagccactat tttcagatgt atcagttgag agtgaactgg 480
cgctagagag tcagaccaaa acttacagag aaaagatgga ttcttgtatt gaagcctttg 540
gtaccaccaa acagaagcga gctctgaaca ccaggagaat gaacagagtt ggcaatgaat 600
ctttgaatcg tgcagtggct aaagctgcag agactatcat tgatacgaag ggtgtgactg 660
ctctggtcag cgatgctatc cacaatgact tgcaagatga ctccctctac cttcctccct 720
gctatgatga tgcagccaag cctgaagacg tgtataaatt tgaagatctt ctttcccctg 780
cggagtatga agctcttcag agcccatctg aagctttcag gaacgtcacg tcagaagaaa 840
tactgaagat gattgaggag aacagccatt gcacctttgt catagaagcg ttgaagtctt 900

```
tgccatcaga tgtggagagc cgagaccgcc aggcccgatg catatggttt ctggataccc     960
tcatcaaatt tcgagctcat agggtagtta agcggaaaag tgctctggga cctggagttc    1020
cccacatcat caacaccaaa ctgctgaagc actttacttg cttgacctac aacaatggca    1080
gattacggaa cttaatttcg gattctatga aggcgaagat tactgcatat gtgatcatac    1140
ttgccttgca catacatgac ttccaaattg acctgacagt gttacagagg gacttgaagc    1200
tcagtgagaa aaggatgatg gagatagcca aagccatgag gctgaagatc tccaaaagaa    1260
gggtgtctgt ggccgccggc agtgaagaag atcacaaact gggcaccctg tccctcccgc    1320
tgcctccagc ccagacctca gaccgcctgg caaagcggag gaagattacc tagacgcatg    1380
ctttccagac agggcgtttt ggctgcatca cagccactgg ctggtcctat tcatttccat    1440
ttttatgtat gttttgaaaa gaaaaggtcc ggggatggtg gctcacacct gaaatcccag    1500
cactttggga ggccgaggca ggaagatcat tgagctcagg agtttgaaac cagtctggac    1560
aacataggga gaccccatct ctaccggagg aaaaaaaaaa gagtcaggcc tggtggtgtg    1620
cgcctgtaat cccagctact cgggaggctg aggcaggacg attacttgag cttgggaaat    1680
caaggttgca gtgagctatg attgtgtggc cacactccat cctgggtcac agagtgagac    1740
cttgtctcaa aaaagtaaca taaggaaaaa agaagccttg ctttagcaca ggtatgaagc    1800
cagaagccag catctcaact gtgcttgtct tatgcagaaa tataaagcga tggccaggtt    1860
ggacttcaaa aaaaaaaaaa aaaa                                            1884
```

<210> SEQ ID NO 28
<211> LENGTH: 3216
<212> TYPE: DNA
<213> ORGANISM: Homo sapiens

<400> SEQUENCE: 28

```
gcggacggtg agtggggatg gactggagtt gaagagctcg agatgaaggg cttgagggcg      60
tgtgttattt gttttcttca agcatttggt cgagattaag aattaaaaat gtcatccaaa     120
caagaaataa tgagtgacca gcggtttaga cgggttgcaa aggacccgag attttgggaa     180
atgccagaaa aggatcgaaa agtcaaaatt gacaagagat ttcgagccat gtttcatgac     240
aagaagttca agttgaacta tgccgtggat aaaagagggc gccccattag ccatagcact     300
acagaggatt tgaagcgttt ttacgacctt tcagattctg attccaatct ctctggtgaa     360
gatagcaaag cattgagtca aaagaaaata aagaagaaaa aaacccagac taaaaaagaa     420
atcgattcaa aaaatctagt tgagaaaaag aaagaaacca agaaggctaa tcacaagggt     480
tctgaaaata aaactgattt agataattct ataggaatta aaaaaatgaa aacctcatgt     540
aaatttaaga tagattcaaa cataagtccg aagaaggata gcaaagaatt tacacaaaaa     600
aataagaaag agaaaaaaaa cattgttcaa catactacag actcttctct cgaagaaaaa     660
caaaggacat tagactcagg cacctctgaa attgtgaaat ctcccagaat cgagtgttct     720
aagacaagaa gagaaatgca atcagtggtt caactcataa tgacaagaga cagtgatggt     780
tatgaaaact caacagatgg tgaaatgtgt gacaaagatg ctctggagga agattcagaa     840
agcgttagtg aaataggaag tgatgaggaa tctgaaaatg aaattacaag tgttggtaga     900
gcttcaggtg atgacgatgg aagtgaagat gatgaagagg aggatgaaga tgaagaggag     960
gatgaagatg aggatagtga ggatgatgat aaaagtgaca gtggccctga tcttgcaagg    1020
ggtaaaggaa atatagaaac tagttctgaa gatgaagatg atacggcaga tttgtttcca    1080
gaagaatctg gttttgagca tgcttggaga gaattagata aagatgctcc tcgtgctgat    1140
```

-continued gagattacac gtcgattagc agtttgtaac atggactggg atagattaaa ggcaaaagat 1200
ttgctggctc tgttcaattc atttaaaccc aaaggaggtg taatattttc cgtcaagata 1260
tatccttcag aatttggaaa ggagaggatg aaggaagagc aagttcaagg accagtagag 1320
ctattaagta ttcctgaaga tgccccagaa aaagactgga cgtctagaga aaaattgaga 1380
gattatcaat tcaaacgact gaagtactat tatgcagtag tagactgtga ttctccggaa 1440
acagctagta aaatttatga ggattgtgat ggcctggaat ttgaaagtag ttgttctttc 1500
atagatctaa ggtttatacc agatgatatt acttttgatg atgagcctaa ggatgtagcc 1560
tcagaagtga atttaacagc atataaacca aaatatttca cttctgctgc aatgggaaca 1620
tcaacggtgg aaatcacttg ggatgagact gatcatgaaa gaattacaat gctcaacagg 1680
aagtttaaaa aggaagagct tttggacatg gattttcaag cctacttagc ttcctctagt 1740
gaagatgaag aggagataga agaggagcta caaggtgatg atggagtcaa tgtagaagaa 1800
gatgggaaaa caaagaaaag tcagaaggat gatgaagaac aaattgctaa atacaggcag 1860
ctcttgcagg ttattcaaga aaaagaaaag aaaggcaaag aaaatgatat ggaaatggaa 1920
attaaatggg ttccaggtct taaagaaagt gcagaagaga tggtcaaaaa caaattggaa 1980
ggaaaggata aactgacccc ttgggaacaa tttttagaga agaagaaaga gaaaaaaaga 2040
ctgaaaagga aacagaaggc tcttgctgaa gaggccagtg aagaggaact tccctctgat 2100
gttgatttga atgacccata ctttgctgaa gaagttaaac aaataggtat aaataaaaaa 2160
tcggtaaaat ctgcaaaaga tggcacatct ccagaagaag aaattgaaat agaaagacaa 2220
aaggctgaaa tggctttgct tatgatggat gaggacgagg acagtaagaa acacttcaat 2280
tacaacaaga ttgtggagca ccagaatctg agcaaaaaga agaaaaagca gctcatgaaa 2340
aagaaggaat taatagagga tgactttgag gtaaatgtta acgatgcacg gtttcaggca 2400
atgtacactt cccacttgtt caatttggac ccctcagatc ccaatttcaa gaaaacaaaa 2460
gctatggaaa aaatccttga ggagaaggcc cggcaaagag aacggaaaga acaagaactt 2520
actcaggcaa taaagaaaaa agagagtgag attgaaaagg aatcacaaag gaagtccatt 2580
gatcctgctt tgtcaatgtt gattaaatct ataaaaacca aaacagagca gtttcaagca 2640
agaaaaaagc aaaaagtcaa ataactggat gttacttatt tttgaactga atacatcttt 2700
tcctaaaatg tacaaaaata ataggaggga atatttattg ggaacaaagc tatctttcaa 2760
gaacatgaat aaaatctttt tctggacata gtaaaatttt tctccataaa taattgtact 2820
taattgtgga tgactgacaa atttttattg tatattccta cagatcagtc ataattaaat 2880
tacctgcatt atagggttta taaaattttt atattttaca atgttcagtt ctaactagtg 2940
gaaagttact ctagcttttt aaaaggctgt ttacaattct gtgtaaaaat agagcagtat 3000
ctactcaagt ttgtgtaaat gttagggata atttgaaaaa tatatatatt taatacatta 3060
atttctctgg aagcaggagg catgtttaaa taactattaa aataatttat ttttctagcc 3120
ataaaggatg gaagtcaaga actttttgtt gtttagtcat gttaagtata gtttatgaaa 3180
ttaacttgta aataaaagtg taaaatattt tcatta 3216

<210> SEQ ID NO 29
<211> LENGTH: 1931
<212> TYPE: DNA
<213> ORGANISM: Homo sapiens

<400> SEQUENCE: 29

```
acttccgggg tcgaggcgag gccaacgata cgcctgctgc agcaggagga gttacgagcc     60
gggccgcgcg ctgcctaaat acctaaacca ggtttagcgc ctgctcatat aaagctctcc    120
taactcgtct tccggtggga atttcttcac gtgggccgga gtcggagact gagtttagct    180
ttactgagga gctctaaatt taggcgggta tgagtgattt cagtgaagaa ttaaaagggc    240
ctgtgacaga tgatgaagaa gtggaaacat ctgtgctcag tggtgcagga atgcattttc    300
cttggcttca aacatacgta gaaactgtgg ccattggagg gaaaaggagg aaggattttg    360
ctcagacaac aagtgcttgt ttaagtttta tccaagaagc tctgctgaag caccaatggc    420
agcaagctgc agaatacatg tacagttatt ttcagacctt ggaagattca gatagctaca    480
aaaggcaggc tgcacctgag attatttgga agctcggaag tgaaattcta ttttatcatc    540
ccaaaagcaa catggagagt ttcaatactt ttgctaaccg gatgaaaaat attggcgtca    600
tgaattattt aaagatctcc ttacaacatg cattatacct tctgcatcat ggaatgctta    660
aagatgctaa gagaaatctg agtgaggcag agacatggag acatggtgaa aatacgtctt    720
cccgggaaat attaatcaac cttattcagg cctataaagg gcttttacag tattatacct    780
ggtctgaaaa gaagatggaa ttgtcaaagc ttgataagga tgattatgct tacaatgcag    840
tagcccagga tgtgttcaac cacagctgga agacatctgc aaatatttct gcattgatta    900
aaattcctgg agtttgggac ccttttgtga agagttatgt agaaatgctg gaattctatg    960
gggatcgaga tggagcccaa gaggtactca ccaattatgc atatgatgaa aagtttccat   1020
caaatccaaa tgcccatatc tacttataca actttctaaa gagacagaag gcaccaagat   1080
caaaattgat aagtgtgctt aagattttgt atcagattgt accatctcat aaattgatgt   1140
tggaattcca tacattactt agaaaatcag aaaaagaaga acaccgtaaa ctggggttgg   1200
aggtattatt tggagtctta gattttgccg gatgcactaa gaatataact gcttggaaat   1260
acttggcaaa atatctgaaa aatatcttaa tgggaaacca ccttgcgtgg gttcaagaag   1320
agtggaactc caggaaaaac tggtggccag gctttcattt cagctacttt tgggcaaaaa   1380
gtgattggaa ggaagataca gctttggcct gtgagaaagc ttttgtggct ggtttactgt   1440
taggaaaagg ttgtagatat ttccggtata ttttaaagca agatcaccaa atcttaggga   1500
agaaaattaa gcggatgaag agatctgtga aaaaatacag tattgtaaat ccaagactct   1560
gatactgaat tttagttatt tcacagttgt agctacacag taagtagctt ggtagatagt   1620
tattgaatgt atttatgtag tgtattaaga agcttatatt actacaaaaa acttattttt   1680
atatattttt atatttttgt attatttata gctagagaaa caatattact gcctttgctc   1740
tttgtaacta tgtctgtttt ctttttgta atgttaaatg ttacatttgt taaggaataa   1800
ttcttcaaat gacaaactaa ttacagaata tagctctaca gcagttattg tttgcaaata   1860
ctttgcctct tgctattgtg taataaactg taacttgtag tgctgtgaaa tgtaaaaaaa   1920
aaaaaaaaaa a                                                        1931
```

<210> SEQ ID NO 30
<211> LENGTH: 409
<212> TYPE: DNA
<213> ORGANISM: Homo sapiens
<220> FEATURE:
<221> NAME/KEY: misc_feature
<222> LOCATION: (190)..(190)
<223> OTHER INFORMATION: n is a, c, g, or t
<220> FEATURE:
<221> NAME/KEY: misc_feature
<222> LOCATION: (200)..(201)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (329)..(329)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (347)..(347)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t

<400> SEQUENCE: 30
aacattcttg agaaagttaa aacaatagca aattgtataa ttgtatccag aaatgtatac 60
tcatcgtatt ttaaagctaa atttattttt taaactagat cccttcatta ttctttatgc 120
cccagagtaa atcccagatg gatcaaagat ctaaacataa tctttcatat gtaaaaatat 180
aaaagtattn gtagaaaacn natatgaatg ctttgatgat cttggaatgg caangtcaat 240
ttttgcagca tatggtggac aaaggagata atttctttaa tgtatcaata gctcttgcaa 300
agcaaacagg anaaaagcaa actgagtang ggatatgana attagtnttc tgagccaccg 360
tgcccagcct aatttttgta actntgtata ntggagactt acacagtgg 409

<210> SEQ ID NO 31
<211> LENGTH: 229
<212> TYPE: DNA
<213> ORGANISM: Homo sapiens

<400> SEQUENCE: 31
tttttttttt tttttttaca aaagaaacta ctactgtatt ttgttgccct gtcccttcaa 60
cttggctcca aattgcttgg ctcatcatca cagtggcctc cagaaggtgg cgagctctgc 120
ttctcaagtt tcaactgtgg aaggcacatc tggtcccaga ggaaggatga ggggctctct 180
ggggcttgag ggcagcccac cttgtgtcct cagaagcccc ctcgtgccg 229

<210> SEQ ID NO 32
<211> LENGTH: 1323
<212> TYPE: DNA
<213> ORGANISM: Homo sapiens

<400> SEQUENCE: 32
gatttcggcc tgactattac ttgggccacg gaaatagcca accctttttct tccgcacggt 60 tggaggaggt cggctggtta tcgggagttg gagggctgag gtcgggaggg tggtgtgtac 120
agagctctag gacaccaggc cagtcgcggg ttttgggccg aggcctgggt tacaagcagc 180
aagtgcgcgg ttggggccac tgcgaggccg ttttagaaaa ctgtttaaaa caaagagcaa 240
ttgatggata aatcaggaat agattctctt gaccatgtga catctgatgc tgtggaactt 300

```
gcaaatcgaa gtgataactc ttctgatagc agcttattta aaactcagtg tatcccttac    360
tcacctaaag gggagaaaag aaaccccatt cgaaaatttg ttcgtacacc tgaaagtgtt    420
cacgcaagtg attcatcaag tgactcatct tttgaaccaa taccattgac tataaaagct    480
atttttgaaa gattcaagaa caggaaaaag agatataaaa aaaagaaaaa gaggaggtac    540
cagccaacag gaagaccacg gggaagacca gaaggaagga gaaatcctat atactcacta    600
atagataaga agaaacaatt tagaagcaga ggatctggct tcccattttt agaatcagag    660
aatgaaaaaa acgcaccttg gagaaaaatt ttaacgtttg agcaagctgt tgcaagagga    720
ttttttaact atattgaaaa actgaagtat gaacaccacc tgaaagaatc attgaagcaa    780
atgaatgttg gtgaagattt agaaaatgaa gattttgaca gtcgtagata caaatttttg    840
gatgatgatg gatccatttc tcctattgag gagtcaacag cagaggatga ggatgcaaca    900
catcttgaag ataacgaatg tgatatcaaa ttggcagggg atagtttcat agtaagttct    960
gaattccctg taagactgag tgtatactta gaagaagagg atattactga agaagctgct   1020
ttgtctaaaa agagagctac aaaagccaaa aatactggac agagaggcct gaaaatgtga   1080
caggatcatg aatgtcaaag gtgaagcata tagaaaaaac gacttcatag aaatgaataa   1140
agataaatgt ggatatatgt accagtctgg tggtgaagaa attctgaaac ccagaacttt   1200
ataacaagaa aaaaaatttt taaccctgtg aagaagtttg tgaaagaaac ttgtgaagta   1260
gtaataatta gaaaaaaaac cattaaaaca ccagagaaaa tacatagaaa aaaaaaaaaa   1320
aaa                                                                 1323
```

<210> SEQ ID NO 33
<211> LENGTH: 2489
<212> TYPE: DNA
<213> ORGANISM: Homo sapiens

<400> SEQUENCE: 33

```
ctccgccgcg ggagggagct gcggctgtgc cggccgagcg ggggagggcg ccgccactca     60
gagccaggga gggagccgct ggagcggaag cccggaggcc gcgctgcgcc ggggtgaggt    120
ggctttgacc ccgggttgcc cggccagcac gaccgaggag gtggctggac agctggagga    180
tgaacggaga agccgactgc cccacagacc tggaaatggc cgcccccaaa ggccaagacc    240
gttggtccca ggaagacatg ctgactttgc tggaatgcat gaagaacaac cttccatcca    300
atgacagctc caagttcaaa accaccgaat cacacatgga ctgggaaaaa gtagcattta    360
aagacttttc tggagacatg tgcaagctca aatgggtgga gatttctaat gaggtgagga    420
agttccgtac attgacagaa ttgatcctcg atgctcagga acatgttaaa aatccttaca    480
aaggcaaaaa actcaagaaa cacccagact tcccaaagaa gcccctgacc ccttatttcc    540
gcttcttcat ggagaagcgg gccaagtatg cgaaactcca ccctgagatg agcaacctgg    600
acctaaccaa gattctgtcc aagaaataca aggagcttcc ggagaagaag aagatgaaat    660
atattcagga cttccagaga gagaaacagg agttcgagcg aaacctggcc cgattcaggg    720
aggatcaccc cgacctaatc cagaatgcca agaaatcgga catcccagag aagcccaaaa    780
ccccccagca gctgtggtac acccacgaga agaaggtgta tctcaaagtg cggccagatg    840
agatcatgag agactatatc cagaagcacc cagagctgaa catcagtgag gagggtatca    900
ccaagtccac cctcaccaag gccgaacgcc agctcaagga caagtttgac gggcgaccca    960
ccaagccacc tccgaacagc tactcgctgt actgcgcaga gctcatggcc aacatgaagg   1020
acgtgcccag cacagagcgc atggtgctgt gcagccagca gtggaagctg ctgtcccaga   1080
```

```
aggagaagga cgcctatcac aagaagtgtg atcagaaaaa gaaagattac gaggtggagc   1140
tgctccgttt cctcgagagc ctgcctgagg aggagcagca gcgggtcttg ggggaagaga   1200
agatgctgaa catcaacaag aagcaggcca ccagccccgc ctccaagaag ccagcccagg   1260
aagggggcaa gggcggctcc gagaagccca agcggcccgt gtcggccatg ttcatcttct   1320
cggaggagaa acggcggcag ctgcaggagg agcggcctga gctctccgag agcgagctga   1380
cccgcctgct ggcccgaatg tggaacgacc tgtctgagaa gaagaaggcc aagtacaagg   1440
cccgagaggc ggcgctcaag gctcagtcgg agaggaagcc cggcggggag cgcgaggaac   1500
ggggcaagct gcccgagtcc cccaaaagag ctgaggagat ctggcaacag agcgttatcg   1560
gcgactacct ggcccgcttc aagaatgacc gggtgaaggc cttgaaagcc atggaaatga   1620
cctggaataa catggaaaag aaggagaaac tgatgtggat taagaaggca gccgaagacc   1680
aaaagcgata tgagagagag ctgagtgaga tgcgggcacc tccagctgct acaaattctt   1740
ccaagaagat gaaattccag ggagaaccca agaagcctcc catgaacggt taccagaagt   1800
tctcccagga gctgctgtcc aatggggagc tgaaccacct gccgctgaag gagcgcatgg   1860
tggagatcgg cagtcgctgg cagcgcatct cccagagcca gaaggagcac tacaaaaagc   1920
tggccgagga gcagcaaaag cagtacaagg tgcacctgga cctctgggtt aagagcctgt   1980
ctccccagga ccgtgcagca tataaagagt acatctccaa taaacgtaag agcatgacca   2040
agctgcgagg cccaaacccc aaatccagcc ggactactct gcagtccaag tcggagtccg   2100
aggaggatga tgaagaggat gaggatgacg aggacgagga tgaagaagag gaagatgatg   2160
agaatgggga ctcctctgaa gatggcggcg actcctctga gtccagcagc gaggacgaga   2220
gcgaggatgg ggatgagaat gaagaggatg acgaggacga agacgacgac gaggatgacg   2280
atgaggatga agataatgag tccgagggca gcagctccag ctcctcctcc tcaggggact   2340
cctcagactc tgactccaac tgaggctcag ccccacccca gggcagccag ggagagccca   2400
ggagctcccc tccccaactg accacctttg tttctccccc atgttctgtc ccttgccccc   2460
ctggcctccc ccactttctt tctttcttt                                      2489
```

<210> SEQ ID NO 34
<211> LENGTH: 3154
<212> TYPE: DNA
<213> ORGANISM: Homo sapiens

<400> SEQUENCE: 34

```
acttccgctt cctcaacagc agcacttccg ggttgggaga aaggtggcgg cgctttcgga     60
gggaataaaa tggaaggaga atcaagcaga tttgaaatcc acactccagt ttctgacaag    120
aaaaagaaaa agtgttctat acataaggaa agacctcaga aacattccca cgaaattttc    180
agagactcct ccctggtgaa tgaacagtct caaataacta ggaggaaaaa gaggaaaaaa    240
gatttccagc atctcatttc ttctcctttg aaaaaatcca gaatctgtga tgagactgca    300
aatgccactt ccacactcaa aaagagaaaa aagagaagat atagtgcttt ggaggtggac    360
gaggaagcag gtgttacagt tgtccttgtg gataaagaaa atattaacaa cacaccaaag    420
cattttagaa aggatgttga tgttgtttgt gttgatatga gcatagaaca gaagttacca    480
agaaagccta aaacagacaa atttcaggta cttgctaagt cacatgcaca taaatcagaa    540
gccctgcaca gtaaagttag ggagaaaaag aataaaaagc atcagaggaa agctgcatcc    600
tgggagagcc agcgggcaag ggacaccctg cctcagtcag aatcccacca ggaggagtcc    660
```

-continued

```
tggctttctg tgggtccagg gggtgaaatt acagaactac cagcatctgc tcataaaaac    720
aagtctaaga aaaaaaagaa aaagtccagt aaccgggaat atgagacact ggccatgcct    780
gaaggatcgc aagcaggcag agaggccggg actgatatgc aggaatccca gcctactgtg    840
ggcttggatg atgaaactcc acaactacta ggacctactc acaaaaaaaa gtctaagaaa    900
aaaaagaaga aaaagtccaa tcaccaggaa tttgaggcat tggccatgcc tgaaggatca    960
caagtgggca gtgaggttgg ggctgatatg caggaatccc ggcctgctgt gggcctgcat   1020
ggtgaaactg caggaatacc agcacctgct tataaaaaca agtctaagaa aaaaaagaaa   1080
aagtccaatc accaggaatt tgaggcagtg gccatgcctg agagcctcga gagtgcatac   1140
cctgaaggat cacaggtggg cagtgaggtt gggactgtgg aaggcagtac agctcttaaa   1200
gggttcaagg aatccaacag tacaaagaag aagtctaaga aaaggaagct tacgtctgtc   1260
aaaagggcac gagtgtctgg tgatgatttt tcagtgccca gtaagaactc tgagagcaca   1320
ctctttgatt cagtagaagg tgatggcgcc atgatggaag aaggtgtgaa atctaggccc   1380
cgacaaaaga aaacccaggc ctgtttggca agcaagcacg tgcaagaggc gccaaggtta   1440
gaacctgcaa atgaagaaca caatgtggaa acagctgaag attccgaaat aagatactta   1500
tctgcagatt caggagatgc cgatgattca gatgcggatt tgggttctgc cgtgaaacag   1560
cttcaggagt tcattcctaa catcaaggac agggccacca gcacaatcaa gcggatgtac   1620
cgggacgact tggaacggtt taaggaattt aaagcacaag gtgtcgctat taaatttggc   1680
aagtttttctg taaaggaaaa taagcagtta gagaaaaatg tggaagactt tctagccctg   1740
acaggcattg agagtgcaga caagctgctg tacacggaca gatatcctga ggaaaaatct   1800
gtgatcacca acttaaaaag gagatactcg tttagattac acattggtag gaacattgcc   1860
cggccctgga aacttatata ctatcgagca aagaagatgt tcgatgtcaa caattacaaa   1920
ggcaggtata gcgaaggaga tactgagaag ttaaagatgt accattctct ccttgggaat   1980
gactggaaga cgattggtga gatggtggcc cgaagtagcc tctccgtggc cctcaagttc   2040
tcacagatca gcagtcaaag aaatcgtggt gcttggagta agtctgaaac ccggaaacta   2100
atcaaggctg tcgaagaagt gattctgaag aagatgtctc cccaggagtt aaaagaggtg   2160
gattccaaac tccaagaaaa tcctgaaagt tgcctatcaa ttgttcggga aaaactctac   2220
aagggcatat cttgggtaga agtagaagct aaagtgcaaa ccagaaattg gatgcagtgt   2280
aaaagtaagt ggacagaaat tctaaccaag aggatgacta atggtcggcg tatctactat   2340
ggcatgaatg ccctgcgggc caaggtcagc cttattgaaa ggttgtatga aataaatgtg   2400
gaagatacta atgaaataga ctgggaagat cttgctagtg ccataggtga tgttcctcca   2460
tcttacgttc aaactaaatt ttctaggctg aaagctgtct atgttccatt ttggcagaaa   2520
aagacttttc cagagatcat cgactacctt tatgagacga ctctaccttt gctgaaggaa   2580
aagttagaaa aaatgatgga gaaaaaaggc actaaaatcc agactcctgc agcacccaag   2640
caagttttcc catttcgaga catcttttat tatgaagacg atagtgaagg agaggacata   2700
gaaaaagaaa gcgaaggcca ggcgccatgc atggctcacg cctgtaattc cagtactttg   2760
ggaggccaag gccggtggat catctgaggt caggagttcg agaccggcct gaccaacatg   2820
gtgaagacct gtcactatta aaaatgcaaa aattagccgg gtgtggtagt gcacacctgt   2880
aatttcaact acttgggagg ctgaggcagg agaattgctt gaacccagga ggtggaggtt   2940
gcagtgagcc aagatcgcac caccgcatga gagagagaga ttactatttc ttgtcccttt   3000
ttctcagttt gattatattt atatacatat gtcagtaaat ctgttttcag tattgatgtt   3060
```

taataaagaa tgtacaatgg ccagagttct actctttcct ctggagcatt aaaatatatt 3120
gccattccta ttaaaacgta tttgaatgtg aaaa 3154

<210> SEQ ID NO 35
<211> LENGTH: 2362
<212> TYPE: DNA
<213> ORGANISM: Homo sapiens

<400> SEQUENCE: 35
acctgattcc gttcctcagc tcgcattcct ccgcccgtcc cgctcccgcc gccagcggag 60
gccctagtct cccgctccaa ctattccaac catcccggga agggtggggc gctcggctct 120
tgggtccccc tccgccgccc cgcctcgtcg atctcccctt ctaccccggt ccctcccttt 180
ctggggtggg gccagccaat cagcgatcag actccggagt ttggcccggg agctggggag 240
ctcaccgatc ccccgcccag cagttctggc cgctgtcccg gtgcgcacgg acgtggctcg 300
agtttcctct gctctccgct ctcgcccgct agctctcctc ccttccgctc ctgcttctct 360
ccgggtctcc cgctccagct ccagccccac ccggccggtc ccgcacggct ccgggtagcc 420
atggaggacc ccacgctcta tattgtcgag cggccgcttc ccgggtaccc cgacgccgag 480
gccccggagc cttcctccgc tggggctcag gcagcggagg agccgtcggg ggccggctca 540
gaagagctga tcaagtcgga ccaggtgaac ggcgtgctgg tgctgagcct cctggacaaa 600
atcatcgggg ccgtagacca gatccagctg actcaagcac agctggagga gcggcaggcg 660
gagatggagg gcgcagtgca gagcatccag ggcgagctga gcaagctggg caaggcgcac 720
gccaccacga gcaatacggt gagcaagctg ctggagaagg tgcgcaaggt cagcgtcaac 780
gtgaagaccg tgcgcggcag cctggagcgc caggcggggc agatcaagaa gctggaggtc 840
aacgaggccg agctgctgcg gcgccgcaac tttaaagtca tgatctacca ggatgaagtg 900
aagctgccgg ccaaactgag catcagcaaa tcgctgaaag agtcggaggc gctgccagag 960
aaggagggcg aggagctggg cgagggcgag cggcccgagg aggacgcagc ggcgctggag 1020
ctttcgtcgg acgaagcggt ggaggttgag gaggttattg aggagtcccg cgcaaagcgt 1080
atcaagcgca gcggcctgcg gcgcgtggac gacttcaaga aggccttctc caaggagaag 1140
atggagaaga ccaaggtgcg tacccgcgag aacctggaga agacgcgcct caagaccaag 1200
gaaaacctgg agaagacgcg gcacaccctg gagaagcgca tgaacaagct gggcacgcgc 1260
ctggtgcccg ccgagcggcg cgagaaactg aagacgtcgc gggacaagtt gcgcaaatcc 1320
ttcacgcccg accacgtggt gtacgcgcgc tccaagaccg cggtctacaa ggtgccaccc 1380
ttcaccttcc acgtcaagaa gatccgcgag ggccaggtgg aagtgctcaa ggccaccgag 1440
atggtggagg tgggcgccga cgacgacgag ggcggcgcgg agcgcgggga ggccggcgac 1500
ctgcggcgcg ggagcagccc cgacgtgcac gcgctgctgg agatcaccga ggagtcggac 1560
gccgtgctgg tggacaagag cgacagcgac tgagccgccc ccgctgccac ccaccccatt 1620
cctcgctcct tccgaacttc ctctttcgca ttctctctcg gctcgagctg gctgagattt 1680
ttctaaattg aaaacacgcc cccctcccca cacctccagg aactccactc ccagtcttag 1740
agctgttagg acccgatggg gaggcagccc ccgcagtgga cagcccccgc ttggacacag 1800
tccgagtgga atgggaaggg aatggtcaat ccctgtcctg gttgtccaag tcgggatctc 1860
agaggaaatt gcagtgattc cacggttagg ccccccctggg ggggctgcct tcccctcagc 1920
ctctccccac accacccacc cagctgctgt cattccgctc actgagctct tcttcattct 1980

-continued

```
caccctgatc cctgggggac tcaaagccaa aactgcccaa agaggaaaga ttgaatccta   2040

aaggggatcc ttgcccccat gggaggcccc ctactagaag gacgtgaaag cagcttttgg   2100

gggaaactga ggcagtgggg aagacagagc agaatgagcc ctcaccctgg ctgggggtcc   2160

agcacaggct gtatctgcag agggtcccag aggaacgctg gagccaagag aagccctggg   2220

aaggaggggt ggggaacgac atgcatgtga gggatggcac actgatgtgt ttatgcacct   2280

gtacacagga gcgcatggcc atggctttgg aaaggagaat ggaaaaatag aagaaggtcg   2340

gccgggcttg gtggcttatg cc                                            2362
```

<210> SEQ ID NO 36
<211> LENGTH: 2328
<212> TYPE: DNA
<213> ORGANISM: Homo sapiens

<400> SEQUENCE: 36

```
gtggccgtgg ctaccgatgg gatagtcgcc gcggtcgcca tcttcccagc aacaacgtca     60

cttcccttcc ggaccacaag gggcgctgac tccgaactta ggacaggaag aaacaggcac    120

atttccggtc tctatgcttt ctcatccggc cggcttgctt tcccctgcgg tcgtccagac    180

tattgggcgc tagcgagacg aactattggt acggggctag agaggaaggc tttgggattg    240

ccggggagca gcgagcgacc gacttccgtt tccagttacc aaggcacgag gatccggtgt    300

tccaacccag gggaaaaaat gcggcctttg actgaagagg agacccgtgt catgtttgag    360

aagatagcga aatacattgg ggagaatctt caactgctgg tggaccggcc cgatggcacc    420

tactgtttcc gtctgcacaa cgaccgggtg tactatgtga gtgagaagat tatgaagctg    480

gccgccaata tttccgggga caagctggtg tcgctgggga cctgctttgg aaaattcact    540

aaaacccaca agtttcggtt gcacgtcaca gctctggatt accttgcacc ttatgccaag    600

tataaagttt ggataaagcc tggtgcagag cagtccttcc tgtatgggaa ccatgtgttg    660

aaatctggtc tgggtcgaat cactgaaaat acttctcagt accagggcgt ggtggtgtac    720

tccatggcag acatcccttt gggttttggg gtggcagcca aatctacaca agactgcaga    780

aaagtagacc ccatggcgat tgtggtattt catcaagcag acattgggga atatgtgcgg    840

catgaagaga cgttgactta aaacgaagcc attccaagga cagacggctg tatggaaagg    900

ccgagctttg tttcctgtgt ttgtgtggac tccaccatca tgttgaattt tgtcaacact    960

ctggcctctt cagggacttc ttatttactg tactctctat cactgacaaa tgcaggctgg   1020

attcttatta tatacagaga tggctcaaaa atggggtttc agatctttgt gacgaaatag   1080

aatactgttt catatttgaa tcagagggct tcttgttctg agaaataggt tcaaaatcat   1140

tggaaccagg aacaagaata gcttattgtt atctgtgata acactgtttt ctaaacacaa   1200

ggattttctt ttttattaat atgcaacata gacattgcca taacagaata ataaaccaca   1260

tgtggggttt taaaaatgaa atttggctaa taggagcaat tcagctattt ttctatacag   1320

taattggtgt gtggtataga agaaaaacgg gttcaaaccc cacttctgcc acctaccagc   1380

tatatggcct tgaatgagtc attcagcttt aataaggttc attttcttct gtttaaaaag   1440

acacaaaact tgaaaatcag ctttggccat ctacctgaga attagaaagt ctgatttttg   1500

gaattagaaa tcatgattgt aggctgggca cagtggctcg cgcctgtaat cccagcactt   1560

tgggaggcca aggcggacgg atcacttgag gttaggagtt tgagaccagc ctggccaaca   1620

tggtgaaacc ccatctctac taaaaaaaaa aaaaaaatta ggtgtggtga cacatggctg   1680

tggtcctagt tacttgggag gctgaggcag gagaatggct tgaactgggg aagcagagct   1740
```

```
tgcagtgagc caagatggtg ccattgcact ccagcctggg cgtgacagag tgagactcca   1800

tctgattgta aagcatctag tacagtgtac agtgccttgg aaatgatagg tatggaataa   1860

atggtaatta tttttatatt atatatatta tgtattcctg ttattaagtg tagagtttta   1920

tgagtataat ttgattttat taccttcttt tttacaagct gttttctcag tatttttctt   1980

ggatgggatg acgctaggct ggaaagtttt tttcatcact atgattttat aaaacaattt   2040

tttctatgaa cctttactta cttgactgga ttggactaaa agcactgatc agaggccacg   2100

acataaaaat tcagtccctt tgtccttccc cgtgcctccc aaagttactt taagatcctt   2160

agaatatttc tttaaatatt ttatagacaa aaaatttaaa gactatctgt attgcaaaat   2220

taaactattt ctttaatgaa tatattgctt attttaagtt ccaaaggtga agtctttaag   2280

aataaaacat taccaactcc tgcttttata tgtaagcaaa aaaaaaaa                2328


<210> SEQ ID NO 37
<211> LENGTH: 13357
<212> TYPE: DNA
<213> ORGANISM: Homo sapiens

<400> SEQUENCE: 37

gctgacacgc tgtcctctgg cgacctgtcg ctggagaggt tgggcctccg gatgcgcgcg     60

gggctctggc ctaccggtga cccggctagc cggccgcgct cctgcttgag ccgcctgccg    120

gggcccgcgg gcctgctgtt ctctcgcgcg tccgagcgtc ccgactcccg gtgccggccc    180

gggtccgggt ctctgaccca cccgggggcg gcggggaagg cggcgagggc caccgtgccc    240

ccgtgcgctc tccgctgcgg gcgcccgggg cggccgcgac aaccccaccc cgctggctcc    300

gtgccgtgcg tgtcaggcgt tctcgtctcc gcggggttgt ccgccgcccc ttccccggag    360

tggggggttg gccggagccg atcggctcgc tggccggccg gccggcctcc gctcccgggg    420

ggctcttcgt gatcgatgtg gtgacgtcgt gctctcccgg gccgggtccg agccgcgacg    480

ggcgaggggc ggacgttcgt ggcgaacggg accgtccttc tcgctccgcc ccgcgggggt    540

cccctcgtct ctcctctccc cgcccgccgg cggtgcgtgt gggaaggcgt ggggtgcgga    600

ccccggcccg acctcgccgt cccgcccgcc gccttctgcg tcgcggggcg ggccggcggg    660

gtcctctgac gcggcagaca gccctcgctg tcgcctccag tggttgtcga cttgcgggcg    720

gccccccctcc gcggcggtgg gggtgccgtc ccgccggccc gtcgtgctgc cctctcgggg    780

ggtttgcgcg agcgtcggct ccgcctgggc ccttgcggtg ctcctggagc gctccgggtt    840

gtccctcagg tgcccgaggc cgaacggtgg tgtgtcgttc ccgcccccgg cgccccctcc    900

tccggtcgcc gccgcggtgt ccgcgcgtgg gtcctgaggg agctcgtcgg tgtggggttc    960

gaggcggttt gagtgagacg agacgagacg cgcccctccc acgcggggaa gggcgcccgc   1020

ctgctctcgg tgagcgcacg tcccgtgctc ccctctggcg ggtgcgcgcg ggccgtgtga   1080

gcgatcgcgg tgggttcggg ccggtgtgac gcgtgcgccg gccggccgcc gaggggctgc   1140

cgttctgcct ccgaccggtc gtgtgtgggt tgacttcgga ggcgctctgc ctcggaagga   1200

aggaggtggg tggacggggg ggcctggtgg ggttgcgcgc acgcgcgcac cggccgggcc   1260

cccgccctga acgcgaacgc tcgaggtggc cgcgcgcagg tgtttcctcg taccgcaggg   1320

ccccctccct tccccaggcg tccctcggcg cctctgcggg cccgaggagg agcggctggc   1380

gggtgggggg agtgtgaccc accctcggtg agaaaagcct tctctagcga tctgagaggc   1440

gtgccttggg ggtaccggat cccccgggcc gccgcctctg tctctgcctc cgttatggta   1500
```

-continued

```
gcgctgccgt agcgacccgc tcgcagagga ccctcctccg cttccccctc gacggggttg   1560
gggggagaa gcgagggttc cgccggccac cgcggtggtg gccgagtgcg gctcgtcgcc   1620
tactgtggcc cgcgcctccc ccttccgagt cgggggagga tcccgccggg ccgggcccgg   1680
cgttcccagc gggttgggac gcggcggccg gcgggcggtg ggtgtgcgcg cccggcgctc   1740
tgtccggcgc gtgacccct ccgccgcgag tcggctctcc gcccgctccc gtgccgagtc   1800
gtgaccggtg ccgacgaccg cgtttgcgtg gcacggggtc gggcccgcct ggccctggga   1860
aagcgtccca cggtgggggc gcgccggtct cccggagcgg gaccgggtcg gaggatggac   1920
gagaatcacg agcgacggtg gtgcgggcgt gtcgggttcg tggctgcggt cgctccgggg   1980
cccccggtgg cggggccccg gggctcgcga ggcggttctc ggtgggggcc gagggccgtc   2040
cggcgtccca ggcggggcgc cgcgggaccg ccctcgtgtc tgtggcggtg ggatcccgcg   2100
gccgtgtttt cctggtggcc cggccgtgcc tgaggtttct ccccgagccg ccgcctctgc   2160
gggctcccgg gtgcccttgc cctcgcggtc cccggccctc gcccgtctgt gccctcttcc   2220
ccgcccgccg cccgccgatc ctcttcttcc ccccgagcgg ctcaccggct tcacgtccgt   2280
tggtggcccc gcctgggacc gaacccggca ccgcctcgtg gggcgccgcc gccggccact   2340
gatcggcccg gcgtccgcgt cccccggcgc gcgccttggg gaccgggtcg gtggcgcccc   2400
gcgtggggcc cggtgggctt cccggagggt tccgggggtc ggcctgcggc gcgtgcgggg   2460
gaggagacgg ttccgggggga ccggccgcga ctgcggcggc ggtggtgggg gcagccgcgg   2520
ggatcgccga gggccggtcg gccgccccgg gtgccgcgcg gtgccgccgg cggcggtgag   2580
gccccgcgcg tgtgtcccgg ccgcggtcgg ccgcgctcga ggggtccccg tggcgtcccc   2640
ttccccgccg gccgcctttc tcgcgccttc cccgtcgccc cggcctcgcc cgtggtctct   2700
cgtcttctcc cggcccgctc ttccgaaccg ggtcggcgcg tcccccgggt gcgcctcgct   2760
tcccgggcct gccgcggccc ttccccgagg cgtccgtccc gggcgtcggc gtcggggaga   2820
gcccgtcctc cccgcgtggc gtcgccccgt tcggcgcgcg cgtgcgcccg agcgcggccc   2880
ggtggtccct gccggacagg cgttcgtgcg acgtgtggcg tgggtcgacc tccgccttgc   2940
cggtcgctcg ccctttcccc gggtcggggg gtggggcccg ggccggggcc tcggccccgg   3000
tcgcggtccc ccgtcccggg cgggggcggg cgcgccggcc ggcctcggtc ggccctccct   3060
tggccgtcgt gtggcgtgtg ccacccctgc gcccgcgccc gccggcgggg ctcggagccg   3120
ggcttcggcc gggccccggg ccctcgaccg gaccggtgcg cgggcgctgc ggccgcacgg   3180
cgcgactgtc cccgggccgg gcaccgcggt ccgcctctcg ctcgccgccc ggacgtcggg   3240
gccgccccgc ggggcgggcg gagcgccgtc cccgcctcgc cgccgcccgc gggcgccggc   3300
cgcgcgcgcg cgcgcgtggc cgccggtccc tcccggccgc cgggcgcggg tcgggccgtc   3360
cgcctcctcg cgggcgggcg cgacgaagaa gcgtcgcggg tctgtggcgc ggggccccgg   3420
tggtcgtgtc gcgtgggggg cgggtggttg gggcgtccgg ttcgccgcgc cccgccccgg   3480
ccccaccggt cccggccgcc gcccccgcgc ccgctcgctc cctcccgtcc gcccgtccgc   3540
ggcccgtccg tccgtccgtc gtcctcctcg cttgcggggc gccgggcccg tcctcgcgag   3600
gccccccggc cggccgtccg gccgcgtcgg ggcctcgccg cgctctacct tacctacctg   3660
gttgatcctg ccagtagcat atgcttgtct caaagattaa gccatgcatg tctgagtacg   3720
cacggccggt acagtgaaac tgcgaatggc tcattaaatc agttatggtt cctttggtcg   3780
ctcgctcctc tcctacttgg ataactgtgg taattctaga gctaatacat gccgacgggc   3840
gctgaccccc ttcgcggggg ggatgcgtgc atttatcaga tcaaaaccaa cccggtcagc   3900
```

-continued

```
ccctctccgg ccccggccgg ggggcgggcg ccggcggctt tggtgactct agataacctc   3960
gggccgatcg cacgcccccc gtggcggcga cgacccattc gaacgtctgc cctatcaact   4020
ttcgatggta gtcgccgtgc ctaccatggt gaccacgggt gacggggaat cagggttcga   4080
ttccggagag ggagcctgag aaacggctac cacatccaag gaaggcagca ggcgcgcaaa   4140
ttacccactc ccgacccggg gaggtagtga cgaaaaataa caatacagga ctctttcgag   4200
gccctgtaat tggaatgagt ccactttaaa tcctttaacg aggatccatt ggagggcaag   4260
tctggtgcca gcagccgcgg taattccagc tccaatagcg tatattaaag ttgctgcagt   4320
taaaaagctc gtagttggat cttgggagcg ggcgggcggt ccgccgcgag gcgagccacc   4380
gcccgtcccc gccccttgcc tctcggcgcc ccctcgatgc tcttagctga gtgtcccgcg   4440
gggcccgaag cgtttacttt gaaaaaatta gagtgttcaa agcaggcccg agccgcctgg   4500
ataccgcagc taggaataat ggaataggac cgcggttcta ttttgttggt tttcggaact   4560
gaggccatga ttaagaggga cggccggggg cattcgtatt gcgccgctag aggtgaaatt   4620
cttggaccgg cgcaagacgg accagagcga aagcatttgc caagaatgtt ttcattaatc   4680
aagaacgaaa gtcggaggtt cgaagacgat cagataccgt cgtagttccg accataaacg   4740
atgccgaccg gcgatgcggc ggcgttattc ccatgacccg ccgggcagct tccgggaaac   4800
caaagtcttt gggttccggg gggagtatgg ttgcaaagct gaaacttaaa ggaattgacg   4860
gaagggcacc accaggagtg gagcctgcgg cttaatttga ctcaacacgg gaaacctcac   4920
ccggcccgga cacggacagg attgacagat tgatagctct ttctcgattc cgtgggtggt   4980
ggtgcatggc cgttcttagt tggtggagcg atttgtctgg ttaattccga taacgaacga   5040
gactctggca tgctaactag ttacgcgacc cccgagcggt cggcgtcccc caacttctta   5100
gagggacaag tggcgttcag ccacccgaga ttgagcaata acaggtctgt gatgccctta   5160
gatgtccggg gctgcacgcg cgctacactg actggctcag cgtgtgccta ccctacgccg   5220
gcaggcgcgg gtaacccgtt gaaccccatt cgtgatgggg atcggggatt gcaattattc   5280
cccatgaacg aggaattccc agtaagtgcg ggtcataagc ttgcgttgat taagtccctg   5340
ccctttgtac acaccgcccg tcgctactac cgattggatg gtttagtgag gccctcggat   5400
cggccccgcc ggggtcggcc cacggccctg gcggagcgct gagaagacgg tcgaacttga   5460
ctatctagag gaagtaaaag tcgtaacaag gtttccgtag gtgaacctgc ggaaggatca   5520
ttaacggagc ccggagggcg aggcccgcgg cggcgccgcc gccgccgcgc gcttccctcc   5580
gcacacccac ccccccaccg cgacgcggcg cgtgcgcggg cggggcccgc gtgcccgttc   5640
gttcgctcgc tcgttcgttc gccgcccggc cccgccggcc gcgagagccg gagaactcgg   5700
gagggagacg gggggagagag agagagagag agaaagagaa agaagggcgt gtcgttggtg   5760
tgcgcgtgtc gtggggccgg cgggcggcgg ggagcggtcc ccggccgcgg ccccgacgac   5820
gtgggtgtcg gcgggcgcgg gggcggttct cggcggcgtc gcggcgggtc tggggggggtc   5880
tcggtgccct cctccccgcc ggggcccgtc gtccggcccc gccgcgccgg ctccccgtct   5940
tcggggccgg ccggattccc gtcgcctccg ccgcgccgct ccgcgccgcc gggcacggcc   6000
ccgctcgctc tccccggcct tcccgctagg gcgtctcgag ggtcgggggc cggacgccgg   6060
tcccctcccc cgcctcctcg tccgccccccc cgccgtccag gtacctagcg cgttccggcg   6120
cggaggttta aagacccctt ggggggatcg cccgtccgcc cgtgggtcgg gggcggtggt   6180
gggcccgcgg gggagtcccg tcgggagggg cccggcccct cccgcgcctc caccgcggac   6240
```

-continued

```
tccgctcccc ggccggggcc gcgccgccgc cgccgccgcg gcggccgtcg ggtgggggct   6300
ttacccggcg gccgtcgcgc gcctgccgcg cgtgtggcgt gcgccccgcg ccgtgggggc   6360
gggaaccccc gggcgcctgt ggggtggtgt ccgcgctcgc cccgcgtgg gcggcgcgcg   6420
cctccccgtg gtgtgaaacc ttccgacccc tctccggagt ccggtcccgt ttgctgtctc   6480
gtctggccgg cctgaggcaa ccccctctcc tcttgggcgg gggggggggg gacgtgccgc   6540
gccaggaagg gcctcctccc ggtgcgtcgt cgggagcgcc ctcgccaaat cgacctcgta   6600
cgactcttag cggtggatca ctcggctcgt gcgtcgatga agaacgcagc tagctgcgag   6660
aattaatgtg aattgcagga cacattgatc atcgacactt cgaacgcact tgcggccccg   6720
ggttcctccc ggggctacgc ctgtctgagc gtcgcttgcc gatcaatcgc cccgggggt   6780
gcctccgggc tcctcggggt gcgcggctgg gggttccctc gcagggcccg ccgggggccc   6840
tccgtccccc taagcgcaga cccggcggcg tccgccctcc tcttgccgcc gcgcccgccc   6900
cttcccctc cccccgcggg ccctgcgtgg tcacgcgtcg ggtggcgggg gggagagggg   6960
ggcgcgcccg gctgagagag acggggaggg cggcgccgcc gccgcccgcg aagacggaga   7020
gggaaagaga gagccggctc gggccgagtt cccgtggccg ccgcctgcgg tccgggttcc   7080
tccctcgggg ggctccctcg cgccgcgcgc ggctcggggt tcggggttcg tcggccccgg   7140
ccgggtggaa ggtcccgtgc ccgtcgtcgt cgtcgtcgtc gcgcgtcgtc ggcggtgggg   7200
gcgtgttgcg tgcggtgtgg tggtggggga ggaggaaggc gggtccggaa ggggaagggt   7260
gccggcgggg agagagggtc gggggagcgc gtcccggtcg ccgcggttcg ccgcccgccc   7320
ccggtggcgg cccggcgtcc ggccgaccgc cgctcccgcg cccctcctcc tccccgccgc   7380
ccctcctccg aggccccgcc cgtcctcctc gccctccccg cgcgtacgcg cgcccgcccg   7440
cccggctcgc ctcgcggcgc gtcggccggg gccgggagcc cgccccgcgg cccgcccggc   7500
cgcgcccgtg gccgcggcgc cggggttcgc gtgtccccgg cggcgacccg cgggacgccg   7560
cggtgtcgtc cgccgtcgcg cgcccgcctc cggctcgcgg ccgcgccgcg ccgcgccggg   7620
gccccgtccc gagcttccgc gtcggggcgg ggcggctccg ccgccgcgtc ctcggacccg   7680
tccccccgac ctccgcgggg gagacgggtc ggggcgtgcg gcgcccgtcc cgcccccggc   7740
ccgtgcccct ccctccggtc gtcccgctcc ggcggggcgg cgcgggggtg ccgccggccg   7800
cgcgctctct ctcccgtcgc ctctccccct cgccgggccc gtctcccgac ggagcgtcgg   7860
gcgggcggtc gggccggcgc gattccgtcc gtccgtccgc cgagcggccc gtccccctcc   7920
gagacgcgac ctcagatcag acgtggcgac ccgctgaatt taagcatatt agtcagcgga   7980
ggagaagaaa ctaaccagga ttccctcagt aacggcgagt gaacagggaa gagcccagcg   8040
ccgaatcccc gccccgcggc ggggcgcggg acatgtggcg tacggaagac ccgctccccg   8100
gcgccgctcg tgggggggccc aagtccttct gatcgaggcc cagcccgtgg acggtgtgag   8160
gccggtagcg gcccccggcg cgccgggccc gggtcttccc ggagtcgggt tgcttgggaa   8220
tgcagcccaa agcgggtggt aaactccatc taaggctaaa taccggcacg agaccgatag   8280
tcaacaagta ccgtaaggga aagttgaaaa gaactttgaa gagagagttc aagagggcgt   8340
gaaaccgtta agaggtaaac gggtggggtc cgcgcagtcc gcccggagga ttcaacccgg   8400
cggcgggtcc ggccgtgtcg gcggcccggc ggatctttcc cgcccccgt tcctcccgac   8460
ccctccaccc gccctccctt cccccgccgc ccctcctcct cctccccgga gggggcgggc   8520
tccggcgggt gcgggggtgg gcgggcgggg ccgggggtgg ggtcggcggg ggaccgtccc   8580
ccgaccggcg accggccgcc gccgggcgca tttccaccgc ggcggtgcgc cgcgaccggc   8640
```

-continued

```
tccgggacgg ctgggaaggc ccggcgggga aggtggctcg gggggccccg tccgtccgtc   8700
cgtccgtcct cctcctcccc cgtctccgcc ccccggcccc gcgtcctccc tcgggagggc   8760
gcgcgggtcg gggcggcggc ggcggcggcg gtggcggcgg cggcggcggc ggcgggaccg   8820
aaaccccccc cgagtgttac agcccccccg gcagcagcac tcgccgaatc ccggggccga   8880
gggagcgaga cccgtcgccg cgctctcccc cctcccggcg cccacccccg cggggaatcc   8940
cccgcgaggg gggtctcccc cgcgggggcg cgccggcgtc tcctcgtggg ggggccgggc   9000
cacccctccc acggcgcgac cgctctccca cccctcctcc ccgcgccccc gccccggcga   9060
cgggggggggt gccgcgcgcg ggtcgggggg cggggcggac tgtccccagt gcgccccggg   9120
cgggtcgcgc cgtcgggccc gggggaggtt ctctcggggc cacgcgcgcg tcccccgaag   9180
agggggacgg cggagcgagc gcacggggtc ggcggcgacg tcggctaccc acccgacccg   9240
tcttgaaaca cggaccaagg agtctaacac gtgcgcgagt cgggggctcg cacgaaagcc   9300
gccgtggcgc aatgaaggtg aaggccggcg cgctcgccgg ccgaggtggg atcccgaggc   9360
ctctccagtc cgccgagggc gcaccaccgg cccgtctcgc ccgccgcgcc ggggaggtgg   9420
agcacgagcg cacgtgttag gacccgaaag atggtgaact atgcctgggc agggcgaagc   9480
cagaggaaac tctggtggag gtccgtagcg gtcctgacgt gcaaatcggt cgtccgacct   9540
gggtataggg gcgaaagact aatcgaacca tctagtagct ggttccctcc gaagtttccc   9600
tcaggatagc tggcgctctc gcagacccga cgcacccccg ccacgcagtt ttatccggta   9660
aagcgaatga ttagaggtct tggggccgaa acgatctcaa cctattctca aactttaaat   9720
gggtaagaag cccggctcgc tggcgtggag ccgggcgtgg aatgcgagtg cctagtgggc   9780
cacttttggt aagcagaact ggcgctgcgg gatgaaccga acgccgggtt aaggcgcccg   9840
atgccgacgc tcatcagacc ccagaaaagg tgttggttga tatagacagc aggacggtgg   9900
ccatggaagt cggaatccgc taaggagtgt gtaacaactc acctgccgaa tcaactagcc   9960
ctgaaaatgg atggcgctgg agcgtcgggc ccatacccgg ccgtcgccgg cagtcgagag  10020
tggacgggag cggcgggggc ggcgcgcgcg cgcgcgcgtg tggtgtgcgt cggagggcgg  10080
cggcggcggc ggcggcgggg gtgtggggtc cttcccccgc cccccccccc acgcctcctc  10140
ccctcctccc gcccacgccc cgctccccgc ccccggagcc ccgcggacgc tacgccgcga  10200
cgagtaggag ggccgctgcg gtgagccttg aagcctaggg cgcgggcccg ggtggagccg  10260
ccgcaggtgc agatcttggt ggtagtagca aatattcaaa cgagaacttt gaaggccgaa  10320
gtggagaagg gttccatgtg aacagcagtt gaacatgggt cagtcggtcc tgagagatgg  10380
gcgagcgccg ttccgaaggg acgggcgatg gcctccgttg ccctcggccg atcgaaaggg  10440
agtcgggttc agatccccga atccggagtg gcggagatgg gcgccgcgag gcgtccagtg  10500
cggtaacgcg accgatcccg gagaagccgg cgggagcccc ggggagagtt ctcttttctt  10560
tgtgaagggc agggcgccct ggaatgggtt cgccccgaga gaggggcccg tgccttggaa  10620
agcgtcgcgg ttccggcggc gtccggtgag ctctcgctgg cccttgaaaa tccgggggag  10680
agggtgtaaa tctcgcgccg ggccgtaccc atatccgcag caggtctcca aggtgaacag  10740
cctctggcat gttggaacaa tgtaggtaag ggaagtcggc aagccggatc cgtaacttcg  10800
ggataaggat tggctctaag ggctgggtcg gtcgggctgg ggcgcgaagc ggggctgggc  10860
gcgcgccgcg gctggacgag gcgccgccgc ccccccacg cccggggcac ccccctcgcg  10920
gccctccccc gccccacccc gcgcgcgccg ctcgctccct ccccgccccg cgccctctct  10980
```

-continued ctctctctct cccccgctcc ccgtcctccc ccctccccgg gggagcgccg cgtgggggcg 11040
gcggcggggg gagaagggtc ggggcggcag gggccggcgg cggcccgccg cggggccccg 11100
gcggcggggg cacggtcccc cgcgaggggg gcccgggcac ccggggggcc ggcggcggcg 11160
gcgactctgg acgcgagccg ggcccttccc gtggatcgcc ccagctgcgg cgggcgtcgc 11220
ggccgccccc ggggagcccg gcgggcgccg gcgcgccccc ccccccaccc cacgtctcgt 11280
cgcgcgcgcg tccgctgggg gcggggagcg gtcgggcggc ggcggtcggc gggcggcggg 11340
gcggggcggt tcgtcccccc gccctacccc cccggccccg tccgcccccc gttccccccct 11400
cctcctcggc gcgcggcggc ggcggcggca ggcggcggag gggccgcggg ccggtccccc 11460
ccgccgggtc cgcccccggg gccgcggttc cgcgcggcgc ctcgcctcgg ccggcgccta 11520
gcagccgact tagaactggt gcggaccagg ggaatccgac tgtttaatta aaacaaagca 11580
tcgcgaaggc ccgcggcggg tgttgacgcg atgtgatttc tgcccagtgc tctgaatgtc 11640
aaagtgaaga aattcaatga agcgcgggta aacggcggga gtaactatga ctctcttaag 11700
gtagccaaat gcctcgtcat ctaattagtg acgcgcatga atggatgaac gagattccca 11760
ctgtccctac ctactatcca gcgaaaccac agccaaggga acgggcttgg cggaatcagc 11820
ggggaaagaa gaccctgttg agcttgactc tagtctggca cggtgaagag acatgagagg 11880
tgtagaataa gtgggaggcc cccggcgccc ccccggtgtc cccgcgaggg gcccggggcg 11940
gggtccgccg gccctgcggg ccgccggtga aataccacta ctctgatcgt tttttcactg 12000
acccggtgag gcgggggggc gagccccgag gggctctcgc ttctggcgcc aagcgcccgg 12060
ccgcgcgccg gccgggcgcg acccgctccg gggacagtgc caggtgggga gtttgactgg 12120
ggcggtacac ctgtcaaacg gtaacgcagg tgtcctaagg cgagctcagg gaggacagaa 12180
acctcccgtg gagcagaagg gcaaaagctc gcttgatctt gattttcagt acgaatacag 12240
accgtgaaag cggggcctca cgatccttct gaccttttgg gttttaagca ggaggtgtca 12300
gaaaagttac cacagggata actggcttgt ggcggccaag cgttcatagc gacgtcgctt 12360
tttgatcctt cgatgtcggc tcttcctatc attgtgaagc agaattcacc aagcgttgga 12420
ttgttcaccc actaataggg aacgtgagct gggtttagac cgtcgtgaga caggttagtt 12480
ttaccctact gatgatgtgt tgttgccatg gtaatcctgc tcagtacgag aggaaccgca 12540
ggttcagaca tttggtgtat gtgcttggct gaggagccaa tggggcgaag ctaccatctg 12600
tgggattatg actgaacgcc tctaagtcag aatcccgccc aggcggaacg atacggcagc 12660
gccgcggagc ctcggttggc ctcggatagc cggtccccccg cctgtccccg ccggcgggcc 12720
gccccccccc tccacgcgcc ccgcgcgcgc gggagggcgc gtgccccgcc gcgcgccggg 12780
accggggtcc ggtgcggagt gcccttcgtc ctgggaaacg gggcgcggcc ggagaggcgg 12840
ccgccccctc gcccgtcacg caccgcacgt tcgtggggaa cctggcgcta aaccattcgt 12900
agacgacctg cttctgggtc ggggtttcgt acgtagcaga gcagctccct cgctgcgatc 12960
tattgaaagt cagccctcga cacaagggtt tgtccgcgcg cgcgcgcgcg cgcgcgtgcg 13020
gggggcccgg cggggcgtgc gcgtccggcg ccgtccgtcc ttccgttcgt cttcctccct 13080
cccggcctct cccgccgacc gcgggcgtgg tggtgggggt gtggggggga gggcgcgcga 13140
ccccggtcgg cgcgccccgc ttcttcggtt cccgcctcct ccccgttcac cgccggggcg 13200
gctcgtccgc tccgggccgg gacggggtcc ggggagcgtg gtttgggagc cgcggaggcg 13260
gccgcgccga gccgggcccg tggcccgccg gtccccgtcc cgggggttgg ccgcgcgggc 13320
cccggtgggg cggccacccg gggtcccggc cctcgcg 13357

<210> SEQ ID NO 38
<211> LENGTH: 651
<212> TYPE: PRT
<213> ORGANISM: Homo sapiens

<400> SEQUENCE: 38

```
Met Ala Ala Pro Leu Leu His Thr Arg Leu Pro Gly Asp Ala Ala Ala
1               5                   10                  15

Ser Ser Ser Ala Val Lys Lys Leu Gly Ala Ser Arg Thr Gly Ile Ser
            20                  25                  30

Asn Met Arg Ala Leu Glu Asn Asp Phe Phe Asn Ser Pro Pro Arg Lys
        35                  40                  45

Thr Val Arg Phe Gly Gly Thr Val Thr Glu Val Leu Leu Lys Tyr Lys
    50                  55                  60

Lys Gly Glu Thr Asn Asp Phe Glu Leu Leu Lys Asn Gln Leu Leu Asp
65                  70                  75                  80

Pro Asp Ile Lys Asp Asp Gln Ile Ile Asn Trp Leu Leu Glu Phe Arg
                85                  90                  95

Ser Ser Ile Met Tyr Leu Thr Lys Asp Phe Glu Gln Leu Ile Ser Ile
            100                 105                 110

Ile Leu Arg Leu Pro Trp Leu Asn Arg Ser Gln Thr Val Val Glu Glu
        115                 120                 125

Tyr Leu Ala Phe Leu Gly Asn Leu Val Ser Ala Gln Thr Val Phe Leu
    130                 135                 140

Arg Pro Cys Leu Ser Met Ile Ala Ser His Phe Val Pro Pro Arg Val
145                 150                 155                 160

Ile Ile Lys Glu Gly Asp Val Asp Val Ser Asp Ser Asp Asp Glu Asp
                165                 170                 175

Asp Asn Leu Pro Ala Asn Phe Asp Thr Cys His Arg Ala Leu Gln Ile
            180                 185                 190

Ile Ala Arg Tyr Val Pro Ser Thr Pro Trp Phe Leu Met Pro Ile Leu
        195                 200                 205

Val Glu Lys Phe Pro Phe Val Arg Lys Ser Glu Arg Thr Leu Glu Cys
    210                 215                 220

Tyr Val His Asn Leu Leu Arg Ile Ser Val Tyr Phe Pro Thr Leu Arg
225                 230                 235                 240

His Glu Ile Leu Glu Leu Ile Ile Glu Lys Leu Leu Lys Leu Asp Val
                245                 250                 255

Asn Ala Ser Arg Gln Gly Ile Glu Asp Ala Glu Glu Thr Ala Thr Gln
            260                 265                 270

Thr Cys Gly Gly Thr Asp Ser Thr Glu Gly Leu Phe Asn Met Asp Glu
        275                 280                 285

Asp Glu Glu Thr Glu His Glu Thr Lys Ala Gly Pro Glu Arg Leu Asp
    290                 295                 300

Gln Met Val His Pro Val Ala Glu Arg Leu Asp Ile Leu Met Ser Leu
305                 310                 315                 320

Val Leu Ser Tyr Met Lys Asp Val Cys Tyr Val Asp Gly Lys Val Asp
                325                 330                 335

Asn Gly Lys Thr Lys Asp Leu Tyr Arg Asp Leu Ile Asn Ile Phe Asp
            340                 345                 350

Lys Leu Leu Leu Pro Thr His Ala Ser Cys His Val Gln Phe Phe Met
        355                 360                 365

Phe Tyr Leu Cys Ser Phe Lys Leu Gly Phe Ala Glu Ala Phe Leu Glu
```

-continued

```
    370                 375                 380

His Leu Trp Lys Lys Leu Gln Asp Pro Ser Asn Pro Ala Ile Ile Arg
385                 390                 395                 400

Gln Ala Ala Gly Asn Tyr Ile Gly Ser Phe Leu Ala Arg Ala Lys Phe
                405                 410                 415

Ile Pro Leu Ile Thr Val Lys Ser Cys Leu Asp Leu Leu Val Asn Trp
            420                 425                 430

Leu His Ile Tyr Leu Asn Asn Gln Asp Ser Gly Thr Lys Ala Phe Cys
        435                 440                 445

Asp Val Ala Leu His Gly Pro Phe Tyr Ser Ala Cys Gln Ala Val Phe
    450                 455                 460

Tyr Thr Phe Val Phe Arg His Lys Gln Leu Leu Ser Gly Asn Leu Lys
465                 470                 475                 480

Glu Gly Leu Gln Tyr Leu Gln Ser Leu Asn Phe Glu Arg Ile Val Met
                485                 490                 495

Ser Gln Leu Asn Pro Leu Lys Ile Cys Leu Pro Ser Val Val Asn Phe
            500                 505                 510

Phe Ala Ala Ile Thr Asn Lys Tyr Gln Leu Val Phe Cys Tyr Thr Ile
        515                 520                 525

Ile Glu Arg Asn Asn Arg Gln Met Leu Pro Val Ile Arg Ser Thr Ala
    530                 535                 540

Gly Gly Asp Ser Val Gln Ile Cys Thr Asn Pro Leu Asp Thr Phe Phe
545                 550                 555                 560

Pro Phe Asp Pro Cys Val Leu Lys Arg Ser Lys Lys Phe Ile Asp Pro
                565                 570                 575

Ile Tyr Gln Val Trp Glu Asp Met Ser Ala Glu Glu Leu Gln Glu Phe
            580                 585                 590

Lys Lys Pro Met Lys Lys Asp Ile Val Glu Asp Glu Asp Asp Asp Phe
        595                 600                 605

Leu Lys Gly Glu Val Pro Gln Asn Asp Thr Val Ile Gly Ile Thr Pro
    610                 615                 620

Ser Ser Phe Asp Thr His Phe Arg Ser Pro Ser Ser Ser Val Gly Ser
625                 630                 635                 640

Pro Pro Val Leu Tyr Met Gln Pro Ser Pro Leu
                645                 650


<210> SEQ ID NO 39
<211> LENGTH: 1394
<212> TYPE: PRT
<213> ORGANISM: Homo sapiens

<400> SEQUENCE: 39

Met Ala Ala Leu Leu Arg Ser Ala Arg Trp Leu Leu Arg Ala Gly Ala
1               5                   10                  15

Ala Pro Arg Leu Pro Leu Ser Leu Arg Leu Leu Pro Gly Gly Pro Gly
            20                  25                  30

Arg Leu His Ala Ala Ser Tyr Leu Pro Ala Ala Arg Ala Gly Pro Val
        35                  40                  45

Ala Gly Gly Leu Leu Ser Pro Ala Arg Leu Tyr Ala Ile Ala Ala Lys
    50                  55                  60

Glu Lys Asp Ile Gln Glu Glu Ser Thr Phe Ser Ser Arg Lys Ile Ser
65                  70                  75                  80

Asn Gln Phe Asp Trp Ala Leu Met Arg Leu Asp Leu Ser Val Arg Arg
                85                  90                  95
```

-continued

```
Thr Gly Arg Ile Pro Lys Lys Leu Leu Gln Lys Val Phe Asn Asp Thr
            100                 105                 110

Cys Arg Ser Gly Gly Leu Gly Gly Ser His Ala Leu Leu Leu Leu Arg
        115                 120                 125

Ser Cys Gly Ser Leu Leu Pro Glu Leu Lys Leu Glu Glu Arg Thr Glu
    130                 135                 140

Phe Ala His Arg Ile Trp Asp Thr Leu Gln Lys Leu Gly Ala Val Tyr
145                 150                 155                 160

Asp Val Ser His Tyr Asn Ala Leu Leu Lys Val Tyr Leu Gln Asn Glu
                165                 170                 175

Tyr Lys Phe Ser Pro Thr Asp Phe Leu Ala Lys Met Glu Glu Ala Asn
            180                 185                 190

Ile Gln Pro Asn Arg Val Thr Tyr Gln Arg Leu Ile Ala Ser Tyr Cys
        195                 200                 205

Asn Val Gly Asp Ile Glu Gly Ala Ser Lys Ile Leu Gly Phe Met Lys
    210                 215                 220

Thr Lys Asp Leu Pro Val Thr Glu Ala Val Phe Ser Ala Leu Val Thr
225                 230                 235                 240

Gly His Ala Arg Ala Gly Asp Met Glu Asn Ala Glu Asn Ile Leu Thr
                245                 250                 255

Val Met Arg Asp Ala Gly Ile Glu Pro Gly Pro Asp Thr Tyr Leu Ala
            260                 265                 270

Leu Leu Asn Ala Tyr Ala Glu Lys Gly Asp Ile Asp His Val Lys Gln
        275                 280                 285

Thr Leu Glu Lys Val Glu Lys Ser Glu Leu His Leu Met Asp Arg Asp
    290                 295                 300

Leu Leu Gln Ile Ile Phe Ser Phe Ser Lys Ala Gly Tyr Pro Gln Tyr
305                 310                 315                 320

Val Ser Glu Ile Leu Glu Lys Val Thr Cys Glu Arg Arg Tyr Ile Pro
                325                 330                 335

Asp Ala Met Asn Leu Ile Leu Leu Leu Val Thr Glu Lys Leu Glu Asp
            340                 345                 350

Val Ala Leu Gln Ile Leu Leu Ala Cys Pro Val Ser Lys Glu Asp Gly
        355                 360                 365

Pro Ser Val Phe Gly Ser Phe Phe Leu Gln His Cys Val Thr Met Asn
    370                 375                 380

Thr Pro Val Glu Lys Leu Thr Asp Tyr Cys Lys Lys Leu Lys Glu Val
385                 390                 395                 400

Gln Met His Ser Phe Pro Leu Gln Phe Thr Leu His Cys Ala Leu Leu
                405                 410                 415

Ala Asn Lys Thr Asp Leu Ala Lys Ala Leu Met Lys Ala Val Lys Glu
            420                 425                 430

Glu Gly Phe Pro Ile Arg Pro His Tyr Phe Trp Pro Leu Leu Val Gly
        435                 440                 445

Arg Arg Lys Glu Lys Asn Val Gln Gly Ile Ile Glu Ile Leu Lys Gly
    450                 455                 460

Met Gln Glu Leu Gly Val His Pro Asp Gln Glu Thr Tyr Thr Asp Tyr
465                 470                 475                 480

Val Ile Pro Cys Phe Asp Ser Val Asn Ser Ala Arg Ala Ile Leu Gln
                485                 490                 495

Glu Asn Gly Cys Leu Ser Asp Ser Asp Met Phe Ser Gln Ala Gly Leu
            500                 505                 510

Arg Ser Glu Ala Ala Asn Gly Asn Leu Asp Phe Val Leu Ser Phe Leu
```

-continued

```
        515                 520                 525

Lys Ser Asn Thr Leu Pro Ile Ser Leu Gln Ser Ile Arg Ser Ser Leu
    530                 535                 540

Leu Leu Gly Phe Arg Arg Ser Met Asn Ile Asn Leu Trp Ser Glu Ile
545                 550                 555                 560

Thr Glu Leu Leu Tyr Lys Asp Gly Arg Tyr Cys Gln Glu Pro Arg Gly
                565                 570                 575

Pro Thr Glu Ala Val Gly Tyr Phe Leu Tyr Asn Leu Ile Asp Ser Met
            580                 585                 590

Ser Asp Ser Glu Val Gln Ala Lys Glu Glu His Leu Arg Gln Tyr Phe
        595                 600                 605

His Gln Leu Glu Lys Met Asn Val Lys Ile Pro Glu Asn Ile Tyr Arg
    610                 615                 620

Gly Ile Arg Asn Leu Leu Glu Ser Tyr His Val Pro Glu Leu Ile Lys
625                 630                 635                 640

Asp Ala His Leu Leu Val Glu Ser Lys Asn Leu Asp Phe Gln Lys Thr
                645                 650                 655

Val Gln Leu Thr Ser Ser Glu Leu Glu Ser Thr Leu Glu Thr Leu Lys
            660                 665                 670

Ala Glu Asn Gln Pro Ile Arg Asp Val Leu Lys Gln Leu Ile Leu Val
        675                 680                 685

Leu Cys Ser Glu Glu Asn Met Gln Lys Ala Leu Glu Leu Lys Ala Lys
    690                 695                 700

Tyr Glu Ser Asp Met Val Thr Gly Gly Tyr Ala Ala Leu Ile Asn Leu
705                 710                 715                 720

Cys Cys Arg His Asp Lys Val Glu Asp Ala Leu Asn Leu Lys Glu Glu
                725                 730                 735

Phe Asp Arg Leu Asp Ser Ser Ala Val Leu Asp Thr Gly Lys Tyr Val
            740                 745                 750

Gly Leu Val Arg Val Leu Ala Lys His Gly Lys Leu Gln Asp Ala Ile
        755                 760                 765

Asn Ile Leu Lys Glu Met Lys Glu Lys Asp Val Leu Ile Lys Asp Thr
    770                 775                 780

Thr Ala Leu Ser Phe Phe His Met Leu Asn Gly Ala Ala Leu Arg Gly
785                 790                 795                 800

Glu Ile Glu Thr Val Lys Gln Leu His Glu Ala Ile Val Thr Leu Gly
                805                 810                 815

Leu Ala Glu Pro Ser Thr Asn Ile Ser Phe Pro Leu Val Thr Val His
            820                 825                 830

Leu Glu Lys Gly Asp Leu Ser Thr Ala Leu Glu Val Ala Ile Asp Cys
        835                 840                 845

Tyr Glu Lys Tyr Lys Val Leu Pro Arg Ile His Asp Val Leu Cys Lys
    850                 855                 860

Leu Val Glu Lys Gly Glu Thr Asp Leu Ile Gln Lys Ala Met Asp Phe
865                 870                 875                 880

Val Ser Gln Glu Gln Gly Glu Met Val Met Leu Tyr Asp Leu Phe Phe
                885                 890                 895

Ala Phe Leu Gln Thr Gly Asn Tyr Lys Glu Ala Lys Lys Ile Ile Glu
            900                 905                 910

Thr Pro Gly Ile Arg Ala Arg Ser Ala Arg Leu Gln Trp Phe Cys Asp
        915                 920                 925

Arg Cys Val Ala Asn Asn Gln Val Glu Thr Leu Glu Lys Leu Val Glu
    930                 935                 940
```

```
Leu Thr Gln Lys Leu Phe Glu Cys Asp Arg Asp Gln Met Tyr Tyr Asn
945                 950                 955                 960

Leu Leu Lys Leu Tyr Lys Ile Asn Gly Asp Trp Gln Arg Ala Asp Ala
                965                 970                 975

Val Trp Asn Lys Ile Gln Glu Glu Asn Val Ile Pro Arg Glu Lys Thr
            980                 985                 990

Leu Arg Leu Leu Ala Glu Ile Leu  Arg Glu Gly Asn Gln  Glu Val Pro
        995                 1000                 1005

Phe Asp  Val Pro Glu Leu Trp  Tyr Glu Asp Glu Lys  His Ser Leu
    1010                 1015                 1020

Asn Ser  Ser Ser Ala Ser Thr  Thr Glu Pro Asp Phe  Gln Lys Asp
    1025                 1030                 1035

Ile Leu  Ile Ala Cys Arg Leu  Asn Gln Lys Lys Gly  Ala Tyr Asp
    1040                 1045                 1050

Ile Phe  Leu Asn Ala Lys Glu  Gln Asn Ile Val Phe  Asn Ala Glu
    1055                 1060                 1065

Thr Tyr  Ser Asn Leu Ile Lys  Leu Leu Met Ser Glu  Asp Tyr Phe
    1070                 1075                 1080

Thr Gln  Ala Met Glu Val Lys  Ala Phe Ala Glu Thr  His Ile Lys
    1085                 1090                 1095

Gly Phe  Thr Leu Asn Asp Ala  Ala Asn Ser Arg Leu  Ile Ile Thr
    1100                 1105                 1110

Gln Val  Arg Arg Asp Tyr Leu  Lys Glu Ala Val Thr  Thr Leu Lys
    1115                 1120                 1125

Thr Val  Leu Asp Gln Gln Gln  Thr Pro Ser Arg Leu  Ala Val Thr
    1130                 1135                 1140

Arg Val  Ile Gln Ala Leu Ala  Met Lys Gly Asp Val  Glu Asn Ile
    1145                 1150                 1155

Glu Val  Val Gln Lys Met Leu  Asn Gly Leu Glu Asp  Ser Ile Gly
    1160                 1165                 1170

Leu Ser  Lys Met Val Phe Ile  Asn Asn Ile Ala Leu  Ala Gln Ile
    1175                 1180                 1185

Lys Asn  Asn Asn Ile Asp Ala  Ala Ile Glu Asn Ile  Glu Asn Met
    1190                 1195                 1200

Leu Thr  Ser Glu Asn Lys Val  Ile Glu Pro Gln Tyr  Phe Gly Leu
    1205                 1210                 1215

Ala Tyr  Leu Phe Arg Lys Val  Ile Glu Glu Gln Leu  Glu Pro Ala
    1220                 1225                 1230

Val Glu  Lys Ile Ser Ile Met  Ala Glu Arg Leu Ala  Asn Gln Phe
    1235                 1240                 1245

Ala Ile  Tyr Lys Pro Val Thr  Asp Phe Phe Leu Gln  Leu Val Asp
    1250                 1255                 1260

Ala Gly  Lys Val Asp Asp Ala  Arg Ala Leu Leu Gln  Arg Cys Gly
    1265                 1270                 1275

Ala Ile  Ala Glu Gln Thr Pro  Ile Leu Leu Leu Phe  Leu Leu Arg
    1280                 1285                 1290

Asn Ser  Arg Lys Gln Gly Lys  Ala Ser Thr Val Lys  Ser Val Leu
    1295                 1300                 1305

Glu Leu  Ile Pro Glu Leu Asn  Glu Lys Glu Glu Ala  Tyr Asn Ser
    1310                 1315                 1320

Leu Met  Lys Ser Tyr Val Ser  Glu Lys Asp Val Thr  Ser Ala Lys
    1325                 1330                 1335
```

```
Ala Leu  Tyr Glu His Leu Thr  Ala Lys Asn Thr Lys  Leu Asp Asp
    1340                 1345                 1350

Leu Phe  Leu Lys Arg Tyr Ala  Ser Leu Leu Lys Tyr  Ala Gly Glu
    1355                 1360                 1365

Pro Val  Pro Phe Ile Glu Pro  Pro Glu Ser Phe Glu  Phe Tyr Ala
    1370                 1375                 1380

Gln Gln  Leu Arg Lys Leu Arg  Glu Asn Ser Ser
    1385                 1390


<210> SEQ ID NO 40
<211> LENGTH: 1079
<212> TYPE: PRT
<213> ORGANISM: Homo sapiens

<400> SEQUENCE: 40

Met Asp Pro Gly Ser Arg Trp Arg Asn Leu Pro Ser Gly Pro Ser Leu
1               5                   10                  15

Lys His Leu Thr Asp Pro Ser Tyr Gly Ile Pro Arg Glu Gln Gln Lys
            20                  25                  30

Ala Ala Leu Gln Glu Leu Thr Arg Ala His Val Glu Ser Phe Asn Tyr
        35                  40                  45

Ala Val His Glu Gly Leu Gly Leu Ala Val Gln Ala Asp Ile Asn Trp
    50                  55                  60

Ala Val Asn Gly Ile Ser Lys Gly Ile Ile Lys Gln Phe Leu Gly Tyr
65                  70                  75                  80

Val Pro Ile Met Val Lys Ser Lys Leu Cys Asn Leu Arg Asn Leu Pro
                85                  90                  95

Pro Gln Ala Leu Ile Glu His His Glu Glu Ala Glu Glu Met Gly Gly
            100                 105                 110

Tyr Phe Ile Ile Asn Gly Ile Glu Lys Val Ile Arg Met Leu Ile Met
        115                 120                 125

Pro Arg Arg Asn Phe Pro Ile Ala Met Ile Arg Pro Lys Trp Lys Thr
    130                 135                 140

Arg Gly Pro Gly Tyr Thr Gln Tyr Gly Val Ser Met His Cys Val Arg
145                 150                 155                 160

Glu Glu His Ser Ala Val Asn Met Asn Leu His Tyr Leu Glu Asn Gly
                165                 170                 175

Thr Val Met Leu Asn Phe Ile Tyr Arg Lys Glu Leu Phe Phe Leu Pro
            180                 185                 190

Leu Gly Phe Ala Leu Lys Ala Leu Val Ser Phe Ser Asp Tyr Gln Ile
        195                 200                 205

Phe Gln Glu Leu Ile Lys Gly Lys Glu Asp Asp Ser Phe Leu Arg Asn
    210                 215                 220

Ser Val Ser Gln Met Leu Arg Ile Val Met Glu Glu Gly Cys Ser Thr
225                 230                 235                 240

Gln Lys Gln Val Leu Asn Tyr Leu Gly Glu Cys Phe Arg Val Lys Leu
                245                 250                 255

Asn Val Pro Asp Trp Tyr Pro Asn Glu Gln Ala Ala Glu Phe Leu Phe
            260                 265                 270

Asn Gln Cys Ile Cys Ile His Leu Lys Ser Asn Thr Glu Lys Phe Tyr
        275                 280                 285

Met Leu Cys Leu Met Thr Arg Lys Leu Phe Ala Leu Ala Lys Gly Glu
    290                 295                 300

Cys Met Glu Asp Asn Pro Asp Ser Leu Val Asn Gln Glu Val Leu Thr
305                 310                 315                 320
```

-continued

```
Pro Gly Gln Leu Phe Leu Met Phe Leu Lys Glu Lys Leu Glu Gly Trp
                325                 330                 335

Leu Val Ser Ile Lys Ile Ala Phe Asp Lys Lys Ala Gln Lys Thr Ser
            340                 345                 350

Val Ser Met Asn Thr Asp Asn Leu Met Arg Ile Phe Thr Met Gly Ile
        355                 360                 365

Asp Leu Thr Lys Pro Phe Glu Tyr Leu Phe Ala Thr Gly Asn Leu Arg
    370                 375                 380

Ser Lys Thr Gly Leu Gly Leu Leu Gln Asp Ser Gly Leu Cys Val Val
385                 390                 395                 400

Ala Asp Lys Leu Asn Phe Ile Arg Tyr Leu Ser His Phe Arg Cys Val
                405                 410                 415

His Arg Gly Ala Asp Phe Ala Lys Met Arg Thr Thr Thr Val Arg Arg
            420                 425                 430

Leu Leu Pro Glu Ser Trp Gly Phe Leu Cys Pro Val His Thr Pro Asp
        435                 440                 445

Gly Glu Pro Cys Gly Leu Met Asn His Leu Thr Ala Val Cys Glu Val
    450                 455                 460

Val Thr Gln Phe Val Tyr Thr Ala Ser Ile Pro Ala Leu Leu Cys Asn
465                 470                 475                 480

Leu Gly Val Thr Pro Ile Asp Gly Ala Pro His Arg Ser Tyr Ser Glu
                485                 490                 495

Cys Tyr Pro Val Leu Leu Asp Gly Val Met Val Gly Trp Val Asp Lys
            500                 505                 510

Asp Leu Ala Pro Gly Ile Ala Asp Ser Leu Arg His Phe Lys Val Leu
        515                 520                 525

Arg Glu Lys Arg Ile Pro Pro Trp Met Glu Val Val Leu Ile Pro Met
    530                 535                 540

Thr Gly Lys Pro Ser Leu Tyr Pro Gly Leu Phe Leu Phe Thr Thr Pro
545                 550                 555                 560

Cys Arg Leu Val Arg Pro Val Gln Asn Leu Ala Leu Gly Lys Glu Glu
                565                 570                 575

Leu Ile Gly Thr Met Glu Gln Ile Phe Met Asn Val Ala Ile Phe Glu
            580                 585                 590

Asp Glu Val Phe Ala Gly Val Thr Thr His Gln Glu Leu Phe Pro His
        595                 600                 605

Ser Leu Leu Ser Val Ile Ala Asn Phe Ile Pro Phe Ser Asp His Asn
    610                 615                 620

Gln Ser Pro Arg Asn Met Tyr Gln Cys Gln Met Gly Lys Gln Thr Met
625                 630                 635                 640

Gly Phe Pro Leu Leu Thr Tyr Gln Asp Arg Ser Asp Asn Lys Leu Tyr
                645                 650                 655

Arg Leu Gln Thr Pro Gln Ser Pro Leu Val Arg Pro Ser Met Tyr Asp
            660                 665                 670

Tyr Tyr Asp Met Asp Asn Tyr Pro Ile Gly Thr Asn Ala Ile Val Ala
        675                 680                 685

Val Ile Ser Tyr Thr Gly Tyr Asp Met Glu Asp Ala Met Ile Val Asn
    690                 695                 700

Lys Ala Ser Trp Glu Arg Gly Phe Ala His Gly Ser Val Tyr Lys Ser
705                 710                 715                 720

Glu Phe Ile Asp Leu Ser Glu Lys Ile Lys Gln Gly Asp Ser Ser Leu
                725                 730                 735
```

```
Val Phe Gly Ile Lys Pro Gly Asp Pro Arg Val Leu Gln Lys Leu Asp
            740                 745                 750

Asp Asp Gly Leu Pro Phe Ile Gly Ala Lys Leu Gln Tyr Gly Asp Pro
        755                 760                 765

Tyr Tyr Ser Tyr Leu Asn Leu Asn Thr Gly Glu Ser Phe Val Met Tyr
    770                 775                 780

Tyr Lys Ser Lys Glu Asn Cys Val Val Asp Asn Ile Lys Val Cys Ser
785                 790                 795                 800

Asn Asp Thr Gly Ser Gly Lys Phe Lys Cys Val Cys Ile Thr Met Arg
                805                 810                 815

Val Pro Arg Asn Pro Thr Ile Gly Asp Lys Phe Ala Ser Arg His Gly
            820                 825                 830

Gln Lys Gly Ile Leu Ser Arg Leu Trp Pro Ala Glu Asp Met Pro Phe
        835                 840                 845

Thr Glu Ser Gly Met Val Pro Asp Ile Leu Phe Asn Pro His Gly Phe
    850                 855                 860

Pro Ser Arg Met Thr Ile Gly Met Leu Ile Glu Ser Met Ala Gly Lys
865                 870                 875                 880

Ser Ala Ala Leu His Gly Leu Cys His Asp Ala Thr Pro Phe Ile Phe
                885                 890                 895

Ser Glu Glu Asn Ser Ala Leu Glu Tyr Phe Gly Glu Met Leu Lys Ala
            900                 905                 910

Ala Gly Tyr Asn Phe Tyr Gly Thr Glu Arg Leu Tyr Ser Gly Ile Ser
        915                 920                 925

Gly Leu Glu Leu Glu Ala Asp Ile Phe Ile Gly Val Val Tyr Tyr Gln
    930                 935                 940

Arg Leu Arg His Met Val Ser Asp Lys Phe Gln Val Arg Thr Thr Gly
945                 950                 955                 960

Ala Arg Asp Arg Val Thr Asn Gln Pro Ile Gly Gly Arg Asn Val Gln
                965                 970                 975

Gly Gly Ile Arg Phe Gly Glu Met Glu Arg Asp Ala Leu Leu Ala His
            980                 985                 990

Gly Thr Ser Phe Leu Leu His Asp  Arg Leu Phe Asn Cys  Ser Asp Arg
        995                 1000                1005

Ser Val  Ala His Val Cys Val  Lys Cys Gly Ser Leu  Leu Ser Pro
    1010                 1015                 1020

Leu Leu  Glu Lys Pro Pro Pro  Ser Trp Ser Ala Met  Arg Asn Arg
    1025                 1030                 1035

Lys Tyr  Asn Cys Thr Leu Cys  Ser Arg Ser Asp Thr  Ile Asp Thr
    1040                 1045                 1050

Val Ser  Val Pro Tyr Val Phe  Arg Tyr Phe Val Ala  Glu Leu Ala
    1055                 1060                 1065

Ala Met  Asn Ile Lys Val Lys  Leu Asp Val Val
    1070                 1075


<210> SEQ ID NO 41
<211> LENGTH: 1135
<212> TYPE: PRT
<213> ORGANISM: Homo sapiens

<400> SEQUENCE: 41

Met Asp Pro Gly Ser Arg Trp Arg Asn Leu Pro Ser Gly Pro Ser Leu
1               5                   10                  15

Lys His Leu Thr Asp Pro Ser Tyr Gly Ile Pro Arg Glu Gln Gln Lys
            20                  25                  30
```

```
Ala Ala Leu Gln Glu Leu Thr Arg Ala His Val Glu Ser Phe Asn Tyr
        35                  40                  45

Ala Val His Glu Gly Leu Gly Leu Ala Val Gln Ala Ile Pro Pro Phe
    50                  55                  60

Glu Phe Ala Phe Lys Asp Glu Arg Ile Ser Phe Thr Ile Leu Asp Ala
65                  70                  75                  80

Val Ile Ser Pro Pro Thr Val Pro Lys Gly Thr Ile Cys Lys Glu Ala
                85                  90                  95

Asn Val Tyr Pro Ala Glu Cys Arg Gly Arg Arg Ser Thr Tyr Arg Gly
            100                 105                 110

Lys Leu Thr Ala Asp Ile Asn Trp Ala Val Asn Gly Ile Ser Lys Gly
        115                 120                 125

Ile Ile Lys Gln Phe Leu Gly Tyr Val Pro Ile Met Val Lys Ser Lys
    130                 135                 140

Leu Cys Asn Leu Arg Asn Leu Pro Pro Gln Ala Leu Ile Glu His His
145                 150                 155                 160

Glu Glu Ala Glu Glu Met Gly Gly Tyr Phe Ile Ile Asn Gly Ile Glu
                165                 170                 175

Lys Val Ile Arg Met Leu Ile Met Pro Arg Arg Asn Phe Pro Ile Ala
            180                 185                 190

Met Ile Arg Pro Lys Trp Lys Thr Arg Gly Pro Gly Tyr Thr Gln Tyr
        195                 200                 205

Gly Val Ser Met His Cys Val Arg Glu Glu His Ser Ala Val Asn Met
    210                 215                 220

Asn Leu His Tyr Leu Glu Asn Gly Thr Val Met Leu Asn Phe Ile Tyr
225                 230                 235                 240

Arg Lys Glu Leu Phe Phe Leu Pro Leu Gly Phe Ala Leu Lys Ala Leu
                245                 250                 255

Val Ser Phe Ser Asp Tyr Gln Ile Phe Gln Glu Leu Ile Lys Gly Lys
            260                 265                 270

Glu Asp Asp Ser Phe Leu Arg Asn Ser Val Ser Gln Met Leu Arg Ile
        275                 280                 285

Val Met Glu Glu Gly Cys Ser Thr Gln Lys Gln Val Leu Asn Tyr Leu
    290                 295                 300

Gly Glu Cys Phe Arg Val Lys Leu Asn Val Pro Asp Trp Tyr Pro Asn
305                 310                 315                 320

Glu Gln Ala Ala Glu Phe Leu Phe Asn Gln Cys Ile Cys Ile His Leu
                325                 330                 335

Lys Ser Asn Thr Glu Lys Phe Tyr Met Leu Cys Leu Met Thr Arg Lys
            340                 345                 350

Leu Phe Ala Leu Ala Lys Gly Glu Cys Met Glu Asp Asn Pro Asp Ser
        355                 360                 365

Leu Val Asn Gln Glu Val Leu Thr Pro Gly Gln Leu Phe Leu Met Phe
    370                 375                 380

Leu Lys Glu Lys Leu Glu Gly Trp Leu Val Ser Ile Lys Ile Ala Phe
385                 390                 395                 400

Asp Lys Lys Ala Gln Lys Thr Ser Val Ser Met Asn Thr Asp Asn Leu
                405                 410                 415

Met Arg Ile Phe Thr Met Gly Ile Asp Leu Thr Lys Pro Phe Glu Tyr
            420                 425                 430

Leu Phe Ala Thr Gly Asn Leu Arg Ser Lys Thr Gly Leu Gly Leu Leu
        435                 440                 445
```

-continued

```
Gln Asp Ser Gly Leu Cys Val Val Ala Asp Lys Leu Asn Phe Ile Arg
    450                 455                 460

Tyr Leu Ser His Phe Arg Cys Val His Arg Gly Ala Asp Phe Ala Lys
465                 470                 475                 480

Met Arg Thr Thr Thr Val Arg Arg Leu Leu Pro Glu Ser Trp Gly Phe
                485                 490                 495

Leu Cys Pro Val His Thr Pro Asp Gly Glu Pro Cys Gly Leu Met Asn
            500                 505                 510

His Leu Thr Ala Val Cys Glu Val Val Thr Gln Phe Val Tyr Thr Ala
        515                 520                 525

Ser Ile Pro Ala Leu Leu Cys Asn Leu Gly Val Thr Pro Ile Asp Gly
    530                 535                 540

Ala Pro His Arg Ser Tyr Ser Glu Cys Tyr Pro Val Leu Leu Asp Gly
545                 550                 555                 560

Val Met Val Gly Trp Val Asp Lys Asp Leu Ala Pro Gly Ile Ala Asp
                565                 570                 575

Ser Leu Arg His Phe Lys Val Leu Arg Glu Lys Arg Ile Pro Pro Trp
            580                 585                 590

Met Glu Val Val Leu Ile Pro Met Thr Gly Lys Pro Ser Leu Tyr Pro
        595                 600                 605

Gly Leu Phe Leu Phe Thr Thr Pro Cys Arg Leu Val Arg Pro Val Gln
    610                 615                 620

Asn Leu Ala Leu Gly Lys Glu Glu Leu Ile Gly Thr Met Glu Gln Ile
625                 630                 635                 640

Phe Met Asn Val Ala Ile Phe Glu Asp Glu Val Phe Ala Gly Val Thr
                645                 650                 655

Thr His Gln Glu Leu Phe Pro His Ser Leu Leu Ser Val Ile Ala Asn
            660                 665                 670

Phe Ile Pro Phe Ser Asp His Asn Gln Ser Pro Arg Asn Met Tyr Gln
        675                 680                 685

Cys Gln Met Gly Lys Gln Thr Met Gly Phe Pro Leu Leu Thr Tyr Gln
    690                 695                 700

Asp Arg Ser Asp Asn Lys Leu Tyr Arg Leu Gln Thr Pro Gln Ser Pro
705                 710                 715                 720

Leu Val Arg Pro Ser Met Tyr Asp Tyr Tyr Asp Met Asp Asn Tyr Pro
                725                 730                 735

Ile Gly Thr Asn Ala Ile Val Ala Val Ile Ser Tyr Thr Gly Tyr Asp
            740                 745                 750

Met Glu Asp Ala Met Ile Val Asn Lys Ala Ser Trp Glu Arg Gly Phe
        755                 760                 765

Ala His Gly Ser Val Tyr Lys Ser Glu Phe Ile Asp Leu Ser Glu Lys
    770                 775                 780

Ile Lys Gln Gly Asp Ser Ser Leu Val Phe Gly Ile Lys Pro Gly Asp
785                 790                 795                 800

Pro Arg Val Leu Gln Lys Leu Asp Asp Asp Gly Leu Pro Phe Ile Gly
                805                 810                 815

Ala Lys Leu Gln Tyr Gly Asp Pro Tyr Tyr Ser Tyr Leu Asn Leu Asn
            820                 825                 830

Thr Gly Glu Ser Phe Val Met Tyr Tyr Lys Ser Lys Glu Asn Cys Val
        835                 840                 845

Val Asp Asn Ile Lys Val Cys Ser Asn Asp Thr Gly Ser Gly Lys Phe
    850                 855                 860

Lys Cys Val Cys Ile Thr Met Arg Val Pro Arg Asn Pro Thr Ile Gly
```

-continued

```
865                 870                 875                 880

Asp Lys Phe Ala Ser Arg His Gly Gln Lys Gly Ile Leu Ser Arg Leu
                885                 890                 895

Trp Pro Ala Glu Asp Met Pro Phe Thr Glu Ser Gly Met Val Pro Asp
            900                 905                 910

Ile Leu Phe Asn Pro His Gly Phe Pro Ser Arg Met Thr Ile Gly Met
        915                 920                 925

Leu Ile Glu Ser Met Ala Gly Lys Ser Ala Ala Leu His Gly Leu Cys
    930                 935                 940

His Asp Ala Thr Pro Phe Ile Phe Ser Glu Glu Asn Ser Ala Leu Glu
945                 950                 955                 960

Tyr Phe Gly Glu Met Leu Lys Ala Ala Gly Tyr Asn Phe Tyr Gly Thr
                965                 970                 975

Glu Arg Leu Tyr Ser Gly Ile Ser Gly Leu Glu Leu Glu Ala Asp Ile
            980                 985                 990

Phe Ile Gly Val Val Tyr Tyr Gln  Arg Leu Arg His Met  Val Ser Asp
        995                 1000                1005

Lys Phe  Gln Val Arg Thr Thr  Gly Ala Arg Asp Arg  Val Thr Asn
    1010                1015                1020

Gln Pro  Ile Gly Gly Arg Asn  Val Gln Gly Gly Ile  Arg Phe Gly
    1025                1030                1035

Glu Met  Glu Arg Asp Ala Leu  Leu Ala His Gly Thr  Ser Phe Leu
    1040                1045                1050

Leu His  Asp Arg Leu Phe Asn  Cys Ser Asp Arg Ser  Val Ala His
    1055                1060                1065

Val Cys  Val Lys Cys Gly Ser  Leu Leu Ser Pro Leu  Leu Glu Lys
    1070                1075                1080

Pro Pro  Pro Ser Trp Ser Ala  Met Arg Asn Arg Lys  Tyr Asn Cys
    1085                1090                1095

Thr Leu  Cys Ser Arg Ser Asp  Thr Ile Asp Thr Val  Ser Val Pro
    1100                1105                1110

Tyr Val  Phe Arg Tyr Phe Val  Ala Glu Leu Ala Ala  Met Asn Ile
    1115                1120                1125

Lys Val  Lys Leu Asp Val Val
    1130                1135
```

<210> SEQ ID NO 42
<211> LENGTH: 346
<212> TYPE: PRT
<213> ORGANISM: Homo sapiens

<400> SEQUENCE: 42

```
Met Ala Ala Ser Gln Ala Val Glu Glu Met Arg Ser Arg Val Val Leu
1               5                   10                  15

Gly Glu Phe Gly Val Arg Asn Val His Thr Thr Asp Phe Pro Gly Asn
            20                  25                  30

Tyr Ser Gly Tyr Asp Asp Ala Trp Asp Gln Asp Arg Phe Glu Lys Asn
        35                  40                  45

Phe Arg Val Asp Val Val His Met Asp Glu Asn Ser Leu Glu Phe Asp
    50                  55                  60

Met Val Gly Ile Asp Ala Ala Ile Ala Asn Ala Phe Arg Arg Ile Leu
65                  70                  75                  80

Leu Ala Glu Val Pro Thr Met Ala Val Glu Lys Val Leu Val Tyr Asn
                85                  90                  95
```

Asn Thr Ser Ile Val Gln Asp Glu Ile Leu Ala His Arg Leu Gly Leu
100 105 110

Ile Pro Ile His Ala Asp Pro Arg Leu Phe Glu Tyr Arg Asn Gln Gly
115 120 125

Asp Glu Glu Gly Thr Glu Ile Asp Thr Leu Gln Phe Arg Leu Gln Val
130 135 140

Arg Cys Thr Arg Asn Pro His Ala Ala Lys Asp Ser Ser Asp Pro Asn
145 150 155 160

Glu Leu Tyr Val Asn His Lys Val Tyr Thr Arg His Met Thr Trp Ile
165 170 175

Pro Leu Gly Asn Gln Ala Asp Leu Phe Pro Glu Gly Thr Ile Arg Pro
180 185 190

Val His Asp Asp Ile Leu Ile Ala Gln Leu Arg Pro Gly Gln Glu Ile
195 200 205

Asp Leu Leu Met His Cys Val Lys Gly Ile Gly Lys Asp His Ala Lys
210 215 220

Phe Ser Pro Val Ala Thr Ala Ser Tyr Arg Leu Leu Pro Asp Ile Thr
225 230 235 240

Leu Leu Glu Pro Val Glu Gly Glu Ala Ala Glu Glu Leu Ser Arg Cys
245 250 255

Phe Ser Pro Gly Val Ile Glu Val Gln Glu Val Gln Gly Lys Lys Val
260 265 270

Ala Arg Val Ala Asn Pro Arg Leu Asp Thr Phe Ser Arg Glu Ile Phe
275 280 285

Arg Asn Glu Lys Leu Lys Lys Val Val Arg Leu Ala Arg Val Arg Asp
290 295 300

His Tyr Ile Phe Ser Val Glu Ser Thr Gly Val Leu Pro Pro Asp Val
305 310 315 320

Leu Val Ser Glu Ala Ile Lys Val Leu Met Gly Lys Cys Arg Arg Phe
325 330 335

Leu Asp Glu Leu Asp Ala Val Gln Met Asp
340 345

<210> SEQ ID NO 43
<211> LENGTH: 133
<212> TYPE: PRT
<213> ORGANISM: Homo sapiens

<400> SEQUENCE: 43

Met Glu Glu Asp Gln Glu Leu Glu Arg Lys Ile Ser Gly Leu Lys Thr
1 5 10 15

Ser Met Ala Glu Gly Glu Arg Lys Thr Ala Leu Glu Met Val Gln Ala
20 25 30

Ala Gly Thr Asp Arg His Cys Val Thr Phe Val Leu His Glu Glu Asp
35 40 45

His Thr Leu Gly Asn Ser Leu Arg Tyr Met Ile Met Lys Asn Pro Glu
50 55 60

Val Glu Phe Cys Gly Tyr Thr Thr Thr His Pro Ser Glu Ser Lys Ile
65 70 75 80

Asn Leu Arg Ile Gln Thr Arg Gly Thr Leu Pro Ala Val Glu Pro Phe
85 90 95

Gln Arg Gly Leu Asn Glu Leu Met Asn Val Cys Gln His Val Leu Asp
100 105 110

Lys Phe Glu Ala Ser Ile Lys Asp Tyr Lys Asp Gln Lys Ala Ser Arg
115 120 125

```
Asn Glu Ser Thr Phe
    130


<210> SEQ ID NO 44
<211> LENGTH: 122
<212> TYPE: PRT
<213> ORGANISM: Homo sapiens

<400> SEQUENCE: 44

Met Glu Glu Asp Gln Glu Leu Glu Arg Lys Ala Ile Glu Glu Leu Leu
1               5                   10                  15

Lys Glu Ala Lys Arg Gly Lys Thr Arg Ala Glu Thr Met Gly Pro Met
            20                  25                  30

Gly Trp Met Lys Cys Pro Leu Ala Ser Thr Asn Lys Arg Phe Leu Ile
        35                  40                  45

Asn Thr Ile Lys Asn Thr Leu Pro Ser His Lys Glu Gln Asp His Glu
    50                  55                  60

Gln Lys Glu Gly Asp Lys Glu Pro Ala Lys Ser Gln Ala Gln Lys Glu
65                  70                  75                  80

Glu Asn Pro Lys Lys His Arg Ser His Pro Tyr Lys His Ser Phe Arg
                85                  90                  95

Ala Arg Gly Ser Ala Ser Tyr Ser Pro Pro Arg Lys Arg Ser Ser Gln
            100                 105                 110

Asp Lys Tyr Glu Lys Arg Ser Asn Arg Arg
        115                 120


<210> SEQ ID NO 45
<211> LENGTH: 710
<212> TYPE: PRT
<213> ORGANISM: Homo sapiens

<400> SEQUENCE: 45

Met Val Lys Leu Ala Lys Ala Gly Lys Asn Gln Gly Asp Pro Lys Lys
1               5                   10                  15

Met Ala Pro Pro Pro Lys Glu Val Glu Glu Asp Ser Glu Asp Glu Glu
            20                  25                  30

Met Ser Glu Asp Glu Glu Asp Asp Ser Ser Gly Glu Glu Val Val Ile
        35                  40                  45

Pro Gln Lys Lys Gly Lys Lys Ala Ala Ala Thr Ser Ala Lys Lys Val
    50                  55                  60

Val Val Ser Pro Thr Lys Lys Val Ala Val Ala Thr Pro Ala Lys Lys
65                  70                  75                  80

Ala Ala Val Thr Pro Gly Lys Lys Ala Ala Ala Thr Pro Ala Lys Lys
                85                  90                  95

Thr Val Thr Pro Ala Lys Ala Val Thr Thr Pro Gly Lys Lys Gly Ala
            100                 105                 110

Thr Pro Gly Lys Ala Leu Val Ala Thr Pro Gly Lys Lys Gly Ala Ala
        115                 120                 125

Ile Pro Ala Lys Gly Ala Lys Asn Gly Lys Asn Ala Lys Lys Glu Asp
    130                 135                 140

Ser Asp Glu Glu Glu Asp Asp Asp Ser Glu Glu Asp Glu Glu Asp Asp
145                 150                 155                 160

Glu Asp Glu Asp Glu Asp Glu Asp Glu Ile Glu Pro Ala Ala Met Lys
                165                 170                 175

Ala Ala Ala Ala Ala Pro Ala Ser Glu Asp Glu Asp Asp Glu Asp Asp
            180                 185                 190
```

```
Glu Asp Asp Glu Asp Asp Asp Asp Asp Glu Glu Asp Asp Ser Glu Glu
        195                 200                 205

Glu Ala Met Glu Thr Thr Pro Ala Lys Gly Lys Lys Ala Ala Lys Val
    210                 215                 220

Val Pro Val Lys Ala Lys Asn Val Ala Glu Asp Glu Asp Glu Glu Glu
225                 230                 235                 240

Asp Asp Glu Asp Glu Asp Asp Asp Asp Asp Glu Asp Asp Glu Asp Asp
                245                 250                 255

Asp Asp Glu Asp Asp Glu Glu Glu Glu Glu Glu Glu Glu Glu Glu Pro
            260                 265                 270

Val Lys Glu Ala Pro Gly Lys Arg Lys Lys Glu Met Ala Lys Gln Lys
        275                 280                 285

Ala Ala Pro Glu Ala Lys Lys Gln Lys Val Glu Gly Thr Glu Pro Thr
    290                 295                 300

Thr Ala Phe Asn Leu Phe Val Gly Asn Leu Asn Phe Asn Lys Ser Ala
305                 310                 315                 320

Pro Glu Leu Lys Thr Gly Ile Ser Asp Val Phe Ala Lys Asn Asp Leu
                325                 330                 335

Ala Val Val Asp Val Arg Ile Gly Met Thr Arg Lys Phe Gly Tyr Val
            340                 345                 350

Asp Phe Glu Ser Ala Glu Asp Leu Glu Lys Ala Leu Glu Leu Thr Gly
        355                 360                 365

Leu Lys Val Phe Gly Asn Glu Ile Lys Leu Glu Lys Pro Lys Gly Lys
    370                 375                 380

Asp Ser Lys Lys Glu Arg Asp Ala Arg Thr Leu Leu Ala Lys Asn Leu
385                 390                 395                 400

Pro Tyr Lys Val Thr Gln Asp Glu Leu Lys Glu Val Phe Glu Asp Ala
                405                 410                 415

Ala Glu Ile Arg Leu Val Ser Lys Asp Gly Lys Ser Lys Gly Ile Ala
            420                 425                 430

Tyr Ile Glu Phe Lys Thr Glu Ala Asp Ala Glu Lys Thr Phe Glu Glu
        435                 440                 445

Lys Gln Gly Thr Glu Ile Asp Gly Arg Ser Ile Ser Leu Tyr Tyr Thr
    450                 455                 460

Gly Glu Lys Gly Gln Asn Gln Asp Tyr Arg Gly Gly Lys Asn Ser Thr
465                 470                 475                 480

Trp Ser Gly Glu Ser Lys Thr Leu Val Leu Ser Asn Leu Ser Tyr Ser
                485                 490                 495

Ala Thr Glu Glu Thr Leu Gln Glu Val Phe Glu Lys Ala Thr Phe Ile
            500                 505                 510

Lys Val Pro Gln Asn Gln Asn Gly Lys Ser Lys Gly Tyr Ala Phe Ile
        515                 520                 525

Glu Phe Ala Ser Phe Glu Asp Ala Lys Glu Ala Leu Asn Ser Cys Asn
    530                 535                 540

Lys Arg Glu Ile Glu Gly Arg Ala Ile Arg Leu Glu Leu Gln Gly Pro
545                 550                 555                 560

Arg Gly Ser Pro Asn Ala Arg Ser Gln Pro Ser Lys Thr Leu Phe Val
                565                 570                 575

Lys Gly Leu Ser Glu Asp Thr Thr Glu Glu Thr Leu Lys Glu Ser Phe
            580                 585                 590

Asp Gly Ser Val Arg Ala Arg Ile Val Thr Asp Arg Glu Thr Gly Ser
        595                 600                 605
```

-continued

Ser Lys Gly Phe Gly Phe Val Asp Phe Asn Ser Glu Glu Asp Ala Lys
610 615 620

Ala Ala Lys Glu Ala Met Glu Asp Gly Glu Ile Asp Gly Asn Lys Val
625 630 635 640

Thr Leu Asp Trp Ala Lys Pro Lys Gly Glu Gly Gly Phe Gly Gly Arg
645 650 655

Gly Gly Gly Arg Gly Gly Phe Gly Gly Arg Gly Gly Gly Arg Gly Gly
660 665 670

Arg Gly Gly Phe Gly Gly Arg Gly Arg Gly Gly Phe Gly Gly Arg Gly
675 680 685

Gly Phe Arg Gly Gly Arg Gly Gly Gly Gly Asp His Lys Pro Gln Gly
690 695 700

Lys Lys Thr Lys Phe Glu
705 710

<210> SEQ ID NO 46
<211> LENGTH: 6637
<212> TYPE: PRT
<213> ORGANISM: Homo sapiens

<400> SEQUENCE: 46

Ala Thr Thr Gly Gly Cys Thr Gly Ala Ala Gly Cys Gly Gly Ala Ala
1 5 10 15

Gly Ala Ala Gly Ala Cys Gly Ala Ala Ala Gly Cys Ala Ala Thr Cys
20 25 30

Ala Thr Ala Ala Ala Ala Thr Gly Gly Gly Ala Gly Gly Thr Thr Gly
35 40 45

Cys Ala Ala Gly Cys Thr Cys Ala Thr Gly Gly Thr Thr Thr Gly Ala
50 55 60

Ala Ala Gly Ala Cys Thr Thr Cys Gly Thr Cys Ala Cys Gly Gly Ala
65 70 75 80

Ala Gly Cys Thr Ala Ala Ala Ala Gly Cys Thr Cys Thr Ala Thr Ala
85 90 95

Cys Ala Cys Cys Cys Gly Ala Thr Thr Thr Gly Cys Cys Thr Cys Gly
100 105 110

Gly Ala Gly Gly Ala Ala Thr Thr Thr Thr Cys Cys Thr Ala Ala Ala
115 120 125

Thr Gly Ala Thr Thr Ala Thr Thr Thr Thr Gly Ala Thr Gly Thr Cys
130 135 140

Thr Thr Ala Thr Ala Thr Ala Thr Cys Thr Thr Thr Gly Ala Thr Thr
145 150 155 160

Gly Thr Thr Thr Thr Cys Ala Ala Ala Ala Cys Ala Ala Ala Ala Gly
165 170 175

Ala Gly Cys Gly Ala Gly Cys Ala Gly Ala Gly Ala Gly Thr Cys Gly
180 185 190

Thr Ala Cys Ala Ala Cys Thr Ala Thr Thr Thr Gly Thr Thr Cys Cys
195 200 205

Cys Cys Cys Cys Cys Cys Ala Thr Gly Thr Ala Gly Ala Ala Gly Thr
210 215 220

Gly Ala Thr Cys Thr Cys Ala Thr Cys Cys Ala Cys Gly Thr Ala Ala
225 230 235 240

Ala Thr Gly Thr Cys Gly Thr Thr Cys Cys Thr Gly Cys Gly Ala Cys
245 250 255

Cys Gly Cys Thr Thr Cys Cys Gly Cys Gly Cys Gly Cys Ala Ala Gly
260 265 270

```
Cys Gly Cys Ala Cys Gly Thr Thr Gly Ala Ala Thr Cys Gly Cys Gly
        275                 280                 285

Thr Gly Gly Thr Gly Ala Cys Thr Cys Cys Gly Gly Gly Cys Thr Thr
    290                 295                 300

Gly Ala Gly Gly Thr Thr Gly Ala Ala Thr Thr Ala Ala Gly Ala Ala
305                 310                 315                 320

Thr Ala Gly Thr Cys Ala Gly Gly Thr Gly Gly Thr Gly Ala Gly Thr
                325                 330                 335

Gly Gly Ala Ala Cys Gly Thr Cys Thr Cys Thr Thr Gly Gly Gly Gly
            340                 345                 350

Thr Gly Thr Cys Gly Gly Ala Ala Thr Thr Cys Ala Ala Ala Ala Cys
        355                 360                 365

Gly Gly Ala Cys Cys Thr Gly Gly Ala Gly Gly Ala Thr Gly Thr Thr
    370                 375                 380

Gly Ala Thr Cys Thr Cys Cys Ala Ala Gly Ala Ala Cys Ala Thr Gly
385                 390                 395                 400

Cys Cys Cys Thr Gly Gly Cys Gly Gly Cys Gly Gly Cys Thr Gly Cys
                405                 410                 415

Ala Gly Gly Gly Cys Ala Thr Thr Thr Cys Cys Thr Thr Cys Gly Gly
            420                 425                 430

Gly Ala Thr Gly Thr Ala Thr Thr Cys Gly Gly Cys Thr Gly Ala Ala
        435                 440                 445

Gly Ala Gly Cys Thr Cys Ala Ala Gly Ala Ala Ala Thr Thr Ala Ala
    450                 455                 460

Gly Thr Gly Thr Thr Ala Ala Ala Thr Cys Cys Ala Thr Thr Ala Cys
465                 470                 475                 480

Gly Ala Ala Cys Cys Cys Thr Cys Gly Ala Thr Ala Cys Cys Thr Gly
                485                 490                 495

Gly Ala Cys Ala Gly Cys Cys Thr Gly Gly Gly Gly Ala Ala Cys Cys
            500                 505                 510

Cys Ala Thr Cys Gly Gly Cys Ala Ala Ala Cys Gly Gly Cys Cys Thr
        515                 520                 525

Gly Thr Ala Cys Gly Ala Thr Thr Thr Ala Gly Cys Thr Thr Thr Gly
    530                 535                 540

Gly Gly Cys Cys Cys Thr Gly Cys Ala Gly Ala Thr Thr Cys Cys Ala
545                 550                 555                 560

Ala Ala Gly Ala Gly Gly Thr Gly Thr Gly Cys Thr Cys Cys Ala Cys
                565                 570                 575

Cys Thr Gly Cys Gly Thr Gly Cys Ala Gly Gly Ala Cys Thr Thr Cys
            580                 585                 590

Ala Gly Cys Ala Ala Cys Thr Gly Thr Thr Cys Thr Gly Gly Gly Cys
        595                 600                 605

Ala Cys Cys Thr Gly Gly Gly Cys Cys Ala Cys Ala Thr Thr Gly Ala
    610                 615                 620

Gly Cys Thr Cys Cys Cys Ala Cys Thr Cys Ala Cys Ala Gly Thr Gly
625                 630                 635                 640

Thr Ala Thr Ala Ala Cys Cys Cys Thr Cys Thr Cys Cys Thr Cys Thr
                645                 650                 655

Thr Cys Gly Ala Thr Ala Ala Gly Cys Thr Gly Thr Ala Cys Cys Thr
            660                 665                 670

Gly Cys Thr Gly Cys Thr Thr Cys Gly Gly Gly Gly Cys Thr Cys Thr
        675                 680                 685
```

-continued

```
Thr Gly Thr Thr Thr Ala Ala Ala Cys Thr Gly Cys Cys Ala Cys Ala
    690                 695                 700

Thr Gly Cys Thr Gly Ala Cys Thr Thr Gly Thr Cys Cys Cys Cys Gly
705                 710                 715                 720

Gly Gly Cys Cys Gly Thr Gly Ala Thr Thr Cys Ala Cys Cys Thr Cys
                725                 730                 735

Thr Thr Ala Cys Thr Cys Thr Gly Cys Cys Ala Gly Cys Thr Gly Ala
            740                 745                 750

Gly Gly Gly Thr Thr Cys Thr Gly Gly Ala Ala Gly Thr Cys Gly Gly
        755                 760                 765

Gly Gly Cys Cys Cys Thr Ala Cys Ala Ala Gly Cys Ala Gly Thr Cys
    770                 775                 780

Thr Ala Cys Gly Ala Gly Cys Thr Thr Gly Ala Gly Ala Gly Ala Ala
785                 790                 795                 800

Thr Thr Cys Thr Gly Ala Ala Cys Ala Gly Gly Thr Thr Thr Cys Thr
                805                 810                 815

Gly Gly Ala Ala Gly Ala Ala Ala Ala Thr Cys Cys Cys Gly Ala Thr
            820                 825                 830

Cys Cys Cys Thr Cys Thr Gly Cys Cys Thr Cys Thr Gly Ala Ala Ala
        835                 840                 845

Thr Thr Cys Gly Gly Gly Ala Gly Gly Ala Ala Thr Thr Ala Gly Ala
    850                 855                 860

Ala Cys Ala Ala Thr Ala Cys Ala Cys Ala Ala Cys Thr Gly Ala Ala
865                 870                 875                 880

Ala Thr Thr Gly Thr Gly Cys Ala Gly Ala Ala Cys Ala Ala Cys Cys
                885                 890                 895

Thr Cys Cys Thr Gly Gly Gly Gly Thr Cys Cys Cys Ala Gly Gly Gly
            900                 905                 910

Cys Gly Cys Ala Cys Ala Thr Gly Thr Ala Ala Ala Gly Ala Ala Cys
        915                 920                 925

Gly Thr Gly Thr Gly Thr Gly Ala Gly Ala Gly Cys Ala Ala Gly Ala
    930                 935                 940

Gly Cys Ala Ala Gly Cys Thr Cys Ala Thr Thr Gly Cys Thr Cys Thr
945                 950                 955                 960

Cys Thr Thr Cys Thr Gly Gly Ala Ala Gly Gly Cys Ala Cys Ala Thr
                965                 970                 975

Ala Thr Gly Ala Ala Thr Gly Cys Thr Ala Ala Gly Cys Gly Cys Thr
            980                 985                 990

Gly Thr Cys Cys Cys Cys Ala Cys  Thr Gly Cys Ala Ala  Gly Ala Cys
        995                 1000                 1005

Cys Gly  Gly Gly Cys Gly Ala  Thr Cys Cys Gly Thr  Thr Gly Thr
    1010                 1015                 1020

Cys Cys  Gly Ala Ala Ala Gly  Gly Ala Ala Cys Ala  Cys Ala Ala
    1025                 1030                 1035

Cys Ala  Gly Cys Ala Ala Gly  Thr Thr Gly Ala Cys  Thr Ala Thr
    1040                 1045                 1050

Cys Ala  Cys Gly Thr Thr Thr  Cys Cys Ala Gly Cys  Cys Ala Thr
    1055                 1060                 1065

Gly Gly  Thr Gly Cys Ala Cys  Ala Gly Gly Ala Cys  Ala Gly Cys
    1070                 1075                 1080

Thr Gly  Gly Cys Cys Ala Gly  Ala Ala Gly Gly Ala  Cys Thr Cys
    1085                 1090                 1095

Thr Gly  Ala Gly Cys Cys Cys  Cys Thr Gly Gly Gly  Ala Ala Thr
```

```
    1100                1105                1110

Thr Gly  Ala Gly Gly Ala Ala  Gly Cys Thr Cys Ala  Gly Ala Thr
    1115                1120                1125

Ala Gly  Gly Ala Ala Ala Ala  Cys Gly Ala Gly Gly  Ala Thr Ala
    1130                1135                1140

Cys Thr  Thr Ala Ala Cys Ala  Cys Cys Cys Ala Cys  Cys Ala Gly
    1145                1150                1155

Thr Gly  Cys Cys Cys Gly Cys  Gly Ala Ala Cys Ala  Cys Cys Thr
    1160                1165                1170

Thr Thr  Cys Thr Gly Cys Cys  Cys Thr Gly Thr Gly  Gly Ala Ala
    1175                1180                1185

Gly Ala  Ala Thr Gly Ala Ala  Gly Gly Ala Thr Thr  Cys Thr Thr
    1190                1195                1200

Thr Cys  Thr Gly Ala Ala Cys  Thr Ala Cys Cys Thr  Thr Thr Thr
    1205                1210                1215

Thr Thr  Cys Gly Gly Gly Ala  Ala Thr Gly Gly Ala  Thr Gly Ala
    1220                1225                1230

Thr Gly  Ala Thr Gly Gly Thr  Ala Thr Gly Gly Ala  Ala Thr Cys
    1235                1240                1245

Cys Ala  Gly Ala Thr Thr Cys  Ala Ala Thr Cys Cys  Cys Ala Gly
    1250                1255                1260

Thr Gly  Thr Gly Thr Thr Cys  Thr Thr Thr Cys Thr  Ala Gly Ala
    1265                1270                1275

Thr Thr  Thr Cys Thr Thr Gly  Gly Thr Gly Gly Thr  Gly Cys Cys
    1280                1285                1290

Gly Cys  Cys Cys Thr Cys Ala  Ala Gly Gly Thr Ala  Thr Cys Gly
    1295                1300                1305

Cys Cys  Cys Ala Gly Thr Cys  Ala Gly Thr Cys Gly  Cys Cys Thr
    1310                1315                1320

Ala Gly  Gly Ala Gly Ala Cys  Cys Ala Gly Ala Thr  Gly Thr Thr
    1325                1330                1335

Thr Ala  Cys Thr Ala Ala Thr  Gly Gly Cys Cys Ala  Gly Ala Cys
    1340                1345                1350

Gly Gly  Thr Gly Ala Ala Cys  Thr Thr Gly Cys Ala  Gly Gly Cys
    1355                1360                1365

Thr Gly  Thr Cys Ala Thr Gly  Ala Ala Gly Gly Ala  Thr Gly Thr
    1370                1375                1380

Ala Gly  Thr Thr Cys Thr Gly  Ala Thr Thr Cys Gly  Ala Ala Ala
    1385                1390                1395

Ala Cys  Thr Thr Cys Thr Gly  Gly Cys Ala Thr Thr  Gly Ala Thr
    1400                1405                1410

Gly Gly  Cys Cys Cys Ala Ala  Gly Ala Ala Cys Ala  Gly Ala Ala
    1415                1420                1425

Gly Thr  Thr Gly Cys Cys Ala  Gly Ala Gly Gly Ala  Ala Gly Thr
    1430                1435                1440

Gly Gly  Cys Cys Ala Cys Ala  Cys Cys Cys Ala Cys  Thr Ala Cys
    1445                1450                1455

Ala Gly  Ala Thr Gly Ala Gly  Gly Ala Ala Ala Ala  Ala Gly Ala
    1460                1465                1470

Cys Thr  Cys Thr Thr Thr Gly  Ala Thr Thr Gly Cys  Thr Ala Thr
    1475                1480                1485

Thr Gly  Ala Cys Cys Gly Ala  Thr Cys Cys Thr Thr  Thr Thr Thr
    1490                1495                1500
```

Gly Ala Gly Thr Ala Cys Ala Cys Thr Thr Cys Cys Ala Gly Gly
1505 1510 1515

Cys Cys Ala Gly Thr Cys Cys Cys Thr Cys Ala Thr Ala Gly Ala
1520 1525 1530

Cys Ala Ala Ala Cys Thr Thr Thr Ala Cys Ala Ala Cys Ala Thr
1535 1540 1545

Thr Thr Gly Gly Ala Thr Thr Cys Gly Cys Cys Thr Thr Cys Ala
1550 1555 1560

Gly Ala Gly Cys Cys Ala Cys Gly Thr Cys Ala Ala Thr Ala Thr
1565 1570 1575

Thr Gly Thr Gly Thr Thr Thr Gly Ala Thr Ala Gly Cys Gly Ala
1580 1585 1590

Gly Ala Thr Gly Gly Ala Cys Ala Ala Ala Cys Thr Ala Ala Thr
1595 1600 1605

Gly Ala Thr Gly Gly Ala Cys Ala Ala Gly Thr Ala Cys Cys Cys
1610 1615 1620

Ala Gly Gly Cys Ala Thr Thr Ala Gly Gly Cys Ala Gly Ala Thr
1625 1630 1635

Cys Cys Thr Gly Gly Ala Gly Ala Ala Gly Ala Ala Ala Gly Ala
1640 1645 1650

Ala Gly Gly Cys Cys Thr Gly Thr Thr Cys Cys Gly Ala Ala Ala
1655 1660 1665

Ala Cys Ala Cys Ala Thr Gly Ala Thr Gly Gly Gly Ala Ala Ala
1670 1675 1680

Gly Cys Gly Ala Gly Thr Gly Gly Ala Cys Thr Ala Cys Gly Cys
1685 1690 1695

Thr Gly Cys Gly Cys Gly Cys Thr Cys Ala Gly Thr Cys Ala Thr
1700 1705 1710

Cys Thr Gly Cys Cys Cys Ala Gly Ala Cys Ala Thr Gly Thr Ala
1715 1720 1725

Cys Ala Thr Cys Ala Ala Cys Ala Cys Cys Ala Ala Cys Gly Ala
1730 1735 1740

Ala Ala Thr Thr Gly Gly Ala Ala Thr Thr Cys Cys Cys Ala Thr
1745 1750 1755

Gly Gly Thr Gly Thr Thr Thr Gly Cys Cys Ala Cys Ala Ala Ala
1760 1765 1770

Ala Cys Thr Gly Ala Cys Cys Thr Ala Cys Cys Cys Ala Cys Ala
1775 1780 1785

Gly Cys Cys Ala Gly Thr Thr Ala Cys Cys Cys Cys Ala Thr Gly
1790 1795 1800

Gly Ala Ala Thr Gly Thr Thr Cys Ala Gly Gly Ala Ala Cys Thr
1805 1810 1815

Thr Ala Gly Gly Cys Ala Ala Gly Cys Gly Gly Thr Cys Ala Thr
1820 1825 1830

Cys Ala Ala Cys Gly Gly Cys Cys Cys Thr Ala Ala Thr Gly Thr
1835 1840 1845

Gly Cys Ala Cys Cys Cys Ala Gly Gly Ala Gly Cys Cys Thr Cys
1850 1855 1860

Cys Ala Thr Gly Gly Thr Cys Ala Thr Cys Ala Ala Thr Gly Ala
1865 1870 1875

Gly Gly Ala Cys Gly Gly Cys Ala Gly Cys Cys Gly Cys Ala Cys
1880 1885 1890

-continued

```
Ala Gly  Cys Cys Cys Thr Gly  Ala Gly Cys Gly Cys  Thr Gly Thr
    1895                 1900                 1905

Gly Gly  Ala Cys Ala Thr Gly  Ala Cys Cys Cys Ala  Gly Cys Gly
    1910                 1915                 1920

Ala Gly  Ala Gly Gly Cys Cys  Gly Thr Gly Gly Cys  Cys Ala Ala
    1925                 1930                 1935

Gly Cys  Ala Gly Cys Thr Thr  Cys Thr Gly Ala Cys  Cys Cys Cys
    1940                 1945                 1950

Ala Gly  Cys Cys Ala Cys Gly  Gly Gly Gly Gly Cys  Ala Cys Cys
    1955                 1960                 1965

Thr Ala  Ala Gly Cys Cys Cys  Cys Ala Gly Gly Gly  Gly Ala Cys
    1970                 1975                 1980

Ala Ala  Ala Ala Ala Thr Thr  Gly Thr Gly Thr Gly  Cys Cys Gly
    1985                 1990                 1995

Gly Cys  Ala Thr Gly Thr Gly  Ala Ala Gly Ala Ala  Thr Gly Gly
    2000                 2005                 2010

Gly Gly  Ala Cys Ala Thr Thr  Cys Thr Gly Cys Thr  Ala Cys Thr
    2015                 2020                 2025

Gly Ala  Ala Cys Cys Gly Ala  Cys Ala Gly Cys Cys  Cys Ala Cys
    2030                 2035                 2040

Ala Cys  Thr Gly Cys Ala Cys  Ala Gly Ala Cys Cys  Cys Thr Cys
    2045                 2050                 2055

Cys Ala  Thr Cys Cys Ala Gly  Gly Cys Cys Cys Ala  Cys Cys Gly
    2060                 2065                 2070

Thr Gly  Cys Cys Cys Gly Cys  Ala Thr Cys Cys Thr  Gly Cys Cys
    2075                 2080                 2085

Thr Gly  Ala Ala Gly Ala Gly  Ala Ala Ala Gly Thr  Gly Cys Thr
    2090                 2095                 2100

Gly Cys  Gly Gly Cys Thr Cys  Cys Ala Cys Thr Ala  Thr Gly Cys
    2105                 2110                 2115

Cys Ala  Ala Cys Thr Gly Cys  Ala Ala Gly Gly Cys  Cys Thr Ala
    2120                 2125                 2130

Thr Ala  Ala Thr Gly Cys Cys  Gly Ala Cys Thr Thr  Thr Gly Ala
    2135                 2140                 2145

Thr Gly  Gly Ala Gly Ala Cys  Gly Ala Gly Ala Thr  Gly Ala Ala
    2150                 2155                 2160

Thr Gly  Cys Cys Cys Ala Thr  Thr Thr Cys Cys Cys  Cys Cys Ala
    2165                 2170                 2175

Gly Ala  Gly Thr Gly Ala Gly  Cys Thr Gly Gly Gly  Cys Cys Gly
    2180                 2185                 2190

Gly Gly  Cys Cys Gly Ala Gly  Gly Cys Cys Thr Ala  Cys Gly Thr
    2195                 2200                 2205

Cys Cys  Thr Gly Gly Cys Cys  Thr Gly Cys Ala Cys  Thr Gly Ala
    2210                 2215                 2220

Thr Cys  Ala Gly Cys Ala Gly  Thr Ala Cys Cys Thr  Thr Gly Thr
    2225                 2230                 2235

Thr Cys  Cys Cys Ala Ala Gly  Gly Ala Thr Gly Gly  Cys Cys Ala
    2240                 2245                 2250

Ala Cys  Cys Ala Thr Thr Gly  Gly Cys Gly Gly Gly  Ala Cys Thr
    2255                 2260                 2265

Gly Ala  Thr Cys Cys Ala Gly  Gly Ala Thr Cys Ala  Cys Ala Thr
    2270                 2275                 2280

Gly Gly  Thr Thr Thr Cys Ala  Gly Gly Gly Gly Cys  Ala Ala Gly
```

2285 2290 2295

Cys Ala Thr Gly Ala Cys Thr Ala Cys Thr Cys Gly Gly Gly Gly
2300 2305 2310

Thr Thr Gly Cys Thr Thr Thr Thr Thr Cys Ala Cys Cys Cys Gly
2315 2320 2325

Gly Gly Ala Gly Cys Ala Cys Thr Ala Thr Ala Thr Gly Gly Ala
2330 2335 2340

Gly Cys Thr Gly Gly Thr Gly Thr Ala Cys Cys Gly Ala Gly Gly
2345 2350 2355

Ala Cys Thr Cys Ala Cys Gly Gly Ala Cys Ala Ala Ala Gly Thr
2360 2365 2370

Gly Gly Gly Gly Cys Gly Cys Gly Thr Gly Ala Ala Gly Cys Thr
2375 2380 2385

Cys Cys Thr Thr Thr Cys Thr Cys Cys Thr Thr Cys Cys Ala Thr
2390 2395 2400

Cys Cys Thr Gly Ala Ala Gly Cys Cys Cys Thr Thr Thr Cys Cys
2405 2410 2415

Gly Cys Thr Gly Thr Gly Gly Ala Cys Ala Gly Gly Ala Ala Ala
2420 2425 2430

Ala Cys Ala Gly Gly Thr Thr Gly Thr Gly Thr Cys Ala Ala Cys
2435 2440 2445

Gly Cys Thr Gly Cys Thr Cys Ala Thr Ala Ala Ala Thr Ala Thr
2450 2455 2460

Ala Ala Thr Cys Cys Cys Ala Gly Ala Gly Gly Ala Cys Cys Ala
2465 2470 2475

Cys Ala Thr Cys Cys Cys Ala Cys Thr Gly Ala Ala Cys Thr Thr
2480 2485 2490

Ala Thr Cys Thr Gly Gly Ala Ala Ala Gly Gly Cys Gly Ala Ala
2495 2500 2505

Ala Ala Thr Cys Ala Cys Thr Gly Gly Gly Ala Ala Ala Gly Cys
2510 2515 2520

Cys Thr Gly Gly Gly Thr Gly Ala Ala Gly Gly Ala Ala Ala Cys
2525 2530 2535

Thr Cys Cys Thr Cys Gly Ala Thr Cys Cys Gly Thr Thr Cys Cys
2540 2545 2550

Thr Gly Gly Cys Thr Thr Thr Ala Ala Cys Cys Cys Thr Gly Ala
2555 2560 2565

Cys Thr Cys Gly Ala Thr Gly Thr Gly Cys Gly Ala Gly Thr Cys
2570 2575 2580

Cys Cys Ala Gly Gly Thr Gly Ala Thr Cys Ala Thr Cys Ala Gly
2585 2590 2595

Gly Gly Ala Ala Gly Gly Gly Gly Ala Gly Cys Thr Gly Cys Thr
2600 2605 2610

Cys Thr Gly Cys Gly Gly Ala Gly Thr Gly Cys Thr Gly Gly Ala
2615 2620 2625

Cys Ala Ala Gly Gly Cys Gly Cys Ala Cys Thr Ala Thr Gly Gly
2630 2635 2640

Gly Ala Gly Cys Thr Cys Cys Gly Cys Cys Thr Ala Cys Gly Gly
2645 2650 2655

Cys Cys Thr Gly Gly Thr Cys Cys Ala Cys Thr Gly Cys Thr Gly
2660 2665 2670

Cys Thr Ala Thr Gly Ala Gly Ala Thr Cys Thr Ala Thr Gly Gly
2675 2680 2685

```
Ala Gly Gly Cys Gly Ala Gly Ala Cys Cys Ala Gly Cys Gly Gly
    2690                2695                2700

Cys Ala Ala Gly Gly Thr Thr Cys Thr Ala Ala Cys Cys Thr Gly
    2705                2710                2715

Cys Cys Thr Gly Gly Cys Cys Cys Gly Cys Cys Thr Cys Thr Thr
    2720                2725                2730

Cys Ala Cys Cys Gly Cys Cys Thr Ala Cys Cys Thr Gly Cys Ala
    2735                2740                2745

Gly Cys Thr Cys Thr Ala Cys Ala Gly Ala Gly Gly Cys Thr Thr
    2750                2755                2760

Cys Ala Cys Cys Thr Thr Gly Gly Gly Cys Gly Thr Gly Gly Ala
    2765                2770                2775

Ala Gly Ala Cys Ala Thr Thr Thr Thr Gly Gly Thr Gly Ala Ala
    2780                2785                2790

Gly Cys Cys Ala Ala Ala Gly Gly Cys Ala Gly Ala Thr Gly Thr
    2795                2800                2805

Cys Ala Ala Gly Ala Gly Gly Cys Ala Ala Cys Gly Thr Ala Thr
    2810                2815                2820

Cys Ala Thr Thr Gly Ala Ala Gly Ala Ala Thr Cys Cys Ala Cys
    2825                2830                2835

Cys Cys Ala Cys Thr Gly Cys Gly Gly Gly Cys Cys Cys Cys Ala
    2840                2845                2850

Gly Gly Cys Thr Gly Thr Cys Ala Gly Gly Gly Cys Thr Gly Cys
    2855                2860                2865

Ala Thr Thr Ala Ala Ala Cys Cys Thr Gly Cys Cys Ala Gly Ala
    2870                2875                2880

Ala Gly Cys Cys Gly Cys Ala Thr Cys Ala Thr Ala Thr Gly Ala
    2885                2890                2895

Thr Gly Ala Gly Gly Thr Cys Cys Gly Ala Gly Gly Ala Ala Ala
    2900                2905                2910

Ala Thr Gly Gly Cys Ala Gly Gly Ala Thr Gly Cys Cys Cys Ala
    2915                2920                2925

Thr Cys Thr Gly Gly Gly Cys Ala Ala Gly Gly Ala Cys Cys Ala
    2930                2935                2940

Gly Ala Gly Gly Gly Ala Thr Thr Thr Thr Ala Ala Cys Ala Thr
    2945                2950                2955

Gly Ala Thr Thr Gly Ala Thr Cys Thr Gly Ala Ala Gly Thr Thr
    2960                2965                2970

Cys Ala Ala Gly Gly Ala Gly Gly Ala Ala Gly Thr Gly Ala Ala
    2975                2980                2985

Cys Cys Ala Thr Thr Ala Cys Ala Gly Cys Ala Ala Thr Gly Ala
    2990                2995                3000

Gly Ala Thr Thr Ala Ala Cys Ala Ala Gly Gly Cys Ala Thr Gly
    3005                3010                3015

Cys Ala Thr Gly Cys Cys Thr Thr Thr Thr Gly Gly Cys Cys Thr
    3020                3025                3030

Ala Cys Ala Cys Ala Gly Ala Cys Ala Gly Thr Thr Cys Cys Cys
    3035                3040                3045

Ala Gly Ala Gly Ala Ala Cys Ala Gly Cys Cys Thr Gly Cys Ala
    3050                3055                3060

Gly Ala Thr Gly Ala Thr Gly Gly Thr Gly Cys Ala Gly Thr Cys
    3065                3070                3075
```

-continued

```
Gly Gly Gly Ala Gly Cys Cys Ala Ala Ala Gly Gly Thr Thr Cys
    3080                3085                3090

Ala Ala Cys Thr Gly Thr Gly Ala Ala Cys Ala Cys Gly Ala Thr
    3095                3100                3105

Gly Cys Ala Gly Ala Thr Cys Thr Cys Gly Thr Gly Cys Cys Thr
    3110                3115                3120

Gly Cys Thr Gly Gly Gly Cys Cys Ala Gly Ala Thr Thr Gly Ala
    3125                3130                3135

Ala Cys Thr Gly Gly Ala Ala Gly Gly Thr Cys Gly Gly Ala Gly
    3140                3145                3150

Ala Cys Cys Cys Cys Cys Gly Cys Thr Gly Ala Thr Gly Gly Cys
    3155                3160                3165

Gly Thr Cys Thr Gly Gly Cys Ala Ala Gly Thr Cys Ala Cys Thr
    3170                3175                3180

Gly Cys Cys Cys Thr Gly Cys Thr Thr Thr Gly Ala Gly Cys Cys
    3185                3190                3195

Thr Thr Ala Thr Gly Ala Gly Thr Thr Cys Ala Cys Cys Cys Cys
    3200                3205                3210

Cys Ala Gly Gly Gly Cys Thr Gly Gly Thr Gly Gly Cys Thr Thr
    3215                3220                3225

Thr Gly Thr Cys Ala Cys Thr Gly Gly Cys Ala Gly Gly Thr Thr
    3230                3235                3240

Cys Cys Thr Cys Ala Cys Cys Gly Gly Cys Ala Thr Cys Ala Ala
    3245                3250                3255

Ala Cys Cys Thr Cys Cys Thr Gly Ala Gly Thr Thr Cys Thr Thr
    3260                3265                3270

Cys Thr Thr Cys Cys Ala Cys Thr Gly Cys Ala Thr Gly Gly Cys
    3275                3280                3285

Ala Gly Gly Ala Cys Gly Ala Gly Ala Gly Gly Gly Cys Cys Thr
    3290                3295                3300

Gly Gly Thr Gly Gly Ala Cys Ala Cys Thr Gly Cys Thr Gly Thr
    3305                3310                3315

Gly Ala Ala Ala Ala Cys Cys Ala Gly Cys Cys Gly Cys Thr Cys
    3320                3325                3330

Ala Gly Gly Cys Thr Ala Thr Cys Thr Cys Cys Ala Ala Ala Gly
    3335                3340                3345

Gly Thr Gly Cys Ala Thr Cys Ala Thr Cys Ala Ala Gly Cys Ala
    3350                3355                3360

Cys Cys Thr Ala Gly Ala Gly Gly Gly Gly Cys Thr Gly Gly Thr
    3365                3370                3375

Cys Gly Thr Gly Cys Ala Gly Thr Ala Thr Gly Ala Thr Cys Thr
    3380                3385                3390

Cys Ala Cys Gly Gly Thr Cys Cys Gly Thr Gly Ala Cys Ala Gly
    3395                3400                3405

Thr Gly Ala Cys Gly Gly Cys Ala Gly Thr Gly Thr Gly Gly Thr
    3410                3415                3420

Gly Cys Ala Gly Thr Thr Cys Cys Thr Gly Thr Ala Thr Gly Gly
    3425                3430                3435

Gly Gly Ala Gly Gly Ala Thr Gly Gly Cys Cys Thr Gly Gly Ala
    3440                3445                3450

Cys Ala Thr Cys Cys Cys Cys Ala Ala Gly Ala Cys Ala Cys Ala
    3455                3460                3465

Gly Thr Thr Cys Cys Thr Gly Cys Ala Gly Cys Cys Cys Ala Ala
```

```
    3470                3475                3480

Gly Cys  Ala Gly Thr Thr Cys  Cys Cys Cys Thr Thr  Cys Cys Thr
    3485                3490                3495

Gly Gly  Cys Cys Ala Gly Cys  Ala Ala Cys Thr Ala  Cys Gly Ala
    3500                3505                3510

Gly Gly  Thr Gly Ala Thr Ala  Ala Thr Gly Ala Ala  Ala Thr Cys
    3515                3520                3525

Ala Cys  Ala Gly Cys Ala Thr  Cys Thr Cys Cys Ala  Thr Gly Ala
    3530                3535                3540

Ala Gly  Thr Thr Thr Thr Ala  Thr Cys Cys Ala Gly  Ala Gly Cys
    3545                3550                3555

Ala Gly  Ala Thr Cys Cys Cys  Ala Ala Ala Ala Ala  Ala Gly Cys
    3560                3565                3570

Thr Cys  Thr Cys Cys Ala Cys  Cys Ala Cys Thr Thr  Cys Ala Gly
    3575                3580                3585

Ala Gly  Cys Thr Ala Thr Cys  Ala Ala Ala Ala Ala  Ala Thr Gly
    3590                3595                3600

Gly Cys  Ala Ala Ala Gly Cys  Ala Ala Gly Cys Ala  Cys Cys Cys
    3605                3610                3615

Cys Ala  Ala Cys Ala Cys Cys  Cys Thr Gly Cys Thr  Gly Ala Gly
    3620                3625                3630

Ala Ala  Gly Ala Gly Gly Cys  Gly Cys Cys Thr Thr  Cys Thr Thr
    3635                3640                3645

Gly Ala  Gly Thr Thr Ala Thr  Thr Cys Cys Cys Ala  Gly Ala Ala
    3650                3655                3660

Ala Ala  Thr Thr Cys Ala Gly  Gly Ala Ala Gly Cys  Thr Gly Thr
    3665                3670                3675

Gly Ala  Ala Ala Gly Cys Cys  Cys Thr Gly Ala Ala  Ala Cys Thr
    3680                3685                3690

Thr Gly  Ala Gly Ala Gly Thr  Gly Ala Ala Ala Ala  Cys Cys Gly
    3695                3700                3705

Cys Ala  Ala Thr Gly Gly Cys  Cys Gly Cys Ala Gly  Cys Cys Cys
    3710                3715                3720

Thr Gly  Gly Gly Ala Cys Thr  Cys Ala Gly Gly Ala  Gly Ala Thr
    3725                3730                3735

Gly Cys  Thr Gly Ala Gly Gly  Ala Thr Gly Thr Gly  Gly Thr Ala
    3740                3745                3750

Thr Gly  Ala Gly Thr Thr Gly  Gly Ala Thr Gly Ala  Gly Gly Ala
    3755                3760                3765

Ala Ala  Gly Cys Cys Gly Ala  Ala Gly Gly Ala Ala  Ala Thr Ala
    3770                3775                3780

Cys Cys  Ala Gly Ala Ala Gly  Ala Ala Gly Gly Cys  Gly Gly Cys
    3785                3790                3795

Cys Gly  Cys Thr Thr Gly Thr  Cys Cys Thr Gly Ala  Cys Cys Cys
    3800                3805                3810

Cys Ala  Gly Thr Cys Thr Gly  Thr Cys Thr Gly Thr  Cys Thr Gly
    3815                3820                3825

Gly Cys  Gly Thr Cys Cys Thr  Gly Ala Cys Ala Thr  Cys Thr Ala
    3830                3835                3840

Cys Thr  Thr Thr Gly Cys Ala  Thr Cys Ala Gly Thr  Gly Thr Cys
    3845                3850                3855

Ala Gly  Ala Ala Ala Cys Ala  Thr Thr Thr Gly Ala  Ala Ala Cys
    3860                3865                3870
```

```
Ala Ala  Ala Gly Gly Thr Thr  Gly Ala Thr Gly Ala  Cys Thr Ala
    3875                 3880                 3885

Cys Ala  Gly Thr Cys Ala Ala  Gly Ala Gly Thr Gly  Gly Gly Cys
    3890                 3895                 3900

Ala Gly  Cys Thr Cys Ala Ala  Ala Cys Ala Gly Ala  Gly Ala Ala
    3905                 3910                 3915

Gly Ala  Gly Thr Thr Ala Thr  Gly Ala Gly Ala Ala  Ala Thr Cys
    3920                 3925                 3930

Ala Gly  Ala Gly Cys Thr Thr  Thr Cys Thr Cys Thr  Cys Gly Ala
    3935                 3940                 3945

Cys Ala  Gly Gly Thr Thr Gly  Ala Gly Gly Ala Cys  Cys Thr Thr
    3950                 3955                 3960

Gly Cys  Thr Gly Cys Ala Gly  Cys Thr Gly Ala Ala  Gly Thr Gly
    3965                 3970                 3975

Gly Cys  Ala Gly Cys Gly Cys  Thr Cys Ala Cys Thr  Gly Thr Gly
    3980                 3985                 3990

Thr Gly  Ala Gly Cys Cys Gly  Gly Gly Cys Gly Ala  Gly Gly Cys
    3995                 4000                 4005

Thr Gly  Thr Gly Gly Gly Cys  Cys Thr Gly Cys Thr  Gly Gly Cys
    4010                 4015                 4020

Thr Gly  Cys Cys Cys Ala Gly  Ala Gly Cys Ala Thr  Cys Gly Gly
    4025                 4030                 4035

Ala Gly  Ala Gly Cys Cys Cys  Thr Cys Cys Ala Cys  Cys Cys Ala
    4040                 4045                 4050

Gly Ala  Thr Gly Ala Cys Cys  Cys Thr Cys Ala Ala  Cys Ala Cys
    4055                 4060                 4065

Cys Thr  Thr Cys Cys Ala Cys  Thr Thr Thr Gly Cys  Ala Gly Gly
    4070                 4075                 4080

Cys Ala  Gly Ala Gly Gly Cys  Gly Ala Gly Ala Thr  Gly Ala Ala
    4085                 4090                 4095

Cys Gly  Thr Cys Ala Cys Cys  Cys Thr Gly Gly Gly  Cys Ala Thr
    4100                 4105                 4110

Thr Cys  Cys Ala Ala Gly Gly  Thr Thr Gly Cys Gly  Gly Gly Ala
    4115                 4120                 4125

Gly Ala  Thr Thr Cys Thr Cys  Ala Thr Gly Gly Thr  Gly Gly Cys
    4130                 4135                 4140

Cys Ala  Gly Cys Gly Cys Cys  Ala Ala Cys Ala Thr  Cys Ala Ala
    4145                 4150                 4155

Gly Ala  Cys Ala Cys Cys Cys  Ala Thr Gly Ala Thr  Gly Ala Gly
    4160                 4165                 4170

Cys Gly  Thr Gly Cys Cys Cys  Gly Thr Gly Cys Thr  Cys Ala Ala
    4175                 4180                 4185

Cys Ala  Cys Cys Ala Ala Gly  Ala Ala Ala Gly Cys  Cys Cys Thr
    4190                 4195                 4200

Gly Ala  Ala Gly Ala Gly Ala  Gly Thr Gly Ala Ala  Ala Ala Gly
    4205                 4210                 4215

Cys Cys  Thr Gly Ala Ala Gly  Ala Ala Gly Cys Ala  Ala Cys Thr
    4220                 4225                 4230

Cys Ala  Cys Cys Ala Gly Gly  Gly Thr Gly Thr Gly  Cys Thr Thr
    4235                 4240                 4245

Gly Gly  Gly Gly Gly Ala Gly  Gly Thr Gly Thr Thr  Gly Cys Ala
    4250                 4255                 4260
```

Gly Ala Ala Ala Ala Thr Thr Gly Ala Cys Gly Thr Cys Cys Ala
4265 4270 4275

Gly Gly Ala Gly Thr Cys Cys Thr Thr Cys Thr Gly Thr Ala Thr
4280 4285 4290

Gly Gly Ala Ala Gly Ala Ala Ala Ala Ala Cys Ala Gly Ala Ala
4295 4300 4305

Cys Ala Ala Ala Thr Thr Cys Cys Ala Gly Gly Thr Gly Thr Ala
4310 4315 4320

Cys Cys Ala Gly Cys Thr Gly Cys Gly Gly Thr Thr Thr Cys Ala
4325 4330 4335

Gly Thr Thr Cys Cys Thr Gly Cys Cys Ala Cys Ala Thr Gly Cys
4340 4345 4350

Ala Thr Ala Thr Thr Ala Cys Cys Ala Gly Cys Ala Gly Gly Ala
4355 4360 4365

Gly Ala Ala Gly Thr Gly Cys Cys Thr Gly Ala Gly Ala Cys Cys
4370 4375 4380

Cys Gly Ala Gly Gly Ala Cys Ala Thr Cys Cys Thr Gly Cys Gly
4385 4390 4395

Cys Thr Thr Cys Ala Thr Gly Gly Ala Ala Ala Cys Ala Ala Gly
4400 4405 4410

Ala Thr Thr Cys Thr Thr Thr Ala Ala Ala Cys Thr Thr Cys Thr
4415 4420 4425

Gly Ala Thr Gly Gly Ala Ala Thr Cys Cys Ala Thr Cys Ala Ala
4430 4435 4440

Ala Ala Ala Gly Ala Ala Gly Ala Ala Thr Ala Ala Thr Ala Ala
4445 4450 4455

Ala Gly Cys Ala Thr Cys Ala Gly Cys Thr Thr Thr Cys Ala Gly
4460 4465 4470

Gly Ala Ala Cys Gly Thr Ala Ala Ala Cys Ala Cys Thr Cys Gly
4475 4480 4485

Ala Ala Gly Ala Gly Cys Thr Ala Cys Ala Cys Ala Gly Cys Gly
4490 4495 4500

Gly Gly Ala Thr Cys Thr Gly Gly Ala Cys Ala Ala Cys Gly Cys
4505 4510 4515

Thr Gly Gly Gly Gly Ala Gly Thr Thr Gly Gly Gly Gly Ala Gly
4520 4525 4530

Gly Ala Gly Thr Cys Gly Gly Gly Gly Ala Gly Ala Gly Cys Ala
4535 4540 4545

Gly Gly Ala Gly Gly Gly Thr Gly Ala Thr Gly Ala Gly Gly Ala
4550 4555 4560

Ala Gly Ala Gly Gly Ala Gly Gly Gly Gly Cys Ala Cys Ala Thr
4565 4570 4575

Thr Gly Thr Gly Gly Ala Thr Gly Cys Thr Gly Ala Ala Gly Cys
4580 4585 4590

Thr Gly Ala Gly Gly Ala Gly Gly Gly Gly Gly Ala Cys Gly Cys
4595 4600 4605

Cys Gly Ala Thr Gly Cys Cys Thr Cys Thr Gly Ala Thr Gly Cys
4610 4615 4620

Cys Ala Ala Ala Cys Gly Cys Ala Ala Gly Gly Ala Gly Ala Ala
4625 4630 4635

Gly Cys Ala Gly Gly Ala Gly Gly Ala Gly Gly Ala Gly Gly Thr
4640 4645 4650

Thr Gly Ala Thr Thr Ala Thr Gly Ala Gly Ala Gly Thr Gly Ala

-continued

```
    4655                4660                4665

Gly Gly  Ala Ala Gly Ala Gly  Gly Ala Gly Gly Ala  Gly Ala Gly
    4670                4675                4680

Gly Gly  Ala Gly Gly Gly Cys  Gly Ala Gly Gly Ala  Gly Ala Ala
    4685                4690                4695

Cys Gly  Ala Cys Gly Ala Thr  Gly Ala Ala Gly Ala  Cys Ala Thr
    4700                4705                4710

Gly Cys  Ala Gly Gly Ala Gly  Gly Ala Ala Cys Gly  Ala Ala Ala
    4715                4720                4725

Thr Cys  Cys Cys Cys Ala Cys  Ala Gly Gly Gly Ala  Ala Gly Gly
    4730                4735                4740

Thr Gly  Cys Thr Cys Gly Ala  Ala Ala Gly Ala Cys  Cys Cys Ala
    4745                4750                4755

Ala Gly  Ala Gly Cys Ala Ala  Gly Ala Thr Gly Ala  Ala Gly Ala
    4760                4765                4770

Gly Gly  Thr Gly Gly Gly Cys  Thr Thr Ala Gly Gly  Cys Ala Cys
    4775                4780                4785

Thr Gly  Ala Gly Gly Ala Gly  Gly Ala Cys Cys Cys  Gly Thr Cys
    4790                4795                4800

Cys Cys  Thr Thr Cys Cys Cys  Gly Cys Cys Cys Thr  Cys Cys Thr
    4805                4810                4815

Gly Ala  Cys Gly Cys Ala Gly  Cys Cys Cys Cys Gly  Gly Ala Ala
    4820                4825                4830

Ala Cys  Cys Cys Ala Cys Cys  Cys Ala Cys Ala Gly  Cys Cys Ala
    4835                4840                4845

Gly Gly  Ala Gly Cys Cys Cys  Cys Ala Gly Gly Gly  Gly Cys Cys
    4850                4855                4860

Cys Gly  Ala Gly Gly Cys Cys  Ala Thr Gly Gly Ala  Gly Cys Gly
    4865                4870                4875

Cys Cys  Gly Gly Gly Thr Cys  Cys Ala Gly Gly Cys  Thr Gly Thr
    4880                4885                4890

Gly Cys  Gly Thr Gly Ala Gly  Ala Thr Cys Cys Ala  Cys Cys Cys
    4895                4900                4905

Gly Thr  Thr Cys Ala Thr Ala  Gly Ala Thr Gly Ala  Cys Thr Ala
    4910                4915                4920

Cys Cys  Ala Gly Thr Ala Cys  Gly Ala Cys Ala Cys  Cys Gly Ala
    4925                4930                4935

Gly Gly  Ala Gly Ala Gly Cys  Cys Thr Gly Thr Gly  Gly Thr Gly
    4940                4945                4950

Cys Cys  Ala Gly Gly Thr Gly  Ala Cys Ala Gly Thr  Gly Ala Ala
    4955                4960                4965

Gly Cys  Thr Cys Cys Cys Thr  Cys Thr Gly Ala Thr  Gly Ala Ala
    4970                4975                4980

Gly Ala  Thr Cys Ala Ala Cys  Thr Thr Thr Gly Ala  Cys Ala Thr
    4985                4990                4995

Gly Ala  Gly Cys Thr Cys Cys  Cys Thr Gly Gly Thr  Ala Gly Thr
    5000                5005                5010

Ala Thr  Cys Thr Thr Thr Gly  Gly Cys Cys Cys Ala  Thr Gly Gly
    5015                5020                5025

Thr Gly  Cys Cys Gly Thr Cys  Ala Thr Cys Thr Ala  Thr Gly Cys
    5030                5035                5040

Gly Ala  Cys Cys Ala Ala Gly  Gly Gly Cys Ala Thr  Cys Ala Cys
    5045                5050                5055
```

-continued

Thr Cys Gly Gly Thr Gly Cys Cys Thr Cys Cys Thr Gly Ala Ala
5060 5065 5070

Thr Gly Ala Ala Ala Cys Ala Ala Cys Cys Ala Ala Cys Ala Ala
5075 5080 5085

Thr Ala Ala Gly Ala Ala Cys Gly Ala Gly Ala Ala Gly Gly Ala
5090 5095 5100

Gly Cys Thr Thr Gly Thr Gly Cys Thr Ala Ala Ala Cys Ala Cys
5105 5110 5115

Ala Gly Ala Ala Gly Gly Ala Ala Thr Cys Ala Ala Cys Cys Thr
5120 5125 5130

Cys Cys Cys Ala Gly Ala Gly Cys Thr Ala Thr Thr Cys Ala Ala
5135 5140 5145

Gly Thr Ala Thr Gly Cys Ala Gly Ala Gly Gly Thr Cys Cys Thr
5150 5155 5160

Gly Gly Ala Thr Cys Thr Gly Cys Gly Cys Cys Gly Cys Cys Thr
5165 5170 5175

Cys Thr Ala Cys Thr Cys Cys Ala Ala Cys Gly Ala Cys Ala Thr
5180 5185 5190

Cys Cys Ala Cys Gly Cys Cys Ala Thr Ala Gly Cys Cys Ala Ala
5195 5200 5205

Cys Ala Cys Gly Thr Ala Thr Gly Gly Cys Ala Thr Thr Gly Ala
5210 5215 5220

Gly Gly Cys Cys Gly Cys Gly Cys Thr Gly Cys Gly Gly Gly Thr
5225 5230 5235

Gly Ala Thr Cys Gly Ala Gly Ala Ala Gly Gly Ala Gly Ala Thr
5240 5245 5250

Cys Ala Ala Gly Gly Ala Thr Gly Thr Gly Thr Thr Thr Gly Cys
5255 5260 5265

Cys Gly Thr Gly Thr Ala Thr Gly Gly Cys Ala Thr Cys Gly Cys
5270 5275 5280

Gly Gly Thr Cys Gly Ala Cys Cys Cys Thr Cys Gly Cys Cys Ala
5285 5290 5295

Thr Cys Thr Cys Thr Cys Cys Cys Thr Gly Gly Thr Thr Gly Cys
5300 5305 5310

Thr Gly Ala Thr Thr Ala Thr Ala Thr Gly Thr Gly Cys Thr Thr
5315 5320 5325

Cys Gly Ala Gly Gly Gly Thr Gly Thr Thr Thr Ala Cys Ala Ala
5330 5335 5340

Gly Cys Cys Ala Cys Thr Gly Ala Ala Thr Cys Gly Cys Thr Thr
5345 5350 5355

Thr Gly Gly Gly Ala Thr Cys Cys Gly Gly Thr Cys Ala Ala Ala
5360 5365 5370

Cys Thr Cys Thr Thr Cys Cys Cys Cys Gly Cys Thr Ala Cys Ala
5375 5380 5385

Gly Cys Ala Gly Ala Thr Gly Ala Cys Ala Thr Thr Thr Gly Ala
5390 5395 5400

Ala Ala Cys Cys Ala Gly Cys Thr Thr Cys Cys Ala Gly Thr Thr
5405 5410 5415

Thr Cys Thr Gly Ala Ala Gly Cys Ala Ala Gly Cys Cys Ala Cys
5420 5425 5430

Cys Ala Thr Gly Cys Thr Gly Gly Gly Ala Thr Cys Cys Cys Ala
5435 5440 5445

Cys Gly Ala Thr Gly Ala Gly Cys Thr Gly Ala Gly Gly Thr Cys
5450 5455 5460

Thr Cys Cys Thr Thr Cys Thr Gly Cys Cys Thr Gly Cys Cys Thr
5465 5470 5475

Thr Gly Thr Gly Gly Thr Cys Gly Gly Gly Ala Ala Gly Gly Thr
5480 5485 5490

Cys Gly Thr Cys Ala Gly Gly Gly Gly Cys Gly Gly Gly Ala Cys
5495 5500 5505

Ala Gly Gly Cys Cys Thr Gly Thr Thr Cys Gly Ala Gly Cys Thr
5510 5515 5520

Cys Ala Ala Gly Cys Ala Gly Cys Cys Thr Cys Thr Gly Ala Gly
5525 5530 5535

Ala Thr Ala Gly Cys Ala Gly Cys Thr Ala Cys Cys Cys Cys Gly
5540 5545 5550

Gly Cys Ala Cys Cys Ala Thr Cys Thr Gly Cys Cys Cys Ala Gly
5555 5560 5565

Cys Thr Cys Cys Ala Ala Gly Gly Ala Cys Cys Cys Thr Thr Gly
5570 5575 5580

Gly Thr Gly Ala Gly Gly Gly Cys Gly Thr Gly Gly Cys Cys Cys
5585 5590 5595

Ala Gly Cys Cys Thr Gly Cys Cys Thr Thr Cys Thr Gly Cys Ala
5600 5605 5610

Thr Gly Ala Gly Ala Gly Gly Ala Cys Cys Ala Gly Gly Ala Gly
5615 5620 5625

Ala Cys Thr Gly Gly Ala Ala Thr Cys Cys Ala Gly Gly Gly Cys
5630 5635 5640

Ala Gly Thr Thr Cys Cys Ala Ala Gly Thr Gly Ala Cys Ala Gly
5645 5650 5655

Thr Ala Cys Ala Gly Ala Gly Cys Ala Cys Ala Gly Cys Ala Gly
5660 5665 5670

Cys Gly Ala Cys Cys Thr Thr Gly Gly Gly Cys Cys Thr Gly Ala
5675 5680 5685

Ala Ala Gly Cys Ala Gly Thr Gly Gly Gly Cys Cys Thr Cys Thr
5690 5695 5700

Gly Ala Gly Cys Thr Gly Gly Gly Cys Cys Ala Gly Cys Thr Thr
5705 5710 5715

Cys Ala Cys Cys Thr Gly Gly Ala Ala Ala Gly Thr Gly Ala Cys
5720 5725 5730

Ala Gly Ala Gly Thr Thr Gly Cys Thr Cys Ala Thr Cys Cys Thr
5735 5740 5745

Thr Gly Cys Cys Cys Cys Thr Cys Cys Cys Thr Gly Thr Cys Thr
5750 5755 5760

Cys Thr Gly Gly Ala Thr Thr Thr Thr Thr Ala Thr Cys Ala Ala
5765 5770 5775

Gly Gly Thr Thr Thr Ala Cys Cys Ala Ala Gly Thr Cys Thr Thr
5780 5785 5790

Cys Thr Gly Ala Gly Thr Cys Cys Cys Cys Cys Thr Gly Ala Gly
5795 5800 5805

Ala Thr Gly Gly Cys Thr Gly Gly Gly Gly Cys Cys Thr Cys Ala
5810 5815 5820

Cys Cys Thr Gly Thr Gly Cys Thr Gly Cys Ala Gly Gly Ala Gly
5825 5830 5835

Gly Cys Cys Thr Cys Thr Gly Thr Gly Gly Cys Ala Thr Ala Ala

```
    5840                5845                5850

Cys Cys  Cys Cys Thr Ala Ala  Gly Gly Ala Gly Ala  Ala Gly Thr
    5855                5860                5865

Cys Cys  Thr Gly Ala Thr Thr  Cys Ala Cys Gly Ala  Thr Thr Cys
    5870                5875                5880

Ala Cys  Thr Gly Ala Gly Ala  Ala Gly Ala Cys Cys  Ala Ala Gly
    5885                5890                5895

Gly Gly  Gly Ala Ala Gly Cys  Cys Ala Thr Gly Cys  Thr Thr Thr
    5900                5905                5910

Gly Cys  Thr Gly Cys Thr Gly  Gly Gly Gly Ala Cys  Cys Cys Cys
    5915                5920                5925

Ala Gly  Gly Cys Ala Cys Cys  Thr Cys Cys Ala Gly  Ala Gly Thr
    5930                5935                5940

Ala Gly  Gly Gly Ala Ala Gly  Cys Gly Gly Gly Gly  Thr Thr Cys
    5945                5950                5955

Thr Thr  Thr Thr Gly Cys Thr  Gly Thr Gly Ala Gly  Thr Gly Gly
    5960                5965                5970

Cys Cys  Ala Gly Gly Gly Ala  Cys Ala Ala Cys Ala  Gly Ala Cys
    5975                5980                5985

Ala Ala  Gly Ala Thr Thr Cys  Cys Thr Gly Gly Gly  Gly Gly Cys
    5990                5995                6000

Thr Cys  Cys Cys Gly Ala Thr  Gly Ala Gly Cys Ala  Gly Gly Ala
    6005                6010                6015

Ala Cys  Gly Thr Gly Gly Ala  Gly Cys Cys Thr Gly  Cys Thr Gly
    6020                6025                6030

Cys Cys  Cys Ala Ala Gly Gly  Cys Cys Thr Gly Cys  Thr Cys Cys
    6035                6040                6045

Thr Thr  Cys Cys Gly Gly Cys  Thr Gly Cys Thr Cys  Cys Ala Gly
    6050                6055                6060

Cys Cys  Cys Cys Thr Gly Gly  Gly Gly Gly Cys Ala  Gly Ala Gly
    6065                6070                6075

Thr Cys  Cys Ala Cys Ala Ala  Ala Gly Ala Gly Thr  Cys Cys Cys
    6080                6085                6090

Cys Ala  Thr Cys Ala Ala Gly  Ala Cys Thr Thr Cys  Thr Thr Cys
    6095                6100                6105

Cys Cys  Thr Gly Ala Gly Thr  Cys Ala Ala Gly Thr  Ala Cys Ala
    6110                6115                6120

Gly Cys  Gly Thr Ala Gly Cys  Ala Thr Ala Gly Thr  Cys Cys Thr
    6125                6130                6135

Cys Cys  Ala Cys Cys Cys Ala  Cys Cys Cys Ala Ala  Cys Cys Thr
    6140                6145                6150

Cys Thr  Cys Thr Gly Cys Cys  Thr Gly Gly Cys Cys  Ala Gly Gly
    6155                6160                6165

Gly Thr  Cys Cys Thr Gly Gly  Cys Cys Cys Thr Gly  Cys Cys Ala
    6170                6175                6180

Cys Thr  Gly Thr Gly Thr Gly  Gly Cys Gly Ala Gly  Gly Thr Gly
    6185                6190                6195

Thr Cys  Cys Thr Thr Cys Thr  Ala Gly Ala Cys Cys  Ala Cys Ala
    6200                6205                6210

Thr Cys  Ala Gly Cys Cys Cys  Cys Ala Ala Gly Gly  Cys Thr Gly
    6215                6220                6225

Gly Gly  Ala Gly Cys Ala Gly  Thr Cys Gly Cys Thr  Cys Cys Ala
    6230                6235                6240
```

-continued

Gly Gly Gly Cys Cys Gly Cys Ala Gly Cys Ala Gly Thr Thr Cys
6245 6250 6255

Ala Cys Thr Cys Cys Cys Ala Cys Ala Cys Ala Thr Ala Gly Ala
6260 6265 6270

Ala Cys Cys Cys Ala Gly Gly Thr Cys Ala Cys Thr Gly Cys Thr
6275 6280 6285

Gly Gly Gly Gly Cys Gly Ala Thr Thr Gly Ala Ala Cys Ala Gly
6290 6295 6300

Gly Thr Thr Gly Cys Cys Thr Gly Gly Cys Thr Thr Thr Thr Cys
6305 6310 6315

Thr Cys Thr Gly Cys Thr Gly Thr Cys Ala Gly Thr Thr Thr Gly
6320 6325 6330

Gly Thr Gly Thr Gly Gly Ala Gly Gly Cys Cys Thr Ala Thr Gly
6335 6340 6345

Thr Thr Cys Thr Gly Cys Cys Cys Cys Ala Thr Ala Cys Ala Cys
6350 6355 6360

Cys Cys Cys Ala Cys Ala Gly Gly Cys Cys Cys Thr Gly Cys Thr
6365 6370 6375

Thr Ala Thr Gly Gly Gly Ala Ala Gly Gly Ala Ala Cys Ala Cys
6380 6385 6390

Ala Gly Gly Cys Cys Thr Cys Cys Ala Gly Cys Cys Cys Ala Gly
6395 6400 6405

Ala Gly Gly Ala Cys Thr Gly Thr Gly Cys Cys Gly Cys Cys Cys
6410 6415 6420

Thr Gly Thr Thr Cys Thr Thr Gly Gly Cys Cys Gly Thr Cys Cys
6425 6430 6435

Ala Cys Gly Thr Thr Thr Cys Cys Thr Cys Thr Cys Cys Cys Thr
6440 6445 6450

Cys Thr Ala Gly Cys Ala Cys Cys Ala Gly Cys Ala Ala Thr Ala
6455 6460 6465

Cys Ala Thr Thr Thr Cys Cys Cys Thr Gly Gly Cys Ala Thr Gly
6470 6475 6480

Gly Ala Cys Ala Gly Ala Ala Ala Ala Gly Ala Cys Ala Gly Ala
6485 6490 6495

Gly Ala Gly Gly Ala Cys Thr Thr Ala Thr Ala Cys Ala Ala Ala
6500 6505 6510

Gly Gly Cys Thr Thr Thr Gly Thr Ala Ala Ala Ala Cys Cys Ala
6515 6520 6525

Gly Ala Gly Gly Cys Thr Ala Gly Cys Thr Thr Cys Thr Ala Thr
6530 6535 6540

Cys Thr Thr Thr Gly Thr Cys Thr Ala Cys Thr Gly Thr Thr Ala
6545 6550 6555

Thr Thr Thr Cys Ala Gly Cys Thr Cys Ala Gly Gly Gly Cys Gly
6560 6565 6570

Gly Gly Thr Ala Ala Thr Thr Ala Ala Cys Ala Thr Cys Ala Thr
6575 6580 6585

Thr Gly Gly Ala Ala Cys Thr Ala Gly Cys Thr Ala Thr Thr Ala
6590 6595 6600

Gly Gly Ala Ala Ala Gly Ala Ala Ala Ala Ala Ala Ala Ala Cys
6605 6610 6615

Thr Thr Gly Gly Thr Thr Thr Thr Thr Thr Thr Thr Ala Cys Ala
6620 6625 6630

```
Ala Cys  Ala Ala
    6635


<210> SEQ ID NO 47
<211> LENGTH: 419
<212> TYPE: PRT
<213> ORGANISM: Homo sapiens

<400> SEQUENCE: 47

Met Ala Ala Glu Val Leu Pro Ser Ala Arg Trp Gln Tyr Cys Gly Ala
1               5                   10                  15

Pro Asp Gly Ser Gln Arg Ala Val Leu Val Gln Phe Ser Asn Gly Lys
            20                  25                  30

Leu Gln Ser Pro Gly Asn Met Arg Phe Thr Leu Tyr Glu Asn Lys Asp
        35                  40                  45

Ser Thr Asn Pro Arg Lys Arg Asn Gln Arg Ile Leu Ala Ala Glu Thr
    50                  55                  60

Asp Arg Leu Ser Tyr Val Gly Asn Asn Phe Gly Thr Gly Ala Leu Lys
65                  70                  75                  80

Cys Asn Thr Leu Cys Arg His Phe Val Gly Ile Leu Asn Lys Thr Ser
                85                  90                  95

Gly Gln Met Glu Val Tyr Asp Ala Glu Leu Phe Asn Met Gln Pro Leu
            100                 105                 110

Phe Ser Asp Val Ser Val Glu Ser Glu Leu Ala Leu Glu Ser Gln Thr
        115                 120                 125

Lys Thr Tyr Arg Glu Lys Met Asp Ser Cys Ile Glu Ala Phe Gly Thr
    130                 135                 140

Thr Lys Gln Lys Arg Ala Leu Asn Thr Arg Arg Met Asn Arg Val Gly
145                 150                 155                 160

Asn Glu Ser Leu Asn Arg Ala Val Ala Lys Ala Ala Glu Thr Ile Ile
                165                 170                 175

Asp Thr Lys Gly Val Thr Ala Leu Val Ser Asp Ala Ile His Asn Asp
            180                 185                 190

Leu Gln Asp Asp Ser Leu Tyr Leu Pro Pro Cys Tyr Asp Asp Ala Ala
        195                 200                 205

Lys Pro Glu Asp Val Tyr Lys Phe Glu Asp Leu Leu Ser Pro Ala Glu
    210                 215                 220

Tyr Glu Ala Leu Gln Ser Pro Ser Glu Ala Phe Arg Asn Val Thr Ser
225                 230                 235                 240

Glu Glu Ile Leu Lys Met Ile Glu Glu Asn Ser His Cys Thr Phe Val
                245                 250                 255

Ile Glu Ala Leu Lys Ser Leu Pro Ser Asp Val Glu Ser Arg Asp Arg
            260                 265                 270

Gln Ala Arg Cys Ile Trp Phe Leu Asp Thr Leu Ile Lys Phe Arg Ala
        275                 280                 285

His Arg Val Val Lys Arg Lys Ser Ala Leu Gly Pro Gly Val Pro His
    290                 295                 300

Ile Ile Asn Thr Lys Leu Leu Lys His Phe Thr Cys Leu Thr Tyr Asn
305                 310                 315                 320

Asn Gly Arg Leu Arg Asn Leu Ile Ser Asp Ser Met Lys Ala Lys Ile
                325                 330                 335

Thr Ala Tyr Val Ile Ile Leu Ala Leu His Ile His Asp Phe Gln Ile
            340                 345                 350

Asp Leu Thr Val Leu Gln Arg Asp Leu Lys Leu Ser Glu Lys Arg Met
        355                 360                 365
```

Met Glu Ile Ala Lys Ala Met Arg Leu Lys Ile Ser Lys Arg Arg Val
    370                 375                 380

Ser Val Ala Ala Gly Ser Glu Glu Asp His Lys Leu Gly Thr Leu Ser
385                 390                 395                 400

Leu Pro Leu Pro Pro Ala Gln Thr Ser Asp Arg Leu Ala Lys Arg Arg
                405                 410                 415

Lys Ile Thr

<210> SEQ ID NO 48
<211> LENGTH: 851
<212> TYPE: PRT
<213> ORGANISM: Homo sapiens

<400> SEQUENCE: 48

Met Ser Ser Lys Gln Glu Ile Met Ser Asp Gln Arg Phe Arg Arg Val
1               5                   10                  15

Ala Lys Asp Pro Arg Phe Trp Glu Met Pro Glu Lys Asp Arg Lys Val
            20                  25                  30

Lys Ile Asp Lys Arg Phe Arg Ala Met Phe His Asp Lys Lys Phe Lys
        35                  40                  45

Leu Asn Tyr Ala Val Asp Lys Arg Gly Arg Pro Ile Ser His Ser Thr
    50                  55                  60

Thr Glu Asp Leu Lys Arg Phe Tyr Asp Leu Ser Asp Ser Asp Ser Asn
65                  70                  75                  80

Leu Ser Gly Glu Asp Ser Lys Ala Leu Ser Gln Lys Lys Ile Lys Lys
                85                  90                  95

Lys Lys Thr Gln Thr Lys Lys Glu Ile Asp Ser Lys Asn Leu Val Glu
            100                 105                 110

Lys Lys Lys Glu Thr Lys Lys Ala Asn His Lys Gly Ser Glu Asn Lys
        115                 120                 125

Thr Asp Leu Asp Asn Ser Ile Gly Ile Lys Lys Met Lys Thr Ser Cys
    130                 135                 140

Lys Phe Lys Ile Asp Ser Asn Ile Ser Pro Lys Lys Asp Ser Lys Glu
145                 150                 155                 160

Phe Thr Gln Lys Asn Lys Lys Glu Lys Lys Asn Ile Val Gln His Thr
                165                 170                 175

Thr Asp Ser Ser Leu Glu Glu Lys Gln Arg Thr Leu Asp Ser Gly Thr
            180                 185                 190

Ser Glu Ile Val Lys Ser Pro Arg Ile Glu Cys Ser Lys Thr Arg Arg
        195                 200                 205

Glu Met Gln Ser Val Val Gln Leu Ile Met Thr Arg Asp Ser Asp Gly
    210                 215                 220

Tyr Glu Asn Ser Thr Asp Gly Glu Met Cys Asp Lys Asp Ala Leu Glu
225                 230                 235                 240

Glu Asp Ser Glu Ser Val Ser Glu Ile Gly Ser Asp Glu Glu Ser Glu
                245                 250                 255

Asn Glu Ile Thr Ser Val Gly Arg Ala Ser Gly Asp Asp Asp Gly Ser
            260                 265                 270

Glu Asp Asp Glu Glu Glu Asp Glu Asp Glu Glu Glu Asp Glu Asp Glu
        275                 280                 285

Asp Ser Glu Asp Asp Asp Lys Ser Asp Ser Gly Pro Asp Leu Ala Arg
    290                 295                 300

Gly Lys Gly Asn Ile Glu Thr Ser Ser Glu Asp Glu Asp Asp Thr Ala
305                 310                 315                 320

-continued

```
Asp Leu Phe Pro Glu Glu Ser Gly Phe Glu His Ala Trp Arg Glu Leu
                325                 330                 335

Asp Lys Asp Ala Pro Arg Ala Asp Glu Ile Thr Arg Arg Leu Ala Val
            340                 345                 350

Cys Asn Met Asp Trp Asp Arg Leu Lys Ala Lys Asp Leu Leu Ala Leu
        355                 360                 365

Phe Asn Ser Phe Lys Pro Lys Gly Gly Val Ile Phe Ser Val Lys Ile
    370                 375                 380

Tyr Pro Ser Glu Phe Gly Lys Glu Arg Met Lys Glu Glu Gln Val Gln
385                 390                 395                 400

Gly Pro Val Glu Leu Leu Ser Ile Pro Glu Asp Ala Pro Glu Lys Asp
                405                 410                 415

Trp Thr Ser Arg Glu Lys Leu Arg Asp Tyr Gln Phe Lys Arg Leu Lys
            420                 425                 430

Tyr Tyr Tyr Ala Val Val Asp Cys Asp Ser Pro Glu Thr Ala Ser Lys
        435                 440                 445

Ile Tyr Glu Asp Cys Asp Gly Leu Glu Phe Glu Ser Ser Cys Ser Phe
    450                 455                 460

Ile Asp Leu Arg Phe Ile Pro Asp Asp Ile Thr Phe Asp Asp Glu Pro
465                 470                 475                 480

Lys Asp Val Ala Ser Glu Val Asn Leu Thr Ala Tyr Lys Pro Lys Tyr
                485                 490                 495

Phe Thr Ser Ala Ala Met Gly Thr Ser Thr Val Glu Ile Thr Trp Asp
            500                 505                 510

Glu Thr Asp His Glu Arg Ile Thr Met Leu Asn Arg Lys Phe Lys Lys
        515                 520                 525

Glu Glu Leu Leu Asp Met Asp Phe Gln Ala Tyr Leu Ala Ser Ser Ser
    530                 535                 540

Glu Asp Glu Glu Glu Ile Glu Glu Glu Leu Gln Gly Asp Asp Gly Val
545                 550                 555                 560

Asn Val Glu Glu Asp Gly Lys Thr Lys Lys Ser Gln Lys Asp Asp Glu
                565                 570                 575

Glu Gln Ile Ala Lys Tyr Arg Gln Leu Leu Gln Val Ile Gln Glu Lys
            580                 585                 590

Glu Lys Lys Gly Lys Glu Asn Asp Met Glu Met Glu Ile Lys Trp Val
        595                 600                 605

Pro Gly Leu Lys Glu Ser Ala Glu Glu Met Val Lys Asn Lys Leu Glu
    610                 615                 620

Gly Lys Asp Lys Leu Thr Pro Trp Glu Gln Phe Leu Glu Lys Lys Lys
625                 630                 635                 640

Glu Lys Lys Arg Leu Lys Arg Lys Gln Lys Ala Leu Ala Glu Glu Ala
                645                 650                 655

Ser Glu Glu Glu Leu Pro Ser Asp Val Asp Leu Asn Asp Pro Tyr Phe
            660                 665                 670

Ala Glu Glu Val Lys Gln Ile Gly Ile Asn Lys Lys Ser Val Lys Ser
        675                 680                 685

Ala Lys Asp Gly Thr Ser Pro Glu Glu Glu Ile Glu Ile Glu Arg Gln
    690                 695                 700

Lys Ala Glu Met Ala Leu Leu Met Met Asp Glu Asp Glu Asp Ser Lys
705                 710                 715                 720

Lys His Phe Asn Tyr Asn Lys Ile Val Glu His Gln Asn Leu Ser Lys
                725                 730                 735
```

```
Lys Lys Lys Lys Gln Leu Met Lys Lys Lys Glu Leu Ile Glu Asp Asp
            740                 745                 750

Phe Glu Val Asn Val Asn Asp Ala Arg Phe Gln Ala Met Tyr Thr Ser
        755                 760                 765

His Leu Phe Asn Leu Asp Pro Ser Asp Pro Asn Phe Lys Lys Thr Lys
    770                 775                 780

Ala Met Glu Lys Ile Leu Glu Glu Lys Ala Arg Gln Arg Glu Arg Lys
785                 790                 795                 800

Glu Gln Glu Leu Thr Gln Ala Ile Lys Lys Lys Glu Ser Glu Ile Glu
                805                 810                 815

Lys Glu Ser Gln Arg Lys Ser Ile Asp Pro Ala Leu Ser Met Leu Ile
            820                 825                 830

Lys Ser Ile Lys Thr Lys Thr Glu Gln Phe Gln Ala Arg Lys Lys Gln
        835                 840                 845

Lys Val Lys
    850


<210> SEQ ID NO 49
<211> LENGTH: 851
<212> TYPE: PRT
<213> ORGANISM: Homo sapiens

<400> SEQUENCE: 49

Met Ser Ser Lys Gln Glu Ile Met Ser Asp Gln Arg Phe Arg Arg Val
1               5                   10                  15

Ala Lys Asp Pro Arg Phe Trp Glu Met Pro Glu Lys Asp Arg Lys Val
            20                  25                  30

Lys Ile Asp Lys Arg Phe Arg Ala Met Phe His Asp Lys Lys Phe Lys
        35                  40                  45

Leu Asn Tyr Ala Val Asp Lys Arg Gly Arg Pro Ile Ser His Ser Thr
    50                  55                  60

Thr Glu Asp Leu Lys Arg Phe Tyr Asp Leu Ser Asp Ser Asp Ser Asn
65                  70                  75                  80

Leu Ser Gly Glu Asp Ser Lys Ala Leu Ser Gln Lys Lys Ile Lys Lys
                85                  90                  95

Lys Lys Thr Gln Thr Lys Lys Glu Ile Asp Ser Lys Asn Leu Val Glu
            100                 105                 110

Lys Lys Lys Glu Thr Lys Lys Ala Asn His Lys Gly Ser Glu Asn Lys
        115                 120                 125

Thr Asp Leu Asp Asn Ser Ile Gly Ile Lys Lys Met Lys Thr Ser Cys
    130                 135                 140

Lys Phe Lys Ile Asp Ser Asn Ile Ser Pro Lys Lys Asp Ser Lys Glu
145                 150                 155                 160

Phe Thr Gln Lys Asn Lys Lys Glu Lys Lys Asn Ile Val Gln His Thr
                165                 170                 175

Thr Asp Ser Ser Leu Glu Glu Lys Gln Arg Thr Leu Asp Ser Gly Thr
            180                 185                 190

Ser Glu Ile Val Lys Ser Pro Arg Ile Glu Cys Ser Lys Thr Arg Arg
        195                 200                 205

Glu Met Gln Ser Val Val Gln Leu Ile Met Thr Arg Asp Ser Asp Gly
    210                 215                 220

Tyr Glu Asn Ser Thr Asp Gly Glu Met Cys Asp Lys Asp Ala Leu Glu
225                 230                 235                 240

Glu Asp Ser Glu Ser Val Ser Glu Ile Gly Ser Asp Glu Glu Ser Glu
                245                 250                 255
```

-continued

```
Asn Glu Ile Thr Ser Val Gly Arg Ala Ser Gly Asp Asp Asp Gly Ser
            260                 265                 270

Glu Asp Asp Glu Glu Glu Asp Glu Asp Glu Glu Glu Asp Glu Asp Glu
        275                 280                 285

Asp Ser Glu Asp Asp Asp Lys Ser Asp Ser Gly Pro Asp Leu Ala Arg
    290                 295                 300

Gly Lys Gly Asn Ile Glu Thr Ser Ser Glu Asp Glu Asp Asp Thr Ala
305                 310                 315                 320

Asp Leu Phe Pro Glu Glu Ser Gly Phe Glu His Ala Trp Arg Glu Leu
                325                 330                 335

Asp Lys Asp Ala Pro Arg Ala Asp Glu Ile Thr Arg Arg Leu Ala Val
            340                 345                 350

Cys Asn Met Asp Trp Asp Arg Leu Lys Ala Lys Asp Leu Leu Ala Leu
        355                 360                 365

Phe Asn Ser Phe Lys Pro Lys Gly Gly Val Ile Phe Ser Val Lys Ile
    370                 375                 380

Tyr Pro Ser Glu Phe Gly Lys Glu Arg Met Lys Glu Glu Gln Val Gln
385                 390                 395                 400

Gly Pro Val Glu Leu Leu Ser Ile Pro Glu Asp Ala Pro Glu Lys Asp
                405                 410                 415

Trp Thr Ser Arg Glu Lys Leu Arg Asp Tyr Gln Phe Lys Arg Leu Lys
            420                 425                 430

Tyr Tyr Tyr Ala Val Val Asp Cys Asp Ser Pro Glu Thr Ala Ser Lys
        435                 440                 445

Ile Tyr Glu Asp Cys Asp Gly Leu Glu Phe Glu Ser Ser Cys Ser Phe
    450                 455                 460

Ile Asp Leu Arg Phe Ile Pro Asp Asp Ile Thr Phe Asp Asp Glu Pro
465                 470                 475                 480

Lys Asp Val Ala Ser Glu Val Asn Leu Thr Ala Tyr Lys Pro Lys Tyr
                485                 490                 495

Phe Thr Ser Ala Ala Met Gly Thr Ser Thr Val Glu Ile Thr Trp Asp
            500                 505                 510

Glu Thr Asp His Glu Arg Ile Thr Met Leu Asn Arg Lys Phe Lys Lys
        515                 520                 525

Glu Glu Leu Leu Asp Met Asp Phe Gln Ala Tyr Leu Ala Ser Ser Ser
    530                 535                 540

Glu Asp Glu Glu Glu Ile Glu Glu Glu Leu Gln Gly Asp Asp Gly Val
545                 550                 555                 560

Asn Val Glu Glu Asp Gly Lys Thr Lys Lys Ser Gln Lys Asp Asp Glu
                565                 570                 575

Glu Gln Ile Ala Lys Tyr Arg Gln Leu Leu Gln Val Ile Gln Glu Lys
            580                 585                 590

Glu Lys Lys Gly Lys Glu Asn Asp Met Glu Met Glu Ile Lys Trp Val
        595                 600                 605

Pro Gly Leu Lys Glu Ser Ala Glu Glu Met Val Lys Asn Lys Leu Glu
    610                 615                 620

Gly Lys Asp Lys Leu Thr Pro Trp Glu Gln Phe Leu Glu Lys Lys Lys
625                 630                 635                 640

Glu Lys Lys Arg Leu Lys Arg Lys Gln Lys Ala Leu Ala Glu Glu Ala
                645                 650                 655

Ser Glu Glu Glu Leu Pro Ser Asp Val Asp Leu Asn Asp Pro Tyr Phe
            660                 665                 670
```

-continued

```
Ala Glu Glu Val Lys Gln Ile Gly Ile Asn Lys Lys Ser Val Lys Ser
        675                 680                 685

Ala Lys Asp Gly Thr Ser Pro Glu Glu Glu Ile Glu Ile Glu Arg Gln
    690                 695                 700

Lys Ala Glu Met Ala Leu Leu Met Met Asp Glu Asp Glu Asp Ser Lys
705                 710                 715                 720

Lys His Phe Asn Tyr Asn Lys Ile Val Glu His Gln Asn Leu Ser Lys
                725                 730                 735

Lys Lys Lys Lys Gln Leu Met Lys Lys Lys Glu Leu Ile Glu Asp Asp
            740                 745                 750

Phe Glu Val Asn Val Asn Asp Ala Arg Phe Gln Ala Met Tyr Thr Ser
        755                 760                 765

His Leu Phe Asn Leu Asp Pro Ser Asp Pro Asn Phe Lys Lys Thr Lys
    770                 775                 780

Ala Met Glu Lys Ile Leu Glu Glu Lys Ala Arg Gln Arg Glu Arg Lys
785                 790                 795                 800

Glu Gln Glu Leu Thr Gln Ala Ile Lys Lys Lys Glu Ser Glu Ile Glu
                805                 810                 815

Lys Glu Ser Gln Arg Lys Ser Ile Asp Pro Ala Leu Ser Met Leu Ile
            820                 825                 830

Lys Ser Ile Lys Thr Lys Thr Glu Gln Phe Gln Ala Arg Lys Lys Gln
        835                 840                 845

Lys Val Lys
    850
```

<210> SEQ ID NO 50
<211> LENGTH: 450
<212> TYPE: PRT
<213> ORGANISM: Homo sapiens

<400> SEQUENCE: 50

```
Met Ser Asp Phe Ser Glu Glu Leu Lys Gly Pro Val Thr Asp Asp Glu
1               5                   10                  15

Glu Val Glu Thr Ser Val Leu Ser Gly Ala Gly Met His Phe Pro Trp
            20                  25                  30

Leu Gln Thr Tyr Val Glu Thr Val Ala Ile Gly Gly Lys Arg Arg Lys
        35                  40                  45

Asp Phe Ala Gln Thr Thr Ser Ala Cys Leu Ser Phe Ile Gln Glu Ala
    50                  55                  60

Leu Leu Lys His Gln Trp Gln Gln Ala Ala Glu Tyr Met Tyr Ser Tyr
65                  70                  75                  80

Phe Gln Thr Leu Glu Asp Ser Asp Ser Tyr Lys Arg Gln Ala Ala Pro
                85                  90                  95

Glu Ile Ile Trp Lys Leu Gly Ser Glu Ile Leu Phe Tyr His Pro Lys
            100                 105                 110

Ser Asn Met Glu Ser Phe Asn Thr Phe Ala Asn Arg Met Lys Asn Ile
        115                 120                 125

Gly Val Met Asn Tyr Leu Lys Ile Ser Leu Gln His Ala Leu Tyr Leu
    130                 135                 140

Leu His His Gly Met Leu Lys Asp Ala Lys Arg Asn Leu Ser Glu Ala
145                 150                 155                 160

Glu Thr Trp Arg His Gly Glu Asn Thr Ser Ser Arg Glu Ile Leu Ile
                165                 170                 175

Asn Leu Ile Gln Ala Tyr Lys Gly Leu Leu Gln Tyr Tyr Thr Trp Ser
            180                 185                 190
```

-continued

```
Glu Lys Lys Met Glu Leu Ser Lys Leu Asp Lys Asp Asp Tyr Ala Tyr
        195                 200                 205

Asn Ala Val Ala Gln Asp Val Phe Asn His Ser Trp Lys Thr Ser Ala
    210                 215                 220

Asn Ile Ser Ala Leu Ile Lys Ile Pro Gly Val Trp Asp Pro Phe Val
225                 230                 235                 240

Lys Ser Tyr Val Glu Met Leu Glu Phe Tyr Gly Asp Arg Asp Gly Ala
                245                 250                 255

Gln Glu Val Leu Thr Asn Tyr Ala Tyr Asp Glu Lys Phe Pro Ser Asn
            260                 265                 270

Pro Asn Ala His Ile Tyr Leu Tyr Asn Phe Leu Lys Arg Gln Lys Ala
        275                 280                 285

Pro Arg Ser Lys Leu Ile Ser Val Leu Lys Ile Leu Tyr Gln Ile Val
    290                 295                 300

Pro Ser His Lys Leu Met Leu Glu Phe His Thr Leu Leu Arg Lys Ser
305                 310                 315                 320

Glu Lys Glu Glu His Arg Lys Leu Gly Leu Glu Val Leu Phe Gly Val
                325                 330                 335

Leu Asp Phe Ala Gly Cys Thr Lys Asn Ile Thr Ala Trp Lys Tyr Leu
            340                 345                 350

Ala Lys Tyr Leu Lys Asn Ile Leu Met Gly Asn His Leu Ala Trp Val
        355                 360                 365

Gln Glu Glu Trp Asn Ser Arg Lys Asn Trp Trp Pro Gly Phe His Phe
    370                 375                 380

Ser Tyr Phe Trp Ala Lys Ser Asp Trp Lys Glu Asp Thr Ala Leu Ala
385                 390                 395                 400

Cys Glu Lys Ala Phe Val Ala Gly Leu Leu Leu Gly Lys Gly Cys Arg
                405                 410                 415

Tyr Phe Arg Tyr Ile Leu Lys Gln Asp His Gln Ile Leu Gly Lys Lys
            420                 425                 430

Ile Lys Arg Met Lys Arg Ser Val Lys Lys Tyr Ser Ile Val Asn Pro
        435                 440                 445

Arg Leu
    450


<210> SEQ ID NO 51
<211> LENGTH: 450
<212> TYPE: PRT
<213> ORGANISM: Homo sapiens

<400> SEQUENCE: 51

Met Ser Asp Phe Ser Glu Glu Leu Lys Gly Pro Val Thr Asp Asp Glu
1               5                   10                  15

Glu Val Glu Thr Ser Val Leu Ser Gly Ala Gly Met His Phe Pro Trp
            20                  25                  30

Leu Gln Thr Tyr Val Glu Thr Val Ala Ile Gly Gly Lys Arg Arg Lys
        35                  40                  45

Asp Phe Ala Gln Thr Thr Ser Ala Cys Leu Ser Phe Ile Gln Glu Ala
    50                  55                  60

Leu Leu Lys His Gln Trp Gln Gln Ala Ala Glu Tyr Met Tyr Ser Tyr
65                  70                  75                  80

Phe Gln Thr Leu Glu Asp Ser Asp Ser Tyr Lys Arg Gln Ala Ala Pro
                85                  90                  95

Glu Ile Ile Trp Lys Leu Gly Ser Glu Ile Leu Phe Tyr His Pro Lys
```

100 105 110

Ser Asn Met Glu Ser Phe Asn Thr Phe Ala Asn Arg Met Lys Asn Ile
115 120 125

Gly Val Met Asn Tyr Leu Lys Ile Ser Leu Gln His Ala Leu Tyr Leu
130 135 140

Leu His His Gly Met Leu Lys Asp Ala Lys Arg Asn Leu Ser Glu Ala
145 150 155 160

Glu Thr Trp Arg His Gly Glu Asn Thr Ser Ser Arg Glu Ile Leu Ile
165 170 175

Asn Leu Ile Gln Ala Tyr Lys Gly Leu Leu Gln Tyr Tyr Thr Trp Ser
180 185 190

Glu Lys Lys Met Glu Leu Ser Lys Leu Asp Lys Asp Asp Tyr Ala Tyr
195 200 205

Asn Ala Val Ala Gln Asp Val Phe Asn His Ser Trp Lys Thr Ser Ala
210 215 220

Asn Ile Ser Ala Leu Ile Lys Ile Pro Gly Val Trp Asp Pro Phe Val
225 230 235 240

Lys Ser Tyr Val Glu Met Leu Glu Phe Tyr Gly Asp Arg Asp Gly Ala
245 250 255

Gln Glu Val Leu Thr Asn Tyr Ala Tyr Asp Glu Lys Phe Pro Ser Asn
260 265 270

Pro Asn Ala His Ile Tyr Leu Tyr Asn Phe Leu Lys Arg Gln Lys Ala
275 280 285

Pro Arg Ser Lys Leu Ile Ser Val Leu Lys Ile Leu Tyr Gln Ile Val
290 295 300

Pro Ser His Lys Leu Met Leu Glu Phe His Thr Leu Leu Arg Lys Ser
305 310 315 320

Glu Lys Glu Glu His Arg Lys Leu Gly Leu Glu Val Leu Phe Gly Val
325 330 335

Leu Asp Phe Ala Gly Cys Thr Lys Asn Ile Thr Ala Trp Lys Tyr Leu
340 345 350

Ala Lys Tyr Leu Lys Asn Ile Leu Met Gly Asn His Leu Ala Trp Val
355 360 365

Gln Glu Glu Trp Asn Ser Arg Lys Asn Trp Trp Pro Gly Phe His Phe
370 375 380

Ser Tyr Phe Trp Ala Lys Ser Asp Trp Lys Glu Asp Thr Ala Leu Ala
385 390 395 400

Cys Glu Lys Ala Phe Val Ala Gly Leu Leu Leu Gly Lys Gly Cys Arg
405 410 415

Tyr Phe Arg Tyr Ile Leu Lys Gln Asp His Gln Ile Leu Gly Lys Lys
420 425 430

Ile Lys Arg Met Lys Arg Ser Val Lys Lys Tyr Ser Ile Val Asn Pro
435 440 445

Arg Leu
450

<210> SEQ ID NO 52
<211> LENGTH: 336
<212> TYPE: PRT
<213> ORGANISM: Homo sapiens

<400> SEQUENCE: 52

Met Glu Ser Phe Asn Thr Phe Ala Asn Arg Met Lys Asn Ile Gly Val
1 5 10 15

Met Asn Tyr Leu Lys Ile Ser Leu Gln His Ala Leu Tyr Leu Leu His
20 25 30

His Gly Met Leu Lys Asp Ala Lys Arg Asn Leu Ser Glu Ala Glu Thr
35 40 45

Trp Arg His Gly Glu Asn Thr Ser Ser Arg Glu Ile Leu Ile Asn Leu
50 55 60

Ile Gln Ala Tyr Lys Gly Leu Leu Gln Tyr Tyr Thr Trp Ser Glu Lys
65 70 75 80

Lys Met Glu Leu Ser Lys Leu Asp Lys Asp Asp Tyr Ala Tyr Asn Ala
85 90 95

Val Ala Gln Asp Val Phe Asn His Ser Trp Lys Thr Ser Ala Asn Ile
100 105 110

Ser Ala Leu Ile Lys Ile Pro Gly Val Trp Asp Pro Phe Val Lys Ser
115 120 125

Tyr Val Glu Met Leu Glu Phe Tyr Gly Asp Arg Asp Gly Ala Gln Glu
130 135 140

Val Leu Thr Asn Tyr Ala Tyr Asp Glu Lys Phe Pro Ser Asn Pro Asn
145 150 155 160

Ala His Ile Tyr Leu Tyr Asn Phe Leu Lys Arg Gln Lys Ala Pro Arg
165 170 175

Ser Lys Leu Ile Ser Val Leu Lys Ile Leu Tyr Gln Ile Val Pro Ser
180 185 190

His Lys Leu Met Leu Glu Phe His Thr Leu Leu Arg Lys Ser Glu Lys
195 200 205

Glu Glu His Arg Lys Leu Gly Leu Glu Val Leu Phe Gly Val Leu Asp
210 215 220

Phe Ala Gly Cys Thr Lys Asn Ile Thr Ala Trp Lys Tyr Leu Ala Lys
225 230 235 240

Tyr Leu Lys Asn Ile Leu Met Gly Asn His Leu Ala Trp Val Gln Glu
245 250 255

Glu Trp Asn Ser Arg Lys Asn Trp Trp Pro Gly Phe His Phe Ser Tyr
260 265 270

Phe Trp Ala Lys Ser Asp Trp Lys Glu Asp Thr Ala Leu Ala Cys Glu
275 280 285

Lys Ala Phe Val Ala Gly Leu Leu Leu Gly Lys Gly Cys Arg Tyr Phe
290 295 300

Arg Tyr Ile Leu Lys Gln Asp His Gln Ile Leu Gly Lys Lys Ile Lys
305 310 315 320

Arg Met Lys Arg Ser Val Lys Lys Tyr Ser Ile Val Asn Pro Arg Leu
325 330 335

<210> SEQ ID NO 53
<211> LENGTH: 588
<212> TYPE: PRT
<213> ORGANISM: Homo sapiens

<400> SEQUENCE: 53

Met Asp Leu Glu Glu Ala Glu Glu Phe Lys Glu Arg Cys Thr Gln Cys
1 5 10 15

Ala Ala Val Ser Trp Gly Leu Thr Asp Glu Gly Lys Tyr Tyr Cys Thr
20 25 30

Ser Cys His Asn Val Thr Glu Arg Tyr Gln Glu Val Thr Asn Thr Asp
35 40 45

Leu Ile Pro Asn Thr Gln Ile Lys Ala Leu Asn Arg Gly Leu Lys Lys
50 55 60

-continued

```
Lys Asn Asn Thr Glu Lys Gly Trp Asp Trp Tyr Val Cys Glu Gly Phe
65                  70                  75                  80

Gln Tyr Ile Leu Tyr Gln Gln Ala Glu Ala Leu Lys Asn Leu Gly Val
                85                  90                  95

Gly Pro Glu Leu Lys Asn Asp Val Leu His Asn Phe Trp Lys Arg Tyr
            100                 105                 110

Leu Gln Lys Ser Lys Gln Ala Tyr Cys Lys Asn Pro Val Tyr Thr Thr
        115                 120                 125

Gly Arg Lys Pro Thr Val Leu Glu Asp Asn Leu Ser His Ser Asp Trp
    130                 135                 140

Ala Ser Glu Pro Glu Leu Leu Ser Asp Val Ser Cys Pro Pro Phe Leu
145                 150                 155                 160

Glu Ser Gly Ala Glu Ser Gln Ser Asp Ile His Thr Arg Lys Pro Phe
                165                 170                 175

Pro Val Ser Lys Ala Ser Gln Ser Glu Thr Ser Val Cys Ser Gly Ser
            180                 185                 190

Leu Asp Gly Val Glu Tyr Ser Gln Arg Lys Glu Lys Gly Ile Val Lys
        195                 200                 205

Met Thr Met Pro Gln Thr Leu Ala Phe Cys Tyr Leu Ser Leu Leu Trp
    210                 215                 220

Gln Arg Glu Ala Ile Thr Leu Ser Asp Leu Leu Arg Phe Val Glu Glu
225                 230                 235                 240

Asp His Ile Pro Tyr Ile Asn Ala Phe Gln His Phe Pro Glu Gln Met
                245                 250                 255

Lys Leu Tyr Gly Arg Asp Arg Gly Ile Phe Gly Ile Glu Ser Trp Pro
            260                 265                 270

Asp Tyr Glu Asp Ile Tyr Lys Lys Thr Ile Glu Val Gly Thr Phe Leu
        275                 280                 285

Asp Leu Pro Arg Phe Pro Asp Ile Thr Glu Asp Cys Tyr Leu His Pro
    290                 295                 300

Asn Ile Leu Cys Met Lys Tyr Leu Met Glu Val Asn Leu Pro Asp Glu
305                 310                 315                 320

Met His Ser Leu Thr Cys His Val Val Lys Met Thr Gly Met Gly Glu
                325                 330                 335

Val Asp Phe Leu Thr Phe Asp Pro Ile Ala Lys Met Ala Lys Thr Val
            340                 345                 350

Lys Tyr Asp Val Gln Ala Val Ala Ile Ile Val Val Val Leu Lys Leu
        355                 360                 365

Leu Phe Leu Leu Asp Asp Ser Phe Glu Trp Ser Leu Ser Asn Leu Ala
    370                 375                 380

Glu Lys His Asn Glu Lys Asn Lys Lys Asp Lys Pro Trp Phe Asp Phe
385                 390                 395                 400

Arg Lys Trp Tyr Gln Ile Met Lys Lys Ala Phe Asp Glu Lys Lys Gln
                405                 410                 415

Lys Trp Glu Glu Ala Arg Ala Lys Tyr Leu Trp Lys Ser Glu Lys Pro
            420                 425                 430

Leu Tyr Tyr Ser Phe Val Asp Lys Pro Val Ala Tyr Lys Lys Arg Glu
        435                 440                 445

Met Val Val Asn Leu Gln Lys Gln Phe Ser Thr Leu Val Glu Ser Thr
    450                 455                 460

Ala Thr Ala Gly Lys Lys Ser Pro Ser Ser Phe Gln Phe Asn Trp Thr
465                 470                 475                 480
```

```
Glu Glu Asp Thr Asp Arg Thr Cys Phe His Gly His Ser Leu Gln Gly
            485                 490                 495

Val Leu Lys Glu Lys Gly Gln Ser Leu Leu Thr Lys Asn Ser Leu Tyr
            500                 505                 510

Trp Leu Ser Thr Gln Lys Phe Cys Arg Cys Tyr Cys Thr His Val Thr
        515                 520                 525

Thr Tyr Glu Glu Ser Asn Tyr Ser Leu Ser Tyr Gln Phe Ile Leu Asn
    530                 535                 540

Leu Phe Ser Phe Leu Leu Arg Ile Lys Thr Ser Leu Leu His Glu Glu
545                 550                 555                 560

Val Ser Leu Val Glu Lys Lys Leu Phe Glu Lys Lys Tyr Ser Val Lys
            565                 570                 575

Arg Lys Lys Ser Arg Ser Lys Lys Val Arg Arg His
            580                 585


<210> SEQ ID NO 54
<211> LENGTH: 843
<212> TYPE: PRT
<213> ORGANISM: Homo sapiens

<400> SEQUENCE: 54

Met Asp Phe Pro Ser Ser Leu Arg Pro Ala Leu Phe Leu Thr Gly Pro
1               5                   10                  15

Leu Gly Leu Ser Asp Val Pro Asp Leu Ser Phe Met Cys Ser Trp Arg
            20                  25                  30

Asp Ala Leu Thr Leu Pro Glu Ala Gln Pro Gln Asn Ser Glu Asn Gly
        35                  40                  45

Ala Leu His Val Thr Lys Asp Leu Leu Trp Glu Pro Ala Thr Pro Gly
    50                  55                  60

Pro Leu Pro Met Leu Pro Pro Leu Ile Asp Pro Trp Asp Pro Gly Leu
65                  70                  75                  80

Thr Ala Arg Asp Leu Leu Phe Arg Gly Gly Tyr Arg Tyr Arg Lys Arg
            85                  90                  95

Pro Arg Val Val Leu Asp Val Thr Glu Gln Ile Ser Arg Phe Leu Leu
            100                 105                 110

Asp His Gly Asp Val Ala Phe Ala Pro Leu Gly Lys Leu Met Leu Glu
        115                 120                 125

Asn Phe Lys Leu Glu Gly Ala Gly Ser Arg Thr Lys Lys Lys Thr Val
    130                 135                 140

Val Ser Val Lys Lys Leu Leu Gln Asp Leu Gly Gly His Gln Pro Trp
145                 150                 155                 160

Gly Cys Pro Trp Ala Tyr Leu Ser Asn Arg Gln Arg Arg Phe Ser Ile
            165                 170                 175

Leu Gly Gly Pro Ile Leu Gly Thr Ser Val Ala Ser His Leu Ala Glu
            180                 185                 190

Leu Leu His Glu Glu Leu Val Leu Arg Trp Glu Gln Leu Leu Leu Asp
        195                 200                 205

Glu Ala Cys Thr Gly Gly Ala Leu Ala Trp Val Pro Gly Arg Thr Pro
    210                 215                 220

Gln Phe Gly Gln Leu Val Tyr Pro Ala Gly Gly Ala Gln Asp Arg Leu
225                 230                 235                 240

His Phe Gln Glu Val Val Leu Thr Pro Gly Asp Asn Pro Gln Phe Leu
            245                 250                 255

Gly Lys Pro Gly Arg Ile Gln Leu Gln Gly Pro Val Arg Gln Val Val
            260                 265                 270
```

```
Thr Cys Thr Val Gln Gly Glu Thr Leu Leu Ala Val Arg Ser Asp Tyr
        275                 280                 285

His Cys Ala Val Trp Lys Phe Gly Lys Gln Trp Gln Pro Thr Leu Leu
    290                 295                 300

Gln Ala Met Gln Val Glu Lys Gly Ala Thr Gly Ile Ser Leu Ser Pro
305                 310                 315                 320

His Leu Pro Gly Glu Leu Ala Ile Cys Ser Arg Ser Gly Ala Val Cys
                325                 330                 335

Leu Trp Ser Pro Glu Asp Gly Leu Arg Gln Ile Tyr Arg Asp Pro Glu
            340                 345                 350

Thr Leu Val Phe Arg Asp Ser Ser Ser Trp Arg Trp Ala Asp Phe Thr
        355                 360                 365

Ala His Pro Arg Val Leu Thr Val Gly Asp Arg Thr Gly Val Lys Met
    370                 375                 380

Leu Asp Thr Gln Gly Pro Pro Gly Cys Gly Leu Leu Leu Phe Arg Leu
385                 390                 395                 400

Gly Ala Glu Ala Ser Cys Gln Lys Gly Glu Arg Val Leu Leu Thr Gln
                405                 410                 415

Tyr Leu Gly His Ser Ser Pro Lys Cys Leu Pro Pro Thr Leu His Leu
            420                 425                 430

Val Cys Thr Gln Phe Ser Leu Tyr Leu Val Asp Glu Arg Leu Pro Leu
        435                 440                 445

Val Pro Met Leu Lys Trp Asn His Gly Leu Pro Ser Pro Leu Leu Leu
    450                 455                 460

Ala Arg Leu Leu Pro Pro Pro Arg Pro Ser Cys Val Gln Pro Leu Leu
465                 470                 475                 480

Leu Gly Gly Gln Gly Gly Gln Leu Gln Leu Leu His Leu Ala Gly Glu
                485                 490                 495

Gly Ala Ser Val Pro Arg Leu Ala Gly Pro Pro Gln Ser Leu Pro Ser
            500                 505                 510

Arg Ile Asp Ser Leu Pro Ala Phe Pro Leu Leu Glu Pro Lys Ile Gln
        515                 520                 525

Trp Arg Leu Gln Glu Arg Leu Lys Ala Pro Thr Ile Gly Leu Ala Ala
    530                 535                 540

Val Val Pro Pro Leu Pro Ser Ala Pro Thr Pro Gly Leu Val Leu Phe
545                 550                 555                 560

Gln Leu Ser Ala Ala Gly Asp Val Phe Tyr Gln Gln Leu Arg Pro Gln
                565                 570                 575

Val Asp Ser Ser Leu Arg Arg Asp Ala Gly Pro Pro Gly Asp Thr Gln
            580                 585                 590

Pro Asp Cys His Ala Pro Thr Ala Ser Trp Thr Ser Gln Asp Thr Ala
        595                 600                 605

Gly Cys Ser Gln Trp Leu Lys Ala Leu Leu Lys Val Pro Leu Ala Pro
    610                 615                 620

Pro Val Trp Thr Ala Pro Thr Phe Thr His Arg Gln Met Leu Gly Ser
625                 630                 635                 640

Thr Glu Leu Arg Arg Glu Glu Glu Glu Gly Gln Arg Leu Gly Val Leu
                645                 650                 655

Arg Lys Ala Met Ala Arg Gly Gln Leu Leu Leu Gln Arg Asp Leu Gly
            660                 665                 670

Ser Leu Pro Ala Ala Glu Pro Pro Pro Ala Pro Glu Ser Gly Leu Glu
        675                 680                 685
```

Asp Lys Leu Ser Glu Arg Leu Gly Glu Ala Trp Ala Gly Arg Gly Ala
690 695 700

Ala Trp Trp Glu Arg Gln Gln Gly Arg Thr Ser Glu Pro Gly Arg Gln
705 710 715 720

Thr Arg Arg Pro Lys Arg Arg Thr Gln Leu Ser Ser Ser Phe Ser Leu
725 730 735

Ser Gly His Val Asp Pro Ser Glu Asp Thr Ser Ser Pro His Ser Pro
740 745 750

Glu Trp Pro Pro Ala Asp Ala Leu Pro Leu Pro Pro Thr Thr Pro Pro
755 760 765

Ser Gln Glu Leu Thr Pro Asp Ala Cys Ala Gln Gly Val Pro Ser Glu
770 775 780

Gln Arg Gln Met Leu Arg Asp Tyr Met Ala Lys Leu Pro Pro Gln Arg
785 790 795 800

Asp Thr Pro Gly Cys Ala Thr Thr Pro Pro His Ser Gln Ala Ser Ser
805 810 815

Val Arg Ala Thr Arg Ser Gln Gln His Thr Pro Val Leu Ser Ser Ser
820 825 830

Gln Pro Leu Arg Lys Lys Pro Arg Met Gly Phe
835 840

<210> SEQ ID NO 55
<211> LENGTH: 537
<212> TYPE: PRT
<213> ORGANISM: Homo sapiens

<400> SEQUENCE: 55

Met Gln Val Glu Lys Gly Ala Thr Gly Ile Ser Leu Ser Pro His Leu
1 5 10 15

Pro Gly Glu Leu Ala Ile Cys Ser Arg Ser Gly Ala Val Cys Leu Trp
20 25 30

Ser Pro Glu Asp Gly Leu Arg Gln Ile Tyr Arg Asp Pro Glu Thr Leu
35 40 45

Val Phe Arg Asp Ser Ser Ser Trp Arg Trp Ala Asp Phe Thr Ala His
50 55 60

Pro Arg Val Leu Thr Val Gly Asp Arg Thr Gly Val Lys Met Leu Asp
65 70 75 80

Thr Gln Gly Pro Pro Gly Cys Gly Leu Leu Leu Phe Arg Leu Gly Ala
85 90 95

Glu Ala Ser Cys Gln Lys Gly Glu Arg Val Leu Leu Thr Gln Tyr Leu
100 105 110

Gly His Ser Ser Pro Lys Cys Leu Pro Pro Thr Leu His Leu Val Cys
115 120 125

Thr Gln Phe Ser Leu Tyr Leu Val Asp Glu Arg Leu Pro Leu Val Pro
130 135 140

Met Leu Lys Trp Asn His Gly Leu Pro Ser Pro Leu Leu Leu Ala Arg
145 150 155 160

Leu Leu Pro Pro Pro Arg Pro Ser Cys Val Gln Pro Leu Leu Leu Gly
165 170 175

Gly Gln Gly Gly Gln Leu Gln Leu Leu His Leu Ala Gly Glu Gly Ala
180 185 190

Ser Val Pro Arg Leu Ala Gly Pro Pro Gln Ser Leu Pro Ser Arg Ile
195 200 205

Asp Ser Leu Pro Ala Phe Pro Leu Leu Glu Pro Lys Ile Gln Trp Arg
210 215 220

Leu Gln Glu Arg Leu Lys Ala Pro Thr Ile Gly Leu Ala Ala Val Val
225 230 235 240

Pro Pro Leu Pro Ser Ala Pro Thr Pro Gly Leu Val Leu Phe Gln Leu
245 250 255

Ser Ala Ala Gly Asp Val Phe Tyr Gln Gln Leu Arg Pro Gln Val Asp
260 265 270

Ser Ser Leu Arg Arg Asp Ala Gly Pro Pro Gly Asp Thr Gln Pro Asp
275 280 285

Cys His Ala Pro Thr Ala Ser Trp Thr Ser Gln Asp Thr Ala Gly Cys
290 295 300

Ser Gln Trp Leu Lys Ala Leu Leu Lys Val Pro Leu Ala Pro Pro Val
305 310 315 320

Trp Thr Ala Pro Thr Phe Thr His Arg Gln Met Leu Gly Ser Thr Glu
325 330 335

Leu Arg Arg Glu Glu Glu Glu Gly Gln Arg Leu Gly Val Leu Arg Lys
340 345 350

Ala Met Ala Arg Gly Gln Leu Leu Leu Gln Arg Asp Leu Gly Ser Leu
355 360 365

Pro Ala Ala Glu Pro Pro Pro Ala Pro Glu Ser Gly Leu Glu Asp Lys
370 375 380

Leu Ser Glu Arg Leu Gly Glu Ala Trp Ala Gly Arg Gly Ala Ala Trp
385 390 395 400

Trp Glu Arg Gln Gln Gly Arg Thr Ser Glu Pro Gly Arg Gln Thr Arg
405 410 415

Arg Pro Lys Arg Arg Thr Gln Leu Ser Ser Ser Phe Ser Leu Ser Gly
420 425 430

His Val Asp Pro Ser Glu Asp Thr Ser Ser Pro His Ser Pro Glu Trp
435 440 445

Pro Pro Ala Asp Ala Leu Pro Leu Pro Pro Thr Thr Pro Pro Ser Gln
450 455 460

Glu Leu Thr Pro Asp Ala Cys Ala Gln Gly Val Pro Ser Glu Gln Arg
465 470 475 480

Gln Met Leu Arg Asp Tyr Met Ala Lys Leu Pro Pro Gln Arg Asp Thr
485 490 495

Pro Gly Cys Ala Thr Thr Pro Pro His Ser Gln Ala Ser Ser Val Arg
500 505 510

Ala Thr Arg Ser Gln Gln His Thr Pro Val Leu Ser Ser Ser Gln Pro
515 520 525

Leu Arg Lys Lys Pro Arg Met Gly Phe
530 535

<210> SEQ ID NO 56
<211> LENGTH: 537
<212> TYPE: PRT
<213> ORGANISM: Homo sapiens

<400> SEQUENCE: 56

Met Gln Val Glu Lys Gly Ala Thr Gly Ile Ser Leu Ser Pro His Leu
1 5 10 15

Pro Gly Glu Leu Ala Ile Cys Ser Arg Ser Gly Ala Val Cys Leu Trp
20 25 30

Ser Pro Glu Asp Gly Leu Arg Gln Ile Tyr Arg Asp Pro Glu Thr Leu
35 40 45

Val Phe Arg Asp Ser Ser Ser Trp Arg Trp Ala Asp Phe Thr Ala His

-continued

```
    50                  55                  60

Pro Arg Val Leu Thr Val Gly Asp Arg Thr Gly Val Lys Met Leu Asp
65                  70                  75                  80

Thr Gln Gly Pro Pro Gly Cys Gly Leu Leu Leu Phe Arg Leu Gly Ala
                85                  90                  95

Glu Ala Ser Cys Gln Lys Gly Glu Arg Val Leu Leu Thr Gln Tyr Leu
            100                 105                 110

Gly His Ser Ser Pro Lys Cys Leu Pro Pro Thr Leu His Leu Val Cys
        115                 120                 125

Thr Gln Phe Ser Leu Tyr Leu Val Asp Glu Arg Leu Pro Leu Val Pro
    130                 135                 140

Met Leu Lys Trp Asn His Gly Leu Pro Ser Pro Leu Leu Leu Ala Arg
145                 150                 155                 160

Leu Leu Pro Pro Pro Arg Pro Ser Cys Val Gln Pro Leu Leu Leu Gly
                165                 170                 175

Gly Gln Gly Gly Gln Leu Gln Leu Leu His Leu Ala Gly Glu Gly Ala
            180                 185                 190

Ser Val Pro Arg Leu Ala Gly Pro Pro Gln Ser Leu Pro Ser Arg Ile
        195                 200                 205

Asp Ser Leu Pro Ala Phe Pro Leu Leu Glu Pro Lys Ile Gln Trp Arg
    210                 215                 220

Leu Gln Glu Arg Leu Lys Ala Pro Thr Ile Gly Leu Ala Ala Val Val
225                 230                 235                 240

Pro Pro Leu Pro Ser Ala Pro Thr Pro Gly Leu Val Leu Phe Gln Leu
                245                 250                 255

Ser Ala Ala Gly Asp Val Phe Tyr Gln Gln Leu Arg Pro Gln Val Asp
            260                 265                 270

Ser Ser Leu Arg Arg Asp Ala Gly Pro Pro Gly Asp Thr Gln Pro Asp
        275                 280                 285

Cys His Ala Pro Thr Ala Ser Trp Thr Ser Gln Asp Thr Ala Gly Cys
    290                 295                 300

Ser Gln Trp Leu Lys Ala Leu Leu Lys Val Pro Leu Ala Pro Pro Val
305                 310                 315                 320

Trp Thr Ala Pro Thr Phe Thr His Arg Gln Met Leu Gly Ser Thr Glu
                325                 330                 335

Leu Arg Arg Glu Glu Glu Glu Gly Gln Arg Leu Gly Val Leu Arg Lys
            340                 345                 350

Ala Met Ala Arg Gly Gln Leu Leu Leu Gln Arg Asp Leu Gly Ser Leu
        355                 360                 365

Pro Ala Ala Glu Pro Pro Pro Ala Pro Glu Ser Gly Leu Glu Asp Lys
    370                 375                 380

Leu Ser Glu Arg Leu Gly Glu Ala Trp Ala Gly Arg Gly Ala Ala Trp
385                 390                 395                 400

Trp Glu Arg Gln Gln Gly Arg Thr Ser Glu Pro Gly Arg Gln Thr Arg
                405                 410                 415

Arg Pro Lys Arg Arg Thr Gln Leu Ser Ser Ser Phe Ser Leu Ser Gly
            420                 425                 430

His Val Asp Pro Ser Glu Asp Thr Ser Ser Pro His Ser Pro Glu Trp
        435                 440                 445

Pro Pro Ala Asp Ala Leu Pro Leu Pro Pro Thr Thr Pro Pro Ser Gln
    450                 455                 460

Glu Leu Thr Pro Asp Ala Cys Ala Gln Gly Val Pro Ser Glu Gln Arg
465                 470                 475                 480
```

```
Gln Met Leu Arg Asp Tyr Met Ala Lys Leu Pro Pro Gln Arg Asp Thr
                485                 490                 495

Pro Gly Cys Ala Thr Thr Pro Pro His Ser Gln Ala Ser Ser Val Arg
            500                 505                 510

Ala Thr Arg Ser Gln Gln His Thr Pro Val Leu Ser Ser Ser Gln Pro
        515                 520                 525

Leu Arg Lys Lys Pro Arg Met Gly Phe
    530                 535


<210> SEQ ID NO 57
<211> LENGTH: 460
<212> TYPE: PRT
<213> ORGANISM: Homo sapiens

<400> SEQUENCE: 57

Met Leu Asp Thr Gln Gly Pro Pro Gly Cys Gly Leu Leu Leu Phe Arg
1               5                   10                  15

Leu Gly Ala Glu Ala Ser Cys Gln Lys Gly Glu Arg Val Leu Leu Thr
            20                  25                  30

Gln Tyr Leu Gly His Ser Ser Pro Lys Cys Leu Pro Pro Thr Leu His
        35                  40                  45

Leu Val Cys Thr Gln Phe Ser Leu Tyr Leu Val Asp Glu Arg Leu Pro
    50                  55                  60

Leu Val Pro Met Leu Lys Trp Asn His Gly Leu Pro Ser Pro Leu Leu
65                  70                  75                  80

Leu Ala Arg Leu Leu Pro Pro Pro Arg Pro Ser Cys Val Gln Pro Leu
                85                  90                  95

Leu Leu Gly Gly Gln Gly Gly Gln Leu Gln Leu Leu His Leu Ala Gly
            100                 105                 110

Glu Gly Ala Ser Val Pro Arg Leu Ala Gly Pro Pro Gln Ser Leu Pro
        115                 120                 125

Ser Arg Ile Asp Ser Leu Pro Ala Phe Pro Leu Leu Glu Pro Lys Ile
    130                 135                 140

Gln Trp Arg Leu Gln Glu Arg Leu Lys Ala Pro Thr Ile Gly Leu Ala
145                 150                 155                 160

Ala Val Val Pro Pro Leu Pro Ser Ala Pro Thr Pro Gly Leu Val Leu
                165                 170                 175

Phe Gln Leu Ser Ala Ala Gly Asp Val Phe Tyr Gln Gln Leu Arg Pro
            180                 185                 190

Gln Val Asp Ser Ser Leu Arg Arg Asp Ala Gly Pro Pro Gly Asp Thr
        195                 200                 205

Gln Pro Asp Cys His Ala Pro Thr Ala Ser Trp Thr Ser Gln Asp Thr
    210                 215                 220

Ala Gly Cys Ser Gln Trp Leu Lys Ala Leu Leu Lys Val Pro Leu Ala
225                 230                 235                 240

Pro Pro Val Trp Thr Ala Pro Thr Phe Thr His Arg Gln Met Leu Gly
                245                 250                 255

Ser Thr Glu Leu Arg Arg Glu Glu Glu Glu Gly Gln Arg Leu Gly Val
            260                 265                 270

Leu Arg Lys Ala Met Ala Arg Gly Gln Leu Leu Leu Gln Arg Asp Leu
        275                 280                 285

Gly Ser Leu Pro Ala Ala Glu Pro Pro Pro Ala Pro Glu Ser Gly Leu
    290                 295                 300

Glu Asp Lys Leu Ser Glu Arg Leu Gly Glu Ala Trp Ala Gly Arg Gly
```

```
305                 310                 315                 320

Ala Ala Trp Trp Glu Arg Gln Gln Gly Arg Thr Ser Glu Pro Gly Arg
                325                 330                 335

Gln Thr Arg Arg Pro Lys Arg Arg Thr Gln Leu Ser Ser Ser Phe Ser
            340                 345                 350

Leu Ser Gly His Val Asp Pro Ser Glu Asp Thr Ser Ser Pro His Ser
        355                 360                 365

Pro Glu Trp Pro Pro Ala Asp Ala Leu Pro Leu Pro Pro Thr Thr Pro
    370                 375                 380

Pro Ser Gln Glu Leu Thr Pro Asp Ala Cys Ala Gln Gly Val Pro Ser
385                 390                 395                 400

Glu Gln Arg Gln Met Leu Arg Asp Tyr Met Ala Lys Leu Pro Pro Gln
                405                 410                 415

Arg Asp Thr Pro Gly Cys Ala Thr Thr Pro Pro His Ser Gln Ala Ser
            420                 425                 430

Ser Val Arg Ala Thr Arg Ser Gln Gln His Thr Pro Val Leu Ser Ser
        435                 440                 445

Ser Gln Pro Leu Arg Lys Lys Pro Arg Met Gly Phe
    450                 455                 460


<210> SEQ ID NO 58
<211> LENGTH: 392
<212> TYPE: PRT
<213> ORGANISM: Homo sapiens

<400> SEQUENCE: 58

Met Leu Lys Trp Asn His Gly Leu Pro Ser Pro Leu Leu Leu Ala Arg
1               5                   10                  15

Leu Leu Pro Pro Pro Arg Pro Ser Cys Val Gln Pro Leu Leu Leu Gly
            20                  25                  30

Gly Gln Gly Gly Gln Leu Gln Leu Leu His Leu Ala Glu Gly Ala Ser
        35                  40                  45

Val Pro Arg Leu Ala Gly Pro Pro Gln Ser Leu Pro Ser Arg Ile Asp
    50                  55                  60

Ser Leu Pro Ala Phe Pro Leu Leu Glu Pro Lys Ile Gln Trp Arg Leu
65                  70                  75                  80

Gln Glu Arg Leu Lys Ala Pro Thr Ile Gly Leu Ala Ala Val Val Pro
                85                  90                  95

Pro Leu Pro Ser Ala Pro Thr Pro Gly Leu Val Leu Phe Gln Leu Ser
            100                 105                 110

Ala Ala Gly Asp Val Phe Tyr Gln Gln Leu Arg Pro Gln Val Asp Ser
        115                 120                 125

Ser Leu Arg Arg Asp Ala Gly Pro Pro Gly Asp Thr Gln Pro Asp Cys
    130                 135                 140

His Ala Pro Thr Ala Ser Trp Thr Ser Gln Asp Thr Ala Gly Cys Ser
145                 150                 155                 160

Gln Trp Leu Lys Ala Leu Leu Lys Val Pro Leu Ala Pro Pro Val Trp
                165                 170                 175

Thr Ala Pro Thr Phe Thr His Arg Gln Met Leu Gly Ser Thr Glu Leu
            180                 185                 190

Arg Arg Glu Glu Glu Glu Gly Gln Arg Leu Gly Val Leu Arg Lys Ala
        195                 200                 205

Met Ala Arg Gly Gln Leu Leu Leu Gln Arg Asp Leu Gly Ser Leu Pro
    210                 215                 220
```

```
Ala Ala Glu Pro Pro Pro Ala Pro Glu Ser Gly Leu Glu Asp Lys Leu
225                 230                 235                 240

Ser Glu Arg Leu Gly Glu Ala Trp Ala Gly Arg Gly Ala Ala Trp Trp
                245                 250                 255

Glu Arg Gln Gln Gly Arg Thr Ser Glu Pro Gly Arg Gln Thr Arg Arg
            260                 265                 270

Pro Lys Arg Arg Thr Gln Leu Ser Ser Ser Phe Ser Leu Ser Gly His
        275                 280                 285

Val Asp Pro Ser Glu Asp Thr Ser Ser Pro His Ser Pro Glu Trp Pro
    290                 295                 300

Pro Ala Asp Ala Leu Pro Leu Pro Pro Thr Thr Pro Pro Ser Gln Glu
305                 310                 315                 320

Leu Thr Pro Asp Ala Cys Ala Gln Gly Val Pro Ser Glu Gln Arg Gln
                325                 330                 335

Met Leu Arg Asp Tyr Met Ala Lys Leu Pro Pro Gln Arg Asp Thr Pro
            340                 345                 350

Gly Cys Ala Thr Thr Pro Pro His Ser Gln Ala Ser Ser Val Arg Ala
        355                 360                 365

Thr Arg Ser Gln Gln His Thr Pro Val Leu Ser Ser Ser Gln Pro Leu
    370                 375                 380

Arg Lys Lys Pro Arg Met Gly Phe
385                 390


<210> SEQ ID NO 59
<211> LENGTH: 278
<212> TYPE: PRT
<213> ORGANISM: Homo sapiens

<400> SEQUENCE: 59

Met Asp Lys Ser Gly Ile Asp Ser Leu Asp His Val Thr Ser Asp Ala
1               5                   10                  15

Val Glu Leu Ala Asn Arg Ser Asp Asn Ser Ser Asp Ser Ser Leu Phe
            20                  25                  30

Lys Thr Gln Cys Ile Pro Tyr Ser Pro Lys Gly Glu Lys Arg Asn Pro
        35                  40                  45

Ile Arg Lys Phe Val Arg Thr Pro Glu Ser Val His Ala Ser Asp Ser
    50                  55                  60

Ser Ser Asp Ser Ser Phe Glu Pro Ile Pro Leu Thr Ile Lys Ala Ile
65                  70                  75                  80

Phe Glu Arg Phe Lys Asn Arg Lys Lys Arg Tyr Lys Lys Lys Lys Lys
                85                  90                  95

Arg Arg Tyr Gln Pro Thr Gly Arg Pro Arg Gly Arg Pro Glu Gly Arg
            100                 105                 110

Arg Asn Pro Ile Tyr Ser Leu Ile Asp Lys Lys Lys Gln Phe Arg Ser
        115                 120                 125

Arg Gly Ser Gly Phe Pro Phe Leu Glu Ser Glu Asn Glu Lys Asn Ala
    130                 135                 140

Pro Trp Arg Lys Ile Leu Thr Phe Glu Gln Ala Val Ala Arg Gly Phe
145                 150                 155                 160

Phe Asn Tyr Ile Glu Lys Leu Lys Tyr Glu His His Leu Lys Glu Ser
                165                 170                 175

Leu Lys Gln Met Asn Val Gly Glu Asp Leu Glu Asn Glu Asp Phe Asp
            180                 185                 190

Ser Arg Arg Tyr Lys Phe Leu Asp Asp Asp Gly Ser Ile Ser Pro Ile
        195                 200                 205
```

```
Glu Glu Ser Thr Ala Glu Asp Glu Asp Ala Thr His Leu Glu Asp Asn
    210                 215                 220

Glu Cys Asp Ile Lys Leu Ala Gly Asp Ser Phe Ile Val Ser Ser Glu
225                 230                 235                 240

Phe Pro Val Arg Leu Ser Val Tyr Leu Glu Glu Glu Asp Ile Thr Glu
                245                 250                 255

Glu Ala Ala Leu Ser Lys Lys Arg Ala Thr Lys Ala Lys Asn Thr Gly
            260                 265                 270

Gln Arg Gly Leu Lys Met
        275


<210> SEQ ID NO 60
<211> LENGTH: 727
<212> TYPE: PRT
<213> ORGANISM: Homo sapiens

<400> SEQUENCE: 60

Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
    50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95

Lys Asn Pro Tyr Lys Gly Lys Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
    130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                165                 170                 175

Ala Arg Phe Arg Glu Asp His Pro Asp Leu Ile Gln Asn Ala Lys Lys
            180                 185                 190

Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Glu Ile Met Arg
    210                 215                 220

Asp Tyr Ile Gln Lys His Pro Glu Leu Asn Ile Ser Glu Glu Gly Ile
225                 230                 235                 240

Thr Lys Ser Thr Leu Thr Lys Ala Glu Arg Gln Leu Lys Asp Lys Phe
                245                 250                 255

Asp Gly Arg Pro Thr Lys Pro Pro Pro Asn Ser Tyr Ser Leu Tyr Cys
            260                 265                 270

Ala Glu Leu Met Ala Asn Met Lys Asp Val Pro Ser Thr Glu Arg Met
        275                 280                 285

Val Leu Cys Ser Gln Gln Trp Lys Leu Leu Ser Gln Lys Glu Lys Asp
```

-continued

```
    290                 295                 300

Ala Tyr His Lys Lys Cys Asp Gln Lys Lys Lys Asp Tyr Glu Val Glu
305                 310                 315                 320

Leu Leu Arg Phe Leu Glu Ser Leu Pro Glu Glu Glu Gln Gln Arg Val
                325                 330                 335

Leu Gly Glu Glu Lys Met Leu Asn Ile Asn Lys Lys Gln Ala Thr Ser
            340                 345                 350

Pro Ala Ser Lys Lys Pro Ala Gln Glu Gly Gly Lys Gly Gly Ser Glu
        355                 360                 365

Lys Pro Lys Arg Pro Val Ser Ala Met Phe Ile Phe Ser Glu Glu Lys
    370                 375                 380

Arg Arg Gln Leu Gln Glu Glu Arg Pro Glu Leu Ser Glu Ser Glu Leu
385                 390                 395                 400

Thr Arg Leu Leu Ala Arg Met Trp Asn Asp Leu Ser Glu Lys Lys Lys
                405                 410                 415

Ala Lys Tyr Lys Ala Arg Glu Ala Ala Leu Lys Ala Gln Ser Glu Arg
            420                 425                 430

Lys Pro Gly Gly Glu Arg Glu Glu Arg Gly Lys Leu Pro Glu Ser Pro
        435                 440                 445

Lys Arg Ala Glu Glu Ile Trp Gln Gln Ser Val Ile Gly Asp Tyr Leu
    450                 455                 460

Ala Arg Phe Lys Asn Asp Arg Val Lys Ala Leu Lys Ala Met Glu Met
465                 470                 475                 480

Thr Trp Asn Asn Met Glu Lys Lys Glu Lys Leu Met Trp Ile Lys Lys
                485                 490                 495

Ala Ala Glu Asp Gln Lys Arg Tyr Glu Arg Glu Leu Ser Glu Met Arg
            500                 505                 510

Ala Pro Pro Ala Ala Thr Asn Ser Ser Lys Lys Met Lys Phe Gln Gly
        515                 520                 525

Glu Pro Lys Lys Pro Pro Met Asn Gly Tyr Gln Lys Phe Ser Gln Glu
    530                 535                 540

Leu Leu Ser Asn Gly Glu Leu Asn His Leu Pro Leu Lys Glu Arg Met
545                 550                 555                 560

Val Glu Ile Gly Ser Arg Trp Gln Arg Ile Ser Gln Ser Gln Lys Glu
                565                 570                 575

His Tyr Lys Lys Leu Ala Glu Glu Gln Gln Lys Gln Tyr Lys Val His
            580                 585                 590

Leu Asp Leu Trp Val Lys Ser Leu Ser Pro Gln Asp Arg Ala Ala Tyr
        595                 600                 605

Lys Glu Tyr Ile Ser Asn Lys Arg Lys Ser Met Thr Lys Leu Arg Gly
    610                 615                 620

Pro Asn Pro Lys Ser Ser Arg Thr Thr Leu Gln Ser Lys Ser Glu Ser
625                 630                 635                 640

Glu Glu Asp Asp Glu Glu Asp Glu Asp Asp Glu Asp Glu Asp Glu Glu
                645                 650                 655

Glu Glu Asp Asp Glu Asn Gly Asp Ser Ser Glu Asp Gly Gly Asp Ser
            660                 665                 670

Ser Glu Ser Ser Ser Glu Asp Glu Ser Glu Asp Gly Asp Glu Asn Glu
        675                 680                 685

Glu Asp Asp Glu Asp Glu Asp Asp Asp Glu Asp Asp Asp Glu Asp Glu
    690                 695                 700

Asp Asn Glu Ser Glu Gly Ser Ser Ser Ser Ser Ser Ser Ser Gly Asp
705                 710                 715                 720
```

Ser Ser Asp Ser Asp Ser Asn
725

<210> SEQ ID NO 61
<211> LENGTH: 727
<212> TYPE: PRT
<213> ORGANISM: Homo sapiens

<400> SEQUENCE: 61

Met Asn Gly Glu Ala Asp Cys Pro Thr Asp Leu Glu Met Ala Ala Pro
1 5 10 15

Lys Gly Gln Asp Arg Trp Ser Gln Glu Asp Met Leu Thr Leu Leu Glu
20 25 30

Cys Met Lys Asn Asn Leu Pro Ser Asn Asp Ser Ser Lys Phe Lys Thr
35 40 45

Thr Glu Ser His Met Asp Trp Glu Lys Val Ala Phe Lys Asp Phe Ser
50 55 60

Gly Asp Met Cys Lys Leu Lys Trp Val Glu Ile Ser Asn Glu Val Arg
65 70 75 80

Lys Phe Arg Thr Leu Thr Glu Leu Ile Leu Asp Ala Gln Glu His Val
85 90 95

Lys Asn Pro Tyr Lys Gly Lys Lys Leu Lys Lys His Pro Asp Phe Pro
100 105 110

Lys Lys Pro Leu Thr Pro Tyr Phe Arg Phe Phe Met Glu Lys Arg Ala
115 120 125

Lys Tyr Ala Lys Leu His Pro Glu Met Ser Asn Leu Asp Leu Thr Lys
130 135 140

Ile Leu Ser Lys Lys Tyr Lys Glu Leu Pro Glu Lys Lys Lys Met Lys
145 150 155 160

Tyr Ile Gln Asp Phe Gln Arg Glu Lys Gln Glu Phe Glu Arg Asn Leu
165 170 175

Ala Arg Phe Arg Glu Asp His Pro Asp Leu Ile Gln Asn Ala Lys Lys
180 185 190

Ser Asp Ile Pro Glu Lys Pro Lys Thr Pro Gln Gln Leu Trp Tyr Thr
195 200 205

His Glu Lys Lys Val Tyr Leu Lys Val Arg Pro Asp Glu Ile Met Arg
210 215 220

Asp Tyr Ile Gln Lys His Pro Glu Leu Asn Ile Ser Glu Glu Gly Ile
225 230 235 240

Thr Lys Ser Thr Leu Thr Lys Ala Glu Arg Gln Leu Lys Asp Lys Phe
245 250 255

Asp Gly Arg Pro Thr Lys Pro Pro Pro Asn Ser Tyr Ser Leu Tyr Cys
260 265 270

Ala Glu Leu Met Ala Asn Met Lys Asp Val Pro Ser Thr Glu Arg Met
275 280 285

Val Leu Cys Ser Gln Gln Trp Lys Leu Leu Ser Gln Lys Glu Lys Asp
290 295 300

Ala Tyr His Lys Lys Cys Asp Gln Lys Lys Lys Asp Tyr Glu Val Glu
305 310 315 320

Leu Leu Arg Phe Leu Glu Ser Leu Pro Glu Glu Glu Gln Gln Arg Val
325 330 335

Leu Gly Glu Glu Lys Met Leu Asn Ile Asn Lys Lys Gln Ala Thr Ser
340 345 350

Pro Ala Ser Lys Lys Pro Ala Gln Glu Gly Gly Lys Gly Gly Ser Glu 355 360 365

Lys Pro Lys Arg Pro Val Ser Ala Met Phe Ile Phe Ser Glu Glu Lys
370 375 380

Arg Arg Gln Leu Gln Glu Glu Arg Pro Glu Leu Ser Glu Ser Glu Leu
385 390 395 400

Thr Arg Leu Leu Ala Arg Met Trp Asn Asp Leu Ser Glu Lys Lys Lys
405 410 415

Ala Lys Tyr Lys Ala Arg Glu Ala Ala Leu Lys Ala Gln Ser Glu Arg
420 425 430

Lys Pro Gly Gly Glu Arg Glu Glu Arg Gly Lys Leu Pro Glu Ser Pro
435 440 445

Lys Arg Ala Glu Glu Ile Trp Gln Gln Ser Val Ile Gly Asp Tyr Leu
450 455 460

Ala Arg Phe Lys Asn Asp Arg Val Lys Ala Leu Lys Ala Met Glu Met
465 470 475 480

Thr Trp Asn Asn Met Glu Lys Lys Glu Lys Leu Met Trp Ile Lys Lys
485 490 495

Ala Ala Glu Asp Gln Lys Arg Tyr Glu Arg Glu Leu Ser Glu Met Arg
500 505 510

Ala Pro Pro Ala Ala Thr Asn Ser Ser Lys Lys Met Lys Phe Gln Gly
515 520 525

Glu Pro Lys Lys Pro Pro Met Asn Gly Tyr Gln Lys Phe Ser Gln Glu
530 535 540

Leu Leu Ser Asn Gly Glu Leu Asn His Leu Pro Leu Lys Glu Arg Met
545 550 555 560

Val Glu Ile Gly Ser Arg Trp Gln Arg Ile Ser Gln Ser Gln Lys Glu
565 570 575

His Tyr Lys Lys Leu Ala Glu Glu Gln Gln Lys Gln Tyr Lys Val His
580 585 590

Leu Asp Leu Trp Val Lys Ser Leu Ser Pro Gln Asp Arg Ala Ala Tyr
595 600 605

Lys Glu Tyr Ile Ser Asn Lys Arg Lys Ser Met Thr Lys Leu Arg Gly
610 615 620

Pro Asn Pro Lys Ser Ser Arg Thr Thr Leu Gln Ser Lys Ser Glu Ser
625 630 635 640

Glu Glu Asp Asp Glu Glu Asp Glu Asp Asp Glu Asp Glu Asp Glu Glu
645 650 655

Glu Glu Asp Asp Glu Asn Gly Asp Ser Ser Glu Asp Gly Gly Asp Ser
660 665 670

Ser Glu Ser Ser Ser Glu Asp Glu Ser Glu Asp Gly Asp Glu Asn Glu
675 680 685

Glu Asp Asp Glu Asp Glu Asp Asp Asp Glu Asp Asp Asp Glu Asp Glu
690 695 700

Asp Asn Glu Ser Glu Gly Ser Ser Ser Ser Ser Ser Ser Ser Gly Asp
705 710 715 720

Ser Ser Asp Ser Asp Ser Asn
725

<210> SEQ ID NO 62
<211> LENGTH: 764
<212> TYPE: PRT
<213> ORGANISM: Homo sapiens

<400> SEQUENCE: 62

-continued

```
Met Asn Gly Glu Ala Asp Cys Pro Thr Asp Leu Glu Met Ala Ala Pro
1               5                   10                  15

Lys Gly Gln Asp Arg Trp Ser Gln Glu Asp Met Leu Thr Leu Leu Glu
            20                  25                  30

Cys Met Lys Asn Asn Leu Pro Ser Asn Asp Ser Ser Lys Phe Lys Thr
        35                  40                  45

Thr Glu Ser His Met Asp Trp Glu Lys Val Ala Phe Lys Asp Phe Ser
    50                  55                  60

Gly Asp Met Cys Lys Leu Lys Trp Val Glu Ile Ser Asn Glu Val Arg
65                  70                  75                  80

Lys Phe Arg Thr Leu Thr Glu Leu Ile Leu Asp Ala Gln Glu His Val
                85                  90                  95

Lys Asn Pro Tyr Lys Gly Lys Lys Leu Lys Lys His Pro Asp Phe Pro
            100                 105                 110

Lys Lys Pro Leu Thr Pro Tyr Phe Arg Phe Phe Met Glu Lys Arg Ala
        115                 120                 125

Lys Tyr Ala Lys Leu His Pro Glu Met Ser Asn Leu Asp Leu Thr Lys
    130                 135                 140

Ile Leu Ser Lys Lys Tyr Lys Glu Leu Pro Glu Lys Lys Lys Met Lys
145                 150                 155                 160

Tyr Ile Gln Asp Phe Gln Arg Glu Lys Gln Glu Phe Glu Arg Asn Leu
                165                 170                 175

Ala Arg Phe Arg Glu Asp His Pro Asp Leu Ile Gln Asn Ala Lys Lys
            180                 185                 190

Ser Asp Ile Pro Glu Lys Pro Lys Thr Pro Gln Gln Leu Trp Tyr Thr
        195                 200                 205

His Glu Lys Lys Val Tyr Leu Lys Val Arg Pro Asp Ala Thr Thr Lys
    210                 215                 220

Glu Val Lys Asp Ser Leu Gly Lys Gln Trp Ser Gln Leu Ser Asp Lys
225                 230                 235                 240

Lys Arg Leu Lys Trp Ile His Lys Ala Leu Glu Gln Arg Lys Glu Tyr
                245                 250                 255

Glu Glu Ile Met Arg Asp Tyr Ile Gln Lys His Pro Glu Leu Asn Ile
            260                 265                 270

Ser Glu Glu Gly Ile Thr Lys Ser Thr Leu Thr Lys Ala Glu Arg Gln
        275                 280                 285

Leu Lys Asp Lys Phe Asp Gly Arg Pro Thr Lys Pro Pro Pro Asn Ser
    290                 295                 300

Tyr Ser Leu Tyr Cys Ala Glu Leu Met Ala Asn Met Lys Asp Val Pro
305                 310                 315                 320

Ser Thr Glu Arg Met Val Leu Cys Ser Gln Gln Trp Lys Leu Leu Ser
                325                 330                 335

Gln Lys Glu Lys Asp Ala Tyr His Lys Lys Cys Asp Gln Lys Lys Lys
            340                 345                 350

Asp Tyr Glu Val Glu Leu Leu Arg Phe Leu Glu Ser Leu Pro Glu Glu
        355                 360                 365

Glu Gln Gln Arg Val Leu Gly Glu Glu Lys Met Leu Asn Ile Asn Lys
    370                 375                 380

Lys Gln Ala Thr Ser Pro Ala Ser Lys Lys Pro Ala Gln Glu Gly Gly
385                 390                 395                 400

Lys Gly Gly Ser Glu Lys Pro Lys Arg Pro Val Ser Ala Met Phe Ile
                405                 410                 415
```

```
Phe Ser Glu Glu Lys Arg Arg Gln Leu Gln Glu Glu Arg Pro Glu Leu
            420                 425                 430

Ser Glu Ser Glu Leu Thr Arg Leu Leu Ala Arg Met Trp Asn Asp Leu
        435                 440                 445

Ser Glu Lys Lys Lys Ala Lys Tyr Lys Ala Arg Glu Ala Ala Leu Lys
    450                 455                 460

Ala Gln Ser Glu Arg Lys Pro Gly Gly Glu Arg Glu Glu Arg Gly Lys
465                 470                 475                 480

Leu Pro Glu Ser Pro Lys Arg Ala Glu Glu Ile Trp Gln Gln Ser Val
                485                 490                 495

Ile Gly Asp Tyr Leu Ala Arg Phe Lys Asn Asp Arg Val Lys Ala Leu
            500                 505                 510

Lys Ala Met Glu Met Thr Trp Asn Asn Met Glu Lys Lys Glu Lys Leu
        515                 520                 525

Met Trp Ile Lys Lys Ala Ala Glu Asp Gln Lys Arg Tyr Glu Arg Glu
    530                 535                 540

Leu Ser Glu Met Arg Ala Pro Pro Ala Ala Thr Asn Ser Ser Lys Lys
545                 550                 555                 560

Met Lys Phe Gln Gly Glu Pro Lys Lys Pro Pro Met Asn Gly Tyr Gln
                565                 570                 575

Lys Phe Ser Gln Glu Leu Leu Ser Asn Gly Glu Leu Asn His Leu Pro
            580                 585                 590

Leu Lys Glu Arg Met Val Glu Ile Gly Ser Arg Trp Gln Arg Ile Ser
        595                 600                 605

Gln Ser Gln Lys Glu His Tyr Lys Lys Leu Ala Glu Glu Gln Gln Lys
    610                 615                 620

Gln Tyr Lys Val His Leu Asp Leu Trp Val Lys Ser Leu Ser Pro Gln
625                 630                 635                 640

Asp Arg Ala Ala Tyr Lys Glu Tyr Ile Ser Asn Lys Arg Lys Ser Met
                645                 650                 655

Thr Lys Leu Arg Gly Pro Asn Pro Lys Ser Ser Arg Thr Thr Leu Gln
            660                 665                 670

Ser Lys Ser Glu Ser Glu Glu Asp Asp Glu Glu Asp Glu Asp Asp Glu
        675                 680                 685

Asp Glu Asp Glu Glu Glu Glu Asp Asp Glu Asn Gly Asp Ser Ser Glu
    690                 695                 700

Asp Gly Gly Asp Ser Ser Glu Ser Ser Ser Glu Asp Glu Ser Glu Asp
705                 710                 715                 720

Gly Asp Glu Asn Glu Glu Asp Asp Glu Asp Glu Asp Asp Asp Glu Asp
                725                 730                 735

Asp Asp Glu Asp Glu Asp Asn Glu Ser Glu Gly Ser Ser Ser Ser Ser
            740                 745                 750

Ser Ser Ser Gly Asp Ser Ser Asp Ser Asp Ser Asn
        755                 760


<210> SEQ ID NO 63
<211> LENGTH: 390
<212> TYPE: PRT
<213> ORGANISM: Homo sapiens

<400> SEQUENCE: 63

Met Tyr Arg Asp Asp Leu Glu Arg Phe Lys Glu Phe Lys Ala Gln Gly
1               5                   10                  15

Val Ala Ile Lys Phe Gly Lys Phe Ser Val Lys Glu Asn Lys Gln Leu
            20                  25                  30
```

-continued

```
Glu Lys Asn Val Glu Asp Phe Leu Ala Leu Thr Gly Ile Glu Ser Ala
        35                  40                  45

Asp Lys Leu Leu Tyr Thr Asp Arg Tyr Pro Glu Glu Lys Ser Val Ile
    50                  55                  60

Thr Asn Leu Lys Arg Arg Tyr Ser Phe Arg Leu His Ile Gly Arg Asn
65                  70                  75                  80

Ile Ala Arg Pro Trp Lys Leu Ile Tyr Tyr Arg Ala Lys Lys Met Phe
                85                  90                  95

Asp Val Asn Asn Tyr Lys Gly Arg Tyr Ser Glu Gly Asp Thr Glu Lys
            100                 105                 110

Leu Lys Met Tyr His Ser Leu Leu Gly Asn Asp Trp Lys Thr Ile Gly
        115                 120                 125

Glu Met Val Ala Arg Ser Ser Leu Ser Val Ala Leu Lys Phe Ser Gln
    130                 135                 140

Ile Ser Ser Gln Arg Asn Arg Gly Ala Trp Ser Lys Ser Glu Thr Arg
145                 150                 155                 160

Lys Leu Ile Lys Ala Val Glu Glu Val Ile Leu Lys Lys Met Ser Pro
                165                 170                 175

Gln Glu Leu Lys Glu Val Asp Ser Lys Leu Gln Glu Asn Pro Glu Ser
            180                 185                 190

Cys Leu Ser Ile Val Arg Glu Lys Leu Tyr Lys Gly Ile Ser Trp Val
        195                 200                 205

Glu Val Glu Ala Lys Val Gln Thr Arg Asn Trp Met Gln Cys Lys Ser
    210                 215                 220

Lys Trp Thr Glu Ile Leu Thr Lys Arg Met Thr Asn Gly Arg Arg Ile
225                 230                 235                 240

Tyr Tyr Gly Met Asn Ala Leu Arg Ala Lys Val Ser Leu Ile Glu Arg
                245                 250                 255

Leu Tyr Glu Ile Asn Val Glu Asp Thr Asn Glu Ile Asp Trp Glu Asp
            260                 265                 270

Leu Ala Ser Ala Ile Gly Asp Val Pro Pro Ser Tyr Val Gln Thr Lys
        275                 280                 285

Phe Ser Arg Leu Lys Ala Val Tyr Val Pro Phe Trp Gln Lys Lys Thr
    290                 295                 300

Phe Pro Glu Ile Ile Asp Tyr Leu Tyr Glu Thr Thr Leu Pro Leu Leu
305                 310                 315                 320

Lys Glu Lys Leu Glu Lys Met Met Glu Lys Lys Gly Thr Lys Ile Gln
                325                 330                 335

Thr Pro Ala Ala Pro Lys Gln Val Phe Pro Phe Arg Asp Ile Phe Tyr
            340                 345                 350

Tyr Glu Asp Asp Ser Glu Gly Glu Asp Ile Glu Lys Glu Ser Glu Gly
        355                 360                 365

Gln Ala Pro Cys Met Ala His Ala Cys Asn Ser Ser Thr Leu Gly Gly
    370                 375                 380

Gln Gly Arg Trp Ile Ile
385                 390
```

<210> SEQ ID NO 64
<211> LENGTH: 905
<212> TYPE: PRT
<213> ORGANISM: Homo sapiens

<400> SEQUENCE: 64

Met Glu Gly Glu Ser Ser Arg Phe Glu Ile His Thr Pro Val Ser Asp
1               5                   10                  15

Lys Lys Lys Lys Lys Cys Ser Ile His Lys Glu Arg Pro Gln Lys His
            20                  25                  30

Ser His Glu Ile Phe Arg Asp Ser Ser Leu Val Asn Glu Gln Ser Gln
        35                  40                  45

Ile Thr Arg Arg Lys Lys Arg Lys Lys Asp Phe Gln His Leu Ile Ser
    50                  55                  60

Ser Pro Leu Lys Lys Ser Arg Ile Cys Asp Glu Thr Ala Asn Ala Thr
65                  70                  75                  80

Ser Thr Leu Lys Lys Arg Lys Lys Arg Arg Tyr Ser Ala Leu Glu Val
                85                  90                  95

Asp Glu Glu Ala Gly Val Thr Val Val Leu Val Asp Lys Glu Asn Ile
            100                 105                 110

Asn Asn Thr Pro Lys His Phe Arg Lys Asp Val Asp Val Val Cys Val
        115                 120                 125

Asp Met Ser Ile Glu Gln Lys Leu Pro Arg Lys Pro Lys Thr Asp Lys
    130                 135                 140

Phe Gln Val Leu Ala Lys Ser His Ala His Lys Ser Glu Ala Leu His
145                 150                 155                 160

Ser Lys Val Arg Glu Lys Lys Asn Lys Lys His Gln Arg Lys Ala Ala
                165                 170                 175

Ser Trp Glu Ser Gln Arg Ala Arg Asp Thr Leu Pro Gln Ser Glu Ser
            180                 185                 190

His Gln Glu Glu Ser Trp Leu Ser Val Gly Pro Gly Gly Glu Ile Thr
        195                 200                 205

Glu Leu Pro Ala Ser Ala His Lys Asn Lys Ser Lys Lys Lys Lys Lys
    210                 215                 220

Lys Ser Ser Asn Arg Glu Tyr Glu Thr Leu Ala Met Pro Glu Gly Ser
225                 230                 235                 240

Gln Ala Gly Arg Glu Ala Gly Thr Asp Met Gln Glu Ser Gln Pro Thr
                245                 250                 255

Val Gly Leu Asp Asp Glu Thr Pro Gln Leu Leu Gly Pro Thr His Lys
            260                 265                 270

Lys Lys Ser Lys Lys Lys Lys Lys Lys Lys Ser Asn His Gln Glu Phe
        275                 280                 285

Glu Ala Leu Ala Met Pro Glu Gly Ser Gln Val Gly Ser Glu Val Gly
    290                 295                 300

Ala Asp Met Gln Glu Ser Arg Pro Ala Val Gly Leu His Gly Glu Thr
305                 310                 315                 320

Ala Gly Ile Pro Ala Pro Ala Tyr Lys Asn Lys Ser Lys Lys Lys Lys
                325                 330                 335

Lys Lys Ser Asn His Gln Glu Phe Glu Ala Val Ala Met Pro Glu Ser
            340                 345                 350

Leu Glu Ser Ala Tyr Pro Glu Gly Ser Gln Val Gly Ser Glu Val Gly
        355                 360                 365

Thr Val Glu Gly Ser Thr Ala Leu Lys Gly Phe Lys Glu Ser Asn Ser
    370                 375                 380

Thr Lys Lys Lys Ser Lys Lys Arg Lys Leu Thr Ser Val Lys Arg Ala
385                 390                 395                 400

Arg Val Ser Gly Asp Asp Phe Ser Val Pro Ser Lys Asn Ser Glu Ser
                405                 410                 415

-continued

```
Thr Leu Phe Asp Ser Val Glu Gly Asp Gly Ala Met Met Glu Glu Gly
            420                 425                 430

Val Lys Ser Arg Pro Arg Gln Lys Lys Thr Gln Ala Cys Leu Ala Ser
        435                 440                 445

Lys His Val Gln Glu Ala Pro Arg Leu Glu Pro Ala Asn Glu Glu His
    450                 455                 460

Asn Val Glu Thr Ala Glu Asp Ser Glu Ile Arg Tyr Leu Ser Ala Asp
465                 470                 475                 480

Ser Gly Asp Ala Asp Asp Ser Asp Ala Asp Leu Gly Ser Ala Val Lys
                485                 490                 495

Gln Leu Gln Glu Phe Ile Pro Asn Ile Lys Asp Arg Ala Thr Ser Thr
            500                 505                 510

Ile Lys Arg Met Tyr Arg Asp Asp Leu Glu Arg Phe Lys Glu Phe Lys
        515                 520                 525

Ala Gln Gly Val Ala Ile Lys Phe Gly Lys Phe Ser Val Lys Glu Asn
    530                 535                 540

Lys Gln Leu Glu Lys Asn Val Glu Asp Phe Leu Ala Leu Thr Gly Ile
545                 550                 555                 560

Glu Ser Ala Asp Lys Leu Leu Tyr Thr Asp Arg Tyr Pro Glu Glu Lys
                565                 570                 575

Ser Val Ile Thr Asn Leu Lys Arg Arg Tyr Ser Phe Arg Leu His Ile
            580                 585                 590

Gly Arg Asn Ile Ala Arg Pro Trp Lys Leu Ile Tyr Tyr Arg Ala Lys
        595                 600                 605

Lys Met Phe Asp Val Asn Asn Tyr Lys Gly Arg Tyr Ser Glu Gly Asp
    610                 615                 620

Thr Glu Lys Leu Lys Met Tyr His Ser Leu Leu Gly Asn Asp Trp Lys
625                 630                 635                 640

Thr Ile Gly Glu Met Val Ala Arg Ser Ser Leu Ser Val Ala Leu Lys
                645                 650                 655

Phe Ser Gln Ile Ser Ser Gln Arg Asn Arg Gly Ala Trp Ser Lys Ser
            660                 665                 670

Glu Thr Arg Lys Leu Ile Lys Ala Val Glu Glu Val Ile Leu Lys Lys
        675                 680                 685

Met Ser Pro Gln Glu Leu Lys Glu Val Asp Ser Lys Leu Gln Glu Asn
    690                 695                 700

Pro Glu Ser Cys Leu Ser Ile Val Arg Glu Lys Leu Tyr Lys Gly Ile
705                 710                 715                 720

Ser Trp Val Glu Val Glu Ala Lys Val Gln Thr Arg Asn Trp Met Gln
                725                 730                 735

Cys Lys Ser Lys Trp Thr Glu Ile Leu Thr Lys Arg Met Thr Asn Gly
            740                 745                 750

Arg Arg Ile Tyr Tyr Gly Met Asn Ala Leu Arg Ala Lys Val Ser Leu
        755                 760                 765

Ile Glu Arg Leu Tyr Glu Ile Asn Val Glu Asp Thr Asn Glu Ile Asp
    770                 775                 780

Trp Glu Asp Leu Ala Ser Ala Ile Gly Asp Val Pro Pro Ser Tyr Val
785                 790                 795                 800

Gln Thr Lys Phe Ser Arg Leu Lys Ala Val Tyr Val Pro Phe Trp Gln
                805                 810                 815

Lys Lys Thr Phe Pro Glu Ile Ile Asp Tyr Leu Tyr Glu Thr Thr Leu
            820                 825                 830
```

```
Pro Leu Leu Lys Glu Lys Leu Glu Lys Met Met Glu Lys Lys Gly Thr
        835                 840                 845

Lys Ile Gln Thr Pro Ala Ala Pro Lys Gln Val Phe Pro Phe Arg Asp
    850                 855                 860

Ile Phe Tyr Tyr Glu Asp Asp Ser Glu Gly Glu Asp Ile Glu Lys Glu
865                 870                 875                 880

Ser Glu Gly Gln Ala Pro Cys Met Ala His Ala Cys Asn Ser Ser Thr
                885                 890                 895

Leu Gly Gly Gln Gly Arg Trp Ile Ile
            900                 905


<210> SEQ ID NO 65
<211> LENGTH: 390
<212> TYPE: PRT
<213> ORGANISM: Homo sapiens

<400> SEQUENCE: 65

Met Glu Asp Pro Thr Leu Tyr Ile Val Glu Arg Pro Leu Pro Gly Tyr
1               5                   10                  15

Pro Asp Ala Glu Ala Pro Glu Pro Ser Ser Ala Gly Ala Gln Ala Ala
            20                  25                  30

Glu Glu Pro Ser Gly Ala Gly Ser Glu Glu Leu Ile Lys Ser Asp Gln
        35                  40                  45

Val Asn Gly Val Leu Val Leu Ser Leu Leu Asp Lys Ile Ile Gly Ala
    50                  55                  60

Val Asp Gln Ile Gln Leu Thr Gln Ala Gln Leu Glu Glu Arg Gln Ala
65                  70                  75                  80

Glu Met Glu Gly Ala Val Gln Ser Ile Gln Gly Glu Leu Ser Lys Leu
                85                  90                  95

Gly Lys Ala His Ala Thr Thr Ser Asn Thr Val Ser Lys Leu Leu Glu
            100                 105                 110

Lys Val Arg Lys Val Ser Val Asn Val Lys Thr Val Arg Gly Ser Leu
        115                 120                 125

Glu Arg Gln Ala Gly Gln Ile Lys Lys Leu Glu Val Asn Glu Ala Glu
    130                 135                 140

Leu Leu Arg Arg Arg Asn Phe Lys Val Met Ile Tyr Gln Asp Glu Val
145                 150                 155                 160

Lys Leu Pro Ala Lys Leu Ser Ile Ser Lys Ser Leu Lys Glu Ser Glu
                165                 170                 175

Ala Leu Pro Glu Lys Glu Gly Glu Glu Leu Gly Glu Gly Glu Arg Pro
            180                 185                 190

Glu Glu Asp Ala Ala Ala Leu Glu Leu Ser Ser Asp Glu Ala Val Glu
        195                 200                 205

Val Glu Glu Val Ile Glu Glu Ser Arg Ala Glu Arg Ile Lys Arg Ser
    210                 215                 220

Gly Leu Arg Arg Val Asp Asp Phe Lys Lys Ala Phe Ser Lys Glu Lys
225                 230                 235                 240

Met Glu Lys Thr Lys Val Arg Thr Arg Glu Asn Leu Glu Lys Thr Arg
                245                 250                 255

Leu Lys Thr Lys Glu Asn Leu Glu Lys Thr Arg His Thr Leu Glu Lys
            260                 265                 270

Arg Met Asn Lys Leu Gly Thr Arg Leu Val Pro Ala Glu Arg Arg Glu
        275                 280                 285

Lys Leu Lys Thr Ser Arg Asp Lys Leu Arg Lys Ser Phe Thr Pro Asp
    290                 295                 300
```

-continued

His Val Val Tyr Ala Arg Ser Lys Thr Ala Val Tyr Lys Val Pro Pro
305 310 315 320

Phe Thr Phe His Val Lys Lys Ile Arg Glu Gly Gln Val Glu Val Leu
325 330 335

Lys Ala Thr Glu Met Val Glu Val Gly Ala Asp Asp Asp Glu Gly Gly
340 345 350

Ala Glu Arg Gly Glu Ala Gly Asp Leu Arg Arg Gly Ser Ser Pro Asp
355 360 365

Val His Ala Leu Leu Glu Ile Thr Glu Glu Ser Asp Ala Val Leu Val
370 375 380

Asp Lys Ser Asp Ser Asp
385 390

<210> SEQ ID NO 66
<211> LENGTH: 133
<212> TYPE: PRT
<213> ORGANISM: Homo sapiens

<400> SEQUENCE: 66

Met Arg Pro Leu Thr Glu Glu Glu Thr Arg Val Met Phe Glu Lys Ile
1 5 10 15

Ala Lys Tyr Ile Gly Glu Asn Leu Gln Leu Leu Val Asp Arg Pro Asp
20 25 30

Gly Thr Tyr Cys Phe Arg Leu His Asn Asp Arg Val Tyr Tyr Val Ser
35 40 45

Glu Lys Ile Met Lys Leu Ala Ala Asn Ile Ser Gly Asp Lys Leu Val
50 55 60

Ser Leu Gly Thr Cys Phe Gly Lys Phe Thr Lys Thr His Lys Phe Arg
65 70 75 80

Leu His Val Thr Ala Leu Asp Tyr Leu Ala Pro Tyr Ala Lys Gly Phe
85 90 95

Gly Val Ala Ala Lys Ser Thr Gln Asp Cys Arg Lys Val Asp Pro Met
100 105 110

Ala Ile Val Val Phe His Gln Ala Asp Ile Gly Glu Tyr Val Arg His
115 120 125

Glu Glu Thr Leu Thr
130

<210> SEQ ID NO 67
<211> LENGTH: 180
<212> TYPE: PRT
<213> ORGANISM: Homo sapiens

<400> SEQUENCE: 67

Met Arg Pro Leu Thr Glu Glu Glu Thr Arg Val Met Phe Glu Lys Ile
1 5 10 15

Ala Lys Tyr Ile Gly Glu Asn Leu Gln Leu Leu Val Asp Arg Pro Asp
20 25 30

Gly Thr Tyr Cys Phe Arg Leu His Asn Asp Arg Val Tyr Tyr Val Ser
35 40 45

Glu Lys Ile Met Lys Leu Ala Ala Asn Ile Ser Gly Asp Lys Leu Val
50 55 60

Ser Leu Gly Thr Cys Phe Gly Lys Phe Thr Lys Thr His Lys Phe Arg
65 70 75 80

Leu His Val Thr Ala Leu Asp Tyr Leu Ala Pro Tyr Ala Lys Tyr Lys
85 90 95

-continued

```
Val Trp Ile Lys Pro Gly Ala Glu Gln Ser Phe Leu Tyr Gly Asn His
            100                 105                 110

Val Leu Lys Ser Gly Leu Gly Arg Ile Thr Glu Asn Thr Ser Gln Tyr
        115                 120                 125

Gln Gly Val Val Val Tyr Ser Met Ala Asp Ile Pro Leu Gly Phe Gly
    130                 135                 140

Val Ala Ala Lys Ser Thr Gln Asp Cys Arg Lys Val Asp Pro Met Ala
145                 150                 155                 160

Ile Val Val Phe His Gln Ala Asp Ile Gly Glu Tyr Val Arg His Glu
                165                 170                 175

Glu Thr Leu Thr
            180


<210> SEQ ID NO 68
<211> LENGTH: 13357
<212> TYPE: DNA
<213> ORGANISM: Homo sapiens

<400> SEQUENCE: 68

gctgacacgc tgtcctctgg cgacctgtcg ctggagaggt tgggcctccg gatgcgcgcg     60

gggctctggc ctaccggtga cccggctagc cggccgcgct cctgcttgag ccgcctgccg    120

gggcccgcgg gcctgctgtt ctctcgcgcg tccgagcgtc ccgactcccg gtgccggccc    180

gggtccgggt ctctgaccca cccgggggcg gcggggaagg cggcgagggc caccgtgccc    240

ccgtgcgctc tccgctgcgg gcgcccgggg cggccgcgac aaccccaccc cgctggctcc    300

gtgccgtgcg tgtcaggcgt tctcgtctcc gcggggttgt ccgccgcccc ttccccggag    360

tggggggttg gccggagccg atcggctcgc tggccggccg gccggcctcc gctcccgggg    420

ggctcttcgt gatcgatgtg gtgacgtcgt gctctcccgg gccgggtccg agccgcgacg    480

ggcgaggggc ggacgttcgt ggcgaacggg accgtccttc tcgctccgcc ccgcgggggt    540

cccctcgtct ctcctctccc cgcccgccgg cggtgcgtgt gggaaggcgt ggggtgcgga    600

ccccggcccg acctcgccgt cccgcccgcc gccttctgcg tcgcggggcg ggccggcggg    660

gtcctctgac gcggcagaca gccctcgctg tcgcctccag tggttgtcga cttgcgggcg    720

gcccccctcc gcggcggtgg gggtgccgtc ccgccggccc gtcgtgctgc cctctcgggg    780

ggtttgcgcg agcgtcggct ccgcctgggc ccttgcggtg ctcctggagc gctccgggtt    840

gtccctcagg tgcccgaggc cgaacggtgg tgtgtcgttc ccgcccccgg cgccccctcc    900

tccggtcgcc gccgcggtgt ccgcgcgtgg gtcctgaggg agctcgtcgg tgtggggttc    960

gaggcggttt gagtgagacg agacgagacg cgcccctccc acgcggggaa gggcgcccgc   1020

ctgctctcgg tgagcgcacg tcccgtgctc ccctctggcg ggtgcgcgcg ggccgtgtga   1080

gcgatcgcgg tgggttcggg ccggtgtgac gcgtgcgccg gccggccgcc gaggggctgc   1140

cgttctgcct ccgaccggtc gtgtgtgggt tgacttcgga ggcgctctgc ctcggaagga   1200

aggaggtggg tggacggggg ggcctggtgg ggttgcgcgc acgcgcgcac cggccgggcc   1260

cccgccctga acgcgaacgc tcgaggtggc cgcgcgcagg tgtttcctcg taccgcaggg   1320

ccccctccct tccccaggcg tccctcggcg cctctgcggg cccgaggagg agcggctggc   1380

gggtgggggg agtgtgaccc accctcggtg agaaaagcct tctctagcga tctgagaggc   1440

gtgccttggg ggtaccggat cccccgggcc gccgcctctg tctctgcctc cgttatggta   1500

gcgctgccgt agcgacccgc tcgcagagga ccctcctccg cttccccctc gacggggttg   1560

ggggggagaa gcgagggttc cgccggccac cgcggtggtg gccgagtgcg gctcgtcgcc   1620
```

-continued

```
tactgtggcc cgcgcctccc ccttccgagt cgggggagga tcccgccggg ccgggcccgg   1680

cgttcccagc gggttgggac gcggcggccg gcgggcggtg ggtgtgcgcg cccggcgctc   1740

tgtccggcgc gtgacccccct ccgccgcgag tcggctctcc gcccgctccc gtgccgagtc   1800

gtgaccggtg ccgacgaccg cgtttgcgtg gcacggggtc gggcccgcct ggccctggga   1860

aagcgtccca cggtgggggc gcgccggtct cccggagcgg gaccgggtcg gaggatggac   1920

gagaatcacg agcgacggtg gtgcgggcgt gtcgggttcg tggctgcggt cgctccgggg   1980

cccccggtgg cggggccccg gggctcgcga ggcggttctc ggtgggggcc gagggccgtc   2040

cggcgtccca ggcggggcgc cgcgggaccg ccctcgtgtc tgtggcggtg ggatcccgcg   2100

gccgtgtttt cctggtggcc cggccgtgcc tgaggtttct ccccgagccg ccgcctctgc   2160

gggctcccgg gtgcccttgc cctcgcggtc cccggccctc gcccgtctgt gccctcttcc   2220

ccgcccgccg cccgccgatc ctcttcttcc ccccgagcgg ctcaccggct tcacgtccgt   2280

tggtggcccc gcctgggacc gaacccggca ccgcctcgtg gggcgccgcc gccggccact   2340

gatcggcccg gcgtccgcgt cccccggcgc gcgccttggg gaccgggtcg gtggcgcccc   2400

gcgtggggcc cggtgggctt cccggagggt tccgggggtc ggcctgcggc gcgtgcgggg   2460

gaggagacgg ttccgggggga ccggccgcga ctgcggcggc ggtggtgggg gcagccgcgg   2520

ggatcgccga gggccggtcg gccgccccgg gtgccgcgcg gtgccgccgg cggcggtgag   2580

gccccgcgcg tgtgtcccgg ccgcggtcgg ccgcgctcga ggggtccccg tggcgtcccc   2640

ttccccgccg gccgcctttc tcgcgccttc cccgtcgccc cggcctcgcc cgtggtctct   2700

cgtcttctcc cggcccgctc ttccgaaccg ggtcggcgcg tcccccgggt gcgcctcgct   2760

tcccgggcct gccgcggccc ttccccgagg cgtccgtccc gggcgtcggc gtcggggaga   2820

gcccgtcctc cccgcgtggc gtcgccccgt tcggcgcgcg cgtgcgcccg agcgcggccc   2880

ggtggtccct gccggacagg cgttcgtgcg acgtgtggcg tgggtcgacc tccgccttgc   2940

cggtcgctcg cccttttcccc gggtcggggg gtggggcccg ggccggggcc tcggccccgg   3000

tcgcggtccc ccgtcccggg cgggggcggg cgcgccggcc ggcctcggtc ggccctccct   3060

tggccgtcgt gtggcgtgtg ccacccctgc gcccgcgccc gccggcgggg ctcggagccg   3120

ggcttcggcc gggccccggg ccctcgaccg gaccggtgcg cgggcgctgc ggccgcacgg   3180

cgcgactgtc cccgggccgg gcaccgcggt ccgcctctcg ctcgccgccc ggacgtcggg   3240

gccgccccgc ggggcgggcg gagcgccgtc cccgcctcgc cgccgcccgc gggcgccggc   3300

cgcgcgcgcg cgcgcgtggc cgccggtccc tcccggccgc cgggcgcggg tcgggccgtc   3360

cgcctcctcg cgggcgggcg cgacgaagaa gcgtcgcggg tctgtggcgc ggggccccgg   3420

tggtcgtgtc gcgtgggggg cgggtggttg gggcgtccgg ttcgccgcgc cccgccccgg   3480

ccccaccggt cccggccgcc gcccccgcgc ccgctcgctc cctcccgtcc gcccgtccgc   3540

ggcccgtccg tccgtccgtc gtcctcctcg cttgcggggc gccgggcccg tcctcgcgag   3600

gcccccccggc cggccgtccg gccgcgtcgg ggcctcgccg cgctctacct tacctacctg   3660

gttgatcctg ccagtagcat atgcttgtct caaagattaa gccatgcatg tctgagtacg   3720

cacggccggt acagtgaaac tgcgaatggc tcattaaatc agttatggtt cctttggtcg   3780

ctcgctcctc tcctacttgg ataactgtgg taattctaga gctaatacat gccgacgggc   3840

gctgaccccc ttcgcggggg ggatgcgtgc atttatcaga tcaaaaccaa cccggtcagc   3900

ccctctccgg ccccggccgg ggggcgggcg ccggcggctt tggtgactct agataacctc   3960

gggccgatcg cacgcccccc gtggcggcga cgacccattc gaacgtctgc cctatcaact   4020
```

ttcgatggta gtcgccgtgc ctaccatggt gaccacgggt gacggggaat cagggttcga 4080
ttccggagag ggagcctgag aaacggctac cacatccaag gaaggcagca ggcgcgcaaa 4140
ttacccactc ccgacccggg gaggtagtga cgaaaaataa caatacagga ctctttcgag 4200
gccctgtaat tggaatgagt ccactttaaa tcctttaacg aggatccatt ggagggcaag 4260
tctggtgcca gcagccgcgg taattccagc tccaatagcg tatattaaag ttgctgcagt 4320
taaaaagctc gtagttggat cttgggagcg ggcgggcggt ccgccgcgag gcgagccacc 4380
gcccgtcccc gccccttgcc tctcggcgcc ccctcgatgc tcttagctga gtgtcccgcg 4440
gggcccgaag cgtttacttt gaaaaaatta gagtgttcaa agcaggcccg agccgcctgg 4500
ataccgcagc taggaataat ggaataggac cgcggttcta ttttgttggt tttcggaact 4560
gaggccatga ttaagaggga cggccggggg cattcgtatt gcgccgctag aggtgaaatt 4620
cttggaccgg cgcaagacgg accagagcga aagcatttgc caagaatgtt ttcattaatc 4680
aagaacgaaa gtcggaggtt cgaagacgat cagataccgt cgtagttccg accataaacg 4740
atgccgaccg gcgatgcggc ggcgttattc ccatgacccg ccgggcagct tccgggaaac 4800
caaagtcttt gggttccggg gggagtatgg ttgcaaagct gaaacttaaa ggaattgacg 4860
gaagggcacc accaggagtg gagcctgcgg cttaatttga ctcaacacgg gaaacctcac 4920
ccggcccgga cacggacagg attgacagat tgatagctct ttctcgattc cgtgggtggt 4980
ggtgcatggc cgttcttagt tggtggagcg atttgtctgg ttaattccga taacgaacga 5040
gactctggca tgctaactag ttacgcgacc cccgagcggt cggcgtcccc caacttctta 5100
gagggacaag tggcgttcag ccacccgaga ttgagcaata acaggtctgt gatgccctta 5160
gatgtccggg gctgcacgcg cgctacactg actggctcag cgtgtgccta ccctacgccg 5220
gcaggcgcgg gtaacccgtt gaaccccatt cgtgatgggg atcggggatt gcaattattc 5280
cccatgaacg aggaattccc agtaagtgcg ggtcataagc ttgcgttgat taagtccctg 5340
ccctttgtac acaccgcccg tcgctactac cgattggatg gtttagtgag gccctcggat 5400
cggccccgcc ggggtcggcc cacggccctg gcggagcgct gagaagacgg tcgaacttga 5460
ctatctagag gaagtaaaag tcgtaacaag gtttccgtag gtgaacctgc ggaaggatca 5520
ttaacggagc ccggagggcg aggcccgcgg cggcgccgcc gccgccgcgc gcttccctcc 5580
gcacacccac ccccccaccg cgacgcggcg cgtgcgcggg cggggcccgc gtgcccgttc 5640
gttcgctcgc tcgttcgttc gccgcccggc cccgccggcc gcgagagccg gagaactcgg 5700
gagggagacg gggagagag agagagagag agaaagagaa agaagggcgt gtcgttggtg 5760
tgcgcgtgtc gtggggccgg cgggcggcgg ggagcggtcc ccggccgcgg ccccgacgac 5820
gtgggtgtcg gcgggcgcgg gggcggttct cggcggcgtc gcggcgggtc tgggggggtc 5880
tcggtgccct cctccccgcc ggggcccgtc gtccggcccc gccgcgccgg ctccccgtct 5940
tcggggccgg ccggattccc gtcgcctccg ccgcgccgct ccgcgccgcc gggcacggcc 6000
ccgctcgctc tccccggcct tcccgctagg gcgtctcgag ggtcgggggc cggacgccgg 6060
tcccctcccc cgcctcctcg tccgcccccc cgccgtccag gtacctagcg cgttccggcg 6120
cggaggttta aagacccctt ggggggatcg cccgtccgcc cgtgggtcgg gggcggtggt 6180
gggcccgcgg gggagtcccg tcgggagggg cccggcccct cccgcgcctc caccgcggac 6240
tccgctcccc ggccggggcc gcgccgccgc cgccgccgcg gcggccgtcg ggtgggggct 6300
ttacccggcg gccgtcgcgc gcctgccgcg cgtgtggcgt gcgccccgcg ccgtgggggc 6360
gggaaccccc gggcgcctgt ggggtggtgt ccgcgctcgc ccccgcgtgg gcggcgcgcg 6420

-continued

```
cctccccgtg gtgtgaaacc ttccgacccc tctccggagt ccggtcccgt ttgctgtctc   6480
gtctggccgg cctgaggcaa ccccctctcc tcttgggcgg gggggggggg gacgtgccgc   6540
gccaggaagg gcctcctccc ggtgcgtcgt cgggagcgcc ctcgccaaat cgacctcgta   6600
cgactcttag cggtggatca ctcggctcgt gcgtcgatga agaacgcagc tagctgcgag   6660
aattaatgtg aattgcagga cacattgatc atcgacactt cgaacgcact tgcggccccg   6720
ggttcctccc ggggctacgc ctgtctgagc gtcgcttgcc gatcaatcgc ccccgggggt   6780
gcctccgggc tcctcggggt gcgcggctgg gggttccctc gcagggcccg ccgggggccc   6840
tccgtccccc taagcgcaga cccggcggcg tccgccctcc tcttgccgcc gcgcccgccc   6900
cttcccccctc cccccgcggg ccctgcgtgg tcacgcgtcg ggtggcgggg gggagagggg   6960
ggcgcgcccg gctgagagag acggggaggg cggcgccgcc gccgcccgcg aagacggaga   7020
gggaaagaga gagccggctc gggccgagtt cccgtggccg ccgcctgcgg tccgggttcc   7080
tccctcgggg ggctccctcg cgccgcgcgc ggctcggggt tcggggttcg tcggccccgg   7140
ccgggtggaa ggtcccgtgc ccgtcgtcgt cgtcgtcgtc gcgcgtcgtc ggcggtgggg   7200
gcgtgttgcg tgcggtgtgg tggtggggga ggaggaaggc gggtccggaa ggggaagggt   7260
gccggcgggg agagagggtc gggggagcgc gtcccggtcg ccgcggttcg ccgcccgccc   7320
ccggtggcgg cccggcgtcc ggccgaccgc cgctcccgcg cccctcctcc tccccgccgc   7380
ccctcctccg aggccccgcc cgtcctcctc gccctccccg cgcgtacgcg cgcccgcccg   7440
cccggctcgc ctcgcggcgc gtcggccggg gccgggagcc cgccccgcgg cccgcccggc   7500
cgcgcccgtg gccgcggcgc cggggttcgc gtgtccccgg cggcgacccg cgggacgccg   7560
cggtgtcgtc cgccgtcgcg cgcccgcctc cggctcgcgg ccgcgccgcg ccgcgccggg   7620
gccccgtccc gagcttccgc gtcggggcgg ggcggctccg ccgccgcgtc ctcggacccg   7680
tccccccgac ctccgcgggg gagacgggtc ggggcgtgcg gcgcccgtcc cgcccccggc   7740
ccgtgcccct ccctccggtc gtcccgctcc ggcggggcgg cgcgggggtg ccgccggccg   7800
cgcgctctct ctcccgtcgc ctctccccct cgccgggccc gtctcccgac ggagcgtcgg   7860
gcgggcggtc gggccggcgc gattccgtcc gtccgtccgc cgagcggccc gtccccctcc   7920
gagacgcgac ctcagatcag acgtggcgac ccgctgaatt taagcatatt agtcagcgga   7980
ggagaagaaa ctaaccagga ttccctcagt aacggcgagt gaacagggaa gagcccagcg   8040
ccgaatcccc gccccgcggc ggggcgcggg acatgtggcg tacggaagac ccgctccccg   8100
gcgccgctcg tgggggggccc aagtccttct gatcgaggcc cagcccgtgg acggtgtgag   8160
gccggtagcg gcccccggcg cgccgggccc gggtcttccc ggagtcgggt tgcttgggaa   8220
tgcagcccaa agcgggtggt aaactccatc taaggctaaa taccggcacg agaccgatag   8280
tcaacaagta ccgtaaggga aagttgaaaa gaactttgaa gagagagttc aagagggcgt   8340
gaaaccgtta agaggtaaac gggtggggtc cgcgcagtcc gcccggagga ttcaacccgg   8400
cggcgggtcc ggccgtgtcg gcggcccggc ggatctttcc cgccccccgt tcctcccgac   8460
ccctccaccc gccctccctt cccccgccgc ccctcctcct cctccccgga gggggcgggc   8520
tccggcgggt gcgggggtgg gcgggcgggg ccgggggtgg ggtcggcggg ggaccgtccc   8580
ccgaccggcg accggccgcc gccgggcgca tttccaccgc ggcggtgcgc cgcgaccggc   8640
tccgggacgg ctgggaaggc ccggcgggga aggtggctcg gggggccccg tccgtccgtc   8700
cgtccgtcct cctcctcccc cgtctccgcc ccccggcccc gcgtcctccc tcgggagggc   8760
gcgcgggtcg gggcggcggc ggcggcggcg gtggcggcgg cggcggcggc ggcgggaccg   8820
```

-continued aaacccccccc cgagtgttac agccccccccg gcagcagcac tcgccgaatc ccggggccga 8880
gggagcgaga cccgtcgccg cgctctcccc cctcccggcg cccaccccccg cggggaatcc 8940 cccgcgaggg gggtctcccc cgcgggggcg cgccggcgtc tcctcgtggg ggggccgggc 9000 caccccctccc acggcgcgac cgctctccca cccctcctcc ccgcgccccc gccccggcga 9060
cggggggggt gccgcgcgcg ggtcgggggg cggggcggac tgtccccagt gcgccccggg 9120
cgggtcgcgc cgtcgggccc gggggaggtt ctctcggggc cacgcgcgcg tcccccgaag 9180
agggggacgg cggagcgagc gcacggggtc ggcggcgacg tcggctaccc acccgacccg 9240
tcttgaaaca cggaccaagg agtctaacac gtgcgcgagt cgggggctcg cacgaaagcc 9300
gccgtggcgc aatgaaggtg aaggccggcg cgctcgccgg ccgaggtggg atcccgaggc 9360
ctctccagtc cgccgagggc gcaccaccgg cccgtctcgc ccgccgcgcc ggggaggtgg 9420
agcacgagcg cacgtgttag gacccgaaag atggtgaact atgcctgggc agggcgaagc 9480
cagaggaaac tctggtggag gtccgtagcg gtcctgacgt gcaaatcggt cgtccgacct 9540
gggtataggg gcgaaagact aatcgaacca tctagtagct ggttccctcc gaagtttccc 9600
tcaggatagc tggcgctctc gcagacccga cgcacccccg ccacgcagtt ttatccggta 9660
aagcgaatga ttagaggtct tggggccgaa acgatctcaa cctattctca aactttaaat 9720
gggtaagaag cccggctcgc tggcgtggag ccgggcgtgg aatgcgagtg cctagtgggc 9780
cacttttggt aagcagaact ggcgctgcgg gatgaaccga acgccgggtt aaggcgcccg 9840
atgccgacgc tcatcagacc ccagaaaagg tgttggttga tatagacagc aggacggtgg 9900
ccatggaagt cggaatccgc taaggagtgt gtaacaactc acctgccgaa tcaactagcc 9960
ctgaaaatgg atggcgctgg agcgtcgggc ccatacccgg ccgtcgccgg cagtcgagag 10020
tggacgggag cggcgggggc ggcgcgcgcg cgcgcgcgtg tggtgtgcgt cggagggcgg 10080
cggcggcggc ggcggcgggg gtgtggggtc cttcccccgc ccccccccccc acgcctcctc 10140 ccctcctccc gcccacgccc cgctccccgc ccccggagcc ccgcggacgc tacgccgcga 10200
cgagtaggag ggccgctgcg gtgagccttg aagcctaggg cgcgggcccg ggtggagccg 10260
ccgcaggtgc agatcttggt ggtagtagca aatattcaaa cgagaacttt gaaggccgaa 10320
gtggagaagg gttccatgtg aacagcagtt gaacatgggt cagtcggtcc tgagagatgg 10380
gcgagcgccg ttccgaaggg acgggcgatg gcctccgttg ccctcggccg atcgaaaggg 10440
agtcgggttc agatccccga atccggagtg gcggagatgg gcgccgcgag gcgtccagtg 10500
cggtaacgcg accgatcccg gagaagccgg cgggagcccc ggggagagtt ctcttttctt 10560
tgtgaagggc agggcgccct ggaatgggtt cgccccgaga gaggggcccg tgccttggaa 10620
agcgtcgcgg ttccggcggc gtccggtgag ctctcgctgg cccttgaaaa tccgggggag 10680
agggtgtaaa tctcgcgccg ggccgtaccc atatccgcag caggtctcca aggtgaacag 10740
cctctggcat gttggaacaa tgtaggtaag ggaagtcggc aagccggatc cgtaacttcg 10800
ggataaggat tggctctaag ggctgggtcg gtcgggctgg ggcgcgaagc ggggctgggc 10860
gcgcgccgcg gctggacgag gcgccgccgc cccccccacg cccggggcac ccccctcgcg 10920
gccctccccc gccccacccc gcgcgcgccg ctcgctccct ccccgccccg cgccctctct 10980
ctctctctct cccccgctcc ccgtcctccc ccctccccgg gggagcgccg cgtgggggcg 11040
gcggcggggg gagaagggtc ggggcggcag ggccggcgg cggcccgccg cggggccccg 11100

-continued gcggcggggg cacggtcccc cgcgaggggg gcccgggcac ccggggggcc ggcggcggcg 11160
gcgactctgg acgcgagccg ggcccttccc gtggatcgcc ccagctgcgg cgggcgtcgc 11220
ggccgccccc ggggagcccg gcgggcgccg gcgcgccccc ccccccaccc cacgtctcgt 11280
cgcgcgcgcg tccgctgggg gcggggagcg gtcgggcggc ggcggtcggc gggcggcggg 11340
gcggggcggt tcgtccccc gccctacccc cccggccccg tccgcccccc gttcccccct 11400
cctcctcggc gcgcggcggc ggcggcggca ggcggcggag gggccgcggg ccggtccccc 11460
ccgccgggtc cgcccccggg gccgcggttc cgcgcggcgc ctcgcctcgg ccggcgccta 11520
gcagccgact tagaactggt gcggaccagg ggaatccgac tgtttaatta aaacaaagca 11580
tcgcgaaggc ccgcggcggg tgttgacgcg atgtgatttc tgcccagtgc tctgaatgtc 11640
aaagtgaaga aattcaatga agcgcgggta aacggcggga gtaactatga ctctcttaag 11700
gtagccaaat gcctcgtcat ctaattagtg acgcgcatga atggatgaac gagattccca 11760
ctgtccctac ctactatcca gcgaaaccac agccaaggga acgggcttgg cggaatcagc 11820
ggggaaagaa gaccctgttg agcttgactc tagtctggca cggtgaagag acatgagagg 11880
tgtagaataa gtgggaggcc cccggcgccc ccccggtgtc cccgcgaggg gcccggggcg 11940
gggtccgccg gccctgcggg ccgccggtga aataccacta ctctgatcgt tttttcactg 12000
acccggtgag gcgggggggc gagccccgag gggctctcgc ttctggcgcc aagcgcccgg 12060
ccgcgcgccg gccgggcgcg acccgctccg ggacagtgc caggtgggga gtttgactgg 12120
ggcggtacac ctgtcaaacg gtaacgcagg tgtcctaagg cgagctcagg gaggacagaa 12180
acctcccgtg gagcagaagg gcaaaagctc gcttgatctt gattttcagt acgaatacag 12240
accgtgaaag cggggcctca cgatccttct gaccttttgg gttttaagca ggaggtgtca 12300
gaaaagttac cacagggata actggcttgt ggcggccaag cgttcatagc gacgtcgctt 12360
tttgatcctt cgatgtcggc tcttcctatc attgtgaagc agaattcacc aagcgttgga 12420
ttgttcaccc actaataggg aacgtgagct gggtttagac cgtcgtgaga caggttagtt 12480
ttaccctact gatgatgtgt tgttgccatg gtaatcctgc tcagtacgag aggaaccgca 12540
ggttcagaca tttggtgtat gtgcttggct gaggagccaa tggggcgaag ctaccatctg 12600
tgggattatg actgaacgcc tctaagtcag aatcccgccc aggcggaacg atacggcagc 12660
gccgcggagc ctcggttggc ctcggatagc cggtccccg cctgtccccg ccggcgggcc 12720
gcccccccc tccacgcgcc ccgcgcgcgc gggagggcgc gtgccccgcc gcgcgccggg 12780
accggggtcc ggtgcggagt gcccttcgtc ctgggaaacg gggcgcggcc ggagaggcgg 12840
ccgccccctc gcccgtcacg caccgcacgt tcgtggggaa cctggcgcta aaccattcgt 12900
agacgacctg cttctgggtc ggggtttcgt acgtagcaga gcagctccct cgctgcgatc 12960
tattgaaagt cagccctcga cacaagggtt tgtccgcgcg cgcgcgcgcg cgcgcgtgcg 13020
gggggcccgg cggggcgtgc gcgtccggcg ccgtccgtcc ttccgttcgt cttcctccct 13080
cccggcctct cccgccgacc gcgggcgtgg tggtgggggt gtggggggga gggcgcgcga 13140
ccccggtcgg cgcgccccgc ttcttcggtt cccgcctcct ccccgttcac cgccggggcg 13200
gctcgtccgc tccgggccgg gacggggtcc ggggagcgtg gtttgggagc cgcggaggcg 13260
gccgcgccga gccgggcccg tggcccgccg gtccccgtcc cgggggttgg ccgcgcgggc 13320
cccggtgggg cggccacccg gggtcccggc cctcgcg 13357

-continued

<210> SEQ ID NO 69
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 69
tttcttgtaa gcgtcgaggt g 21

<210> SEQ ID NO 70
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 70
agcaggcacc taggagacaa 20

<210> SEQ ID NO 71
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 71
tcaggcgttc tcgtctcc 18

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72
caccacatcg atcacgaaga 20

<210> SEQ ID NO 73
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 73
ctatgcgcac ccgttctc 18

<210> SEQ ID NO 74
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 74
gtagcgaagc gagcagga 18